US012329811B2

(12) United States Patent
Nachbagauer et al.

(10) Patent No.: US 12,329,811 B2
(45) Date of Patent: Jun. 17, 2025

(54) SEASONAL RNA INFLUENZA VIRUS VACCINES

(71) Applicant: ModernaTX, Inc., Cambridge, MA (US)

(72) Inventors: Raffael Nachbagauer, Cambridge, MA (US); Carole Henry, Cambridge, MA (US); Patricia Jorquera, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 115 days.

(21) Appl. No.: 17/572,465

(22) Filed: Jan. 10, 2022

(65) Prior Publication Data

US 2023/0000970 A1 Jan. 5, 2023

Related U.S. Application Data

(60) Provisional application No. 63/249,291, filed on Sep. 28, 2021, provisional application No. 63/210,409, filed on Jun. 14, 2021, provisional application No. 63/174,437, filed on Apr. 13, 2021, provisional application No. 63/136,126, filed on Jan. 11, 2021.

(51) Int. Cl.

| | |
|---|---|
| *A61K 39/145* | (2006.01) |
| *A61P 31/16* | (2006.01) |
| *A61K 39/00* | (2006.01) |

(52) U.S. Cl.

CPC ............ *A61K 39/145* (2013.01); *A61P 31/16* (2018.01); *A61K 2039/53* (2013.01); *A61K 2039/6018* (2013.01)

(58) Field of Classification Search

None

See application file for complete search history.

(56) References Cited

U.S. PATENT DOCUMENTS

| | | | |
|---|---|---|---|
| 5,256,555 | A | 10/1993 | Milburn et al. |
| 5,756,264 | A | 5/1998 | Schwartz et al. |
| 6,022,715 | A | 2/2000 | Merenkova et al. |
| 6,040,427 | A | 3/2000 | Locht et al. |
| 6,096,503 | A | 8/2000 | Sutcliffe et al. |
| 6,100,024 | A | 8/2000 | Hudson et al. |
| 6,528,262 | B1 | 3/2003 | Gilad et al. |
| 8,383,340 | B2 | 2/2013 | Ketterer et al. |
| 8,710,200 | B2 | 4/2014 | Schrum et al. |
| 8,754,062 | B2 | 6/2014 | De Fougerolles et al. |
| 8,822,663 | B2 | 9/2014 | Schrum et al. |
| 8,980,864 | B2 | 3/2015 | Hoge et al. |
| 8,999,380 | B2 | 4/2015 | Bancel et al. |
| 9,221,891 | B2 | 12/2015 | Bancel et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,572,896 | B2 | 2/2017 | Bancel et al. |
| 9,597,380 | B2 | 3/2017 | Chakraborty et al. |
| 9,675,668 | B2 | 6/2017 | Bancel et al. |
| 9,868,691 | B2 | 1/2018 | Benenato et al. |
| 9,872,900 | B2 | 1/2018 | Ciaramella et al. |
| 10,023,626 | B2 | 7/2018 | Bolen et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,027,025 | B2 | 6/2021 | Hoge et al. |
| 11,045,540 | B2 | 6/2021 | Ciaramella |
| 11,103,578 | B2 | 8/2021 | Ciaramella et al. |
| 11,266,735 | B2 | 3/2022 | Kallen et al. |
| 11,351,242 | B1 | 6/2022 | Lori et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,564,893 | B2 | 1/2023 | Smith |

(Continued)

FOREIGN PATENT DOCUMENTS

| | | | |
|---|---|---|---|
| CN | 110974954 | A | 4/2020 |
| EP | 2092064 | B1 | 9/2010 |

(Continued)

OTHER PUBLICATIONS

U.S. Appl. No. 16/897,859, filed Jun. 10, 2020, Ciaramella et al.
U.S. Appl. No. 16/897,734, filed Jun. 10, 2020, Ciaramella et al.
U.S. Appl. No. 17/245,973, filed Apr. 30, 2021, Ciaramella.
U.S. Appl. No. 16/965,589, filed Jul. 28, 2020, Ciaramella et al.
U.S. Appl. No. 17/439,198, filed Sep. 14, 2021, Lusso et al.
U.S. Appl. No. 17/737,581, filed May 5, 2022, Panther et al.
International Search Report and Written Opinion for Application No. PCT/US2022/011851, mailed Mar. 25, 2022.
[No Author Listed], "Moderna's (MRNA) Flu Vaccine Data Fails to Impress Investors", Dec. 13, 2021 (Dec. 13, 2021), pp. 1-6. Retrieved from the Internet: URL:https://finance.yahoo.com/news/moderna s-mrna-flu-vaccine-data-153303228.html?guccounter=1&guce_referrer=aHROcHM6Ly93d3cuZ29vZ2xlLmNvbS8&guce_referrer_sig=AQAAAJpn3p7IiHi5Gppdr9ckD_a8FxRTr2MtUAQeqDz37PFJp8H_QTbC2SKOsIbb28wvm7kJTQJcRAdYVNfcXSBAeWKrKRY4HMdkSZGaWdx2fMpYlwKaeGuc4iW6N8k-60f8R7YT HZiINunaCU.

(Continued)

*Primary Examiner* — Benjamin P Blumel

(74) *Attorney, Agent, or Firm* — Foley & Lardner LLP

(57) ABSTRACT

The disclosure provides RNA vaccines for seasonal influenza virus as well as methods of using the vaccines.

24 Claims, 57 Drawing Sheets

Specification includes a Sequence Listing.

(56) References Cited

U.S. PATENT DOCUMENTS 11,576,961 B2 2/2023 Ciaramella et al.
11,643,441 B1 5/2023 Ciaramella et al.
11,696,946 B2 7/2023 Ciaramella
11,752,206 B2 9/2023 Ciaramella et al.
11,786,607 B2 10/2023 Hoge et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 2/2024 Ciaramella et al.
11,912,982 B2 2/2024 Issa et al.
12,070,495 B2 8/2024 Lusso et al.
2001/0001066 A1 5/2001 Cezayirli et al.
2001/0005506 A1 6/2001 Cezayirli et al.
2003/0165849 A1 9/2003 Zhang et al.
2006/0247195 A1 11/2006 Ray
2007/0281336 A1 12/2007 Jendrisak et al.
2008/0220471 A1 9/2008 Davis et al.
2010/0028943 A1 2/2010 Thomas et al.
2010/0048883 A1 2/2010 Ketterer et al.
2010/0291156 A1 11/2010 Barner et al.
2012/0177701 A1 7/2012 Ilyinskii et al.
2012/0301955 A1 11/2012 Thomas et al.
2013/0102034 A1 4/2013 Schrum et al.
2013/0236974 A1 9/2013 De Fougerolles
2013/0245103 A1 9/2013 de Fougerolles et al.
2013/0259923 A1 10/2013 Bancel et al.
2013/0266640 A1 10/2013 De Fougerolles et al.
2014/0142290 A1 5/2014 Madden et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0328825 A1 11/2014 Meis et al.
2014/0378538 A1 12/2014 Bancel
2015/0051268 A1 2/2015 Bancel et al.
2015/0056253 A1 2/2015 Bancel et al.
2015/0141499 A1 5/2015 Bancel et al.
2015/0307542 A1 10/2015 Roy et al.
2015/0315541 A1 11/2015 Bancel et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0194368 A1 7/2016 Hoge et al.
2016/0194625 A1 7/2016 Hoge et al.
2016/0243221 A1 8/2016 Hoge et al.
2016/0317647 A1 11/2016 Ciaramella et al.
2017/0043037 A1 2/2017 Kariko et al.
2017/0202979 A1 7/2017 Chakraborty et al.
2017/0204152 A1 7/2017 Nelson et al.
2017/0130255 A1 10/2017 Wang et al.
2017/0340724 A1 11/2017 Ciaramella et al.
2017/0340725 A1 11/2017 Ciaramella et al.
2018/0000953 A1 1/2018 Almarsson et al.
2018/0002393 A1 1/2018 Bancel et al.
2018/0028645 A1 2/2018 Ciaramella et al.
2018/0028664 A1 2/2018 Besin et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 10/2018 Ciaramella et al.
2018/0296663 A1 10/2018 Hipp et al.
2018/0303929 A1 10/2018 Ciaramella et al.
2018/0311336 A1 11/2018 Ciaramella et al.
2018/0311343 A1 11/2018 Huang et al.
2018/0312549 A1 11/2018 Ciaramella
2018/0318409 A1 11/2018 Valiante et al.
2018/0363019 A1 12/2018 Hoge
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0085368 A1 3/2019 Bancel et al.
2019/0099481 A1 4/2019 Ciaramella et al.
2019/0125839 A1 5/2019 Frederick et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0275170 A1 9/2019 Benenato et al.
2019/0298657 A1 10/2019 Martini et al.
2019/0298658 A1 10/2019 Benenato
2019/0300906 A1 10/2019 Martini et al.
2019/0314292 A1 10/2019 Benenato et al.
2019/0336452 A1 11/2019 Brader
2019/0351040 A1 11/2019 Valiante et al.
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0069599 A1 3/2020 Smith et al.
2020/0071689 A1 3/2020 Miracco
2020/0085916 A1 3/2020 Martini et al.
2020/0109420 A1 4/2020 Brito et al.
2020/0129445 A1 4/2020 Patel et al.
2020/0129608 A1 4/2020 Ciaramella et al.
2020/0129615 A1 4/2020 Ciaramella et al.
2020/0239869 A1 7/2020 Issa et al.
2020/0254086 A1 8/2020 Hoge et al.
2020/0282047 A1 9/2020 Ciaramella et al.
2020/0306191 A1 10/2020 Schariter et al.
2020/0338004 A1 10/2020 Hansson et al.
2020/0368162 A1 11/2020 Martini
2021/0046173 A1 2/2021 Ciaramella et al.
2021/0087135 A1 3/2021 Benenato et al.
2021/0162037 A1 6/2021 Jasny et al.
2021/0163919 A1 6/2021 Issa et al.
2021/0187097 A1 6/2021 Ciaramella et al.
2021/0206818 A1 7/2021 Huang et al.
2021/0217484 A1 7/2021 Giessel et al.
2021/0228707 A1 7/2021 Mektar et al.
2021/0268086 A1 9/2021 Zhong et al.
2021/0309976 A1 10/2021 Dousis et al.
2021/0378980 A1 12/2021 Horhota et al.
2022/0031631 A1 2/2022 Almarsson et al.
2022/0047518 A1 2/2022 Hennessy et al.
2022/0054653 A1 2/2022 Martini et al.
2022/0062175 A1 3/2022 Smith
2022/0062408 A1 3/2022 Kramarczyk et al.
2022/0125899 A1 4/2022 Ashburn et al.
2022/0145381 A1 5/2022 Elich et al.
2022/0236253 A1 7/2022 Hopson
2022/0241399 A1 8/2022 Lusso et al.
2022/0347292 A1 11/2022 Panther et al.
2022/0348900 A1 11/2022 Shamashkin et al.
2022/0349006 A1 11/2022 Amato et al.
2023/0000970 A1 1/2023 Nachbagauer et al.
2023/0142529 A1 5/2023 White et al.
2023/0181481 A1 6/2023 White et al.
2023/0190761 A1 6/2023 Brader et al.
2023/0212645 A1 7/2023 Marquardt et al.
2023/0287437 A1 9/2023 Smith et al.
2023/0338506 A1 10/2023 Shaw et al.
2023/0346914 A1 11/2023 Stewart-Jones et al.
2023/0355743 A1 11/2023 Stewart-Jones et al.
2024/0100145 A1 3/2024 Bollman et al.
2024/0100151 A1 3/2024 Carfi et al.
2024/0139309 A1 5/2024 Carfi et al.
2024/0173400 A1 5/2024 Ciaramella et al.
2024/0181030 A1 6/2024 Himansu et al.
2024/0207392 A1 6/2024 Chandramouli et al.
2024/0209068 A1 6/2024 Deal et al.
2024/0226028 A1 7/2024 Goldman et al.
2024/0226277 A1 7/2024 Nachbagauer et al.

(56) References Cited

U.S. PATENT DOCUMENTS

2024/0229109 A1 7/2024 Rabideau et al.
2024/0238211 A1 7/2024 Brader et al.
2024/0263226 A1 8/2024 Schmitt

FOREIGN PATENT DOCUMENTS

EP 3083578 A1 10/2016
WO WO 2002/48310 A2 6/2002
WO WO 2005/027936 A2 3/2005
WO WO 2005/118813 A2 12/2005
WO WO 2005/118857 A2 12/2005
WO WO 2008/077592 A1 7/2008
WO WO 2008/145129 A2 12/2008
WO WO 2011/071931 A2 6/2011
WO WO 2011/150264 A2 12/2011
WO WO 2012/038450 A1 3/2012
WO WO 2013/090648 A1 6/2013
WO WO 2013/102203 A1 7/2013
WO WO 2014/140211 A1 9/2014
WO WO 2014/144711 A1 9/2014
WO WO 2014/152030 A1 9/2014
WO WO 2014/152966 A1 9/2014
WO WO 2014/159813 A1 10/2014
WO WO 2014/160243 A1 10/2014
WO WO 2015/085318 A2 6/2015
WO WO 2015/143335 A1 9/2015
WO WO 2015/164674 A1 10/2015
WO WO 2015/188933 A1 12/2015
WO WO 2016/138160 A1 9/2016
WO WO 2016/164762 A1 10/2016
WO WO 2016/201377 A1 12/2016
WO WO 2017/011773 A2 1/2017
WO WO 2017/015457 A1 1/2017
WO WO 2017/015463 A1 1/2017
WO WO 2017/019935 A1 2/2017
WO WO 2017/020026 A1 2/2017
WO WO 2017/031232 A1 2/2017
WO WO 2017/031241 A1 2/2017
WO WO 2017/062513 A1 4/2017
WO WO 2017/066789 A1 4/2017
WO WO 2017/070601 A1 4/2017
WO WO 2017/070616 A1 4/2017
WO WO 2017/070618 A1 4/2017
WO WO 2017/070620 A1 4/2017
WO WO 2017/070622 A1 4/2017
WO WO 2017/070623 A1 4/2017
WO WO 2017/075038 A1 5/2017
WO WO 2017/081082 A1 5/2017
WO WO 2017/112865 A1 6/2017
WO WO 2017/127750 A1 7/2017
WO WO 2017/201333 A1 11/2017
WO WO 2017/201340 A1 11/2017
WO WO 2017/201342 A1 11/2017
WO WO 2017/201347 A1 11/2017
WO WO 2018/053209 A1 3/2018
WO WO 2018/075980 A1 4/2018
WO WO 2018/078053 A1 5/2018
WO WO 2018/081459 A1 5/2018
WO WO 2018/081462 A1 5/2018
WO WO 2018/089851 A1 5/2018
WO WO 2018/107088 A1 6/2018
WO WO 2018/111967 A1 6/2018
WO WO 2018/144082 A1 8/2018
WO WO 2018/144778 A1 8/2018
WO WO 2018/157009 A1 8/2018
WO WO 2018/170245 A1 9/2018
WO WO 2018/170256 A1 9/2018
WO WO 2018/170260 A1 9/2018
WO WO 2018/170270 A1 9/2018
WO WO 2018/170347 A1 9/2018
WO WO 2018/175783 A1 9/2018
WO WO 2018/187590 A2 10/2018
WO WO 2018/200737 A1 11/2018
WO WO 2018/232355 A1 12/2018
WO WO 2018/232357 A1 12/2018
WO WO 2019/018765 A1 1/2019
WO WO 2019/036670 A1 2/2019
WO WO 2019/036682 A1 2/2019
WO WO 2019/036683 A1 2/2019
WO WO 2019/036685 A1 2/2019
WO WO 2019/081750 A1 5/2019
WO WO 2019/103993 A1 5/2019
WO WO 2020/056370 A1 3/2020
WO WO 2020/061284 A1 3/2020
WO WO 2020/061295 A1 3/2020
WO WO 2020/061367 A1 3/2020
WO WO 2020/097291 A1 5/2020
WO WO 2020/163719 A2 8/2020
WO WO 2020/172239 A1 8/2020
WO WO 2020/185811 A1 9/2020
WO WO 2020/190750 A1 9/2020
WO WO 2020/243561 A1 12/2020
WO WO 2021/016430 A1 1/2021
WO WO 2021/030533 A1 2/2021
WO WO 2021/050864 A1 3/2021
WO WO 2021/055811 A1 3/2021
WO WO 2021/155243 A1 8/2021
WO WO 2021/155274 A1 8/2021
WO WO 2021/159040 A2 8/2021
WO WO 2021/159130 A2 8/2021
WO WO 2021/204175 A1 10/2021
WO WO 2021/211343 A1 10/2021
WO WO 2021/222304 A1 11/2021
WO WO 2021/231929 A1 11/2021
WO WO 2021/231963 A1 11/2021
WO WO 2021/237084 A1 11/2021
WO WO 2021/239880 A1 12/2021
WO WO 2021/247817 A1 12/2021
WO WO 2022/032154 A2 2/2022
WO WO 2022/067010 A1 3/2022
WO WO 2022/076562 A1 4/2022
WO WO 2022/099003 A1 5/2022
WO WO 2022/137133 A1 6/2022
WO WO 2022/150717 A1 7/2022
WO WO 2022/155524 A1 7/2022
WO WO 2022/155530 A1 7/2022
WO WO 2022/187698 A1 9/2022
WO WO 2022/197624 A1 9/2022
WO WO 2022/204491 A1 9/2022
WO WO 2022/212191 A1 10/2022
WO WO 2022/212442 A1 10/2022
WO WO 2022/212711 A1 10/2022
WO WO 2022/221335 A1 10/2022
WO WO 2022/221336 A1 10/2022
WO WO 2022/221359 A1 10/2022
WO WO 2022/221440 A1 10/2022
WO WO 2022/226277 A1 10/2022
WO WO 2022/226318 A1 10/2022
WO WO 2022/232585 A1 11/2022
WO WO 2022/241103 A1 11/2022
WO WO 2022/245888 A1 11/2022
WO WO 2022/266010 A1 12/2022
WO WO 2022/266012 A1 12/2022
WO WO 2022/266389 A1 12/2022
WO WO 2023/274860 A1 1/2023
WO WO 2023/283642 A1 1/2023
WO WO 2023/283645 1/2023
WO WO 2023/283651 1/2023
WO WO 2023/014649 A1 2/2023
WO WO 2023/018773 A1 2/2023
WO WO 2023/018923 A1 2/2023
WO WO 2023/019181 A1 2/2023
WO WO 2023/056401 A1 4/2023
WO WO 2023/069625 A1 4/2023
WO WO 2023/069895 A1 4/2023
WO WO 2023/069900 A1 4/2023
WO WO 2023/076358 A1 5/2023
WO WO 2023/076658 A1 5/2023
WO WO 2023/081311 A1 5/2023
WO WO 2023/092069 A1 5/2023
WO WO 2023/107999 A2 6/2023
WO WO 2023/114307 A1 6/2023
WO WO 2023/132885 A1 7/2023
WO WO 2023/137149 A1 7/2023

(56) References Cited

FOREIGN PATENT DOCUMENTS

| | | | |
|---|---|---|---|
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |
| WO | WO 2024/123978 | A1 | 6/2024 |
| WO | WO 2024/151811 | A1 | 7/2024 |
| WO | WO 2024/163465 | A1 | 8/2024 |

OTHER PUBLICATIONS

[No Author Listed], MEGAscript Kit Product Manual, Oct. 27, 2009. Ambion/Invitrogen website: http://tools.invitrogen.com/contenl/sfs/manuals/ cms_072987.pdf, (last accessed Mar. 17, 2013). 29 pages.

[No Author Listed], World Health Organization: "Recommended composition of influenza virus vaccines for use in the 2021 southern hemisphere influenza season", Sep. 25, 2020 (Sep. 25, 2020), pp. 1-9, Retrieved from the Internet: URL:https://www.who.int/publications/m/item/recommended-composition-of-influenza-virus-vaccines-for-use-in-the-2022-southern-hemisphere-influenza-season.

Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.

Brennan, Ribonucleoside triphosphate concentration-dependent termination of bacteriophage SP01 transcription in vitro by Bacillus subtilis RNA polymerase. Virology. Jun. 1984;135(2):555-60. doi: 10.1016/0042-6822(84)90211-3.

Devoldere et al., Evading innate immunity in nonviral mRNA delivery: don't shoot the messenger. Drug Discov Today. Jan. 2016;21(1):11-25. doi: 10.1016/j.drudis.2015.07.009. Epub Jul. 23, 2015.

Dolgin, mRNA flu shots move into trials. Nature Reviews Drug Discovery 20, 801-803 (2021).

Easton et al., Rapid, nondenaturing RNA purification using weak anion-exchange fast performance liquid chromatography. RNA. Mar. 2010;16(3):647-53. Epub Jan. 25, 2010.

Freyn et al., A Multi-Targeting, Nucleoside-Modified mRNA Influenza Virus Vaccine Provides Broad Protection in Mice. Mol Ther. Jul. 8, 2020;28(7):1569-1584. doi: 10.1016/j.ymthe.2020.04.018. Epub Apr. 19, 2020.

Furuichi, Caps on Eukaryotic mRNAs. eLS. John Wiley & Sons. Jul. 2014. 1-12.

Georgopoulos et al., Use of high-performance liquid chromatographic fractionation of large RNA molecules in the assay of group I intron ribozyme activity. J Chromatogr A. Jan. 28, 2000;868(1):109-14.

Gruegelsiepe et al., Handbook of RNA Biochemistry, ed. R.K. Hartmann, Part LI, pp. 3-21, 2005.

Hartmann et al., Handbook of RNA Biochemistry, Second Edition, "Part I RNA Synthesis and Detection." 2014. p. 1-27.

Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.

Kariko et al., Generating the optimal mRNA for therapy: HPLC purification eliminates immune activation and improves translation of nucleoside-modified, protein-encoding mRNA. Nucleic Acids Res. Nov. 2011;39(21):e142.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Kern et al., Application of a Fed-Batch System to Produce RNA by in Vitro Transcription. Biotechnol Prog. Mar.-Apr. 1999;15(2):174-84. doi: 10.1021/bp990008g.

Koch, G., et al., Quantitative Studies on the Infectivity of ribonucleic acid from partially purified and highly purified poliovirus preparations. Virology. Mar. 1960; 10(3): 329-343.

Krammer et al., Chimeric hemagglutinin influenza virus vaccine constructs elicit broadly protective stalk-specific antibodies. J Virol. Jun. 2013;87(12):6542-50. doi: 10.1128/JVI.00641-13. Epub Apr. 10, 2013.

Lewandowski, L.J. et al., Separation of the infectious ribonucleic acid of potato spindle tuber virus from double-stranded ribonucleic acid of plant tissue extracts. J Virol. Nov. 1971;8(5):809-12.

Li et al., Lipid-based nanoparticles for nucleic acid delivery. Pharm Res. Mar. 2007;24(3):438-49. doi: 10.1007/s11095-006-9180-5.

Mellits, K.H. et al., Removal of double-stranded contaminants from RNA transcripts: synthesis of adenovirus VA RNAI from a T7 vector. Nucleic Acids Res. Sep. 25, 1990;18(18):5401-6.

Nedialkov et al., NTP-driven translocation by human RNA polymerase II. J Biol Chem. May 16, 2003;278(20):18303-12. doi: 10.1074/jbc.M301103200. Epub Mar. 13, 2003.

Ouranidis et al., Pharma 4.0 Continuous mRNA Drug Products Manufacturing. Pharmaceutics. Aug. 31, 2021;13(9):1371. doi: 10.3390/pharmaceutics13091371.

Sahin et al., mRNA-based therapeutics—developing a new class of drugs. Nat Rev Drug Discov. Oct. 2014;13(10):759-80. doi: 10.1038/nrd4278. Epub Sep. 19, 2014.

Schmidt et al., Fast and Flexible mRNA Vaccine Manufacturing as a Solution to Pandemic Situations by Adopting Chemical Engineering Good Practice—Continuous Autonomous Operation in Stainless Steel Equipment Concepts. Processes. 2021;9(11):1874-93.

Steinle et al., Concise Review: Application of In Vitro Transcribed Messenger RNA for Cellular Engineering and Reprogramming: Progress and Challenges. Stem Cells. Jan. 2017;35(1):68-79. doi: 10.1002/stem.2402. Epub Jun. 20, 2016.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.

Wang et al., Purification of the messenger ribonucleic acid for the lipoprotein of the *Escherichia coli* outer membrane. Biochemistry. Oct. 2, 1979;18(20):4270-7.

Weissman et al., HPLC purification of in vitro transcribed long RNA. Methods Mol Biol. 2013;969:43-54. doi: 10.1007/978-1-62703-260-5_3.

[No Author Listed], Comirnaty (mRNA-1273) EMA SmPC (summary of product characteristics). Published Dec. 1, 2021. 276 pages.

[No Author Listed], Influenza A virus A/Jiangxi/IPB13/2013(H10N8) hemagglutinin protein. UniProtKB Accession: A0A059T4A1. Sep. 3, 2014. 1 page.

[No Author Listed], Moderna Provides Business Update and Announces Three New Development Programs in Infectious Disease Vaccines. Press Release. Jan. 11, 2021. 5 pages.

[No Author Listed], Moderna's COVID-19 Vaccine Candidate Meets its Primary Efficacy Endpoint in the First Interim Analysis of the Phase 3 COVE Study. Press Release. Nov. 16, 2020. pages.

[No Author Listed], Press release, Moderna, "Moderna Announces Publication in The New England Journal of Medicine of Interim Results From Older Adult Age Cohorts in Phase 1 Study of its mRNA Vaccine Against COVID-19 (mRNA-1273)", Sep. 29, 2020. 7 pages.

[No Author Listed], spike glycoprotein [Middle East respiratory syndrome coronavirus]. GenBank Accession No. AGN52936.1. Published Jun. 10, 2013. 2 pages.

[No Author Listed], SPIKE_CVHSA. UniProt KB Accession No. P59594. Published Oct. 14, 2015. 1 page.

[No Author Listed], Spikevax (mRNA-1273) EMA SmPC (summary of product characteristics). Published Jan. 20, 2021. 137 pages.

(56) References Cited

OTHER PUBLICATIONS

[No Author Listed], Who Drug Information, vol. 35, No. 2, 2021, 341 pages.
Abbasi et al., COVID-19 and mRNA Vaccines-First Large Test for a New Approach. JAMA. Sep. 22, 2020;324(12):1125-1127. doi: 10.1001/jama.2020.16866.
Altieri et al., The influence of 4-thiouridine labeling on pre-mRNA splicing outcomes. PLoS One. Dec. 13, 2021;16(12):e0257503. doi: 10.1371/journal.pone.0257503. eCollection 2021.
Atsmon et al., Safety and immunogenicity of multimeric-001—a novel universal influenza vaccine. J Clin Immunol. Jun. 2012;32(3):595-603. doi: 10.1007/s10875-011-9632-5. Epub Feb. 9, 2012.
Buschmann et al, Nanomaterial Delivery Systems for mRNA Vaccines. Vaccines (Basel). Jan. 19, 2021;9(1):65. doi: 10.3390/vaccines9010065.
Chen et al., Vaccine design of hemagglutinin glycoprotein against influenza. Trends Biotechnol. Sep. 2011;29(9):426-34. doi: 10.1016/j.tibtech.2011.04.007.
Cheng et al., Selective ORgan Targeting (SORT) nanoparticles for tissue specific mRNA delivery and CRISPR/Cas gene editing. Nat Nanotechnol. Apr. 2020; 15(4): 313-320.
Choi et al., 2'-O-methylation in mRNA disrupts tRNA decoding during translation elongation. Nat Struct Mol Biol. Mar. 2018;25(3):208-216. doi: 10.1038/s41594-018-0030-z. Epub Feb. 19, 2018.
Cox et al., FluBlok, a recombinant hemagglutinin influenza vaccine. Influenza Other Respir Viruses. Nov. 2008; 2(6): 211-219.
Du et al., The spike protein of SARS-CoV—a target for vaccine and therapeutic development. Nat Rev Microbiol. Mar. 2009;7(3):226-36. doi: 10.1038/nrmicro2090. Epub Feb. 9, 2009.
Ellebedy et al., Influenza Vaccines. Vaccine. Nov. 5, 2009; 27(Suppl 4): D65-D68.
Escriou et al., Protection from SARS coronavirus conferred by live measles vaccine expressing the spike glycoprotein. Virology. Mar. 2014;452-453:32-41. doi: 10.1016/j.virol.2014.01.002. Epub Jan. 28, 2014.
Geall et al., RNA: the new revolution in nucleic acid vaccines. Semin Immunol. Apr. 2013;25(2):152-9. doi: 10.1016/j.smim.2013.05.001. Epub Jun. 2, 2013.
Guevara et al., Advances in Lipid Nanoparticles for mRNA-Based Cancer Immunotherapy. Front Chem. 2020; 8: 589959.
Hashiba et al., The use of design of experiments with multiple responses to determine optimal formulations for in vivo hepatic mRNA delivery. J Control Release. Nov. 10, 2020;327:467-476. doi: 10.1016/j.jconrel.2020.08.031. Epub Aug. 25, 2020.
He et al., Receptor-binding domain of SARS-CoV spike protein induces highly potent neutralizing antibodies: implication for developing subunit vaccine. Biochem Biophys Res Commun. Nov. 12, 2004;324(2):773-81. doi: 10.1016/j.bbrc.2004.09.106.
Hemmer et al., Minimal peptide length requirements for CD4(+) T cell clones—implications for molecular mimicry and T cell survival. Int Immunol. Mar. 2000;12(3):375-83. doi: 10.1093/intimm/12.3.375.
Hoernes et al., Nucleotide modifications within bacterial messenger RNAs regulate their translation and are able to rewire the genetic code. Nucleic Acids Res. Jan. 29, 2016; 44(2): 852-862.
Hörr, RNA vaccine for the induction of specific cytotoxic T lymphocytes (CTL) and antibodies. Eberhard Karls University of Tübingen. Dissertation. English-Language Translation. 1999. 138 Pages.
Hou et al., Lipid nanoparticles for mRNA delivery. Nature Reviews Materials vol. 6, pp. 1078-1094 (2021).
Houser et al., Influenza Vaccines: Challenges and Solutions. Cell Host Microbe. Mar. 11, 2015; 17(3): 295-300. doi: 10.1016/j.chom.2015.02.012.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263.
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Mendonca et al., Design of lipid-based nanoparticles for delivery of therapeutic nucleic acids. Drug Discov Today. Mar. 2023;28(3):103505. doi: 10.1016/j.drudis.2023.103505. Epub Jan. 25, 2023.
Miao et al., Delivery of mRNA vaccines with heterocyclic lipids increases anti-tumor efficacy by STING-mediated immune cell activation. Nat Biotechnol 37, 1174-1185 (2019). https://doi.org/10.1038/s41587-019-0247-3.
Modjarrad, MERS-CoV vaccine candidates in development: The current landscape. Vaccine. Jun. 3, 2016;34(26):2982-2987. doi: 10.1016/j.vaccine.2016.03.104. Epub Apr. 12, 2016.
Muthumani et al., A synthetic consensus anti-spike protein DNA vaccine induces protective immunity against Middle East respiratory syndrome coronavirus in nonhuman primates. Sci Transl Med. Aug. 19, 2015;7(301):301ra132. doi: 10.1126/scitranslmed.aac7462.
Peabody et al., Termination-reinitiation occurs in the translation of mammalian cell mRNAs. Mol Cell Biol. Jul. 1986;6(7):2695-703. doi: 10.1128/mcb.6.7.2695-2703.1986.
Rodriguez-Gascon et al., Development of nucleic acid vaccines: use of self-amplifying RNA in lipid nanoparticles. Int J Nanomedicine. 2014; 9: 1833-1843.
Rossi et al., IRES-based Venezuelan equine encephalitis vaccine candidate elicits protective immunity in mice. Virology. Mar. 15, 2013;437(2):81-8. doi: 10.1016/j.virol.2012.11.013. Epub Jan. 22, 2013.
Schumann et al., Multiple links between 5-methylcytosine content of mRNA and translation. BMC Biol. Apr. 15, 2020;18(1):40. doi: 10.1186/s12915-020-00769-5.
Shim et al. Intranasal immunization with plasmid DNA encoding spike protein of SARS-coronavirus/polyethylenimine nanoparticles elicits antigen-specific humoral and cellular immune responses. BMC Immunol. Dec. 31, 2010;11:65. doi: 10.1186/1471-2172-11-65.
Stephenson et al., Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis. Apr. 15, 2005;191(8):1210-5. doi: 10.1086/428948. Epub Mar. 14, 2005.
Tam et al., Advances in Lipid Nanoparticles for siRNA Delivery. Pharmaceutics. Sep. 18, 2013;5(3):498-507. doi: 10.3390/pharmaceutics5030498.
Tews et al., Chapter 2: Self-Replicating RNA. RNA Vaccines. 2017; 1499: 15-35. Published online Jun. 11, 2016. doi: 10.1007/978-1-4939-6481-9_2.
Ulmer et al., RNA-based vaccines. Vaccine. Jun. 22, 2012;30(30):4414-8. doi: 10.1016/j.vaccine.2012.04.060. Epub Apr. 28, 2012.
Verma et al., Double-headed nucleosides: Synthesis and applications. Beilstein J Org Chem. Jun. 8, 2021;17:1392-1439. doi: 10.3762/bjoc.17.98. eCollection 2021.
Yang et al., A DNA vaccine induces SARS coronavirus neutralization and protective immunity in mice. Nature. Apr. 1, 2004;428(6982):561-4. doi: 10.1038/nature02463.
Yin et al., Non-viral vectors for gene-based therapy. Nat Rev Genet. Aug. 2014;15(8):541-55. doi: 10.1038/nrg3763. Epub Jul. 15, 2014.
[No Author Listed], An Audience with Moncef Slaoui. Nat Rev Drug Discov Jul. 1, 2015;14:452-453. https://doi.org/10.1038/nrd4669.
[No Author Listed], List of past and pending litigations. Prepared Oct. 24, 2023. 1 page.
Aartse et al., Influenza A Virus Hemagglutinin Trimer, Head and Stem Proteins Identify and Quantify Different Hemagglutinin-Specific B Cell Subsets in Humans. Vaccines (Basel). Jul. 2, 2021;9(7):717. doi: 10.3390/vaccines9070717.
*Alnylam Pharmaceuticals, Inc.* v. *Moderna, Inc.* (Fed. Circ. 2023-2357) D.I. 8—Docketing Statement, Sep. 21, 2023. 2 pages.
*Alnylam Pharmaceuticals, Inc.* v. *Moderna, Inc. et al* (D. Del. 23-cv-580-CFC) D.I. 1—Complaint for Patent Infringement, May 26, 2023. 28 pages.
*Alnylam Pharmaceuticals, Inc.* v. *Moderna, Inc. et al* (D. Del. 23-cv-580-CFC) D.I. 12—Answer to the Complaint, Jul. 17, 2023. 37 pages.

(56) References Cited

OTHER PUBLICATIONS

*Alnylam Pharmaceuticals, Inc.* v. *Moderna, Inc. et al.* (D. Del. 22-cv-335-CFC) D.I. 1—Complaint for Patent Infringement, Mar. 17, 2022. 14 pages.
*Alnylam Pharmaceuticals, Inc.* v. *Moderna, Inc. et al.* (D. Del. 22-cv-335-CFC) D.I. 128—Final Judgement, Aug. 30, 2023. 2 pages.
*Alnylam Pharmaceuticals, Inc.* v. *Moderna, Inc. et al.* (D. Del. 22-cv-335-CFC) D.I. 130—Notice of Appeal to the U.S. Court of Appeals for the Federal Circuit, Aug. 31, 2023. 3 pages.
*Alnylam Pharmaceuticals, Inc.* v. *Moderna, Inc. et al.* (D. Del. 22-cv-335-CFC) D.I. 87—Answer to the Complaint, May 10, 2023. 44 pages.
*Arbutus BioPharma Corp. et al.* v. *Moderna, Inc. et al.* (D. Del. 22-cv-252-MSG) D.I. 1—Complaint for Patent Infringement, Feb. 28, 2022. 51 pages.
*Arbutus BioPharma Corp. et al.* v. *Moderna, Inc. et al.* (D. Del. 22-cv-252-MSG) D.I. 31—District Court Memorandum, Nov. 2, 2022. 16 pages.
*Arbutus BioPharma Corp. et al.* v. *Moderna, Inc. et al.* (D. Del. 22-cv-252-MSG) D.I. 35—Answer to the Complaint, Nov. 30, 2022. 83 pages.
*Arbutus BioPharma Corp. et al.* v. *Moderna, Inc. et al.* (D. Del. 22-cv-252-MSG) D.I. 64—District Court Memorandum, Mar. 10, 2023. 4 pages.
Chinnakannan et al., The Design and Development of a Multi-HBV Antigen Encoded in Chimpanzee Adenoviral and Modified Vaccinia Ankara Viral Vectors; A Novel Therapeutic Vaccine Strategy against HBV. Vaccines (Basel) . Apr. 14, 2020;8(2):184. doi: 10.3390/vaccines8020184.
Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.
Dormitzer, Synthetic Vaccinology at Novartis, Presentation at The National Academy of Sciences Forum on Synthetic Biology. Oct. 21, 2013, The Keck Center, Washington, DC. 12 pages.
Engler et al., Half- vs full-dose trivalent inactivated influenza vaccine (2004-2005): age, dose, and sex effects on immune responses. Arch Intern Med. Dec. 8, 2008;168(22):2405-14. doi: 10.1001/archinternmed.2008.513.
Geall et al., Using self-amplifying mRNA vaccines to facilitate a rapid response to pandemic influenza. Eur Pharm Rev. Jul. 3, 2014; 3. 8 pages.
Hanson et al., Identification of Stabilizing Mutations in an H5 Hemagglutinin Influenza Virus Protein. J Virol. Dec. 30, 2015;90(6):2981-92. doi: 10.1128/JVI.02790-15.
He et al., Low molecular weight protamine (LMWP): a nontoxic protamine substitute and an effective cell-penetrating peptide. J Control Release. Nov. 10, 2014;193:63-73. doi: 10.1016/j.jconrel.2014.05.056. Epub Jun. 3, 2014.
Huang et al., Construction and biological characterisation of recombinant porcine circovirus type 2 expressing the V5 epitope tag. Virus Res. Nov. 2011;161(2):115-23. doi: 10.1016/j.virusres.2011.05.015. Epub May 27, 2011.
Impagliazzo et al., A stable trimeric influenza hemagglutinin stem as a broadly protective immunogen. Science. Sep. 18, 2015;349(6254):1301-6. doi: 10.1126/science.aac7263. Epub Aug. 24, 2015.
Johanning et al., A Sindbis virus mRNA polynucleotide vector achieves prolonged and high level heterologous gene expression in vivo. Nucleic Acids Res. May 11, 1995; 23(9): 1495-1501.
Kutikuppala et al., Prospects and Challenges in Developing mRNA Vaccines for Infectious Diseases and Oncogenic Viruses. Med Sci (Basel). May 22, 2024;12(2):28. doi: 10.3390/medsci12020028.
Lee et al., Design and Structure of an Engineered Disulfide-Stabilized Influenza Virus Hemagglutinin Trimer. J Virol. Jul. 2015;89(14):7417-20. doi: 10.1128/JVI.00808-15. Epub Apr. 29, 2015.
Leuschner et al., Therapeutic siRNA silencing in inflammatory monocytes in mice. Nat Biotechnol. Oct. 9, 2011;29(11):1005-10. doi: 10.1038/nbt.1989.
Li et al., Cell Attachment Domains of the Porcine Epidemic Diarrhea Virus Spike Protein are Key Targets of Neutralizing Antibodies. J Virol. May 26, 2017;91(12):e00273-17. doi: 10.1128/JVI.00273-17. Print Jun. 15, 2017.
Lin et al., Progress and challenges of mRNA vaccines. Interdisc Med. Dec. 22, 2022;1(1):e20220008. doi: 10.1002/INMD.20220008.
Lu et al., Production and stabilization of the trimeric influenza hemagglutinin stem domain for potentially broadly protective influenza vaccines. Proc Natl Acad Sci U S A. Jan. 7, 2014;111(1):125-30. doi: 10.1073/pnas.1308701110. Epub Dec. 16, 2013.
Lugovtsev et al., Generation of the influenza B viruses with improved growth phenotype by substitution of specific amino acids of hemagglutinin. Virology. Sep. 1, 2007;365(2):315-23. doi: 10.1016/j.virol.2007.04.006. Epub May 8, 2007.
Milder et al., Universal stabilization of the influenza hemagglutinin by structure-based redesign of the pH switch regions. Proc Natl Acad Sci U S A. Feb. 8, 2022;119(6):e2115379119. doi: 10.1073/pnas.2115379119.
*ModernaTX, Inc. et al.*v. *Pfizer Inc.et al.* (D. Mass. 22-11378-RGS) D.I. 1—Complaint for Patent Infringement, Aug. 26, 2022. 39 pages.
*ModernaTX, Inc. et al.*v. *Pfizer Inc.et al.* (D. Mass. 22-11378-RGS) D.I. 45—Answer to the Complaint, Dec. 5, 2022. 81 pages.
Pascolo., Messenger RNA-based vaccines. Expert Opin Biol Ther. Aug. 2004;4(8):1285-94. doi: 10.1517/14712598.4.8.1285.
Petition for Inter Partes Review of U.S. Pat. No. 10,702,600. *BioNTech SE and Pfizer Inc.* (Petitioners) v. *ModernaTX, Inc.* (Patent Owner). Filed Aug. 28, 2023. 87 pages.
Petition For Inter Partes Review of U.S. Pat. No. 10,933,127. *BioNTech SE and Pfizer Inc.* (Petitioners) v. *ModernaTX, Inc.* (Patent Owner). Filed Aug. 28, 2023. 89 pages.
*Promosome, LLC* v. *Moderna, Inc.* (S.D. Cal. 23-cv-1047-JES-DDL) D.I. 1—Complaint for Patent Infringement, Jun. 6, 2023. 51 pages.
*Promosome, LLC* v. *Moderna, Inc.* (S.D. Cal. 23-cv-1047-JES-DDL) D.I. 30—Notice of Dismissal, Sep. 19, 2023. 4 pages.
Schuurhuis et al., Ins and outs of dendritic cells. Int Arch Allergy Immunol. 2006;140(1):53-72. doi: 10.1159/000092002. Epub Mar. 13, 2006.
Staneková et al., Conserved epitopes of influenza A virus inducing protective immunity and their prospects for universal vaccine development. Virol J. Nov. 30, 2010:7:351. doi: 10.1186/1743-422X-7-351.
Thery et al., The cell biology of antigen presentation in dendritic cells. Curr Opin Immunol. Feb. 2001;13(1):45-51. doi: 10.1016/s0952-7915(00)00180-1.
Walls et al., Crucial steps in the structure determination of a coronavirus spike glycoprotein using cryo-electron microscopy. Protein Sci. Jan. 2017;26(1):113-121. doi: 10.1002/pro.3048. Epub Oct. 18, 2016.
Walls et al., Tectonic conformational changes of a coronavirus spike glycoprotein promote membrane fusion. Proc Natl Acad Sci U S A. Oct. 17, 2017;114(42):11157-11162. doi: 10.1073/pnas.1708727114. Epub Oct. 3, 2017.
Yildiz et al., Trans-Amplifying RNA: A Journey from Alphavirus Research to Future Vaccines. Viruses. Mar. 25, 2024;16(4):503. doi: 10.3390/v16040503.
Zhao et al., Key Aspects of Coronavirus Avian Infectious Bronchitis Virus. Pathogens. May 11, 2023;12(5):698. doi: 10.3390/pathogens12050698.
Ziganshina et al., Antibody-Dependent Enhancement with a Focus on SARS-CoV-2 and Anti-Glycan Antibodies. Viruses. Jul. 20, 2023;15(7):1584. doi: 10.3390/v15071584.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 18/176,014, filed Feb. 28, 2023, Ciaramella.
U.S. Appl. No. 18/365,948, filed Aug. 4, 2023, Ciaramella.

(56) References Cited

OTHER PUBLICATIONS

U.S. Appl. No. 17/819,414, filed Aug. 12, 2022, Ciaramella.
U.S. Appl. No. 18/812,841, filed Aug. 22, 2024, Ciaramella et al.
U.S. Appl. No. 15/767,600, filed Apr. 11, 2018, Ciaramella et al.
U.S. Appl. No. 18/306,082, filed Apr. 24, 2023, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 18/314,980, filed May 10, 2023, Ciaramella et al.
U.S. Appl. No. 15/767,618, filed Apr. 11, 2018, Ciaramella et al.
U.S. Appl. No. 18/481,204, filed Oct. 4, 2023, Ciaramella et al.
U.S. Appl. No. 17/590,479, filed Feb. 1, 2022, Ciaramella et al.
U.S. Appl. No. 18/635,203, filed Apr. 15, 2024, Ciaramella et al.
U.S. Appl. No. 17/737,532, filed May 5, 2022, Ciaramella et al.
U.S. Appl. No. 17/839,401, filed Jun. 13, 2022, Ciaramella et al.
U.S. Appl. No. 18/528,323, filed Dec. 4, 2023, Ciaramella et al.
U.S. Appl. No. 18/322,831, filed May 24, 2023, Ciaramella.
U.S. Appl. No. 18/189,512, filed Mar. 24, 2023, Ciaramella et al.
U.S. Appl. No. 18/055,193, filed Nov. 14, 2022, Ciaramella et al.
U.S. Appl. No. 18/354,574, filed Jul. 18, 2023, Ciaramella et al.
U.S. Appl. No. 17/823,255, filed Aug. 30, 2022, Ciaramella et al.
U.S. Appl. No. 18/796,754, filed Aug. 7, 2024, Ciaramella et al.
U.S. Appl. No. 18/416,835, filed Jan. 18, 2024, Ciaramella.
U.S. Appl. No. 17/938,823, filed Oct. 7, 2022, Ciaramella et al.
U.S. Appl. No. 16/765,285, filed May 19, 2020, Ciaramella et al.
U.S. Appl. No. 17/531,211, filed Nov. 19, 2021, Ciaramella et al.
U.S. Appl. No. 18/418,127, filed Jan. 19, 2024, Ciaramella et al.
U.S. Appl. No. 18/552,346, filed Sep. 25, 2023, Himansu et al.
U.S. Appl. No. 18/771,978, filed Jul. 12, 2024, Lusso et al.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 18/284,919, filed Sep. 29, 2023, Deal et al.
U.S. Appl. No. 17/797,784, filed Aug. 5, 2022, Stewart-Jones et al.
U.S. Appl. No. 18/280,362, filed Sep. 5, 2023, Bollman et al.
U.S. Appl. No. 18/028,126, filed Mar. 23, 2023, Stewart-Jones et al.
U.S. Appl. No. 18/272,512, filed Jul. 14, 2023, Carfi et al.
U.S. Appl. No. 18/286,705, filed Oct. 12, 2023, Chandramouli et al.
U.S. Appl. No. 18/272,496, filed Jul. 14, 2023, Carfi et al.
U.S. Appl. No. 18/284,938, filed Sep. 29, 2023, Rabideau et al.
U.S. Appl. No. 18/569,768, filed Dec. 13, 2023, Stewart-Jones.
U.S. Appl. No. 18/569,776, filed Dec. 13, 2023, Stewart-Jones.
U.S. Appl. No. 18/282,097, filed Sep. 14, 2023, Stewart-Jones et al.
U.S. Appl. No. 18/555,087, filed Oct. 12, 2023, Nachbagauer et al.
U.S. Appl. No. 18/555,130, filed Oct. 12, 2023, Nachbagauer et al.
U.S. Appl. No. 18/577,571, filed Jan. 8, 2024, Stewart-Jones.
U.S. Appl. No. 18/717,792, filed Jun. 7, 2024, Bahl et al.
U.S. Appl. No. 18/577,563, filed Jan. 8, 2024, Stewart-Jones.
U.S. Appl. No. 18/351,843, filed Jul. 13, 2023, Bollman et al.
U.S. Appl. No. 18/351,057, filed Jul. 12, 2023, Bollman et al.
U.S. Appl. No. 18/335,949, filed Jun. 15, 2023, Nasir et al.
U.S. Appl. No. 18/605,658, filed Mar. 14, 2024, Nasir et al.

N1 Wisconsin NA

- PBS
- N1 Wisc WT
- N1 Wisc D151G
- N1 Wisc dcyT
- N1 Wisc stalk d15
- N1 Wisc stalk d30
- N1 Wisc stalk ins15
- N1 Wisc R118K
- N1 Wisc E227D
- N1 Wisc WT + H1 HA
- N1 Wisc D151G + H1 HA
- N1 Wisc dcyT + H1 HA
- N1 Wisc stalk d15 + H1 HA
- N1 Wisc stalk d30 + H1 HA
- N1 Wisc stalk ins15 + H1 HA
- N1 Wisc R118K + H1 HA
- N1 Wisc E227D + H1 HA log10 N1 NA-specific IgG titers 2.5x, 1.5x, 2.8x

H1 Wisconsin HA log10 H1 HA-specific IgG titers

- N1 Wisc WT + H1 HA
- N1 Wisc D151G + H1 HA
- N1 Wisc dcytT + H1 HA
- N1 Wisc stalk d15 + H1 HA
- N1 Wisc stalk d30 + H1 HA
- N1 Wisc stalk ins15 + H1 HA
- N1 Wisc R118K + H1 HA
- N1 Wisc E227D + H1 HA H1 Wisconsin HA N1 Wisc WT + H1 HA
N1 Wisc D15G + H1 HA
N1 Wisc dcytT + H1 HA
N1 Wisc stalk d15 + H1 HA
N1 Wisc stalk d30 + H1 HA
N1 Wisc stalk ins15 + H1 HA
N1 Wisc R118K + H1 HA
N1 Wisc E227D + H1 HA log10 H1 HA-specific IgG titers

| | |
|---|---|
| WT | H3 Hong Kong 2019 |
| 12 | RIIV (SEQ ID NO: 139) + GRFYQ (SEQ ID NO: 140) |
| 13 | RIIV (SEQ ID NO: 139) + CMG |
| 14 | RIIV (SEQ ID NO: 139) + TYDP (SEQ ID NO: 141) |
| 15 | EGLV (SEQ ID NO: 142) + GFRYQ (SEQ ID NO: 143) |
| 17 | EGLV (SEQ ID NO: 142) + TYDP (SEQ ID NO: 141) |
| 22 | RIIV (SEQ ID NO: 139) + EGLV (SEQ ID NO: 142) + TYDP (SEQ ID NO: 141) |
| 23 | RIIV (SEQ ID NO: 139) + EGLV (SEQ ID NO: 142) + GFRYQ (SEQ ID NO: 143) + CMG |
| 24 | RIIV (SEQ ID NO: 139) + EGLV (SEQ ID NO: 142) + GFRYQ (SEQ ID NO: 143) + TYDP (SEQ ID NO: 141) |

SEASONAL RNA INFLUENZA VIRUS VACCINES

RELATED APPLICATIONS

This application claims priority under 35 U.S.C. § 119(e) to U.S. Provisional Patent Application No. 63/136,126, filed Jan. 11, 2021, U.S. Provisional Patent Application No. 63/174,437, filed Apr. 13, 2021, U.S. Provisional Patent Application No. 63/210,409, filed Jun. 14, 2021, and U.S. Provisional Patent Application No. 63/249,291, filed Sep. 28, 2021, which are hereby incorporated by reference in their entireties.

BACKGROUND

Seasonal influenza is an acute respiratory infection caused by influenza viruses—influenza A and influenza B viruses—that circulate in all parts of the world. Seasonal influenza is characterized by a sudden onset of fever, cough (usually dry), headache, muscle and joint pain, severe malaise (feeling unwell), sore throat and a runny nose. In industrialized countries most deaths associated with influenza occur among people age 65 or older. Epidemics can result in high levels of worker/school absenteeism and productivity losses. Clinics and hospitals can be overwhelmed during peak illness periods. The effects of seasonal influenza epidemics in developing countries are not fully known, but research estimates that 99% of deaths in children under 5 years of age with influenza related lower respiratory tract infections are found in developing countries.

Inactivated influenza vaccines are currently available and the most widely used method to prevent influenza outbreaks, particularly in high risk populations, such as the elderly. Vaccines elicit immune responses that attack the viral glycoprotein hemagglutinin (HA) and the viral enzyme neuraminidase (NA) found on the surface of the influenza virus. Anti-hemagglutinin antibodies neutralize viral infectivity, while anti-neuraminidase antibodies decrease the severity of disease. Because HA is the major influenza virus antigen recognized by neutralizing antibodies, this glycoprotein has been the focus of currently available influenza vaccines.

SUMMARY

Influenza vaccination only provides protection against outbreaks involving known viral strains. Because of its penchant to vary its antigenic components from year to year, vaccination against an influenza virus can prove ineffective. Provided herein, in some aspects, are messenger RNA (mRNA) vaccines against influenza virus infection that offer the advantages of high efficacy, speed of development, and production scalability and reliability. The mRNA vaccines of the present disclosure comprise mRNAs encoding unique combinations of HA and/or NA antigens, e.g., antigens from multiple seasonal influenza flu strains, in some embodiments, all formulated in a single lipid nanoparticle. In certain aspects, the mRNA vaccines of the present disclosure comprise mRNAs encoding unique combinations of HA antigens. In other aspects, the mRNA vaccines of the present disclosure comprise mRNAs encoding unique combinations of HA antigens in combination with NA antigens. In certain aspects, the mRNA vaccines of the present disclosure comprise mRNAs encoding both HA and NA (e.g., enzymatically active or inactive) antigens from multiple seasonal influenza flu strains, in some embodiments, all formulated in a single lipid nanoparticle, thus offering a vaccine that not only neutralizes viral infectivity but also decreases the severity of disease.

As discussed in more detail below, due to the constant evolving nature of influenza viruses, the WHO Global Influenza Surveillance and Response System (GISRS)—a system of National Influenza Centers and WHO Collaborating Centers around the world—continuously monitors the influenza viruses circulating in humans and updates the recommended composition of influenza vaccines twice a year. To permit enough time to develop the standard inactivated virus vaccines, this recommendation is made six to seven months prior to the start of the influenza season, which unfortunately allows plenty of time for the influenza viruses to continue to evolve/mutate or change in prevalence. The mRNA vaccine technology provided herein offers the GISRS additional time to monitor circulating viruses and make its recommendation closer to the influenza season. This extension of the GISRS monitoring timeline should allow the GISRS predictions to be more accurate, resulting in more effective vaccines designed to target circulating viruses closer to the influenza season.

In some aspects, the disclosure provides a composition comprising (a) a first messenger ribonucleic acid (mRNA) encoding a hemagglutinin (HA) antigen of a first influenza A virus and a second mRNA encoding an HA antigen of a second influenza A virus, wherein the influenza A HA antigens are of different subtypes; and (b) a third mRNA encoding an HA antigen of a first influenza B virus and a fourth mRNA encoding an HA antigen of a second influenza B virus, wherein the influenza B HA antigens are of different lineages, and wherein the mRNAs of (a) and (b) are in a lipid nanoparticle. In some embodiments, (a) and (b) are in the same lipid nanoparticle. In some embodiments, (a) and (b) are in separate lipid nanoparticles.

In some embodiments, the composition further comprises: (c) a fifth mRNA encoding neuraminidase (NA) antigen of the first influenza A virus and a sixth mRNA encoding an NA antigen of the second influenza A virus, wherein the influenza A NA antigens are of different subtypes; and (d) a seventh mRNA encoding an NA antigen of the first influenza B virus and an eighth mRNA encoding an NA antigen of the second influenza B virus, wherein the influenza B NA antigens are of different lineages, and wherein the mRNAs of (c) and (d) are in the lipid nanoparticle. In some embodiments, (c) and (d) are in the same lipid nanoparticle. In some embodiments, (a), (b), (c), and (d) are in the same lipid nanoparticle. In some embodiments, (c) and (d) are in separate lipid nanoparticles. In some embodiments, (a), (b), (c), and (d) are in separate lipid nanoparticles.

In some embodiments, the ratio of the first:second:third:fourth mRNA is 1:1:1:1. In some embodiments, the ratio of the first:second:third:fourth:fifth:sixth:seventh:eighth mRNAs is 1:1:1:1:1:1:1:1. In some embodiments, the ratio of the first:second:third:fourth:fifth:sixth:seventh:eighth mRNAs is 3:3:3:3:1:1:1:1.

In some embodiments, the HA and NA antigens are recommended by or selected according to standardized criteria used by World Health Organization's Global Influenza Surveillance and Response System (GISRS). In some embodiments, the HA and NA antigens are recommended by GISRS for inclusion in influenza virus vaccines for either Southern or Northern hemisphere influenza vaccines for the year of manufacture and distribution. In some embodiments, the HA and NA antigen(s) are selected using a hemagglutinin inhibition (HAI) assay to identify circulating influenza viruses that are antigenically similar to influenza viruses from a previous season's vaccine, optionally wherein influenza viruses are considered to be antigenically similar if their HAI titers differ by two dilutions or less.

In some embodiments, the first mRNA encodes an influenza A HA antigen of the H1 subtype, and the second mRNA encodes an influenza A HA antigen of the H3 subtype. In some embodiments, the third mRNA encodes an influenza B HA antigen of the B/Yamagata lineage, and the fourth mRNA encodes an influenza B HA antigen of the B/Victoria lineage. In some embodiments, the fifth mRNA encodes an influenza A NA antigen of the N1 subtype, and the sixth mRNA encodes an influenza A NA antigen of the N2 subtype. In some embodiments, the seventh mRNA encodes an influenza B NA antigen of the B/Yamagata lineage, and the eighth mRNA encodes an influenza B NA antigen of the B/Victoria lineage.

In some embodiments, the NA is enzymatically inactive. In some embodiments, the enzymatically inactive NA comprises a mutation in at least one of the following amino acids: R118, D151, and E227. In some embodiments, the enzymatically inactive NA comprises a D151G mutation. In some embodiments, the enzymatically inactive NA comprises a E227D mutation. In some embodiments, the enzymatically inactive NA comprises a R118K mutation. In some embodiments, the enzymatically inactive NA comprises an influenza A NA antigen of the N1 subtype. In some embodiments, the enzymatically inactive NA comprises an influenza A NA antigen of the N2 subtype. In some embodiments, the enzymatically inactive NA comprises an influenza B NA antigen of the B/Yamagata lineage. In some embodiments, the enzymatically inactive NA comprises an influenza B NA antigen of the B/Victoria lineage. In some embodiments, the enzymatically inactive NA comprises the N1_Wisconsin_2019_WT antigen (SEQ ID NO: 46).

In some embodiments, the NA is enzymatically active.

In some embodiments, the enzymatically inactive NA comprises one of the following mutations: a deletion of a cytoplasmic tail, a deletion of amino acids of a stalk region, or an insertion of amino acids in a stalk region. In some embodiments, the enzymatically inactive NA comprises a deletion of the cytoplasmic tail. In some embodiments, the enzymatically inactive NA comprises a deletion of amino acids of the stalk region, optionally wherein 15 or 30 amino acids are deleted. In some embodiments, the enzymatically inactive NA comprises an insertion of amino acids of the stalk region, optionally wherein 15 amino acids are inserted.

In some embodiments, the composition elicits neuraminidase inhibition antibodies at least 2-fold, at least 3-fold, or at least 4-fold higher than a control value (e.g., wild-type neuraminidase inhibition value). In some embodiments, the composition has a neuraminidase inhibition value of at least 50%, at least 60%, at least 70%, at least 80%, at least 90%, or at least 95% of a control value (e.g., of a wild-type neuraminidase inhibition value).

In some embodiments, the HA comprises at least one mutation. In some embodiments, the mutation(s) creates a new disulfide in the HA stem, deletion of a cleavage site, and/or replacement of a polybasic cleavage site (HPAI) by an LPAI sequence. In some embodiments the HA comprises two mutations, optionally wherein the two mutations are a disulfide in the HA stem and deletion of a cleavage site.

In some embodiments, an HA-reactive IgG antibody titer and/or the NA-reactive IgG antibody titer in a subject on day 21 post administration of the composition is at least 2-fold higher than an HA-reactive IgG antibody titer and/or the NA-reactive IgG antibody titer in a subject prior to administration of the composition. In some embodiments, an HA-reactive IgG antibody titer and/or the NA-reactive IgG antibody titer in a subject on day 28 post administration of the composition is at least 2-fold higher or at least 4-fold higher than an HA-reactive IgG antibody titer and/or the NA-reactive IgG antibody titer in a subject prior to administration of the composition. In some embodiments, an HA-reactive IgG antibody titer and/or the NA-reactive IgG antibody titer in a subject on day 36 post administration of the composition is at least 4-fold higher than an HA-reactive IgG antibody titer and/or the NA-reactive IgG antibody titer in a subject prior to administration of the composition.

In some embodiments, the mRNA comprises a 5' untranslated region (UTR), a 3' UTR, and a polyA tail. In some embodiments, the mRNA comprises a 5' cap analog. In some embodiments, the mRNA comprises a chemical modification. In some embodiments, the chemical modification is 1-methylpseudouridine.

In some embodiments, the lipid nanoparticle comprises an ionizable amino lipid, a sterol, a neutral lipid, and a polyethylene glycol (PEG)-modified lipid. In some embodiments, the lipid nanoparticle comprises 40-55 mol % ionizable amino lipid, 30-45 mol % sterol, 5-15 mol % neutral lipid, and 1-5 mol % PEG-modified lipid. In some embodiments, the lipid nanoparticle comprises 45 mol %, 46 mol %, 47 mol %, 48 mol %, 49 mol %, or 50 mol % ionizable amino lipid. In some embodiments, the lipid nanoparticle comprises 48 mol % ionizable amino lipid, 38.5 mol % sterol, 11 mol % neutral lipid, and 2.5 mol % PEG-modified lipid. In some embodiments, the ionizable amino lipid has the structure of Compound 1:

(Compound 1)

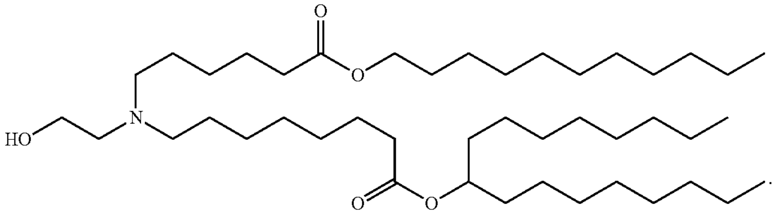

In some embodiments, the sterol is cholesterol. In some embodiments, the neutral lipid is 1,2 distearoyl-sn-glycero-3-phosphocholine (DSPC). In some embodiments, the PEG-modified lipid is 1,2 dimyristoyl-sn-glycerol, methoxypolyethyleneglycol (PEG2000 DMG).

In some embodiments, the disclosure provides a method comprising administering to a subject in need thereof the composition described herein. In some embodiments, the composition is administered in an amount effective to induce a neutralizing antibody response against influenza A H1N1, influenza A H3N2, influenza B/Yamagata, and influenza B/Victoria. In some embodiments, the composition is administered in an amount effective to induce a T cell response against influenza A H1N1, influenza A H3N2, influenza B/Yamagata, and influenza B/Victoria. In some embodiments, the subject is administered two doses of the composition.

Some aspects of the present disclosure provide a composition comprising: an mRNA encoding a HA antigen from a first circulating influenza A virus, an mRNA encoding a HA antigen from a second circulating influenza A virus, an mRNA encoding a HA antigen from a first circulating influenza B virus, and an mRNA encoding a HA antigen from a second circulating influenza B virus; and an mRNA encoding a NA antigen from the first circulating influenza A virus, an mRNA encoding a NA antigen from the second circulating influenza A virus, an mRNA encoding a NA antigen from the first circulating influenza B virus, and an mRNA encoding a NA antigen from the second circulating influenza B virus and a lipid nanoparticle. In some embodiments, the mRNAs are present at a ratio of 1:1:1:1:1:1:1:1. In some embodiments, the mRNAs are present at a ratio of 3:3:3:3:1:1:1:1.

Another aspect of the disclosure provides a composition comprising an mRNA encoding a HA antigen from a first circulating influenza A virus, an mRNA encoding a HA antigen from a second circulating influenza A virus, an mRNA encoding a HA antigen from a first circulating influenza B virus, an mRNA encoding a HA antigen from a second circulating influenza B virus; and a lipid nanoparticle, wherein the mRNAs are present at a ratio of 1:1:1:1.

Other aspects of the present disclosure provide a composition comprising: two or three mRNAs encoding a HA antigen from a first circulating influenza A virus, two or three mRNAs encoding a HA antigen from a second circulating influenza A virus, two or three mRNAs encoding a HA antigen from a first circulating influenza B virus, and two or three mRNAs encoding a HA antigen from a second circulating influenza B virus and a lipid nanoparticle.

Yet other aspects of the present disclosure provide a composition comprising: two or three mRNAs encoding a HA antigen from a first circulating influenza A virus, two or three mRNAs encoding a HA antigen from a second circulating influenza A virus, two or three mRNAs encoding a HA antigen from a first circulating influenza B virus, and two or three mRNAs encoding a HA antigen from a second circulating influenza B virus; and an mRNA encoding a NA antigen from the first circulating influenza A virus, an mRNA encoding a NA antigen from the second circulating influenza A virus, an mRNA encoding a NA antigen from the first circulating influenza B virus, and an mRNA encoding a NA antigen from the second circulating influenza B virus and a lipid nanoparticle. In some embodiments, the mRNAs are present at a ratio of 2:2:2:2:1:1:1:1 or 3:3:3:3:1:1:1:1.

In some embodiments, at least one mRNA further comprises one or more non-coding sequences in an untranslated region (UTR), optionally a 5' UTR or 3' UTR. In some embodiments, all of the mRNAs further comprise one or more non-coding sequences in an UTR, optionally a 5' UTR or 3' UTR.

In some embodiments, the non-coding sequence is positioned in a 3' UTR of an mRNA, upstream of the polyA tail of the mRNA. In some embodiments, the non-coding sequence is positioned in a 3' UTR of an mRNA, downstream of the polyA tail of the mRNA. In some embodiments, the non-coding sequence is positioned in a 3' UTR of an mRNA between the last codon of the ORF of the mRNA and the first "A" of the polyA tail of the mRNA.

In some embodiments, the non-coding sequence comprises between 1 and 10 nucleotides.

In some embodiments, the non-coding sequence comprises one or more RNAse cleavage sites. In some embodiments, the RNAse cleavage site comprises an RNase H cleavage site.

In some embodiments, the ratio is a mass ratio (wt/wt ratio). In some embodiments, the ratio is a molar ratio. In some embodiments, the lipid nanoparticle is a population of lipid nanoparticles. In some embodiments, the composition comprises a population of lipid nanoparticles.

BRIEF DESCRIPTION OF THE DRAWINGS

FIG. 8A shows the HAI titers against H1N1 A/Victoria/2570/2019; FIG. 8B shows the HAI titers against H3N2 A/Hong Kong/2671/2019; FIG. 8C shows the HAI titers B/Washington/02/2019; and FIG. 8D show the HAI titers against B/Phuket/3073/2013.

FIG. 20A shows the HAI titers against H1N1 A/Victoria/2570/2019; FIG. 20B shows the HAI titers against H3N2 A/Hong Kong/2671/2019; FIG. 20C shows the HAI titers against B/Washington/02/2019; and FIG. 20D shows the HAI titers against B/Phuket/3073/2013.

FIG. 23A shows % initial body weight against challenge virus H3N2 Hong Kong/1/1968-MA20 and FIG. 23B shows % initial body weight against challenge virus H1N1 A/Netherlands/602/2009.

FIG. 24A shows % survival against challenge virus H3N2 Hong Kong/1/1968-MA20 and FIG. 24B shows % survival against challenge virus H1N1 A/Netherlands/602/2009.

FIG. 25A shows clinical observations against challenge virus H3N2 Hong Kong/1/1968-MA20 and FIG. 25B shows clinical observations against challenge virus p1N1 A/Netherlands/602/2009.

DETAILED DESCRIPTION

Figure 1:
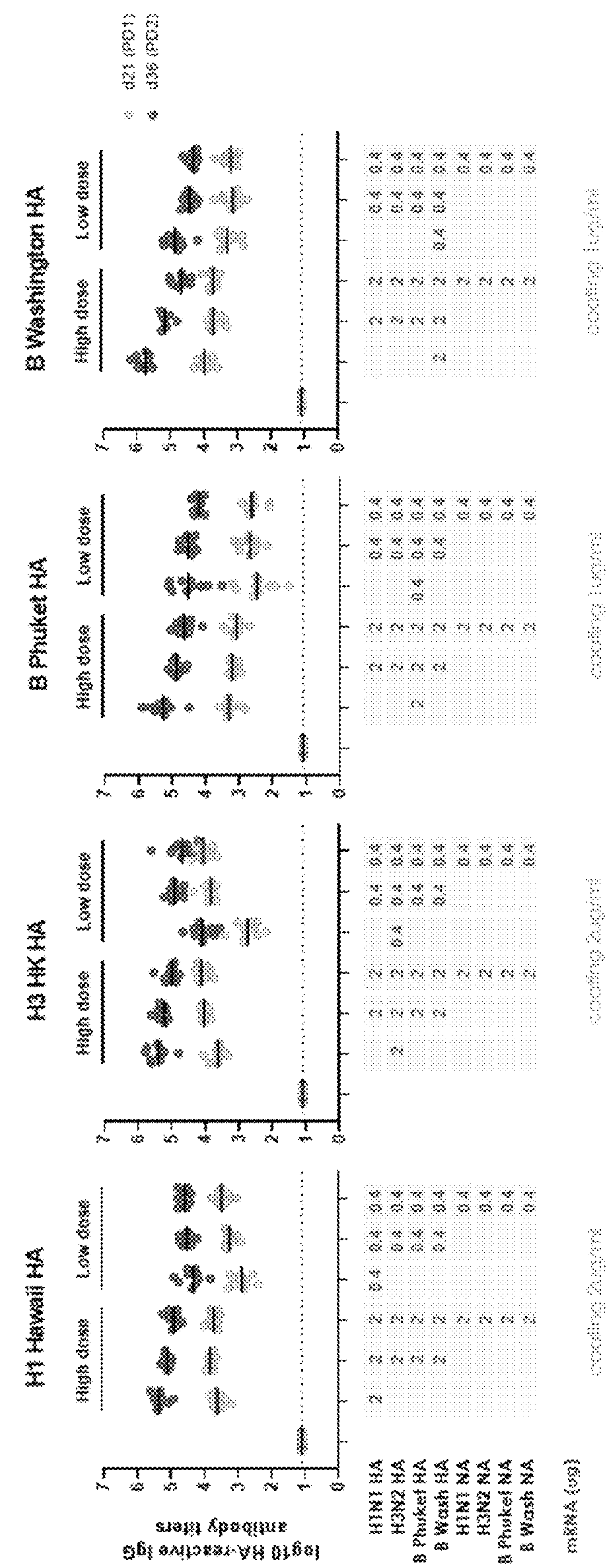
FIG. 1 is a series of graphs showing the hemagglutinin (HA)-reactive IgG antibody titers to each of the four antigens after one (PD1; day 21) or two (PD2; day 36) doses of influenza HA and neuraminidase (NA) formulations or controls. The doses administered are provided in the tables below each graph.

Influenza can cause mild to severe respiratory illness, which can result in hospitalization or death. Older adults and young children are at an increased risk of serious flu complications. The disease burden remains high, as the annual effectiveness of licensed vaccines varies from approximately 30-50%, and there have been 140,000-810,000 hospitalizations and 12,000-61,000 deaths annually in the US from the flu since 2010.

The most effective way to prevent the influenza virus infection is vaccination. Immunity from influenza virus vaccination, however, wanes over time, so annual vaccination is recommended to protect against the virus. Vaccination is most effective when circulating viruses are well-matched with viruses used to develop the vaccines. Due to the constant evolving nature of influenza viruses, the WHO Global Influenza Surveillance and Response System (GISRS)—a system of National Influenza Centers and WHO Collaborating Centers around the world—continuously monitors the influenza viruses circulating in humans and updates the recommended composition of influenza vaccines twice a year. Surveillance is the foundation underpinning all efforts to understand, prevent, and control influenza, and global influenza surveillance—initiated in 1952—has long provided annual information used to select the precise virus strains to be used as the basis of annual vaccines. Such surveillance activities also provide the vital information needed to establish the degree of seasonality of influenza in various parts of the world, and to estimate its impact and burden.

In addition, global influenza surveillance forms the primary line of defense against the occurrence of influenza pandemics by identifying emerging influenza virus strains that pose a potential threat. The importance of this has been demonstrated on numerous occasions, for example in 1997, 2003, and 2004 when influenza A(H5N1) viruses were detected in humans in China, Hong Kong Special Administrative Region (Hong Kong SAR); in 1999 when A(H9N2) was identified in Hong Kong SAR; in 2003 when A(H7N7) was detected in the Netherlands; in 2004 when A(H5N1) was detected in southeast Asia (with subsequent spread to other regions); and in 2009 with the emergence of the declared pandemic of A(H1N1) influenza.

Traditionally, WHO provides a recommendation on the composition of the vaccine that targets the three (3) most representative virus types in circulation (two subtypes of influenza A viruses and one influenza B virus) (a trivalent vaccine). Starting with the 2013-2014 northern hemisphere influenza season, a fourth component was recommended, supporting quadrivalent vaccine development. Quadrivalent vaccines include a second influenza B virus in addition to the viruses in trivalent vaccines and are thought to provide wider protection against influenza B virus infections.

The WHO, through the WHO GISRS system, in collaboration with other partners, monitors influenza activity globally and recommends seasonal influenza vaccine compositions twice a year for the Northern and Southern hemisphere influenza seasons. The WHO also guides countries in tropical and subtropical areas to choose vaccine formulations (Northern hemisphere vs. Southern hemisphere) and supports decisions for timing of vaccination campaigns. The organization also supports Member States to develop prevention and control strategies. The GISRS provides laboratory diagnosis and virological surveillance of circulating influenza viruses—both of which are key elements in influenza vaccine virus selection and the early detection of emerging viruses with pandemic potential.

While a number of inactivated influenza vaccines and recombinant influenza vaccines are available in injectable form, as noted above, the annual vaccines range widely in effectiveness, from 30% to 50%. This is due, in part, to the composition recommendation process. The recommendations are updated twice a year (in February or March for the Northern hemisphere and in September for the Southern hemisphere); however, it is at least six or seven months before the vaccines are administered to the population. The recommendations are made so far in advance so that sufficient numbers of traditional vaccines (e.g., attenuated virus vaccines) can be designed and produced in advance of the flu season. During the six- or seven-month period; however, the influenza viruses may mutate, or other influenza strains may become more prevalent, such that the traditional vaccines become less effective. The traditional vaccines cannot adapt because they are already in production, and it would take an addition six to seven months to design and manufacture a new vaccine. In contrast, the mRNA vaccines described herein are able to overcome these challenges. They can be produced in a matter of weeks, so that they can be designed against the influenza viruses circulating closer to the influenza season. That is, it is thought that prediction of the circulating influenza viruses closer to the influenza season will be more accurate than predictions from six or seven months before the season, and therefore the mRNA vaccines described herein will also be more effective because they are designed to target circulating viruses closer to the influenza season.

Similarly, they can be formulated as a supplemental booster vaccine. For example, if the traditional vaccines are made and further predictions indicate that a different influenza virus is more prevalent or infectious, a supplemental booster mRNA vaccine may be designed and administered, as described herein.

The mRNA vaccines described herein encode multiple antigens from multiple circulating strains in a single lipid nanoparticle (LNP). The mRNA vaccines comprise, in some embodiments, a combination of four hemagglutinin (HA) antigens. The mRNA vaccines comprise, in some embodiments, four hemagglutinin (HA) and four neuraminidase (NA) antigens. While HA is a major surface glycoprotein on the influenza virus and the target of current influenza virus vaccines, NA has not been widely used.

Without wishing to be bound by theory, it is thought that the addition of NA to the vaccines described herein may provide additional protection during well-matched years and "fallback" protection during HA-drift years. Like HA, NA is a major surface glycoprotein, but it has lower antigenic drift than HA. The lack of NA in currently licensed vaccines is largely due to the difficulty of producing correctly folded protein using legacy manufacturing processes. These limitations do not apply to mRNA-based approaches. Vaccination with recombinant NA protein has been shown to protect mice from homologous and heterologous lethal influenza virus challenges within the same subtype (Wohlbold et al., mBio. 2015 Mar. 10; 6(2):e02556). N1 NA delivered as mRNA has been shown to protect against highly lethal viral challenges (up to 500×LD50) and to elicit protective immunity even when administered in doses as low as 50 ng (Freyn et al., Mol Ther. 2020 Jul. 8; 28(7):1569-1584). In guinea pigs, intranasal vaccination with recombinant NA has been shown to reduce transmission of influenza B viruses (McMahon et al., mBio 2019 May 21; 10(3):e00560-19).

NA-based protection in humans has been investigated in human challenge studies in the 1970s either by challenge with a strain that expressed an HA to which the participants did not have measurable antibodies (Murphy et al., N Engl J Med. 1972 Jun. 22; 286(25):1329-32), or by challenge after vaccination with a vaccine that was matched for the NA, but mismatched to the HA of the challenge strain (Couch et al., J Infect Dis. 1974 April; 129(4):411-20). Both studies showed a reduction in illness associated with NA immunity. A more recent set of challenge studies performed at the NIH showed statistically significant correlation of NA inhibition titers (NAI) and protection (Memoli et al., mBio. 2016 Apr. 19; 7(2):e00417-16).

Observational studies have explored the contribution of NA-based immunity to protection. It has been found that anti-NA antibodies in serum and nasal secretions independently correlated with reducing H1N1 infections and serum NAI correlated with reduced illness in infected individuals (Couch et al., J Infect Dis. 2013 Mar. 15; 207(6):974-81) and that NAI independently correlated with protection from infection and further quantified that a 2-fold increase in NAI resulted in a 29% (95% CI: 16-41) increase in effectiveness (Monto et al., J Infect Dis. 2015 Oct. 15; 212(8):1191-9).

Use of the combination of HA and NA antigens, as described in the Examples below, was shown to consistently produce robust immune responses to all components of the vaccine (HA and NA).

In exemplary aspects, the vaccines of the disclosure are designed to combat seasonal influenza, and as such are vaccines for use in an upcoming or forthcoming Northern hemisphere season or Southern hemisphere season. Based on an understanding of circulating influenza viruses (e.g., virus lineages, strains and/or subtypes) at a given point in time, the vaccines are designed to combat such viruses as they are predicted to be those that will be circulating or prevalent in the upcoming or forthcoming influenza season (e.g., the upcoming/forthcoming season in a particular geographic location, for example, northern or southern hemisphere). With existing vaccine technology, for example, cell- or recombinant-based vaccines, the technologies are limited by the length of time required to produce the vaccines. Cell-and-recombinant vaccines take many months to produce, so decisions around antigen inclusion or design have to be made far in advance of the upcoming/forthcoming influenza season. The existing paradigm for deciding which antigens to include in these traditional vaccines involves deciding at least 6 months in advance of the forthcoming season. Inter-seasonal influenza activity is collected and analyses as predictive of the upcoming season. For example, based on data collected through February of a given year (e.g., from September of the prior year through January of the given year), traditional vaccine manufacturers design and begin to manufacture vaccines for the forthcoming northern hemisphere influenza season. Based on data collected through September of a given year, traditional vaccine manufacturers design and begin to manufacture vaccines for the forthcoming northern hemisphere influenza season. By contrast, mRNA vaccines can be designed in a matter of days and a recent vaccine developed by applicant preceded from design to manufactured vaccine in just over 5 weeks. This phenomenal benefit afforded by mRNA vaccine technology allows for significantly more accurate prediction of what will be the circulating viruses for any particular influenza season. Data can be captured and analyzed as to what viruses are circulating and with what prevalence, much closer to the start of an influenza season.

The mRNA vaccines of the instant invention comprise mRNAs encoding HA, and optionally, NA antigens of the influenza viruses circulating at the time of design of the vaccines. Exemplary vaccines of the invention comprise mRNAs encoding HA antigens, and optionally NA antigens of the circulating H1N1 viruses and H3N2 viruses. The vaccines of the invention can comprise mRNAs encoding the HA antigens of each circulating influenza A subtype or of each predominant influenza A subtype in combination with mRNAs encoding the HA antigens of each circulating influenza B lineage (or of each predominant influenza lineage). In exemplary embodiments, the vaccines also comprise mRNAs encoding the NA antigens corresponding to the selected HA antigens. Predominant viruses, or those predominant in circulation, are those detected in the human population at an endemic frequency or at a frequency above a certain threshold understood by the skilled artisan is requisite to evidence that those strain(s) are in circulation within a population, e.g., within populations representative of the Northern or Southern hemisphere.

In exemplary embodiments, an mRNA vaccine of the invention includes mRNA encoding the HA antigen of an influenza A virus strain of the A(H1N1) subtype, mRNA encoding the HA antigen of an influenza A virus strain of the A(H3N2) subtype, mRNA encoding the HA antigen of an influenza B virus strain of the B/Victoria lineage and mRNA encoding the HA antigen of an influenza B virus strain of the B/Yamagata lineage.

The skilled artisan will appreciate a limitation to the traditional cell- or recombinant-based technologies in that selecting circulating or predominant strains of a limited number, e.g., 4 strains selected for design/making tetravalent cell- or recombinant-based will not be representative of all circulating clades and subclades of viruses.

As used herein and as is known in the art, a clade is a taxonomic subdivision of influenza viruses based on the similarity of their HA gene sequences. Viruses within a clade have similar genetic changes (e.g., nucleotide or amino acid mutations) and are therefore, genetically related, but they do not share the exact same viral genome. Viruses within a clade may be further subdivided in sub-clades. While clades and sub-clades may be genetically different from others, they are not necessarily antigenically different. Viruses from a specific clade or sub-clade may not have a mutation that impacts host immunity in comparison to other clades or sub-clades.

The mRNA vaccines of the invention are amenable to inclusion of multiple mRNAs and, as such, can include mRNAs encoding, for example, the HA antigens, and optionally also the corresponding NA antigens, of the most prevalent A/H1N1 strain, A/H3N2 strain, B/Victoria lineage and B/Yamagata lineage, but can further include mRNAs encoding the HA antigens, and optionally also the corresponding NA antigens, of a second prevalent A/H1N1 strain, A/H3N2 strain, B/Victoria lineage and/or B/Yamagata lineage. By virtue of the multiple mRNA format, the vaccines of the invention can encode HA antigens, and optionally corresponding NA antigens, of circulating strains/lineages that represent multiple, distinct influenza clades and sub-clades, producing vaccines more efficacious at combatting an upcoming or forthcoming influenza season.

Seasonal Influenza Virus

Seasonal influenza is an acute respiratory infection caused by influenza viruses that circulate in all parts of the world. Influenza viruses belong to the Orthomyxoviridae family and are divided into types A, B, and C. Influenza types A and B are responsible for epidemics of respiratory illness that are often associated with increased rates of hospitalization and death. Influenza type C is a milder infection that does not cause epidemics, and does not therefore have the severe public health impact of influenza types A and B.

All influenza viruses are negatives-strand RNA viruses with a segmented genome. Influenza type A and B viruses have 8 genes that code for 10 proteins, including the surface proteins hemagglutinin (HA) and neuraminidase (NA). In the case of influenza type A viruses, further subdivision can be made into different subtypes according to differences in these two surface proteins. To date, 16 HA subtypes and 9 NA subtypes have been identified. However, during the 20th century, the only influenza A subtypes that circulated extensively in humans were A(H1N1); A(H1N2); A(H2N2); and A(H3N2). All known subtypes of influenza type A viruses have been isolated from birds and can affect a range of mammal species. As with humans, the number of influenza A subtypes that have been isolated from other mammalian species is limited. Almost all influenza A pandemics have been caused by descendants of the 1918 virus, including "drifted" H1N1 viruses and reassorted H2N2 and H3N2 viruses. Influenza A comprises HA and NA proteins on the surface of its viral envelope. HA allows the virus's recognizing and binding to target cells, and also to infect the cell with viral RNA. NA is critical for the subsequent release of the daughter virus particles created within the infected cell so they can spread to other cells.

Influenza type B viruses almost exclusively infect humans. Influenza B viruses are not classified into subtypes but can be broken down into lineages. Currently circulating influenza type B viruses belong to either B/Yamagata (B/Yamagata/16/88-like) or B/Victoria (B/Victoria/2/87-like) lineage. Influenza virus B mutates at a rate 2 to 3 times slower than type A; however, it significantly impacts children and young adults annually. The influenza B virus capsid is enveloped while its virion consists of an envelope, a matrix protein, a nucleoprotein complex, a nucleocapsid, and a polymerase complex. It can be spherical or filamentous. Its 500 or so surface projections are made of HA and NA. The influenza B virus genome is 14,548 nucleotides long and consists of eight segments of linear negative-sense, single-stranded RNA. The multipartite genome is encapsidated, each segment in a separate nucleocapsid, and the nucleocapsids are surrounded by one envelope.

Virological Surveillance of Influenza

All national and international influenza surveillance systems—including those for monitoring clinical disease—depend fundamentally upon virological surveillance. Within countries, the National Information Center serves as the focal point for coordinating influenza virological surveillance. Some primarily collect specimens directly while others primarily receive virus isolates from other influenza laboratories. The data is then compiled and sent to international surveillance bodies, such as the WHO, for further analysis, as described in more detail below. The WHO then makes two annual recommendations regarding the influenza viruses to be included in the seasonal flu vaccine. The determination of which influenza viruses are included requires antigenic characterization and genetic characterization of the circulating viruses.

Antigenic Characterization

Hemagglutination Inhibition Assay

The hemagglutination inhibition (HAI) test is a classical laboratory procedure for the classification or subtyping of hemagglutinating viruses and further determining the antigenic characteristics of influenza viral isolates provided that the reference antisera used contain antibodies to currently circulating viruses (see, e.g., Pedersen J C *Methods Mol Biol.* 2014; 1161:11-25). The antisera used are based on antigen preparations derived from either the wildtype strain or a high-growth reassortant made using the wild-type strain or an antigenically equivalent strain.

To perform the assay, a serial dilution of virus is prepared across the rows in a U or V-bottom shaped 96-well microtiter plate. As an example, the most concentrated sample in the first well may be diluted to be 1/5× of the stock, and subsequent wells may be two-fold dilutions (1/10, 1/20, 1/40, etc.). The final well serves as a negative control with no virus. Each row of the plate typically has a different virus and the same pattern of dilutions. After serial dilutions, a standardized concentration of red blood cells (RBCs) is added to each well and mixed gently. The plate is incubated at room temperature. Following the incubation period, the assay can be analyzed to distinguish between agglutinated and non-agglutinated wells. The relative concentration, or titer, of the virus sample is based on the well with the last agglutinated appearance, immediately before a pellet is observed.

Serological methods such as the HAI test are essential for many epidemiological and immunological studies and for evaluation of the antibody response following vaccination. Serological methods are also very useful in situations where identification of the virus is not feasible (e.g. after viral shedding has stopped). The HAI test is used to identify circulating influenza viruses that are antigenically similar to influenza viruses from a previous season's vaccine. As used herein "antigenically similar" refers to a virus having an HAI titer that differs by two dilutions or less.

In some embodiments, the HAI assay is used to measure the effectiveness of a candidate vaccine, such as those provided herein. In some embodiments, the mRNA vaccines have an HAI titer that is 2-, 3-, 4-, 5-, 6-, 7-, 8-, 9-, or 10-fold increased relative to a control (e.g., HAI titer from a subject administered a traditional seasonal flu vaccine, such as FLUBLOK®).

In some embodiments, an HA ELISA assay is performed to examine the HA antibody titers resulting from administration of a candidate vaccine (e.g., IgG antibody titers) (see, e.g., Examples 1, 2, 4, 7, and 8). In some embodiments, the mRNA vaccines have an HA IgG antibody titer that is 1-log, 2-log, 3-log, 4-log, 5-log, 6-log, 7-log, 8-log, 9-log, or 10-log increased relative to a control (e.g., PBS). In some embodiments, the control comprises the HA-reactive IgG antibody titer in a subject prior to administration of the composition (e.g., vaccine). In some embodiments, a candidate vaccine has an HA IgG antibody titer that is 1-, 2-, 3-, 4-, 5-, 6-, 7-, 8-, 9-, or 10-fold increased relative to a control.

Neuraminidase Inhibition Assay

The neuraminidase-inhibition (NAI) assay is a laboratory procedure for the identification of the neuraminidase (NA) glycoprotein subtype in influenza viruses or the NA subtype specificity of antibodies to influenza virus (see, e.g., Pedersen J C *Methods Mol Biol.* 2014; 1161:27-36). A serological procedure for subtyping the NA glycoprotein is critical for the identification and classification of avian influenza (AI) viruses.

There are two basic forms of assay for influenza virus NA based on the use of different substrate molecules, a longstanding assay based on the use of a large substrate such as fetuin (e.g., the enzyme-linked lectin assay (ELLA)) and newer assays which utilize small substrate molecules. The fetuin-based method is used to determine the potency of the viral NA and thus the standardized NA dose for use in the NA inhibition (NAI) assay. Once determined, the standardized dose is added to serial dilutions of test antisera, negative control serum and reference anti-NA serum. Any inhibitory effect of the sera on NA activity can then be determined and the NAI titer calculated. The small substrate based method may be a fluorescence assay that uses the substrate 2-(4-methylumbelliferyl)-α-D-N-acetylneuraminic acid (MUNANA). The substrate is added to serially diluted test antisera and cleavage of the MUNANA substrate by NA releases the fluorescent product methylumbelliferone. The inhibitory effect of the sera on the influenza virus NA is determined based on the concentration of the sera that is required to reduce 50% of the NA activity, given as an $IC_{50}$ value. The small substrate based method may, alternatively, be a chemiluminescence-based (CL) assay that uses a sialic acid 1,2-dioxetane derivative (NA-Star) substrate or a modified NA-XTD substrate. The CL assays provide an extended-glow chemiluminescent light signal and neuraminidase inhibitor IC50 values are achieved over a range of virus dilutions.

In some embodiments, the mRNA vaccines have an NAI titer that is 2-, 3-, 4-, 5-, 6-, 7-, 8-, 9-, or 10-fold increased relative to a control. The control, in some embodiments, is a traditional seasonal influenza vaccine that only comprises HA antigens (e.g., does not comprise NA antigens). In some embodiments, the control is a NAI titer value for a wild-type NA. In some embodiments, the mRNA vaccine has an NAI titer that is at least 2-fold higher than a control value. In some embodiments, the vaccine's NAI value is at least 50%, 55%, 60%, 65%, 70%, 75%, 80%, 85%, 90%, 95%, 96%, 97%, 98%, or at least 99% of a control (e.g., the NAI value of a wild-type NA).

In some embodiments, an NA ELISA assay is performed to examine the NA antibody titers resulting from administration of a candidate vaccine (e.g., IgG antibody titers) (see, e.g., Examples 1, 2, 4, 7, and 8). In some embodiments, the mRNA vaccines have an NA IgG antibody titer that is 1-log, 2-log, 3-log, 4-log, 5-log, 6-log, 7-log, 8-log, 9-log, or 10-log increased relative to a control (e.g., PBS). In some embodiments, the control comprises the NA-reactive IgG antibody titer in a subject prior to administration of the composition (e.g., vaccine). In some embodiments, a candidate vaccine has an NA IgG antibody titer that is 1-, 2-, 3-, 4-, 5-, 6-, 7-, 8-, 9-, or 10-fold increased relative to a control.

Microneutralization Assay

Serological methods such as the HAI test rarely yield an early diagnosis of acute influenza virus infection. Although conventional neutralization tests for influenza viruses (based on the inhibition of cytopathogenic effect formation in MDCK cell culture) are productive, a microneutralization assay using microtiter plates in combination with an ELISA to detect virus-infected cells can yield results within two days. The microneutralization assay is a highly sensitive and specific assay for detecting virus-specific neutralizing antibodies to influenza viruses in human and animal sera, and in some embodiments, includes the detection of human antibodies to avian subtypes. Testing can be carried out quickly once a novel virus is identified and often before purified viral proteins become available for use in other assays.

Virus Identification by Immunofluorescence Antibody Staining

Immunofluorescence antibody (IFA) staining of virus-infected cells in original clinical specimens and field isolates is a rapid and sensitive method for diagnosing respiratory and other viral infections. In some embodiments, IFA staining is performed on isolates rather than original clinical specimens, as this allows any virus that is present to first be amplified, and if required used in other studies. As commercially available rapid tests for diagnosing influenza infection differ with regard to the type of specimen required as well as their complexity, specificity and sensitivity, it is recommended that such assays should be used in conjunction with other laboratory tests.

Genetic Characterization

Molecular Identification of Influenza Isolates

The direct molecular identification of influenza isolates is a rapid and powerful technique. The reverse-transcription polymerase chain reaction (RT-PCR) allows template viral RNA to be reverse transcribed producing complementary DNA (cDNA) which can then be amplified and detected. This method can be used directly on clinical samples and the rapid nature of the results can greatly facilitate investigation of outbreaks of respiratory illness (e.g., influenza). For example, genetic analysis of influenza virus genes (especially the HA and NA genes) can be used to identify an unknown influenza virus when the antigenic characteristics cannot be defined. Genetic analyses also can be used to monitor the evolution of influenza viruses and to determine the degree of relatedness between viruses from different geographical areas and those collected at different times of the year.

The hallmark of human influenza viruses is their ability to undergo antigenic change, which occurs in the following two ways: antigenic drift or antigenic shift.

Antigenic Drift

Antigenic drift is a process of gradual and relatively continuous change in the viral HA and NA proteins. It results from the accumulation of point mutations in the HA and NA genes during viral replication. Both influenza type A and B viruses undergo antigenic drift, leading to new virus strains. The emergence of these new strains necessitates the frequent updating of influenza vaccine virus strains. Because antibodies to previous influenza infections may not provide full protection against the new strains resulting from antigenic drift, subjects can have many influenza infections over a lifetime.

Antigenic Shift

In addition to antigenic drift, influenza type A viruses can also undergo a more dramatic and abrupt type of change called antigenic shift. By definition, a shift has occurred when an influenza type A virus emerges among humans bearing either a HA protein or a combination of HA and NA proteins that have not been circulating among humans in recent years. There are at least three possible mechanisms by which antigenic shift can occur: (a) a virus bearing new HA and NA proteins can arise through the genetic reassortment of non-human and human influenza viruses; (b) an influenza virus from other animals (e.g. birds or pigs) can infect a human directly without undergoing genetic reassortment; or (c) a non-human virus may be passed from one type of animal (e.g. birds) through an intermediate animal host (such as a pig) to humans.

Whereas antigenic drift occurs continuously, antigenic shift occurs infrequently and unpredictably. Since antigenic shift results in the emergence of a new influenza virus, a large proportion (or even all) of the world's population will have no antibodies against it. If the new strain is capable of causing illness in humans and sustained chains of human-to-human transmission leading to community-wide outbreaks then such a virus has the potential to spread worldwide, causing a pandemic.

Antigens

Antigens, as used herein, are proteins capable of inducing an immune response (e.g., causing an immune system to produce antibodies against the antigens). The vaccines of the present disclosure provide a unique advantage over traditional protein-based vaccination approaches in which protein antigens are purified or produced in vitro, e.g., recombinant protein production technologies. The vaccines of the present disclosure feature mRNA encoding the desired antigens, which when introduced into the body, i.e., administered to a mammalian subject (for example a human) in vivo, cause the cells of the body to express the desired antigens. In order to facilitate delivery of the mRNAs of the present disclosure to the cells of the body, the mRNAs are encapsulated in lipid nanoparticles (LNPs). Upon delivery and uptake by cells of the body, the mRNAs are translated in the cytosol and protein antigens are generated by the host cell machinery. The protein antigens are presented and elicit an adaptive humoral and cellular immune response. Neutralizing antibodies are directed against the expressed protein antigens and hence the protein antigens are considered relevant target antigens for vaccine development. Herein, use of the term "antigen" encompasses immunogenic proteins and immunogenic fragments (an immunogenic fragment that induces (or is capable of inducing) an immune response to a (at least one) influenza virus), unless otherwise stated. It should be understood that the term "protein" encompasses peptides and the term "antigen" encompasses antigenic fragments. Other molecules may be antigenic such as bacterial polysaccharides or combinations of protein and polysaccharide structures, but for the viral vaccines included herein, viral proteins, fragments of viral proteins and designed and or mutated proteins derived from the influenza virus are the antigens provided herein.

In some embodiments, the influenza antigen is hemagglutinin (HA) or neuraminidase (NA). Exemplary HA and NA antigens are known in the art and are publicly available, for example, NCBI's Influenza Virus Resource (ncbi.nlm.nih.gov/genomes/FLU/Database/nph-select.cgi?go=database), Influenza Research Database fludb.org/brc/home.spg?decorator=influenza), and GISRS (gisaid.org/references/human-influenza-vaccine-composition/). In some embodiments, the vaccine comprises mRNA encoding at least one of the following antigens: A/California/7/2009 (H1N1)pdm09-like virus, A/Switzerland/9715293/2013 (H3N2)-like virus, B/Phuket/3073/2013-like virus, B/Brisbane/60/2008-like virus, A/Hong Kong/4801/2014 (H3N2)-like virus, A/Michigan/45/2015 (H1N1) pdm09-like virus, A/Singapore/INFIMH-16-0019/2016 (H3N2)-like virus, B/Colorado/06/2017-like virus (B/Victoria/2/87 lineage), A/Switzerland/8060/2017 (H3N2)-like virus, A/Brisbane/02/2018 (H1N1)pdm09-like virus, A/Kansas/14/2017 (H3N2)-like virus, A/South Australia/34/2019 (H3N2)-like virus, B/Washington/02/2019-like (B/Victoria lineage) virus, A/Guangdong-Maonan/SWL1536/2019 (H1N1)pdm09-like virus, A/Hong Kong/2671/2019 (H3N2)-like virus, A/Hawaii/70/2019 (H1N1) pdm09-like virus, A/Victoria/2570/2019 (H1N1)pdm09-like virus, A/Wisconsin/588/2019 (H1N1)pdm09-like virus, and A/Cambodia/e0826360/2020 (H3N2)-like virus.

In some embodiments, the influenza antigen is a fragment of, a derivative of, or a modified HA or NA. For example, in some embodiments, the NA is a wild-type NA (e.g., is enzymatically active). In some embodiments, the NA is a modified NA, such as an enzymatically inactive NA. As used herein, "enzymatically inactive NA" refers to a NA that has been mutated such that it possesses no or minimal catalytic activity (see, e.g., Richard et al., J Clin Virol., 2008, 41(1): 20-24; Yen et al., J Virol., 2006, 80(17): 8787-8795). For example, in some embodiments, the enzymatically inactive NA possesses less than 30%, 25%, 20%, 15%, 14%, 13%, 12%, 11%, 10%, 9%, 8%, 7%, 6%, 5%, 4%, 3%, 2%, 1%, or 0% of the catalytic activity of the wild-type NA (e.g., in an enzymatic activity assay, as is known in the art). In some embodiments, at least one of Arg118, Asp151, Arg152, Arg224, Glu276, Arg292, Arg371 and Tyr406 is mutated relative to an influenza A or B neuraminidase wild type sequence. In some embodiments, 1, 2, 3, 4, 5, 6, 7, or all 8 amino acids are mutated. In some embodiments, at least one of Glu119, Arg156, Trp178, Ser179, Asp198, Ile222, Glu227, His274, Glu277, Asn294, and Glu425 is mutated relative to an influenza A or B neuraminidase wild type sequence. In some embodiments, the mutation is R118K, D151G, or E227D. In some embodiments, the mutation is a deletion of the cytoplasmic tail (dcytT). In some embodiments, the mutation is a deletion of amino acids of the stalk region. In some embodiments, the mutation is a deletion of 15 amino acids of the stalk region (stalk_d15). In some embodiments, the mutation is a deletion of 30 amino acids of the stalk region (stalk_d30). In some embodiments, the mutation is an insertion of amino acids of the stalk region. In some embodiments, the mutation is an insertion of 15 amino acids in the stalk region (stalk_ins15). In some embodiments, the mutant NA antigens are combined with HA antigens. In some embodiments, the enzymatically inactive NA comprises an influenza A NA antigen of the N1 subtype (e.g., N1_Wisconsin_2019_WT strain, SEQ ID NO: 46). In some embodiments, the enzymatically inactive NA comprises an influenza A NA antigen of the N2 subtype (e.g., N2 A/Hong Kong/45/2019, SEQ ID NO: 19). In some embodiments, the enzymatically inactive NA comprises an influenza A NA antigen of the N8 subtype (e.g., Astrakhan/2020, SEQ ID NO: 121). In some embodiments, the enzymatically inactive NA comprises an influenza B NA antigen of the B/Yamagata lineage (e.g., NA B/Phuket/3073/2013, SEQ ID NO: 34). In some embodiments, the enzymatically inactive NA comprises an influenza B NA antigen of the B/Victoria lineage (e.g., NA B/Washington/02/2019, SEQ ID NO: 25).

In some embodiments, the HA is a wild-type HA. In some embodiments, the HA is a modified HA. In some embodiments, the HA comprises at least one mutation. In some embodiments, at least one amino acid is mutated relative to an influenza A or B hemagglutination wild type sequence. In some embodiments, the mutation is T2191, H371Y, I494M, H504P, M362L, HA0, ΔPB, TB, or VASP. In some embodiments, more than one amino acid is mutated. In some embodiments, the mutation is selected from the group consisting of creation of a disulfide in the HA stem to link neighboring protomers, deletion of a cleavage site, and replacement of polybasic cleavage site (HPAI) by an LPAI sequence. In some embodiments, the mutation is a disulfide in the HA stem to link neighboring protomers. In some embodiments, the mutation is the deletion of a cleavage site. In some embodiments, the mutation is replacement of polybasic cleavage site (HPAI) by an LPAI sequence.

In some embodiments, the mRNA vaccines of the present disclosure may comprise a combination of mRNAs encoding HA, or modified versions thereof, optionally in combination with mRNAs encoding NA antigens, or fragments, derivatives, or modified versions thereof. In some embodiments, the mRNA vaccine may comprise a combination of mRNAs encoding HA, or modified versions thereof, and mRNAs encoding NA antigens, or fragments, derivatives, or modified versions thereof. In some embodiments, the vaccine comprises mRNAs encoding 1, 2, 3, 4, 5, 6, 7, 8, 9, or 10 HA antigens and/or mRNAs encoding 1, 2, 3, 4, 5, 6, 7, 8, 9, or 10 NA antigens, or any combination thereof (e.g., 4 HA antigens, or 4 HA antigens and 4 NA antigens). In some embodiments, the vaccine comprises mRNA encoding one HA antigen. In some embodiments, the vaccine comprises mRNAs encoding two HA antigens. In some embodiments, the vaccine comprises mRNAs encoding three HA antigens. In some embodiments, the vaccine comprises mRNAs encoding four HA antigens. In some embodiments, the vaccine comprises mRNAs encoding five HA antigens. In some embodiments, the vaccine comprises mRNAs encoding six HA antigens. In some embodiments, the vaccine comprises mRNAs encoding seven HA antigens. In some embodiments, the vaccine comprises mRNAs encoding eight HA antigens. In some embodiments, the vaccine comprises mRNAs encoding nine HA antigens. In some embodiments, the vaccine comprises mRNAs encoding ten or more HA antigens. In some embodiments, the vaccine comprises mRNA encoding one HA antigen and mRNA encoding one NA antigen. In some embodiments, the vaccine comprises mRNAs encoding two HA antigens and mRNAs encoding two NA antigens. In some embodiments, the vaccine comprises mRNAs encoding three HA antigens and mRNAs encoding three NA antigens. In some embodiments, the vaccine comprises mRNAs encoding four HA antigens and mRNAs encoding four NA antigens. In some embodiments, the vaccine comprises mRNAs encoding five HA antigens and mRNAs encoding five NA antigens. In some embodiments, the vaccine comprises mRNAs encoding six HA antigens and mRNAs encoding six NA antigens.

In some embodiments, the mRNAs encoding the antigens are present in the formulation in an equal amount (e.g., a 1:1 weight/weight ratio or a 1:1 molar ratio), for example, a 1:1 ratio of mRNAs encoding distinct HA antigens, or a 1:1 ratio of mRNAs encoding distinct HA and NA antigens. As used herein, a "weight/weight ratio" or wt/wt ratio or wt:wt ratio refers to the ratio between the weights (masses) of the different components. A "molar ratio" refers to the ratio between different components (e.g., the number of mRNA encoding each antigen). In an exemplary vaccine comprising mRNAs encoding four different HA antigens, mRNAs at a "1:1 ratio" would include the mRNAs in a ratio (e.g., wt/wt ratio or molar ratio) of 1:1:1:1 of the first, second, third and fourth mRNA. In an exemplary vaccine comprising mRNAs encoding four different HA antigens and four different NA antigens, mRNAs at a "1:1 ratio" would include the mRNAs encoding the different HA antigens in a ratio of 1:1:1:1 of the first, second, third and fourth mRNA, and would include mRNAs encoding the different NA antigens in a ratio of 1:1:1:1 of the first, second, third and fourth mRNA.

In some embodiments, the ratio of mRNAs encoding the different HA antigens are equivalent to each other (e.g., 1:1:1:1) and the ratio of mRNAs encoding the different NA antigens are equivalent to each other (e.g., 1:1:1:1); however, the ratio of the mRNAs encoding the HA antigens to mRNAs encoding the NA antigens is not 1:1. In an exemplary vaccine comprising mRNAs encoding four different HA antigens and four different NA antigens, mRNAs at a "3:1 ratio" would include the mRNAs encoding the different HA antigens in a ratio of 3:3:3:3 of the first, second, third and fourth mRNA, and would include mRNAs encoding the different NA antigens in a ratio of 1:1:1:1 of the first, second, third and fourth mRNA In some embodiments, the HA:NA ratio is 1:1, 1:2, 1:3, 1:4, 2:1, 3:1, or 4:1. In each embodiment or aspect of the invention, it is understood that the featured vaccines include the mRNAs encapsulated within LNPs. While it is possible to encapsulate each unique mRNA in its own LNP, the mRNA vaccine technology enjoys the significant technological advantage of being able to encapsulate several mRNAs in a single LNP product. In some embodiments, a single LNP comprises 1, 2, 3, 4, 5, 6, 7, 8, 9, 10, 11, or 12 different mRNA polynucleotides. In other embodiments, the mRNAs are each formulated in unique LNPs (e.g., a composition comprises 8 LNPs, each LNP comprising 1 of 8 different mRNA polynucleotides).

In some aspects, compositions of the disclosure comprise at least:
- an mRNA encoding a HA antigen from a first circulating influenza A virus,
- an mRNA encoding a HA antigen from a second circulating influenza A virus,
- an mRNA encoding a HA antigen from a first circulating influenza B virus, and
- an mRNA encoding a HA antigen from a second circulating influenza B virus.

In other aspects, compositions of the disclosure comprise at least:
- an mRNA encoding a HA antigen from a first circulating influenza A virus,
- an mRNA encoding a HA antigen from a second circulating influenza A virus,
- an mRNA encoding a HA antigen from a first circulating influenza B virus, and
- an mRNA encoding a HA antigen from a second circulating influenza B virus; and
- an mRNA encoding a NA antigen from the first circulating influenza A virus,
- an mRNA encoding a NA antigen from the second circulating influenza A virus,
- an mRNA encoding a NA antigen from the first circulating influenza B virus, and
- an mRNA encoding a NA antigen from the second circulating influenza B virus, wherein the
- mRNAs are formulated in a lipid nanoparticle at a ratio of 1:1:1:1:1:1:1:1.

In yet other aspects, compositions of the disclosure comprise at least:
- an mRNA encoding a HA antigen from a first circulating influenza A virus,
- an mRNA encoding a HA antigen from a second circulating influenza A virus,
- an mRNA encoding a HA antigen from a first circulating influenza B virus, and
- an mRNA encoding a HA antigen from a second circulating influenza B virus; and
- an mRNA encoding a NA antigen from the first circulating influenza A virus,
- an mRNA encoding a NA antigen from the second circulating influenza A virus,
- an mRNA encoding a NA antigen from the first circulating influenza B virus, and
- an mRNA encoding a NA antigen from the second circulating influenza B virus.

In other aspects, compositions of the disclosure comprise:
- two or three mRNAs encoding a HA antigen from a first circulating influenza A virus, two or three mRNAs encoding a HA antigen from a second circulating influenza A virus, two or three mRNAs encoding a HA antigen from a first circulating influenza B virus, and two or three mRNAs encoding a HA antigen from a second circulating influenza B virus.

In further aspects, compositions of the disclosure comprise:

two or three mRNAs encoding a HA antigen from a first circulating influenza A virus, two or three mRNAs encoding a HA antigen from a second circulating influenza A virus, two or three mRNAs encoding a HA antigen from a first circulating influenza B virus, and two or three mRNAs encoding a HA antigen from a second circulating influenza B virus; and an mRNA encoding a NA antigen from the first circulating influenza A virus, an mRNA encoding a NA antigen from the second circulating influenza A virus, an mRNA encoding a NA antigen from the first circulating influenza B virus, and an mRNA encoding a NA antigen from the second circulating influenza B virus. In some embodiments, the mRNAs are formulated in a lipid nanoparticle at a ratio of 2:2:2:2:1:1:1:1.

In some embodiments, the mRNAs are formulated in a lipid nanoparticle at a ratio of 3:3:3:3:1:1:1:1.

Circulating influenza A viruses include, for example, influenza A(H1N1)pdm09, A(H3N2), and influenza type B viruses (B/Victoria/2/87 and B/Yamagata/16/88). In some embodiments, the influenza A(H1N1)pdm09 viruses comprise haemagglutinin (HA) genes that belong to phylogenetic clade 6B.1A (e.g., subclades 5A, 5B, and 7). In some embodiments, the influenza A(H3N2) viruses comprise clade 3C.3a or clade 3C.2a and its subclades (e.g., 3C.2a1b). In some embodiments, the influenza B virus of the B/Yamagata lineage belongs to genetic clade 3. In some embodiments, the influenza B virus of the B/Victoria lineage belongs to genetic clade 1A.

In some embodiments, the circulating influenza A(H1N1) pdm09 virus is A/California/07/2009, A/Michigan/45/2015, A/Brisbane/02/2018, A/Hawaii/70/2019, A/Idaho/07/2018, A/Maine/38/2018, A/Nebraska/15/2018, A/Nebraska/14/2019, A/Wisconsin/588/2019, A/Iowa/33/2019, A/Arkansas/28/2019, A/Virginia/41/2019, A/Minnesota/60/2019, A/Alabama/27/2019, or A/Guangdong-Maonan/SWL1536/2019.

In some embodiments, the circulating influenza A(H3N2) virus is A/Iowa/60/2018, A/South Australia/34/2019, A/Hong Kong/45/2019, A/Hong Kong/2671/2019, A/Kansas/14/2017, A/Jamaica/60361/2019, A/Florida/130/2019, A/Laos/1789/2019, A/Vermont/25/2019, A/New Jersey/34/2019, A/California/176/2019, A/Pennsylvania/1026/2019, A/Togo/634/2019, A/Kenya/130/2019, A/Togo/1307/2019, A/Ohio/30/2019, A/Guatemala/93/2019, A/Guatemala/10/2019, A/Hong Kong/4801/2014, or A/Singapore/INFIMH-16-0019-2016.

In some embodiments, the circulating influenza B/Victoria lineage virus is B/Washington/02/2019, B/Colorado/06/2017, B/Brisbane/60/2008, or B/Colorado/06/2019.

In some embodiments, the influenza B/Yamagata lineage virus includes B/Phuket/3073/2013-like virus.

In some embodiments, a vaccine of the disclosure includes mRNAs encoding influenza A HA antigens of the H1-H18 subtype. As used herein, "subtype" refers to the specific HA and/or NA protein of an influenza A virus. There are 18 distinct subtypes of HA (H1-H18) and 11 distinct subtypes of NA (N1-N11) known in the art (CDC, "Types of Influenza Viruses", 2019). In some embodiments, the vaccine comprises an mRNA encoding an influenza A HA antigen of the H1 subtype. In some embodiments, the vaccine comprises an mRNA encoding an influenza A HA antigen of the H3 subtype. In some embodiments, the vaccine comprises an mRNA encoding an influenza A of the H2 subtype. In some embodiments, the vaccine comprises an mRNA encoding an influenza A of the H5 subtype. In some embodiments, the vaccine comprises an mRNA encoding an influenza A of the H7 subtype. In some embodiments, the vaccine comprises an mRNA encoding an influenza A of the H9 subtype. In some embodiments, the vaccine comprises an mRNA encoding an H1 subtype antigen and an mRNA encoding an H3 subtype antigen.

In some embodiments, vaccine of the disclosure includes mRNAs encoding influenza A NA antigens of the N1-N11 subtype. In some embodiments, the vaccine comprises an mRNA encoding an influenza A NA of the N1 subtype. In some embodiments, the vaccine comprises an mRNA encoding an influenza A NA antigen of the N2 subtype. In some embodiments, the vaccine comprises an mRNA encoding an N1 subtype antigen and an mRNA encoding an N2 subtype antigen. In some embodiments, the vaccine comprises an mRNA encoding an influenza A NA antigen of the N8 subtype.

In some embodiments, a vaccine of the disclosure includes mRNAs encoding influenza B antigens. The influenza B antigens may be from any strain known in the art. Examples of influenza B strains include, but are not limited to, strains originating from Aichi, Akita, Alaska, Ann Arbor, Argentina, Bangkok, Beijing, Belgium, Bonn, Brazil, Buenos Aires, Canada, Chaco, Chiba, Chongqing, CNIC, Cordoba, Czechoslovakia, Daeku, Durban, Finland, Fujian, Fukuoka, Genoa, Guangdong, Guangzhou, Hannover, Harbin, Hawaii, Hebei, Henan, Hiroshima, Hong Kong, Houston, Hunan, Ibaraki, India, Israel, Johannesburg, Kagoshima, Kanagawa, Kansas, Khazkov, Kobe, Kouchi, Lazio, Lee, Leningrad, Lissabon, Los Angeles, Lusaka, Lyon, Malaysia, Maputo, Mar del Plata, Maryland, Memphis, Michigan, Mie, Milano, Minsk, Nagasaki, Nagoya, Nanchang, Nashville, Nebraska, The Netherlands, New York, NIB, Ningxia, Norway, Oman, Oregon, Osaka, Oslo, Panama, Paris, Parma, Perugia, Philippines, Pusan, Quebec, Rochester, Roma, Saga, Seoul, Shangdong, Shanghai, Shenzhen, Shiga, Shizuoka, Sichuan, Siena, Singapore, South Carolina, South Dakota, Spain, Stockholm, Switzerland, Taiwan, Texas, Tokushima, Tokyo, Trento, Trieste, United Kingdom, Ushuaia, USSR, Utah, Victoria, Vienna, Wuhan, Xuanwu, Yamagata, Yamanashi, Yunnan, hybrid subtypes, circulating recombinant forms, clinical and field isolates. Exemplary influenza B strains include, but are not limited to: Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV 106/2002, strain Belgium/WV 107/2002, strain Belgium/WV 109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001. Their sequences are known in the art and are available from GenBank.

In some embodiments, a vaccine of the disclosure includes mRNAs encoding an influenza B HA antigen, for example a B/Yamagata antigen or a B/Victoria antigen. In some embodiments, a vaccine of the disclosure includes mRNAs encoding an HA B/Yamagata antigen and an HA B/Victoria antigen. In some embodiments, a vaccine of the disclosure includes mRNAs encoding an influenza B NA antigen, for example an NA B/Yamagata antigen or an NA B/Victoria antigen. In some embodiments, a vaccine of the disclosure includes mRNAs encoding an NA B/Yamagata antigen and an NA B/Victoria antigen.

Therefore, in some embodiments, the vaccine comprises eight antigens: an H1 antigen, and H3 antigen, an N1 antigen, an N2 antigen, an HA B/Yamagata antigen, an HA B/Victoria antigen, an NA B/Yamagata antigen, and an NA B/Victoria antigen.

Exemplary sequences of the influenza virus antigens and the RNA encoding the influenza virus antigens of the compositions of the present disclosure are provided in Tables 4, 6, 7, 9, and 11. In some embodiments, the mRNA vaccines comprise a sequence that has at least 90%, 91%, 92%, 93%, 94%, 95%, 96%, 97%, 98%, or 99% identity to an open reading frame (ORF) sequence selected from SEQ ID NOs: 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, or 126. In some embodiments, the mRNA vaccines encode a polypeptide that is 90%, 91%, 92%, 93%, 94%, 95%, 96%, 97%, 98%, 99% or identical to a sequence selected from SEQ ID NOs: 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, or 127. In some embodiments, the mRNA vaccine comprises a sequence that has at least 90%, 91%, 92%, 93%, 94%, 95%, 96%, 97%, 98%, or 99% identity to a sequence selected according to standardized criteria used by World Health Organization's Global Influenza Surveillance and Response System (GISRS).

Nucleic Acids

The compositions of the present disclosure comprise a (at least one) messenger RNA (mRNA) having an open reading frame (ORF) encoding an influenza virus antigen. In some embodiments, the mRNA further comprises a 5' UTR, 3' UTR, a poly(A) tail and/or a 5' cap analog.

It should also be understood that the influenza virus vaccine of the present disclosure may include any 5' untranslated region (UTR) and/or any 3' UTR. Exemplary UTR sequences include SEQ ID NOs: 1-4; however, other UTR sequences may be used or exchanged for any of the UTR sequences described herein. In some embodiments, a 5' UTR of the present disclosure comprises a sequence selected from SEQ ID NO: 1 (GGGAAAUAAGAGAGAAAAGAAGAGUAAGAAGAAAUAUAAGAGCCACC) and SEQ ID NO: 2 (GGGAAAUAAGAGAGAAAAGAAGAGUAAGAAGAAAUAUAAGACCCCGGCGCCG CCACC). In some embodiments, a 3' UTR of the present disclosure comprises a sequence selected from SEQ ID NO: 3 (UGAUAAUAGGCUGGAGCCUCGGUGGCCAUGCUUCUUGCCCCUUGGGCCUCCCCCCAGCCCCUCCUCCCCUUCCUGCACCCGUACCCC CGUGGUCUUUGAAUAAAGUCUGAGUGGGCGGC) and SEQ ID NO: 4 (UGAUAA UAGGCUGGAGCCUCGGUGGCCUAGCUUCUUGCCCCUUGGGCCUCCCCCCAGCC CCUCCUCCCCUUCCUGCACCCGUACCCCCGUGGUCUUUGAAUAAAGUCUGAGU GGGCGGC). UTRs may also be omitted from the RNA polynucleotides provided herein.

Nucleic acids comprise a polymer of nucleotides (nucleotide monomers). Thus, nucleic acids are also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any RNA that encodes a (at least one) protein (a naturally-occurring, non-naturally-occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents mRNA, the "T"s would be substituted for "U"s. Thus, any of the DNAs disclosed and identified by a particular sequence identification number herein also disclose the corresponding mRNA sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in an RNA polynucleotide of the present disclosure.

Variants

In some embodiments, the compositions of the present disclosure include RNA that encodes an influenza virus antigen variant. Antigen variants or other polypeptide variants refers to molecules that differ in their amino acid sequence from a wild-type, native, or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native, or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a composition comprises an RNA or an RNA ORF that comprises a nucleotide sequence of any one of the sequences provided herein, or comprises a nucleotide sequence at least 90%, at least 95%, at least 96%, at least 97%, at least 98%, or at least 99% identical to a nucleotide sequence of any one of the sequences provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an mRNA vaccine.

As recognized by those skilled in the art, protein fragments, functional protein domains, and homologous proteins are also considered to be within the scope of influenza virus antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the influenza virus. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a composition includes an RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap];G(5')ppp(5')A; G(5')ppp(5')G; m7G(5')ppp(5')A; m7G (5')ppp(5')G (New England BioLabs, Ipswich, MA.). 5'-capping of modified RNA may be completed post-transcriptionally using a Vaccinia Virus Capping Enzyme to generate the "Cap 0" structure: m7G(5')ppp(5')G (New England BioLabs, Ipswich, MA.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, a composition includes a stabilizing element. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, an mRNA includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, an mRNA includes the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, an mRNA does not include a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

An mRNA may or may not contain an enhancer and/or promoter sequence, which may be modified or unmodified or which may be activated or inactivated. In some embodiments, the histone stem-loop is generally derived from histone genes and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, an mRNA has one or more AU-rich sequences removed. These sequences, sometimes referred to as AURES are destabilizing sequences found in the 3'UTR. The AURES may be removed from the RNA vaccines. Alternatively, the AURES may remain in the RNA vaccine.

Signal Peptides

In some embodiments, a composition comprises an mRNA having an ORF that encodes a signal peptide fused to the influenza virus antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by an ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than influenza virus antigens in nature) are known in the art and can be tested for desired properties and then incorporated into a nucleic acid of the disclosure.

Fusion Proteins

In some embodiments, a composition of the present disclosure includes an mRNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the influenza virus antigen. Antigenic fusion proteins, in some embodiments, retain the functional property from each original protein.

Scaffold Moieties

The mRNA vaccines as provided herein, in some embodiments, encode fusion proteins that comprise influenza virus antigens linked to scaffold moieties. In some embodiments, such scaffold moieties impart desired properties to an antigen encoded by a nucleic acid of the disclosure. For example, scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. Computational and Structural Biotechnology Journal 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments, the influenza virus antigen is fused to HBsAG or HBcAG to facilitate self-assembly of nanoparticles displaying the influenza virus antigen.

In some embodiments, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. Flavins and Flavoproteins. Methods and Protocols, Series: Methods in Molecular Biology. 2014). The LS monomer is 150 amino acids long and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. J Mol Biol. 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. Nat Struct Mol Biol. 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. FEBS J. 2013, 280: 2097-2104).

In some embodiments, an RNA of the present disclosure encodes an influenza virus antigen (e.g., HA or NA protein) fused to a foldon domain. The foldon domain may be, for example, obtained from bacteriophage T4 fibritin (see, e.g., Tao Y, et al. Structure. 1997 Jun. 15; 5(6):789-98).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding an influenza virus antigen). In some embodiments, a codon optimized sequence shares less than 90% sequence identity to a naturally-occurring or wild-type sequence (e.g., a naturally-occurring or wild-type mRNA sequence encoding an influenza virus antigen). In some embodiments, a codon optimized sequence shares less than 85% sequence identity to a naturally-occurring or wild-type sequence (e.g., a naturally-occurring or wild-type mRNA sequence encoding an influenza virus antigen). In some embodiments, a codon optimized sequence shares less than 80% sequence identity to a naturally-occurring or wild-type sequence (e.g., a naturally-occurring or wild-type mRNA sequence encoding an influenza virus antigen). In some embodiments, a codon optimized sequence shares less than 75% sequence identity to a naturally-occurring or wild-type sequence (e.g., a naturally-occurring or wild-type mRNA sequence encoding an influenza virus antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an influenza virus antigen). In some embodiments, a codon optimized sequence shares between 65% and 75% or about 80% sequence identity to a naturally-occurring or wild-type sequence (e.g., a naturally-occurring or wild-type mRNA sequence encoding an influenza virus antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an influenza virus antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, an mRNA is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

The compositions of the present disclosure comprise, in some embodiments, an RNA having an open reading frame encoding an influenza virus antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the poly(A) tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 128), where R is a purine (adenine or guanine) three bases upstream of the start codon (AUG), which is followed by another 'G'. 5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 138) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (1743) dehydrogenase 4 gene (HSD17B4) (WO2015024667), or a 5' UTR element derived from the 5' UTR of ATP5A1

(WO2015024667) can be used. In some embodiments, an internal ribosome entry site (IRES) is used instead of a 5' UTR.

In some embodiments, a 5' UTR of the present disclosure comprises a sequence selected from SEQ ID NO: 1 and SEQ ID NO: 2.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-$\alpha$. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3'' UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term “altered” as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an “altered” UTR (whether 3' or 5') comprise a variant UTR.

In some embodiments, a double, triple or quadruple UTR such as a 5' UTR or 3' UTR may be used. As used herein, a “double” UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein “patterned UTRs” are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a “family of proteins” is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

Non-Coding Sequences

Aspects of the disclosure relate to multivalent RNA compositions which comprise mRNAs, e.g., 2-15 mRNA polynucleotides each comprising a distinct open reading frame (ORF) encoding an influenza virus antigenic polypeptide, wherein each mRNA polynucleotide comprises one or more non-coding sequences in an untranslated region (UTR) having unique identifier sequences (non-coding sequences). As used herein, “non-coding sequence” refers to a sequence of a biological molecule (e.g., nucleic acid, protein, etc.) that when combined with the sequence another biological molecule serves to identify the other biological molecule. Typically, a non-coding sequence is a heterologous sequence that is incorporated within or appended to a sequence of a target biological molecule and utilized as a reference in order to identify a target molecule of interest. In some embodiments, a non-coding sequence is a sequence of a nucleic acid (e.g., a heterologous or synthetic nucleic acid) that is incorporated within or appended to a target nucleic acid and utilized as a reference in order to identify the target nucleic acid. In some embodiments, a non-coding sequence is of the formula (N)n. In some embodiments, n is an integer in the range of 5 to 20, 5 to 10, 10 to 20, 7 to 20, or 7 to 30. In some embodiments, n is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more. In some embodiments, each N is a nucleotide that is independently selected from A, G, T, U, and C, or analogues thereof. Thus, some embodiments comprise nucleic acids (e.g., mRNAs) that (i) have a target sequence of interest (e.g., a coding sequence (e.g., that encodes an antigen protein or antigenic polypeptide)); and (ii) comprises a unique non-coding sequence.

In some embodiments, one or more in vitro transcribed mRNAs comprise one or more non-coding sequences in an untranslated region (UTR), such as a 5' UTR or 3' UTR. Inclusion of a non-coding sequence in the UTR of an mRNA prevents non-coding sequence from being translated into a peptide. In some embodiments, a non-coding sequence is positioned in a 3' UTR of an mRNA. In some embodiments, the non-coding sequence is positioned upstream of the polyA tail of the mRNA. In some embodiments, the non-coding sequence is positioned downstream of (e.g., after) the polyA tail of the mRNA. In some embodiments, the non-coding sequence is positioned between the last codon of the ORF of the mRNA and the first "A" of the polyA tail of the mRNA. In some embodiments, a polynucleotide non-coding sequence positioned in a UTR comprises between 1 and 10 nucleotides (e.g., 1, 2, 3, 4, 5, 6, 7, 8, 9, or 10 nucleotides). In some embodiments, UTR comprising a polynucleotide non-coding sequence further comprises one or more (e.g., 1, 2, 3, or more) RNAse cleavage sites, such as RNase H cleavage sites. In some embodiments, each different RNA of a multivalent RNA composition comprises a different (e.g., unique) non-coding sequence. In some embodiments, RNAs of a multivalent RNA composition are detected and/or purified according to the polynucleotide non-coding sequences of the RNAs. In some embodiments, the mRNA non-coding sequences are used to identify the presence of mRNA or determine a relative ratio of different mRNAs in a sample (e.g., a reaction product or a drug product). In some embodiments, the mRNA non-coding sequences are detected using one or more of deep sequencing, PCR, and Sanger sequencing. Exemplary non-coding sequences include: AACGUGAU; AAACAUCG; ATGCCUAA; AGUGGUCA; ACCACUGU; ACAUUGGC; CAGAUCUG; CAUCAAGU; CGCUGAUC; ACAAGCUA; CUGUAGCC; AGUACAAG; AACAACCA; AACCGAGA; AACGCUUA; AAGACGGA; AAGGUACA; ACACAGAA; ACAGCAGA; ACCUCCAA; ACGCUCGA; ACGUAUCA; ACUAUGCA; AGAGUCAA; AGAUCGCA; AGCAGGAA; AGUCACUA; AUCCUGUA; AUUGAGGA; CAACCACA; GACUAGUA; CAAUGGAA; CACUUCGA; CAGCGUUA; CAUACCAA; CCAGUUCA; CCGAAGUA; ACAGUG; CGAUGU; UUAGGC; AUCACG; and UGACCA.

In some embodiments the multivalent RNA composition is produced by a method comprising:

(a) combining a linearized first DNA molecule encoding the first mRNA polynucleotide, a linearized second DNA molecule encoding the second mRNA polynucleotide, and a linearized third, fourth, fifth, sixth, seventh, eighth, ninth or tenth DNA molecule encoding the third, fourth, fifth, sixth, seventh, eighth, ninth or tenth mRNA polynucleotide into a single reaction vessel, wherein the first DNA molecule, the second DNA molecule, and the third, fourth, fifth, sixth, seventh, eighth, ninth or tenth DNA molecule are obtained from different sources; and (b) simultaneously in vitro transcribing the linearized first DNA molecule, the linearized second DNA molecule and the linearized third, fourth, fifth, sixth, seventh, eighth, ninth or tenth DNA molecule to obtain a multivalent RNA composition. The different sources may be bacterial cell cultures which may not be co-cultured. In some embodiments the amounts of the first, second and third, fourth, fifth, sixth, seventh, eighth, ninth or tenth DNA molecules present in the reaction mixture prior to the start of the IVT have been normalized.

In Vitro Transcription of RNA cDNA encoding the polynucleotides described herein may be transcribed using an in vitro transcription (IVT) system. In vitro transcription of RNA is known in the art and is described in International Publication WO 2014/152027, which is incorporated by reference herein in its entirety. In some embodiments, the RNA of the present disclosure is prepared in accordance with any one or more of the methods described in WO 2018/053209 and WO 2019/036682, each of which is incorporated by reference herein.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide, for example, but not limited to influenza virus mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5 ' to and operably linked to the gene of interest.

In some embodiments, an in vitro transcription template encodes a 5' untranslated (UTR) region, contains an open reading frame, and encodes a 3' UTR and a poly(A) tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "poly(A) tail" is a region of mRNA that is downstream, e.g., directly downstream (i.e., 3'), from the 3' UTR that contains multiple, consecutive adenosine monophosphates. A poly(A) tail may contain 10 to 300 adenosine monophosphates. For example, a poly(A) tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a poly(A) tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA.), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the mRNA of the disclosure is formulated in a lipid nanoparticle (LNP). It is to be understood that "a lipid nanoparticle," as used herein refers to a single LNP or a population of LNPs. Lipid nanoparticles typically comprise ionizable amino (cationic) lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticles. The vaccines can be made, for example, using mixing processes such as microfluidics and T-junction mixing of two fluid streams, one of which contains the mRNA and the other has the lipid components. In some embodiments, the vaccines are prepared by combining an ionizable amino lipid, a phospholipid (such as DOPE or DSPC), a PEG lipid (such as 1,2-dimyristoyl-OT-glycerol methoxypoly ethylene glycol, also known as PEG-DMG), and a structural lipid (such as cholesterol) in an alcohol (e.g., ethanol). The lipids may be combined to yield desired molar ratios and diluted with water and alcohol (e.g., ethanol) to a final lipid concentration of between about 5.5 mM and about 25 mM, for example.

Vaccines including mRNA and a lipid component may be prepared, for example, by combining a lipid solution with an mRNA solution at lipid component to mRNA wt:wt ratios of between about 5:1 and about 50:1. The lipid solution may be rapidly injected using a microfluidic based system (e.g., NanoAssemblr) at flow rates between about 10 ml/min and about 18 ml/min, for example, into the mRNA solution to produce a suspension (e.g., with a water to alcohol ratio between about 1:1 and about 4:1).

Vaccines can be processed by dialysis to remove the alcohol (e.g., ethanol) and achieve buffer exchange. Formulations may be dialyzed against phosphate buffered saline (PBS), pH 7.4, for example, at volumes greater than that of the primary product (e.g., using Slide-A-Lyzer cassettes (Thermo Fisher Scientific Inc., Rockford, Ill.)) with a molecular weight cutoff of 10 kD, for example. The forgoing exemplary method induces nanoprecipitation and particle formation. Alternative processes including, but not limited to, T-junction and direct injection, may be used to achieve the same nanoprecipitation.

Vaccines of the present disclosure are typically formulated in lipid nanoparticle. In some embodiments, the lipid nanoparticle comprises at least one ionizable amino lipid, at least one non-cationic lipid, at least one sterol, and/or at least one polyethylene glycol (PEG)-modified lipid.

In some embodiments, the lipid nanoparticle comprises 20-60 mol % ionizable amino lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable amino lipid. In some embodiments, the lipid nanoparticle comprises 20 mol %, 30 mol %, 40 mol %, 50, or 60 mol % ionizable amino lipid.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises 5 mol %, 10 mol %, 15 mol %, 20 mol %, or 25 mol % non-cationic lipid.

In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %. In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises 20-60 mol % ionizable amino lipid, 5-25 mol % non-cationic lipid, 25-55 mol % sterol, and 0.5-15 mol % PEG-modified lipid. In some embodiments, the lipid nanoparticle comprises 40-50 mol % ionizable amino lipid, 5-15 mol % neutral lipid, 20-40 mol % cholesterol, and 0.5-3 mol % PEG-modified lipid. In some embodiments, the lipid nanoparticle comprises 45-50 mol % ionizable amino lipid, 9-13 mol % neutral lipid, 35-45 mol % cholesterol, and 2-3 mol % PEG-modified lipid. In some embodiments, the lipid nanoparticle comprises 48 mol % ionizable amino lipid, 11 mol % neutral lipid, 68.5 mol % cholesterol, and 2.5 mol % PEG-modified lipid.

In some embodiments, an ionizable amino lipid of the disclosure comprises a compound of Formula (I):

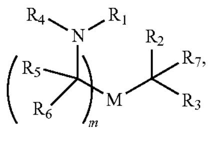

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)N(R)_2$, $—C({=}NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)N(R)_2$, $—C({=}NR_9)R$, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, C1-14 alkyl, C2-14 alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, —C(O)N $(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)R, —C(O)N(R)OR, and —C(=$NR_9$)N$(R)_2$, and each n is independently selected from 1, 2, 3, 4, and 5; and when Q is a 5- to 14-membered heterocycle and (i) $R_4$ is —$(CH_2)_n$Q in which n is 1 or 2, or (ii) $R_4$ is —$(CH_2)_n$CHQR in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of C3-6 carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a C3-6 carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)R, —C(O)N(R)OR, and —C(=$NR_9$)N$(R)_2$, and each n is independently selected from 1, 2, 3, 4, and 5;

each $R_5$ is independently selected from the group consisting of $C_{1-3}$ alkyl, C2-3 alkenyl, and H;

each $R_6$ is independently selected from the group consisting of $C_{1-3}$ alkyl, C2-3 alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, C2-3 alkenyl, and H;

$R_8$ is selected from the group consisting of C3-6 carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —N$(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

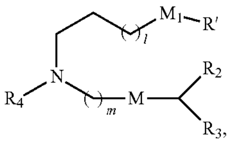

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

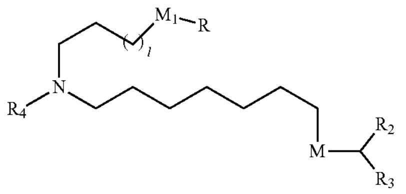

or a salt or isomer thereof, wherein l is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

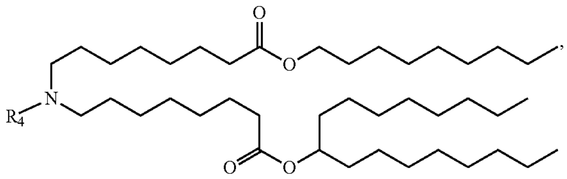

, (IIb)

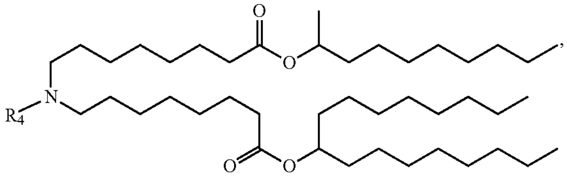

, (IIc)

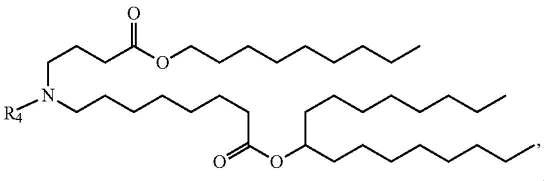

, or (IIe)

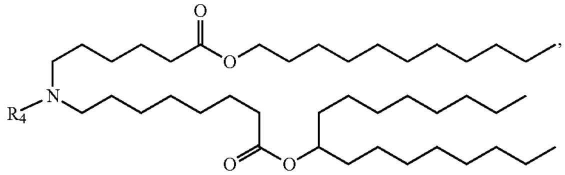

, or a salt or isomer thereof, wherein $R_4$ is as described herein.

In some embodiments, a subset of compounds of Formula (I) includes those of Formula (IId):

(IId)

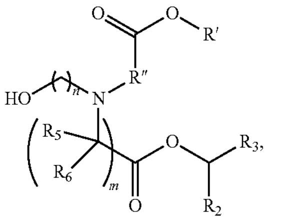

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable amino lipid of the disclosure comprises a compound having structure:

(Compound I)

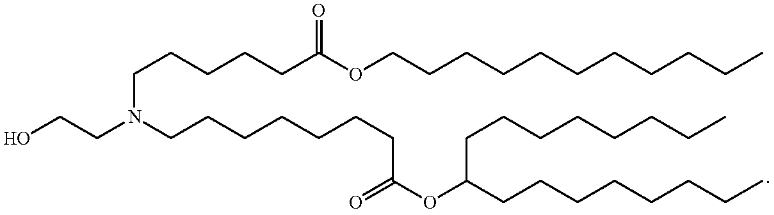

In some embodiments, an ionizable amino lipid of the disclosure comprises a compound having structure:

(Compound II)

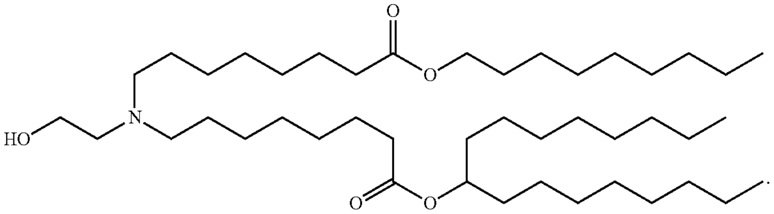

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable amino lipid of Compound 1, wherein the non-cationic lipid is DSPC, the structural lipid that is cholesterol, and the PEG lipid is DMG-PEG (e.g., PEG2000-DMG).

In some embodiments, the lipid nanoparticle comprises 45-55 mole percent (mol %) ionizable amino lipid (e.g., Compound 1). For example, lipid nanoparticle may comprise 45-47, 45-48, 45-49, 45-50, 45-52, 46-48, 46-49, 46-50, 46-52, 46-55, 47-48, 47-49, 47-50, 47-52, 47-55, 48-50, 48-52, 48-55, 49-50, 49-52, 49-55, or 50-55 mol % ionizable amino lipid (e.g., Compound 1). For example, lipid nanoparticle may comprise 45, 46, 47, 48, 49, 50, 51, 52, 53, 54, or 55 mol % ionizable amino lipid.

In some embodiments, the lipid nanoparticle comprises 5-15 mol % non-cationic (neutral) lipid (e.g., DSPC). For example, the lipid nanoparticle may comprise 5-6, 5-7, 5-8, 5-9, 5-10, 5-11, 5-12, 5-13, 5-14, 5-15, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 13-14, 13-15, or 14-15 mol % non-cationic (neutral) lipid (e.g., DSPC). For example, the lipid nanoparticle may comprise 5, 6, 7, 8, 9, 10, 11, 12, 13, 14, or 15 mol % DSPC.

In some embodiments, the lipid nanoparticle comprises 35-40 mol % sterol (e.g., cholesterol). For example, the lipid nanoparticle may comprise 35-36, 35-37, 35-38, 35-39, 35-40, 36-37, 36-38, 36-39, 36-40, 37-38, 37-39, 37-40, 38-39, 38-40, or 39-40 mol % cholesterol. For example, the lipid nanoparticle may comprise 35, 35.5, 36, 36.5, 37, 37.5, 38, 38.5, 39, 39.5, or 40 mol % cholesterol.

In some embodiments, the lipid nanoparticle comprises 1-3 mol % DMG-PEG. For example, the lipid nanoparticle may comprise 1-1.5, 1-2, 1-2.5, 1-3, 1.5-2, 1.5-2.5, 1.5-3, 2-2.5, 2-3, or 2.5-3. mol % DMG-PEG. For example, the lipid nanoparticle may comprise 1, 1.5, 2, 2.5, or 3 mol % DMG-PEG.

In some embodiments, the lipid nanoparticle comprises 50 mol % ionizable amino lipid, 10 mol % DSPC, 38.5 mol % cholesterol, and 1.5 mol % DMG-PEG. In some embodiments, the lipid nanoparticle comprises 48 mol % ionizable amino lipid, 11 mol % DSPC, 38.5 mol % cholesterol, and 2.5 mol % PEG2000-DMG.

In some embodiments, an LNP of the disclosure comprises an N:P ratio of from about 2:1 to about 30:1.

In some embodiments, an LNP of the disclosure comprises an N:P ratio of about 6:1.

In some embodiments, an LNP of the disclosure comprises an N:P ratio of about 3:1.

In some embodiments, an LNP of the disclosure comprises a wt/wt ratio of the ionizable amino lipid component to the RNA of from about 10:1 to about 100:1.

In some embodiments, an LNP of the disclosure comprises a wt/wt ratio of the ionizable amino lipid component to the RNA of about 20:1.

In some embodiments, an LNP of the disclosure comprises a wt/wt ratio of the ionizable amino lipid component to the RNA of about 10:1.

In some embodiments, an LNP of the disclosure has a mean diameter from about 50 nm to about 150 nm.

In some embodiments, an LNP of the disclosure has a mean diameter from about 70 nm to about 120 nm.

Multivalent Vaccines

The compositions, as provided herein, may include RNA or multiple RNAs encoding two or more antigens of the same or different species. In some embodiments, composition includes an RNA or multiple RNAs encoding two or more influenza virus antigens. In some embodiments, the RNA may encode 1, 2, 3, 4, 5, 6, 7, 8, 9, 10, 11, 12, or more influenza virus antigens.

In some embodiments, two or more different mRNA encoding antigens may be formulated in the same lipid nanoparticle (e.g., the four NA antigens and the four HA antigens are formulated in a single lipid nanoparticle). In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The compositions, as provided herein, may include an RNA or multiple RNAs encoding two or more antigens of the same or different viral strains. Also provided herein are combination vaccines that include RNA encoding one or more influenza virus and one or more antigen(s) of a different organism. Thus, the vaccines of the present disclosure may be combination vaccines that target one or more antigens of the same strain/species, or one or more antigens of different strains/species, e.g., antigens which induce immunity to organisms which are found in the same geographic areas where the risk of influenza virus infection is high or organisms to which an individual is likely to be exposed to when exposed to an influenza virus.

Pharmaceutical Formulations

Provided herein are compositions (e.g., pharmaceutical compositions), methods, kits and reagents for prevention or treatment of influenza virus in humans and other mammals, for example. The compositions provided herein can be used as therapeutic or prophylactic agents. They may be used in medicine to prevent and/or treat an influenza virus infection.

In some embodiments, the influenza virus vaccine containing RNA as described herein can be administered to a subject (e.g., a mammalian subject, such as a human subject), and the RNA polynucleotides are translated in vivo to produce an antigenic polypeptide (antigen).

An "effective amount" of a composition (e.g., comprising RNA) is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a composition provides an induced or boosted immune response as a function of antigen production in the cells of the subject. In some embodiments, an effective amount of the composition containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, the compositions (comprising polynucleotides and their encoded polypeptides) in accordance with the present disclosure may be used for treatment or prevention of an influenza virus infection. A composition may be administered prophylactically or therapeutically as part of an active immunization scheme to healthy individuals or early in infection during the incubation phase or during active infection after onset of symptoms. In some embodiments, the amount of RNA provided to a cell, a tissue or a subject may be an amount effective for immune prophylaxis.

A composition may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, or 6 months. In exemplary embodiments, the time of administration between the initial administration of the prophylactic composition and the booster may be, but is not limited to, 1 week, 2 weeks, 3 weeks, 1 month, 2 months, 3 months, or 6 months. the time of administration between the initial administration of the prophylactic composition and the booster is 21 days. In some embodiments, the time of administration between the initial administration of the prophylactic composition and the booster is 28 days. In some embodiments, the time of administration between the initial administration of the prophylactic composition and the booster is 36 days.

In some embodiments, a composition may be administered intramuscularly, intranasally or intradermally, similarly to the administration of inactivated vaccines known in the art.

A composition may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including RNA and/or complexes optionally in combination with one or more pharmaceutically acceptable excipients.

The RNA may be formulated or administered alone or in conjunction with one or more other components. For example, an immunizing composition may comprise other components including, but not limited to, adjuvants.

In some embodiments, an immunizing composition does not include an adjuvant (they are adjuvant free).

An RNA may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, an immunizing composition is administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, an RNA is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the RNA (e.g., for transplantation into a subject), hyaluronidase, nanoparticle mimics and combinations thereof.

Dosing/Administration

Provided herein are immunizing compositions (e.g., RNA vaccines), methods, kits and reagents for prevention and/or treatment of influenza virus infection in humans and other mammals. Immunizing compositions can be used as therapeutic or prophylactic agents. In some embodiments, immunizing compositions are used to provide prophylactic protection from influenza virus infection. In some embodiments, immunizing compositions are used to treat an influenza virus infection. In some embodiments, embodiments, immunizing compositions are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, an immunizing composition (e.g., RNA a vaccine) is administered to a subject (e.g., a mammalian subject, such as a human subject) in an effective amount to induce an antigen-specific immune response. The RNA encoding the influenza virus antigen is expressed and translated in vivo to produce the antigen, which then stimulates an immune response in the subject.

Prophylactic protection from an influenza virus can be achieved following administration of an immunizing composition (e.g., an RNA vaccine) of the present disclosure. Immunizing compositions can be administered once, twice, three times, four times or more but it is likely sufficient to administer the vaccine once (optionally followed by a single booster). It is possible, although less desirable, to administer an immunizing compositions to an infected individual to achieve a therapeutic response. Dosing may need to be adjusted accordingly.

A method of eliciting an immune response in a subject against an influenza virus antigen (or multiple antigens) is provided in aspects of the present disclosure. In some embodiments, a method involves administering to the subject an immunizing composition comprising a mRNA having an open reading frame encoding an influenza virus antigen, thereby inducing in the subject an immune response specific to the influenza virus antigen, wherein anti-antigen antibody titer in the subject is increased following vaccination relative to anti-antigen antibody titer in a subject vaccinated with a prophylactically effective dose of a traditional vaccine against the antigen. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the influenza virus or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the influenza virus or an unvaccinated subject.

A method of eliciting an immune response in a subject against an influenza virus is provided in other aspects of the disclosure. The method involves administering to the subject an immunizing composition (e.g., an RNA vaccine) comprising a RNA polynucleotide comprising an open reading frame encoding an influenza virus antigen, thereby inducing in the subject an immune response specific to the influenza virus, wherein the immune response in the subject is equivalent to an immune response in a subject vaccinated with a traditional vaccine against the influenza virus at 2 times to 100 times the dosage level relative to the immunizing composition.

In some embodiments, the immune response in the subject is equivalent to an immune response in a subject vaccinated with a traditional vaccine at twice the dosage level relative to an immunizing composition of the present disclosure. In some embodiments, the immune response in the subject is equivalent to an immune response in a subject vaccinated with a traditional vaccine at three times the dosage level relative to an immunizing composition of the present disclosure. In some embodiments, the immune response in the subject is equivalent to an immune response in a subject vaccinated with a traditional vaccine at 4 times, 5 times, 10 times, 50 times, or 100 times the dosage level relative to an immunizing composition of the present disclosure. In some embodiments, the immune response in the subject is equivalent to an immune response in a subject vaccinated with a traditional vaccine at 10 times to 1000 times the dosage level relative to an immunizing composition of the present disclosure. In some embodiments, the immune response in the subject is equivalent to an immune response in a subject vaccinated with a traditional vaccine at 100 times to 1000 times the dosage level relative to an immunizing composition of the present disclosure.

In other embodiments, the immune response is assessed by determining [protein] antibody titer in the subject. In other embodiments, the ability to promote a robust T cell response(s) is measured using art recognized techniques.

Other aspects the disclosure provide methods of eliciting an immune response in a subject against an influenza virus by administering to the subject an immunizing composition (e.g., an RNA vaccine) comprising an RNA having an open reading frame encoding an influenza virus antigen, thereby inducing in the subject an immune response specific to the influenza virus antigen, wherein the immune response in the subject is induced 2 days to 10 weeks earlier relative to an immune response induced in a subject vaccinated with a prophylactically effective dose of a traditional vaccine against the influenza virus. In some embodiments, the immune response in the subject is induced in a subject vaccinated with a prophylactically effective dose of a traditional vaccine at 2 times to 100 times the dosage level relative to an immunizing composition of the present disclosure.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against an influenza virus by administering to the subject an RNA having an open reading frame encoding a first antigen, wherein the RNA does not include a stabilization element, and wherein an adjuvant is not co-formulated or co-administered with the vaccine.

An immunizing composition (e.g., an RNA vaccine) may be administered by any route that results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The RNA is typically formulated in dosage unit form for ease of administration and uniformity of dosage. It will be understood, however, that the total daily usage of the RNA may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of the RNA, as provided herein, may be as low as 50 μg (total mRNA), administered for example as a single dose or as two 25 μg doses. A "dose" as used herein, represents the sum total of RNA in the composition (e.g., including all of the NA antigens and/or HA antigens in the formulation). In some embodiments, the effective amount is a total dose of 50 μg-300 μg, 100 μg-300 μg, 150 μg-300 μg, 200 μg-300 μg, 250 μg-300 μg, 150 μg-200 μg, 150 μg-250 μg, 150 μg-300 μg, 200 μg-250 μg, or 250 μg-300 μg. For example, the effective amount may be a total dose of 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, or 300 μg. In some embodiments, the effective amount is a total dose of 66 μg. In some embodiments, the effective amount is a total dose of 67 μg. In some embodiments, the effective amount is a total dose of 68 μg. In some embodiments, the effective amount is a total dose of 132 μg. In some embodiments, the effective amount is a total dose of 133 μg. In some embodiments, the effective amount is a total dose of 134 μg. In some embodiments, the effective amount is a total dose of 266 μg. In some embodiments, the effective amount is a total dose of 267 μg. In some embodiments, the effective amount is a total dose of 268 μg. In some embodiments, the effective amount is a total dose of 100 μg. In some embodiments, the effective amount is a total dose of 200 μg. In some embodiments, the effective amount is a total dose of 300 μg.

The RNA described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the immunizing compositions (e.g., RNA vaccines), wherein the RNA is formulated in an effective amount to produce an antigen specific immune response in a subject (e.g., production of antibodies specific to an influenza virus antigen). "An effective amount" is a dose of the RNA effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) influenza virus protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-influenza virus antigen antibody titer produced in a subject administered an immunizing composition as provided herein. An antibody titer is a measurement of the amount of antibodies within a subject, for example, antibodies that are specific to a particular antigen or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by an immunizing composition (e.g., RNA vaccine).

In some embodiments, an anti-influenza virus antigen antibody titer produced in a subject is increased by at least 1 log relative to a control. For example, anti-influenza virus antigen antibody titer produced in a subject may be increased by at least 1.5, at least 2, at least 2.5, or at least 3 log relative to a control. In some embodiments, the anti-influenza virus antigen antibody titer produced in the subject is increased by 1, 1.5, 2, 2.5 or 3 log relative to a control. In some embodiments, the anti-influenza virus antigen antibody titer produced in the subject is increased by 1-3 log relative to a control. For example, the anti-influenza virus antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-influenza virus antigen antibody titer produced in a subject is increased at least 2 times relative to a control. For example, the anti-influenza virus antigen n antibody titer produced in a subject may be increased at least 3 times, at least 4 times, at least 5 times, at least 6 times, at least 7 times, at least 8 times, at least 9 times, or at least 10 times relative to a control. In some embodiments, the anti-influenza virus antigen antibody titer produced in the subject is increased 2, 3, 4, 5, 6, 7, 8, 9, or 10 times relative to a control. In some embodiments, the anti-influenza virus antigen antibody titer produced in a subject is increased 2-10 times relative to a control. For example, the anti-influenza virus antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to influenza virus. A geometric mean titer (GMT) is the average antibody titer for a group of subjects calculated by multiplying all values and taking the nth root of the number, where n is the number of subjects with available data.

A control, in some embodiments, is an anti-influenza virus antigen antibody titer produced in a subject who has not been administered an immunizing composition (e.g., RNA vaccine). In some embodiments, a control is an anti-influenza virus antigen antibody titer produced in a subject administered a recombinant or purified protein vaccine. Recombinant protein vaccines typically include protein antigens that either have been produced in a heterologous expression system (e.g., bacteria or yeast) or purified from large amounts of the pathogenic organism.

In some embodiments, the ability of an immunizing composition (e.g., RNA vaccine) to be effective is measured in a murine model. For example, an immunizing composition may be administered to a murine model and the murine model assayed for induction of neutralizing antibody titers. Viral challenge studies may also be used to assess the efficacy of a vaccine of the present disclosure. For example, an immunizing composition may be administered to a murine model, the murine model challenged with virus, and the murine model assayed for survival and/or immune response (e.g., neutralizing antibody response, T cell response (e.g., cytokine response)).

A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified protein vaccine, or a live attenuated or inactivated vaccine, or a VLP vaccine, that a physician/clinician or other medical professional would administer to a subject to treat or prevent influenza virus infection or a related condition, while following the standard of care guideline for treating or preventing influenza virus infection or a related condition.

In some embodiments, the anti-influenza virus antigen antibody titer produced in a subject administered an effective amount of an immunizing composition is equivalent to an anti-influenza virus antigen antibody titer produced in a control subject administered a standard of care dose of a recombinant or purified protein vaccine, or a live attenuated or inactivated vaccine, or a VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100; \text{ and}$$

$$\text{Efficacy}=(1-\text{RR})\times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, efficacy of the immunizing composition (e.g., RNA vaccine) is at least 60% relative to unvaccinated control subjects. For example, efficacy of the immunizing composition may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of an immunizing composition of the present disclosure is sufficient to provide sterilizing immunity in the subject for at least 1 year. For example, the effective amount of an immunizing composition of the present disclosure is sufficient to provide sterilizing immunity in the subject for at least 2 years, at least 3 years, at least 4 years, or at least 5 years. In some embodiments, the effective amount of an immunizing composition of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of an immunizing composition of the present disclosure is sufficient to produce detectable levels of influenza virus antigen as measured in serum of the subject at 1-72 hours post administration.

Titer. An antibody titer is a measurement of the amount of antibodies within a subject, for example, antibodies that are specific to a particular antigen (e.g., an anti-influenza virus antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of an immunizing composition of the present disclosure is sufficient to produce a 1,000-10,000 neutralizing antibody titer produced by neutralizing antibody against the influenza virus antigen as measured in serum of the subject at 1-72 hours post administration. In some embodiments, the effective amount is sufficient to produce a 1,000-5,000 neutralizing antibody titer produced by neutralizing antibody against the influenza virus antigen as measured in serum of the subject at 1-72 hours post administration. In some embodiments, the effective amount is sufficient to produce a 5,000-10,000 neutralizing antibody titer produced by neutralizing antibody against the influenza virus antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-influenza virus antigen antibody titer produced in the subject is increased by at least 1 log relative to a control. For example, an anti-influenza virus antigen antibody titer produced in the subject may be increased by at least 2, 3, 4, 5, 6, 7, 8, 9 or 10 log relative to a control.

In some embodiments, an anti-influenza virus antigen antibody titer produced in the subject is increased at least 2 times relative to a control. For example, an anti-influenza virus antigen antibody titer produced in the subject is increased by at least 3, 4, 5, 6, 7, 8, 9 or 10 times relative to a control.

A control may be, for example, an unvaccinated subject, or a subject administered a live attenuated viral vaccine, an inactivated viral vaccine, or a protein subunit vaccine.

EXAMPLES

Example 1. Multiantigen Dose Response and Immune Interference Analysis Using Northern Hemisphere Influenza Strains In this example, multiple influenza virus HA and NA antigens administered as mRNA vaccines were evaluated for immunogenicity, dose response, and immunological interference between the antigens. Further, the data was examined for any dampening of immune response towards one antigen over another different antigen when all antigens were co-administered simultaneously as mRNA vaccines formulated in lipid nanoparticles (LNPs). For this study, the antigens were formulated separately into different LNPs and mixed before administration. In all cases, the NA protein was rendered enzymatically inactive by catalytic site residue mutation prior to inclusion in the vaccine. The experiment was carried out as shown below in Tables 1 and 2 in both a high dose version and a low dose version using the similar experimental design shown below.

TABLE 1

Study Design—High Dose

| Group | No. Animals | Antigen (encoded by mRNA) | Dose (μgram) mRNA/animal |
|---|---|---|---|
| GR1 | 5 | PBS control | — |
| GR2 | 10 | A/Hawaii/70/2019 H1N1 WT HA | 2 |
| GR3 | 10 | A/Hawaii/70/2019 H1N1 WT HA | 0.4 |
| GR4 | 10 | A/Hong Kong/45/2019 H3N2 WT HA | 2 |
| GR5 | 10 | B/Washington/02/2019 (B/Vic) WT HA | 2 |
| GR6 | 10 | B/Phuket/3073/2013 (B/Yam) WT HA | 2 |
| GR7 | 10 | A/Hawaii/70/2019 H1N1 mut NA | 2 |
| GR8 | 10 | A/Hong Kong/45/2019 H3N2 mut NA | 2 |
| GR9 | 10 | B/Washington/02/2019 (B/Vic) mut NA | 2 |
| GR10 | 10 | B/Phuket/3073/2013 (B/Yam) mut NA | 2 |
| GR11 | 10 | 1:1 ratio 4 × HAs (H1N1, H3N2, B/Vic, B/Yam | 4 |
| GR12 | 10 | 1:1 ratio 4 × HAs & 4 × NAs (H1N1, H3N2, B/Vic, B/Yam) | 16 |

TABLE 2

Study Design—Low Dose

| Group | No. Animals | Antigen (encoded by mRNA) | Dose (μgram) mRNA/animal |
|---|---|---|---|
| GR1 | 5 | PBS control | — |
| GR2 | 10 | A/Hawaii/70/2019 H1N1 WT HA | 2 |
| GR3 | 10 | A/Hawaii/70/2019 H1N1 WT HA | 0.4 |
| GR4 | 10 | A/Hong Kong/45/2019 H3N2 WT HA | 0.4 |
| GR5 | 10 | B/Washington/02/2019 (B/Vic) WT HA | 0.4 |
| GR6 | 10 | B/Phuket/3073/2013 (B/Yam) WT HA | 0.4 |
| GR7 | 10 | A/Hawaii/70/2019 H1N1 mut NA | 0.4 |
| GR8 | 10 | A/Hong Kong/45/2019 H3N2 mut NA | 0.4 |
| GR9 | 10 | B/Washington/02/2019 (B/Vic) mut NA | 0.4 |
| GR10 | 10 | B/Phuket/3073/2013 (B/Yam) mut NA | 0.4 |
| GR11 | 10 | 1:1 ratio 4 × HAs (H1N1, H3N2, B/Vic, B/Yam | 1.6 |
| GR12 | 10 | 1:1 ratio 4 × HAs & 4 × NAs (H1N1, H3N2, B/Vic, B/Yam) | 3.2 |

In some embodiments, a geometric mean, which is the nth root of the product of n numbers, is generally used to describe proportional growth. Geometric mean, in some embodiments, is used to characterize antibody titer produced in a subject.

As shown in the study design above, this study evaluated the dose response and any immune interference between antigens. There were 8 different flu glycoprotein antigens tested individually (4 HA antigens, 4 NA antigens). Also tested were four HAs combined in ratios (e.g., mass ratios) of 1:1:1:1 to evaluate interference between HAs. Finally, there were 4 HAs combined with 4 NAs in an 8-antigen mixture (i.e., 1:1:1:1:1:1:1:1) to evaluate any interference between HAs in the presence of NAs. The doses administered were as specified in the Tables above and in FIGS. 1 and 2. The immunization regimen was a prime on day 1 and boost on day 21 with the same amount of specified vaccine. Antibody responses were evaluated by ELISA (IgG antibody binding titers represented in FIGS. 1 and 2) on day 21 (3 weeks post dose 1) and day 36 (2 weeks post dose 2).

Antibody Responses to mRNA Vaccines

ELISA assays to determine IgG antibody titers to each different influenza glycoprotein antigen were run using individual mouse serum samples on day 21 (3 weeks post-prime) and day 36 (2 weeks post-boost). The ELISA plates were coated with individual recombinant HA or NA protein antigens at various concentrations specified in the tables under each antibody titer plot as 5 μg/ml, 2 μg/ml, or 1 μg/ml. See FIG. 1 and FIG. 2. The amount of each mRNA used to immunize mice (2 μg versus 0.4 μg) and the number of antigens used to immunize each animal in a particular group is shown below the antibody titers (single construct versus 4 HAs versus 4HAs+4NAs). Antibody titers were determined using a four-parameter logistic curve fit in GraphPad Prism (GraphPad Software, Inc.) and defined as the reciprocal dilution at approximately $OD_{450nm}$=1.5 (normalized to a mouse standard on each plate). See FIG. 1 and FIG. 2.

Figure 2:
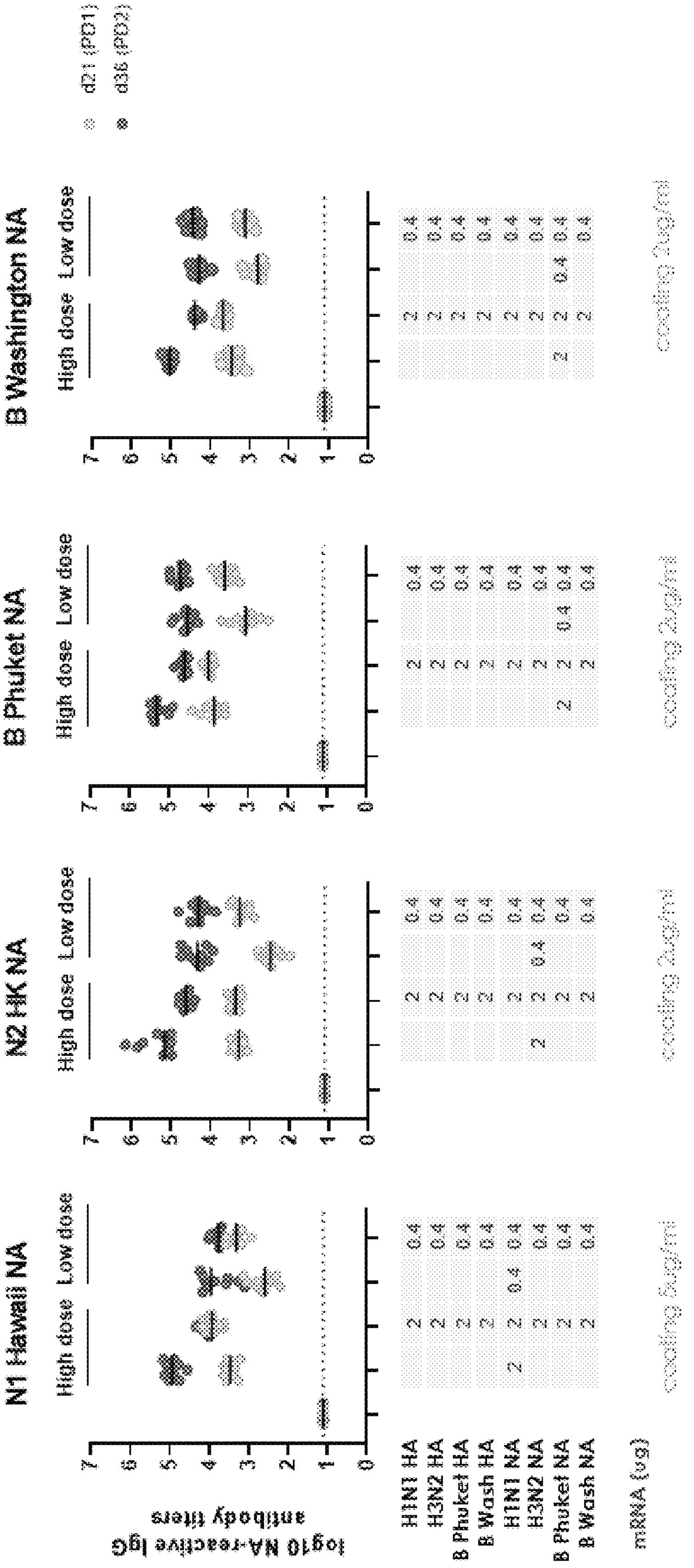
FIG. 2 is a series of graphs showing the NA-reactive IgG antibody titers to each of the four antigens after one (PD1; day 21) or two (PD2; day 36) doses of influenza HA and NA formulations or controls. The doses administered are provided in the tables below each graph.

The antibody responses against each of the different HA antigens were substantial whether the mice were immunized with one single mRNA encoded HA antigen, a combination of 4 different mRNA encoded HA antigens, or a combination of 4 different mRNA encoded HA antigens and 4 different mRNA encoded NA antigens. FIG. 1 shows that similarly high responses were obtained after the first dose to all 4 different HA antigens, demonstrating that there is no indication of deleterious immunological interference between different antigens when an animal was immunized with vaccine candidates containing multiple different mRNAs expressing different HAs present at the same time after dose 1. Furthermore, the addition of 4 different mRNA encoded NA antigens at the same time did not inhibit the response to the HAs present in the vaccine after dose 1. See FIG. 1. A clear dose response was obtained in every case, usually increasing the antibody response by one to two login in antibody titer. The only indication of slight antigen interference effects when antigens were co-administered occurred in the high dose groups, but the responses were robust so any potential interference was not considered problematic for vaccine development.

Antibody responses to the individual NA antigens were also very good and not apparently subject to detrimental immunological interference between antigens present in the same vaccine administered to a single animal or group of mice. See FIG. 2. The antibody responses to NA were robust and a dose response was observed in every case.

Example 2. Evaluation of the Immunogenicity of Ratios of HA/NA Antigens in mRNA Vaccines for Influenza Viruses Circulating in Northern and Southern Hemisphere In this example, the immunogenicity of various mass ratios of HA to NA antigens administered using mRNA in LNPs, was measured as antibody titers in Balb/c mice immunized with the vaccines shown in Table 3 below. The immunogenicity of multiple influenza virus HA and NA antigens as mRNA vaccines were evaluated for antibody titers and dose responses, between the 1:1, 2:1, 3:1, 4:1 and 1:2 ratios of HA/NA antigens administered in the mRNA vaccines. In particular, the data was examined for any favorable distribution of immune responses to one antigen over another when all antigens were co-administered simultaneously as mRNA vaccines formulated in lipid nanoparticles (LNPs). For this experiment, the antigens were formulated separately into different LNPs and mixed before administration. In all cases, the NA protein was rendered enzymatically inactive by catalytic site residue mutation prior to inclusion in the vaccine, except for the final group in each graph (Group 10), where wild type NA was used (denoted "WY" in the table below each graph). The experiment was carried out as shown below in the experimental design described in Table 3.

TABLE 3

| Antigen Ratios | | | |
|---|---|---|---|
| Group | No. Animals | Antigen (encoded by mRNA) | Dose (μgram) mRNA/animal |
| GR1 | 5 | PBS control | — |
| GR2 | 10 | 1:1:1:1 ratio 4 × HAs Northern Hemisphere (1.2 μg each) | 4.8 |
| GR3 | 10 | 1:1:1:1 ratio 4 × HAs Southern Hemisphere (1.2 μg each) | 4.8 |
| GR4 | 10 | 1:1 ratio 4 × HA and 4x mut NAs NH* | 9.6 |
| GR5 | 10 | 1:1 ratio 4 × HA and 4x mut NAs SH* | 9.6 |
| GR6 | 10 | 2:1 ratio 4 × HA and 4x mut NAs SH* | 7.2 |
| GR7 | 10 | 3:1 ratio 4 × HA and 4x mut NAs SH* | 6.4 |
| GR8 | 10 | 4:1 ratio 4 × HA and 4x mut NAs SH* | 6.0 |
| GR9 | 10 | 1:2 ratio 4 × HA and 4x mut NAs SH* | 14.4 |
| GR10 | 10 | 1:1 ratio 4 × HAs and 4 × WT NAs SH* | 9.6 |

*NH—Northern Hemisphere, SH—Southern Hemisphere, mut—enzymatically inactive NA (catalytic site mutation)

Antibody Responses to mRNA Vaccines

ELISA assays to determine IgG antibody titers to each different influenza glycoprotein antigen were run using individual mouse serum samples on day 21 (3 weeks post-prime) and day 36 (2 weeks post-boost). The ELISA plates were coated with individual recombinant HA or NA protein antigens at various concentrations specified in the tables under each antibody titer plot as either 5 μg/ml, 2 μg/ml, or 1 μg/ml. See FIG. 3. The amount of each mRNA used to immunize mice (2 μg versus 0.4 μg) and the number of different antigens included in the vaccine used to immunize each animal in a particular group is shown below the antibody titers (4 HAs versus 4HAs+4NAs at various ratios). Antibody titers were determined using a four-parameter logistic curve fit in GraphPad Prism (GraphPad Software, Inc.) and defined as the reciprocal dilution at approximately $OD_{450nm}$=1.5 (normalized to a mouse standard on each plate).

Figure 3:
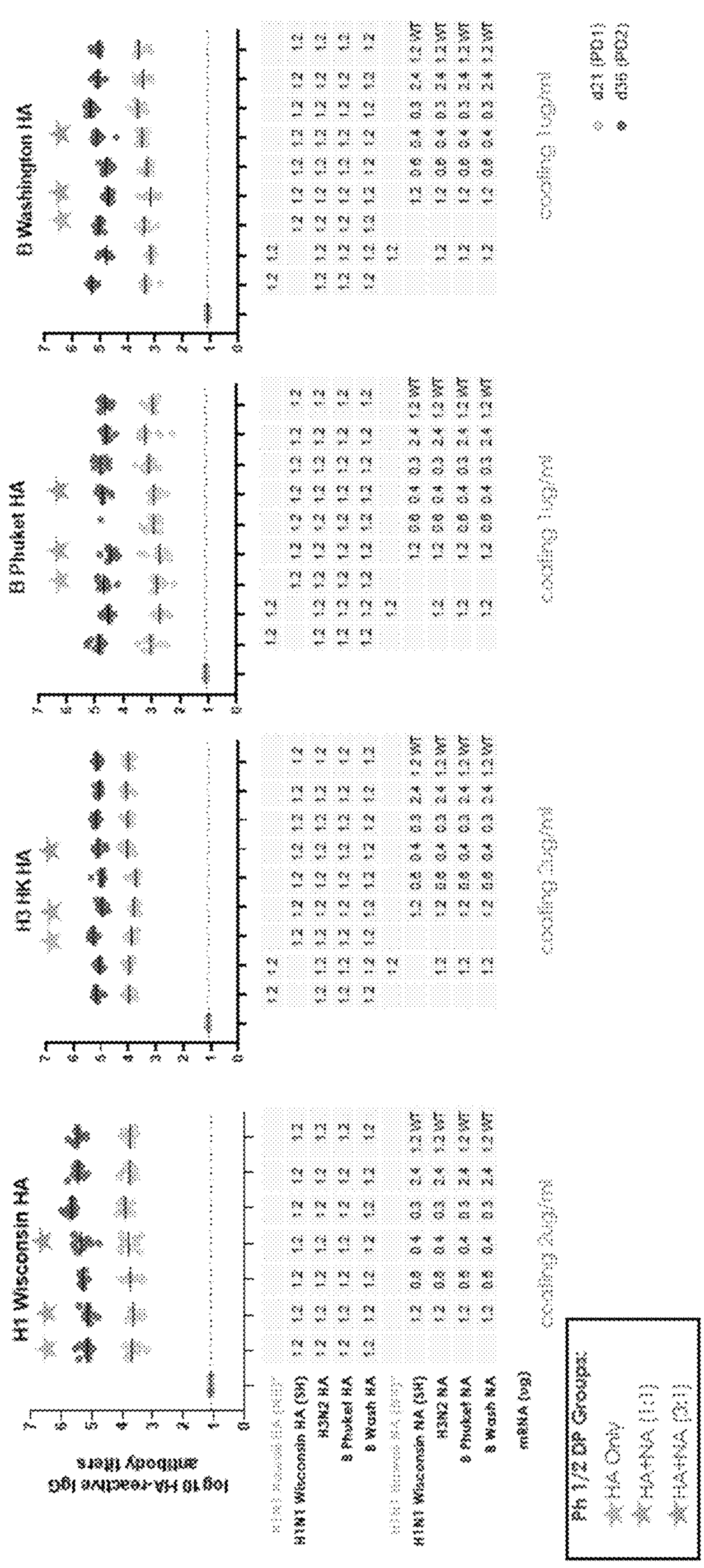
FIG. 3 is a series of graphs showing the HA-reactive IgG antibody titers to each of four antigens after one (PD1; day 21) or two (PD2; day 36) doses of influenza HA and NA formulations or controls. The doses administered are provided in the tables below each graph. The asterisk (*) indicates a dose where the data is not available.

The HA antibody titer results shown in FIG. 3 demonstrate a slight dose effect with increasing HA titers as the ratio of HA:NA increased 1:1 to 3:1. See the stars above the antibody responses to HAs in FIG. 3 for the mice immunized with HA only, 1:1 ratio of HA:NA, 3:1 ratio of HA:NA. The group receiving enhanced levels of NA in the vaccine with HA:NA in the ratio of 1:2 did not show the same effect on HA antibody titers; however, the antibody responses to HA glycoprotein antigens at all combinations or ratios of mRNAs tested were very robust.

Figure 4:
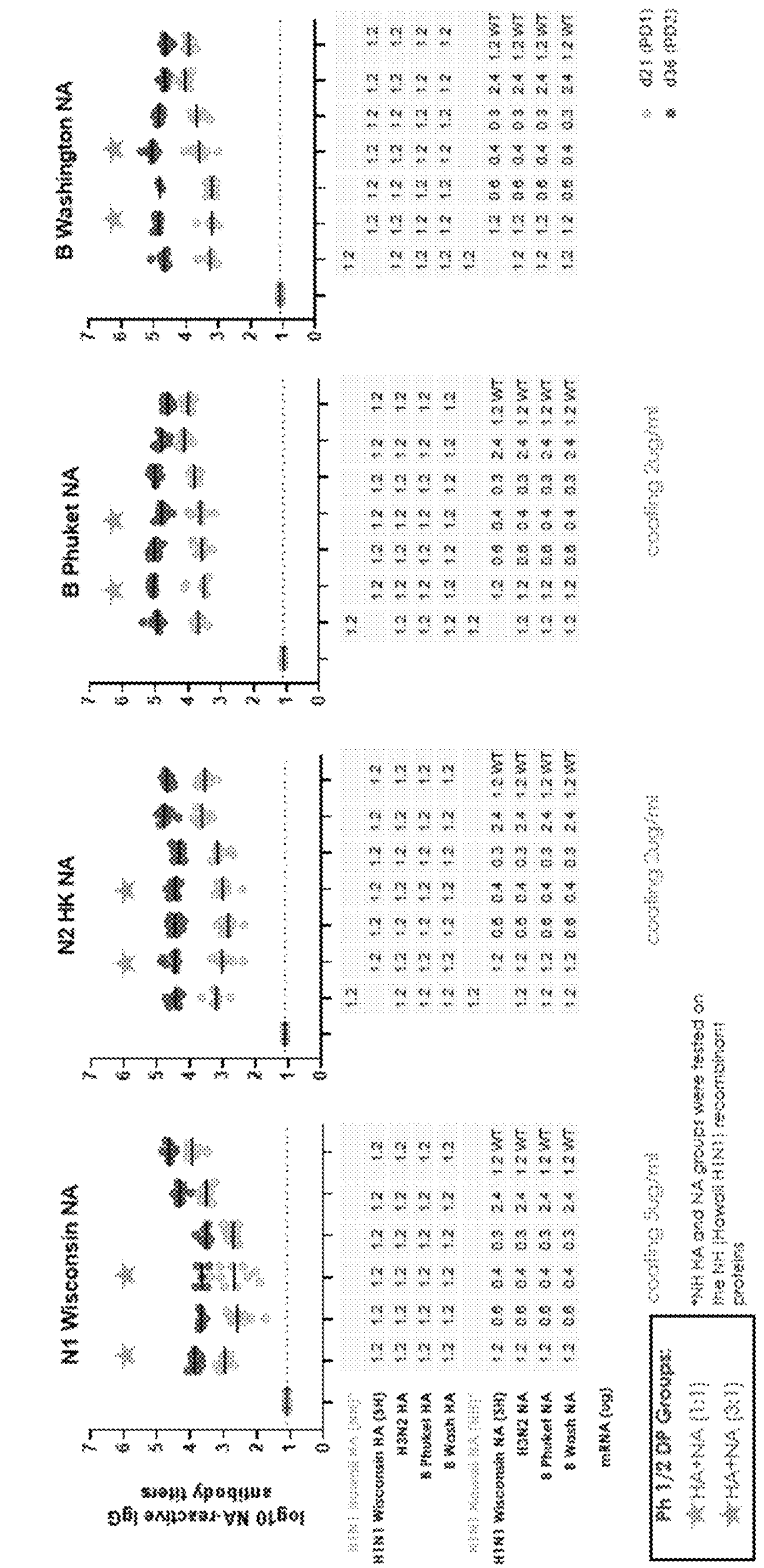
FIG. 4 is a series of graphs showing the hemagglutinin (HA)-reactive IgG antibody titers after one (PD1; day 21) or two (PD2; day 36) doses of influenza HA and neuraminidase (NA) formulations to each of the four antigens. The doses administered are provided in the tables below each graph. The asterisk (*) indicates a dose where the data is not available.

FIG. 4 shows the NA antibody titers and dose responses observed between the 1:1, 2:1, 3:1, 4:1 and 1:2 ratios of HA:NA antigens administered in the mRNA vaccines. In this example, antibody responses to NA were generally lower than HA responses and somewhat insensitive to the relative proportion of NA to HA. The antibody titer to NA was very good across all the groups tested including groups in which the amount of NA was less than that of HA in the vaccine. Compare NA titers where the immunizing vaccine contained HA:NA ratios 1:1 to 3:1. See FIG. 4.

Example 3. Evaluation of the Immunogenicity and Dose Response of HA/NA Antigens in mRNA Vaccines for Influenza Viruses Circulating in Northern and Southern Hemisphere In this example, the immunogenicity of various doses of mRNA vaccines encoding HA antigens and optionally, NA antigens, in LNPs was measured. The vaccines comprised mRNA encoding four HA antigens at a 1:1:1:1 ratio (SEQ ID NOs: 7, 16, 25, and 34) or four HA antigens and four NA antigens at a 1:1:1:1:1:1:1:1 ratio (SEQ ID NOs: 7, 16, 25, 34, 10, 19, 28, and 37, respectively), or four HA antigens and four NA antigens at a 3:3:3:3:1:1:1:1 ratio (SEQ ID NOs: 7, 16, 25, 34, 10, 19, 28, and 37, respectively). Balb/c mice were immunized with PBS (control, n=4), or 16 μg, 8 μg, 4 μg, 2 μg, 1 μg, 0.5 μg, 0.25 μg, 0.125 μg, 0.0625 μg, or 0.0313 μg of mRNA vaccine (n=8/group) on day 1 and day 22. Serum samples were collected on day 21 and day 36 and ELISAs were undertaken to measure the immunogenicity of multiple influenza virus HA and NA antigens as mRNA vaccines were evaluated for antibody titers and dose responses.

Briefly, 96-well microtiter plates (Thermo, #439454) were coated with 1 μg/mL, 2 μg/mL or 5 μg/mL recombinant protein (based on the antigen, HA or NA, and the strain). After overnight incubation at 4° C., the plates were washed 4 times with PBS/0.05% Tween-20 and blocked for 2 hours at 37° C. (SuperBlock—Pierce #37515). After washing, 5-fold serial dilutions of mouse sera were added (assay diluent—PBS+0.05% Tween-20+5% goat serum). Plates were incubated for 2 hours at 37° C., washed, and HRP-conjugated goat anti-mouse IgG (Southern Biotech, #1030-05) was added at a 1:10,000 dilution in assay diluent. Plates were incubated for 1 hour at 37° C., washed and bound antibody was detected with TMB substrate (SeraCare #5120-0077). After incubation for 10 minutes at room temperature, the reaction was stopped by adding TMB stop solution (SeraCare #5150-0021) and the absorbance was measured at $OD_{450nm}$. Titers were determined using a four-parameter logistic curve fit in GraphPad Prism (GraphPad Software, Inc.) and defined as the reciprocal dilution at approximately $OD_{450nm}$=1.5 (normalized to a mouse standard on each plate).

Figure 5:
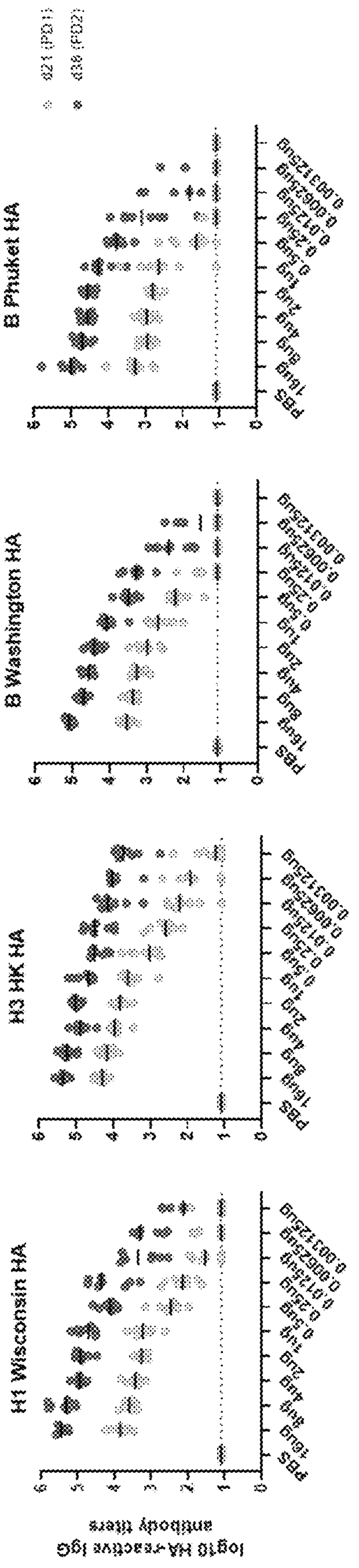
FIG. 5 is a series of graphs showing the hemagglutinin (HA)-reactive IgG antibody titers after one (PD1; day 21) or two (PD2; day 36) doses of influenza HA ("HA only").
Figure 6A:
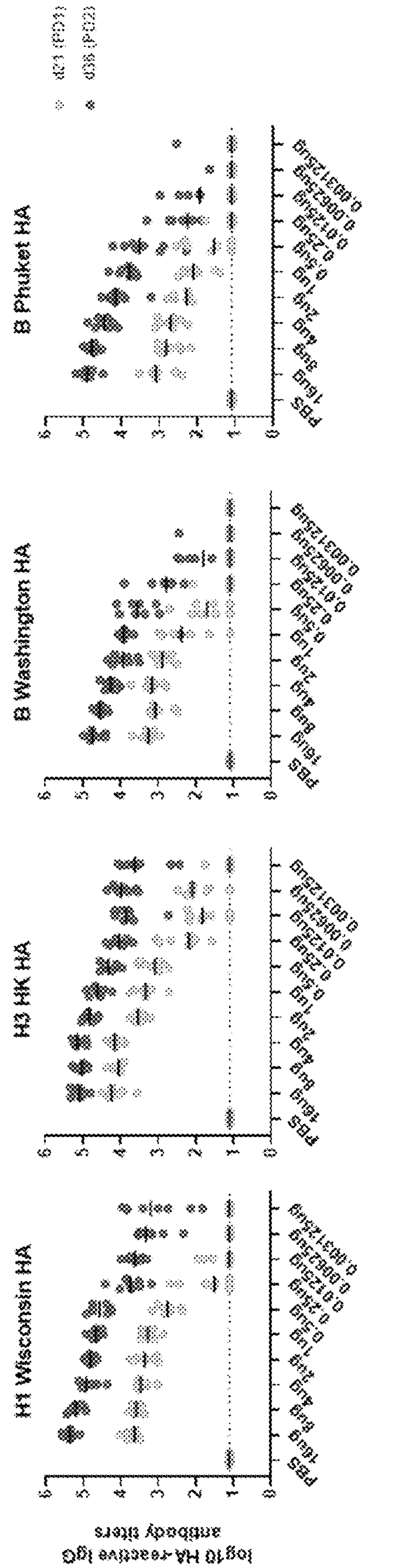
FIGS. 6A-6D are a series of graphs showing the hemagglutinin (HA)-reactive IgG antibody titers and the neuraminidase (NA)-reactive IgG antibody titers after one (PD1; day 21) or two (PD2; day 36) doses of influenza hemagglutinin (HA)/neuraminidase (NA) ("HA/NA") formulations to each of the eight HA and NA antigens. A 1:1:1:1:1:1:1:1 (H1 Wisconsin HA:H3 HK HA:B Washington HA:B Phuket HA:N1 Wisconsin NA:N2 HK NA:B Washington NA:B Phuket NA) ratio was tested in FIGS. 6A-6B, and a 3:3:3:3:1:1:1:1 (H1 Wisconsin HA:H3 HK HA:B Washington HA:B Phuket HA:N1 Wisconsin NA:N2 HK NA:B Washington NA:B Phuket NA) ratio was tested in FIGS. 6C-6D.
Figure 6B:
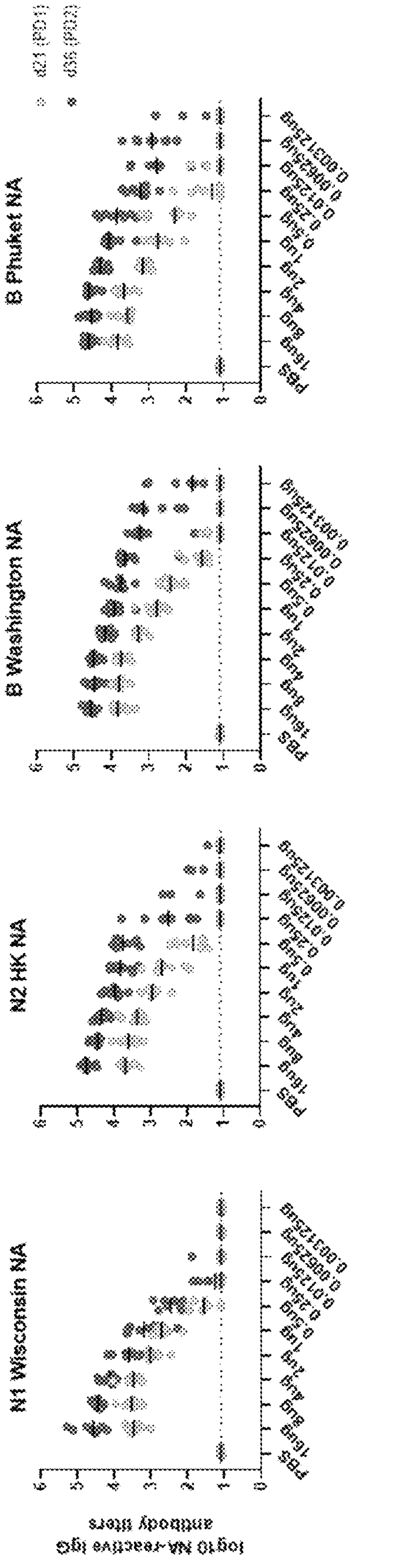
Figure 6C:
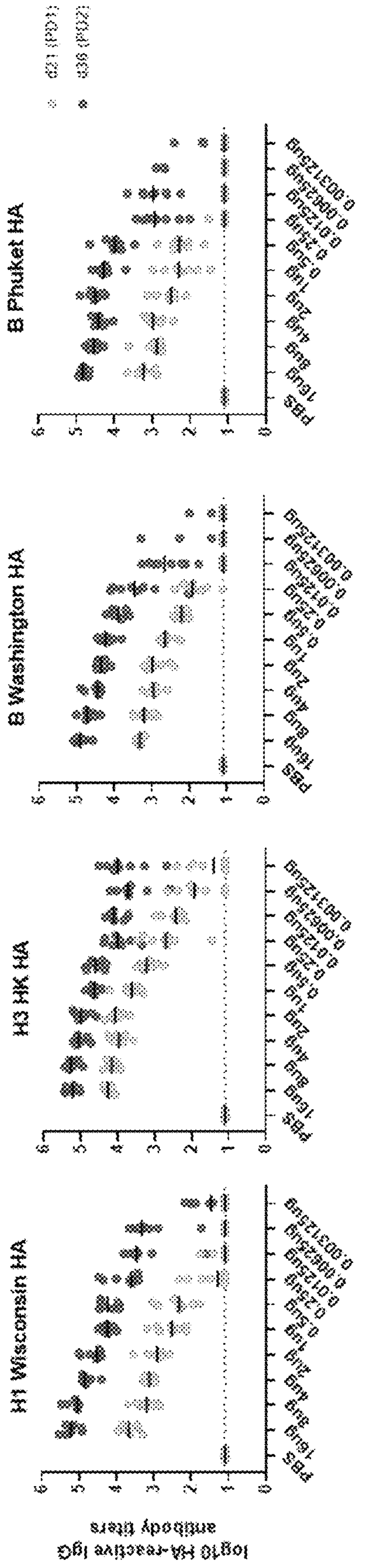
Figure 6D:
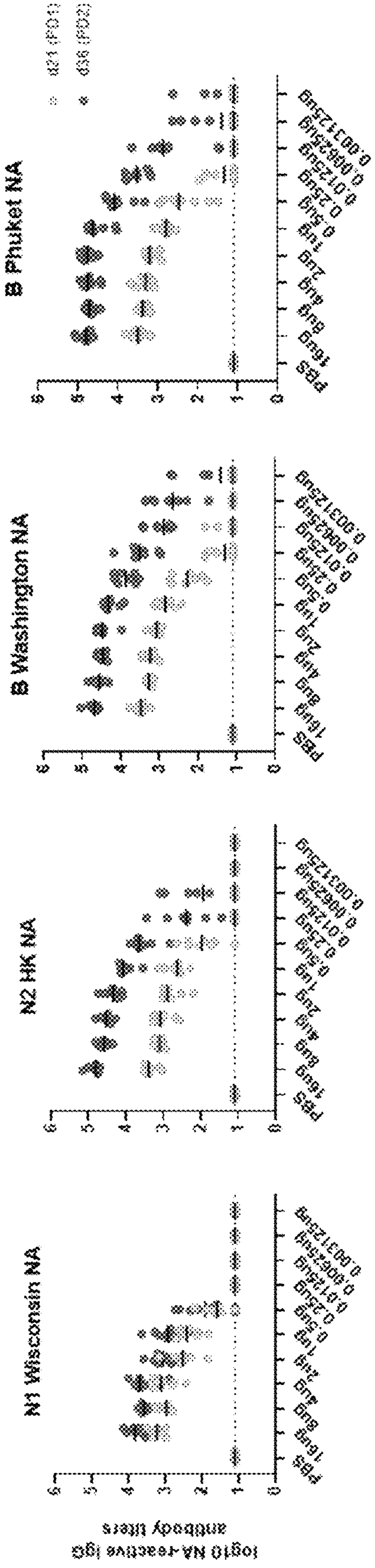

As shown in FIG. 5, a dose response was observed for the vaccine comprising mRNA encoding four HA antigens at a 1:1:1:1 ratio against each of the HA antigens. FIGS. 6A and 6B show a dose response for the vaccine comprising four HA antigens and four NA antigens at a 1:1:1:1:1:1:1:1 ratio, against the HA antigens (FIG. 6A) and the NA antigens (FIG. 6B). FIGS. 6C and 6D show a dose response for the vaccine comprising four HA antigens and four NA antigens at a 3:3:3:3:1:1:1:1 ratio, against the HA antigens (FIG. 6C) and the NA antigens (FIG. 6D).

Figure 7:
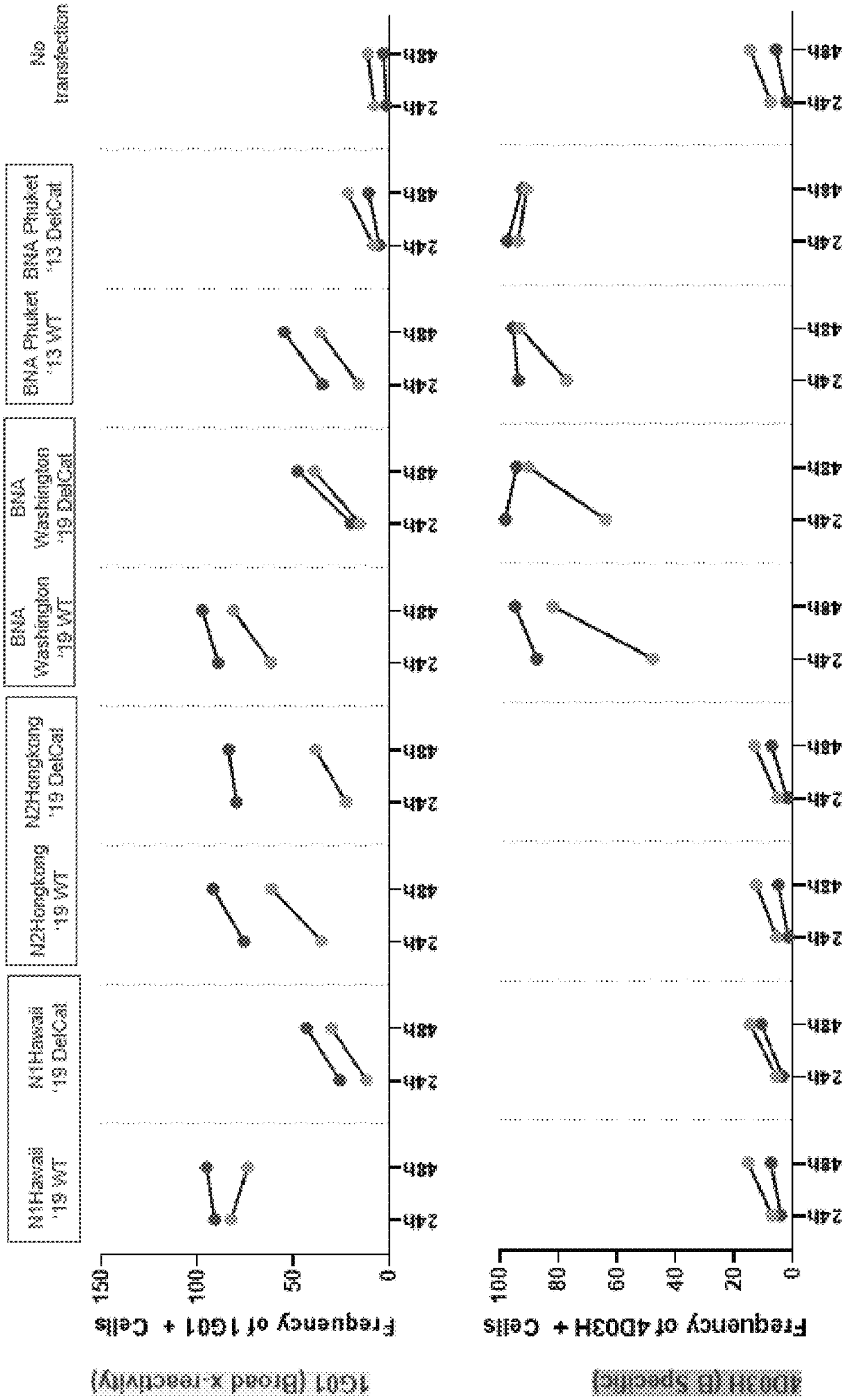
FIG. 7 includes two graphs showing the frequency of NA-expressing cells at 24 and 48 hours post-transfection. HEK293T cells were transfected with a high (100 ng, shown in black) or low (25 ng, shown in gray) dose of mRNA encoding a wild-type (WT) NA or NA-D151G(DelGat) and expression was measured by flow cytometry. The top graph shows the frequency of NA-expressing cells using the antibody 1G01 (a broadly NA-reactive antibody) and the bottom graph shows the frequency of NA-expressing cells using antibody 4D03 (a B NA-reactive antibody).
Figure 8A:
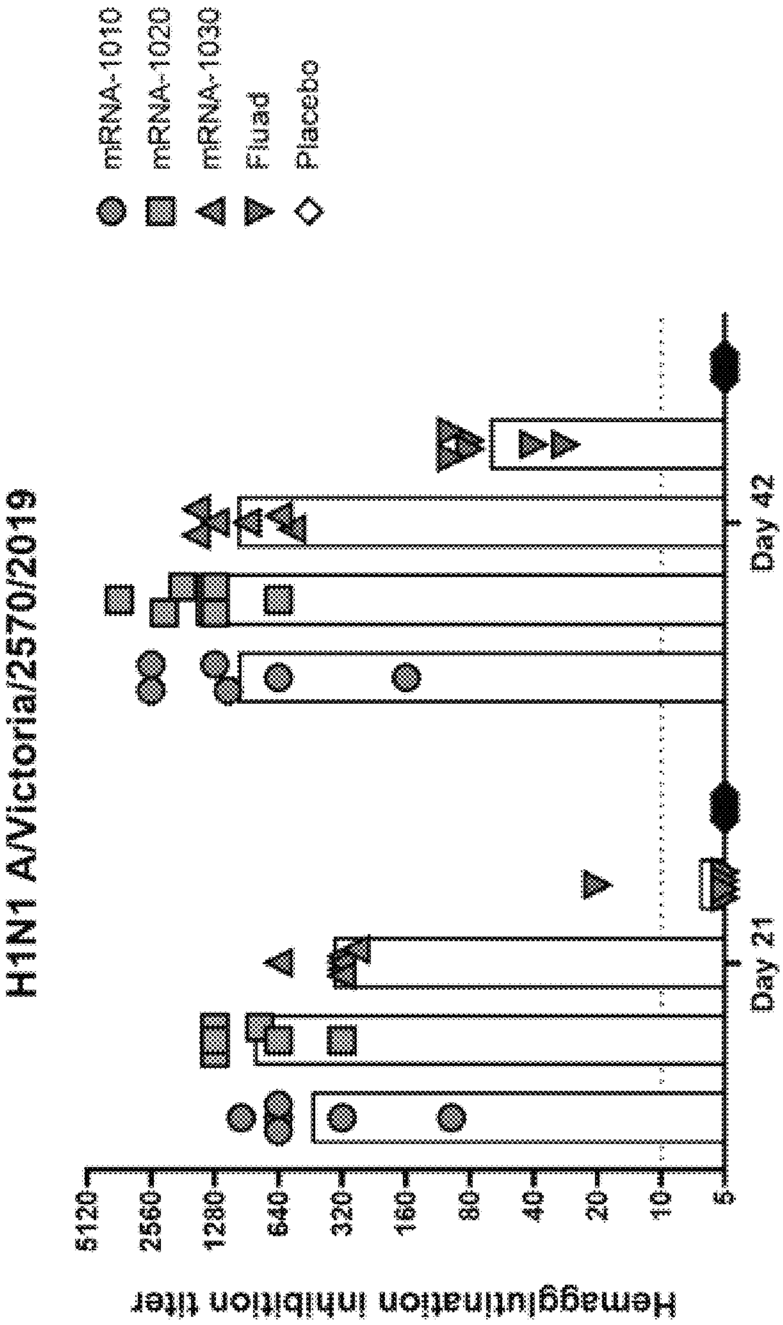
FIGS. 8A-8D are a series of graphs showing the hemagglutinin (HA) inhibition (HAI) titers for different formulations of mRNA vaccines. mRNA-1010 comprises a 1:1:1:1 ratio of H1 A/Victoria HA:H3 HK HA:B Washington HA:B Phuket HA. mRNA-1020 comprises a 1:1:1:1:1:1:1:1 ratio of H1 A/Victoria HA:H3 HK HA:B Washington HA:B Phuket HA:N1 Victoria NA:N2 HK NA:B Washington NA:B Phuket NA. mRNA-1030 comprises a 3:3:3:3:1:1:1:1 ratio of H1 Victoria HA:H3 HK HA:B Washington HA:B Phuket HA:N1 Wisconsin NA:N2 HK NA:B Washington NA:B Phuket NA. Fluad is an adjuvanted seasonal vaccine comparator and the placebo is PBS.
Figure 8B:
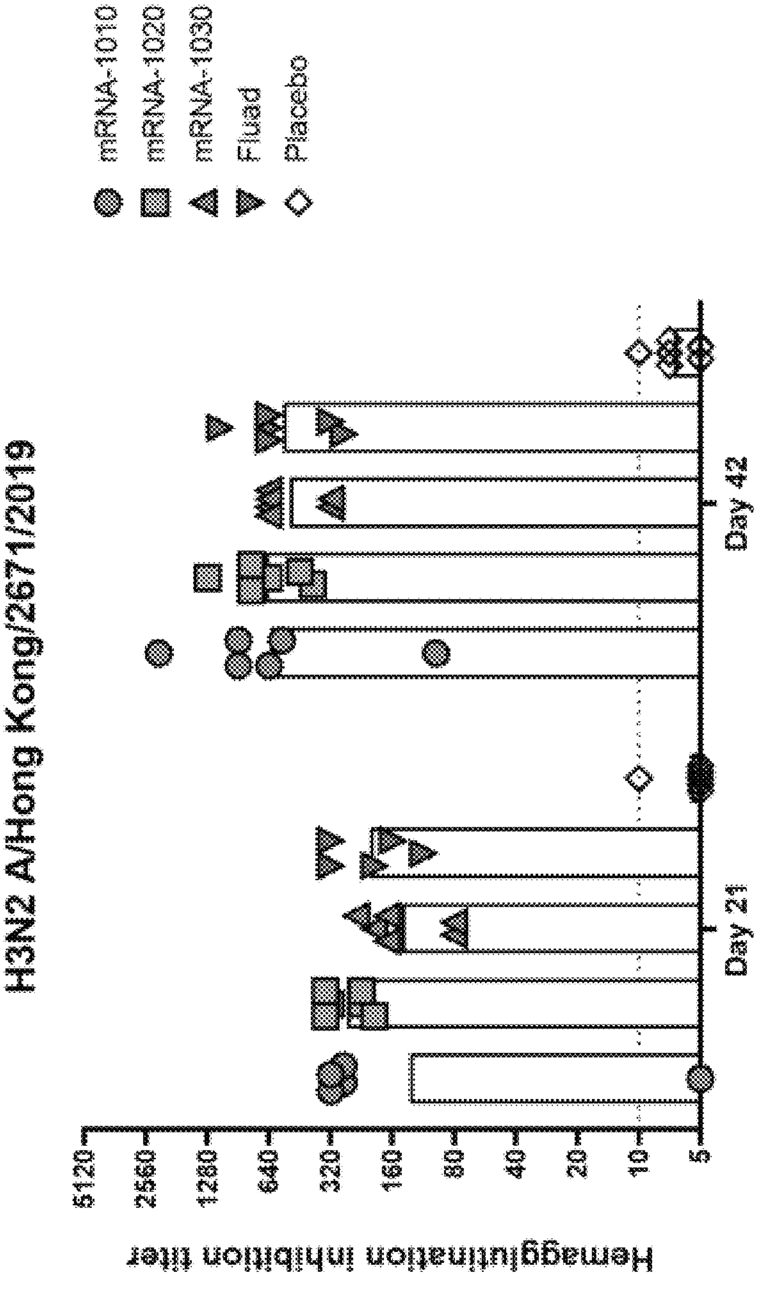
Figure 8C:
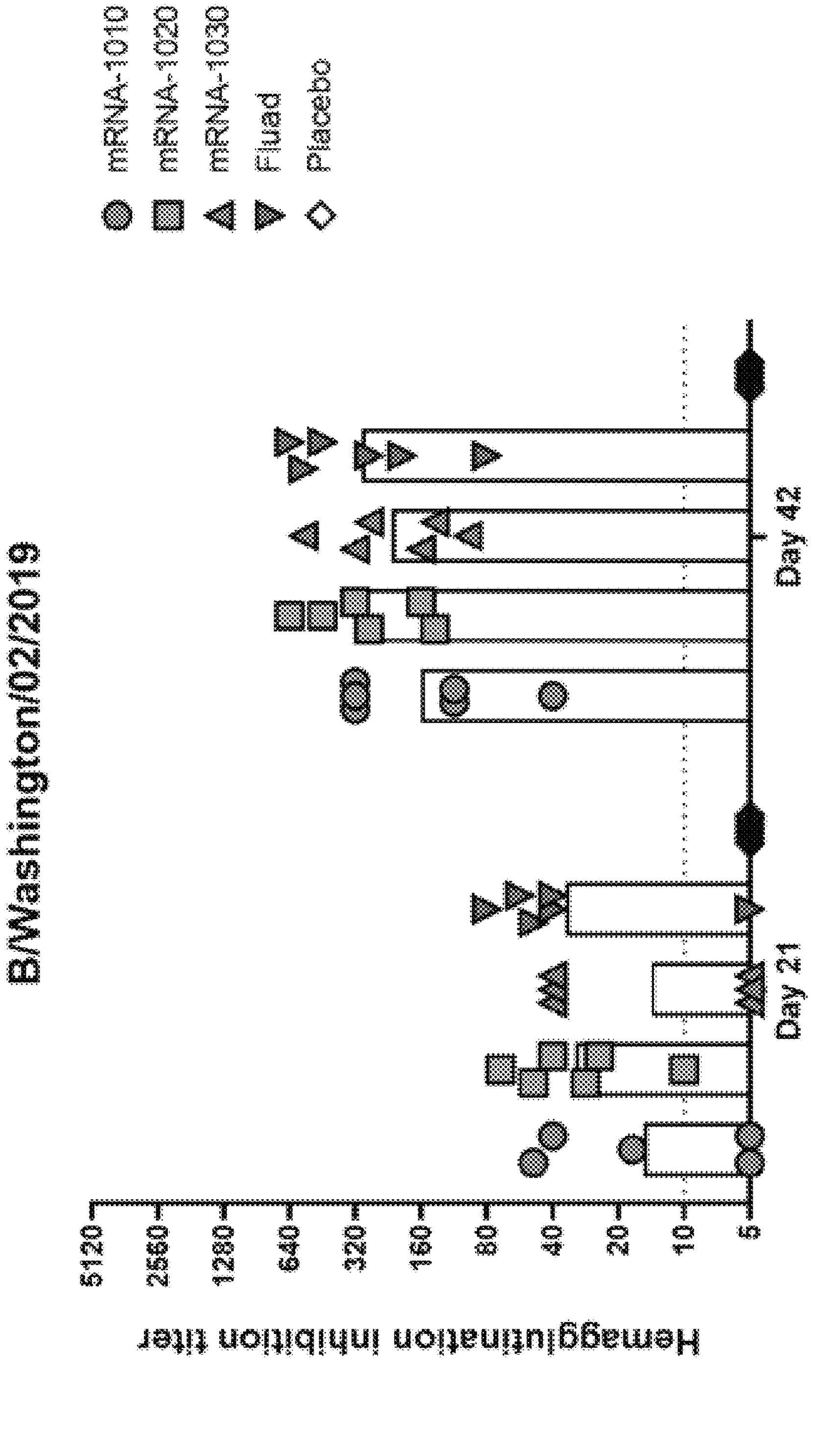
Figure 8D:
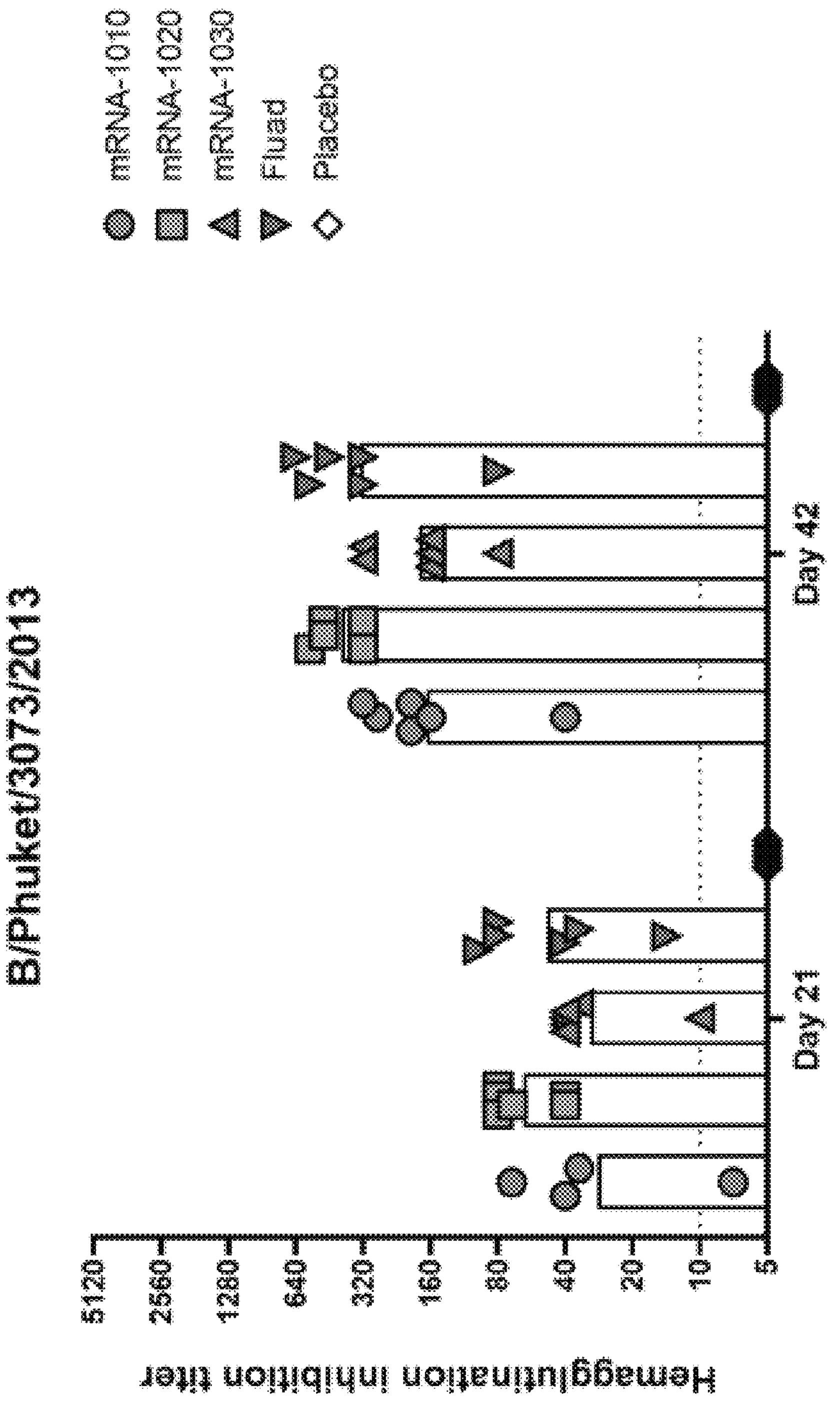

Example 4. Evaluation of the Immunogenicity and Dose Response of N1 NA Mutant Constructs In this example, expression screening was undertaken to determine whether a mutation in the catalytic domain of an NA antigen would have an effect. Different potential mutants included the following: extended NA stalk (may improve immunogenicity), shortened NA stalk (may improve expression and/or stability), remove cytoplasmic tail (may change surface distribution of NA), and catalytic mutants (may reduce NA reactogenicity, NA stability, and/or NA expression). HEK293t cells were plated (30,000 cells/well) in a 96-well plate. Doses of 100 ng or 25 ng mRNA were added to each well. Primary antibodies, include mAb-1G01 (human broadly cross-reactive NA antibody) and mAb 4D03 (human B cell antibody) were used, and readouts were performed at 24 hours and 48 hours. The mRNAs tested include (from left to right) SEQ ID NOs: 9, 12, 18, 21, 27, 30, 36, and 39. As shown in FIG. 7, the mutated NA (D151G) antigen results in approximately the same frequency of NA positive cells (lower graph) as the wild-type NA, except for N1 NA. The antibody 1G01 used in this experiment binds around the catalytic site of NA and residue Arg151 is part of the epitope targeted by this antibody, explaining, in part, the decreased signal observed in the experiment.

In addition, the immunogenicity of mRNA vaccines encoding mutant N1 NA (A/Wisconsin/588/2019) antigens in LNPs was tested in mice. The mutations tested are shown in Table 4 below, and include D151G substitution (del cat), deletion of the cytoplasmic tail (dcytT), deletion of 15 amino acids of the stalk region (stalk_d15), deletion of 30 amino acids of the stalk region (stalk_d30), insertion of 15 amino acids in the stalk region (stalk_ins15), R118K substitution, and E227D substitution. In some groups, the mutant N1 NA antigens were administered with HA antigens (H1 HA antigen), as shown in the table, at a 1:1 ratio. Balb/c mice were immunized with PBS or the dose of mRNA vaccine (n=8/group) shown in Table 4 on day 1 and day 22. Serum samples were collected on day 21 and day 36 and ELISAs were performed to measure the immunogenicity of the A/Wisconsin/588/2019 influenza virus HA and NA antigens.

TABLE 4

| Experimental Groups | | | | |
|---|---|---|---|---|
| Group | No. Animals | Antigen (encoded by mRNA) | SEQ ID NO: | Dose (μg) mRNA/animal |
| GR1 | 4 | PBS control | — | — |
| GR2 | 8 | N1_Wisconsin_WT | 46 | 1 |
| GR3 | 8 | N1_Wisconsin_del cat | 49 | 1 |
| GR4 | 8 | N1_Wisconsin_dcyT | 61 | 1 |
| GR5 | 8 | N1_Wisconsin_stalk_d15 | 64 | 1 |
| GR6 | 8 | N1_Wisconsin_stalk_d30 | 67 | 1 |
| GR7 | 8 | N1_Wisconsin_stalk_ins15 | 70 | 1 |
| GR8 | 8 | N1_Wisconsin_R118K | 73 | 1 |
| GR9 | 8 | N1_Wisconsin_E227D | 76 | 1 |
| GR10 | 8 | N1_Wisconsin_WT + H1 HA | 46 + 6 | 2 |
| GR11 | 8 | N1_Wisconsin_del cat + H1 HA | 49 + 6 | 2 |
| GR12 | 8 | N1_Wisconsin_dcyT + H1 HA | 61 + 6 | 2 |
| GR13 | 8 | N1_Wisconsin_stalk_d15 + H1 HA | 64 + 6 | 2 |
| GR14 | 8 | N1_Wisconsin_stalk_d30 + H1 HA | 67 + 6 | 2 |
| GR15 | 8 | N1_Wisconsin_stalk_ins15 + H1 HA | 70 + 6 | 2 |
| GR16 | 8 | N1_Wisconsin_R118K + H1 HA | 73 + 6 | 2 |
| GR17 | 8 | N1_Wisconsin_E227D + H1 HA | 76 + 6 | 2 |

Figure 14A:
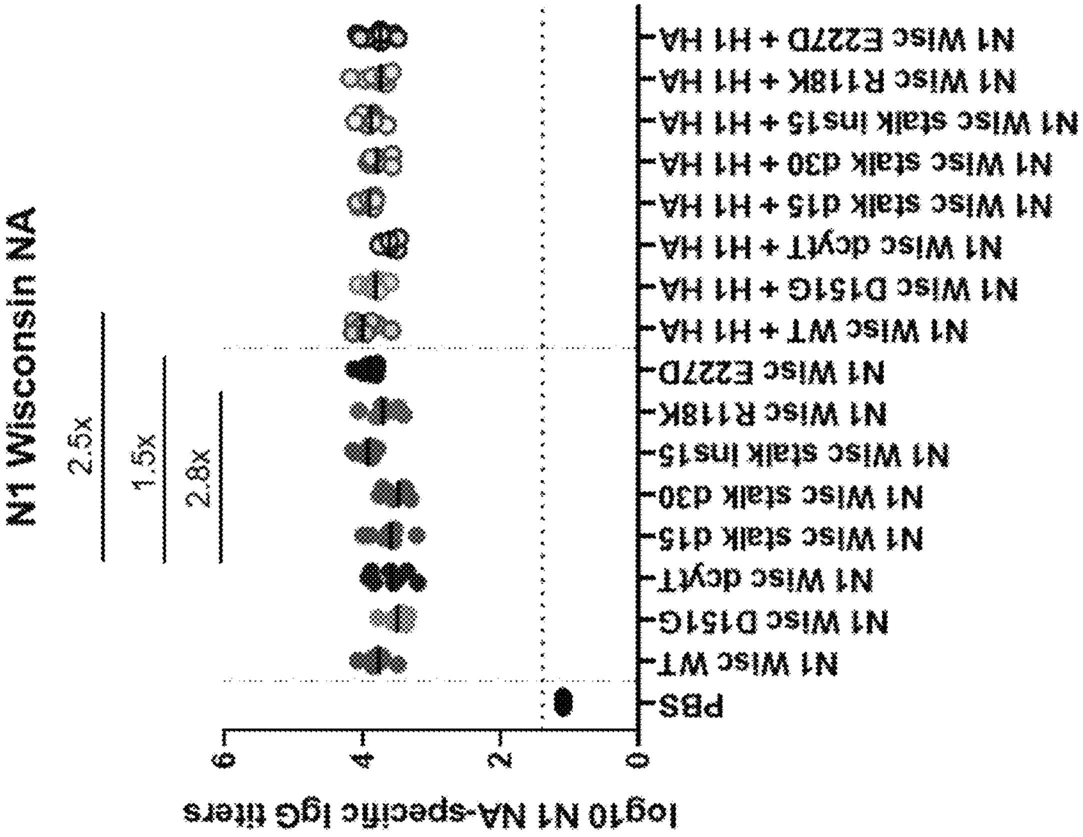
FIGS. 14A-14B are graphs depicting the NA-specific IgG titers (FIG. 14A) and HA-specific IgG titers (FIG. 14B) in mice after one dose (day 21) of the mRNA vaccine shown on the x-axis.
Figure 14B:
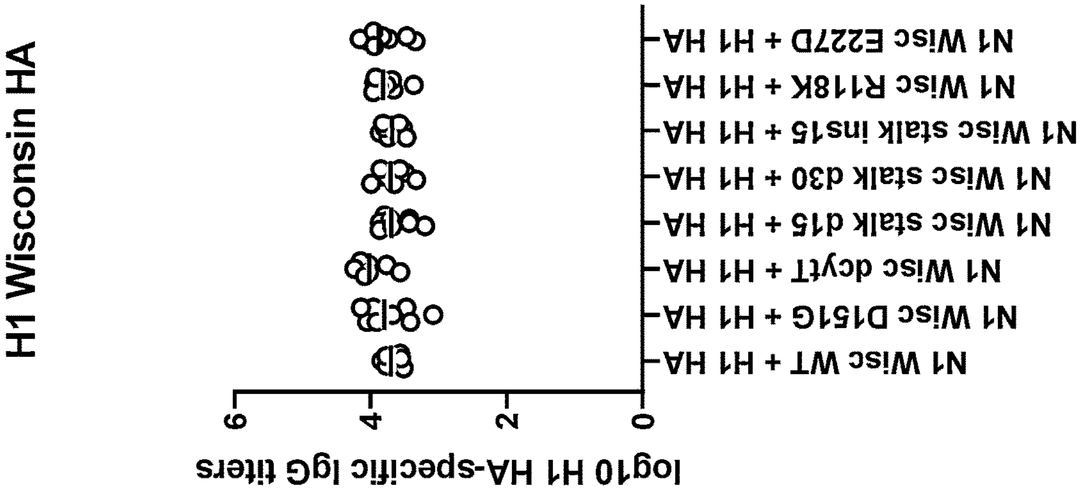
Figure 15A:
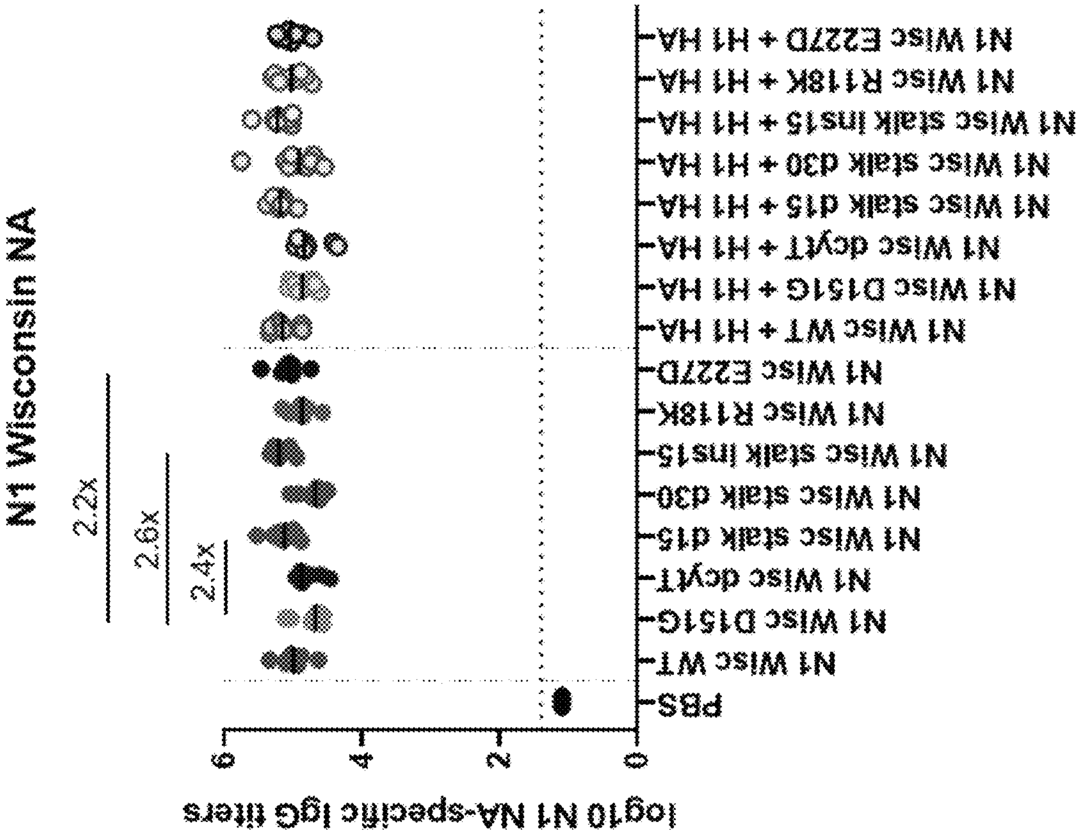
FIGS. 15A-15B are graphs depicting the NA-specific IgG titers (FIG. 15A) and HA-specific IgG titers (FIG. 15B) in mice after two doses (day 36) of the mRNA vaccine shown on the x-axis.
Figure 15B:
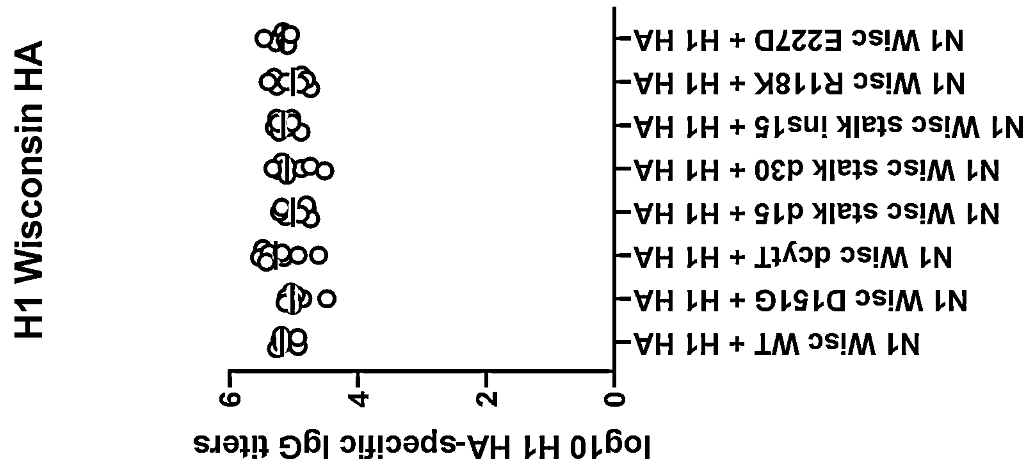

The results are shown in FIGS. 14A, 14B, 15A, and 15B. As shown in FIG. 14A, the immunogenicity of the constructs varied between 1.5× to 2.8× between certain constructs with respect the N1 NA-specific IgG titers after the first dose. The H1 HA-specific IgG titers after the first dose are shown in FIG. 14B. Following the second dose (day 36), differences in the N1 NA-specific IgG titers were observed, as well as a global increase in titers compared to the post-first dose data (FIG. 15A). Similarly, in FIG. 15B, H1 HA-specific IgG titers were found to increase relative to post-first dose levels.

Figure 16A:
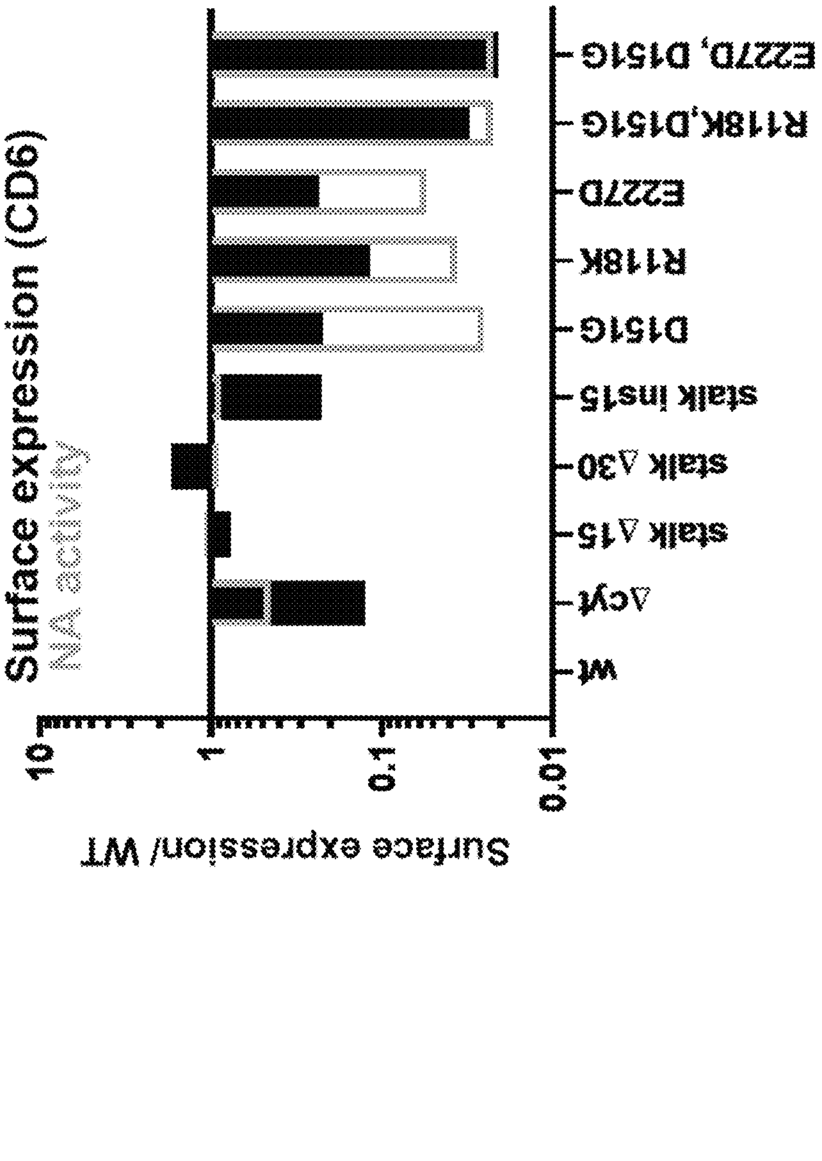
FIGS. 16A-16B are graphs showing surface expression (NA activity) of different NA mutants relative to a wild-type NA (FIG. 16A) and active site binding (NA activity) of different NA mutants relative to a wild-type NA (FIG. 16B).
Figure 16B:
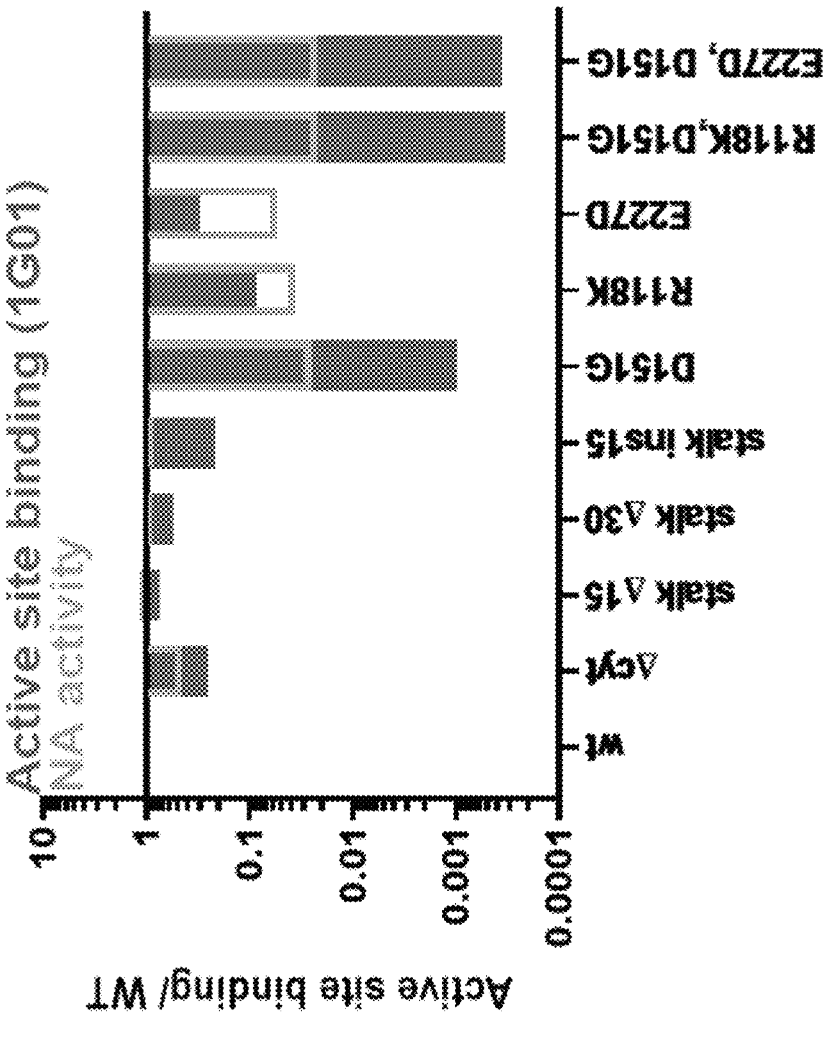

Moreover, it was found that changes to the stalk length did not affect NA catalytic activity, although StalkΔ30 exhibited slightly increased expression. The deletion of the cytoplasmic tail reduced surface expression and affected NA activity. All catalytic mutations severely impacted sialidase activity, and dual mutants showed further reduced activity as compared to single mutants (FIG. 16A). The D151G mutation was found to reduce NA activity and to affect loop-150, a major antigenic site (FIG. 16B).

Example 5. Multiantigen Dose Response and Immune Interference Analysis Using 2021 Southern Hemisphere Influenza Strains (Ferrets)

Figure 9:
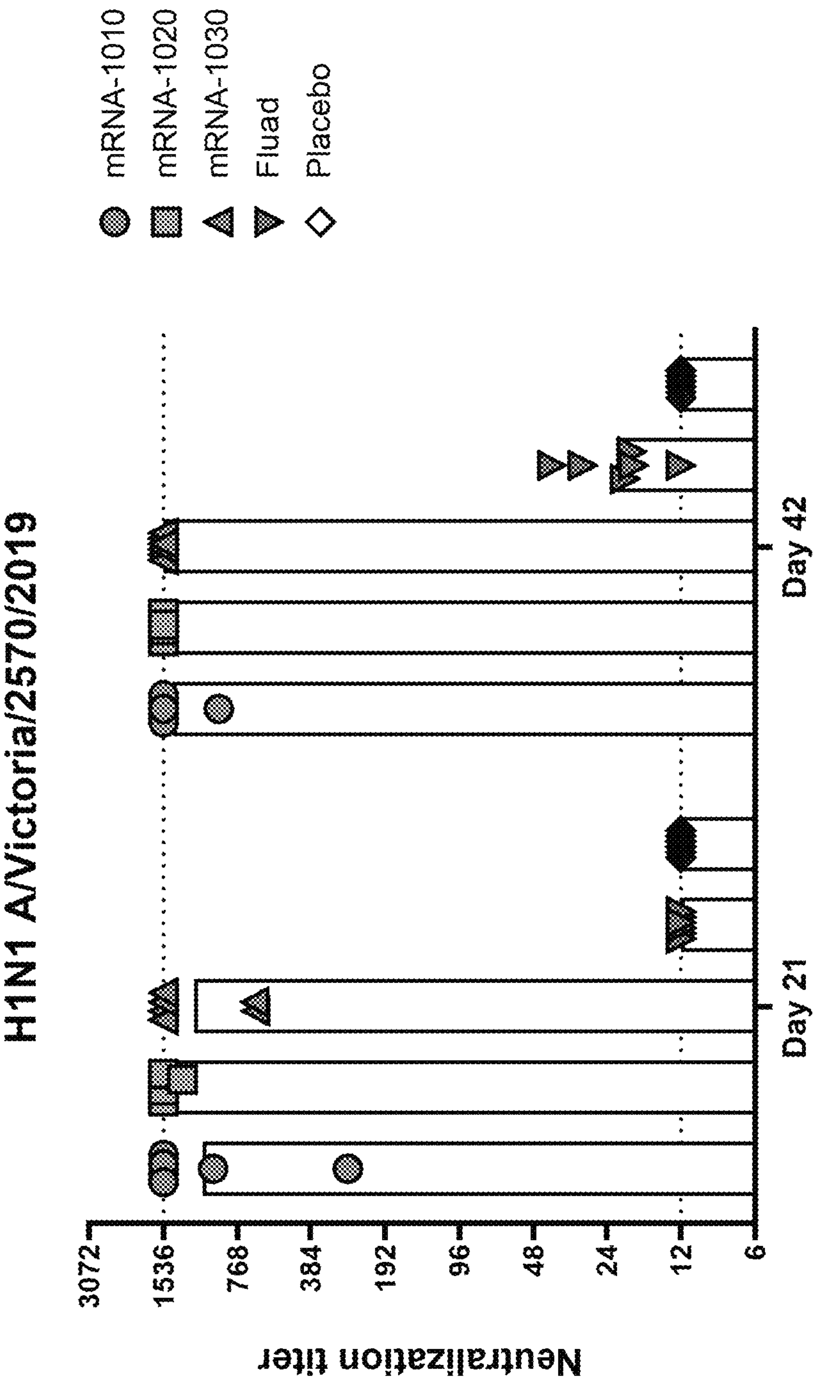
FIG. 9 is a graph showing neutralizing titers against H1N1 A/Victoria/2570/2019 for mRNA-1010, mRNA-1020, mRNA-1030, Fluad (an adjuvanted seasonal vaccine comparator), and a placebo (PBS).

In this example, multiple influenza virus HA and NA antigens administered as mRNA vaccines were evaluated for immunogenicity and immunological interference between the antigens. Further, the data was examined for any dampening of immune response towards one antigen over another different antigen when all antigens were co-administered simultaneously as mRNA vaccines formulated in lipid nanoparticles (LNPs). For this study, the antigens were formulated separately into different LNPs and mixed before administration. In all cases, the NA protein was rendered enzymatically inactive by catalytic site residue mutation prior to inclusion in the vaccine. Briefly, ferrets were injected with one of the following compositions: mRNA-1010 (a 1:1:1:1 ratio of H1 A/Victoria HA:H3 HK HA:B Washington HA:B Phuket HA), mRNA-1020 (a 1:1:1:1:1:1:1:1 ratio of H1 A/Victoria HA:H3 HK HA:B Washington HA:B Phuket HA:N1 Victoria NA:N2 HK NA:B Washington NA:B Phuket NA), mRNA-1030 (a 3:3:3:3:1:1:1:1 ratio of H1 Victoria HA:H3 HK HA:B Washington HA:B Phuket HA:N1 Wisconsin NA:N2 HK NA:B Washington NA:B Phuket NA), Fluad (an adjuvanted 2020/21 Northern Hemisphere composition mismatched for the H1N1 strain compared to the mRNA vaccines), or a PBS control. The total mRNA dose was higher in the mRNA-1020 group (25 μg/HA and 25 μg/NA) than the other two groups (mRNA-1010, 25 μg/HA; mRNA-1030, 25 μg/HA; 8.3 μg/NA). The ferrets were administered the composition on a prime/boost vaccination schedule on Day 0 (D0) and Day 21 (D21). On D21 and D42, a hemagglutination inhibition (HAI) assay was performed. The results are shown in FIGS. 8A-8D, which demonstrate that HAI antibodies elicited in ferrets are comparable to an enhanced (adjuvanted) seasonal comparator vaccine (Fluad). No interference due to addition of neuraminidase antigens was observed. Neutralizing titers were also measured and high neutralizing titers against the challenge virus strain were measured (FIG. 9). Note that, in FIG. 9, the upper limit of detection of the assay prevented comparison of neutralizing titers after two doses.

Figure 10A:
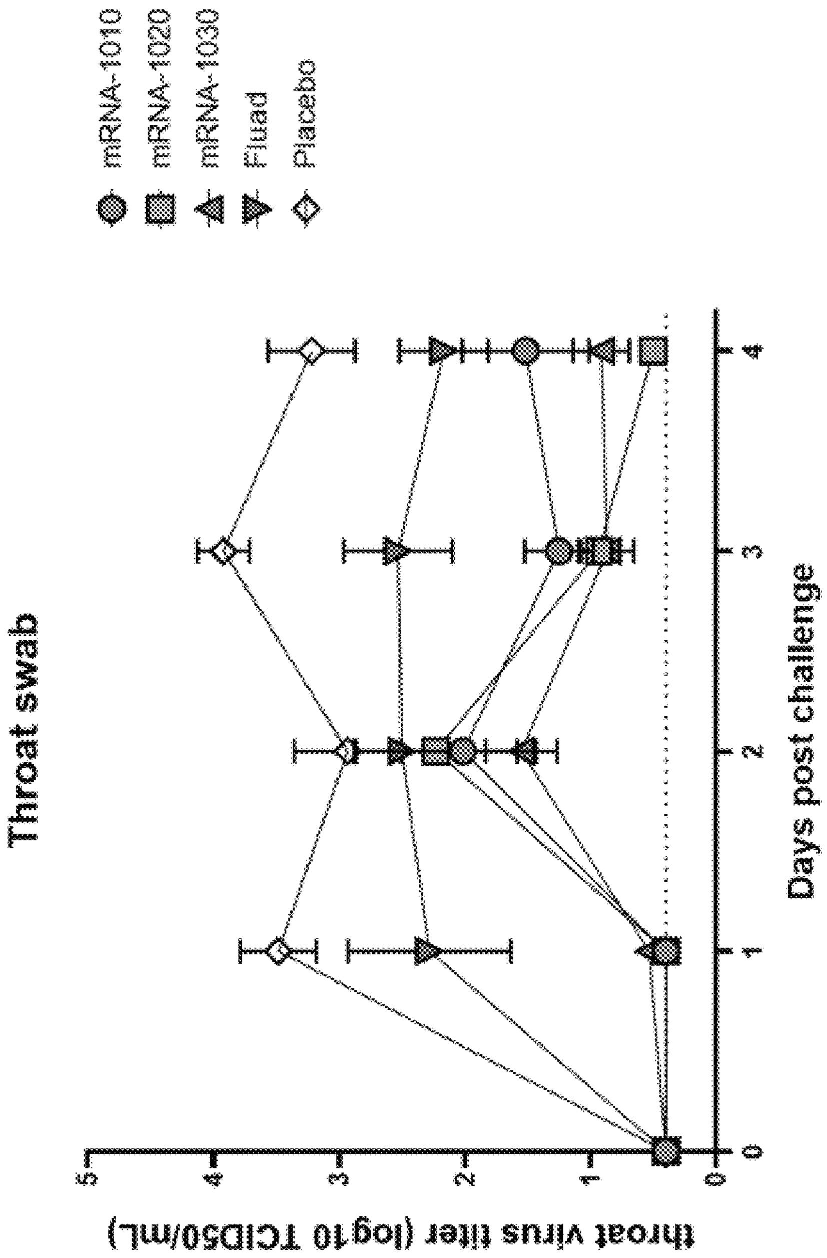
FIGS. 10A-10C are graphs showing throat virus titers (FIG. 10A), nose virus titers (FIG. 10B), and results from the tissue culture infectious dose ($TCID_{50}$) assay of the nasal turbinate sample (FIG. 10C) in ferrets treated with mRNA-1010, mRNA-1020, mRNA-1030, Fluad (an adjuvanted seasonal vaccine comparator), or a placebo (PBS).
Figure 10B:
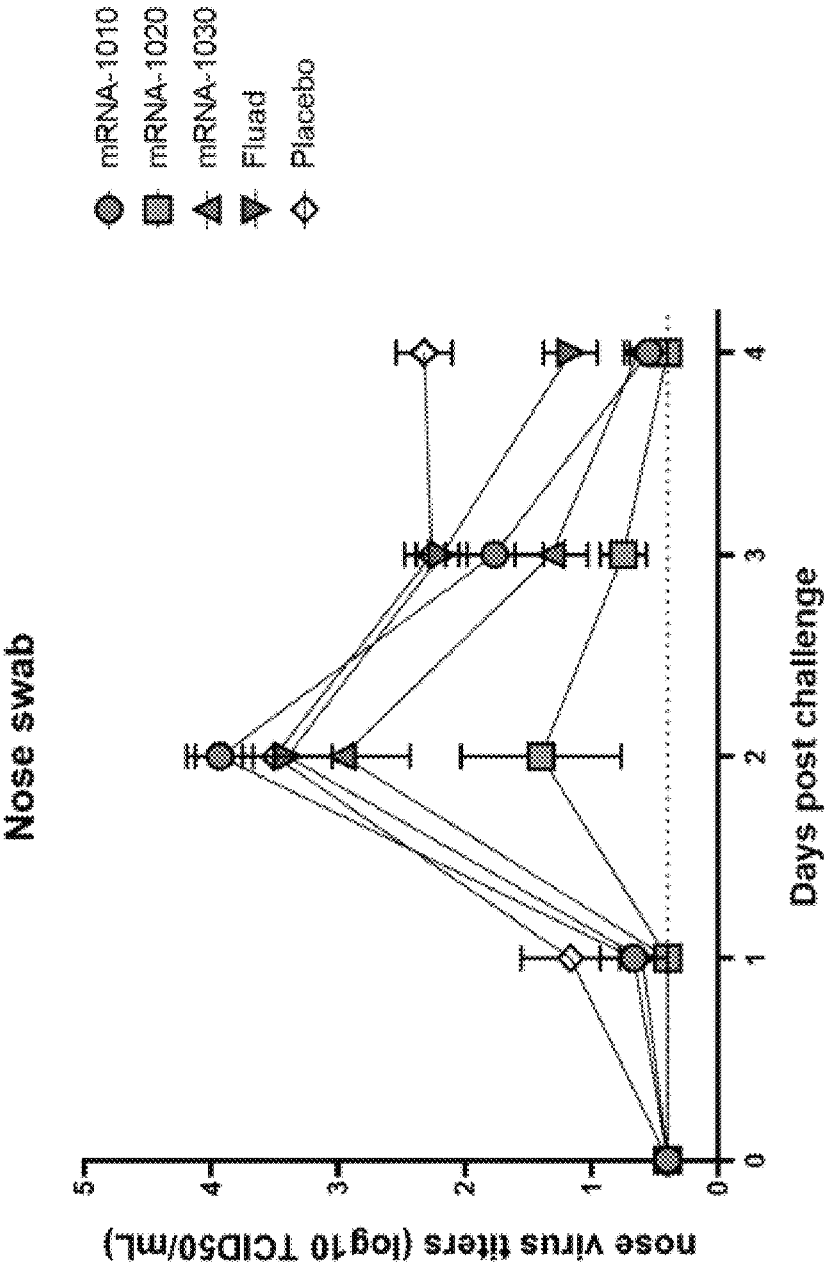
Figure 10C:
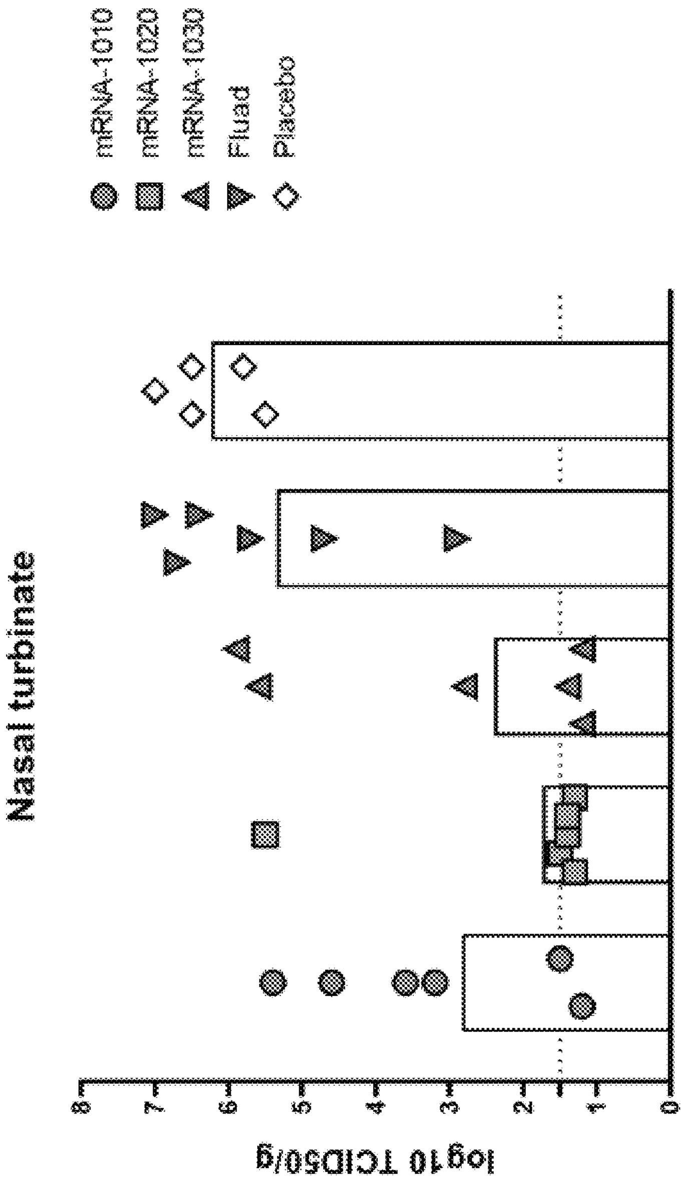
Figure 11:
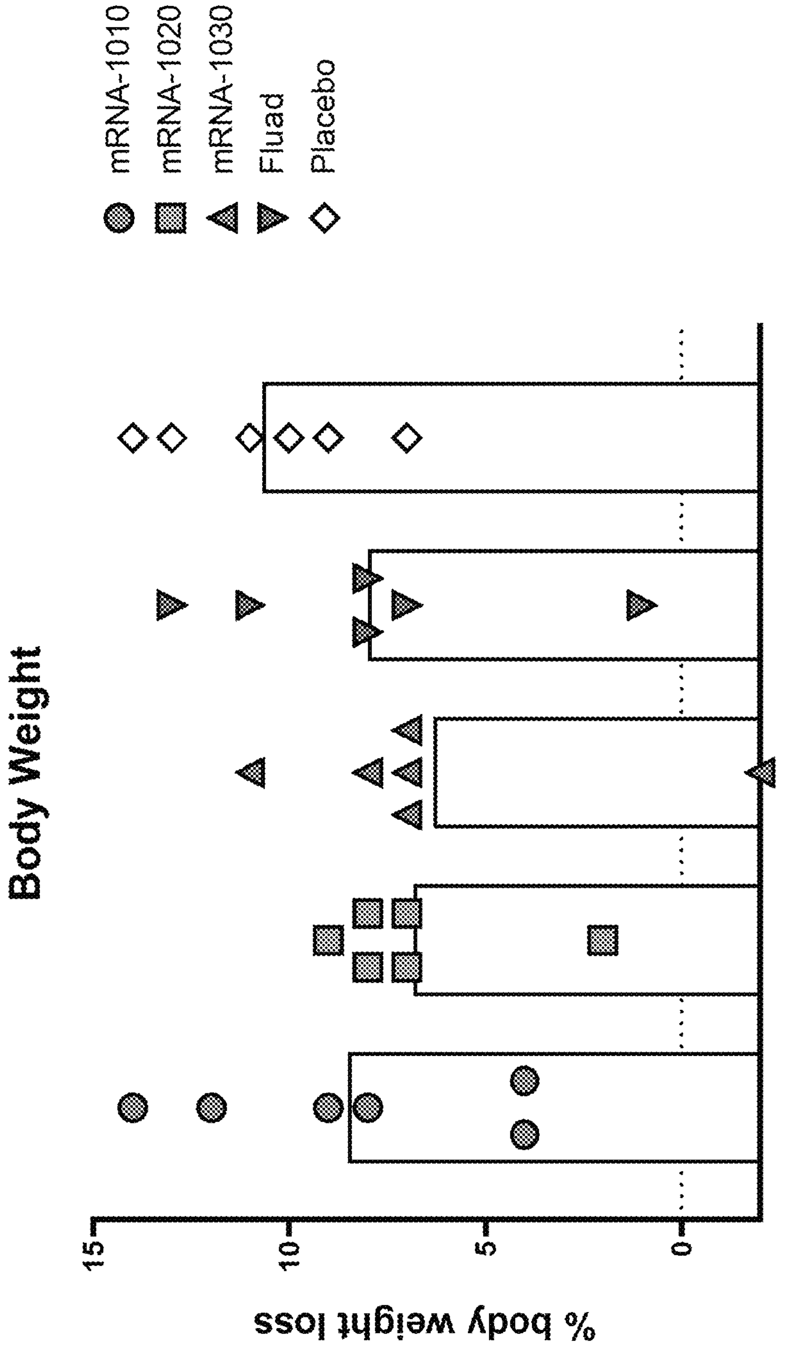
FIG. 11 is a graph showing the body weight of ferrets following administration of mRNA vaccines: mRNA-1010, mRNA-1020, mRNA-1030, Fluad (an adjuvanted seasonal vaccine comparator), or a placebo (PBS).
Figure 12:
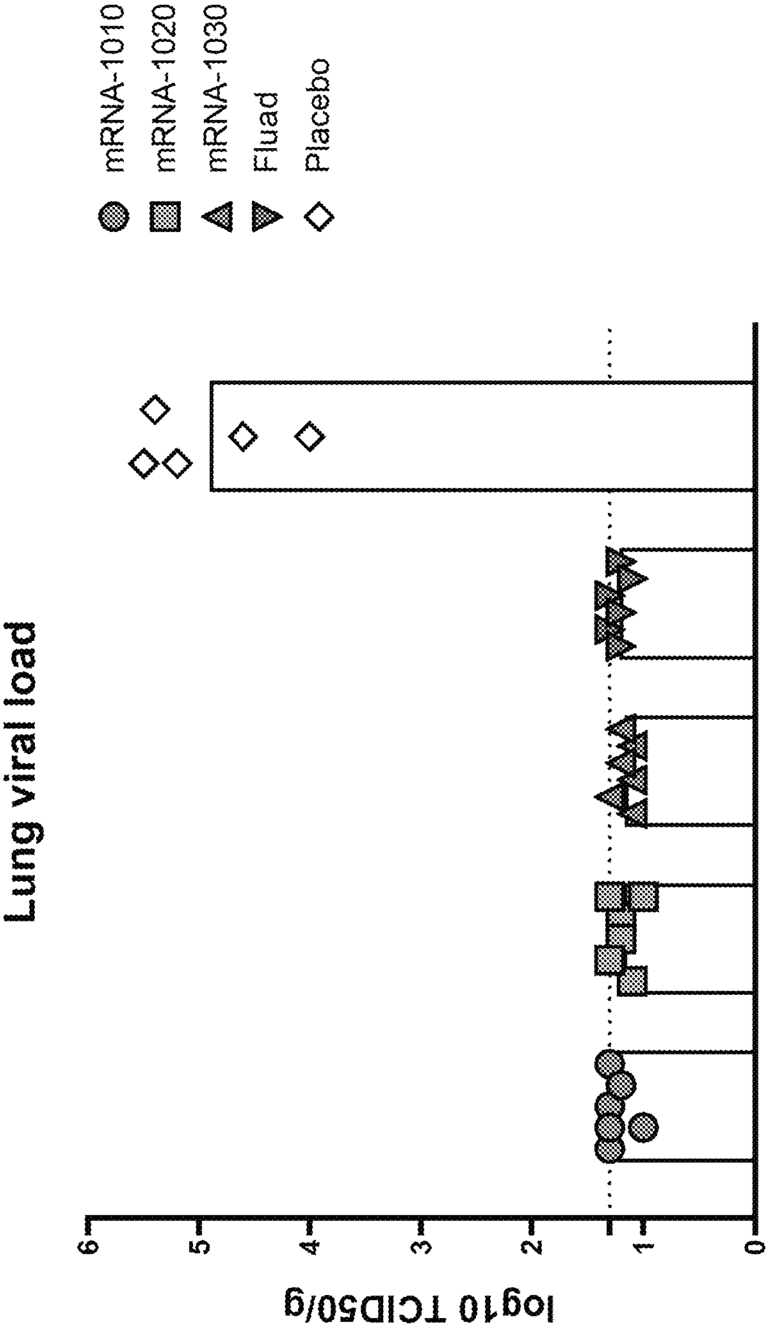
FIG. 12 is a graph showing the lung viral load of ferrets following administration of mRNA-1010, mRNA-1020, mRNA-1030, Fluad (an adjuvanted seasonal vaccine comparator), and a placebo (PBS).

On D42, a non-lethal challenge was performed and, for four days post-challenge, the ferrets were followed for viral shedding in untranslated regions (UTRs) and body weight. Necropsies were performed on day 4 to obtain viral titers and gross histopathology of the upper respiratory tract (URT) and lower respiratory tract (LRT). As shown in FIGS. 10A-10C, viral shedding in the URT of ferrets is difficult to suppress with intramuscular vaccination (FIG. 10B). mRNA-1010 was found to comparable to (mismatched) Fluad, whereas mRNA-1020 showed an impressive reduction in viral shedding. Body weight loss was found to be reduced after challenge (FIG. 11) in the mRNA vaccine groups compared to the control (PBS). With respect to the LRT, it was found that the mRNA vaccines completely protected the region after H1N1 challenge (FIG. 12). Lung titers were at or below the limit of detection in all vaccinated ferrets on day 5 post-challenge. It is noted that protection of the lower respiratory tract is generally thought to prevent severe influenza.

Overall, it was found that immunization with mRNA-1010, mRNA-1020, and mRNA-1030 induced functional antibody responses after one dose that were further boosted after the second immunization. Upon live virus challenge, animals that received mRNA vaccines had lower detectable virus loads across multiple tissues compared to Fluad-vaccinated animals or animals in the placebo group. Also, vaccination with mRNA-1020 resulted in reduced viral shedding in the URT. No virus was detected in the lungs of the vaccinated animals four days post-challenge.

Example 6. Screening of Mouse T Cell Epitopes in H1N1 and H3N2

Figure 13:
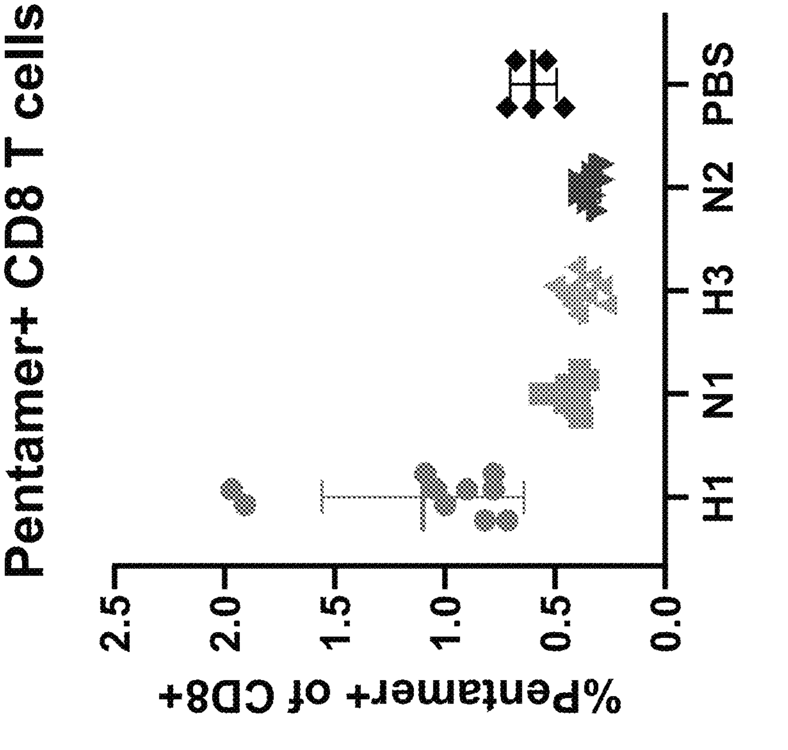
FIG. 13 is a graph showing the percent of pentamer-positive CD8+ T cells in pooled samples. The pentamer used, IYSTVASSL (SEQ ID NO: 137) (contained in H1), was conjugated to APC.

In this example, flu peptides generated by Genscript in A/Wisconsin/2019 H1N1 and A/HongKong/2019 H3N2 were screened. Female Balb/c mice (n=10/experimental group; n=4, PBS) were administered 5 μg of mRNA (A/Wisconsin/2019 H1N1 HAWT, A/Wisconsin/2019 N1 del cat, A/Hong Kong/2019/H3 HA WT, or A/Hong Kong/2019/N2NA WT) formulated in SM102 lipid nanoparticles or PBS on day 1 and on day 22. On day 29, spleens were removed for FACS intracellular cytokine staining (ICS) and a pentamer stain assay (IYSTVASSL (SEQ ID NO: 137)—contained in H1 and conjugated to APC). As shown in FIG. 13, the percent of pentamer-positive CD8+ T cells was increased in the A/Wisconsin/2019 H1 group (i.e., the group had more CD8 T cells that recognized and bound to the H1 pentamer than the other groups).

Example 7. Evaluation of Immunogenicity Using 2021/2022 Northern Hemisphere Influenza Strains (Mice)

In this example, multiple influenza virus HA and NA antigens administered as mRNA vaccines were evaluated for immunogenicity and immunological interference between the antigens. In particular, the immunogenicity of various doses of Northern Hemisphere 2021/2022 influenza strains (e.g., H3N2 Cambodia) was evaluated and compared to the immunogenicity of the Southern Hemisphere 2021 influenza strains (e.g., H3N2 HK). Further, the data was examined for any dampening of immune response towards one antigen over another different antigen when all antigens are co-administered simultaneously as mRNA vaccines formulated in lipid nanoparticles (LNPs). For this study, the antigens were formulated separately into different LNPs and mixed before administration. In all cases, the NA protein was rendered enzymatically inactive by catalytic site residue mutation prior to inclusion in the vaccine. Briefly, Balb/c mice were injected with one of the following constructs: mRNA-1010 (a 1:1:1:1 ratio of 4 HA antigens, 2021/2022 NH strains), mRNA-1010 (a 1:1:1:1 ratio of 4HA, 2021 SH strains), mRNA-1020 (a 1:1:1:1:1:1:1:1 ratio of 4 HA antigens+4 NA antigens, 2021/2022 NH strains), mRNA-1020 (a 1:1:1:1:1:1:1:1 ratio of 4 HA antigens+4 NA antigens, 2021 SH strains), mRNA-1030 (a 3:3:3:3:1:1:1:1 ratio of 4 HA antigens+4 NA antigens, 2021/2022 NH strains), mRNA-1030 (a 3:3:3:3:1:1:1:1 ratio of 4 HA antigens+4 NA antigens, 2021 SH strains), a 1:1:1:1:1 ratio of 5 HA antigens, or a PBS control, at the amounts shown in Table 5 below.

TABLE 5

| Experimental Groups | | | |
|---|---|---|---|
| Group | No. Animals | Antigen (encoded by mRNA) | Mass |
| GR1 | 4 | PBS control | — |
| GR2 | 8 | 4 × HA 2021/2022 NH strains (Cambodia)* | 4.8 μg |
| GR3 | 8 | 4 × HA 2021 SH strains (HK)* | 4.8 μg |
| GR4 | 30 | 1:1 ratio 4 × HA + 4 × NA 2021/2022 NH strains (Cambodia)* | 9.6 μg |

TABLE 5-continued

| Experimental Groups | | | |
|---|---|---|---|
| Group | No. Animals | Antigen (encoded by mRNA) | Mass |
| GR5 | 8 | 1:1 ratio 4 × HA + 4 × NA 2021 SH strains (HK)* | 9.6 μg |
| GR6 | 8 | 3:1 ratio 4 × HA + 4 × NA 2021/2022 NH strains (Cambodia)* | 6.4 μg |
| GR7 | 8 | 3:1 ratio 4 × HA + 4 × NA 2021 SH strains (HK)* | 6.4 μg |
| GR8 | 8 | 5 × HA (2021 SH strains + Cambodia HA)* | 6 μg |

*NH—Northern Hemisphere, SH—Southern Hemisphere

The mice received a prime dose on Day 1 and a boost dose on Day 22. Sera were collected on Day 21 and on Day 36 and ELISA assays were performed to examine antibody binding to recombinant HA and NA (FIGS. 28 and 29).

Figure 28:
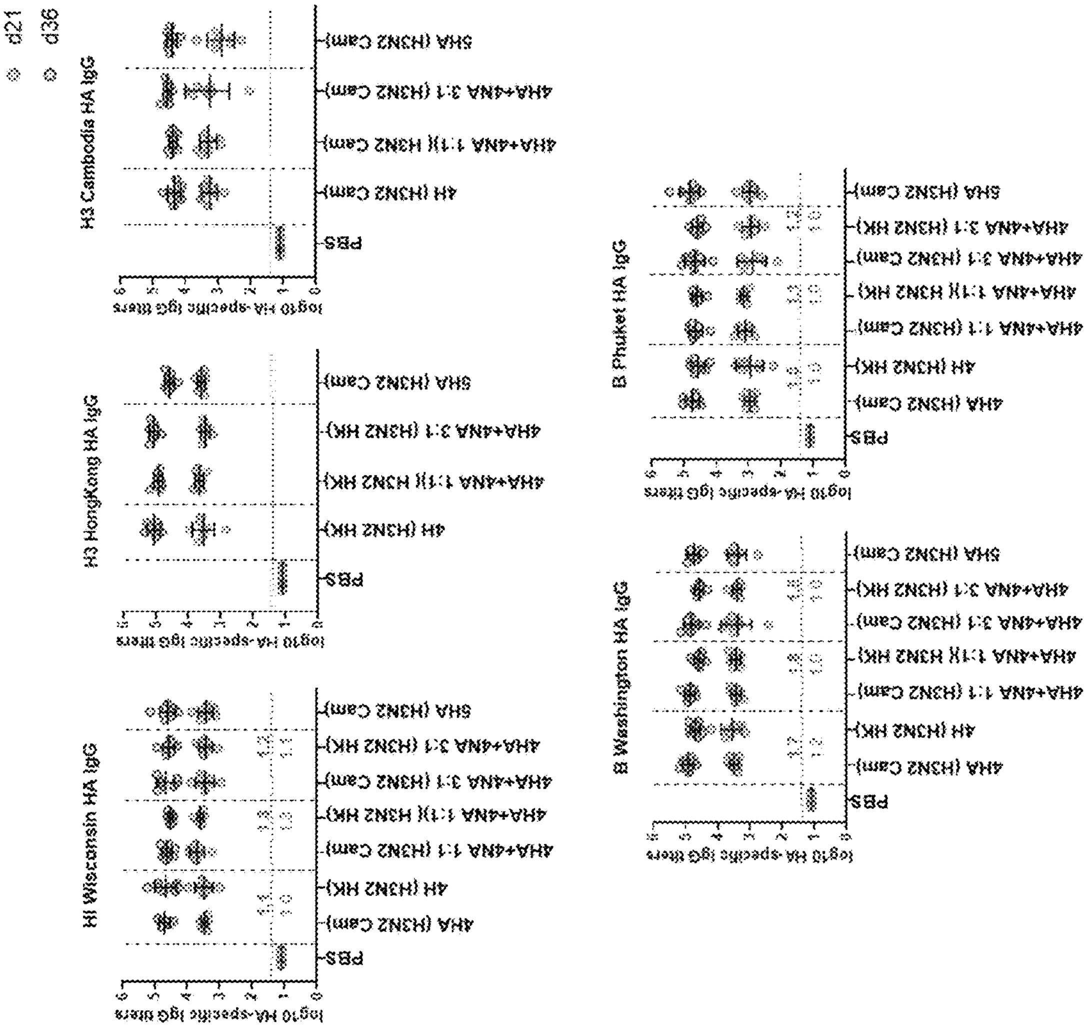
FIG. 28 is a graph showing the hemagglutinin (HA)-reactive IgG antibody titers to five different influenza antigens (N1 Wisconsin, N2 Cambodia, H2 Hong Kong, B Washington, and B Phuket) after one (PD1; day 21) or two (PD2; day 36) doses of influenza HA and neuraminidase (NA) formulations or controls.
Figure 29:
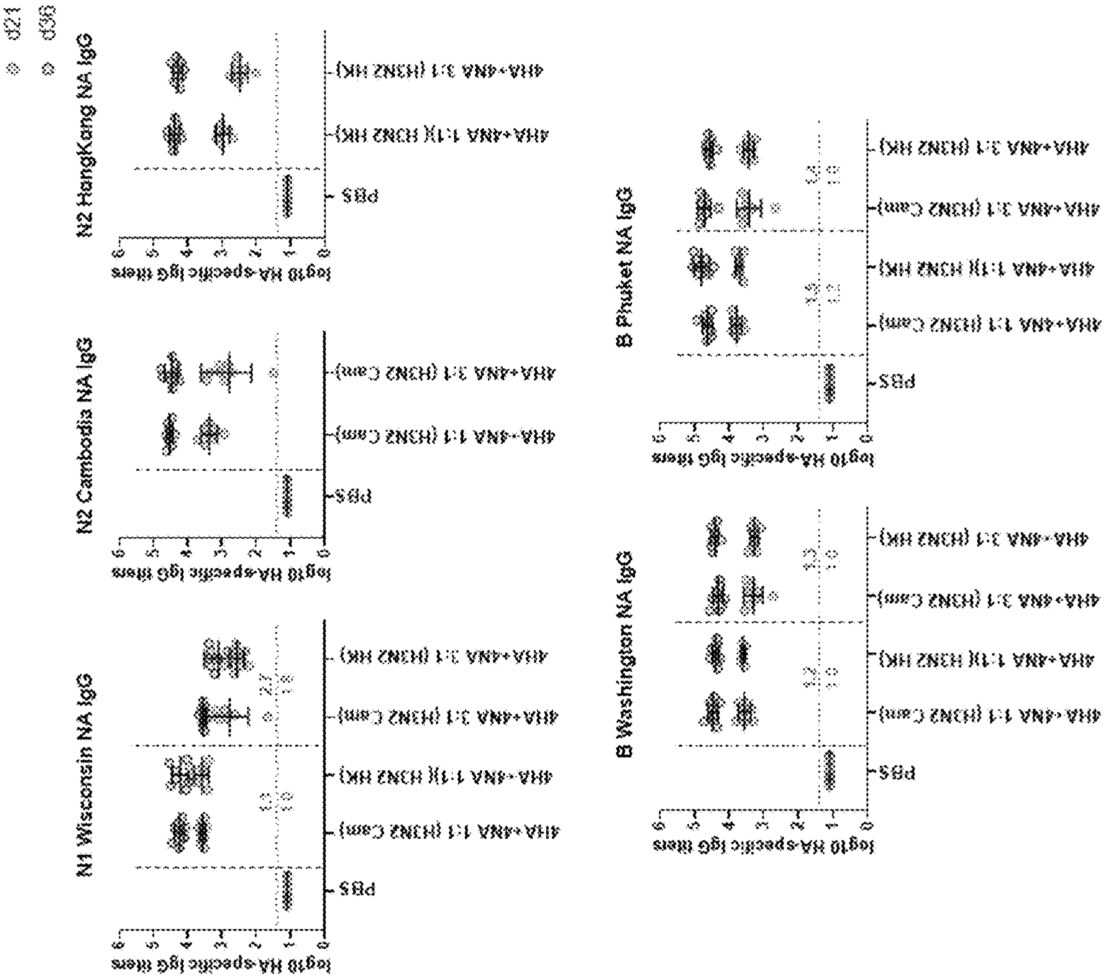
FIG. 29 is a graph showing the NA-reactive IgG antibody titers to five different influenza antigens (N1 Wisconsin, N2 Cambodia, H2 Hong Kong, B Washington, and B Phuket) after one (PD1; day 21) or two (PD2; day 36) doses of influenza HA and NA formulations or controls.

As shown in FIGS. 28 and 29, the antibody responses to HA and NA glycoprotein antigens at all combinations or ratios of mRNAs tested were robust, even with the updated strain change. The HA ELISA data was all within a 2-fold change (FIG. 28) and the NA ELISA data showed high response at both ratios tested (mRNA-1020 and mRNA-1030) (FIG. 29).

Additionally, HAI, microneutralization, and NAI assays are performed.

Example 8. Evaluation of Immunogenicity of E227D Mutation Across all Neuraminidases In this example, multiple influenza virus HA and NA antigens administered as mRNA vaccines were evaluated for immunogenicity, in particular, the immunogenicity of E227D mutated NA compared to D151G for all four seasonal strains. Further, the data was examined for any dampening of immune response towards one antigen over another different antigen when all antigens are co-administered simultaneously as mRNA vaccines formulated in lipid nanoparticles (LNPs). For this study, the antigens were formulated separately into different LNPs and mixed before administration. In all cases, the NA protein was rendered enzymatically inactive by catalytic site residue mutation prior to inclusion in the vaccine. Briefly, Balb/c mice were injected with the constructs and at the amounts shown in Table 6 below. The constructs included individual NA antigens as well as combinations of NA with HA (mRNA-1020 and mRNA-1030).

TABLE 6

| Experimental Groups | | | |
|---|---|---|---|
| Group | No. Animals | Antigen (encoded by mRNA) | Dose (μg) mRNA/animal |
| GR1 | 4 | PBS control | — |
| GR2 | 8 | N1 Wisconsin D151G | 1 |
| GR3 | 8 | N1 Wisconsin E227D | 1 |
| GR4 | 8 | N2 Cambodia D151G | 1 |
| GR5 | 8 | N2 Cambodia E227D | 1 |
| GR6 | 8 | B Phuket NA D151G | 1 |
| GR7 | 8 | B Phuket NA E227D | 1 |
| GR8 | 8 | B Washington NA D151G | 1 |
| GR9 | 8 | B Washington NA E227D | 1 |
| GR10 | 8 | mRNA-1020-NH21/22 D151G | 8 |
| GR11 | 8 | mRNA-1020-NH21/22 E227D | 8 |
| GR12 | 8 | mRNA-1030-NH21/22 D151G | 5.33 |
| GR13 | 8 | mRNA-1030-NH21/22 E227D | 5.33 |

The mice received a single dose of the mRNA composition and sera was collected on Day 21. ELISAs were performed to examine antibody binding to recombinant HA and NA, as well as NAI assays.

Figure 30:
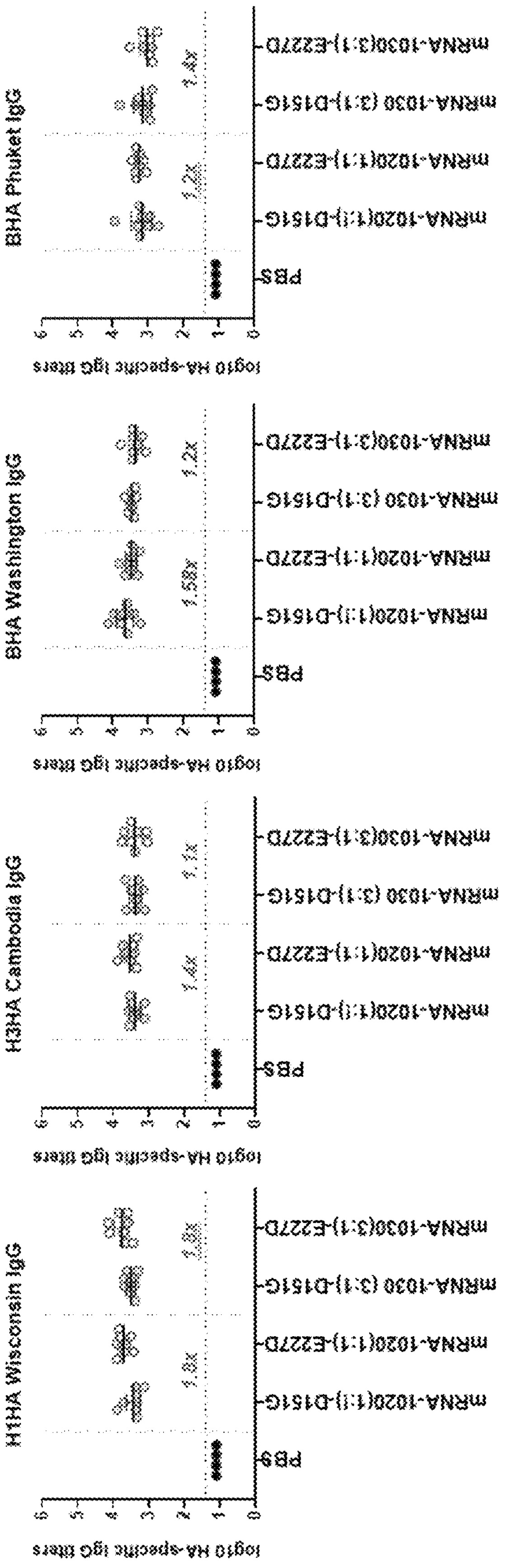
FIG. 30 is a graph showing the HA-specific IgG titers in mice after one dose of the mRNA vaccine or placebo (PBS) shown on the x-axis.
Figure 31:
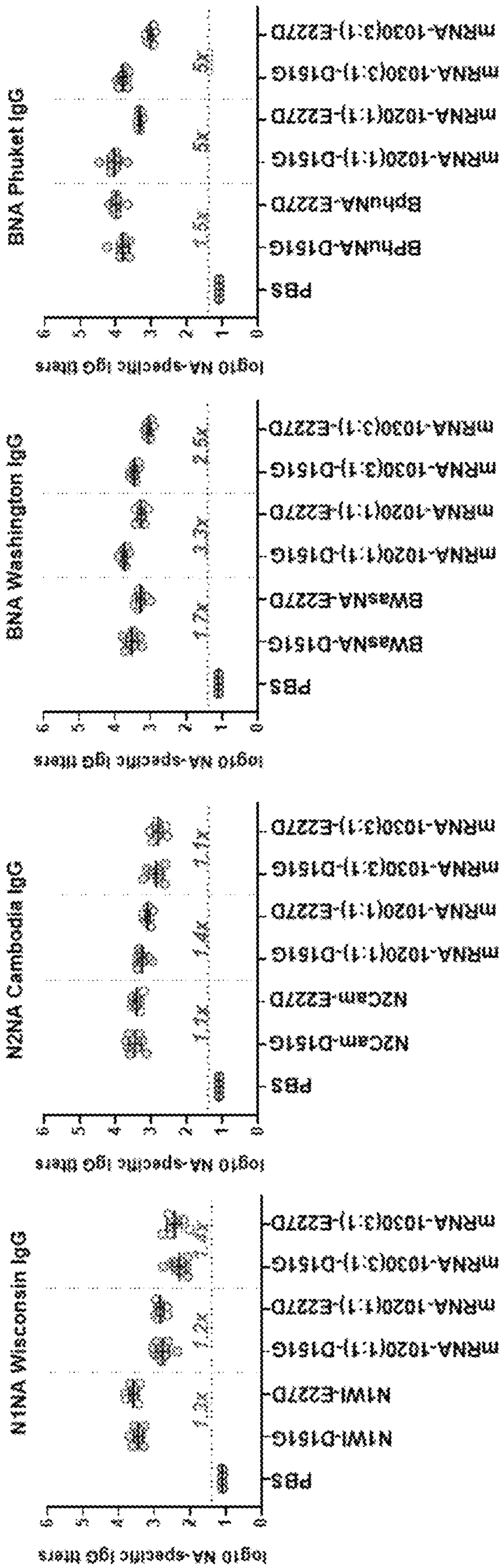
FIG. 31 is a graph showing the NA-specific IgG titers in mice after one dose of the mRNA vaccine or placebo (PBS) shown on the x-axis.

The results demonstrate that, when the HA and NA antigens were combined in mRNA-1020 and mRNA-1030, the E227D mutation showed a decreased response compared to the D151G mutation (see, e.g., BHA Washington (FIG. 30) and N2NA Cambodia, BNA Washington, and BNA Phuket (FIG. 31)). When the individual NA antigens were tested (N1NA Wisconsin, N2NA Cambodia, BNA Phucket, and BNA Washington), mRNA encoding NA antigens having the E227D mutation had a comparable response to WT and the D151G mutation (FIG. 31).

Figure 32A:
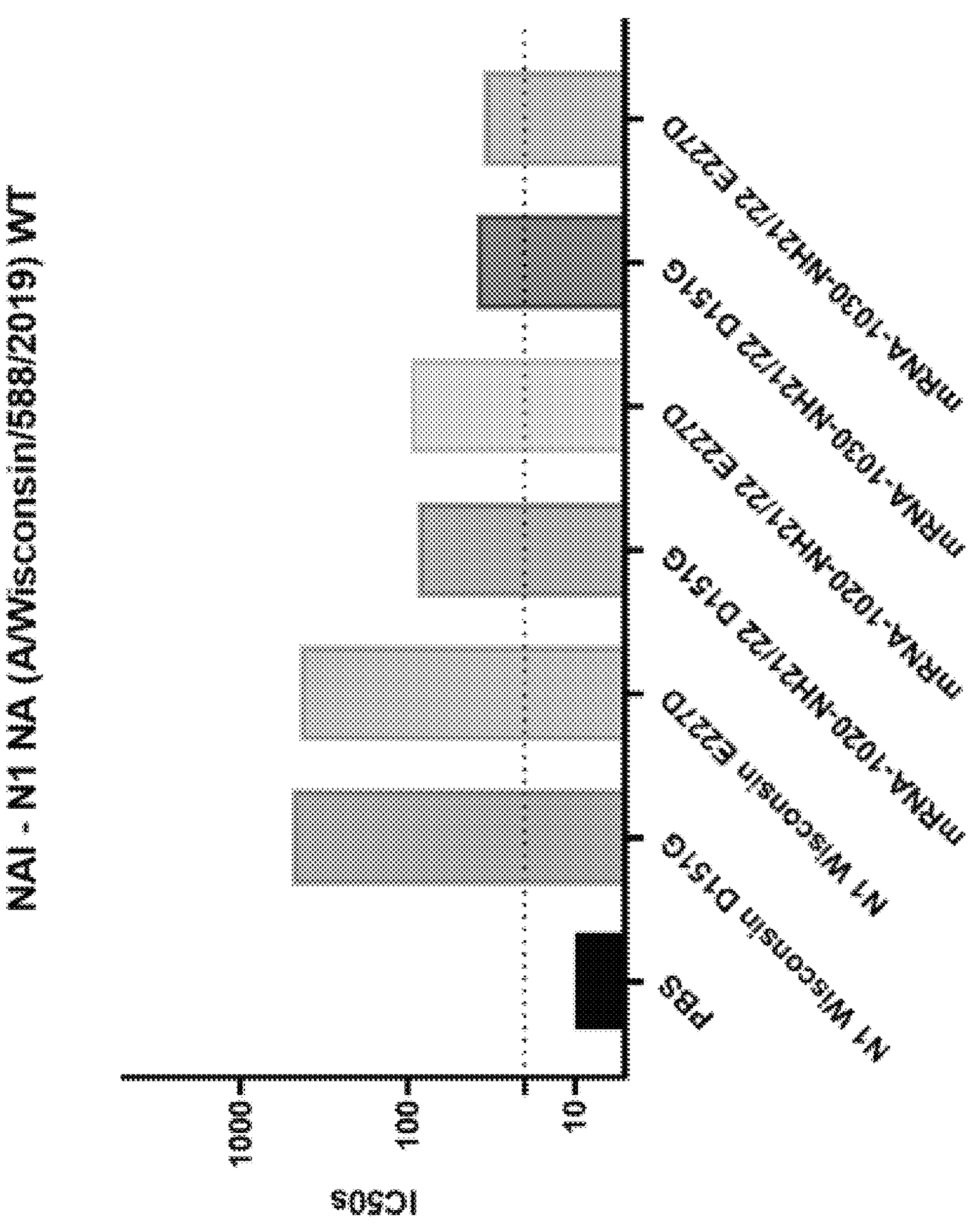
FIGS. 32A-32C are graphs showing $IC_{50}$ titers following a neuraminidase inhibition (NAI) assay against N1 NA (A/Wisconsin/588/2019) (FIG. 32A), B/Washington (FIG. 32B), and B/Phuket (FIG. 32C).
Figure 32B:
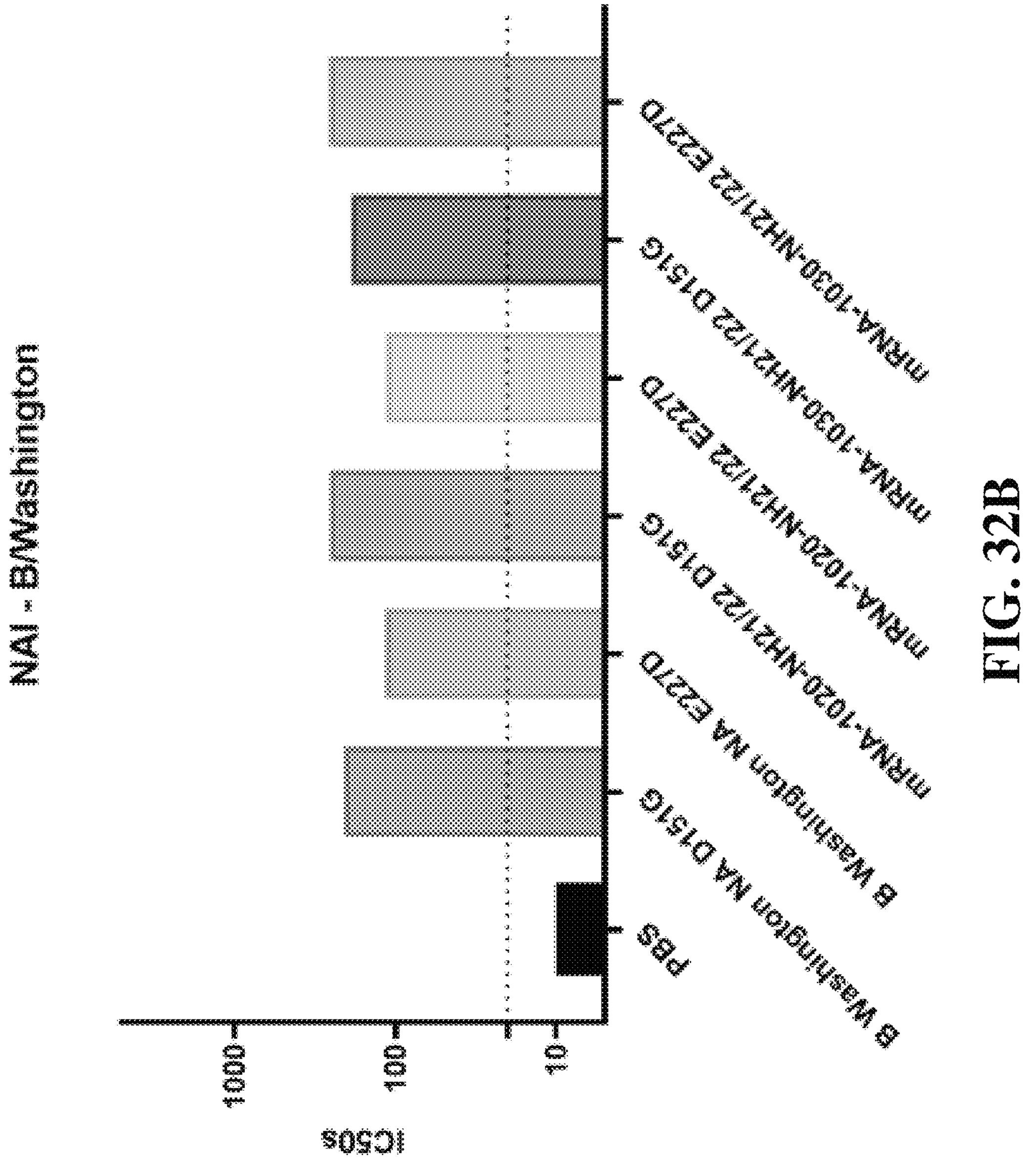
Figure 32C:
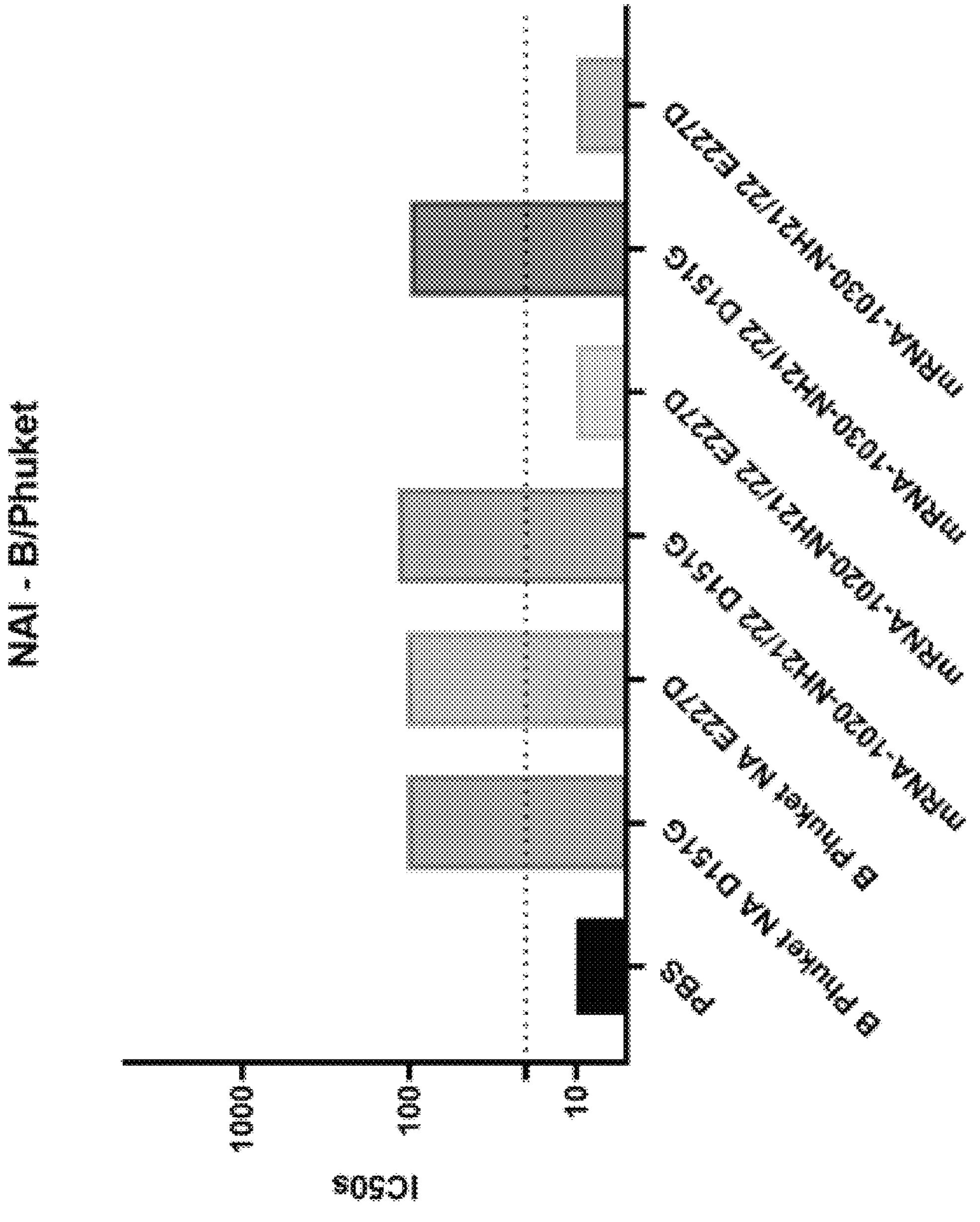

The NAI assay showed decreased titers at Day 21 (D21) for mRNA-1020 and mRNA-1030 after one dose (FIGS. 32A-32C). Additionally, HAI and microneutralization assays are performed.

Example 9: H3 Variant Screening by Fluorescence-Activated Cell Sorting (FACS)

In vitro screening was performed to compare expression of selected H3 variant designs (see Table 7 below) to that of wild-type (H3 Hong Kong 2019) using EXPI293 cells in 6-well plates. In each well, 5 mL of culture (1e6 cells/mL) was shaken at 120 rpm. The TRANSIT®-mRNA Transfection Kit (2 ul per 1 ug mRNA) was used and mRNA (2.5 μg/well; 250 ng/1 million cells) was added to each well. Cells were harvested at 24, 48, and 72 hours, and then fixed with CYTOFIX™ (BD Biosciences) and stained (the primary antibody, which is H3-specific, was mAb 41-5E04 (Genscript) and the secondary antibody was goat anti-human IgG AF647).

TABLE 7

Experimental Groups

| # | HA0 | 33 | 46 | 219 | 362 | 369 | 371 | 392 | 447 | 464 | 467 | 494 | 504 | predicted effect |
|---|---|---|---|---|---|---|---|---|---|---|---|---|---|---|
| WT | H3_HK/45/2019_WT | H | T | T | M | F | H | Q | L | F | T | I | H | x |
| 1 | H3_HK/45/2019_1_ H17aY | Y | . | . | . | . | . | . | . | . | . | . | . | stabilizing |
| 2 | H3_HK/45/2019_2_ T203aI | . | . | I | . | . | . | . | . | . | . | . | . | stabilizing |
| 3 | H3_HK/45/2019_3_ M17bL | . | . | . | L | . | . | . | . | . | . | . | . | stabilizing |
| 4 | H3_HK/45/2019_4_ F24B_Y | . | . | . | . | Y | . | . | . | . | . | . | . | |
| 5 | H3_HK/45/2019_5_ H26B_Y | . | . | . | . | . | Y | . | . | . | . | . | . | stabilizing |
| 6 | H3_HK/45/2019_6_ L102B_M | . | . | . | . | . | . | . | M | . | . | . | . | |
| 7 | H3_HK/45/2019_7_ F119B_Y | . | . | . | . | . | . | . | . | Y | . | . | . | |
| 8 | H3_HK/45/2019_8_ T122B_V | . | . | . | . | . | . | . | . | . | V | . | . | |
| 9 | H3_HK/45/2019_9_ I149B_M | . | . | . | . | . | . | . | . | . | . | M | . | |
| 10 | H3_HK/45/2019_10_ H159B_P | . | . | . | . | . | . | . | . | . | . | . | P | |
| 11 | H3_HK/45/2019_11 | . | . | I | L | . | . | . | . | . | . | . | . | |
| 12 | H3_HK/45/2019_12 | . | . | I | . | . | Y | . | . | . | . | . | . | |
| 13 | H3_HK/45/2019_13 | . | . | I | . | . | . | . | . | . | . | M | . | |
| 14 | H3_HK/45/2019_14 | . | . | I | . | . | . | . | . | . | . | . | P | |
| 15 | H3_HK/45/2019_15 | . | . | . | L | . | Y | . | . | . | . | . | . | |
| 16 | H3_HK/45/2019_16 | . | . | . | L | . | . | . | . | . | . | M | . | |
| 17 | H3_HK/45/2019_17 | . | . | . | L | . | . | . | . | . | . | . | P | |
| 18 | H3_HK/45/2019_18 | . | . | . | . | . | Y | . | . | . | . | M | . | |
| 19 | H3_HK/45/2019_19 | . | . | . | . | Y | . | . | . | . | . | . | P | |
| 20 | H3_HK/45/2019_20 | . | . | I | L | . | Y | . | . | . | . | . | . | |
| 21 | H3_HK/45/2019_21 | . | . | I | L | . | . | . | . | . | . | M | . | |
| 22 | H3_HK/45/2019_22 | . | . | I | L | . | . | . | . | . | . | . | P | |
| 23 | H3_HK/45/2019_23 | . | . | I | L | . | Y | . | . | . | . | M | . | |
| 24 | H3_HK/45/2019_24 | . | . | I | L | . | . | . | . | . | . | . | P | |
| 25 | H3_HK/45/2019_25 | . | . | I | L | . | Y | . | . | . | . | M | P | |
| 26 | H3_HK/45/2019_26_ ΔCT | . | . | . | . | . | . | . | . | . | . | . | . | delta cyt tail |
| 27 | H3_HK/45/2019_27_ T30C, Q47C | . | C | . | . | . | . | C | . | . | . | . | . | |

Figure 17:
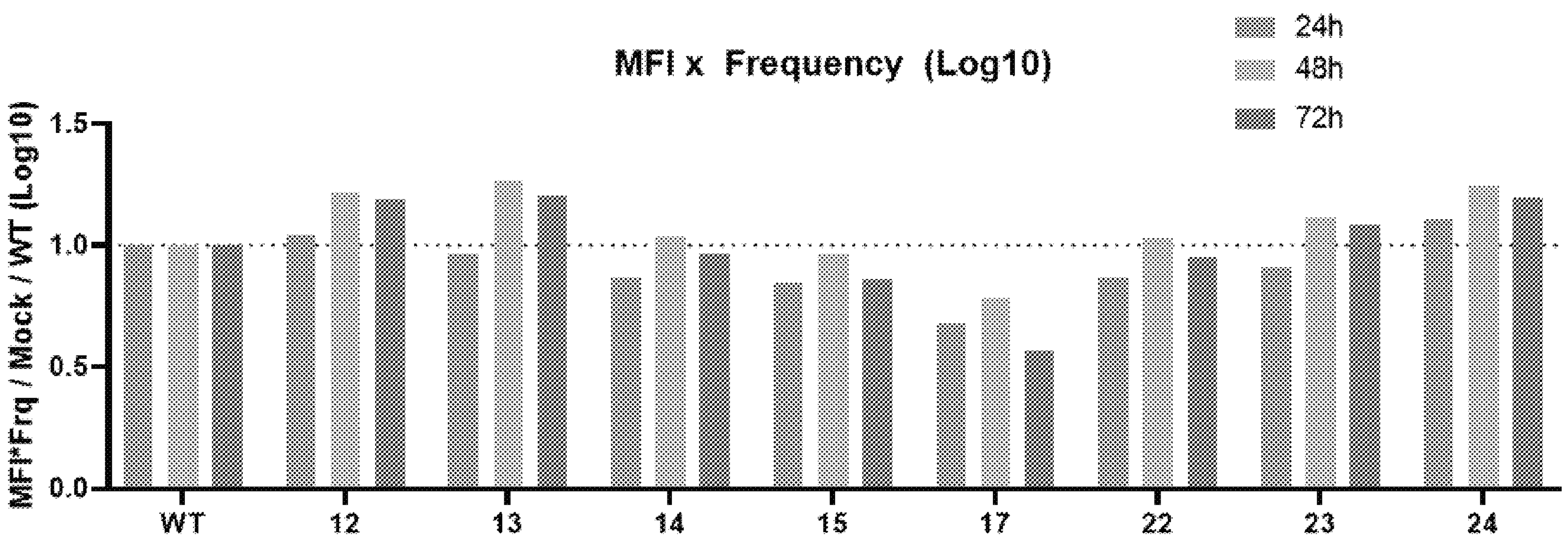
FIG. 17 is a graph showing relative expression of H3 antigens as the mean fluorescence intensity (MFI)×frequency normalized to wild-type at 24, 48, and 72 hours post-mRNA transfection.

The cells were analyzed by flow cytometry using an LSR Fortessa. Frequency (%) of positive cells and mean fluorescent intensity (MFI) at 72 hours were calculated for all H3 designs (data not shown). Expression of higher expressor designs (designs 12-24) was confirmed in a second experiment. Frequency (%) of positive cells and mean fluorescent intensity (MFI) at 24, 48 and 72 hours were calculated (data not shown). Mean fluorescence intensity (MFI)×frequency was normalized to wild-type at 24, 48, and 72 hours of the different H3 variants (FIG. 17). As shown in FIG. 17, there was very little change in expression compared to the wild-type H3 protein. GR15 and GR17 variants had lower expression than the wild-type. None of these mutations were found to be deleterious or to impact expression levels negatively.

Example 10: H1, H3N2, H5N8 Protein Production

Different H5, N8, H1, H3, and N2 proteins were designed and produced, generating the yields shown in Table 8 below.

TABLE 8

| Experimental Yields (Protein) | |
|---|---|
| Design | Yield mg/L |
| H5/Astrakhan/2020 _Th_Fd_H6_St | 3.2 mg |
| H5/Astrakhan/2020_APB_Th_Fd_H6_St | 5.8 mg |
| N8/Astrakhan/2020 _N_HisSt_VASP_Th_(64-Cterm) | 1.2 mg |
| N8/Astrakhan/2020 _N_HisSt_TB_Th_(64-Cterm) | 7.6 mg |
| H1/Wisconsin_WT_Th-Fd-H6-St | 4.6 mg |
| H1/Wisconsin_E22C,K375C_Th-Fd-H6-St | 2.0 mg |
| H1/Wisconsin_ HA0_E22C, K375C_ Th-Fd-H6-St | 2.64 mg |
| H3/Cambodia/2020 _Th-Fd-H6-St | 3 mg |
| N2/Cambodia/2020 N_HisSt_VASP_Th_(83-Cterm) | 3.2 mg |

The resulting proteins were then run through an SDS-PAGE gel and visualized with a Coomassie stain under reducing conditions (reducing gels were run under boiled conditions; 5 ug of protein loaded per well) and non-reducing conditions, which demonstrated that the correct proteins were generated (data not shown).

Figure 18A:
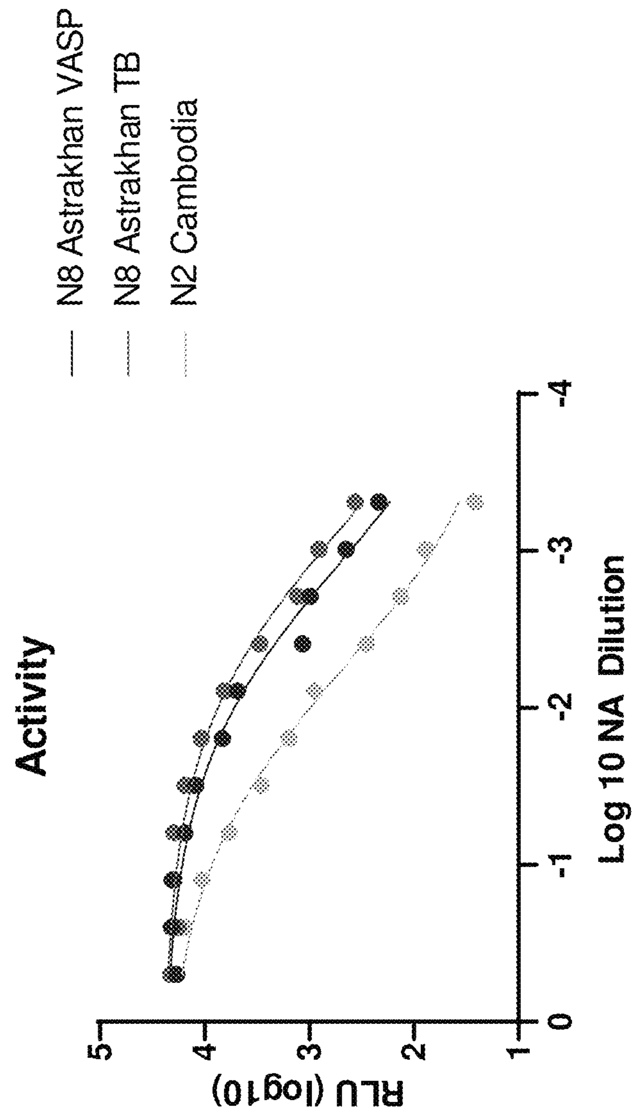
FIGS. 18A-18B are graphs showing neuraminidase activity (FIG. 18A) and activity titers (FIG. 18B) of three different neuraminidase variants.
Figure 18B:
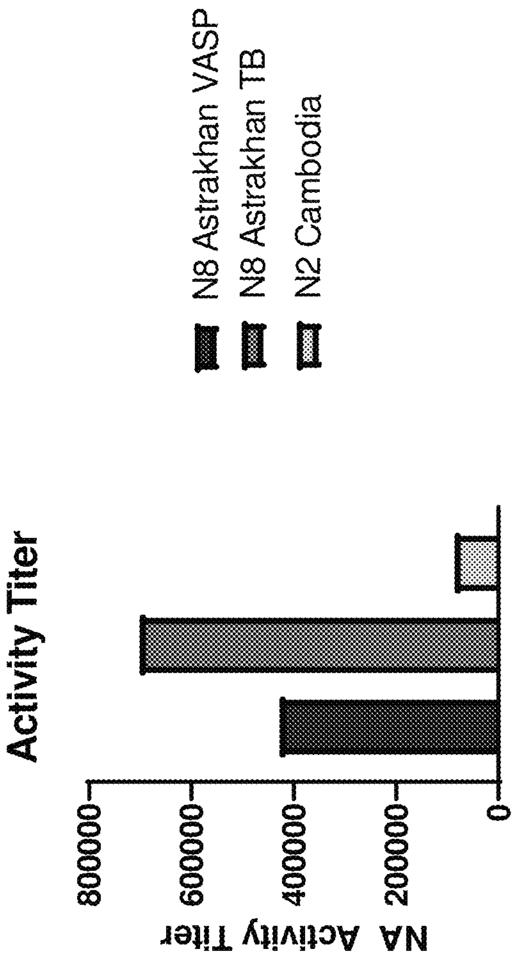
Figure 19A:
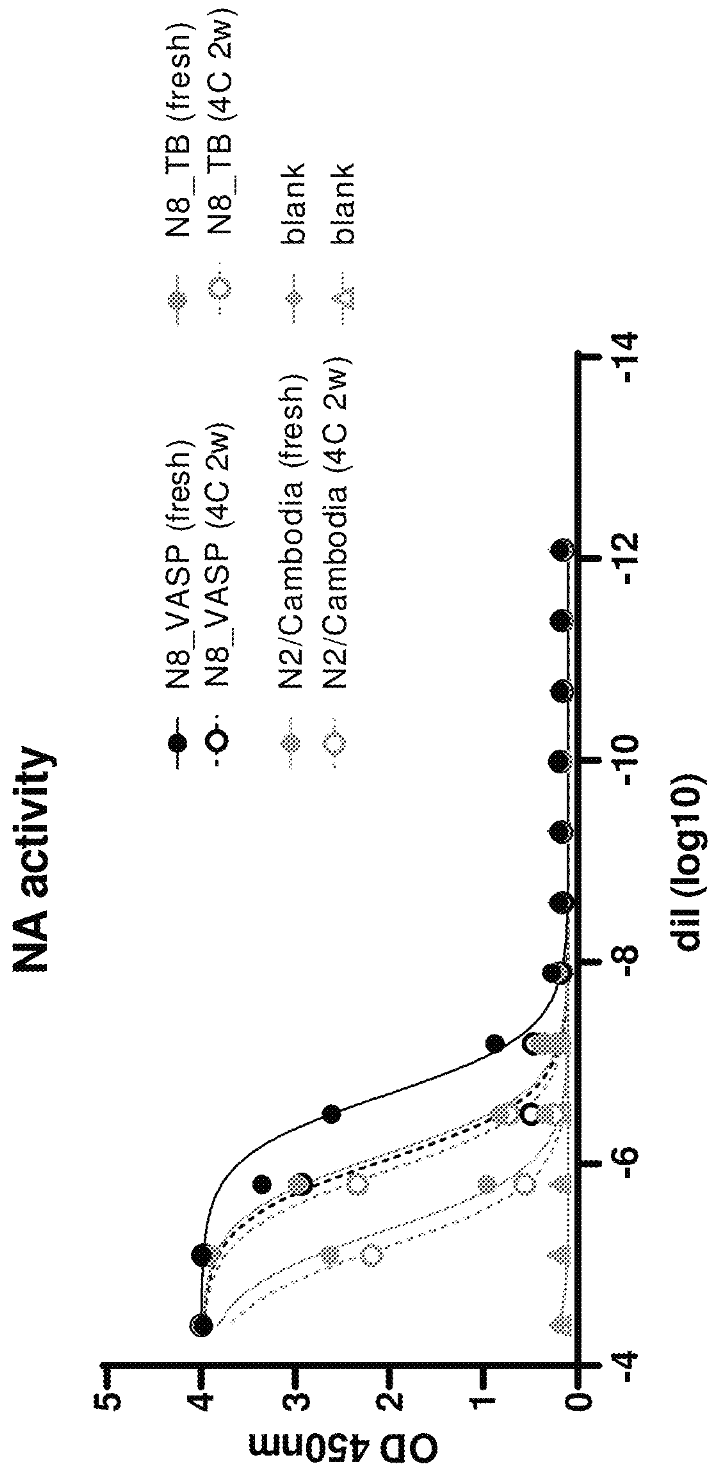
FIGS. 19A-19B are graphs showing neuraminidase activity (FIG. 19A) and fetuin cleavage (FIG. 19B) of three different neuraminidase variants, each of which was either "fresh" or stored for two weeks at 4° C.
Figure 19B:
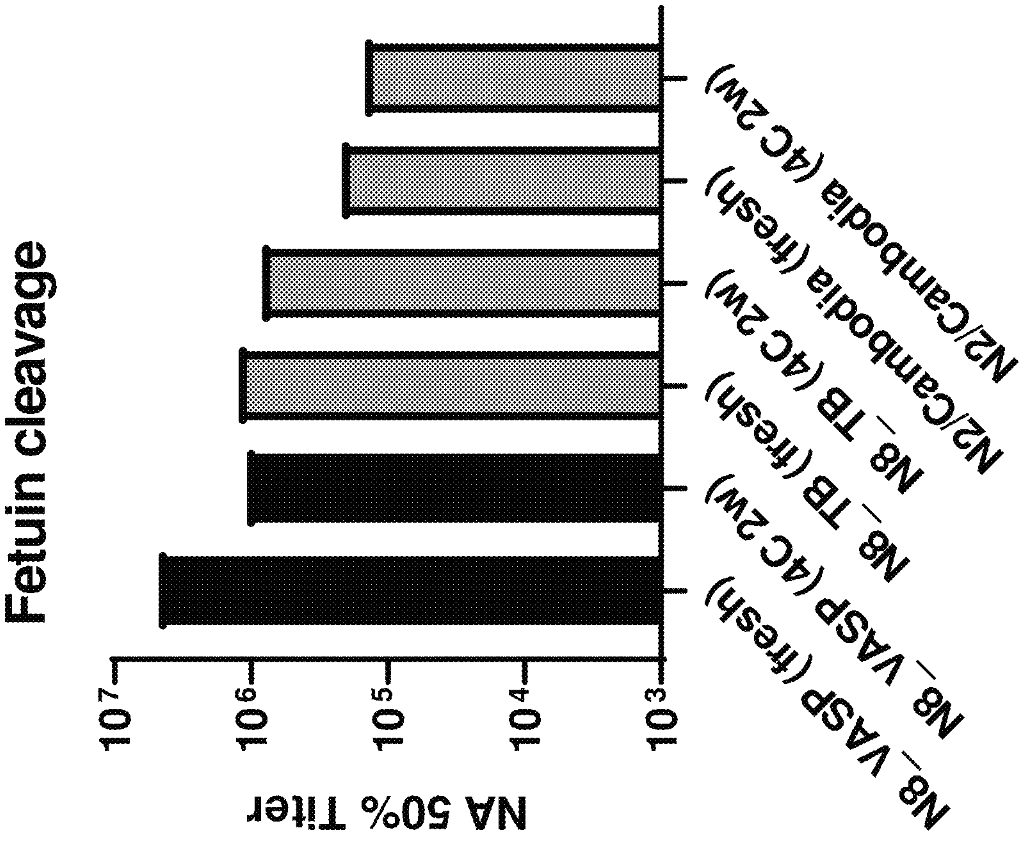
Figure 20A:
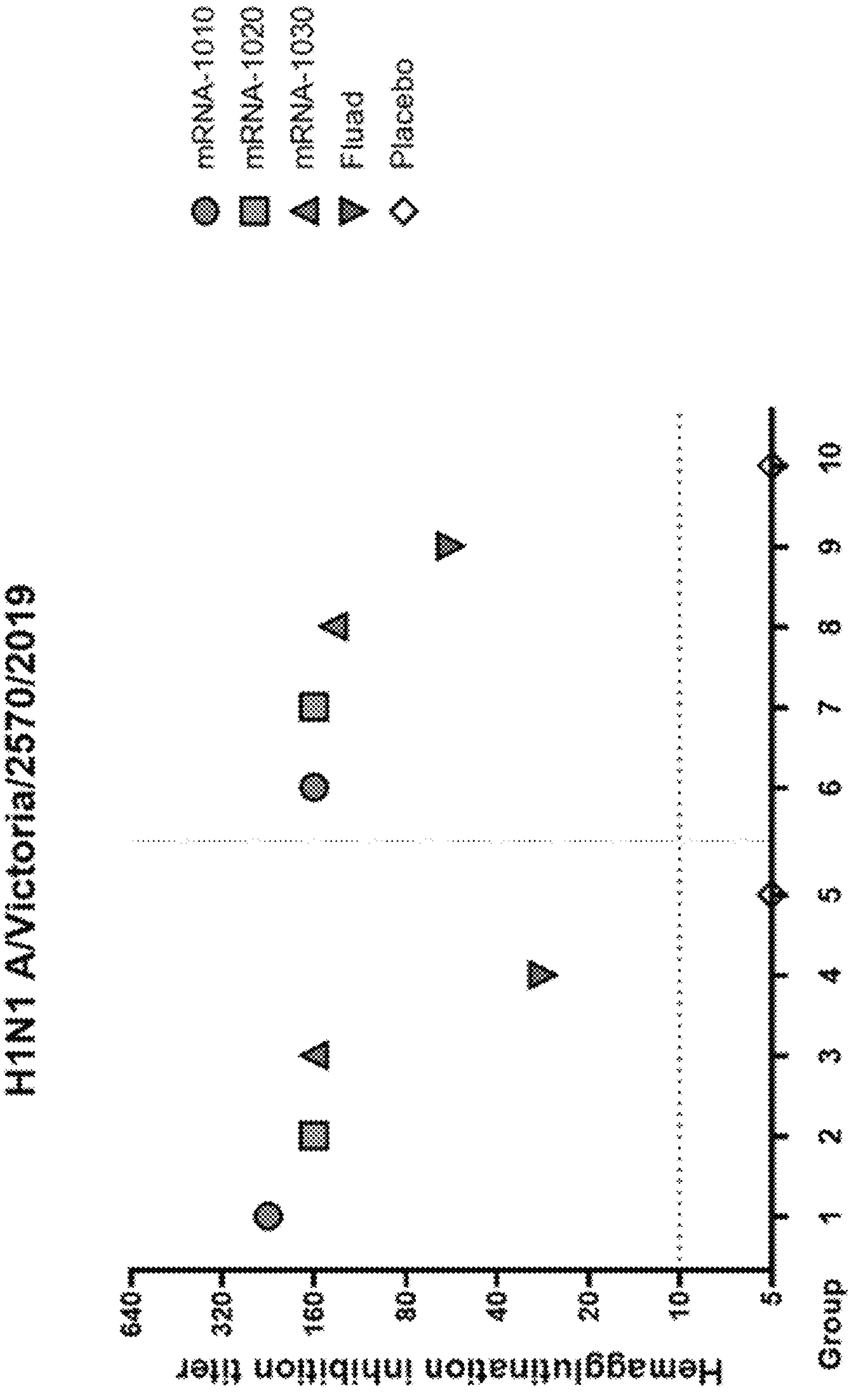
FIGS. 20A-20D are graphs showing the hemagglutinin (HA) inhibition (HAI) titers for different formulations of mRNA vaccines (mRNA-1010, mRNA-1020, and mRNA-1030).
Figure 20B:
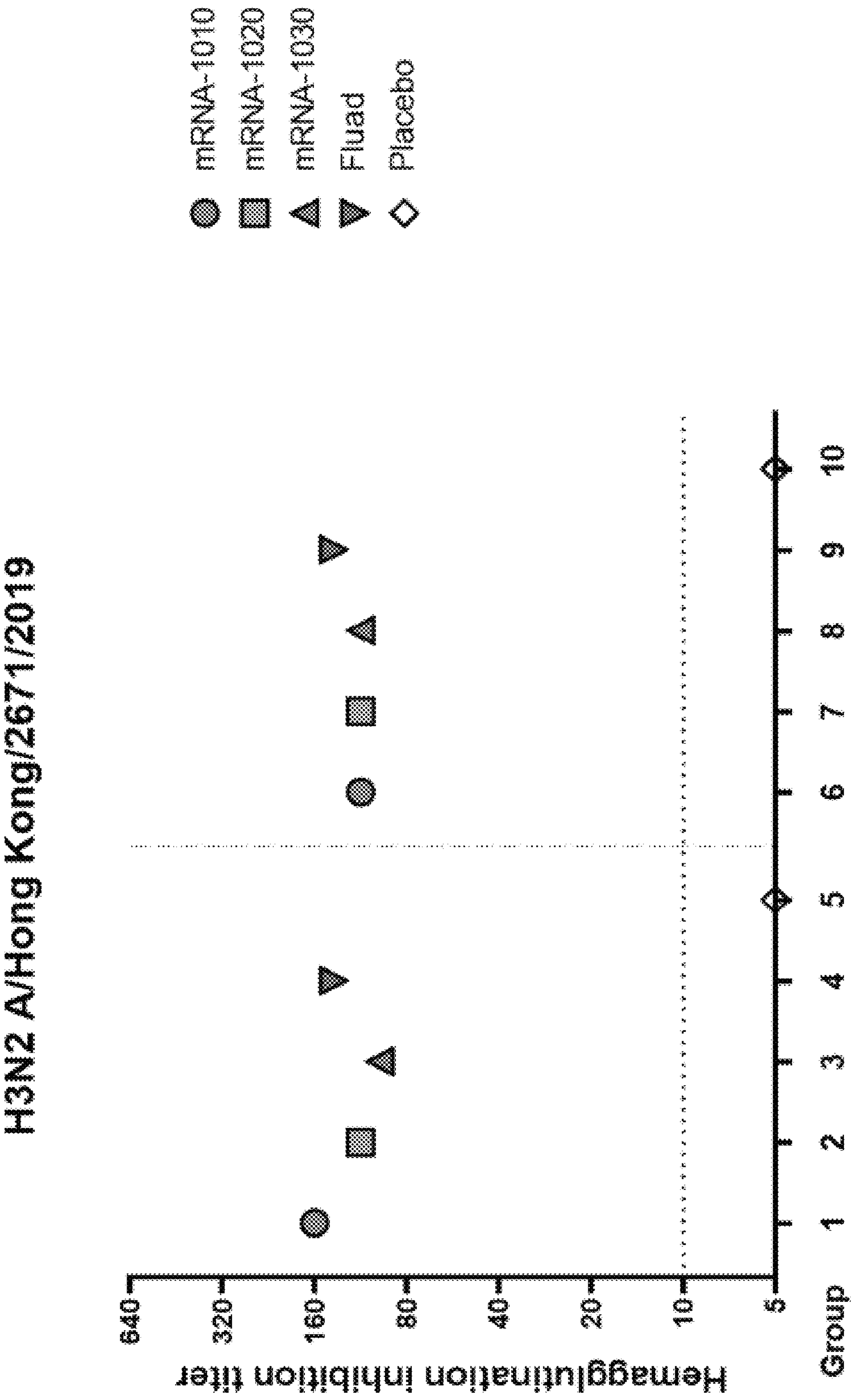
Figure 20C:
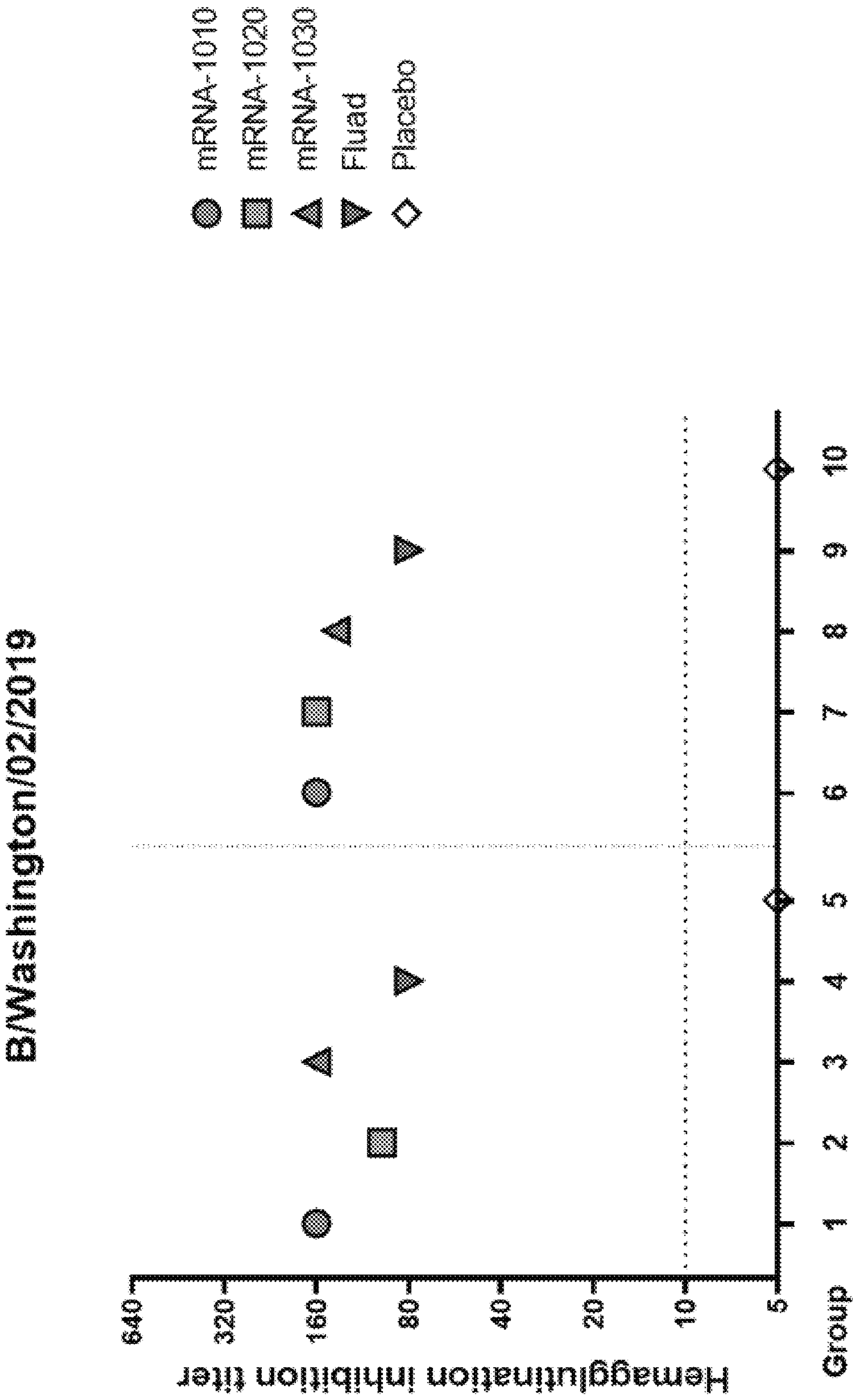
Figure 20D:
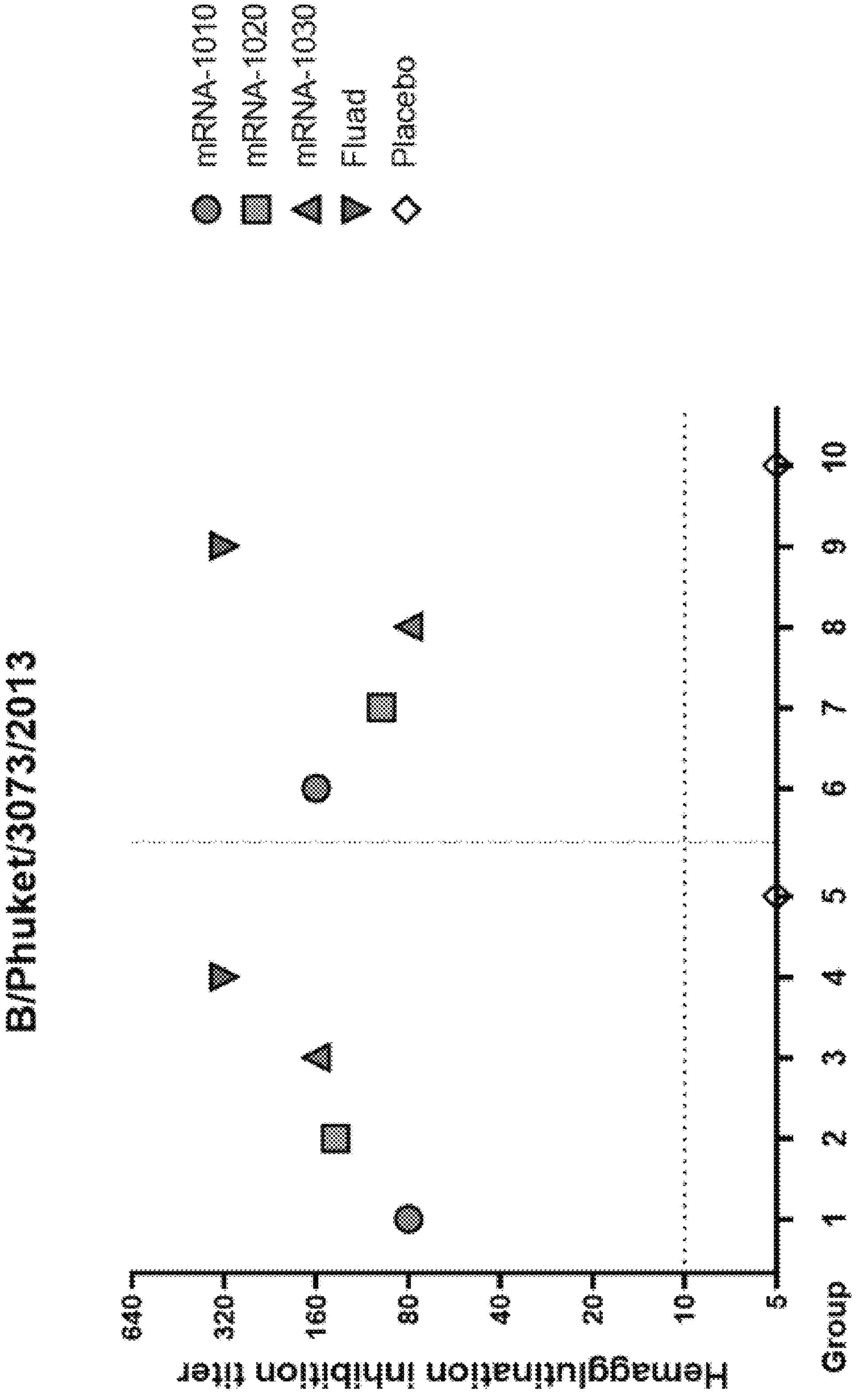
Figure 21A:
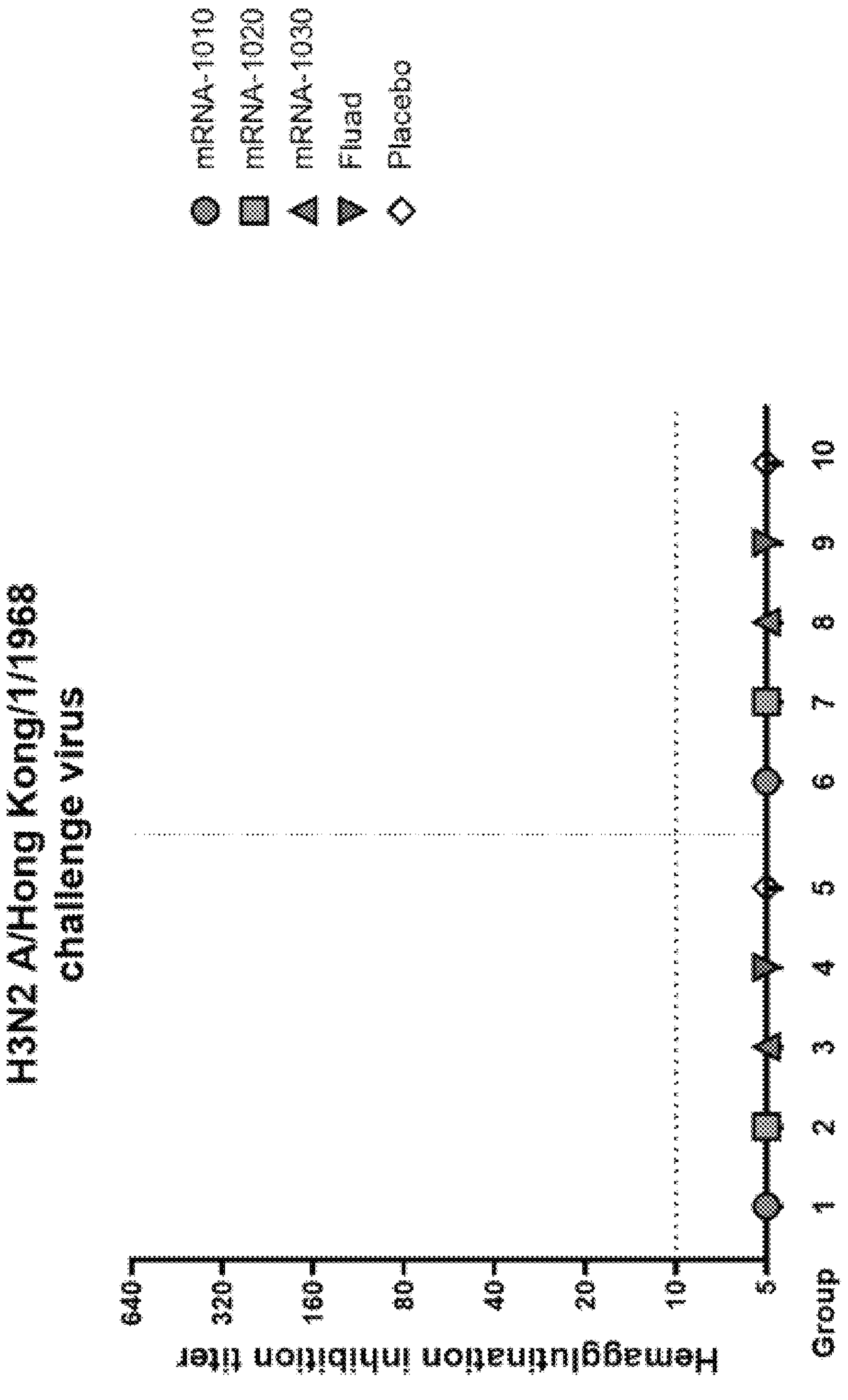
FIGS. 21A-21B are graphs showing HAI titers for different formulations of mRNA vaccines (mRNA-1010, mRNA-1020, and mRNA-1030) against challenge viruses H3N2 Hong Kong/1/1968-MA20 (FIG. 21A) and pH1N1 A/Netherlands/602/2009 (FIG. 21B).
Figure 21B:
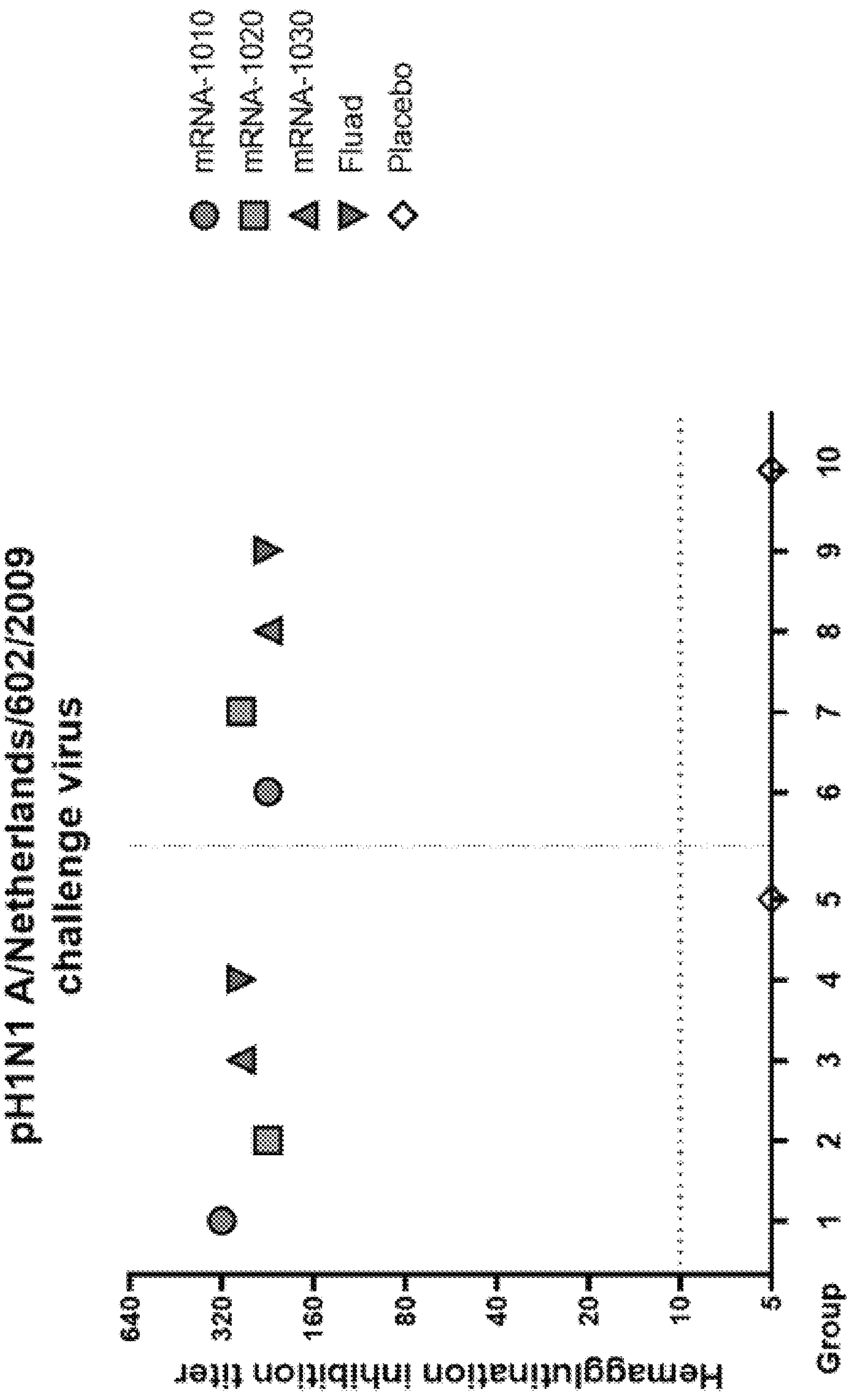
Figure 22A:
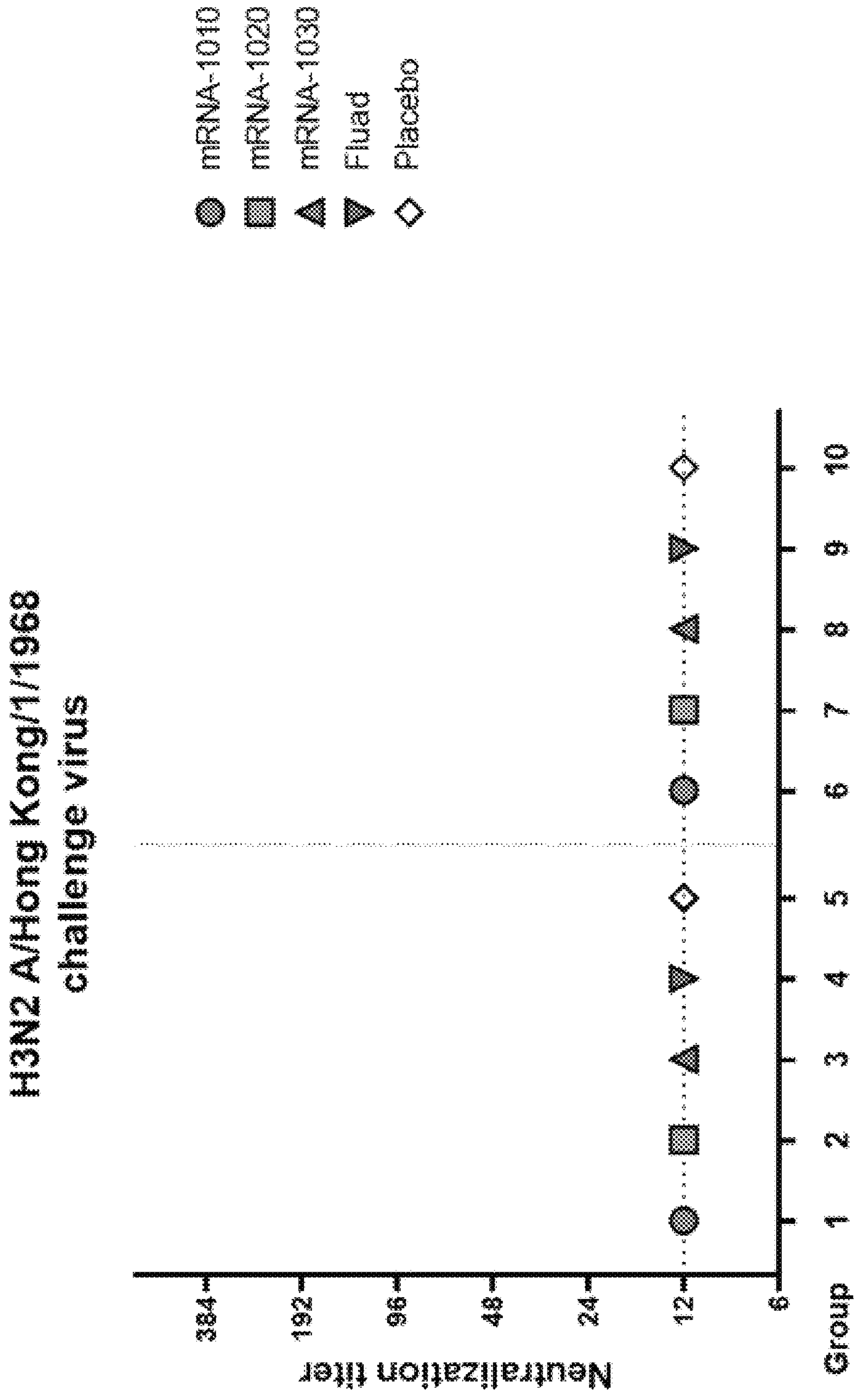
FIGS. 22A-22B are graphs showing microneutralization titers for different formulations of mRNA vaccines (mRNA-1010, mRNA-1020, and mRNA-1030) against challenge viruses H3N2 Hong Kong/1/1968-MA20 (FIG. 22A) and pH1N1 A/Netherlands/602/2009 (FIG. 22B).
Figure 22B:
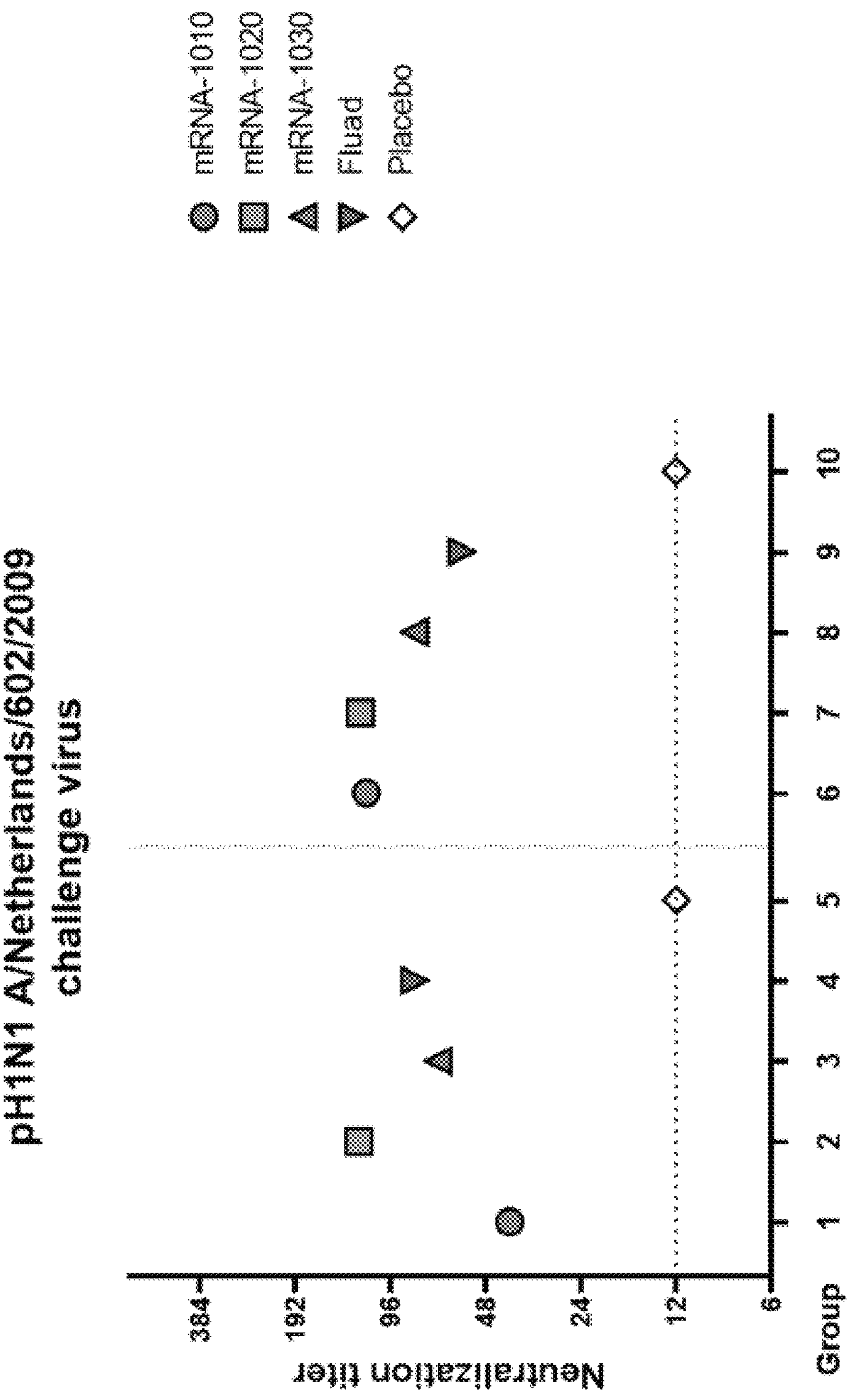

A 2-(4-methylumbelliferyl)-α-D-N-acetylneuraminic acid (MUNANA) fluorescence-based assay was performed to test the neuraminidase (NA) activity of different proteins. In FIGS. 18A-18B, samples were normalized to 0.6 mg/ml, then pre-diluted 1/500, followed by a two-fold dilution. As can be seen in FIGS. 18A and 18B, the two N8 proteins were found to have greater NA activity than the N2 protein. In FIGS. 19A-19B, an enzyme-linked lectin assay (ELLA) was performed. The same three proteins were assayed for NA activity, but the impact of cold storage (4° C. for two weeks) was examined. As can be seen in FIG. 19A, cold storage slightly reduced the NA activity in each group tested. NA is known to cleave sialic acids on fetuin. FIG. 19B shows measurements of NA activity (fetuin cleavage), demonstrating a slight decrease in NA activity in the groups that had undergone cold storage compared to the "fresh" groups.

Example 11: Multiantigen Dose Response and Immune Interference Analysis Using 2021 Southern Hemisphere Influenza Strains (Mice)

In this example, multiple influenza virus HA and NA antigens administered as mRNA vaccines were evaluated for immunogenicity and immunological interference between the antigens. Further, the data was examined for any dampening of immune response towards one antigen over another different antigen when all antigens were co-administered simultaneously as mRNA vaccines formulated in lipid nanoparticles (LNPs). For this study, the antigens were formulated separately into different LNPs and mixed before administration. In all cases, the NA protein was rendered enzymatically inactive by catalytic site residue mutation prior to inclusion in the vaccine. Briefly, mice were injected with one of the following compositions: mRNA-1010 (a 1:1:1:1 ratio of H1 A/Victoria HA:H3 HK HA:B Washington HA:B Phuket HA), mRNA-1020 (a 1:1:1:1:1:1:1:1 ratio of H1 A/Victoria HA:H3 HK HA:B Washington HA:B Phuket HA:N1 Victoria NA:N2 HK NA:B Washington NA:B Phuket NA), mRNA-1030 (a 3:3:3:3:1:1:1:1 ratio of H1 Victoria HA:H3 HK HA:B Washington HA:B Phuket HA:N1 Wisconsin NA:N2 HK NA:B Washington NA:B Phuket NA), Fluad (an adjuvanted seasonal vaccine comparator, Northern Hemisphere composition mismatched for the H1N1 strain compared to the mRNA vaccines), or a PBS control. The total mRNA dose was higher in the mRNA-1020 group (2.5 μg/HA and 2.5 μg/NA) than the other two groups (mRNA-1010, 2.5 μg/HA; mRNA-1030, 2.5 μg/HA; 0.83 μg/NA). The mice were administered the composition on a prime only vaccination schedule on Day 0 (D0). On Day 21 (D21), a hemagglutination inhibition (HAI) assay was performed. The results are shown in FIGS. 20A-20D, which demonstrate that the mRNA vaccines elicited robust hemagglutination inhibition titers after a single dose. The results also show that HAI antibodies elicited in mice are comparable to the adjuvanted seasonal comparator vaccine (Fluad). No interference due to addition of NA antigens was observed. HAI and microneutralization titers were also measured against H3N2 (Groups 1-5) and H1N1 (Groups 6-10) challenge virus strains (mouse-adapted viruses based on isolates from 1968 and 2009, respectively) (FIGS. 21A-21B and 22A-22B). The H1N1 and H3N2 challenge viruses were mismatched from the vaccine strains by approximately 10 and 50 years of antigenic drift respectively. The HAI and MN titers against the H3N2 challenge strain were not detectable due to the substantial antigenic mismatch to the vaccine. However, HAI and MN antibodies were elicited in mice against mismatched H1N1 challenge virus.

Figure 23A:
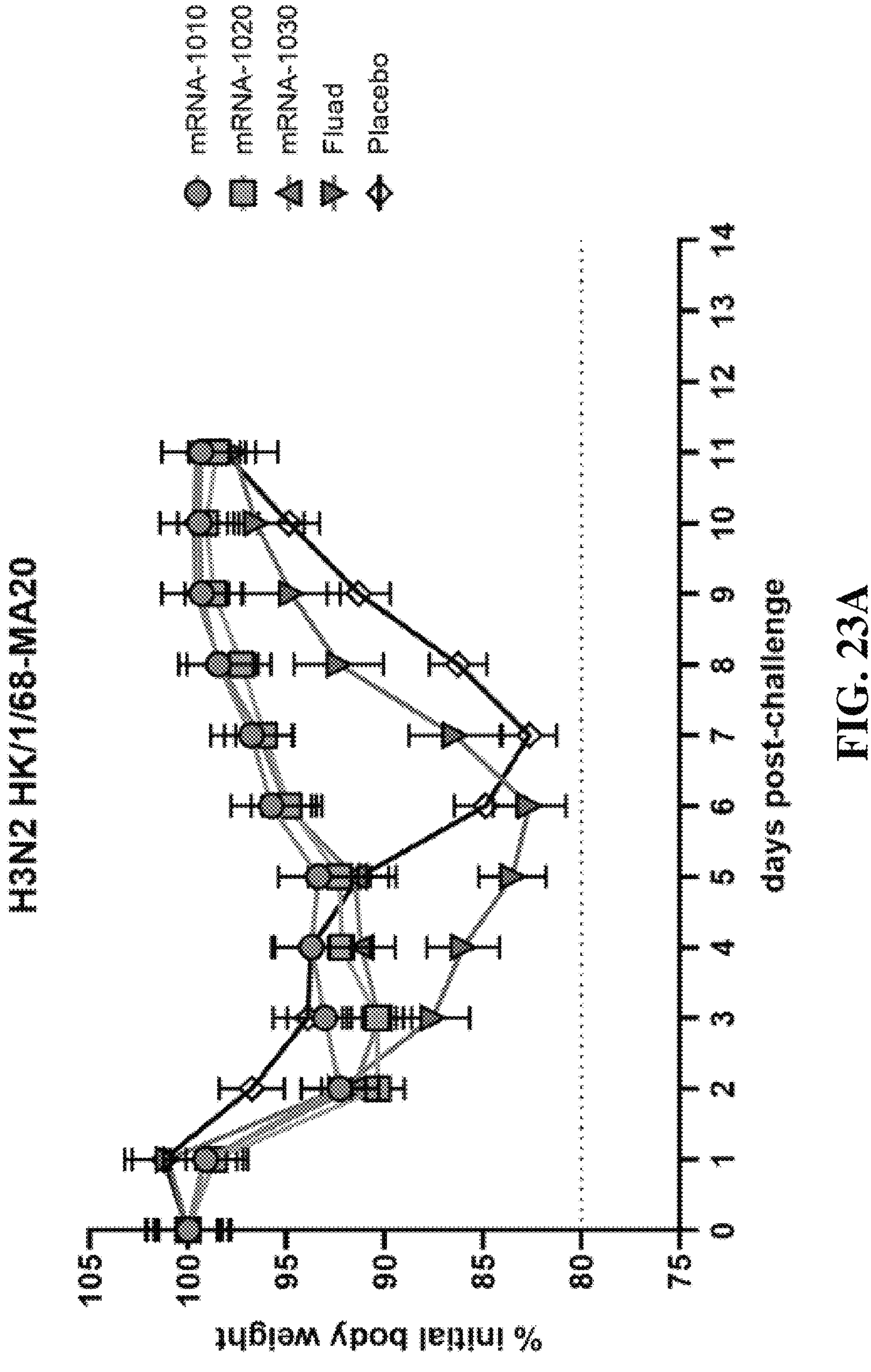
FIGS. 23A-23B are graphs showing % initial body weight of mice post-lethal challenge following administration of mRNA vaccines: mRNA-1010, mRNA-1020, mRNA-1030, Fluad (an adjuvanted seasonal vaccine comparator), or a placebo (PBS).
Figure 23B:
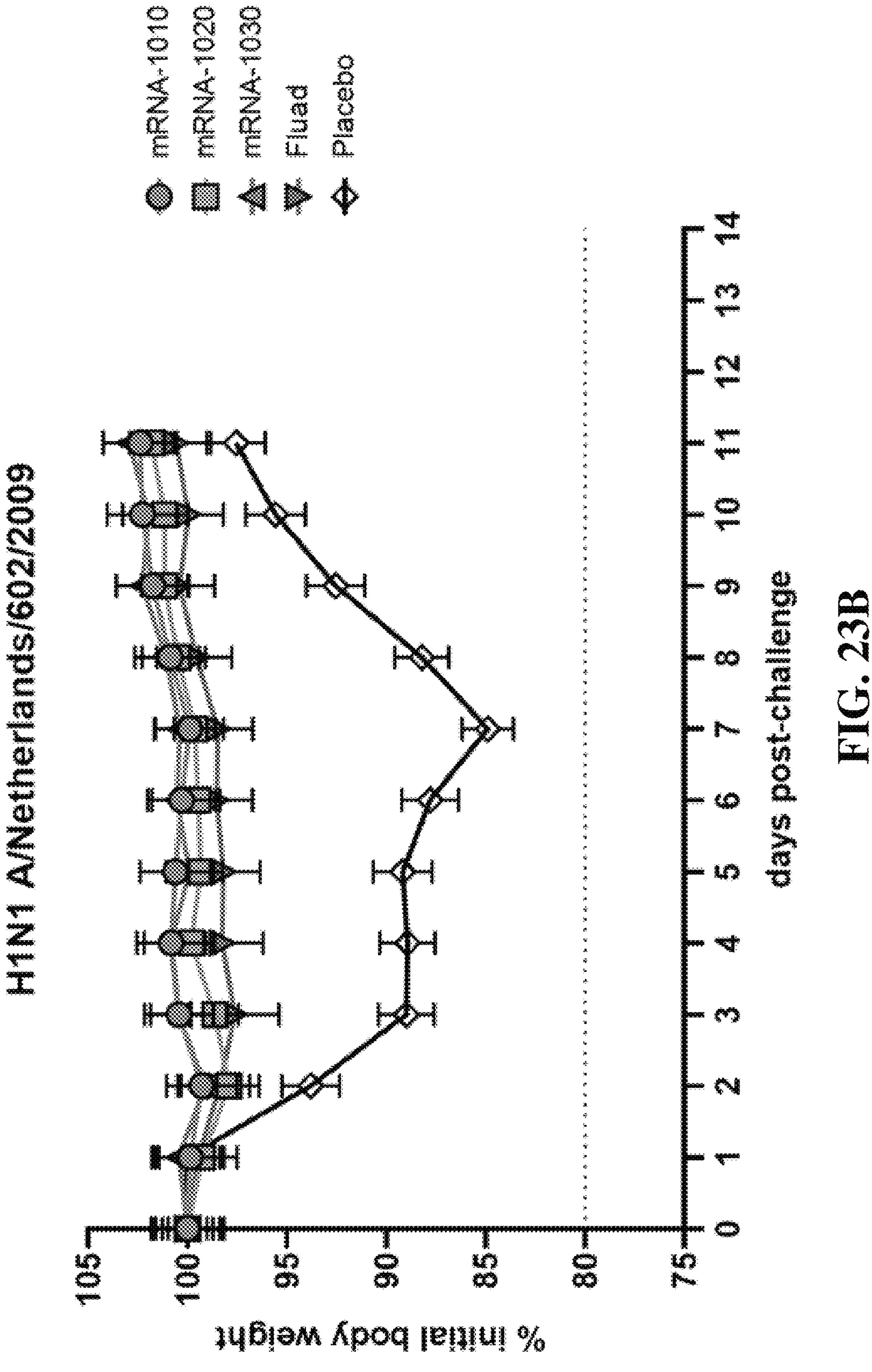
Figure 24A:
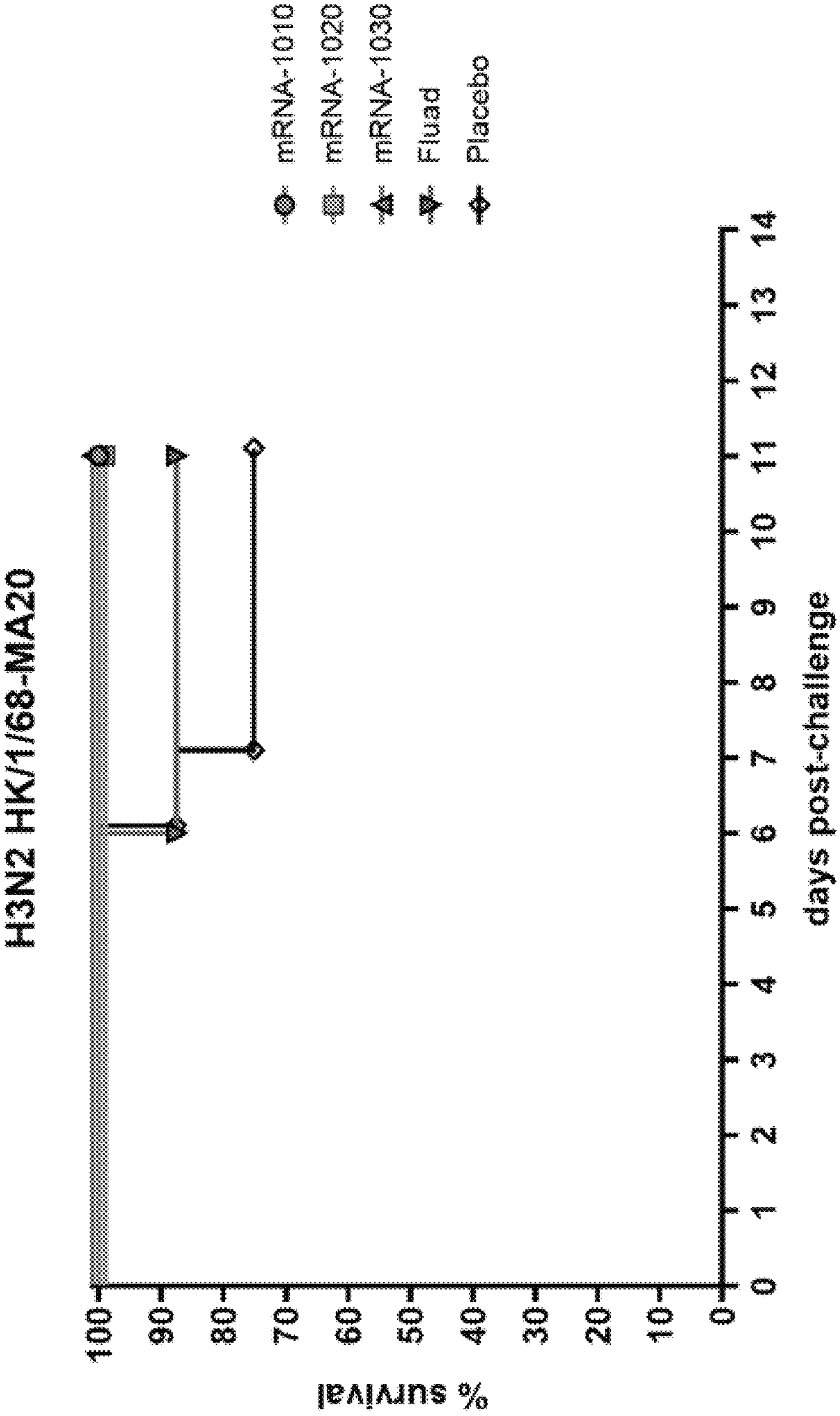
FIGS. 24A-24B are graphs showing % survival of mice post-lethal challenge following administration of mRNA vaccines: mRNA-1010, mRNA-1020, mRNA-1030, Fluad (an adjuvanted seasonal vaccine comparator), or a placebo (PBS).
Figure 24B:
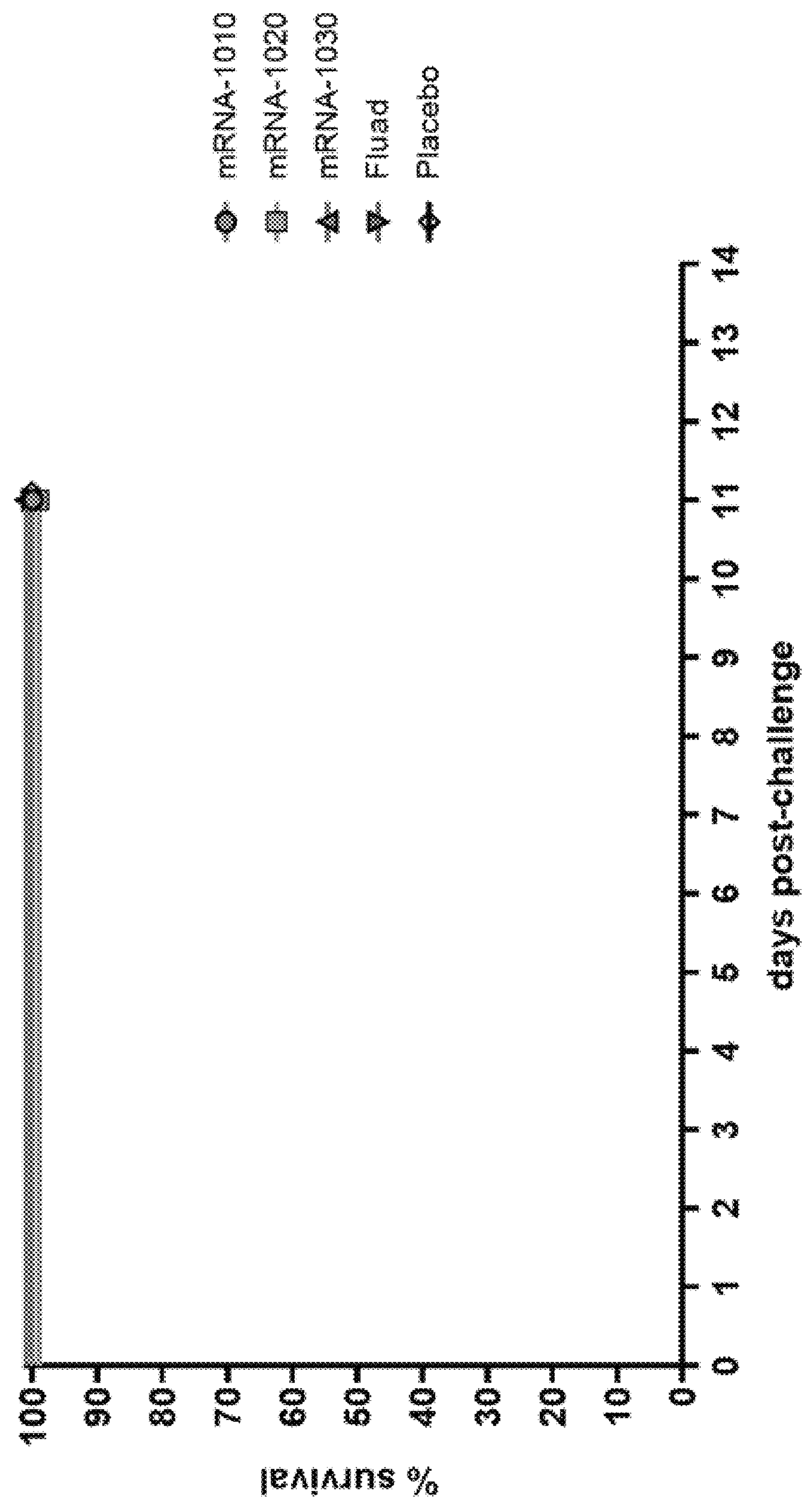
Figure 25A:
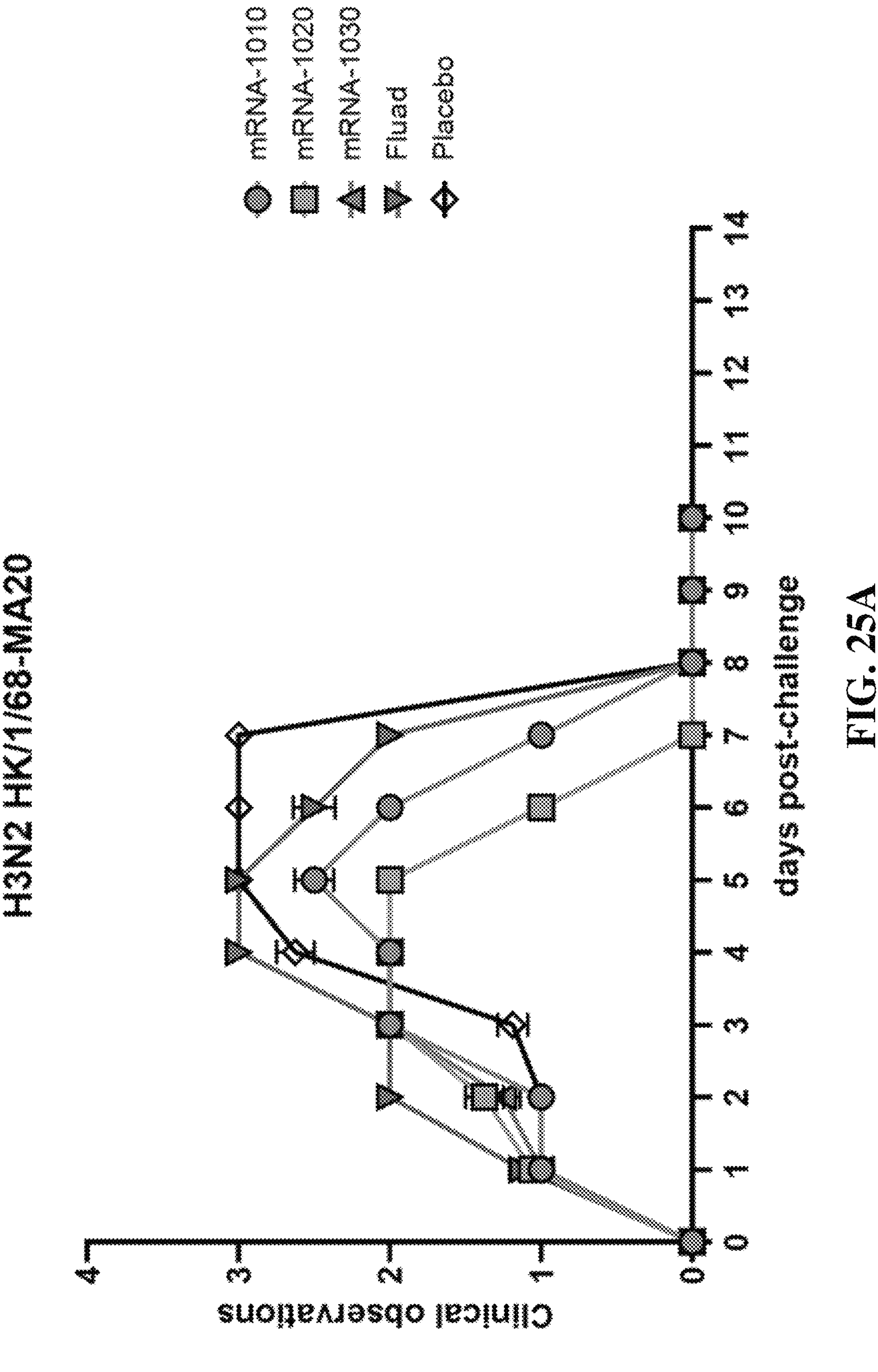
FIGS. 25A-25B are graphs showing clinical observations of mice post lethal challenge following administration of mRNA vaccines: mRNA-1010, mRNA-1020, mRNA-1030, Fluad (an adjuvanted seasonal vaccine comparator), or a placebo (PBS).
Figure 25B:
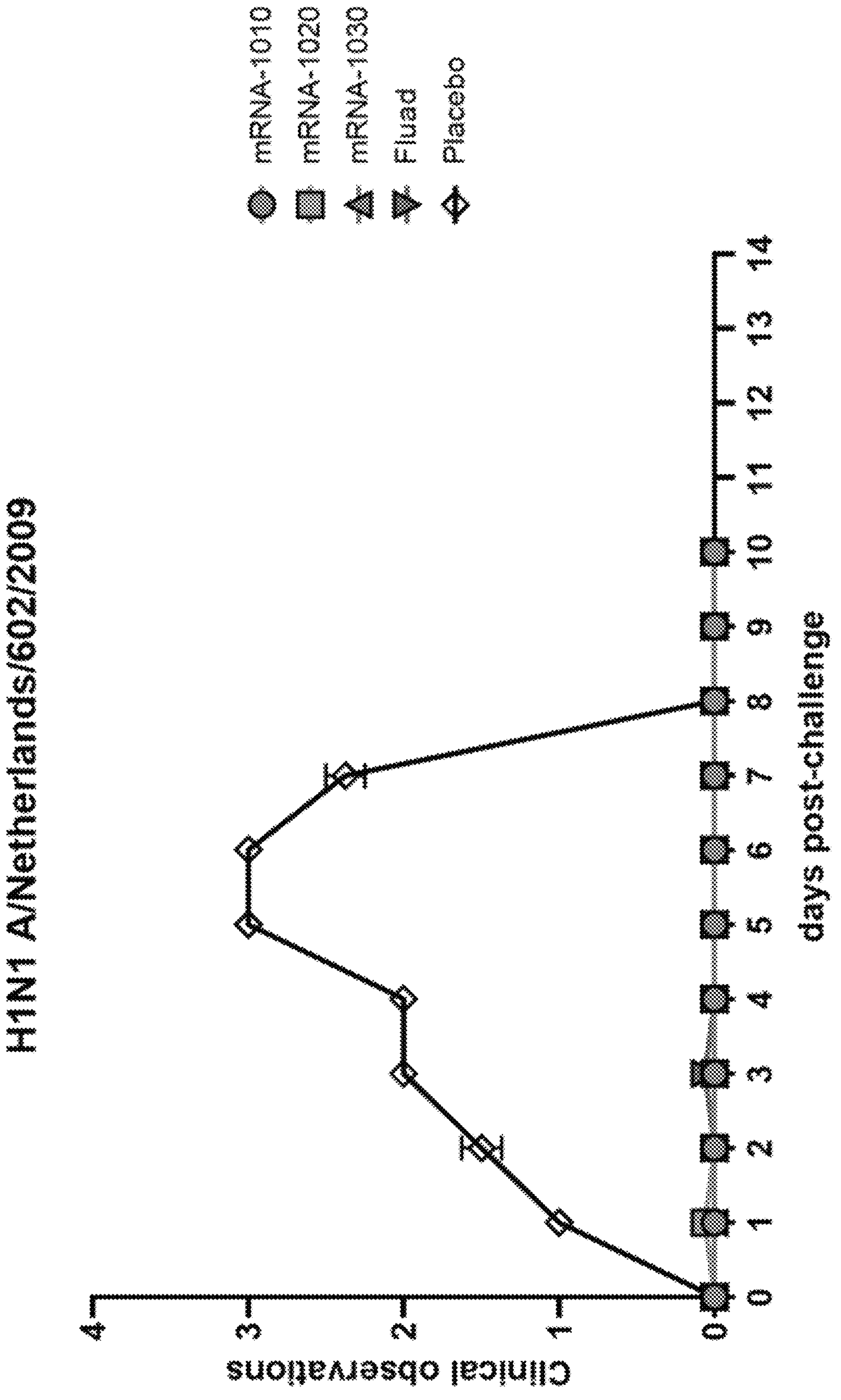

On D21, a lethal challenge was performed. The H1N1 (Groups 1-5) and H3N2 (Groups 6-10) challenge viruses were selected because they cause morbidity in mice. For fourteen days post-challenge, the mice were followed for weight loss assessment, survival, and clinical observations. Weight loss was found to be reduced in mice that received the mRNA vaccines compared to those that received the adjuvanted seasonal comparator, Fluad, after the H3N2 challenge, and those that received the control (PBS) after both H1N1 and H3N2 virus challenges (FIGS. 23A-23B). It was found that in the absence of detectable functional antibodies, the mRNA vaccines conferred superior protection against the H3N2 virus challenge. mRNA vaccination induced protective responses against the H1N1 challenge comparable to the adjuvanted seasonal comparator, Fluad, and completely protected against morbidity (FIGS. 24A-24B). It was also found that there were fewer scorable clinical symptoms in mice that received the mRNA vaccines after the H3N2 challenge (FIGS. 25A-25B).

Overall, it was found that immunization with mRNA-1010, mRNA-1020, and mRNA-1030 induced functional antibody responses after a single dose. Upon live virus challenge, mice that received mRNA vaccines lost less weight and showered fewer clinical symptoms compared to Fluad-vaccinated mice or mice in the placebo group. Also, mice that received mRNA vaccines or Fluad were fully protected against the H1N1 challenge and showed no scorable clinical symptoms.

Example 12: Evaluation of Cell Surface Expression of H3N2, H5N8 and H1 HA Mutant Constructs In this example, expression screening was undertaken to determine whether a mutation in the catalytic domain of an HA antigen would have an effect. Different potential mutants included the following: H1 Wisconsin E22C, K375C (new disulfide into the HA stem to link neighboring protomers), H1 Wisconsin E22C, K375C, HA0 (new disulfide into the HA stem to link neighboring protomers and deletion of cleavage site), and H5 Astrakhan ΔPB (replacement of polybasic cleavage site (HPAI) by LPAI sequence). HEK293t cells were plated (30,000 cells/well) in a 96-well plate. Doses of 100 ng or 500 ng mRNA were added to each well. Primary antibody mAb-CR9114 was used, and readouts were performed at 48 hours. The mRNAs tested include (from left to right) SEQ ID NOs: 86, 89, 92, 95, 98, 104, and 101 (FIGS. 26A-26C and Table 9).

TABLE 9

| Experimental Groups | |
|---|---|
| Antigen (encoded by mRNA) | SEQ ID NO: |
| H3 Hongkong WT | 86 |
| H3_Cambodia_WT | 89 |
| H1_Wisconsin_WT | 92 |
| H1_Wisconsin_E22C_K375C | 95 |
| H1_Wisconsin_E22C_K375C_HA0 | 98 |
| H5_Astrakhan_WT | 104 |
| H5_Astrakhan_APB | 101 |

Figure 26A:
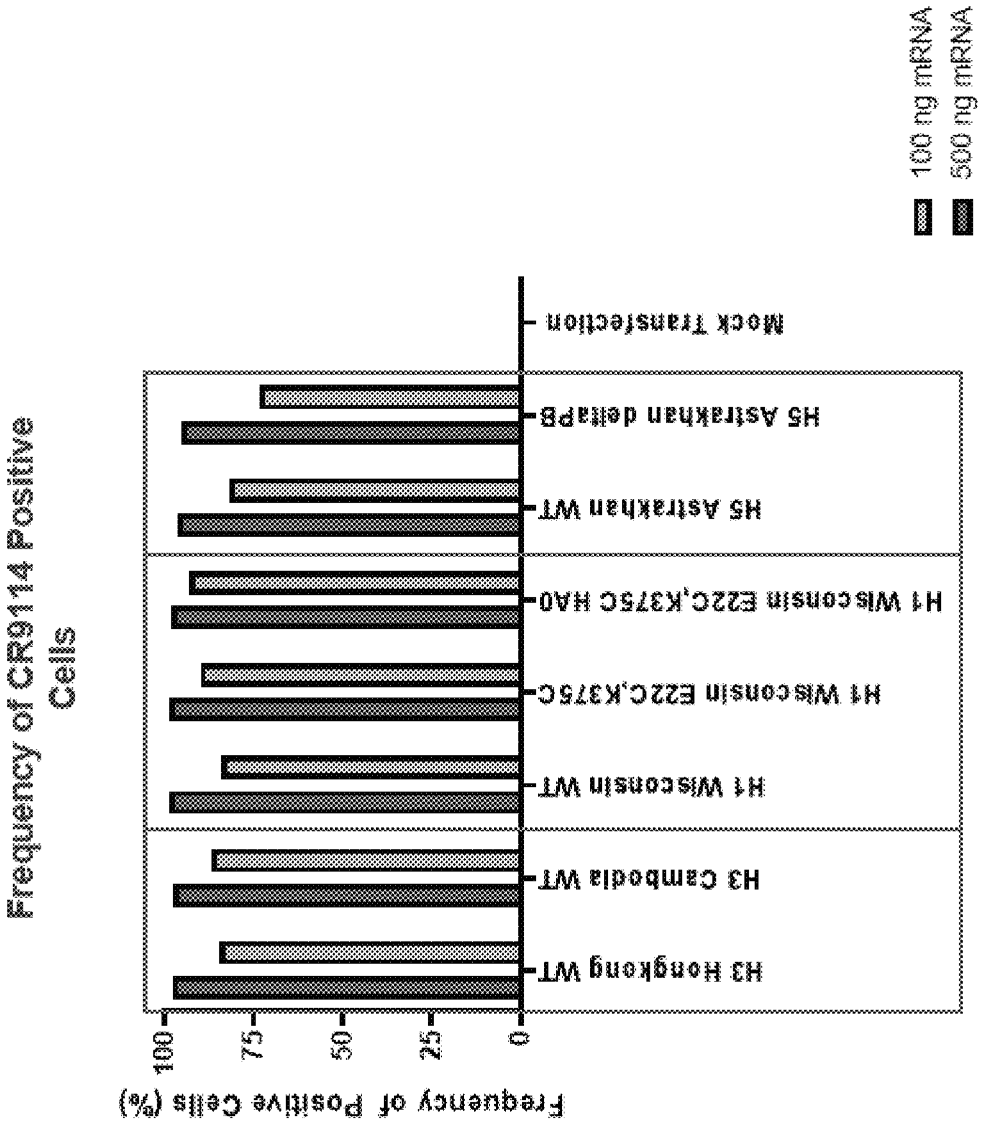
FIGS. 26A-26C are graphs showing frequency of CR9114 positive cells (FIG. 26A), the mean fluorescence intensity (MFI) of CR9114 positive cells (FIG. 26B), and frequency× MFI of CR9114 positive cells normalized to wild-type at 48 hours of the different influenza antigens and variants (H3 Hong Kong WT, H3 Cambodia WT, H1 Wisconsin WT, H1 Wisconsin E22C, K375C, H1 Wisconsin E22C, K375C, HA0, H5 Astrakhan WT, and H5 Astrakhan ΔPB) (FIG. 26C).
Figure 26B:
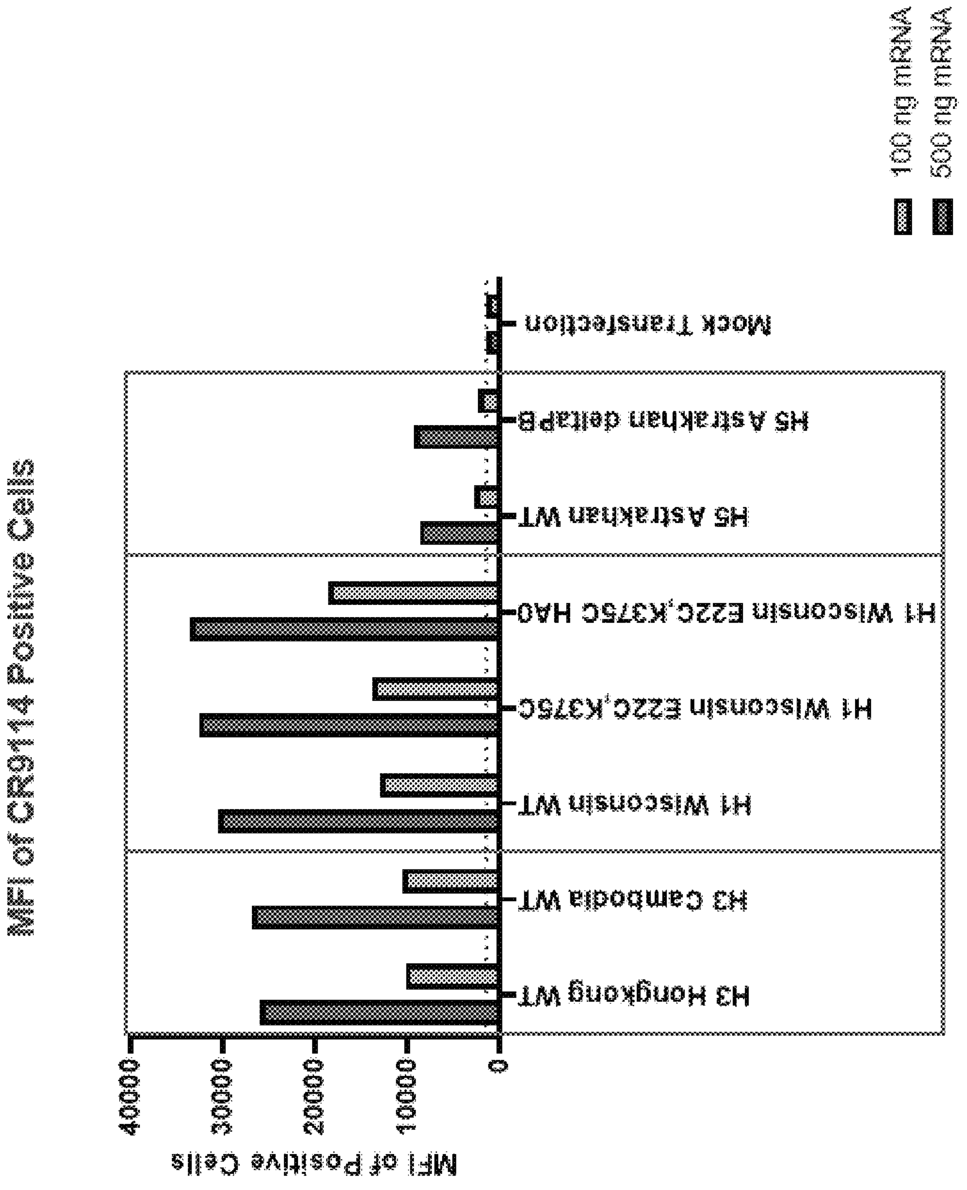
Figure 26C:
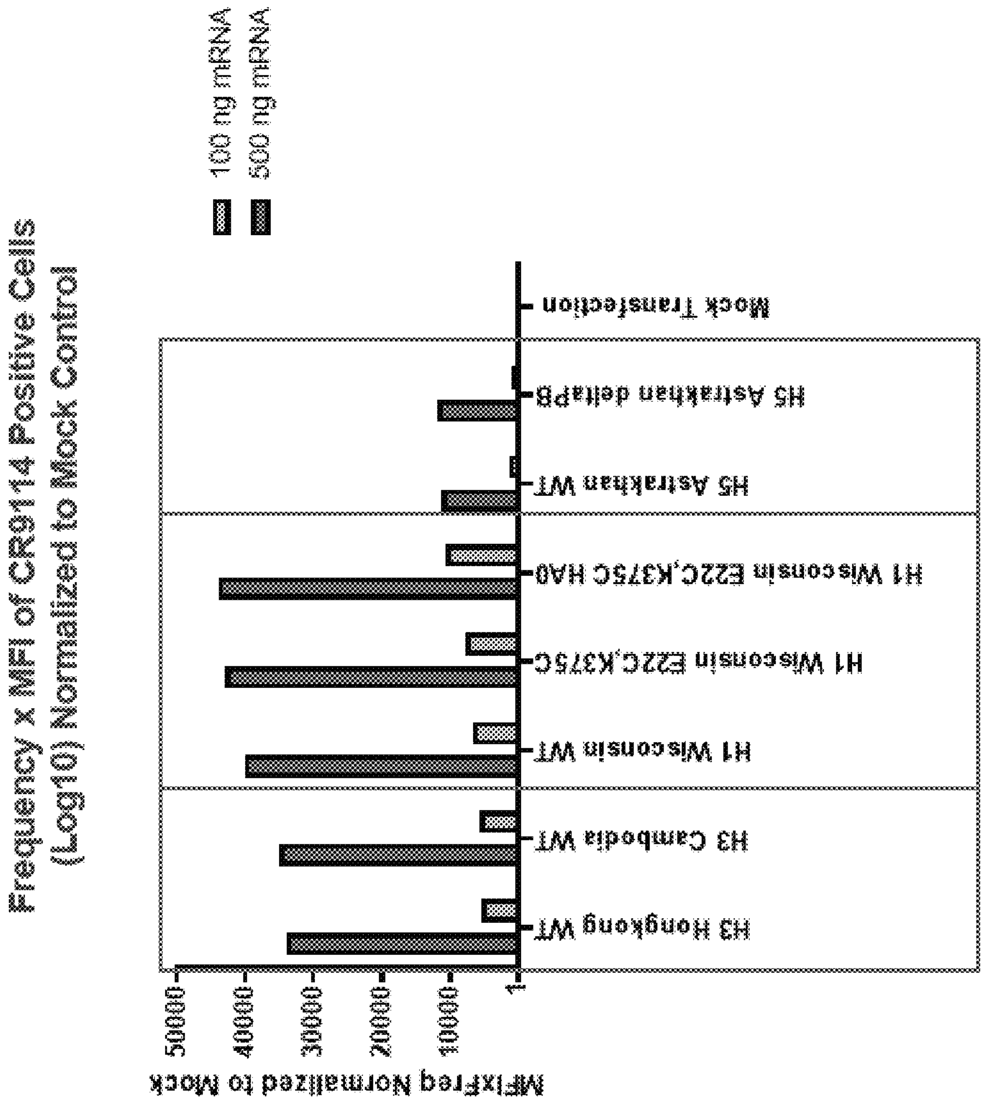

Frequency (%) of CR9114 positive cells and mean fluorescent intensity (MFI) at 48 hours is shown in FIGS. 26A and 26B, respectively. Mean fluorescence intensity (MFI)× frequency was normalized to wild-type at 42 hours of the different variants (FIG. 26C). As shown in FIG. 26A, the mutated HA antigens resulted in approximately the same frequency of HA positive cells as the wild-type HA. The H5 constructs showed lower signal (MFI) compared to H1 and H3 constructs, which may be due to its affinity with the CR9114 antibody (FIG. 26B). Therefore, the constructs all showed similar expression to their respective controls and none of these mutations are shown to be deleterious or impact expression levels negatively (FIG. 26C).

Further expression screenings were taken for the following NA mutants: N2_Cambodia_with D151G mutation, N2_Cambodia_with E227D mutation, N8_Astrakhan_with D151G mutation, and N8 Astrakhan with E227D mutation. HEK293t cells were plated (30,000 cells/well) in a 96-well plate. Doses of 100 ng or 500 ng mRNA were added to each well. Primary antibody mAb-1G01 (human broadly cross-reactive NA antibody) was used, and readouts were performed at 48 hours. The mRNAs tested include (from left to right) SEQ ID NOs: 107, 110, 113, 116, 119, 122, and 125 (FIGS. 27A-27C and Table 10).

TABLE 10

| Experimental Groups | |
|---|---|
| Antigen (encoded by mRNA) | SEQ ID NO: |
| N2_Hongkong_WT | 107 |
| N2_Cambodia_WT | 110 |
| N2_Cambodia_D151G | 113 |
| N2_Cambodia_E227D | 116 |
| N8_Astrakhan_WT | 119 |
| N8_Astrakhan_D151G | 122 |
| N8_Astrakhan_E227D | 125 |

Figure 27A:
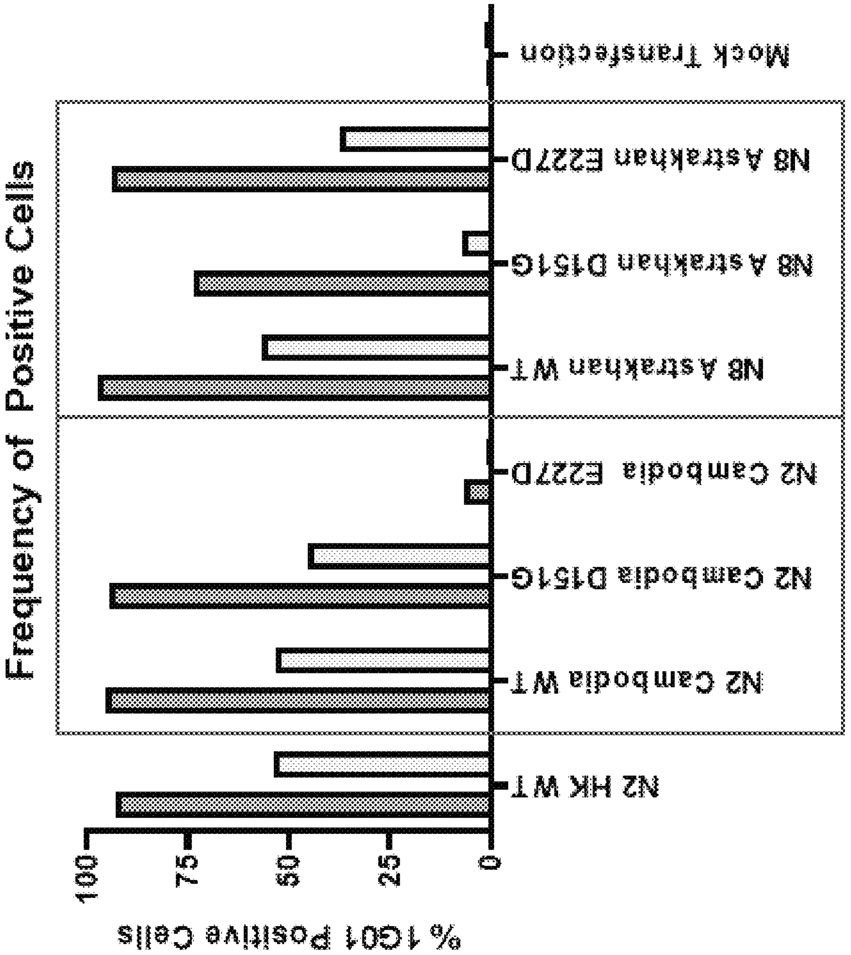
FIGS. 27A-27C are graphs showing frequency of 1G01 positive cells (FIG. 27A), the mean fluorescence intensity (MFI) of 1G01 positive cells (FIG. 27B), and frequency× MFI of 1G01 positive cells normalized to wild-type at 48 hours (FIG. 27C) of the different influenza antigens and variants (N2 Hong Kong WT, N2 Cambodia WT, N2 Cambodia D151G, N2 Cambodia E227D, N8 Astrakhan WT, N8 Astrakhan D151G, and N8 Astrakhan E227D).
Figure 27B:
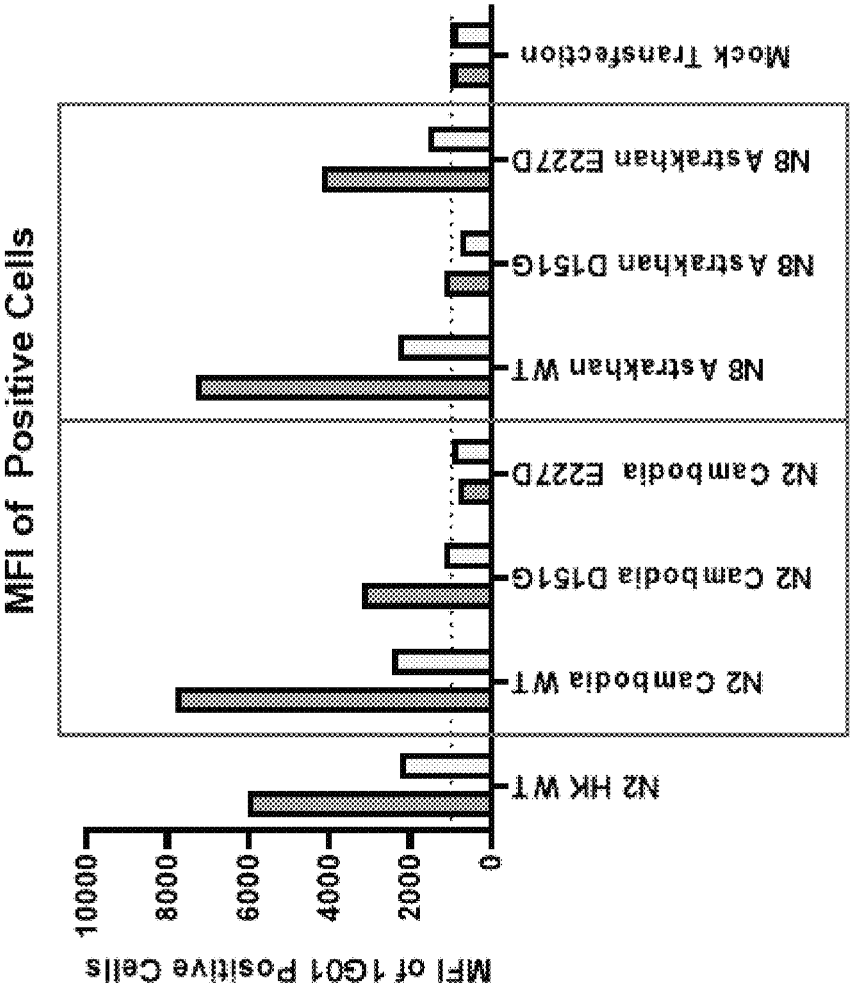
Figure 27C:
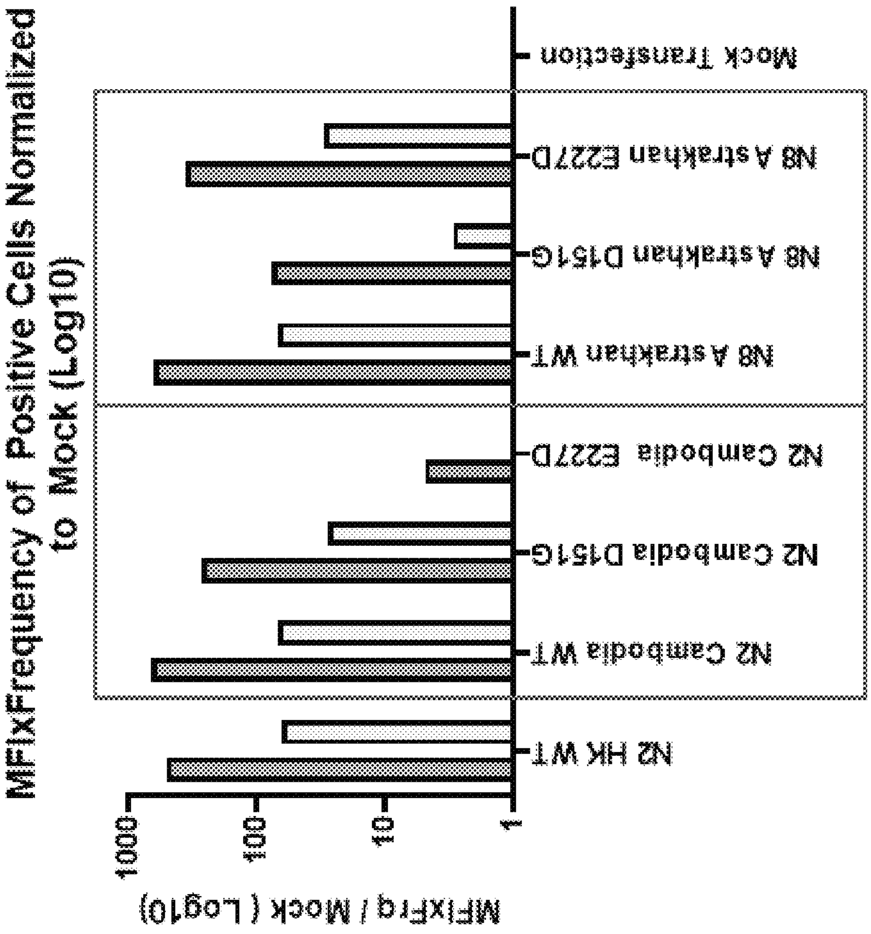

Frequency (%) of 1G01 positive cells and mean fluorescent intensity (MFI) at 48 hours is shown in FIGS. 27A and 27B, respectively. Mean fluorescence intensity (MFI)×frequency was normalized to wild-type at 42 hours of the different variants (FIG. 27C). Results show that no loss of 1G01 binding with mutated N2 D151G antigen was observed, but a decrease with the mutated N2 E227D antigen was observed (FIGS. 27A-27C). This appears to be a D151G trend previously demonstrated with N2 Hong Kong (see above and FIG. 7). There was a slight decrease in binding of 1G01 against mutated N8 D151G antigen but binding of 1G01 was with the mutated N8 E227D antibody was maintained (FIG. 27A-27C). The N2 and N8 mutant constructs showed lower signal (MFI) compared to WT antigens (FIG. 27B). Overall, the mutant constructs showed a decrease in expression compared to their respective controls.

SEQUENCE LISTING

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a poly(A) tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:

(SEQ ID NO: 1)

GGGAAAUAAGAGAGAAAAGAAGAGUAAGAAGAAAUAUAAGAGCCACC

5' UTR:

(SEQ ID NO: 2)

GGGAAAUAAGAGAGAAAAGAAGAGUAAGAAGAAAUAUAAGACCCCGGCG

CCGCCACC

3' UTR:

(SEQ ID NO: 3)

UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUG

AAUAAAGUCUGAGUGGGCGGC

3' UTR:

(SEQ ID NO: 4)

UGAUAAUAGGCUGGAGCCUCGGUGGCCUAGCUUCUUGCCCCUUGGGCCU

CCCCCCAGCCCCUCCUCCCCUUCCUGCACCCGUACCCCCGUGGUCUUUG

AAUAAAGUCUGAGUGGGCGGC

TABLE 11

| | SEQ ID NO: |
|---|---|
| H1_Hawaii_2019_WT | |
| SEQ ID NO: 5 consists of from 5' end to 3' end: 5' UTR SEQ ID NO: 2, mRNA ORF SEQ ID NO: 6, and 3' UTR SEQ ID NO: 4. | 5 |

TABLE 11-continued

| | | SEQ ID NO: |
|---|---|---|
| Chemistry<br>Cap | 1-methylpseudouridine<br>C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGCUGCUGUACACCUUCACCACCGCCAACGCCGACACCCUGUGCAUC<br>GGCUACCACGCCAACAACAGCACCGACACCGUGGACACCGUGCUGGAGAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAAGGGCGUGACAGCAGCCUGUCCA<br>CACGCCGGAGCCAAGAGCUUCUACAAGAACCUGAUCUGGCUGGUGAAGAAGGGCAACAGCUACCCC<br>AAACUGAACCAGACCUACAUCAACGACAAGGGCAAGGAGGUGCUGGUGCUGUGGGGCAUCCACCAC<br>CCACCUACCAUCGCCGCCCAGGAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC<br>CGGAUGAACUACUACUGGACCCUGGUGGAGCCCGGAGACAAGAUUACCUUCGAGGCCACCGGCAAC<br>CUGGUGGUGCCCCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAAGCCGGGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACAAGAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGAGAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | 6 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAILVVLLYTFTTANADTLCIGYHANNSTDTVDTVLEKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDKGVTAACPHAGAKSFYKNLIWLVKKGNSYPKLNQTYINDKGKEVLVLWGIHH<br>PPTIAAQESLYQNADAYVFVGTSRYSKKFKPEIATRPKVRDQEGRMNYYWTLVEPGDKITFEATGN<br>LVVPRYAFTMERDAGSGIIISDTPVHDCNTTCQTPEGAINTSLPFQNVHPITIGKCPKYVKSTKLR<br>LATGLRNVPSIQSRGLFGAIAGFIEGGWTGMVDGWYGYHHQNEQGSGYAADLKSTQNAIDKITNKV<br>NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLESTRIY<br>QILAIYSTVASSLVLVVSLGAISFWMCSNGSLQCRICI | 7 |
| PolyA tail | 100 nt | |
| | N1_Hawaii_2019_WT | |
| SEQ ID NO: 8 consists of from 5' end to 3' end: 5' UTR SEQ ID NO: 2, mRNA ORF SEQ ID NO: 9, and 3' UTR SEQ ID NO: 4. | | 8 |
| Chemistry<br>Cap | 1-methylpseudouridine<br>C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCAUGGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAACGUGAUCACCUACGAGAACAACACCUGGGUGAACCAGACCUAC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCCGGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGACCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAACAUCCUGCGGACCCAGGAGAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC<br>UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC | 9 |

TABLE 11-continued

| | | SEQ ID NO: |
|---|---|---|
| | AGCAGCAUCAGCUUCUGCGGCGUGGACAGCGAUAUCGUGGGCUGGAGCUGGCCAGACGGAGCCGAG<br>CUGCCCUUCACCAUCGACAAG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGMANLILQIGNIISIWVSHSIQIGNQSQIETCNKNVITYENNTWVNQTY<br>VNISNTNSAARQSVASVKLAGNSSLCPVSGWAIYSKDNSVRIGSKGDVFVIREPFISCSPLECRTF<br>FLTQGALLNDKHSNGTIKDRSPYRTLMSCPIGEVPSPYNSRFESVAWSASACHDGTNWLTIGISGP<br>DSGAVAVLKYNGIITDTIKSWRNNILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 10 |
| PolyA tail | 100 nt | |
| | N1_Hawaii_2019_del_cat | |
| SEQ ID NO: 11 consists of from 5' end to 3' end: 5' UTR SEQ ID NO: 2, mRNA ORF SEQ ID NO: 12, and 3' UTR SEQ ID NO: 4. | | 11 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACCAUGAACCCC | 2 |
| ORF of mRNA Construct (excluding the stop codon) | AACCAGAAGAUCAUCACCAUCGGCAGCAUCUGCAUGACCAUCGGCAUGGCCAACCUGAUCCUGCAA<br>AUCGGCAACAUCAUCAGCAUCUGGGUGAGCCACAGCAUCCAGAUCGGCAACCAGAGCCAGAUCGAG<br>ACCUGCAACAAGAACGUGAUCACCUACGAGAACAACACCUGGGUGAACCAGACCUACGUGAACAUC<br>AGCAACACCAACAGCGCCGCUCGGCAGUCAGUGGCCAGCGUGAAGCUGGCCGGCAACAGCAGCCUG<br>UGCCCCGUUAGUGGCUGGGCCAUCUACAGCAAGGACAACAGCGUGCGGAUCGGCAGCAAGGGCGAC<br>GUGUUCGUGAUCCGGGAGCCCUUCAUCAGCUGCAGCCCGCUUGAGUGCCGCACCUUCUUCCUGACC<br>CAGGGCGCUCUGCUGAACGACAAGCACAGCAACGGCACCAUCAAGGGCCGGAGCCCCUAUCGGACC<br>CUGAUGAGCUGCCCCAUUGGCGAGGUGCCCAGCCCCUACAACAGCCGGUUCGAGUCUGUGGCCUGG<br>AGCGCCUCUGCCUGCCACGACGGCACCAACUGGCUGACCAUCGGGAUCAGCGGACCCGAUAGCGGA<br>GCAGUGGCCGUGCUGAAGUACAACGGCAUCAUCACCGACACCAUCAAGAGCUGGCGGAACAACAUC<br>CUGCGGACCCAGGAGAGCGAGUGCGCCUGCGUGAACGGCAGCUGCUUCACCAUCAUGACCGACGGC<br>CCUAGCGACGGACAGGCCAGCUACAAGAUCUUCCGGAUCGAGAAGGGCAAGAUCAUCAAGAGCGUG<br>GAGAUGAAGGCACCCAACUACCACUACGAGGAGUGCAGCUGCUACCCCGACAGCAGCGAGAUCACC<br>UGCGUGUGCCGGGACAACUGGCACGGGAGCAACAGGCCCUGGGUGAGCUUCAACCAGAACCUGGAG<br>UACCAGAUGGGCUACAUCUGCAGCGGCGUGUUCGGCGACAACCCACGGCCCAACGACAAGACUGGC<br>AGCUGCGGUCCGGUGAGCAGCAACGGCGCCAACGGCGUGAAGGGCUUCAGCUUCAAGUACGGCAAC<br>GGCGUGUGGAUCGGCCGGACCAAGAGCAUCAGCAGCCGGAAGGGCUUCGAGAUGAUCUGGGACCCC<br>AACGGCUGGACCGGCACCGACAACAAGUUCAGCAAGAAGCAGGACAUCGUGGGCAUCAACGAGUGG<br>AGCGGCUACAGCGGCAGCUUCGUGCAGCACCCCGAGCUGACUGGCCUGAACUGCAUCCGGCCCUGC<br>UUCUGGGUGGAACUGAUACGGGGACGGCCCGAGGAGAACACCAUCUGGACCAGCGGCAGCAGCAUC<br>AGCUUCUGCGGCGUGGACAGCGAUAUCGUGGGCUGGAGCUGGCCAGACGGAGCCGAGCUGCCCUUC<br>ACCAUCGACAAG | 12 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGMANLILQIGNIISIWVSHSIQIGNQSQIETCNKNVITYENNTWVNQTY<br>VNISNTNSAARQSVASVKLAGNSSLCPVSGWAIYSKDNSVRIGSKGDVFVIREPFISCSPLECRTF<br>FLTQGALLNDKHSNGTIKGRSPYRTLMSCPIGEVPSPYNSRFESVAWSASACHDGTNWLTIGISGP<br>DSGAVAVLKYNGIITDTIKSWRNNILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 13 |
| PolyA tail | 100 nt | |
| | H3_Hongkong_2019_WT | |
| SEQ ID NO: 14 consists of from 5' end to 3' end: 5' UTR SEQ ID NO: 2, mRNA ORF SEQ ID NO: 15, and 3' UTR SEQ ID NO: 4. | | 14 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC | 15 |

TABLE 11-continued

| | | SEQ ID NO: |
|---|---|---|
| | AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUC | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNSTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICI | 16 |
| PolyA tail | 100 nt | |
| N2_Hongkong_2019_WT | | |
| SEQ ID NO: 17 consists of from 5' end to 3' end: 5' UTR SEQ ID NO: 2, mRNA ORF SEQ ID NO: 18, and 3' UTR SEQ ID NO: 4. | | 17 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CUGCCCAACAACCAGGUGAUGCUGUGCGAGCCCACCAUCAUCGAGCGGAACAUCACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGACCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGAGAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC<br>ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGCUACGUGUGCAGCGGUCUGGUGGGCGACACUCCCCGGAAGAGCGAC<br>AGCAGCUCCAGCAGCCACUGCCUGAACCCCAACAACGAGGAGGGUGGUCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>GAUCUGAACCUGAUGCACAUC | 18 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSVSLTISTICFFMQIAILITTVTLHFKQYEFNSLPNNQVMLCEPTIIERNITEIV<br>YLTNTTIEKEICPKPAEYRNWSKPQCGITGFAPFSKDNSIRLSAGGDIWVTREPYVSCDLDKCYQF<br>ALGQGTTLNNVHSNNTVRDRTPYRTLLMNELGVPFHLGTKQVCIAWSSSSCHDGKAWLHVCITGDD<br>KNATASFIYNGRLVDSVVSWSNDILRTQESECVCINGTCTVVMTDGNATGKADTKILFIEEGKIVH<br>TSKLSGSAQHVEECSCYPRYPGVRCVCRDNWKGSNRPIIDINIKDHSIVSSYVCSGLVGDTPRKSD | 19 |

TABLE 11-continued

| | | SEQ ID NO: |
|---|---|---|
| | SSSSSHCLNPNNEEGGHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>DLNLMHI | |
| PolyA tail | 100 nt | |
| | N2_Hongkong_2019_del_cat | |
| SEQ ID NO: 20 consists of from 5' end to 3' end: 5' UTR SEQ ID NO: 2, mRNA ORF SEQ ID NO: 21, and 3' UTR SEQ ID NO: 4. | | 20 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CUGCCCAACAACCAGGUGAUGCUGUGCGAGCCCACCAUCAUCGAGCGGAACAUCACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGGCCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGAGAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC<br>ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGCUACGUGUGCAGCGGUCUGGUGGGCGACACUCCCCGGAAGAGCGAC<br>AGCAGCUCCAGCAGCCACUGCCUGAACCCCAACAACGAGGAGGGUGGUCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>GAUCUGAACCUGAUGCACAUC | 21 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSVSLTISTICFFMQIAILITTVTLHFKQYEFNSLPNNQVMLCEPTIIERNITEIV<br>YLTNTTIEKEICPKPAEYRNWSKPQCGITGFAPFSKDNSIRLSAGGDIWVTREPYVSCDLDKCYQF<br>ALGQGTTLNNVHSNNTVRGRTPYRTLLMNELGVPFHLGTKQVCIAWSSSSCHDGKAWLHVCITGDD<br>KNATASFIYNGRLVDSVVSWSNDILRTQESECVCINGTCTVVMTDGNATGKADTKILFIEEGKIVH<br>TSKLSGSAQHVEECSCYPRYPGVRCVCRDNWKGSNRPIIDINIKDHSIVSSYVCSGLVGDTPRKSD<br>SSSSSHCLNPNNEEGGHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>DLNLMHI | 22 |
| PolyA tail | 100 nt | |
| | B_HA_Washington_2019_WT | |
| SEQ ID NO: 23 consists of from 5' end to 3' end: 5' UTR SEQ ID NO: 2, mRNA ORF SEQ ID NO: 24, and 3' UTR SEQ ID NO: 4. | | 23 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCAUCGUGCUGUUAAUGGUGGUGACCAGCAACGCCGACCGGAUCUGCACCGGCAUC<br>ACCUCUAGCAACAGCCCUCACGUGGUGAAGACCGCCACACAGGGCGAGGUGAACGUGACCGGCGUG<br>AUUCCCCUGACCACCACCCCUACCAAGAGCCACUUCGCCAACCUGAAGGGAACCGAGACCCGGGGC<br>AAGCUGUGUCCCAAGUGCCUGAACUGCACCGACCUGGACGUGGCCCUGGGCAGACCCAAGUGCACC<br>GGCAAGAUCCCCAGCGCCCGGGUGUCUAUCCUGCACGAAGUGCGGCCCGUGACUAGCGGCUGCUUC<br>CCCAUCAUGCACGACCGGACCAAGAUCCGGCAGCUGCCCAACCUGCUGCGGGGCUACGAGCACGUG<br>CGGCUGAGCACCCACAACGUGAUCAACGCCGAAGACGCACCCGGGAGACCAUACGAGAUCGGCACC<br>AGCGGCUCUUGCCCCAACAUCACCAACGGCAACGGCUUCUUCGCUACCAUGGCCUGGGCCGUGCCA<br>AAGAACAAGACUGCCACCAACCCUCUGACCAUCGAGGUGCCCUACAUCUGCACCGAGGGCGAGGAC<br>CAGAUCACCGUGUGGGGCUUCCACAGCGACAGCGAGACCCAGAUGGCCAAGCUGUACGGCGACAGC<br>AAGCCCCAGAAGUUCACCAGCAGCGCCAACGGCGUGACCACCCACUACGUGAGCCAGAUCGGCGGC<br>UUCCCCAACCAGACCGAGGACGGCGGCUUACCCCAGAGCGGCCGGAUCGUGGUGGACUACAUGGUG<br>CAGAAGAGCGGCAAGACCGGCACCAUCACCUACCAGCGGGGCAUCCUGCUGCCACAGAAGGUGUGG<br>UGCGCCUCAGGGCGGUCAAAGGUGAUCAAGGGCAGCCUGCCACUGAUUGGCGAGGCCGACUGCCUG<br>CACGAGAAGUACGGCGGCCUGAACAAGAGCAAGCCCUACUACACCGGCGAGCACGCCAAGGCAAUC<br>GGCAACUGCCCCAUCUGGGUGAAGACACCCCUGAAGCUGGCCAACGGCACCAAGUACCGGCCACCC | 24 |

TABLE 11-continued

| | | SEQ ID NO: |
|---|---|---|
| | GCCAAACUGCUGAAGGAGCGGGGCUUCUUCGGCGCCAUUGCCGGCUUCCUCGAAGGCGGUUGGGAG<br>GGCAUGAUCGCCGGCUGGCACGGCUACACUAGCCACGGCGCACACGGAGUAGCAGUGGCCGCCGAC<br>CUGAAGAGCACCCAGGAGGCCAUCAACAAGAUCACCAAGAACCUGAACAGCCUGAGCGAGCUGGAG<br>GUGAAGAAUCUGCAGCGGCUGUCUGGCGCUAUGGACGAGCUGCACAACGAGAUCCUGGAGCUGGAC<br>GAGAAGGUGGACGACUUACGGGCCGACACCAUCAGCAGCCAGAUCGAGCUGGCCGUGCUG8CUGAG<br>CAACGAGGGCAUCAUCAACAGCGAGGACGAGCACCUGCUGGCCCUGGAGGGAAGCUGAAGAAGAUG<br>CUGGGCCCUUCUGCCGUGGAGAUCGGUAACGGCUGCUUCGAGACCAAGCACAAGUGCAACCAGACC<br>UGCCUGGAUCGGAUCGCAGCCGGCACCUUUGACGCCGGGGAGUUCAGCCUGCCCACCUUCGACAGC<br>CUGAACAUCACCGCCGCCAGCCUGAACGACGACGGCCUGGACAACCACACCAUCCUGCUGUACUAC<br>UCUACAGCCGCUAGCAGCCUGGCCGUGACCCUGAUGAUCGCCAUCUUCGUGGUGUACAUGGUGAGC<br>CGGGACAACGUGAGCUGCAGCAUCUGCCUG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAIIVLLMVVTSNADRICTGITSSNSPHVVKTATQGEVNVTGVIPLTTTPTKSHFANLKGTETRG<br>KLCPKCLNCTDLDVALGRPKCTGKIPSARVSILHEVRPVTSGCFPIMHDRTKIRQLPNLLRGYEHV<br>RLSTHNVINAEDAPGRPYEIGTSGSCPNITNGNGFFATMAWAVPKNKTATNPLTIEVPYICTEGED<br>QITVWGFHSDSETQMAKLYGDSKPQKFTSSANGVTTHYVSQIGGFPNQTEDGGLPQSGRIVVDYMV<br>QKSGKTGTITYQRGILLPQKVWCASGRSKVIKGSLPLIGEADCLHEKYGGLNKSKPYYTGEHAKAI<br>GNCPIWVKTPLKLANGTKYRPPAKLLKERGFFGAIAGFLEGGWEGMIAGWHGYTSHGAHGVAVAAD<br>LKSTQEAINKITKNLNSLSELEVKNLQRLSGAMDELHNEILELDEKVDDLRADTISSQIELAVLLS<br>NEGIINSEDEHLLALERKLKKMLGPSAVEIGNGCFETKHKCNQTCLDRIAAGTFDAGEFSLPTFDS<br>LNITAASLNDDGLDNHTILLYYSTAASSLAVTLMIAIFVVYMVSRDNVSCSICL | 25 |
| PolyA tail | 100 nt | |
| | B_NA_Washington_2019_WT | |
| SEQ ID NO: 26 consists of from 5' end to 3' end: 5' UTR SEQ ID NO: 2, mRNA ORF SEQ ID NO: 27, and 3' UTR SEQ ID NO: 4. | | 26 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGCUGCCCAGCACCAUCCAGACCCUGACCCUGUUUCUGACCAGCGGAGGCGUGCUGCUGAGCCUG<br>UACGUGAGCGCCAGCCUGAGCUACCUGCUGUACAGCGACAUCCUGCUGAAGUUCAGCCCCACCGAG<br>AUCACCGCACCCACCAUGCCCCUGGACUGCGCCAACGCCAGCAACGUGCAGGCCGUGAACCGGAGC<br>GCCACAAAGGGCGUGACCCUGCUGCUGCCCGAGCCAGAGUGGACAUAUCCUCGGCUGAGCUGCCCU<br>GGCAGCACCUUCCAGAAGGCCCUGCUGAUCAGCCCACACCGGUUCGGCGAGACCAAGGGCAACAGC<br>GCACCCCUGAUCAUCCGGGAGCCCUUCGUGGCCUGUGGCCCCAACGAGUGCAAGCACUUCGCCCUG<br>ACACACUACGCUGCUCAGCCCGGUGGCUACUACAACGGCACCCGGGGUGAUCGGAACAAGCUGCGG<br>CACCUGAUCAGCGUGAAGCUGGGCAAGAUCCCCACCGUGGAGAACAGCAUCUUCCACAUGGCCGCC<br>UGGUCAGGAAGCGCCUGCCACGACGGCAAGGAGUGGACCUACAUCGGCGUGGACGGCCCUGACAAC<br>AACGCCCUGCUGAAGGUGAAGUACGGCGAGGCCUACACCGACACCUACCACAGCUACGCCAACAAC<br>AUCCUGCGGACCCAGGAGAGCGCCUGCAACUGCAUCGGCGGCAACUGCUACCUGAUGAUCACCGAC<br>GGCAGCGCUUCUGGCGUGAGCGAGUGCCGGUUCCUGAAGAUCCGGGAGGGCCGGAUCAUCAAGGAG<br>AUCUUUCCCACCGGCCGGGUGAAGCACACCGAGGAGUGCACCUGCGGCUUCGCCAGCAACAAGACC<br>AUCGAGUGCGCCUGCCGGGACAAUCGGUACACCGCCAAGCGGCCCUUCGUGAAGCUGAACGUGGAG<br>ACCGACACCGCCGAGAUCCGGCUGAUGUGCACCGACACUUAUCUGGACACCCCUCGGCCUAACGAC<br>GGCAGCAUCACCGGCCCUUGCGAGAGCGACGGCGACAAGGGAAGCGGCGGCAUCAAGGGCGGUUUC<br>GUGCACCAGCGGAUGAAGAGCAAGAUCGGCCGGUGGUACAGCCGGACCAUGAGCAAGACCGAGCGG<br>AUGGGCAUGGGCCUGUACGUAAAGUACGGAGGGGAUCCCUGGGCUGACAGCGACGCCCUGACCUUC<br>AGCGGCGUGAUGGUGAGCAUGAAGGAGCCCGGCUGGUACAGCUUCGGCUUCGAGAUCAAGGACAAG<br>AAGUGCGACGUGCCCUGCAUCGGCAUCGAGAUGGUGCACGACGGCGGCAAGGAGACCUGGCACUCU<br>GCCGCCACUGCCAUCUACUGCCUGAUGGGCAGCGGCCAGCUGCUGUGGGACACCGUGACCGGCGUG<br>GACAUGGCCCUG | 27 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MLPSTIQTLTLFLTSGGVLLSLYVSASLSYLLYSDILLKFSPTEITAPTMPLDCANASNVQAVNRS<br>ATKGVTLLLPEPEWTYPRLSCPGSTFQKALLISPHRFGETKGNSAPLIIREPFVACGPNECKHFAL<br>THYAAQPGGYYNGTRGDRNKLRHLISVKLGKIPTVENSIFHMAAWSGSACHDGKEWTYIGVDGPDN<br>NALLKVKYGEAYTDTYHSYANNILRTQESACNCIGGNCYLMITDGSASGVSECRFLKIREGRIIKE<br>IFPTGRVKHTEECTCGFASNKTIECACRDNRYTAKRPFVKLNVETDTAEIRLMCTDTYLDTPRPND<br>GSITGPCESDGDKGSGGIKGGFVHQRMKSKIGRWYSRTMSKTERMGMGLYVKYGGDPWADSDALTF<br>SGVMVSMKEPGWYSFGFEIKDKKCDVPCIGIEMVHDGGKETWHSAATAIYCLMGSGQLLWDTVTGV<br>DMAL | 28 |
| PolyA tail | 100 nt | |
| | B_N A_ Washington_2019_del_cat | |
| SEQ ID NO: 29 consists of from 5' end to 3' end: 5' UTR SEQ ID NO: 2, mRNA ORF SEQ ID NO: 30, and 3' UTR SEQ ID NO: 4. | | 29 |

TABLE 11-continued

| | | SEQ ID NO: |
|---|---|---|
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of<br>mRNA<br>Construct<br>(excluding the<br>stop codon) | AUGCUGCCCAGCACCAUCCAGACCCUGACCCUGUUUCUGACCAGCGGAGGCGUGCUGCUGAGCCUG<br>UACGUGAGCGCCAGCCUGAGCUACCUGCUGUACAGCGACAUCCUGCUGAAGUUCAGCCCCACCGAG<br>AUCACCGCACCCACCAUGCCCCUGGACUGCGCCAACGCCAGCAACGUGCAGGCCGUGAACCGGAGC<br>GCCACAAAGGGCGUGACCCUGCUGCUGCCCGAGCCAGAGUGGACAUAUCCUCGGCUGAGCUGCCCU<br>GGCAGCACCUUCCAGAAGGCCCUGCUGAUCAGCCCACACCGGUUCGGCGAGACCAAGGGCAACAGC<br>GCACCCCUGAUCAUCCGGGAGCCCUUCGUGGCCUGUGGCCCCAACGAGUGCAAGCACUUCGCCCUG<br>ACACACUACGCUGCUCAGCCCGGUGGCUACUACAACGGCACCCGGGGUGGCCGGAACAAGCUGCGG<br>CACCUGAUCAGCGUGAAGCUGGGCAAGAUCCCCACCGUGGAGAACAGCAUCUUCCACAUGGCCGCC<br>UGGUCAGGAAGCGCCUGCCACGACGGCAAGGAGUGGACCUACAUCGGCGUGGACGGCCCUGACAAC<br>AACGCCCUGCUGAAGGUGAAGUACGGCGAGGCCUACACCGACACCUACCACAGCUACGCCAACAAC<br>AUCCUGCGGACCCAGGAGAGCGCCUGCAACUGCAUCGGCGGCAACUGCUACCUGAUGAUCACCGAC<br>GGCAGCGCUUCUGGCGUGAGCGAGUGCCGGUUCCUGAAGAUCCGGGAGGGCCGGAUCAUCAAGGAG<br>AUCUUUCCCACCGGCCGGGUGAAGCACACCGAGGAGUGCACCUGCGGCUUCGCCAGCAACAAGACC<br>AUCGAGUGCGCCUGCCGGGACAAUCGGUACACCGCCAAGCGGCCCUUCGUGAAGCUGAACGUGGAG<br>ACCGACACCGCCGAGAUCCGGCUGAUGUGCACCGACACUUAUCUGGACACCCCUCGGCCUAACGAC<br>GGCAGCAUCACCGGCCCUUGCGAGAGCGACGGCGACAAGGGAAGCGGCGGCAUCAAGGGCGGUUUC<br>GUGCACCAGCGGAUGAAGAGCAAGAUCGGCCGGUGGUACAGCCGGACCAUGAGCAAGACCGAGCGG<br>AUGGGCAUGGGCCUGUACGUAAAGUACGGAGGGGAUCCCUGGGCUGACAGCGACGCCCUGACCUUC<br>AGCGGCGUGAUGGUGAGCAUGAAGGAGCCCGGCUGGUACAGCUUCGGCUUCGAGAUCAAGGACAAG<br>AAGUGCGACGUGCCCUGCAUCGGCAUCGAGAUGGUGCACGACGGCGGCAAGGAGACCUGGCACUCU<br>GCCGCCACUGCCAUCUACUGCCUGAUGGGCAGCGGCCAGCUGCUGUGGGACACCGUGACCGGCGUG<br>GACAUGGCCCUG | 30 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding<br>amino acid<br>sequence | MLPSTIQTLTLFLTSGGVLLSLYVSASLSYLLYSDILLKFSPTEITAPTMPLDCANASNVQAVNRS<br>ATKGVTLLLPEPEWTYPRLSCPGSTFQKALLISPHRFGETKGNSAPLIIREPFVACGPNECKHFAL<br>THYAAQPGGYYNGTRGGRNKLRHLISVKLGKIPTVENSIFHMAAWSGSACHDGKEWTYIGVDGPDN<br>NALLKVKYGEAYTDTYHSYANNILRTQESACNCIGGNCYLMITDGSASGVSECRFLKIREGRIIKE<br>IFPTGRVKHTEECTCGFASNKTIECACRDNRYTAKRPFVKLNVETDTAEIRLMCTDTYLDTPRPND<br>GSITGPCESDGDKGSGGIKGGFVHQRMKSKIGRWYSRTMSKTERMGMGLYVKYGGDPWADSDALTF<br>SGVMVSMKEPGWYSFGFEIKDKKCDVPCIGIEMVHDGGKETWHSAATAIYCLMGSGQLLWDTVTGV<br>DMAL | 31 |
| PolyA tail | 100 nt | |
| | B_HA_Phuket_2013_WT | |
| SEQ ID NO: 32 consists of from 5' end to 3' end: 5' UTR SEQ ID NO: 2, mRNA ORF SEQ ID NO: 33, and 3' UTR SEQ ID NO: 4. | | 32 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of<br>mRNA<br>Construct<br>(excluding the<br>stop codon) | AUGAAGGCCAUCAUCGUGCUACUGAUGGUGGUGACCAGCAACGCCGACCGGAUCUGCACCGGCAUC<br>ACCAGCAGCAACAGCCCGCACGUGGUGAAGACCGCCACCCAAGGCGAGGUGAACGUGACCGGCGUG<br>AUCCCACUGACCACCACUCCCACCAAGAGCUACUUCGCCAACCUGAAGGGCACACGGACUCGGGGC<br>AAGCUGUGCCCCGACUGCCUGAACUGCACCGACCUGGACGUGGCCCUGGGCAGACCCAUGUGCGUG<br>GGCACCACCCCUUCUGCCAAGGCCAGCAUCCUGCACGAGGUGAGACCCGUGACCAGCGGGUGCUUC<br>CCCAUCAUGCACGACCGGACCAAGAUCCGGCAGCUGCCCAACCUGCUGCGGGGCUACGAGAAGAUC<br>CGGCUGAGCACCCAGAACGUGAUCGACGCCGAGAAGGCCCCUGGAGGUCCCUACCGGCUGGGCACC<br>AGCGGAAGCUGCCCCAACGCCACCAGCAAGAUCGGCUUCUUCGCCACCAUGGCCUGGGCUGUGCCC<br>AAGGACAACUACAAGAACGCCACCAAUCCCCUGACCGUGGAGGUGCCCUACAUCUGCACCGAGGGC<br>GAGGACCAGAUCACCGUGUGGGGCUUCCACAGCGACAACAAGACCCAGAUGAAGAGCCUGUACGGC<br>GACAGCAAUCCCCAGAAGUUCACAAGCAGCGCCAACGGCGUGACCACCCACUACGUGAGCCAGAUC<br>GGCGACUUCCCCGACCAGACCGAGGACGGAGGGCUGCCUCAGAGUGGCCGGAUCGUGGUGGACUAC<br>AUGAUGCAGAAGCCCGGCAAGACCGGCACCAUCGUGUACCAGCGGGGCGUGCUGUUGCCUCAGAAA<br>GUUUGGUGUGCCAGCGGCAGGAGCAAGGUGAUCAAGGGCAGCCUGCCCCUGAUCGGCGAGGCAGAC<br>UGCCUCCACGAGGAGUACGGCGGCCUGAACAAGAGCAAGCCCUACUACACCGGCAAGCACGCCAAG<br>GCCAUCGGCAACUGCCCCAUCUGGGUGAAGACCCCUCUGAAGCUGGCCAACGGCACCAAGUACCGG<br>CCACCAGCCAAGCUGCUGAAGGAGCGGGGCUUCUUUGGCGCCAUUGCCGGCUUCCUCGAGGGAGGC<br>UGGGAGGGCAUGAUCGCCGGCUGGCACGGCUACACAAGCCACGGCGCACACGGAGUGGCUGUGGCU<br>GCCGACCUGAAGAGCACCCAGGAGGCCAUCAACAAGAUCACCAAGAACCUGAACAGCCUGAGCGAG<br>CUGGAGGUGAAGAACCUGCAGCGGCUGUCAGGCGCCAUGGACGAGCUGCACAACGAGAUCCUGGAG<br>CUGGACGAGAAGGUGGACGACCUGCGUGCCGACACCAUCAGCAGCCAGAUCGAGCUGGCCGUGCUG<br>CUGAGCAACGAGGGCAUCAUCAACAGCGAGGACGAGCACCUGCUGGCCCUGGAGCGGAAACUGAAG<br>AAGAUGCUGGGACCCUCUGCCGUGGACAUCGGCAACGGCUGCUUCGAGACCAAGCACAAGUGCAAC<br>CAGACCUGCCUGGAUCGGAUCGCCGCCGGAACCUUCAACGCCGGCGAGUUCAGCCUGCCCACCUUC<br>GACAGCCUGAACAUCACCGCCGCCAGCCUGAACGACGACGGCCUGGACAACCACACCAUCCUGCUG | 33 |

TABLE 11-continued

| | | SEQ ID NO: |
|---|---|---|
| | UACUACAGCACUGCCGCCUCAAGCCUGGCCGUGACCCUGAUGCUGGCCAUCUUCAUCGUGUACAUG GUGAGCCGGGACAACGUGAGCUGCAGCAUCUGCCUG | |
| 3' UTR | UGAUAAUAGGCUGGAGCCUCGGUGGCCUAGCUUCUUGCCCCUUGGGCCUCCCCCCAGCCCCUCCUC CCCUUCCUGCACCCGUACCCCCGUGGUCUUUGAAUAAAGUCUGAGUGGGCGGC | 4 |
| Corresponding amino acid sequence | MKAIIVLLMVVTSNADRICTGITSSNSPHVVKTATQGEVNVTGVIPLTTTPTKSYFANLKGTRTRG KLCPDCLNCTDLDVALGRPMCVGTTPSAKASILHEVRPVTSGCFPIMHDRTKIRQLPNLLRGYEKI RLSTQNVIDAEKAPGGPYRLGTSGSCPNATSKIGFFATMAWAVPKDNYKNATNPLTVEVPYICTEG EDQITVWGFHSDNKTQMKSLYGDSNPQKFTSSANGVTTHYVSQIGDFPDQTEDGGLPQSGRIVVDY MMQKPGKTGTIVYQRGVLLPQKVWCASGRSKVIKGSLPLIGEADCLHEEYGGLNKSKPYYTGKHAK AIGNCPIWVKTPLKLANGTKYRPPAKLLKERGFFGAIAGFLEGGWEGMIAGWHGYTSHGAHGVAVA ADLKSTQEAINKITKNLNSLSELEVKNLQRLSGAMDELHNEILELDEKVDDLRADTISSQIELAVL LSNEGIINSEDEHLLALERKLKKMLGPSAVDIGNGCFETKHKCNQTCLDRIAAGTFNAGEFSLPTF DSLNITAASLNDDGLDNHTILLYYSTAASSLAVTLMLAIFIVYMVSRDNVSCSICL | 34 |
| PolyA tail | 100 nt | |
| | **B_NA_Phuket_2013_WT** | |
| SEQ ID NO: 35 consists of from 5' end to 3' end: 5' UTR SEQ ID NO: 2, mRNA ORF SEQ ID NO: 36, and 3' UTR SEQ ID NO: 4. | | 35 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGCUGCCCAGCACCAUCCAGACCCUGACCCUGUUCCUGACCAGCGGAGGCGUGCUGCUGAGCCUG UACGUCAGCGCCAGCCUGAGCUACCUGCUGUACAGCGACAUCCUGCUGAAGUUCAGCCGGACCGAG GUGACCGCUCCCAUCAUGCCCCUGGACUGCGCCAACGCCAGCAACGUGCAGGCCGUGAAUCGGAGC GCCACCAAGGGCGUGACUCCCCUGCUGCCCGAGCCUGAGUGGACUUAUCCUCGGCUGAGCUGCCCA GGCAGCACCUUCCAGAAGGCCCUGCUGAUCAGCCCACACCGGUUCGGCGAGACCAAGGGCAACAGC GCUCCCCUGAUCAUCCGGGAGCCCUUCAUCGCCUGCGGCCCCAAGGAGUGCAAGCACUUCGCCCUG ACCCACUACGCUGCCCAACCCGGAGGCUACUACAACGGCACCAGAGAGGACCGGAACAAGCUGCGG CACCUGAUCAGCGUGAAGCUGGGCAAGAUCCCCACCGUGGAGAACAGCAUCUUCCACAUGGCUGCU UGGUCUGGAAGUGCUUGUCACGACGGCCGGGAGUGGACCUACAUCGGCGUGGACGGCCCAGACAGC AACGCCCUGCUGAAGAUCAAGUACGGCGAGGCCUACACCGACACCUACCACAGCUACGCCAAGAAC AUCCUGCGGACCCAGGAGAGCGCCUGCAACUGCAUCGGCGGCGACUGCUACCUGAUGAUCACCGAC GGCCCAGCAUCUGGCAUCAGCGAGUGCCGGUUCCUGAAGAUCCGGGAGGGCCGGAUCAUCAAGGAG AUCUUCCCCACCGGGAGAGUGAAGCACACCGAGGAGUGCACCUGCGGCUUCGCCAGCAACAAGACC AUCGAGUGCGCCUGCCGGGACAACAGCUACACCGCCAAGCGGCCCUUCGUGAAGCUGAACGUGGAG ACCGACACCGCCGAGAUCCGGCUGAUGUGCACCAAGACCUACCUGGACACCCCUCGGCCCAACGAC GGAAGCAUCACCGGACCCUGCGAGAGCGACGGGGACGAAGGAAGCGGCGGAAUCAAGGGCGGCUUC GUGCACCAGCGGAUGGCCAGCAAGAUCGGCCGGUGGUACAGCCGGACCAUGAGCAAGACCAAGCGG AUGGGCAUGGGCCUGUACGUGAAGUACGACGGCGACCCCUGGACAGACAGCGAAGCCCUGGCCCUG UCUGGCGUGAUGGUGAGCAUGGAGGAGCCCGGCUGGUACAGCUUCGGCUUCGAGAUCAAGGACAAG AAGUGCGACGUGCCCUGCAUCGGCAUCGAGAUGGUGCACGACGGCGGCAAGACCACCUGGCAUAGC GCCGCAACCGCGAUCUACUGCCUGAUGGGCAGCGGCCAGCUGCUGUGGGACACCGUGACCGGCGUG AACAUGACCCUG | 36 |
| 3' UTR | UGAUAAUAGGCUGGAGCCUCGGUGGCCUAGCUUCUUGCCCCUUGGGCCUCCCCCCAGCCCCUCCUC CCCUUCCUGCACCCGUACCCCCGUGGUCUUUGAAUAAAGUCUGAGUGGGCGGC | 4 |
| Corresponding amino acid sequence | MLPSTIQTLTLFLTSGGVLLSLYVSASLSYLLYSDILLKFSRTEVTAPIMPLDCANASNVQAVNRS ATKGVTPLLPEPEWTYPRLSCPGSTFQKALLISPHRFGETKGNSAPLIIREPFIACGPKECKHFAL THYAAQPGGYYNGTREDRNKLRHLISVKLGKIPTVENSIFHMAAWSGSACHDGREWTYIGVDGPDS NALLKIKYGEAYTDTYHSYAKNILRTQESACNCIGGDCYLMITDGPASGISECRFLKIREGRIIKE IFPTGRVKHTEECTCGFASNKTIECACRDNSYTAKRPFVKLNVETDTAEIRLMCTKTYLDTPRPND GSITGPCESDGDEGSGGIKGGFVHQRMASKIGRWYSRTMSKTKRMGMGLYVKYDGDPWTDSEALAL SGVMVSMEEPGWYSFGFEIKDKKCDVPCIGIEMVHDGGKTTWHSAATAIYCLMGSGQLLWDTVTGV NMTL | 37 |
| PolyA tail | 100 nt | |
| | **B_NA_Phuket_2013_del_cat** | |
| SEQ ID NO: 38 consists of from 5' end to 3' end: 5' UTR SEQ ID NO: 2, mRNA ORF SEQ ID NO: 39, and 3' UTR SEQ ID NO: 4. | | 38 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct | AUGCUGCCCAGCACCAUCCAGACCCUGACCCUGUUCCUGACCAGCGGAGGCGUGCUGCUGAGCCUG UACGUCAGCGCCAGCCUGAGCUACCUGCUGUACAGCGACAUCCUGCUGAAGUUCAGCCGGACCGAG GUGACCGCUCCCAUCAUGCCCCUGGACUGCGCCAACGCCAGCAACGUGCAGGCCGUGAAUCGGAGC | 39 |

TABLE 11-continued

| | | SEQ ID NO: |
|---|---|---|
| (excluding the stop codon) | GCCACCAAGGGCGUGACUCCCCUGCUGCCCGAGCCUGAGUGGACUUAUCCUCGGCUGAGCUGCCCA<br>GGCAGCACCUUCCAGAAGGCCCUGCUGAUCAGCCCACACCGGUUCGGCGAGACCAAGGGCAACAGC<br>GCUCCCCUGAUCAUCCGGGAGCCCUUCAUCGCCUGCGGCCCCAAGGAGUGCAAGCACUUCGCCCUG<br>ACCCACUACGCUGCCCAACCCGGAGGCUACUACAACGGCACCAGAGAGGGCCGGAACAAGCUGCGG<br>CACCUGAUCAGCGUGAAGCUGGGCAAGAUCCCCACCGUGGAGAACAGCAUCUUCCACAUGGCUGCU<br>UGGUCUGGAAGUGCUUGUCACGACGGCCGGGAGUGGACCUACAUCGGCGUGGACGGCCCAGACAGC<br>AACGCCCUGCUGAAGAUCAAGUACGGCGAGGCCUACACCGACACCUACCACAGCUACGCCAAGAAC<br>AUCCUGCGGACCCAGGAGAGCGCCUGCAACUGCAUCGGCGGCGACUGCUACCUGAUGAUCACCGAC<br>GGCCCAGCAUCUGGCAUCAGCGAGUGCCGGUUCCUGAAGAUCCGGGAGGGCCGGAUCAUCAAGGAG<br>AUCUUCCCCACCGGGAGAGUGAAGCACACCGAGGAGUGCACCUGCGGCUUCGCCAGCAACAAGACC<br>AUCGAGUGCGCCUGCCGGGACAACAGCUACACCGCCAAGCGGCCCUUCGUGAAGCUGAACGUGGAG<br>ACCGACACCGCCGAGAUCCGGCUGAUGUGCACCAAGACCUACCUGGACACCCCUCGGCCCAACGAC<br>GGAAGCAUCACCGGACCCUGCGAGAGCGACGGGGACGAAGGAAGCGGCGGAAUCAAGGGCGGCUUC<br>GUGCACCAGCGGAUGGCCAGCAAGAUCGGCCGGUGGUACAGCCGGACCAUGAGCAAGACCAAGCGG<br>AUGGGCAUGGGCCUGUACGUGAAGUACGACGGCGACCCCUGGACAGACAGCGAAGCCCUGGCCCUG<br>UCUGGCGUGAUGGUGAGCAUGGAGGAGCCCGGCUGGUACAGCUUCGGCUUCGAGAUCAAGGACAAG<br>AAGUGCGACGUGCCCUGCAUCGGCAUCGAGAUGGUGCACGACGGCGGCAAGACCACCUGGCAUAGC<br>GCCGCAACCGCGAUCUACUGCCUGAUGGGCAGCGGCCAGCUGCUGUGGGACACCGUGACCGGCGUG<br>AACAUGACCCUG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MLPSTIQTLTLFLTSGGVLLSLYVSASLSYLLYSDILLKFSRTEVTAPIMPLDCANASNVQAVNRS<br>ATKGVTPLLPEPEWTYPRLSCPGSTFQKALLISPHRFGETKGNSAPLIIREPFIACGPKECKHFAL<br>THYAAQPGGYYNGTREGRNKLRHLISVKLGKIPTVENSIFHMAAWSGSACHDGREWTYIGVDGPDS<br>NALLKIKYGEAYTDTYHSYAKNILRTQESACNCIGGDCYLMITDGPASGISECRFLKIREGRIIKE<br>IFPTGRVKHTEECTCGFASNKTIECACRDNSYTAKRPFVKLNVETDTAEIRLMCTKTYLDTPRPND<br>GSITGPCESDGDEGSGGIKGGFVHQRMASKIGRWYSRTMSKTKRMGMGLYVKYDGDPWTDSEALAL<br>SGVMVSMEEPGWYSFGFEIKDKKCDVPCIGIEMVHDGGKTTWHSAATAIYCLMGSGQLLWDTVTGV<br>NMTL | 40 |
| PolyA tail | 100 nt | |
| | H1_Wisconsin_2019_WT | |
| SEQ ID NO: 41 consists of from 5' end to 3' end: 5' UTR SEQ ID NO: 2, mRNA ORF SEQ ID NO: 42, and 3' UTR SEQ ID NO: 4. | | 41 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGAUGCUGUACACCUUCACCACCGCCAACGCCGACACCCUGUGCAUC<br>GGCUACCACGCCAACAACAGCACCGACACCGUGGACACCGUGCUGGAGAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAACGGCGUGACAGCAGCCUGUCCA<br>CACGCCGGAGCCAAGAGCUUCUACAAGAACCUGAUCUGGCUGGUGAAGAAGGGCAAGAGCUACCCC<br>AAGAUCAACCAGACCUACAUCAACGACAAGGGCAAGGAGGUGCUGGUGCUGUGGGGCAUCCACCAC<br>CCACCUACCAUCGCCGACCAGCAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC<br>CGGAUGAACUACUACUGGACCCUGGUGGAGCCCGGAGACAAGAUUACCUUCGAGGCCACCGGCAAC<br>CUGGUGGCCCCUCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAAGCCGGGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACAAGAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGACAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | 42 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAILVVMLYTFTTANADTLCIGYHANNSTDTVDTVLEKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDNGVTAACPHAGAKSFYKNLIWLVKKGKSYPKINQTYINDKGKEVLVLWGIHH<br>PPTIADQQSLYQNADAYVFVGTSRYSKKFKPEIATRPKVRDQEGRMNYYWTLVEPGDKITFEATGN | 42 |

TABLE 11-continued

| | | SEQ ID NO: |
|---|---|---|
| | LVAPRYAFTMERDAGSGIIISDTPVHDCNTTCQTPEGAINTSLPFQNVHPITIGKCPKYVKSTKLR<br>LATGLRNVPSIQSRGLFGAIAGFIEGGWTGMVDGWYGYHHQNEQGSGYAADLKSTQNAIDKITNKV<br>NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLDSTRIY<br>QILAIYSTVASSLVLVVSLGAISFWMCSNGSLQCRICI | |
| PolyA tail | 100 nt | |
| | N1_Wisconsin_2019_WT | |
| SEQ ID NO: 44 consists of from 5' end to 3' end: 5' UTR SEQ ID NO: 2, mRNA ORF SEQ ID NO: 45, and 3' UTR SEQ ID NO: 4. | | 44 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCCGGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGACCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGAGAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC<br>UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC<br>AGCAGCAUCAGCUUCUGCGGCGUGGACAGCGAUAUCGUGGGCUGGAGCUGGCCAGACGGAGCCGAG<br>CUGCCCUUCACCAUCGACAAG | 45 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIREPFISCSPLECRTF<br>FLTQGALLNDKHSNGTIKDRSPYRTLMSCPIGEVPSPYNSRFESVAWSASACHDGTNWLTIGISGP<br>DSGAVAVLKYNGIITDTIKSWRNKILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 46 |
| PolyA tail | 100 nt | |
| | N1_Wisconsin_2019_del_cat | |
| SEQ ID NO: 47 consists of from 5' end to 3' end: 5' UTR SEQ ID NO: 2, mRNA ORF SEQ ID NO: 48, and 3' UTR SEQ ID NO: 4. | | 47 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCCGGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGGCCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGAGACGCGAGUGCGCCUGCGUGAACGGCAGCUGCUUCACCAUCAU<br>GACCGACGGCCCUACGCGACGGACAGGCCAGCUACAAGAUCUUCCGGAUCGAGAAGGGCAAGAUCA<br>UCAAGAGCGUGGAGAUGAAGGCACCCAACUACCACUACGAGGAGUGCAGCUGCUACCCCGACAGCA<br>GCGAGAUCACCUGCGUGUGCCGGGACAACUGGCACGGGAGCAACAGGCCCUGGGUGAGCUUCAACC | 48 |

TABLE 11-continued

| | | SEQ ID NO: |
|---|---|---|
| | AGAACCUGGAGUACCAGAUGGGCUACAUCUGCAGCGGCGUGUUCGGCGACAACCCACGGCCCAACG<br>ACAAGACUGGCAGCUGCGGUCCGGUGAGCAGCAACGGCGCCAACGGCGUGAAGGGCUUCAGCUUCA<br>AGUACGGCAACGGCGUGUGGAUCGGCCGGACCAAGAGCAUCAGCAGCCGGAAGGGCUUCGAGAUGA<br>UCUGGGACCCCAACGGCUGGACCGGCACCGACAACAAGUUCAGCAAGAAGCAGGACAUCGUGGGCA<br>UCAACGAGUGGAGCGGCUACAGCGGCAGCUUCGUGCAGCACCCCGAGCUGACUGGCCUGAACUGCA<br>UCCGGCCCUGCUUCUGGGUGGAACUGAUACGGGGACGGCCCGAGGAGAACACCAUCUGGACCAGCG<br>GCAGCAGCAUCAGCUUCUGCGGCGUGGACAGCGAUAUCGUGGGCUGGAGCUGGCCAGACGGAGCCG<br>AGCUGCCCUUCACCAUCGACAAG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIREPFISCSPLECRTF<br>FLTQGALLNDKHSNGTIKGRSPYRTLMSCPIGEVPSPYNSRFESVAWSASACHDGTNWLTIGISGP<br>DSGAVAVLKYNGIITDTIKSWRNKILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 49 |
| PolyA tail | 100 nt | |
| | H3_Hongkong_2019_WT_5UTRSSU | |
| SEQ ID NO: 50 consists of from 5' end to 3' end: 5' UTR SEQ ID NO: 2, mRNA ORF SEQ ID NO: 51, and 3' UTR SEQ ID NO: 4. | | 50 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUC | 51 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNSTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICI | 52 |
| PolyA tail | 100 nt | |

TABLE 11-continued

| | | SEQ ID NO: |
|---|---|---|
| | H3_Hongkong_2019_heterogeneousLoc_S25M_5UTRv1.1 | |
| SEQ ID NO: 53 consists of from 5' end to 3' end: 5' UTR SEQ ID NO: 2, mRNA ORF SEQ ID NO: 54, and 3' UTR SEQ ID NO: 4. | | 53 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAUGACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUC | 54 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNMTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICI | 55 |
| PolyA tail | 100 nt | |
| | H3_Hongkong_2019_heterogeneousLoc_S25M_5UTRSSU | |
| SEQ ID NO: 56 consists of from 5' end to 3' end: 5' UTR SEQ ID NO: 2, mRNA ORF SEQ ID NO: 57, and 3' UTR SEQ ID NO: 4. | | 56 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAUGACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC | 57 |

TABLE 11-continued

| | | SEQ ID NO: |
|---|---|---|
| | GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUC | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNMTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICI | 58 |
| PolyA tail | 100 nt | |
| | N1_Wisconsin_dcytT | |
| SEQ ID NO: 59 consists of from 5' end to 3' end: 5' UTR SEQ ID NO: 2, mRNA ORF SEQ ID NO: 60, and 3' UTR SEQ ID NO: 4. | | 59 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAUCAUCACCAUCGGCAGCAUCUGCAUGACCAUCGGCACCGCCAACCUGAUCCUGCAAAUCGGC<br>AACAUCAUCAGCAUCUGGGUGAGCCACAGCAUCCAGAUCGGCAACCAGAGCCAGAUCGAGACCUGC<br>AACAAGAGCGUGAUCACCUACGAGAACAACACCUGGGUGAACCAGACCUUCGUGAACAUCAGCAAC<br>ACCAACAGCGCCGCUCGGCAGUCAGUGGCCAGCGUGAAGCUGGCCGGCAACAGCAGCCUGUGCCCC<br>GUUAGUGGCUGGGCCAUCUACAGCAAGGACAACAGCGUGCGGAUCGGCAGCAAGGGCGACGUGUUC<br>GUGAUCCGGGAGCCCUUCAUCAGCUGCAGCCCGCUUGAGUGCCGCACCUUCUUCCUGACCCAGGGC<br>GCUCUGCUGAACGACAAGCACAGCAACGGCACCAUCAAGGACCGGAGCCCCUAUCGGACCCUGAUG<br>AGCUGCCCCAUUGGCGAGGUGCCCAGCCCCUACAACAGCCGGUUCGAGUCUGUGGCCUGGAGCGCC<br>UCUGCCUGCCACGACGGCACCAACUGGCUGACCAUCGGGAUCAGCGGACCCGAUAGCGGAGCAGUG<br>GCCGUGCUGAAGUACAACGGCAUCAUCACCGACACCAUCAAGAGCUGGCGGAACAAGAUCCUGCGG<br>ACCCAGGAGAGCGAGUGCGCCUGCGUGAACGGCAGCUGCUUCACCAUCAUGACCGACGGCCCUAGC<br>GACGGACAGGCCAGCUACAAGAUCUUCCGGAUCGAGAAGGGCAAGAUCAUCAAGAGCGUGGAGAUG<br>AAGGCACCCAACUACCACUACGAGGAGUGCAGCUGCUACCCCGACAGCAGCGAGAUCACCUGCGUG<br>UGCCGGGACAACUGGCACGGGAGCAACAGGCCCUGGGUGAGCUUCAACCAGAACCUGGAGUACCAG<br>AUGGGCUACAUCUGCAGCGGCGUGUUCGGCGACAACCCACGGCCCAACGACAAGACUGGCAGCUGC<br>GGUCCGGUGAGCAGCAACGGCGCCAACGGCGUGAAGGGCUUCAGCUUCAAGUACGGCAACGGCGUG<br>UGGAUCGGCCGGACCAAGAGCAUCAGCAGCCGGAAGGGCUUCGAGAUGAUCUGGGACCCCAACGGC<br>UGGACCGGCACCGACAACAAGUUCAGCAAGAAGCAGGACAUCGUGGGCAUCAACGAGUGGAGCGGC<br>UACAGCGGCAGCUUCGUGCAGCACCCCGAGCUGACUGGCCUGAACUGCAUCCGGCCCUGCUUCUGG<br>GUGGAACUGAUACGGGGACGGCCCGAGGAGAACACCAUCUGGACCAGCGGCAGCAGCAUCAGCUUC<br>UGCGGCGUGGACAGCGAUAUCGUGGGCUGGAGCUGGCCAGACGGAGCCGAGCUGCCCUUCACCAUC<br>GACAAG | 60 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MIITIGSICMTIGTANLILQIGNIISIWVSHSIQIGNQSQIETCNKSVITYENNTWVNQTFVNISN<br>TNSAARQSVASVKLAGNSSLCPVSGWAIYSKDNSVRIGSKGDVFVIREPFISCSPLECRTFFLTQG<br>ALLNDKHSNGTIKDRSPYRTLMSCPIGEVPSPYNSRFESVAWSASACHDGTNWLTIGISGPDSGAV<br>AVLKYNGIITDTIKSWRNKILRTQESECACVNGSCFTIMTDGPSDGQASYKIFRIEKGKIIKSVEM<br>KAPNYHYEECSCYPDSSEITCVCRDNWHGSNRPWVSFNQNLEYQMGYICSGVFGDNPRPNDKTGSC<br>GPVSSNGANGVKGFSFKYGNGVWIGRTKSISSRKGFEMIWDPNGWTGTDNKFSKKQDIVGINEWSG<br>YSGSFVQHPELTGLNCIRPCFWVELIRGRPEENTIWTSGSSISFCGVDSDIVGWSWPDGAELPFTI<br>DK | 61 |
| PolyA tail | 100 nt | |
| | N1_Wisconsin_stalk_dl5 | |
| SEQ ID NO: 62 consists of from 5' end to 3' end: 5' UTR SEQ ID NO: 2, mRNA ORF SEQ ID NO: 63, and 3' UTR SEQ ID NO: 4. | | 62 |
| Chemistry | 1-methylpseudouridine | |
| Cap | C1 | |

TABLE 11-continued

| | | SEQ ID NO: |
|---|---|---|
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG AUCCUGCAAAUCGGCAACAUCAUCAGCAUCUGGGUGAGCCACAGCAUCCAGACCGGCAGCCAGAGC CAGAUCGAGACCUGCAACCAGAGCAUUAUCACCUACGAGAAUAACACCUGGGUGAAGGACACCACC AGCGUGAUCCUGACCGGCAACAGCAGCCUGUGCCCCGUUAGUGGCUGGGCCAUCUACAGCAAGGAC AACAGCGUGCGGAUCGGCAGCAAGGGCGACGUGUUCGUGAUCCGGGAGCCCUUCAUCAGCUGCAGC CCGCUUGAGUGCCGCACCUUCUUCCUGACCCAGGGCGCUCUGCUGAACGACAAGCACAGCAACGGC ACCAUCAAGGACCGGAGCCCCUAUCGGACCCUGAUGAGCUGCCCCAUUGGCGAGGUGCCCAGCCCC UACAACAGCCGGUUCGAGUCUGUGGCCUGGAGCGCCUCUGCCUGCCACGACGGCACCAACUGGCUG ACCAUCGGGAUCAGCGGACCCGAUAGCGGAGCAGUGGCCGUGCUGAAGUACAACGGCAUCAUCACC GACACCAUCAAGAGCUGGCGGAACAAGAUCCUGCGGACCCAGGAGAGCGAGUGCGCCUGCGUGAAC GGCAGCUGCUUCACCAUCAUGACCGACGGCCCUAGCGACGGACAGGCCAGCUACAAGAUCUUCCGG AUCGAGAAGGGCAAGAUCAUCAAGAGCGUGGAGAUGAAGGCACCCAACUACCACUACGAGGAGUGC AGCUGCUACCCCGACAGCAGCGAGAUCACCUGCGUGUGCCGGGACAACUGGCACGGGAGCAACAGG CCCUGGGUGAGCUUCAACCAGAACCUGGAGUACCAGAUGGGCUACAUCUGCAGCGGCGUGUUCGGC GACAACCCACGGCCCAACGACAAGACUGGCAGCUGCGGUCCGGUGAGCAGCAACGGCGCCAACGGC GUGAAGGGCUUCAGCUUCAAGUACGGCAACGGCGUGUGGAUCGGCCGGACCAAGAGCAUCAGCAGC CGGAAGGGCUUCGAGAUGAUCUGGGACCCCAACGGCUGGACCGGCACCGACAACAAGUUCAGCAAG AAGCAGGACAUCGUGGGCAUCAACGAGUGGAGCGGCUACAGCGGCAGCUUCGUGCAGCACCCCGAG CUGACUGGCCUGAACUGCAUCCGGCCCUGCUUCUGGGUGGAACUGAUACGGGGACGGCCCGAGGAG AACACCAUCUGGACCAGCGGCAGCAGCAUCAGCUUCUGCGGCGUGGACAGCGAUAUCGUGGGCUGG AGCUGGCCAGACGGAGCCGAGCUGCCCUUCACCAUCGACAAG | 63 |
| 3' UTR | UGAUAAUAGGCUGGAGCCUCGGUGGCCUAGCUUCUUGCCCCUUGGGCCUCCCCCCAGCCCCUCCUC CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQTGSQSQIETCNQSIITYENNTWVKDTT SVILTGNSSLCPVSGWAIYSKDNSVRIGSKGDVFVIREPFISCSPLECRTFFLTQGALLNDKHSNG TIKDRSPYRTLMSCPIGEVPSPYNSRFESVAWSASACHDGTNWLTIGISGPDSGAVAVLKYNGIIT DTIKSWRNKILRTQESECACVNGSCFTIMTDGPSDGQASYKIFRIEKGKIIKSVEMKAPNYHYEEC SCYPDSSEITCVCRDNWHGSNRPWVSFNQNLEYQMGYICSGVFGDNPRPNDKTGSCGPVSSNGANG VKGFSFKYGNGVWIGRTKSISSRKGFEMIWDPNGWTGTDNKFSKKQDIVGINEWSGYSGSFVQHPE LTGLNCIRPCFWVELIRGRPEENTIWTSGSSISFCGVDSDIVGWSWPDGAELPFTIDK | 64 |
| PolyA tail | 100 nt | |
| N1_Wisconsin_stalk_d30 | | |
| SEQ ID NO: 65 consists of from 5' end to 3' end: 5' UTR SEQ ID NO: 2, mRNA ORF SEQ ID NO: 66, and 3' UTR SEQ ID NO: 4. | | 65 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG AUCCUGCAAAUCGGCAACAUCAUCAGCAUCUGGGUGAGCCACAGCAUCCAGAUCGGCAACCAGAGC CAGAUCGAGACCUGCAACCAGAGCGUGAUCCUGACCGGCAACAGCAGCCUGUGCCCCGUUAGUGGC UGGGCCAUCUACAGCAAGGACAACAGCGUGCGGAUCGGCAGCAAGGGCGACGUGUUCGUGAUCCGG GAGCCCUUCAUCAGCUGCAGCCCGCUUGAGUGCCGCACCUUCUUCCUGACCCAGGGCGCUCUGCUG AACGACAAGCACAGCAACGGCACCAUCAAGGACCGGAGCCCCUAUCGGACCCUGAUGAGCUGCCCC AUUGGCGAGGUGCCCAGCCCCUACAACAGCCGGUUCGAGUCUGUGGCCUGGAGCGCCUCUGCCUGC CACGACGGCACCAACUGGCUGACCAUCGGGAUCAGCGGACCCGAUAGCGGAGCAGUGGCCGUGCUG AAGUACAACGGCAUCAUCACCGACACCAUCAAGAGCUGGCGGAACAAGAUCCUGCGGACCCAGGAG AGCGAGUGCGCCUGCGUGAACGGCAGCUGCUUCACCAUCAUGACCGACGGCCCUAGCGACGGACAG GCCAGCUACAAGAUCUUCCGGAUCGAGAAGGGCAAGAUCAUCAAGAGCGUGGAGAUGAAGGCACCC AACUACCACUACGAGGAGUGCAGCUGCUACCCCGACAGCAGCGAGAUCACCUGCGUGUGCCGGGAC AACUGGCACGGGAGCAACAGGCCCUGGGUGAGCUUCAACCAGAACCUGGAGUACCAGAUGGGCUAC AUCUGCAGCGGCGUGUUCGGCGACAACCCACGGCCCAACGACAAGACUGGCAGCUGCGGUCCGGUG AGCAGCAACGGCGCCAACGGCGUGAAGGGCUUCAGCUUCAAGUACGGCAACGGCGUGUGGAUCGGC CGGACCAAGAGCAUCAGCAGCCGGAAGGGCUUCGAGAUGAUCUGGGACCCCAACGGCUGGACCGGC ACCGACAACAAGUUCAGCAAGAAGCAGGACAUCGUGGGCAUCAACGAGUGGAGCGGCUACAGCGGC AGCUUCGUGCAGCACCCCGAGCUGACUGGCCUGAACUGCAUCCGGCCCUGCUUCUGGGUGGAACUG AUACGGGGACGGCCCGAGGAGAACACCAUCUGGACCAGCGGCAGCAGCAUCAGCUUCUGCGGCGUG GACAGCGAUAUCGUGGGCUGGAGCUGGCCAGACGGAGCCGAGCUGCCCUUCACCAUCGACAAG | 66 |
| 3' UTR | UGAUAAUAGGCUGGAGCCUCGGUGGCCUAGCUUCUUGCCCCUUGGGCCUCCCCCCAGCCCCUCCUC CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNQSVILTGNSSLCPVSG WAIYSKDNSVRIGSKGDVFVIREPFISCSPLECRTFFLTQGALLNDKHSNGTIKDRSPYRTLMSCP IGEVPSPYNSRFESVAWSASACHDGTNWLTIGISGPDSGAVAVLKYNGIITDTIKSWRNKILRTQE SECACVNGSCFTIMTDGPSDGQASYKIFRIEKGKIIKSVEMKAPNYHYEECSCYPDSSEITCVCRD NWHGSNRPWVSFNQNLEYQMGYICSGVFGDNPRPNDKTGSCGPVSSNGANGVKGFSFKYGNGVWIG | 67 |

TABLE 11-continued

| | | SEQ ID NO: |
|---|---|---|
| | RTKSISSRKGFEMIWDPNGWTGTDNKFSKKQDIVGINEWSGYSGSFVQHPELTGLNCIRPCFWVEL<br>IRGRPEENTIWTSGSSISFCGVDSDIVGWSWPDGAELPFTIDK | |
| PolyA tail | 100 nt | |
| | N1_Wisconsin_stalk_ins15 | |
| SEQ ID NO: 68 consists of from 5' end to 3' end: 5' UTR SEQ ID NO: 2, mRNA ORF SEQ ID NO: 69, and 3' UTR SEQ ID NO: 4. | | 68 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGAACAUCACCGAGAUCGUGUACCUGACCAACACC<br>ACCAUCGAGAAACAGUCAGUGGCCAGCGUGAAGCUGGCCGGCAACAGCAGCCUGUGCCCCGUUAGU<br>GGCUGGGCCAUCUACAGCAAGGACAACAGCGUGCGGAUCGGCAGCAAGGGCGACGUGUUCGUGAUC<br>CGGGAGCCCUUCAUCAGCUGCAGCCCGCUUGAGUGCCGCACCUUCUUCCUGACCCAGGGCGCUCUG<br>CUGAACGACAAGCACAGCAACGGCACCAUCAAGGACCGGAGCCCCUAUCGGACCCUGAUGAGCUGC<br>CCCAUUGGCGAGGUGCCCAGCCCCUACAACAGCCGGUUCGAGUCUGUGGCCUGGAGCGCCUCUGCC<br>UGCCACGACGGCACCAACUGGCUGACCAUCGGGAUCAGCGGACCCGAUAGCGGAGCAGUGGCCGUG<br>CUGAAGUACAACGGCAUCAUCACCGACACCAUCAAGAGCUGGCGGAACAAGAUCCUGCGGACCCAG<br>GAGAGCGAGUGCGCCUGCGUGAACGGCAGCUGCUUCACCAUCAUGACCGACGGCCCUAGCGACGGA<br>CAGGCCAGCUACAAGAUCUUCCGGAUCGAGAAGGGCAAGAUCAUCAAGAGCGUGGAGAUGAAGGCA<br>CCCAACUACCACUACGAGGAGUGCAGCUGCUACCCCGACAGCAGCGAGAUCACCUGCGUGUGCCGG<br>GACAACUGGCACGGGAGCAACAGGCCCUGGGUGAGCUUCAACCAGAACCUGGAGUACCAGAUGGGC<br>UACAUCUGCAGCGGCGUGUUCGGCGACAACCCACGGCCCAACGACAAGACUGGCAGCUGCGGUCCG<br>GUGAGCAGCAACGGCGCCAACGGCGUGAAGGGCUUCAGCUUCAAGUACGGCAACGGCGUGUGGAUC<br>GGCCGGACCAAGAGCAUCAGCAGCCGGAAGGGCUUCGAGAUGAUCUGGGACCCCAACGGCUGGACC<br>GGCACCGACAACAAGUUCAGCAAGAAGCAGGACAUCGUGGGCAUCAACGAGUGGAGCGGCUACAGC<br>GGCAGCUUCGUGCAGCACCCCGAGCUGACUGGCCUGAACUGCAUCCGGCCCUGCUUCUGGGUGGAA<br>CUGAUACGGGGACGGCCCGAGGAGAACACCAUCUGGACCAGCGGCAGCAGCAUCAGCUUCUGCGGC<br>GUGGACAGCGAUAUCGUGGGCUGGAGCUGGCCAGACGGAGCCGAGCUGCCCUUCACCAUCGACAAG | 69 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARNITEIVYLTNTTIEKQSVASVKLAGNSSLCPVSGWAIYSKDNSVRIGSKGDVFVI<br>REPFISCSPLECRTFFLTQGALLNDKHSNGTIKDRSPYRTLMSCPIGEVPSPYNSRFESVAWSASA<br>CHDGTNWLTIGISGPDSGAVAVLKYNGIITDTIKSWRNKILRTQESECACVNGSCFTIMTDGPSDG<br>QASYKIFRIEKGKIIKSVEMKAPNYHYEECSCYPDSSEITCVCRDNWHGSNRPWVSFNQNLEYQMG<br>YICSGVFGDNPRPNDKTGSCGPVSSNGANGVKGFSFKYGNGVWIGRTKSISSRKGFEMIWDPNGWT<br>GTDNKFSKKQDIVGINEWSGYSGSFVQHPELTGLNCIRPCFWVELIRGRPEENTIWTSGSSISFCG<br>VDSDIVGWSWPDGAELPFTIDK | 70 |
| PolyA tail | 100 nt | |
| | N1_Wisconsin_R118K | |
| SEQ ID NO: 71 consists of from 5' end to 3' end: 5' UTR SEQ ID NO: 2, mRNA ORF SEQ ID NO: 72, and 3' UTR SEQ ID NO: 4. | | 71 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCAAGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGACCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGAGAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC | 72 |

TABLE 11-continued

| | | SEQ ID NO: |
|---|---|---|
| | UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC<br>AGCAGCAUCAGCUUCUGCGGCGUGGACAGCGAUAUCGUGGGCUGGAGCUGGCCAGACGGAGCCGAG<br>CUGCCCUUCACCAUCGACAAG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIKEPFISCSPLECRTF<br>FLTQGALLNDKHSNGTIKDRSPYRTLMSCPIGEVPSPYNSRFESVAWSASACHDGTNWLTIGISGP<br>DSGAVAVLKYNGIITDTIKSWRNKILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 73 |
| PolyA tail | 100 nt | |
| | N1_Wisconsin_E227D | |
| SEQ ID NO: 74 consists of from 5' end to 3' end: 5' UTR SEQ ID NO: 2, mRNA ORF SEQ ID NO: 75, and 3' UTR SEQ ID NO: 4. | | 74 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCCGGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGACCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGACAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC<br>UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC<br>AGCAGCAUCAGCUUCUGCGGCGUGGACAGCGAUAUCGUGGGCUGGAGCUGGCCAGACGGAGCCGAG<br>CUGCCCUUCACCAUCGACAAG | 75 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIREPFISCSPLECRTF<br>FLTQGALLNDKHSNGTIKDRSPYRTLMSCPIGEVPSPYNSRFESVAWSASACHDGTNWLTIGISGP<br>DSGAVAVLKYNGIITDTIKSWRNKILRTQDSECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 76 |
| PolyA tail | 100 nt | |
| | N1_Wisconsin_R118K + D151G | |
| SEQ ID NO: 77 consists of from 5' end to 3' end: 5' UTR SEQ ID NO: 2, mRNA ORF SEQ ID NO: 78, and 3' UTR SEQ ID NO: 4. | | 77 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC | 78 |

TABLE 11-continued

| | | SEQ ID NO: |
|---|---|---|
| Construct (excluding the stop codon) | CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCAAGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGGCCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGAGAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC<br>UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC<br>AGCAGCAUCAGCUUCUGCGGCGUGGACAGCGAUAUCGUGGGCUGGAGCUGGCCAGACGGAGCCGAG<br>CUGCCCUUCACCAUCGACAAG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIKEPFISCSPLECRTF<br>FLTQGALLNDKHSNGTIKGRSPYRTLMSCPIGEVPSPYNSRFESVAWSASACHDGTNWLTIGISGP<br>DSGAVAVLKYNGIITDTIKSWRNKILRTQESECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI<br>NEWSGYSGSFVQHPELTGLNCIRPCFWVELIRGRPEENTIWTSGSSISFCGVDSDIVGWSWPDGAE<br>LPFTIDK | 79 |
| PolyA tail | 100 nt | |
| | N1_Wisconsin_D151G + E227D | |
| SEQ ID NO: 80 consists of from 5' end to 3' end: 5' UTR SEQ ID NO: 2, mRNA ORF SEQ ID NO: 81, and 3' UTR SEQ ID NO: 4. | | 80 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCCAACCAGAAGAUCAUCACCAUCGGCAGCAUCUGCAUGACCAUCGGCACCGCCAACCUG<br>AUCCUGCAAAUCGGCAACAUCAUCAGCAUCUGGGUGAGCCACAGCAUCCAGAUCGGCAACCAGAGC<br>CAGAUCGAGACCUGCAACAAGAGCGUGAUCACCUACGAGAACAACACCUGGGUGAACCAGACCUUC<br>GUGAACAUCAGCAACACCAACAGCGCCGCUCGGCAGUCAGUGGCCAGCGUGAAGCUGGCCGGCAAC<br>AGCAGCCUGUGCCCCGUUAGUGGCUGGGCCAUCUACAGCAAGGACAACAGCGUGCGGAUCGGCAGC<br>AAGGGCGACGUGUUCGUGAUCCGGGAGCCCUUCAUCAGCUGCAGCCCGCUUGAGUGCCGCACCUUC<br>UUCCUGACCCAGGGCGCUCUGCUGAACGACAAGCACAGCAACGGCACCAUCAAGGGCCGGAGCCCC<br>UAUCGGACCCUGAUGAGCUGCCCCAUUGGCGAGGUGCCCAGCCCCUACAACAGCCGGUUCGAGUCU<br>GUGGCCUGGAGCGCCUCUGCCUGCCACGACGGCACCAACUGGCUGACCAUCGGGAUCAGCGGACCC<br>GAUAGCGGAGCAGUGGCCGUGCUGAAGUACAACGGCAUCAUCACCGACACCAUCAAGAGCUGGCGG<br>AACAAGAUCCUGCGGACCCAGGACAGCGAGUGCGCCUGCGUGAACGGCAGCUGCUUCACCAUCAUG<br>ACCGACGGCCCUAGCGACGGACAGGCCAGCUACAAGAUCUUCCGGAUCGAGAAGGGCAAGAUCAUC<br>AAGAGCGUGGAGAUGAAGGCACCCAACUACCACUACGAGGAGUGCAGCUGCUACCCCGACAGCAGC<br>GAGAUCACCUGCGUGUGCCGGGACAACUGGCACGGGAGCAACAGGCCCUGGGUGAGCUUCAACCAG<br>AACCUGGAGUACCAGAUGGGCUACAUCUGCAGCGGCGUGUUCGGCGACAACCCACGGCCCAACGAC<br>AAGACUGGCAGCUGCGGUCCGGUGAGCAGCAACGGCGCCAACGGCGUGAAGGGCUUCAGCUUCAAG<br>UACGGCAACGGCGUGUGGAUCGGCCGGACCAAGAGCAUCAGCAGCCGGAAGGGCUUCGAGAUGAUC<br>UGGGACCCCAACGGCUGGACCGGCACCGACAACAAGUUCAGCAAGAAGCAGGACAUCGUGGGCAUC<br>AACGAGUGGAGCGGCUACAGCGGCAGCUUCGUGCAGCACCCCGAGCUGACUGGCCUGAACUGCAUC<br>CGGCCCUGCUUCUGGGUGGAACUGAUACGGGGACGGCCCGAGGAGAACACCAUCUGGACCAGCGGC<br>AGCAGCAUCAGCUUCUGCGGCGUGGACAGCGAUAUCGUGGGCUGGAGCUGGCCAGACGGAGCCGAG<br>CUGCCCUUCACCAUCGACAAG | 81 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSICMTIGTANLILQIGNIISIWVSHSIQIGNQSQIETCNKSVITYENNTWVNQTF<br>VNISNTNSAARQSVASVKLAGNSSLCPVSGWAIYSKDNSVRIGSKGDVFVIREPFISCSPLECRTF<br>FLTQGALLNDKHSNGTIKGRSPYRTLMSCPIGEVPSPYNSRFESVAWSASACHDGTNWLTIGISGP<br>DSGAVAVLKYNGIITDTIKSWRNKILRTQDSECACVNGSCFTIMTDGPSDGQASYKIFRIEKGKII<br>KSVEMKAPNYHYEECSCYPDSSEITCVCRDNWHGSNRPWVSFNQNLEYQMGYICSGVFGDNPRPND<br>KTGSCGPVSSNGANGVKGFSFKYGNGVWIGRTKSISSRKGFEMIWDPNGWTGTDNKFSKKQDIVGI | 82 |

TABLE 11-continued

| | | SEQ ID NO: |
|---|---|---|
| | NEWSGYSGSFVQHPELTGLNCIRPCFWVELIRGRPEENTIWTSGSSISFCGVDSDIVGWSWPDGAE<br>LPFTIDK | |
| PolyA tail | 100 nt | |
| | H3_HA_GCC | |
| SEQ ID NO: 83 consists of from 5' end to 3' end: 5' UTR SEQ ID NO: 2, mRNA ORF SEQ ID NO: 84, and 3' UTR SEQ ID NO: 4. | | 83 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUCGGCUCUGGCAGCGGCAGC<br>ACCAGCCUGCUGGGACUGGCCGUGCGGCUGCUGCUGUUUCAGCCUGCCCUGAUGGUGUUCUGGGCA<br>AGCCAGGUGCGGCAGAACUGCCGGAACGGCAGCUACGAGAUCAGCGUGCUGAUGAUGGACAACAGC<br>GCCUACAAGGAGCCCAUGCAGAACCUGCGGGAGGCCGUGGAGGAGGGCCUGGACAUCGUGCGGAAG<br>CGGCUGCGGGAAGCCGACCUGAACGUGACCGUGAACGCCACCUUCAUCUACAGCGACGGCCUGAUC<br>CACAAGAGCGGCGACUGCCGGAGCAGCACCUGCGAGGGGCUGGACCUGCUGCGGGAGAUCACCCGG<br>GACCACAAGAUGGGCUGCGCCCUGAUGGGCCCCAGCUGCACCUACAGCACUUUCCAGAUGUACCUG<br>GACACCGAGCUGAACUACCCCAUGAUCAGCGCAGGCAGCUACGGCCUGAGCUGCGACUACAAGGAG<br>ACCCUGACCCGGAUCCUGCCACCCGCCCGGAAGCUGAUGUACUUCCUCGUGGACUUCUGGAAGGUG<br>AACAACGCCAGCUUCAAGCCCUUCAGCUGGAACAGCAGCUACGUGUACAAGAACGGCAGCGAGCCC<br>GAGGACUGCUUCUGGUACCUGAACGCUCUGGAGGCCGGGGUGAGCUACUUCAGCGAGGUGCUGAAC<br>UUCAAGGACGUGCUGCGGCGGAGCGAGCAGUUCCAGGAGAUCCUGACCGGCCACAACCGGAAGAGC<br>AACGUGAUCGUGAUGUGCGGCACCCCGGAGAGCUUCUACGACGUGAAGGGCGACCUGCAGGUGGCC<br>GAGGACACCGUGGUGAUCCUGGUGGACCUGUUCAGCAACCACUACUUCGAGGAGAACACCACCGCC<br>CCUGAGUACAUGGACAACGUGCUGGUGCUGACCCUGCCCAGCGAGCAGAGCACCAGCAACACCAGC<br>GUGGCCGAGCGGUUCAGCAGCGGCCGGAGCGACUUCAGCCUGGCCUACCUGGAGGGCACCCUGCUG<br>UUCGGCCACAUGCUGCAGACCUUCCUGGAGAACGGCGAGAACGUAACCGGCCCCAAGUUCGCCCGG<br>GCCUUCCGGAACCUGACCUUCCAGGGCUUCGCAGGCCCCGUGACCCUGGACGACAGCGGCGACAUC<br>GACAACAUCAUGAGCCUGCUGUACGUGAGCCUGGACACCCGGAAGUACAAGGUGCUGAUGAAGUAC<br>GACACCCACAAGAACAAGACCAUCCCCGUGGCCGAGAACCCCAACUUCAUCUGGAAGAACCACAAG<br>CUGCCCAACGACGUGCCCGGUCUGGGACCGCAGAUCCUGAUGAUCGCCGUGUUCACCCUGACCGGC<br>AUCCUGGUGGUGCUGCUGCUGAUCGCCCUGCUGGUCCUGCGGAAGUACCGGCGGGACCAC | 84 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNSTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICIGSGSGSTSLLGLAVRLLLFQPALMVFWA<br>SQVRQNCRNGSYEISVLMMDNSAYKEPMQNLREAVEEGLDIVRKRLREADLNVTVNATFIYSDGLI<br>HKSGDCRSSTCEGLDLLREITRDHKMGCALMGPSCTYSTFQMYLDTELNYPMISAGSYGLSCDYKE<br>TLTRILPPARKLMYFLVDFWKVNNASFKPFSWNSSYVYKNGSEPEDCFWYLNALEAGVSYFSEVLN | 85 |

TABLE 11-continued

| | | SEQ ID NO: |
|---|---|---|
| | FKDVLRRSEQFQEILTGHNRKSNVIVMCGTPESFYDVKGDLQVAEDTVVILVDLFSNHYFEENTTA<br>PEYMDNVLVLTLPSEQSTSNTSVAERFSSGRSDFSLAYLEGTLLFGHMLQTFLENGENVTGPKFAR<br>AFRNLTFQGFAGPVTLDDSGDIDNIMSLLYVSLDTRKYKVLMKYDTHKNKTIPVAENPNFIWKNHK<br>LPNDVPGLGPQILMIAVFTLTGILVVLLLIALLVLRKYRRDH | |
| Poly A tail | 100 nt | |
| | H3 Hongkong WT | |
| SEQ ID NO: 86 consists of from 5' end to 3' end: 5' UTR SEQ ID NO: 2, mRNA ORF SEQ ID NO: 87, and 3' UTR SEQ ID NO: 4. | | 86 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGGCUUCACCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGAAGUGGGACCUGUUCGUGGAGAGAUCGCGGGCCUAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGGCCGGCGUGACCCAGAACGGCAAGUCAUUCAGC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAAGGAGCAGUUCGACAAGCUGUACAUCUGGGGAGUG<br>CACCAUCCCGGCACCGACAAGGACCAGAUUAGCCUGUACGCCCAGUCUAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAACACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUCUCCUGCUUCCUGCUGUGCGUGGCCCUGCUGGGUUUC<br>AUCAUGUGGGCCUGCCAGAAGGGCAACAUCCGGUGCAACAUCUGCAUC | 87 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLGFTQKIPGNDNSTATLCLGHHAVPNGTIVKTITNDRIEVTNATELVQNSSIGE<br>ICDSPHQILDGGNCTLIDALLGDPQCDGFQNKKWDLFVERSRAYSNCYPYDVPDYASLRSLVASSG<br>TLEFKNESFNWAGVTQNGKSFSCIRGSSSSFFSRLNWLTHLNYTYPALNVTMPNKEQFDKLYIWGV<br>HHPGTDKDQISLYAQSSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQNTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAISCFLLCVALLGFIMWACQKGNIRCNICI | 88 |
| PolyA tail | 100 nt | |
| | H3_Cambodia_WT | |
| SEQ ID NO: 89 consists of from 5' end to 3' end: 5' UTR SEQ ID NO: 2, mRNA ORF SEQ ID NO: 90, and 3' UTR SEQ ID NO: 4. | | 89 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGUGUUCGCCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGGAGUGGGACCUGUUCGUGGAGAGAUCGCGGGCCAAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGACCGGCGUGAAGCAGAACGGCACCUCAAGCGCC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAACGAGCAGUUCGACAAGCUGUACAUCUGGGGAGUG<br>CACCAUCCCAGCACCGACAAGGACCAGAUUAGCCUGUUCGCCCAGCCCAGCGGCCGGAUCACCGUG | 90 |

TABLE 11-continued

| | | SEQ ID NO: |
|---|---|---|
| | AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAGCACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUGUCCUGCUUCCUGCUGUGCAUCGCCCUGCUGGGUUUC<br>AUCAUGUGGGCCUGCCAGAAGGGCAACAUCCGGUGCAACAUCUGCAUC | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKTIIALSYILCLVFAQKIPGNDNSTATLCLGHHAVPNGTIVKTITNDRIEVTNATELVQNSSIGE<br>ICDSPHQILDGGNCTLIDALLGDPQCDGFQNKEWDLFVERSRANSNCYPYDVPDYASLRSLVASSG<br>TLEFKNESFNWTGVKQNGTSSACIRGSSSSFFSRLNWLTHLNYTYPALNVTMPNNEQFDKLYIWGV<br>HHPSTDKDQISLFAQPSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQSTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAMSCFLLCIALLGFIMWACQKGNIRCNICI | 91 |
| PolyA tail | 100 nt | |
| H1_Wisconsin_WT | | |
| SEQ ID NO: 92 consists of from 5' end to 3' end: 5' UTR SEQ ID NO: 2, mRNA ORF SEQ ID NO: 93, and 3' UTR SEQ ID NO: 4. | | 92 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGAUGCUGUACACCUUCACCACCGCCAACGCCGACACCCUGUGCAUC<br>GGCUACCACGCCAACAACAGCACCGACACCGUGGACACCGUGCUGGAGAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAACGGCGUGACAGCAGCCUGUCCA<br>CACGCCGGAGCCAAGAGCUUCUACAAGAACCUGAUCUGGCUGGUGAAGAAGGGCAAGAGCUACCCC<br>AAGAUCAACCAGACCUACAUCAACGACAAGGGCAAGGAGGUGCUGGUGCUGUGGGGCAUCCACCAC<br>CCACCUACCAUCGCCGACCAGCAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC<br>CGGAUGAACUACUACUGGACCCUGGUGGAGCCCGGAGACAAGAUUACCUUCGAGGCCACCGGCAAC<br>CUGGUGGCCCCUCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAAGCCGGGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACAAGAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGACAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | 93 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAILVVMLYTFTTANADTLCIGYHANNSTDTVDTVLEKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDNGVTAACPHAGAKSFYKNLIWLVKKGKSYPKINQTYINDKGKEVLVLWGIHH<br>PPTIADQQSLYQNADAYVFVGTSRYSKKFKPEIATRPKVRDQEGRMNYYWTLVEPGDKITFEATGN<br>LVAPRYAFTMERDAGSGIIISDTPVHDCNTTCQTPEGAINTSLPFQNVHPITIGKCPKYVKSTKLR<br>LATGLRNVPSIQSRGLFGAIAGFIEGGWTGMVDGWYGYHHQNEQGSGYAADLKSTQNAIDKITNKV | 94 |

TABLE 11-continued

| | | SEQ ID NO: |
|---|---|---|
| | NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLDSTRIY<br>QILAIYSTVASSLVLVVSLGAISFWMCSNGSLQCRICI | |
| Poly A tail | 100 nt | |
| | H1_Wisconsin_E22C_K375C | |
| SEQ ID NO: 95 consists of from 5' end to 3' end: 5' UTR SEQ ID NO: 2, mRNA ORF SEQ ID NO: 96, and 3' UTR SEQ ID NO: 4. | | 95 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGAUGCUGUACACCUUCACCACCGCCAACGCCGACACCCUGUGCAUC<br>GGCUACCACGCCAACAACAGCACCGACACCGUGGACACCGUGCUGUGCAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAACGGCGUGACAGCAGCCUGUCCA<br>CACGCCGGAGCCAAGAGCUUCUACAAGAACCUGAUCUGGCUGGUGAAGAAGGGCAAGAGCUACCCC<br>AAGAUCAACCAGACCUACAUCAACGACAAGGGCAAGGAGGUGCUGGUGCUGUGGGGCAUCCACCAC<br>CCACCUACCAUCGCCGACCAGCAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC<br>CGGAUGAACUACUACUGGACCCUGGUGGAGCCCGGAGACAAGAUUACCUUCGAGGCCACCGGCAAC<br>CUGGUGGCCCCUCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAAGCCGGGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACUGCAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGACAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | 96 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAILVVMLYTFTTANADTLCIGYHANNSTDTVDTVLCKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDNGVTAACPHAGAKSFYKNLIWLVKKGKSYPKINQTYINDKGKEVLVLWGIHH<br>PPTIADQQSLYQNADAYVFVGTSRYSKKFKPEIATRPKVRDQEGRMNYYWTLVEPGDKITFEATGN<br>LVAPRYAFTMERDAGSGIIISDTPVHDCNTTCQTPEGAINTSLPFQNVHPITIGKCPKYVKSTKLR<br>LATGLRNVPSIQSRGLFGAIAGFIEGGWTGMVDGWYGYHHQNEQGSGYAADLKSTQNAIDCITNKV<br>NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLDSTRIY<br>QILAIYSTVASSLVLVVSLGAISFWMCSNGSLQCRICI | 97 |
| PolyA tail | 100 nt | |
| | H1_Wisconsin_ E22C_K375C_HA0 | |
| SEQ ID NO: 98 consists of from 5' end to 3' end: 5' UTR SEQ ID NO: 2, mRNA ORF SEQ ID NO: 99, and 3' UTR SEQ ID NO: 4. | | 98 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGAUGCUGUACACCUUCACCACCGCCAACGCCGACACCCUGUGCAUC<br>GGCUACCACGCCAACAACAGCACCGACACCGUGGACACCGUGCUGUGCAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAACGGCGUGACAGCAGCCUGUCCA<br>CACGCCGGAGCCAAGAGCUUCUACAAGAACCUGAUCUGGCUGGUGAAGAAGGGCAAGAGCUACCCC<br>AAGAUCAACCAGACCUACAUCAACGACAAGGGCAAGGAGGUGCUGGUGCUGUGGGGCAUCCACCAC<br>CCACCUACCAUCGCCGACCAGCAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC | 99 |

TABLE 11-continued

| | | SEQ ID NO: |
|---|---|---|
| | CGGAUGAACUACUACUGGACCCUGGUGGAGCCCGGAGACAAGAUUACCUUCGAGGCCACCGGCAAC<br>CUGGUGGCCCCUCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAGCCGCCGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACUGCAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGACAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MKAILVVMLYTFTTANADTLCIGYHANNSTDTVDTVLCKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDNGVTAACPHAGAKSFYKNLIWLVKKGKSYPKINQTYINDKGKEVLVLWGIHH<br>PPTIADQQSLYQNADAYVFVGTSRYSKKFKPEIATRPKVRDQEGRMNYYWTLVEPGDKITFEATGN<br>LVAPRYAFTMERDAGSGIIISDTPVHDCNTTCQTPEGAINTSLPFQNVHPITIGKCPKYVKSTKLR<br>LATGLRNVPSIQAAGLFGAIAGFIEGGWTGMVDGWYGYHHQNEQGSGYAADLKSTQNAIDCITNKV<br>NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLDSTRIY<br>QILAIYSTVASSLVLVVSLGAISFWMCSNGSLQCRICI | 100 |
| PolyA tail | 100 nt | |

H5_Astrakhan_APB

| | | |
|---|---|---|
| SEQ ID NO: 101 consists of from 5' end to 3' end: 5' UTR SEQ ID NO: 2, mRNA ORF SEQ ID NO: 102, and 3' UTR SEQ ID NO: 4. | | 101 |
| Chemistry | 1-methylpseudouridine | |
| Cap | C2 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGGAGAACAUUGUGUUACUGCUGGCCAUUGUGUCACUGGUGAAAUCCGACCAGAUUUGCAUUGGU<br>UACCACGCCAAUAACUCAACCGAGCAGGUGGAUACUAUCAUGGAGAAGAACGUAACCGUCACCCAC<br>GCCCAGGACAUUUUGGAGAAGACACAUAACGGUAAACUCUGUGACCUGAACGGGGUGAAGCCCUUG<br>AUACUGAAGGAUUGCUCUGUAGCGGGCUGGCUACUCGGAAAUCCUAUGUGCGACGAAUUUAUUCGC<br>GUACCUGAGUGGAGUUAUAUCGUUGAGAGAGCCAAUCCAGCUAACGAUCUGUGCUAUCCUGGCAGU<br>CUGAACGAUUACGAAGAGCUUAAACACCUCCUGUCCCGGAUUAACCAUUUCGAGAAGAUAUUGAUA<br>AUCCCGAAGAGCAGCUGGCCAAAUCACGAAACCUCCCUGGGAGUGAGCGCUGCUUGCCCCUACCAG<br>GGAGCCCCUUCAUUCUUCAGGAACGUGGUUUGGCUGAUCAAGAAGAACGACGCAUACCCAACUAUU<br>AAGAUCUCCUACAAUAAUACCAACCGGGAGGACCUGCUAAUCUUGUGGGGUAUCCAUCACAGCAAC<br>AACGCAGAAGAGCAAACUAACCUGUAUAAGAACCCGACCACCUAUAUCUCGGUCGGAACAAGCACG<br>UUAAACCAGCGGUUGGUCCCGAAGAUCGCCACAAGGUCUCAGGUGAACGGCCAGAGAGGAAGAAUG<br>GACUUCUUCUGGACCAUAUUGAAGCCAGACGACGCAAUACAUUUCGAGUCUAACGGAAACUUCAUU<br>GCUCCGGAAUACGCGUACAAGAUUGUUAAGAAGGGCGAUUCGACCAUUAUGAAAUCAGGGGUGGAA<br>UACGGUCACUGUAACACCAAGUGCCAAACUCCUGUGGGCGCUAUUAACUCAUCAAUGCCCUUCCAC<br>AAUAUUCACCCACUGACUAUUGGUGAGUGCCCGAAAUACGUAAAGUCUAAUAAACUCGUGUUGGCG<br>ACCGGCCUAAGAAACAGCCCACAGAUCGAGACCAGGGGCUUGUUUGGGGCGAUUGCAGGAUUUAUC<br>GAAGGCGGCUGGCAGGGUAUGGUGGACGGCUGGUACGGAUAUCAUCACAGCAACGAACAAGGGUCA<br>GGAUACGCCGCAGACAAAGAAUCGACUCAGAAAGCUAUAGACGGAGUGACGAACAAAGUGAACUCG<br>AUCAUUGAUAAGAUGAAUACACAGUUUGAAGCGGUCGGCAGAGAAUUUAACAACUUGGAACGGAGA<br>AUUGAGAAUCUGAACAAGAAGAUGGAGGACGGCUUUCUGGACGUGUGGACUUAUAACGCCGAGCUC<br>CUCGUGCUGAUGGAGAACGAAAGGACUCUUGACUUUCACGAUUCAAACGUCAAGAACCUGUACGAC<br>AAGGUUAGAUUGCAGCUGCGGGACAACGCCAAAGAACUGGGUAACGGCUGUUUCGAGUUCUACCAU<br>AAGUGCGAUAACGAGUGCAUGGAAUCUGUCAGAAACGGUACCUACGACUAUCCCCAGUAUUCUGAA<br>GAGGCCCGCCUCAAACGAGAGGAGAUCUCUGGAGUGAAGCUGGAGUCCAUUGGCACGUACCAAAUU<br>CUGUCAAUCUACUCCACCGCUGCAUCAAGCCUAGCUCUGGCGAUCAUGAUGGCGGGGCUCAGUCUG<br>UGGAUGUGUUCAAACGGUUCCCUGCAGUGUCGCAUUUGUAUC | 102 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MENIVLLLAIVSLVKSDQICIGYHANNSTEQVDTIMEKNVTVTHAQDILEKTHNGKLCDLNGVKPL<br>ILKDCSVAGWLLGNPMCDEFIRVPEWSYIVERANPANDLCYPGSLNDYEELKHLLSRINHFEKILI<br>IPKSSWPNHETSLGVSAACPYQGAPSFFRNVVWLIKKNDAYPTIKISYNNTNREDLLILWGIHHSN<br>NAEEQTNLYKNPTTYISVGTSTLNQRLVPKIATRSQVNGQRGRMDFFWTILKPDDAIHFESNGNFI<br>APEYAYKIVKKGDSTIMKSGVEYGHCNTKCQTPVGAINSSMPFHNIHPLTIGECPKYVKSNKLVLA<br>TGLRNSPQIETRGLFGAIAGFIEGGWQGMVDGWYGYHHSNEQGSGYAADKESTQKAIDGVTNKVNS<br>IIDKMNTQFEAVGREFNNLERRIENLNKKMEDGFLDVWTYNAELLVLMENERTLDFHDSNVKNLYD | 103 |

TABLE 11-continued

| | | SEQ ID NO: |
|---|---|---|
| | KVRLQLRDNAKELGNGCFEFYHKCDNECMESVRNGTYDYPQYSEEARLKREEISGVKLESIGTYQI<br>LSIYSTAASSLALAIMMAGLSLWMCSNGSLQCRICI | |
| PolyA tail | 100 nt | |
| | H5_Astrakham _WT | |
| SEQ ID NO: 104 consists of from 5' end to 3' end: 5' UTR SEQ ID NO: 2, mRNA ORF SEQ ID NO: 105, and 3' UTR SEQ ID NO: 4. | | 104 |
| Chemistry | 1-methylpseudouridine | |
| Cap | C2 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGGAGAACAUUGUGUUACUGCUGGCCAUUGUGUCACUGGUGAAAUCCGACCAGAUUUGCAUUGGU<br>UACCACGCCAAUAACUCAACCGAGCAGGUGGAUACUAUCAUGGAGAAGAACGUAACCGUCACCCAC<br>GCCCAGGACAUUUUGGAGAAGACACAUAACGGUAAACUCUGUGACCUGAACGGGGUGAAGCCCUUG<br>AUACUGAAGGAUUGCUCUGUAGCGGGCUGGCUACUCGGAAAUCCUAUGUGCGACGAAUUUAUUCGC<br>GUACCUGAGUGGAGUUAUAUCGUUGAGAGAGCCAAUCCAGCUAACGAUCUGUGCUAUCCUGGCAGU<br>CUGAACGAUUACGAAGAGCUUAAACACCUCCUGUCCCGGAUUAACCAUUUCGAGAAGAUAUUGAUA<br>AUCCCGAAGAGCAGCUGGCCAAAUCACGAAACCUCCCUGGGAGUGAGCGCUGCUUGCCCCUACCAG<br>GGAGCCCCUUCAUUCUUCAGGAACGUGGUUUGGCUGAUCAAGAAGAACGACGCAUACCCAACUAUU<br>AAGAUCUCCUACAAUAAUACCAACCGGGAGGACCUGCUAAUCUUGUGGGGUAUCCAUCACAGCAAC<br>AACGCAGAAGAGCAAACUAACCUGUAUAAGAACCCGACCACCUAUAUCUCGGUCGGAACAAGCACG<br>UUAAACCAGCGGUUGGUCCCGAAGAUCGCCACAAGGUCUCAGGUGAACGGCCAGAGAGGAAGAAUG<br>GACUUCUUCUGGACCAUAUUGAAGCCAGACGACGCAAUACAUUUCGAGUCUAACGGAAACUUCAUU<br>GCUCCGGAAUACGCGUACAAGAUUGUUAAGAAGGGCGAUUCGACCAUUAUGAAAUCAGGGGUGGAA<br>UACGGUCACUGUAACACCAAGUGCCAAACUCCUGUGGGCGCUAUUAACUCAUCAAUGCCCUUCCAC<br>AAUAUUCACCCACUGACUAUUGGUGAGUGCCCGAAAUACGUAAAGUCUAAUAAACUCGUGUUGGCG<br>ACCGGCCUAAGAAACAGCCCACUUCGCGAGAAGAGGCGGAAGAGGGGCUUGUUUGGGGCGAUUGCA<br>GGAUUUAUCGAAGGCGGCUGGCAGGGUAUGGUGGACGGCUGGUACGGAUAUCAUCACAGCAACGAA<br>CAAGGGUCAGGAUACGCCGCAGACAAAGAAUCGACUCAGAAAGCUAUAGACGGAGUGACGAACAAA<br>GUGAACUCGAUCAUUGAUAAGAUGAAUACACAGUUUGAAGCGGUCGGCAGAGAAUUUAACAACUUG<br>GAACGGAGAAUUGAGAAUCUGAACAAGAAGAUGGAGGACGGCUUUCUGGACGUGUGGACUUAUAAC<br>GCCGAGCUCCUCGUGCUGAUGGAGAACGAAAGGACUCUUGACUUUCACGAUUCAAACGUCAAGAAC<br>CUGUACGACAAGGUUAGAUUGCAGCUGCGGGACAACGCCAAAGAACUGGGUAACGGCUGUUUCGAG<br>UUCUACCAUAAGUGCGAUAACGAGUGCAUGGAAUCUGUCAGAAACGGUACCUACGACUAUCCCCAG<br>UAUUCUGAAGAGGCCCGCCUCAAACGAGAGGAGAUCUCUGGAGUGAAGCUGGAGUCCAUUGGCACG<br>UACCAAAUUCUGUCAAUCUACUCCACCGCUGCAUCAAGCCUAGCUCUGGCGAUCAUGAUGGCGGGG<br>CUCAGUCUGUGGAUGUGUUCAAACGGUUCCCUGCAGUGUCGCAUUUGUAUC | 105 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MENIVLLLAIVSLVKSDQICIGYHANNSTEQVDTIMEKNVTVTHAQDILEKTHNGKLCDLNGVKPL<br>ILKDCSVAGWLLGNPMCDEFIRVPEWSYIVERANPANDLCYPGSLNDYEELKHLLSRINHFEKILI<br>IPKSSWPNHETSLGVSAACPYQGAPSFFRNVVWLIKKNDAYPTIKISYNNTNREDLLILWGIHHSN<br>NAEEQTNLYKNPTTYISVGTSTLNQRLVPKIATRSQVNGQRGRMDFFWTILKPDDAIHFESNGNFI<br>APEYAYKIVKKGDSTIMKSGVEYGHCNTKCQTPVGAINSSMPFHNIHPLTIGECPKYVKSNKLVLA<br>TGLRNSPLREKRRKRGLFGAIAGFIEGGWQGMVDGWYGYHHSNEQGSGYAADKESTQKAIDGVTNK<br>VNSIIDKMNTQFEAVGREFNNLERRIENLNKKMEDGFLDVWTYNAELLVLMENERTLDFHDSNVKN<br>LYDKVRLQLRDNAKELGNGCFEFYHKCDNECMESVRNGTYDYPQYSEEARLKREEISGVKLESIGT<br>YQILSIYSTAASSLALAIMMAGLSLWMCSNGSLQCRICI | 106 |
| PolyA tail | 100 nt | |
| | N2_Hongkong_WT | |
| SEQ ID NO: 107 consists of from 5' end to 3' end: 5' UTR SEQ ID NO: 2, mRNA ORF SEQ ID NO: 108, and 3' UTR SEQ ID NO: 4. | | 107 |
| Chemistry | 1-methylpseudouridine | |
| Cap | C3 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CUGCCCAACAACCAGGUGAUGCUGUGCGAGCCCACCAUCAUCGAGCGGAACAUCACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGACCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGAGAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC | 108 |

TABLE 11-continued

| | | SEQ ID NO: |
|---|---|---|
| | ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGCUACGUGUGCAGCGGUCUGGUGGGCGACACUCCCCGGAAGAGCGAC<br>AGCAGCUCCAGCAGCCACUGCCUGAACCCCAACAACGAGGAGGGUGGUCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>GAUCUGAACCUGAUGCACAUC | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSVSLTISTICFFMQIAILITTVTLHFKQYEFNSLPNNQVMLCEPTIIERNITEIV<br>YLTNTTIEKEICPKPAEYRNWSKPQCGITGFAPFSKDNSIRLSAGGDIWVTREPYVSCDLDKCYQF<br>ALGQGTTLNNVHSNNTVRDRTPYRTLLMNELGVPFHLGTKQVCIAWSSSSCHDGKAWLHVCITGDD<br>KNATASFIYNGRLVDSVVSWSNDILRTQESECVCINGTCTVVMTDGNATGKADTKILFIEEGKIVH<br>TSKLSGSAQHVEECSCYPRYPGVRCVCRDNWKGSNRPIIDINIKDHSIVSSYVCSGLVGDTPRKSD<br>SSSSSHCLNPNNEEGGHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>DLNLMHI | 109 |
| PolyA tail | 100 nt | |
| | N2_Cambodia_WT | |
| SEQ ID NO: 110 consists of from 5' end to 3' end: 5' UTR SEQ ID NO: 2, mRNA ORF SEQ ID NO: 111, and 3' UTR SEQ ID NO: 4. | | 110 |
| Chemistry | 1-methylpseudouridine | |
| Cap | C4 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CCUCCCAACAACCAGGUGAUGCUGUGCGAGCCCACCAUCAUCGAGCGGAACAUGACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGACCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGAGAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC<br>ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGAUACGUGUGCAGCGGUCUGGUGGGCGACACUCCCCGGAAGAGCGAC<br>AGCAGCUCCAGCAGCCACUGCCUGAACCCCAACAACGAGAAGGGUGACCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>AACCUGAGCCUGAUGCACAUC | 111 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSVSLTISTICFFMQIAILITTVTLHFKQYEFNSPPNNQVMLCEPTIIERNMTEIV<br>YLTNTTIEKEICPKPAEYRNWSKPQCGITGFAPFSKDNSIRLSAGGDIWVTREPYVSCDLDKCYQF<br>ALGQGTTLNNVHSNNTVRDRTPYRTLLMNELGVPFHLGTKQVCIAWSSSSCHDGKAWLHVCITGDD<br>KNATASFIYNGRLVDSVVSWSNDILRTQESECVCINGTCTVVMTDGNATGKADTKILFIEEGKIVH<br>TSKLSGSAQHVEECSCYPRYPGVRCVCRDNWKGSNRPIIDINIKDHSIVSRYVCSGLVGDTPRKSD<br>SSSSSHCLNPNNEKGDHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>NLSLMHI | 112 |
| PolyA tail | 100 nt | |
| | N2_Cambodia_D151G | |
| SEQ ID NO: 113 consists of from 5' end to 3' end: 5' UTR SEQ ID NO: 2, mRNA ORF SEQ ID NO: 114, and 3' UTR SEQ ID NO: 4. | | 113 |
| Chemistry | 1-methylpseudouridine | |
| Cap | C4 | |

TABLE 11-continued

| | | SEQ ID NO: |
|---|---|---|
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CCUCCCAACAACCAGGUGAUGCUGUGCGAGCCCACCAUCAUCGAGCGGAACAUGACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGGCCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGAGAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC<br>ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGAUACGUGUGCAGCGGUCUGGUGGGCGACACUCCCCGGAAGAGCGAC<br>AGCAGCUCCAGCAGCCACUGCCUGAACCCCAACAACGAGAAGGGUGACCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>AACCUGAGCCUGAUGCACAUC | 114 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIITIGSVSLTISTICFFMQIAILITTVTLHFKQYEFNSPPNNQVMLCEPTIIERNMTEIV<br>YLTNTTIEKEICPKPAEYRNWSKPQCGITGFAPFSKDNSIRLSAGGDIWVTREPYVSCDLDKCYQF<br>ALGQGTTLNNVHSNNTVRGRTPYRTLLMNELGVPFHLGTKQVCIAWSSSSCHDGKAWLHVCITGDD<br>KNATASFIYNGRLVDSVVSWSNDILRTQESECVCINGTCTVVMTDGNATGKADTKILFIEEGKIVH<br>TSKLSGSAQHVEECSCYPRYPGVRCVCRDNWKGSNRPIIDINIKDHSIVSRYVCSGLVGDTPRKSD<br>SSSSSHCLNPNNEKGDHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>NLSLMHI | 115 |
| PolyA tail | 100 nt | |

N2_Cambodia_E227D

| | | |
|---|---|---|
| SEQ ID NO: 116 consists of from 5' end to 3' end: 5' UTR SEQ ID NO: 2, mRNA ORF SEQ ID NO: 117, and 3' UTR SEQ ID NO: 4. | | 116 |
| Chemistry | 1-methylpseudouridine | |
| Cap | C5 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCGAACCAGAAGAUCAUCACCAUCGGCAGCGUGAGCCUGACCAUCAGCACCAUCUGCUUC<br>UUCAUGCAGAUCGCCAUCCUGAUCACCACCGUGACCCUGCACUUCAAGCAGUACGAGUUCAACAGC<br>CCUCCCAACAACCAGGUGAUGCUGUGCGAGCCCACCAUCAUCGAGCGGAACAUGACCGAGAUCGUG<br>UACCUGACCAACACCACCAUCGAGAAGGAGAUCUGCCCCAAGCCCGCCGAGUACCGGAACUGGAGC<br>AAGCCCCAGUGCGGCAUCACCGGCUUCGCCCCAUUCAGCAAGGACAACAGCAUCAGACUGAGUGCC<br>GGCGGCGACAUCUGGGUGACCCGGGAGCCCUACGUGAGCUGCGACCUGGACAAGUGCUACCAGUUC<br>GCCCUGGGACAGGGCACCACCCUGAACAACGUGCACAGCAACAACACUGUGCGGGACCGGACCCCA<br>UACCGGACCCUGCUGAUGAACGAGCUGGGCGUGCCCUUCCACCUGGGCACCAAGCAGGUGUGCAUC<br>GCCUGGAGCAGCAGCAGCUGCCACGACGGCAAGGCCUGGCUGCACGUGUGCAUUACCGGCGACGAC<br>AAGAACGCCACCGCCAGCUUCAUCUACAACGGCAGGCUGGUGGACAGCGUGGUGAGCUGGAGCAAC<br>GACAUCCUGCGGACCCAGGACAGCGAGUGCGUGUGCAUCAACGGCACCUGCACCGUGGUGAUGACU<br>GACGGCAACGCCACCGGCAAGGCCGACACCAAGAUCCUGUUCAUCGAGGAGGGGAAGAUCGUGCAC<br>ACCAGCAAGCUGUCUGGCAGCGCCCAGCACGUGGAGGAGUGCAGCUGCUACCCUCGGUACCCCGGC<br>GUGAGGUGCGUGUGCCGGGACAACUGGAAGGGCAGCAACCGGCCCAUCAUCGACAUCAACAUCAAG<br>GACCACAGCAUAGUGAGCAGAUACGUGUGCAGCGGUCUGGUGGGCGACACUCCCCGGAAGAGCGAC<br>AGCAGCUCCAGCAGCCACUGCCUGAACCCCAACAACGAGAAGGGUGACCACGGCGUGAAGGGCUGG<br>GCCUUCGACGACGGCAACGACGUGUGGAUGGGCCGGACCAUCAACGAGACCAGCAGACUGGGCUAC<br>GAGACCUUCAAGGUGGUGGAGGGCUGGAGCAAUCCCAAGAGCAAGCUGCAGAUCAACCGGCAGGUG<br>AUCGUCGAUCGGGGCGAUCGGAGCGGCUACAGCGGCAUCUUCAGCGUGGAGGGCAAGAGCUGCAUC<br>AACCGGUGCUUCUACGUGGAGCUGAUCCGGGGCCGGAAGGAGGAGACCGAGGUGCUGUGGACCAGC<br>AACAGCAUCGUGGUGUUCUGCGGCACCAGCGGCACCUACGGCACCGGAUCCUGGCCAGACGGCGCC<br>AACCUGAGCCUGAUGCACAUC | 117 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid | MNPNQKIITIGSVSLTISTICFFMQIAILITTVTLHFKQYEFNSPPNNQVMLCEPTIIERNMTEIV<br>YLTNTTIEKEICPKPAEYRNWSKPQCGITGFAPFSKDNSIRLSAGGDIWVTREPYVSCDLDKCYQF | 118 |

TABLE 11-continued

| | | SEQ ID NO: |
|---|---|---|
| sequence | ALGQGTTLNNVHSNNTVRDRTPYRTLLMNELGVPFHLGTKQVCIAWSSSSCHDGKAWLHVCITGDD<br>KNATASFIYNGRLVDSVVSWSNDILRTQDSECVCINGTCTVVMTDGNATGKADTKILFIEEGKIVH<br>TSKLSGSAQHVEECSCYPRYPGVRCVCRDNWKGSNRPIIDINIKDHSIVSRYVCSGLVGDTPRKSD<br>SSSSSHCLNPNNEKGDHGVKGWAFDDGNDVWMGRTINETSRLGYETFKVVEGWSNPKSKLQINRQV<br>IVDRGDRSGYSGIFSVEGKSCINRCFYVELIRGRKEETEVLWTSNSIVVFCGTSGTYGTGSWPDGA<br>NLSLMHI | |
| PolyA tail | 100 nt | |
| | N8_Astrakhan_WT | |
| SEQ ID NO: 119 consists of from 5' end to 3' end: 5' UTR SEQ ID NO: 2, mRNA ORF SEQ ID NO: 120, and 3' UTR SEQ ID NO: 4. | | 119 |
| Chemistry | 1-methylpseudouridine | |
| Cap | C6 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCUAAUCAGAAGAUUGCGACCAUUGGCAGCAUUUCUCUUGGCCUCGUGGUGUUCAACGUC<br>UUGCUGCACGCCCUAUCCAUCAUCCUCAUGGUCCUGGCCCUUGGUAAGAGCGAGAACAACGGUAUU<br>UGUAAGGGAACAAUCAUCAGAGAGUACAACGAGACCGUUCGGAUCGAGAAGGUAACACAGUGGUAC<br>AAUACGUCAGUUGUGGAGUACGUGCCGCACUGGAACGAGGGCGCUUAUAUUAACAACACCGAGCCA<br>AUCUGCGACGUGAAGGGCUUUGCGCCUUUUAGCAAAGACAACGGAAUCCGAAUCGGAAGCAGAGGG<br>CAUAUCUUUGUUAUUAGGGAACCAUUUGUGUCUUGUAGUCCCGUCGAGUGCCGAACCUUCUUCCUU<br>ACACAGGGCGCAUUGCUGAACGAUAAGCAUUCCAACGGCACCGUUAAGGACAGGAGCCCAUUCAGG<br>ACACUGAUGUCAGUGGAAGUUGGUCAAUCGCCUAACGUUUAUCAGGCACGCUUUGAGGCCGUGGCC<br>UGGAGUGCAACCGCCUGUCACGACGGCAAGAAGUGGAUGACAAUUGGGGUGACUGGUCCUGACAGC<br>AAGGCAAUCGCAGUUGUUCACUACGGCGGUGUCCCCACGGACAUCGUGAAUUCGUGGGCCGGAGAC<br>AUCCUGCGGACUCAGGAAUCUUCGUGUACCUGCAUCCAGGGCAACUGUUACUGGGUAAUGACUGAC<br>GGUCCUAGUAACCGUCAGGCCCAAUAUAGAAUAUACAAGGCCAACCAGGGCAAGAUUAUUGACCAA<br>GCCGACGUAUCCUUCUCCGGCGGCCAUAUCGAGGAGUGCUCUUGUUAUCCUAACGACGGAAAGGUC<br>GAGUGUGUGUGCCGCGACAACUGGAUCGGGACCAACCGCCCUGUGCUGGUCAUAUCUCCUGAUCUG<br>UCAUAUCGUGUGGGAUAUCUUUGUGCAGGAUUGCCAUCCGAUACACCCCGAGGUGAGGACGCCCAG<br>UUCGUAGGGAGCUGUACUAGCCCUAUGGGAAAUCAGGGAUACGGCGUUAAGGGUUUUGGAUUCCGC<br>CAAGGUACCGACGUCUGGAUGGGCAGGACCAUAAGCAGGACCAGCAGAUCCGGAUUUGAAAUCAUC<br>AGGAUCAAGAACGGGUGGACCCAGACGUCUAAAGAGCAAAUUCGUCGGCAAGUGGUUGUAGACAAU<br>CUAAAUUGGUCUGGCUAUAGCGGAAGUUUCACUCUUCCAGUUGAACUCAGCGGCCGUGAGUGUCUG<br>GUGCCGUGCUUUUGGGUGGAAAUGAUCAGAGGCAGGCCCGAGGAGCGUACAAUCUGGACAUCUUCU<br>UCCUCCAUCGUGAUGUGUGGGGUUGAUCACGAGAUCGCAGACUGGAGCUGGCACGACGGUGCGAUA<br>CUGCCAUUCGACAUUGACGGAAUG | 120 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIATIGSISLGLVVFNVLLHALSIILMVLALGKSENNGICKGTIIREYNETVRIEKVTQWY<br>NTSVVEYVPHWNEGAYINNTEPICDVKGFAPFSKDNGIRIGSRGHIFVIREPFVSCSPVECRTFFL<br>TQGALLNDKHSNGTVKDRSPFRTLMSVEVGQSPNVYQARFEAVAWSATACHDGKKWMTIGVTGPDS<br>KAIAVVHYGGVPTDIVNSWAGDILRTQESSCTCIQGNCYWVMTDGPSNRQAQYRIYKANQGKIIDQ<br>ADVSFSGGHIEECSCYPNDGKVECVCRDNWIGTNRPVLVISPDLSYRVGYLCAGLPSDTPRGEDAQ<br>FVGSCTSPMGNQGYGVKGFGFRQGTDVWMGRTISRTSRSGFEIIRIKNGWTQTSKEQIRRQVVVDN<br>LNWSGYSGSFTLPVELSGRECLVPCFWVEMIRGRPEERTIWTSSSSIVMCGVDHEIADWSWHDGAI<br>LPFDIDGM | 121 |
| PolyA tail | 100 nt | |
| | N8_Astrakhan_D151G | |
| SEQ ID NO: 122 consists of from 5' end to 3' end: 5' UTR SEQ ID NO: 2, mRNA ORF SEQ ID NO: 123, and 3' UTR SEQ ID NO: 4. | | 122 |
| Chemistry | 1-methylpseudouridine | |
| Cap | C6 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCUAAUCAGAAGAUUGCGACCAUUGGCAGCAUUUCUCUUGGCCUCGUGGUGUUCAACGUC<br>UUGCUGCACGCCCUAUCCAUCAUCCUCAUGGUCCUGGCCCUUGGUAAGAGCGAGAACAACGGUAUU<br>UGUAAGGGAACAAUCAUCAGAGAGUACAACGAGACCGUUCGGAUCGAGAAGGUAACACAGUGGUAC<br>AAUACGUCAGUUGUGGAGUACGUGCCGCACUGGAACGAGGGCGCUUAUAUUAACAACACCGAGCCA<br>AUCUGCGACGUGAAGGGCUUUGCGCCUUUUAGCAAAGACAACGGAAUCCGAAUCGGAAGCAGAGGG<br>CAUAUCUUUGUUAUUAGGGAACCAUUUGUGUCUUGUAGUCCCGUCGAGUGCCGAACCUUCUUCCUU<br>ACACAGGGCGCAUUGCUGAACGAUAAGCAUUCCAACGGCACCGUUAAGGGCAGGAGCCCAUUCAGG<br>ACACUGAUGUCAGUGGAAGUUGGUCAAUCGCCUAACGUUUAUCAGGCACGCUUUGAGGCCGUGGCC<br>UGGAGUGCAACCGCCUGUCACGACGGCAAGAAGUGGAUGACAAUUGGGGUGACUGGUCCUGACAGC<br>AAGGCAAUCGCAGUUGUUCACUACGGCGGUGUCCCCACGGACAUCGUGAAUUCGUGGGCCGGAGAC<br>AUCCUGCGGACUCAGGAAUCUUCGUGUACCUGCAUCCAGGGCAACUGUUACUGGGUAAUGACUGAC<br>GGUCCUAGUAACCGUCAGGCCCAAUAUAGAAUAUACAAGGCCAACCAGGGCAAGAUUAUUGACCAA<br>GCCGACGUAUCCUUCUCCGGCGGCCAUAUCGAGGAGUGCUCUUGUUAUCCUAACGACGGAAAGGUC | 123 |

TABLE 11-continued

| | | SEQ ID NO: |
|---|---|---|
| | GAGUGUGUGUGCCGCGACAACUGGAUCGGGACCAACCGCCCUGUGCUGGUCAUAUCUCCUGAUCUG<br>UCAUAUCGUGUGGGAUAUCUUUGUGCAGGAUUGCCAUCCGAUACACCCCGAGGUGAGGACGCCCAG<br>UUCGUAGGGAGCUGUACUAGCCCUAUGGGAAAUCAGGGAUACGGCGUUAAGGGUUUUGGAUUCCGC<br>CAAGGUACCGACGUCUGGAUGGGCAGGACCAUAAGCAGGACCAGCAGAUCCGGAUUUGAAAUCAUC<br>AGGAUCAAGAACGGGUGGACCCAGACGUCUAAAGAGCAAAUUCGUCGGCAAGUGGUUGUAGACAAU<br>CUAAAUUGGUCUGGCUAUAGCGGAAGUUUCACUCUUCCAGUUGAACUCAGCGGCCGUGAGUGUCUG<br>GUGCCGUGCUUUUGGGUGGAAAUGAUCAGAGGCAGGCCCGAGGAGCGUACAAUCUGGACAUCUUCU<br>UCCUCCAUCGUGAUGUGUGGGGUUGAUCACGAGAUCGCAGACUGGAGCUGGCACGACGGUGCGAUA<br>CUGCCAUUCGACAUUGACGGAAUG | |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIATIGSISLGLVVFNVLLHALSIILMVLALGKSENNGICKGTIIREYNETVRIEKVTQWY<br>NTSVVEYVPHWNEGAYINNTEPICDVKGFAPFSKDNGIRIGSRGHIFVIREPFVSCSPVECRTFFL<br>TQGALLNDKHSNGTVKGRSPFRTLMSVEVGQSPNVYQARFEAVAWSATACHDGKKWMTIGVTGPDS<br>KAIAVVHYGGVPTDIVNSWAGDILRTQESSCTCIQGNCYWVMTDGPSNRQAQYRIYKANQGKIIDQ<br>ADVSFSGGHIEECSCYPNDGKVECVCRDNWIGTNRPVLVISPDLSYRVGYLCAGLPSDTPRGEDAQ<br>FVGSCTSPMGNQGYGVKGFGFRQGTDVWMGRTISRTSRSGFEIIRIKNGWTQTSKEQIRRQVVVDN<br>LNWSGYSGSFTLPVELSGRECLVPCFWVEMIRGRPEERTIWTSSSSIVMCGVDHEIADWSWHDGAI<br>LPFDIDGM | 124 |
| PolyA tail | 100 nt | |
| | N8_Astrakhan_E227D | |
| SEQ ID NO: 125 consists of from 5' end to 3' end: 5' UTR SEQ ID NO: 2, mRNA ORF SEQ ID NO: 126, and 3' UTR SEQ ID NO: 4. | | 125 |
| Chemistry | 1-methylpseudouridine | |
| Cap | C7 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAACCCUAAUCAGAAGAUUGCGACCAUUGGCAGCAUUUCUCUUGGCCUCGUGGUGUUCAACGUC<br>UUGCUGCACGCCCUAUCCAUCAUCCUCAUGGUCCUGGCCCUUGGUAAGAGCGAGAACAACGGUAUU<br>UGUAAGGGAACAAUCAUCAGAGAGUACAACGAGACCGUUCGGAUCGAGAAGGUAACACAGUGGUAC<br>AAUACGUCAGUUGUGGAGUACGUGCCGCACUGGAACGAGGGCGCUUAUAUUAACAACACCGAGCCA<br>AUCUGCGACGUGAAGGGCUUUGCGCCUUUUAGCAAAGACAACGGAAUCCGAAUCGGAAGCAGAGGG<br>CAUAUCUUUGUUAUUAGGGAACCAUUUGUGUCUUGUAGUCCCGUCGAGUGCCGAACCUUCUUCCUU<br>ACACAGGGCGCAUUGCUGAACGAUAAGCAUUCCAACGGCACCGUUAAGGACAGGAGCCCAUUCAGG<br>ACACUGAUGUCAGUGGAAGUUGGUCAAUCGCCUAACGUUUAUCAGGCACGCUUUGAGGCCGUGGCC<br>UGGAGUGCAACCGCCUGUCACGACGGCAAGAAGUGGAUGACAAUUGGGGUGACUGGUCCUGACAGC<br>AAGGCAAUCGCAGUUGUUCACUACGGCGGUGUCCCCACGGACAUCGUGAAUUCGUGGGCCGGAGAC<br>AUCCUGCGGACUCAGGACUCUUCGUGUACCUGCAUCCAGGGCAACUGUUACUGGGUAAUGACUGAC<br>GGUCCUAGUAACCGUCAGGCCCAAUAUAGAAUAUACAAGGCCAACCAGGGCAAGAUUAUUGACCAA<br>GCCGACGUAUCCUUCUCCGGCGGCCAUAUCGAGGAGUGCUCUUGUUAUCCUAACGACGGAAAGGUC<br>GAGUGUGUGUGCCGCGACAACUGGAUCGGGACCAACCGCCCUGUGCUGGUCAUAUCUCCUGAUCUG<br>UCAUAUCGUGUGGGAUAUCUUUGUGCAGGAUUGCCAUCCGAUACACCCCGAGGUGAGGACGCCCAG<br>UUCGUAGGGAGCUGUACUAGCCCUAUGGGAAAUCAGGGAUACGGCGUUAAGGGUUUUGGAUUCCGC<br>CAAGGUACCGACGUCUGGAUGGGCAGGACCAUAAGCAGGACCAGCAGAUCCGGAUUUGAAAUCAUC<br>AGGAUCAAGAACGGGUGGACCCAGACGUCUAAAGAGCAAAUUCGUCGGCAAGUGGUUGUAGACAAU<br>CUAAAUUGGUCUGGCUAUAGCGGAAGUUUCACUCUUCCAGUUGAACUCAGCGGCCGUGAGUGUCUG<br>GUGCCGUGCUUUUGGGUGGAAAUGAUCAGAGGCAGGCCCGAGGAGCGUACAAUCUGGACAUCUUCU<br>UCCUCCAUCGUGAUGUGUGGGGUUGAUCACGAGAUCGCAGACUGGAGCUGGCACGACGGUGCGAUA<br>CUGCCAUUCGACAUUGACGGAAUG | 126 |
| 3' UTR | UGAUAAUAGGCUGGAGCCUCGGUGGCCUAGCUUCUUGCCCCUUGGGCCUCCCCCCAGCCCCUCCUC<br>CCCUUCCUGCACCCGUACCCCCGUGGUCUUUGAAUAAAGUCUGAGUGGGCGGC | 4 |
| Corresponding amino acid sequence | MNPNQKIATIGSISLGLVVFNVLLHALSIILMVLALGKSENNGICKGTIIREYNETVRIEKVTQWY<br>NTSVVEYVPHWNEGAYINNTEPICDVKGFAPFSKDNGIRIGSRGHIFVIREPFVSCSPVECRTFFL<br>TQGALLNDKHSNGTVKDRSPFRTLMSVEVGQSPNVYQARFEAVAWSATACHDGKKWMTIGVTGPDS<br>KAIAVVHYGGVPTDIVNSWAGDILRTQDSSCTCIQGNCYWVMTDGPSNRQAQYRIYKANQGKIIDQ<br>ADVSFSGGHIEECSCYPNDGKVECVCRDNWIGTNRPVLVISPDLSYRVGYLCAGLPSDTPRGEDAQ<br>FVGSCTSPMGNQGYGVKGFGFRQGTDVWMGRTISRTSRSGFEIIRIKNGWTQTSKEQIRRQVVVDN<br>LNWSGYSGSFTLPVELSGRECLVPCFWVEMIRGRPEERTIWTSSSSIVMCGVDHEIADWSWHDGAI<br>LPFDIDGM | 127 |
| PolyA tail | 100 nt | |
| | H3_Cambodia_WT (NCS) | |
| SEQ ID NO: 129 consists of from 5' end to 3' end: 5' UTR SEQ ID NO: 2, mRNA ORF SEQ ID NO: 90, and 3' UTR SEQ ID NO: 130. | | 129 |
| Chemistry | 1-methylpseudouridine | |
| Cap | C1 | |

TABLE 11-continued

| | | SEQ ID NO: |
|---|---|---|
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGACCAUCAUCGCCCUGAGCUACAUCCUGUGCCUGGUGUUCGCCCAGAAGAUCCCCGGCAAC<br>GAUAACAGCACCGCCACCCUGUGUCUGGGACACCACGCCGUGCCCAACGGCACCAUCGUGAAGACU<br>AUCACCAACGACCGGAUCGAGGUGACCAACGCCACCGAGCUGGUGCAGAACAGCAGCAUCGGCGAG<br>AUCUGCGACAGCCCUCACCAGAUCCUGGACGGCGGCAACUGCACCCUGAUCGACGCACUGCUGGGC<br>GACCCUCAGUGCGACGGCUUUCAGAACAAGGAGUGGGACCUGUUCGUGGAGAGAUCGCGGGCCAAC<br>AGCAACUGCUACCCCUACGACGUCCCCGACUACGCAAGCCUGAGAAGCCUCGUGGCCUCAAGCGGC<br>ACCCUGGAGUUCAAGAACGAGAGCUUCAACUGGACCGGCGUGAAGCAGAACGGCACCUCAAGCGCC<br>UGCAUCCGGGGCUCCAGCAGCAGCUUCUUCUCACGGCUGAACUGGCUGACCCACCUGAACUACACC<br>UACCCCGCCCUGAACGUGACCAUGCCCAACAACGAGCAGUUCGACAAGCUGUACAUCUGGGGAGUG<br>CACCAUCCCAGCACCGACAAGGACCAGAUUAGCCUGUUCGCCCAGCCCAGCGGCCGGAUCACCGUG<br>AGCACCAAGCGGAGCCAGCAGGCCGUGAUCCCCAACAUCGGCUCUCGGCCCAGAAUCCGGGACAUC<br>CCCAGCCGGAUCAGCAUCUACUGGACCAUUGUGAAGCCCGGCGACAUCCUGCUGAUCAACUCCACC<br>GGCAACCUGAUCGCCCCUCGGGGCUAUUUCAAGAUCCGGAGCGGCAAGAGCAGCAUCAUGCGGAGC<br>GACGCCCCUAUCGGCAAGUGCAAGAGCGAGUGCAUCACACCCAACGGAAGCAUCCCCAACGACAAG<br>CCCUUCCAGAACGUGAACCGGAUAACCUACGGCGCCUGCCCUAGAUACGUGAAGCAGAGCACCCUG<br>AAGCUGGCCACCGGCAUGCGGAACGUGCCCGAGAAGCAGACUCGGGGCAUCUUCGGCGCCAUCGCC<br>GGCUUCAUCGAGAACGGCUGGGAGGGCAUGGUGGACGGCUGGUACGGCUUCCGGCACCAGAACUCU<br>GAGGGCAGAGGACAGGCCGCAGACCUGAAGAGCACCCAGGCCGCCAUCGACCAGAUCAACGGCAAG<br>CUGAACCGGCUGAUCGGCAAGACCAACGAGAAGUUCCACCAGAUCGAGAAGGAGUUCAGCGAGGUG<br>GAGGGCAGGGUACAGGACCUGGAGAAGUACGUGGAGGACACCAAGAUCGACCUGUGGAGCUACAAC<br>GCCGAGCUGCUGGUAGCCCUGGAGAACCAGCACACCAUCGACCUGACCGACAGCGAGAUGAACAAG<br>CUGUUCGAGAAGACCAAGAAGCAGCUGCGGGAGAACGCCGAGGACAUGGGCAACGGCUGCUUCAAG<br>AUCUACCACAAGUGCGACAACGCCUGCAUCGGCAGCAUCCGGAACGAGACCUACGACCACAACGUG<br>UACCGGGACGAGGCCCUGAACAACCGGUUCCAGAUCAAGGGCGUGGAGCUGAAGAGCGGCUACAAG<br>GACUGGAUCCUGUGGAUCAGCUUCGCCAUGUCCUGCUUCCUGCUGUGCAUCGCCCUGCUGGGUUUC<br>AUCAUGUGGGCCUGCCAGAAGGGCAACAUCCGGUGCAACAUCUGCAUC | 90 |
| 3' UTR | UGAUAAUAGGCUGGAGCCUCGGUGGCACGAGAACGGCACCAUCACCCCUCCCCCCAGCCCCUCCUC<br>CCCUUCCUGCAGGAAGUGGUCUUUGAAUAAAGUCUGAGUGGGCGGC | 130 |
| Corresponding amino acid sequence | MKTIIALSYILCLVFAQKIPGNDNSTATLCLGHHAVPNGTIVKTITNDRIEVTNATELVQNSSIGE<br>ICDSPHQILDGGNCTLIDALLGDPQCDGFQNKEWDLFVERSRANSNCYPYDVPDYASLRSLVASSG<br>TLEFKNESFNWTGVKQNGTSSACIRGSSSSFFSRLNWLTHLNYTYPALNVTMPNNEQFDKLYIWGV<br>HHPSTDKDQISLFAQPSGRITVSTKRSQQAVIPNIGSRPRIRDIPSRISIYWTIVKPGDILLINST<br>GNLIAPRGYFKIRSGKSSIMRSDAPIGKCKSECITPNGSIPNDKPFQNVNRITYGACPRYVKQSTL<br>KLATGMRNVPEKQTRGIFGAIAGFIENGWEGMVDGWYGFRHQNSEGRGQAADLKSTQAAIDQINGK<br>LNRLIGKTNEKFHQIEKEFSEVEGRVQDLEKYVEDTKIDLWSYNAELLVALENQHTIDLTDSEMNK<br>LFEKTKKQLRENAEDMGNGCFKIYHKCDNACIGSIRNETYDHNVYRDEALNNRFQIKGVELKSGYK<br>DWILWISFAMSCFLLCIALLGFIMWACQKGNIRCNICI | 91 |
| PolyA tail | 100 nt | |

B_HA_Washington_2019_WT (NCS)

| | | |
|---|---|---|
| SEQ ID NO: 131 SEQ ID NO: 24, | consists of from 5' end to 3' end: 5' UTR SEQ ID NO: 2, mRNA ORF and 3' UTR SEQ ID NO: 132. | 131 |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCAUCGUGCUGUUAAUGGUGGUGACCAGCAACGCCGACCGGAUCUGCACCGGCAUC<br>ACCUCUAGCAACAGCCCUCACGUGGUGAAGACCGCCACACAGGGCGAGGUGAACGUGACCGGCGUG<br>AUUCCCCUGACCACCACCCCUACCAAGAGCCACUUCGCCAACCUGAAGGGAACCGAGACCCGGGGC<br>AAGCUGUGUCCCAAGUGCCUGAACUGCACCGACCUGGACGUGGCCCUGGGCAGACCCAAGUGCACC<br>GGCAAGAUCCCCAGCGCCCGGGUGUCUAUCCUGCACGAAGUGCGGCCCGUGACUAGCGGCUGCUUC<br>CCCAUCAUGCACGACCGGACCAAGAUCCGGCAGCUGCCCAACCUGCUGCGGGGCUACGAGCACGUG<br>CGGCUGAGCACCCACAACGUGAUCAACGCCGAAGACGCACCCGGGAGACCAUACGAGAUCGGCACC<br>AGCGGCUCUUGCCCCAACAUCACCAACGGCAACGGCUUCUUCGCUACCAUGGCCUGGGCCGUGCCA<br>AAGAACAAGACUGCCACCAACCCUCUGACCAUCGAGGUGCCCUACAUCUGCACCGAGGGCGAGGAC<br>CAGAUCACCGUGUGGGGCUUCCACAGCGACAGCGAGACCCAGAUGGCCAAGCUGUACGGCGACAGC<br>AAGCCCCAGAAGUUCACCAGCAGCGCCAACGGCGUGACCACCCACUACGUGAGCCAGAUCGGCGGC<br>UUCCCCAACCAGACCGAGGACGGCGGCUUACCCCAGAGCGGCCGGAUCGUGGUGGACUACAUGGUG<br>CAGAAGAGCGGCAAGACCGGCACCAUCACCUACCAGCGGGGCAUCCUGCUGCCACAGAAGGUGUGG<br>UGCGCCUCAGGGCGGUCAAAGGUGAUCAAGGGCAGCCUGCCACUGAUUGGCGAGGCCGACUGCCUG<br>CACGAGAAGUACGGCGGCCUGAACAAGAGCAAGCCCUACUACACCGGCGAGCACGCCAAGGCAAUC<br>GGCAACUGCCCCAUCUGGGUGAAGACACCCCUGAAGCUGGCCAACGGCACCAAGUACCGGCCACCC<br>GCCAAACUGCUGAAGGAGCGGGGCUUCUUCGGCGCCAUUGCCGGCUUCCUCGAAGGCGGUUGGGAG<br>GGCAUGAUCGCCGGCUGGCACGGCUACACUAGCCACGGCGCACACGGAGUAGCAGUGGCCGCCGAC<br>CUGAAGAGCACCCAGGAGGCCAUCAACAAGAUCACCAAGAACCUGAACAGCCUGAGCGAGCUGGAG<br>GUGAAGAAUCUGCAGCGGCUGUCUGGCGCUAUGGACGAGCUGCACAACGAGAUCCUGGAGCUGGAC<br>GAGAAGGUGGACGACUUACGGGCCGACACCAUCAGCAGCCAGAUCGAGCUGGCCGUGCUG8CUGAG<br>CAACGAGGGCAUCAUCAACAGCGAGGACGAGCACCUGCUGGCCCUGGAGGGAAGCUGAAGAAGAUG<br>CUGGGCCCUUCUGCCGUGGAGAUCGGUAACGGCUGCUUCGAGACCAAGCACAAGUGCAACCAGACC<br>UGCCUGGAUCGGAUCGCAGCCGGCACCUUUGACGCCGGGGAGUUCAGCCUGCCCACCUUCGACAGC | 24 |

TABLE 11-continued

| | | SEQ ID NO: |
|---|---|---|
| | CUGAACAUCACCGCCGCCAGCCUGAACGACGACGGCCUGGACAACCACACCAUCCUGCUGUACUAC<br>UCUACAGCCGCUAGCAGCCUGGCCGUGACCCUGAUGAUCGCCAUCUUCGUGGUGUACAUGGUGAGC<br>CGGGACAACGUGAGCUGCAGCAUCUGCCUG | |
| 3' UTR | UGAUAAUAGGCUGGAGCCUCGGUGGCAACCUACGCCGAAGACCACGCCUCCCCCCAGCCCCUCCUC<br>CCCUUCCUGCAGGUUAGUGGUCUUUGAAUAAAGUCUGAGUGGGCGGC | 132 |
| Corresponding amino acid sequence | MKAIIVLLMVVTSNADRICTGITSSNSPHVVKTATQGEVNVTGVIPLTTTPTKSHFANLKGTETRG<br>KLCPKCLNCTDLDVALGRPKCTGKIPSARVSILHEVRPVTSGCFPIMHDRTKIRQLPNLLRGYEHV<br>RLSTHNVINAEDAPGRPYEIGTSGSCPNITNGNGFFATMAWAVPKNKTATNPLTIEVPYICTEGED<br>QITVWGFHSDSETQMAKLYGDSKPQKFTSSANGVTTHYVSQIGGFPNQTEDGGLPQSGRIVVDYMV<br>QKSGKTGTITYQRGILLPQKVWCASGRSKVIKGSLPLIGEADCLHEKYGGLNKSKPYYTGEHAKAI<br>GNCPIWVKTPLKLANGTKYRPPAKLLKERGFFGAIAGFLEGGWEGMIAGWHGYTSHGAHGVAVAAD<br>LKSTQEAINKITKNLNSLSELEVKNLQRLSGAMDELHNEILELDEKVDDLRADTISSQIELAVLLS<br>NEGIINSEDEHLLALERKLKKMLGPSAVEIGNGCFETKHKCNQTCLDRIAAGTFDAGEFSLPTFDS<br>LNITAASLNDDGLDNHTILLYYSTAASSLAVTLMIAIFVVYMVSRDNVSCSICL | 25 |
| PolyA tail | 100 nt | |
| | B_HA_Phuket_2013_WT (NCS) | |
| SEQ ID NO: 133 | consists of from 5' end to 3' end: 5' UTR SEQ ID NO: 2, mRNA ORF | 133 |
| SEQ ID NO: 33, | and 3' UTR SEQ ID NO: 134. | |
| Chemistry | 1-methylpseudouridine | |
| Cap | C1 | |
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCAUCGUGCUACUGAUGGUGGUGACCAGCAACGCCGACCGGAUCUGCACCGGCAUC<br>ACCAGCAGCAACAGCCCGCACGUGGUGAAGACCGCCACCCAAGGCGAGGUGAACGUGACCGGCGUG<br>AUCCCACUGACCACCACUCCCACCAAGAGCUACUUCGCCAACCUGAAGGGCACACGGACUCGGGGC<br>AAGCUGUGCCCCGACUGCCUGAACUGCACCGACCUGGACGUGGCCCUGGGCAGACCCAUGUGCGUG<br>GGCACCACCCCUUCUGCCAAGGCCAGCAUCCUGCACGAGGUGAGACCCGUGACCAGCGGGUGCUUC<br>CCCAUCAUGCACGACCGGACCAAGAUCCGGCAGCUGCCCAACCUGCUGCGGGGCUACGAGAAGAUC<br>CGGCUGAGCACCCAGAACGUGAUCGACGCCGAGAAGGCCCCUGGAGGUCCCUACCGGCUGGGCACC<br>AGCGGAAGCUGCCCCAACGCCACCAGCAAGAUCGGCUUCUUCGCCACCAUGGCCUGGGCUGUGCCC<br>AAGGACAACUACAAGAACGCCACCAAUCCCCUGACCGUGGAGGUGCCCUACAUCUGCACCGAGGGC<br>GAGGACCAGAUCACCGUGUGGGGCUUCCACAGCGACAACAAGACCCAGAUGAAGAGCCUGUACGGC<br>GACAGCAAUCCCCAGAAGUUCACAAGCAGCGCCAACGGCGUGACCACCCACUACGUGAGCCAGAUC<br>GGCGACUUCCCCGACCAGACCGAGGACGGAGGGCUGCCUCAGAGUGGCCGGAUCGUGGUGGACUAC<br>AUGAUGCAGAAGCCCGGCAAGACCGGCACCAUCGUGUACCAGCGGGGCGUGCUGUUGCCUCAGAAA<br>GUUUGGUGUGCCAGCGGCAGGAGCAAGGUGAUCAAGGGCAGCCUGCCCCUGAUCGGCGAGGCAGAC<br>UGCCUCCACGAGGAGUACGGCGGCCUGAACAAGAGCAAGCCCUACUACACCGGCAAGCACGCCAAG<br>GCCAUCGGCAACUGCCCCAUCUGGGUGAAGACCCCUCUGAAGCUGGCCAACGGCACCAAGUACCGG<br>CCACCAGCCAAGCUGCUGAAGGAGCGGGGCUUCUUUGGCGCCAUUGCCGGCUUCCUCGAGGGAGGC<br>UGGGAGGGCAUGAUCGCCGGCUGGCACGGCUACACAAGCCACGGCGCACACGGAGUGGCUGUGGCU<br>GCCGACCUGAAGAGCACCCAGGAGGCCAUCAACAAGAUCACCAAGAACCUGAACAGCCUGAGCGAG<br>CUGGAGGUGAAGAACCUGCAGCGGCUGUCAGGCGCCAUGGACGAGCUGCACAACGAGAUCCUGGAG<br>CUGGACGAGAAGGUGGACGACCUGCGUGCCGACACCAUCAGCAGCCAGAUCGAGCUGGCCGUGCUG<br>CUGAGCAACGAGGGCAUCAUCAACAGCGAGGACGAGCACCUGCUGGCCCUGGAGCGGAAACUGAAG<br>AAGAUGCUGGGACCCUCUGCCGUGGACAUCGGCAACGGCUGCUUCGAGACCAAGCACAAGUGCAAC<br>CAGACCUGCCUGGAUCGGAUCGCCGCCGGAACCUUCAACGCCGGCGAGUUCAGCCUGCCCACCUUC<br>GACAGCCUGAACAUCACCGCCGCCAGCCUGAACGACGACGGCCUGGACAACCACACCAUCCUGCUG<br>UACUACAGCACUGCCGCCUCAAGCCUGGCCGUGACCCUGAUGCUGGCCAUCUUCAUCGUGUACAUG<br>GUGAGCCGGGACAACGUGAGCUGCAGCAUCUGCCUG | 33 |
| 3' UTR | UGAUAAUAGGCUGGAGCCUCGGUGGCAACGACCCUGCCGCAGCAAACCUCCCCCCAGCCCCUCCUC<br>CCCUUCCUGCAGGACCAGUGGUCUUUGAAUAAAGUCUGAGUGGGCGGC | 134 |
| Corresponding amino acid sequence | MKAIIVLLMVVTSNADRICTGITSSNSPHVVKTATQGEVNVTGVIPLTTTPTKSYFANLKGTRTRG<br>KLCPDCLNCTDLDVALGRPMCVGTTPSAKASILHEVRPVTSGCFPIMHDRTKIRQLPNLLRGYEKI<br>RLSTQNVIDAEKAPGGPYRLGTSGSCPNATSKIGFFATMAWAVPKDNYKNATNPLTVEVPYICTEG<br>EDQITVWGFHSDNKTQMKSLYGDSNPQKFTSSANGVTTHYVSQIGDFPDQTEDGGLPQSGRIVVDY<br>MMQKPGKTGTIVYQRGVLLPQKVWCASGRSKVIKGSLPLIGEADCLHEEYGGLNKSKPYYTGKHAK<br>AIGNCPIWVKTPLKLANGTKYRPPAKLLKERGFFGAIAGFLEGGWEGMIAGWHGYTSHGAHGVAVA<br>ADLKSTQEAINKITKNLNSLSELEVKNLQRLSGAMDELHNEILELDEKVDDLRADTISSQIELAVL<br>LSNEGIINSEDEHLLALERKLKKMLGPSAVDIGNGCFETKHKCNQTCLDRIAAGTFNAGEFSLPTF<br>DSLNITAASLNDDGLDNHTILLYYSTAASSLAVTLMLAIFIVYMVSRDNVSCSICL | 34 |
| PolyA tail | 100 nt | |
| | H1_Wisconsin_2019_WT (NCS) | |
| SEQ ID NO: 135 | consists of from 5' end to 3' end: 5' UTR SEQ ID NO: 2, mRNA ORF | 135 |
| SEQ ID NO: 42, | and 3' UTR SEQ ID NO: 136. | |
| Chemistry | 1-methylpseudouridine | |
| Cap | C1 | |

TABLE 11-continued

| | | SEQ ID NO: |
|---|---|---|
| 5' UTR | GGGAAAUAAGAGAGAAAAGAAGAGUAAGAAGAAAUAUAAGACCCCGGCGCCGCCACC | 2 |
| ORF of mRNA Construct (excluding the stop codon) | AUGAAGGCCAUCCUGGUCGUGAUGCUGUACACCUUCACCACCGCCAACGCCGACACCCUGUGCAUC<br>GGCUACCACGCCAACAACAGCACCGACACCGUGGACACCGUGCUGGAGAAGAACGUGACCGUGACC<br>CACAGCGUGAACCUGCUGGAGGACAAGCACAACGGCAAGCUGUGCAAGCUGAGGGGAGUGGCACCC<br>CUGCACCUGGGCAAGUGCAACAUCGCCGGCUGGAUCCUGGGCAACCCCGAGUGCGAGAGCCUGAGC<br>ACAGCCCGGAGCUGGAGCUACAUCGUGGAGACCAGCAACAGCGACAACGGCACCUGUUACCCCGGC<br>GACUUCAUCAACUACGAGGAGCUGCGGGAGCAGCUGAGCAGCGUGAGCAGCUUCGAGCGGUUCGAG<br>AUCUUCCCCAAGACCAGCAGCUGGCCCAACCACGACAGCGACAACGGCGUGACAGCAGCCUGUCCA<br>CACGCCGGAGCCAAGAGCUUCUACAAGAACCUGAUCUGGCUGGUGAAGAAGGGCAAGAGCUACCCC<br>AAGAUCAACCAGACCUACAUCAACGACAAGGGCAAGGAGGUGCUGGUGCUGUGGGGCAUCCACCAC<br>CCACCUACCAUCGCCGACCAGCAGAGCCUGUACCAGAACGCCGACGCCUACGUGUUCGUGGGCACC<br>AGCCGGUACAGCAAGAAGUUCAAGCCAGAGAUCGCCACCCGGCCCAAGGUGAGAGACCAGGAGGGC<br>CGGAUGAACUACUACUGGACCCUGGUGGAGCCCGGAGACAAGAUUACCUUCGAGGCCACCGGCAAC<br>CUGGUGGCCCCUCGGUACGCCUUCACCAUGGAACGGGACGCUGGCAGCGGCAUCAUCAUCAGCGAC<br>ACUCCCGUGCACGACUGCAACACCACCUGCCAGACUCCCGAGGGCGCUAUCAACACCAGCCUGCCC<br>UUCCAGAACGUGCACCCCAUCACCAUCGGCAAGUGCCCCAAGUACGUAAAGAGCACCAAAUUGCGG<br>CUGGCCACCGGACUCAGGAACGUGCCCAGCAUCCAAAGCCGGGGCCUGUUUGGCGCAAUCGCCGGC<br>UUCAUCGAGGGCGGCUGGACUGGCAUGGUGGACGGCUGGUACGGCUACCACCACCAGAACGAACAG<br>GGGAGCGGCUACGCAGCUGACCUGAAGAGCACCCAGAACGCCAUCGACAAGAUCACCAACAAGGUG<br>AACAGCGUGAUCGAGAAGAUGAACACCCAGUUCACCGCCGUGGGCAAGGAGUUCAACCACCUGGAG<br>AAGCGGAUCGAGAACCUGAACAAGAAGGUGGACGACGGCUUCCUGGACAUCUGGACCUACAACGCC<br>GAGCUGCUGGUUCUGCUGGAGAACGAGCGGACCCUGGACUAUCACGACAGCAACGUGAAGAACCUG<br>UACGAGAAGGUGCGGAACCAGCUGAAGAACAACGCCAAGGAGAUCGGCAACGGCUGCUUCGAGUUC<br>UACCACAAGUGCGACAACACCUGCAUGGAGAGCGUGAAGAACGGCACCUACGACUACCCCAAGUAC<br>AGCGAGGAGGCCAAGCUGAACCGGGAGAAGAUCGACGGCGUGAAGCUGGACAGCACCCGGAUCUAC<br>CAGAUCCUGGCCAUCUACAGCACCGUGGCCAGCAGCCUGGUGCUGGUGGUGAGCCUGGGCGCCAUC<br>AGCUUCUGGAUGUGCAGCAACGGCAGCCUGCAGUGCCGGAUCUGCAUC | 42 |
| 3' UTR | UGAUAAUAGGCUGGAGCCUCGGUGGCCACCGAAGCAGCCAUCAGCACCUCCCCCCAGCCCCUCCUC<br>CCCUUCCUGCAGGCCAAAGUGGUCUUUGAAUAAAGUCUGAGUGGGCGGC | 136 |
| Corresponding amino acid sequence | MKAILVVMLYTFTTANADTLCIGYHANNSTDTVDTVLEKNVTVTHSVNLLEDKHNGKLCKLRGVAP<br>LHLGKCNIAGWILGNPECESLSTARSWSYIVETSNSDNGTCYPGDFINYEELREQLSSVSSFERFE<br>IFPKTSSWPNHDSDNGVTAACPHAGAKSFYKNLIWLVKKGKSYPKINQTYINDKGKEVLVLWGIHH<br>PPTIADQQSLYQNADAYVFVGTSRYSKKFKPEIATRPKVRDQEGRMNYYWTLVEPGDKITFEATGN<br>LVAPRYAFTMERDAGSGIIISDTPVHDCNTTCQTPEGAINTSLPFQNVHPITIGKCPKYVKSTKLR<br>LATGLRNVPSIQSRGLFGAIAGFIEGGWTGMVDGWYGYHHQNEQGSGYAADLKSTQNAIDKITNKV<br>NSVIEKMNTQFTAVGKEFNHLEKRIENLNKKVDDGFLDIWTYNAELLVLLENERTLDYHDSNVKNL<br>YEKVRNQLKNNAKEIGNGCFEFYHKCDNTCMESVKNGTYDYPKYSEEAKLNREKIDGVKLDSTRIY<br>QILAIYSTVASSLVLVVSLGAISFWMCSNGSLQCRICI | 42 |
| PolyA tail | 100 nt | |

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean ±10% of the recited numerical value.

Where a range of values is provided, each value between and including the upper and lower ends of the range are specifically contemplated and described herein.

What is claimed is:

1. A composition comprising:

(a) a first messenger ribonucleic acid (mRNA) comprising a first open reading frame (ORF) encoding a first hemagglutinin (HA) protein of a first influenza A virus;

(b) a second mRNA comprising a second ORF encoding a second HA protein of a second influenza A virus;

wherein the first and second influenza A viruses are of different subtypes, (c) a third mRNA comprising a third ORF encoding a third HA protein of a first influenza B virus;

(d) a fourth mRNA comprising a fourth ORF encoding a first neuraminidase (NA) protein of the first influenza A virus;

(e) a fifth mRNA comprising a fifth ORF encoding a second NA protein of the second influenza A virus; and (f) a sixth mRNA comprising a sixth ORF encoding a third NA protein of the first influenza B virus, wherein the first mRNA, second mRNA, third mRNA, fourth mRNA, fifth mRNA, and sixth mRNA are in the lipid nanoparticle, wherein each ORF comprises nucleosides consisting of N1-methylpseudouridine, adenosine, guanosine, and cytidine, wherein the first mRNA, second mRNA, third mRNA, fourth mRNA, fifth mRNA, and sixth mRNA are at a 1:1:1:1:1:1 mass ratio, wherein the lipid nanoparticle comprises an ionizable amino lipid, a sterol, a neutral lipid, and a polyethylene glycol (PEG)-modified lipid, wherein the ionizable amino lipid comprises a compound of Formula (I):

(I)

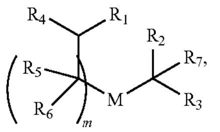

or a salt thereof, wherein:

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is —$(CH_2)_nQ$, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl;

m is selected from 5, 6, 7, 8, 9, 10, 11, 12, and 13.

2. The composition of claim 1, wherein the first HA protein is an H1 subtype HA protein, and the second HA protein is an H3 subtype HA protein.

3. The composition of claim 2, wherein the first NA protein is an N1 subtype NA protein, and the second NA protein is an N2 subtype NA protein.

4. The composition of claim 3, wherein the third HA protein is a B/Victoria lineage HA protein, and the third NA protein is a B/Victoria lineage NA protein.

5. The composition of claim 4, wherein the lipid nanoparticle comprises 40-55 mol % ionizable amino lipid, 30-45 mol % sterol, 5-15 mol % neutral lipid, and 1-5 mol % PEG-modified lipid.

6. A composition comprising:

a first mRNA comprising a first open reading frame (ORF) encoding a hemagglutinin (HA) antigen from a first seasonal influenza A virus;

a second mRNA comprising a second ORF encoding an HA antigen from a second seasonal influenza A virus of a different subtype than the first seasonal influenza A virus;

a third mRNA comprising a third ORF encoding an HA antigen from a first seasonal influenza B virus;

a fourth mRNA comprising a fourth ORF encoding a neuraminidase (NA) antigen from the first seasonal circulating influenza A virus;

a fifth mRNA comprising a fifth ORF encoding an NA antigen from the second seasonal influenza A virus;

a sixth mRNA comprising a sixth ORF encoding an NA antigen from the first seasonal influenza B virus; and a lipid nanoparticle, wherein the first mRNA, second mRNA, third mRNA, fourth mRNA, fifth mRNA, and sixth mRNA are at a 1:1:1:1:1:1 mass ratio or a 3:3:3:1:1:1 mass ratio, wherein each ORF comprises nucleosides consisting of N1-methylpseudouridine, adenosine, guanosine, and cytidine, wherein the lipid nanoparticle comprises an ionizable amino lipid, a sterol, a neutral lipid, and a polyethylene glycol (PEG)-modified lipid, wherein the ionizable amino lipid comprises a compound of Formula (I):

(I)

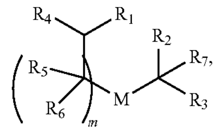

or a salt thereof, wherein:

$R_1$ is selected from the group consisting of $C_{5-30}$ alkyl, $C_{5-20}$ alkenyl, and —R″M′R′;

$R_2$ and $R_3$ are independently selected from the group consisting of $C_{1-14}$ alkyl and $C_{2-14}$ alkenyl;

$R_4$ is —$(CH_2)_n$Q, wherein Q is —OR, and n is selected from 1, 2, 3, 4, and 5;

each $R_5$ is H;

each $R_6$ is H;

M and M′ are independently selected from —C(O)O— and —OC(O)—;

$R_7$ is H;

R is H;

R′ is selected from the group consisting of $C_{1-18}$ alkyl and $C_{2-18}$ alkenyl;

R″ is selected from the group consisting of $C_{3-14}$ alkyl and $C_{3-14}$ alkenyl;

m is selected from 5, 6, 7, 8, 9, 10, 11, 12, and 13.

7. The composition of claim 6, wherein the first mRNA, second mRNA, third mRNA, fourth mRNA, fifth mRNA, and sixth mRNA are at a 1:1:1:1:1:1 mass ratio.

8. The composition of claim 6, wherein:

(a) the first seasonal influenza A virus is an influenza A/(H1N1)pdm09 virus;

(b) the second seasonal influenza A virus is an influenza A/(H3N2) virus; and (c) the first seasonal influenza B virus is a B/Victoria lineage virus.

9. The composition of claim 6, wherein the first mRNA, second mRNA, third mRNA, fourth mRNA, fifth mRNA, and sixth mRNA are at a 3:3:3:1:1:1 mass ratio.

10. The composition of claim 5, wherein the ionizable amino lipid comprises Compound 1:

(Compound 1)

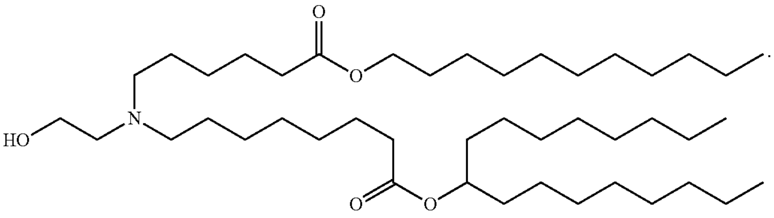

11. The composition of claim 4, wherein the composition comprises a seventh mRNA comprising a seventh ORF encoding a fourth HA protein of a third influenza A virus, wherein the fourth HA protein is an H3 subtype HA protein, wherein the seventh mRNA is in the lipid nanoparticle, wherein the first mRNA, second mRNA, third mRNA, fourth mRNA, fifth mRNA, sixth mRNA, and seventh mRNA are at a 1:1:1:1:1:1:1 mass ratio.

12. The composition of claim 11, wherein the composition comprises an eighth mRNA comprising an eighth ORF encoding a fifth HA protein of a fourth influenza A virus, wherein the fifth HA protein is an H3 subtype HA protein, wherein the eighth mRNA is in the lipid nanoparticle, wherein the first mRNA, second mRNA, third mRNA, fourth mRNA, fifth mRNA, sixth mRNA, seventh mRNA, and eighth mRNA are at a 1:1:1:1:1:1:1:1 mass ratio.

13. The composition of claim 4, wherein the composition comprises:

(g) a seventh mRNA comprising a seventh ORF encoding a fourth HA protein of a third influenza A virus, wherein the fourth HA protein is an H3 subtype HA protein; and (h) an eighth mRNA comprising an eighth ORF encoding a fourth NA protein of the third influenza A virus, wherein the fourth NA protein is an N2 subtype NA protein, wherein the seventh mRNA and the eighth mRNA are in the lipid nanoparticle, wherein the first mRNA, second mRNA, third mRNA, fourth mRNA, fifth mRNA, sixth mRNA, seventh mRNA, and eighth mRNA are at a 1:1:1:1:1:1:1:1 mass ratio.

14. The composition of claim 13, wherein the composition comprises:

(i) a ninth mRNA comprising a ninth ORF encoding a fifth HA protein of a fourth influenza A virus, wherein the fifth HA protein is an H3 subtype HA protein; and (j) a tenth mRNA comprising a tenth ORF encoding a fifth NA protein of the fourth influenza A virus, wherein the fifth NA protein is an N2 subtype NA protein, wherein the ninth mRNA and the tenth mRNA are in the lipid nanoparticle, wherein the first mRNA, second mRNA, third mRNA, fourth mRNA, fifth mRNA, sixth mRNA, seventh mRNA, eighth mRNA, ninth mRNA, and tenth mRNA are at a 1:1:1:1:1:1:1:1:1:1 mass ratio.

15. The composition of claim 4, wherein the composition comprises:

(g) a seventh mRNA comprising a seventh ORF encoding a fourth HA protein of an influenza B/Yamagata lineage virus; and (h) an eighth mRNA comprising an eighth ORF encoding a fourth NA protein of an influenza B/Yamagata lineage virus, wherein the seventh mRNA and the eighth mRNA are in the lipid nanoparticle, wherein the first mRNA, second mRNA, third mRNA, fourth mRNA, fifth mRNA, sixth mRNA, seventh mRNA, and eighth mRNA are at a 1:1:1:1:1:1:1:1 mass ratio.

16. A composition comprising:

(a) a first messenger ribonucleic acid (mRNA) comprising a first open reading frame (ORF) encoding a first hemagglutinin (HA) protein of a first influenza A virus;

(b) a second mRNA comprising a second ORF encoding a second HA protein of a second influenza A virus, wherein the first and second influenza A viruses are of different subtypes;

(c) a third mRNA comprising a third ORF encoding a third HA protein of a first influenza B virus;

(d) a fourth mRNA comprising a fourth ORF encoding a first neuraminidase (NA) protein of the first influenza A virus;

(e) a fifth mRNA comprising a fifth ORF encoding a second NA protein of the second influenza A virus; and (f) a sixth mRNA comprising a sixth ORF encoding a third NA protein of the first influenza B virus, wherein the first mRNA, second mRNA, third mRNA, fourth mRNA, fifth mRNA, and sixth mRNA are in the lipid nanoparticle, wherein the first mRNA, second mRNA, third mRNA, fourth mRNA, fifth mRNA, and sixth mRNA are at a 3:3:3:1:1:1 mass ratio, wherein each ORF comprises nucleosides consisting of N1-methylpseudouridine, adenosine, guanosine, and cytidine, wherein the lipid nanoparticle comprises an ionizable amino lipid, a sterol, a neutral lipid, and a polyethylene glycol (PEG)-modified lipid, wherein the ionizable amino lipid comprises a compound of Formula (I):

(I)

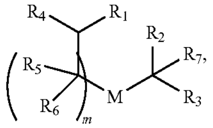

or a salt thereof, wherein:

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is $—(CH_2)_nQ$, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl;

m is selected from 5, 6, 7, 8, 9, 10, 11, 12, and 13.

17. The composition of claim 16, wherein:

the first HA protein is an H1 subtype HA protein and the first NA protein is an N1 subtype NA protein;

the second HA protein is an H3 subtype HA protein and the second NA protein is an N2 subtype NA protein; and the third HA protein is a B/Victoria lineage HA protein and the third NA protein is a B/Victoria lineage NA protein.

18. The composition of claim 17, wherein the composition comprises a seventh mRNA comprising a seventh ORF encoding a fourth HA protein of a third influenza A virus, wherein the fourth HA protein is an H3 subtype HA protein, wherein the seventh mRNA is in the lipid nanoparticle, wherein the first mRNA, second mRNA, third mRNA, fourth mRNA, fifth mRNA, sixth mRNA, and seventh mRNA are at a 3:3:3:1:1:1:3 mass ratio.

19. The composition of claim 18, wherein the composition comprises an eighth mRNA comprising an eighth ORF encoding a fifth HA protein of a fourth influenza A virus, wherein the fifth HA protein is an H3 subtype HA protein, wherein the eighth mRNA is in the lipid nanoparticle, wherein the first mRNA, second mRNA, third mRNA, fourth mRNA, fifth mRNA, sixth mRNA, seventh mRNA, and eighth mRNA are at a 3:3:3:1:1:1:3:3 mass ratio.

20. The composition of claim 17, wherein the composition comprises:

(g) a seventh mRNA comprising a seventh ORF encoding a fourth HA protein of a third influenza A virus, wherein the fourth HA protein is an H3 subtype HA protein; and (h) an eighth mRNA comprising an eighth ORF encoding a fourth NA protein of the third influenza A virus, wherein the fourth NA protein is an N2 subtype NA protein, wherein seventh mRNA and the eighth mRNA are in the lipid nanoparticle, wherein the first mRNA, second mRNA, third mRNA, fourth mRNA, fifth mRNA, sixth mRNA, seventh mRNA, and eighth mRNA are at a 3:3:3:1:1:1:3:1 mass ratio.

21. The composition of claim 20, wherein the composition comprises:

(i) a ninth mRNA comprising a ninth ORF encoding a fifth HA protein of a fourth influenza A virus, wherein the fourth HA protein is an H3 subtype HA protein; and (j) a tenth mRNA comprising a tenth ORF encoding a fifth NA protein of the fourth influenza A virus, wherein the fifth NA protein is an N2 subtype NA protein, wherein ninth mRNA and the tenth mRNA are in the lipid nanoparticle, wherein the first mRNA, second mRNA, third mRNA, fourth mRNA, fifth mRNA, sixth mRNA, seventh mRNA, eighth mRNA, ninth mRNA, and tenth mRNA are at a 3:3:3:1:1:1:3:1:3:1 mass ratio.

22. The composition of claim 17, wherein the composition comprises:

(g) a seventh mRNA comprising a seventh ORF encoding a fourth HA protein of an influenza B/Yamagata lineage virus; and (h) an eighth mRNA comprising an eighth ORF encoding a fourth NA protein of an influenza B/Yamagata lineage virus, wherein the seventh mRNA and the eighth mRNA are in the lipid nanoparticle, wherein the first mRNA, second mRNA, third mRNA, fourth mRNA, fifth mRNA, sixth mRNA, seventh mRNA, and eighth mRNA are at a 3:3:3:1:1:1:3:1 mass ratio.

23. The composition of claim 17, wherein the lipid nanoparticle comprises 40-55 mol % ionizable amino lipid, 30-45 mol % sterol, 5-15 mol % neutral lipid, and 1-5 mol % PEG-modified lipid.

24. The composition of claim 18, wherein the ionizable amino lipid comprises Compound 1:

(Compound 1)

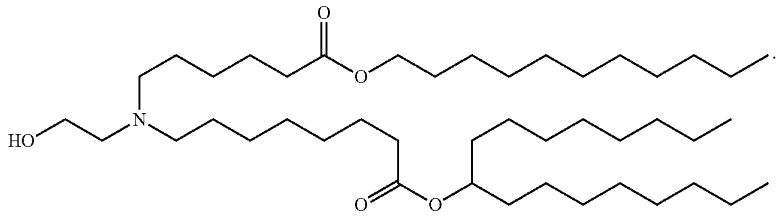

* * * * *

SEQUENCE LISTING

<160> NUMBER OF SEQ ID NOS: 143

<210> SEQ ID NO 1
<211> LENGTH: 47
<212> TYPE: RNA
<213> ORGANISM: Artificial Sequence
<220> FEATURE:
<223> OTHER INFORMATION: Synthetic

<400> SEQUENCE: 1
gggaaauaag agagaaaaga agaguaagaa gaaauauaag agccacc 47

<210> SEQ ID NO 2
<211> LENGTH: 57
<212> TYPE: RNA
<213> ORGANISM: Artificial Sequence
<220> FEATURE:
<223> OTHER INFORMATION: Synthetic

<400> SEQUENCE: 2
gggaaauaag agagaaaaga agaguaagaa gaaauauaag accccggcgc cgccacc 57

<210> SEQ ID NO 3
<211> LENGTH: 119
<212> TYPE: RNA
<213> ORGANISM: Artificial Sequence
<220> FEATURE:
<223> OTHER INFORMATION: Synthetic

<400> SEQUENCE: 3
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 4
<211> LENGTH: 119
<212> TYPE: RNA
<213> ORGANISM: Artificial Sequence
<220> FEATURE:
<223> OTHER INFORMATION: Synthetic

<400> SEQUENCE: 4
ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 5
<211> LENGTH: 1874
<212> TYPE: RNA
<213> ORGANISM: Artificial Sequence
<220> FEATURE:
<223> OTHER INFORMATION: Synthetic

<400> SEQUENCE: 5
gggaaauaag agagaaaaga agaguaagaa gaaauauaag accccggcgc cgccaccaug 60
aaggccaucc uggucgugcu gcuguacacc uucaccaccg ccaacgccga cacccugugc 120
aucggcuacc acgccaacaa cagcaccgac accguggaca ccgugcugga gaagaacgug 180
accgugaccc acagcgugaa ccugcuggag gacaagcaca acggcaagcu gugcaagcug 240
aggggagugg caccccugca ccugggcaag ugcaacaucg ccggcuggau ccugggcaac 300
cccgagugcg agagccugag cacagcccgg agcuggagcu acaucgugga gaccagcaac 360
agcgacaacg gcaccuguua ccccggcgac uucaucaacu acgaggagcu gcgggagcag 420
cugagcagcg ugagcagcuu cgagcgguuc gagaucuucc ccaagaccag cagcuggccc 480
aaccacgaca gcgacaaggg cgugacagca gccuguccac acgccggagc caagagcuuc 540
uacaagaacc ugaucuggcu ggugaagaag ggcaacagcu accccaaacu gaaccagacc 600
uacaucaacg acaagggcaa ggaggugcug gugcuguggg gcauccacca cccaccuacc 660

```
aucgccgccc aggagagccu guaccagaac gccgacgccu acguguucgu gggcaccagc     720
cgguacagca agaaguucaa gccagagauc gccacccggc ccaaggugag agaccaggag     780
ggccggauga acuacuacug gacccuggug gagcccggag acaagauuac cuucgaggcc     840
accggcaacc ugguggugcc ccgguacgcc uucaccaugg aacgggacgc uggcagcggc     900
aucaucauca gcgacacucc cgugcacgac ugcaacacca ccugccagac ucccgagggc     960
gcuaucaaca ccagccugcc cuuccagaac gugcaccccca ucaccaucgg caagugcccc   1020
aaguacguaa agagcaccaa auugcggcug gccaccggac ucaggaacgu gcccagcauc    1080
caaagccggg gccuguuugg cgcaaucgcc ggcuucaucg agggcggcug gacuggcaug    1140
guggacggcu gguacggcua ccaccaccag aacgaacagg ggagcggcua cgcagcugac    1200
cugaagagca cccagaacgc caucgacaag aucaccaaca aggugaacag cgugaucgag    1260
aagaugaaca cccaguucac cgccgugggc aaggaguuca accaccugga gaagcggauc    1320
gagaaccuga acaagaaggu ggacgacggc uuccuggaca ucuggaccua caacgccgag    1380
cugcugguuc ugcuggagaa cgagcggacc cuggacuauc acgacagcaa cgugaagaac    1440
cuguacgaga aggugcggaa ccagcugaag aacaacgcca aggagaucgg caacggcugc    1500
uucgaguucu accacaagug cgacaacacc ugcauggaga gcgugaagaa cggcaccuac    1560
gacuacccca aguacagcga ggaggccaag cugaaccggg agaagaucga cggcgugaag    1620
cuggagagca cccggaucua ccagauccug gccaucuaca gcaccguggc cagcagccug    1680
gugcuggugg ugagccuggg cgccaucagc uucuggaugu gcagcaacgg cagccugcag    1740
ugccggaucu gcaucugaua auaggcugga gccucggugg ccuagcuucu ugccccuugg    1800
gccucccccc agccccuccu ccccuuccug cacccguacc cccguggucu uugaauaaag    1860
ucugaguggg cggc                                                      1874
```

<210> SEQ ID NO 6
<211> LENGTH: 1698
<212> TYPE: RNA
<213> ORGANISM: Artificial Sequence
<220> FEATURE:
<223> OTHER INFORMATION: Synthetic

<400> SEQUENCE: 6

```
augaaggcca uccuggucgu gcugcuguac accuucacca ccgccaacgc cgacacccug      60
ugcaucggcu accacgccaa caacagcacc gacaccgugg acaccgugcu ggagaagaac     120
gugaccguga cccacagcgu gaaccugcug gaggacaagc acaacggcaa gcugugcaag     180
cugaggggag uggcaccccu gcaccugggc aagugcaaca ucgccggcug gauccugggc     240
aaccccgagu gcgagagccu gagcacagcc cggagcugga gcuacaucgu ggagaccagc     300
aacagcgaca acggcaccug uuaccccggc gacuucauca acuacgagga gcugcgggag     360
cagcugagca gcgugagcag cuucgagcgg uucgagaucu uccccaagac cagcagcugg     420
cccaaccacg acagcgacaa gggcgugaca gcagccuguc cacacgccgg agccaagagc     480
uucuacaaga accugaucug gcuggugaag aagggcaaca gcuaccccaa acugaaccag     540
accuacauca acgacaaggg caaggaggug cuggugcugu ggggcaucca ccacccaccu     600
accaucgccg cccaggagag ccuguaccag aacgccgacg ccuacguguu cgugggcacc     660
agccgguaca gcaagaaguu caagccagag aucgccaccc ggcccaaggu gagagaccag     720
gagggccgga ugaacuacua cuggacccug guggagcccg gagacaagau uaccuucgag     780
gccaccggca accugguggu gccccgguac gccuucacca uggaacggga cgcuggcagc     840
```

ggcaucauca ucagcgacac ucccgugcac gacugcaaca ccaccugcca gacuccccgag 900 ggcgcuauca acaccagccu gcccuuccag aacgugcacc ccaucaccau cggcaagugc 960
cccaaguacg uaaagagcac caaauugcgg cuggccaccg gacucaggaa cgugcccagc 1020
auccaaagcc ggggccuguu uggcgcaauc gccggcuuca ucgagggcgg cuggacuggc 1080
augguggacg gcugguacgg cuaccaccac cagaacgaac aggggagcgg cuacgcagcu 1140
gaccugaaga gcacccagaa cgccaucgac aagaucacca acaaggugaa cagcgugauc 1200
gagaagauga acacccaguu caccgccgug ggcaaggagu ucaaccaccu ggagaagcgg 1260
aucgagaacc ugaacaagaa gguggacgac ggcuuccugg acaucuggac cuacaacgcc 1320
gagcugcugg uucugcugga gaacgagcgg acccuggacu aucacgacag caacgugaag 1380
aaccuguacg agaaggugcg gaaccagcug aagaacaacg ccaaggagau cggcaacggc 1440
ugcuucgagu ucuaccacaa gugcgacaac accugcaugg agagcgugaa gaacggcacc 1500
uacgacuacc ccaaguacag cgaggaggcc aagcugaacc gggagaagau cgacggcgug 1560
aagcuggaga gcacccggau cuaccagauc cuggccaucu acagcaccgu ggccagcagc 1620
cuggugcugg uggugagccu gggcgccauc agcuucugga ugugcagcaa cggcagccug 1680
cagugccgga ucugcauc 1698

<210> SEQ ID NO 7
<211> LENGTH: 566
<212> TYPE: PRT
<213> ORGANISM: Artificial Sequence
<220> FEATURE:
<223> OTHER INFORMATION: Synthetic

<400> SEQUENCE: 7

Met Lys Ala Ile Leu Val Val Leu Leu Tyr Thr Phe Thr Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Arg Ser Trp Ser Tyr Ile
85 90 95

Val Glu Thr Ser Asn Ser Asp Asn Gly Thr Cys Tyr Pro Gly Asp Phe
100 105 110

Ile Asn Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asp Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Asn Gln Thr Tyr Ile Asn Asp Lys Gly Lys Glu Val Leu Val
180 185 190

Leu Trp Gly Ile His His Pro Pro Thr Ile Ala Ala Gln Glu Ser Leu
195 200 205

-continued

```
Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asp Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 8
<211> LENGTH: 1583
<212> TYPE: RNA
<213> ORGANISM: Artificial Sequence
<220> FEATURE:
<223> OTHER INFORMATION: Synthetic

<400> SEQUENCE: 8

```
gggaaauaag agagaaaaga agaguaagaa gaaauauaag accccggcgc cgccaccaug     60
aaccccaacc agaagaucau caccaucggc agcaucugca ugaccaucgg cauggccaac    120
cugauccugc aaaucggcaa caucaucagc aucugggga gccacagcau ccagaucggc    180
aaccagagcc agaucgagac cugcaacaag aacgugauca ccuacgagaa caacaccugg    240
gugaaccaga ccuacgugaa caucagcaac accaacagcg ccgcucggca gucaguggcc    300
agcgugaagc uggccggcaa cagcagccug ugccccguua guggcugggc caucuacagc    360
aaggacaaca gcgugcggau cggcagcaag ggcgacgugu ucgugauccg ggagcccuuc    420
aucagcugca gcccgcuuga gugccgcacc uucuuccuga cccagggcgc ucugcugaac    480
gacaagcaca gcaacggcac caucaaggac cggagccccu aucggacccu gaugagcugc    540
cccauuggcg aggugcccag ccccuacaac agccgguucg agucuguggc cuggagcgcc    600
ucugccugcc acgacggcac caacuggcug accaucggga ucagcggacc cgauagcgga    660
gcaguggccg ugcugaagua caacggcauc aucaccgaca ccaucaagag cuggcggaac    720
aacauccugc ggacccagga gagcgagugc gccugcguga acggcagcug cuucaccauc    780
augaccgacg gcccuagcga cggacaggcc agcuacaaga ucuuccggau cgagaagggc    840
aagaucauca agagcgugga gaugaaggca cccaacuacc acuacgagga gugcagcugc    900
uaccccgaca gcagcgagau caccugcgug ugccgggaca acuggcacgg gagcaacagg    960
cccugggguga gcuucaacca gaaccuggag uaccagaugg gcuacaucug cagcggcgug   1020
uucggcgaca acccacggcc caacgacaag acuggcagcu gcgguccggu gagcagcaac   1080
ggcgccaacg gcgugaaggg cuucagcuuc aaguacggca acggcgugug gaucggccgg   1140
accaagagca ucagcagccg gaagggcuuc gagaugaucu gggaccccaa cggcuggacc   1200
ggcaccgaca acaaguucag caagaagcag gacaucgugg gcaucaacga guggagcggc   1260
uacagcggca gcuucgugca gcaccccgag cugacuggcc ugaacugcau ccggcccugc   1320
uucugggugg aacugauacg gggacggccc gaggagaaca ccaucuggac cagcggcagc   1380
agcaucagcu ucugcggcgu ggacagcgau aucgugggcu ggagcuggcc agacggagcc   1440
gagcugcccu ucaccaucga caagugauaa uaggcuggag ccucggugge cuagcuucuu   1500
gccccuuggg ccucccccca gccccuccuc cccuuccugc acccguaccc ccguggucuu   1560
ugaauaaagu cugagugggc ggc                                            1583
```

<210> SEQ ID NO 9
<211> LENGTH: 1407
<212> TYPE: RNA
<213> ORGANISM: Artificial Sequence
<220> FEATURE:
<223> OTHER INFORMATION: Synthetic

<400> SEQUENCE: 9

```
augaacccca accagaagau caucaccauc ggcagcaucu gcaugaccau cggcauggcc     60
aaccugaucc ugcaaaucgg caacaucauc agcaucuggg ugagccacag cauccagauc    120
ggcaaccaga gccagaucga gaccugcaac aagaacguga ucaccuacga gaacaacacc    180
ugggugaacc agaccuacgu gaacaucagc aacaccaaca gcgccgcucg gcagucagug    240
gccagcguga agcuggccgg caacagcagc cugugccccg uuaguggcug ggccaucuac    300
agcaaggaca acagcgugcg gaucggcagc aagggcgacg uguucgugau ccgggagccc    360
uucaucagcu gcagcccgcu ugagugccgc accuucuucc ugacccaggg cgcucugcug    420
```

```
aacgacaagc acagcaacgg caccaucaag gaccggagcc ccuaucggac ccugaugagc    480

ugccccauug gcgaggugcc cagccccuac aacagccggu ucgagucugu ggccuggagc    540

gccucugccu gccacgacgg caccaacugg cugaccaucg ggaucagcgg acccgauagc    600

ggagcagugg ccgugcugaa guacaacggc aucaucaccg acaccaucaa gagcuggcgg    660

aacaacaucc ugcggaccca ggagagcgag ugcgccugcg ugaacggcag cugcuucacc    720

aucaugaccg acggcccuag cgacggacag gccagcuaca agaucuuccg gaucgagaag    780

ggcaagauca ucaagagcgu ggagaugaag gcacccaacu accacuacga ggagugcagc    840

ugcuaccccg acagcagcga gaucaccugc gugugccggg acaacuggca cgggagcaac    900

aggcccuggg ugagcuucaa ccagaaccug gaguaccaga ugggcuacau cugcagcggc    960

guguucggcg acaacccacg gcccaacgac aagacuggca gcugcggucc ggugagcagc   1020

aacggcgcca acggcgugaa gggcuucagc uucaaguacg gcaacggcgu guggaucggc   1080

cggaccaaga gcaucagcag ccggaagggc uucgagauga ucugggaccc caacggcugg   1140

accggcaccg acaacaaguu cagcaagaag caggacaucg ugggcaucaa cgaguggagc   1200

ggcuacagcg gcagcuucgu gcagcacccc gagcugacug gccugaacug cauccggccc   1260

ugcuucuggg uggaacugau acggggacgg cccgaggaga acaccaucug gaccagcggc   1320

agcagcauca gcuucugcgg cguggacagc gauaucgugg gcuggagcug gccagacgga   1380

gccgagcugc ccuucaccau cgacaag                                        1407
```

<210> SEQ ID NO 10
<211> LENGTH: 469
<212> TYPE: PRT
<213> ORGANISM: Artificial Sequence
<220> FEATURE:
<223> OTHER INFORMATION: Synthetic

<400> SEQUENCE: 10

```
Met Asn Pro Asn Gln Lys Ile Ile Thr Ile Gly Ser Ile Cys Met Thr
1               5                   10                  15

Ile Gly Met Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Lys Asn Val Ile Thr Tyr Glu Asn Asn Thr Trp Val Asn Gln
    50                  55                  60

Thr Tyr Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190
```

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465

<210> SEQ ID NO 11
<211> LENGTH: 1583
<212> TYPE: RNA
<213> ORGANISM: Artificial Sequence
<220> FEATURE:
<223> OTHER INFORMATION: Synthetic

<400> SEQUENCE: 11
gggaaauaag agagaaaaga agaguaagaa gaaauauaag accccggcgc cgccaccaug 60
aaccccaacc agaagaucau caccaucggc agcaucugca ugaccaucgg cauggccaac 120
cugauccugc aaaucggcaa caucaucagc aucuggguga gccacagcau ccagaucggc 180
aaccagagcc agaucgagac cugcaacaag aacgugauca ccuacgagaa caacaccugg 240
gugaaccaga ccuacgugaa caucagcaac accaacagcg ccgcucggca gucaguggcc 300
agcgugaagc uggccggcaa cagcagccug ugccccguua guggcugggc caucuacagc 360
aaggacaaca gcgugcggau cggcagcaag ggcgacgugu ucgugauccg ggagcccuuc 420

-continued aucagcugca gcccgcuuga gugccgcacc uucuuccuga cccagggcgc ucugcugaac 480
gacaagcaca gcaacggcac caucaagggc cggagccccu aucggacccu gaugagcugc 540
cccauuggcg aggugcccag ccccuacaac agccgguucg agucuguggc cuggagcgcc 600
ucugccugcc acgacggcac caacuggcug accaucggga ucagcggacc cgauagcgga 660
gcaguggccg ugcugaagua caacggcauc aucaccgaca ccaucaagag cuggcggaac 720
aacauccugc ggacccagga gagcgagugc gccugcguga acggcagcug cuucaccauc 780
augaccgacg gcccuagcga cggacaggcc agcuacaaga ucuuccggau cgagaagggc 840
aagaucauca agagcgugga gaugaaggca cccaacuacc acuacgagga gugcagcugc 900
uaccccgaca gcagcgagau caccugcgug ugccgggaca acuggcacgg gagcaacagg 960
cccuggguga gcuucaacca gaaccuggag uaccagaugg gcuacaucug cagcggcgug 1020
uucggcgaca acccacggcc caacgacaag acuggcagcu gcgguccggu gagcagcaac 1080
ggcgccaacg gcgugaaggg cuucagcuuc aaguacggca acggcgugug gaucggccgg 1140
accaagagca ucagcagccg gaagggcuuc gagaugaucu gggaccccaa cggcuggacc 1200
ggcaccgaca acaaguucag caagaagcag gacaucgugg gcaucaacga guggagcggc 1260
uacagcggca gcuucgugca gcaccccgag cugacuggcc ugaacugcau ccggcccugc 1320
uucugggugg aacugauacg gggacggccc gaggagaaca ccaucuggac cagcggcagc 1380
agcaucagcu ucugcggcgu ggacagcgau aucgugggcu ggagcuggcc agacggagcc 1440
gagcugcccu ucaccaucga caagugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 12
<211> LENGTH: 1407
<212> TYPE: RNA
<213> ORGANISM: Artificial Sequence
<220> FEATURE:
<223> OTHER INFORMATION: Synthetic

<400> SEQUENCE: 12
augaacccca accagaagau caucaccauc ggcagcaucu gcaugaccau cggcauggcc 60
aaccugaucc ugcaaaucgg caacaucauc agcaucuggg ugagccacag cauccagauc 120
ggcaaccaga gccagaucga gaccugcaac aagaacguga ucaccuacga gaacaacacc 180
ugggugaacc agaccuacgu gaacaucagc aacaccaaca gcgccgcucg gcagucagug 240
gccagcguga agcuggccgg caacagcagc cugugccccg uuaguggcug ggccaucuac 300
agcaaggaca acagcgugcg gaucggcagc aagggcgacg uguucgugau ccgggagccc 360
uucaucagcu gcagcccgcu ugagugccgc accuucuucc ugacccaggg cgcucugcug 420
aacgacaagc acagcaacgg caccaucaag ggccggagcc ccuaucggac ccugaugagc 480
ugccccauug gcgaggugcc cagccccuac aacagccggu ucgagucugu ggccuggagc 540
gccucugccu gccacgacgg caccaacugg cugaccaucg ggaucagcgg acccgauagc 600
ggagcagugg ccgugcugaa guacaacggc aucaucaccg acaccaucaa gagcuggcgg 660
aacaacaucc ugcggaccca ggagagcgag ugcgccugcg ugaacggcag cugcuucacc 720
aucaugaccg acggcccuag cgacggacag gccagcuaca agaucuuccg gaucgagaag 780
ggcaagauca ucaagagcgu ggagaugaag gcacccaacu accacuacga ggagugcagc 840
ugcuaccccg acagcagcga gaucaccugc gugugccggg acaacuggca cgggagcaac 900

```
aggcccuggg ugagcuucaa ccagaaccug gaguaccaga ugggcuacau cugcagcggc    960

guguucggcg acaacccacg gcccaacgac aagacuggca gcugcggucc ggugagcagc   1020

aacggcgcca acggcgugaa gggcuucagc uucaaguacg gcaacggcgu guggaucggc   1080

cggaccaaga gcaucagcag ccggaagggc uucgagauga ucugggaccc caacggcugg   1140

accggcaccg acaacaaguu cagcaagaag caggacaucg ugggcaucaa cgaguggagc   1200

ggcuacagcg gcagcuucgu gcagcacccc gagcugacug gccugaacug cauccggccc   1260

ugcuucuggg uggaacugau acggggacgg cccgaggaga acaccaucug gaccagcggc   1320

agcagcauca gcuucugcgg cguggacagc gauaucgugg gcuggagcug gccagacgga   1380

gccgagcugc ccuucaccau cgacaag                                       1407


<210> SEQ ID NO 13
<211> LENGTH: 469
<212> TYPE: PRT
<213> ORGANISM: Artificial Sequence
<220> FEATURE:
<223> OTHER INFORMATION: Synthetic

<400> SEQUENCE: 13

Met Asn Pro Asn Gln Lys Ile Ile Thr Ile Gly Ser Ile Cys Met Thr
1               5                   10                  15

Ile Gly Met Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Lys Asn Val Ile Thr Tyr Glu Asn Asn Thr Trp Val Asn Gln
    50                  55                  60

Thr Tyr Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Gly Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270
```

-continued

```
Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465
```

```
<210> SEQ ID NO 14
<211> LENGTH: 1874
<212> TYPE: RNA
<213> ORGANISM: Artificial Sequence
<220> FEATURE:
<223> OTHER INFORMATION: Synthetic

<400> SEQUENCE: 14

gggaaauaag agagaaaaga agaguaagaa gaaauauaag accccggcgc cgccaccaug      60

aagaccauca ucgcccugag cuacaauccug ugccugggcu ucacccagaa gaucccccggc    120

aacgauaaca gcaccgccac ccugugucug ggacaccacg ccgugcccaa cggcaccauc     180

gugaagacua ucaccaacga ccggaucgag gugaccaacg ccaccgagcu ggugcagaac     240

agcagcaucg gcgagaucug cgacagcccu caccagaucc uggacggcgg caacugcacc     300

cugaucgacg cacugcuggg cgacccucag ugcgacggcu uucagaacaa gaagugggac     360

cuguucgugg agagaucgcg ggccuacagc aacugcuacc ccuacgacgu ccccgacuac     420

gcaagccuga gaagccucgu ggccucaagc ggcacccugg aguucaagaa cgagagcuuc     480

aacugggccg gcgugaccca gaacggcaag ucauucagcu gcauccgggg cuccagcagc     540

agcuucuucu cacggcugaa cuggcugacc caccugaacu acaccuaccc cgcccugaac     600

gugaccaugc ccaacaagga gcaguucgac aagcuguaca ucuggggagu gcaccauccc     660

ggcaccgaca aggaccagau uagccuguac gcccagucua gcggccggau caccgugagc     720

accaagcgga gccagcaggc cgugaucccc aacaucggcu cucggcccag aauccgggac     780

auccccagcc ggaucagcau cuacuggacc auugugaagc ccggcgacau ccugcugauc     840

aacuccaccg gcaaccugau cgccccucgg ggcuauuuca agauccggag cggcaagagc     900
```

-continued

```
agcaucaugc ggagcgacgc cccuaucggc aagugcaaga gcgagugcau cacacccaac    960
ggaagcaucc ccaacgacaa gcccuuccag aacgugaacc ggauaaccua cggcgccugc   1020
ccuagauacg ugaagcagaa cacccugaag cuggccaccg gcaugcggaa cgugcccgag   1080
aagcagacuc ggggcaucuu cggcgccauc gccggcuuca ucgagaacgg cugggagggc   1140
augguggacg gcugguacgg cuuccggcac cagaacucug agggcagagg acaggccgca   1200
gaccugaaga gcacccaggc cgccaucgac cagaucaacg gcaagcugaa ccggcugauc   1260
ggcaagacca acgagaaguu ccaccagauc gagaaggagu ucagcgaggu ggagggcagg   1320
guacaggacc uggagaagua cguggaggac accaagaucg accuguggag cuacaacgcc   1380
gagcugcugg uagcccugga gaaccagcac accaucgacc ugaccgacag cgagaugaac   1440
aagcuguucg agaagaccaa gaagcagcug cgggagaacg ccgaggacau gggcaacggc   1500
ugcuucaaga ucuaccacaa gugcgacaac gccugcaucg gcagcauccg gaacgagacc   1560
uacgaccaca acguguaccg ggacgaggcc cugaacaacc gguuccagau caagggcgug   1620
gagcugaaga gcggcuacaa ggacuggauc cuguggauca gcuucgccau cuccugcuuc   1680
cugcugugcg uggcccugcu ggguuucauc auguggccu gccagaaggg caacauccgg    1740
ugcaacaucu gcaucugaua auaggcugga gccucggugg ccuagcuucu ugccccuugg   1800
gccucccccc agccccuccu ccccuuccug cacccguacc cccguggucu uugaauaaag   1860
ucugaguggg cggc                                                     1874
```

<210> SEQ ID NO 15
<211> LENGTH: 1698
<212> TYPE: RNA
<213> ORGANISM: Artificial Sequence
<220> FEATURE:
<223> OTHER INFORMATION: Synthetic

<400> SEQUENCE: 15

```
augaagacca ucaucgcccu gagcuacauc cugugccugg gcuucaccca gaagaucccc     60
ggcaacgaua acagcaccgc cacccugugu cugggacacc acgccgugcc caacggcacc    120
aucgugaaga cuaucaccaa cgaccggauc gaggugacca acgccaccga gcuggugcag    180
aacagcagca ucggcgagau cugcgacagc ccucaccaga uccuggacgg cggcaacugc    240
acccugaucg acgcacugcu gggcgacccu cagugcgacg gcuuucagaa caagaagugg    300
gaccuguucg uggagagauc gcgggccuac agcaacugcu accccuacga cguccccgac    360
uacgcaagcc ugagaagccu cguggccuca agcggcaccc uggaguucaa gaacgagagc    420
uucaacuggg ccggcgugac ccagaacggc aagucauuca gcugcauccg gggcuccagc    480
agcagcuucu ucucacggcu gaacuggcug acccaccuga acuacaccua ccccgcccug    540
aacgugacca ugcccaacaa ggagcaguuc gacaagcugu acaucugggg agugcaccau    600
cccggcaccg acaaggacca gauuagccug uacgcccagu cuagcggccg gaucaccgug    660
agcaccaagc ggagccagca ggccgugauc cccaacaucg gcucucggcc cagaauccgg    720
gacaucccca gccggaucag caucuacugg accauuguga agcccggcga cauccugcug    780
aucaacucca ccggcaaccu gaucgccccu cggggcuauu ucaagauccg gagcggcaag    840
agcagcauca ugcggagcga cgccccuauc ggcaagugca agagcgagug caucacaccc    900
aacggaagca uccccaacga caagcccuuc cagaacguga accggauaac cuacggcgcc    960
ugcccuagau acgugaagca gaacacccug aagcuggcca ccggcaugcg gaacgugccc   1020
```

```
gagaagcaga cucggggcau cuucggcgcc aucgccggcu ucaucgagaa cggcugggag   1080

ggcauggugg acggcuggua cggcuuccgg caccagaacu cugagggcag aggacaggcc   1140

gcagaccuga agagcaccca ggccgccauc gaccagauca acggcaagcu gaaccggcug   1200

aucggcaaga ccaacgagaa guuccaccag aucgagaagg aguucagcga gguggagggc   1260

aggguacagg accuggagaa guacguggag gacaccaaga ucgaccugug gagcuacaac   1320

gccgagcugc ugguagcccu ggagaaccag cacaccaucg accugaccga cagcgagaug   1380

aacaagcugu ucgagaagac caagaagcag cugcgggaga acgccgagga caugggcaac   1440

ggcugcuuca agaucuacca caagugcgac aacgccugca ucggcagcau ccggaacgag   1500

accuacgacc acaacgugua ccgggacgag gcccugaaca accgguucca gaucaagggc   1560

guggagcuga agagcggcua caaggacugg auccugugga ucagcuucgc caucuccugc   1620

uuccugcugu gcguggcccu gcuggguuuc aucauguggg ccugccagaa gggcaacauc   1680

cggugcaaca ucugcauc                                                 1698
```

<210> SEQ ID NO 16
<211> LENGTH: 566
<212> TYPE: PRT
<213> ORGANISM: Artificial Sequence
<220> FEATURE:
<223> OTHER INFORMATION: Synthetic

<400> SEQUENCE: 16

```
Met Lys Thr Ile Ile Ala Leu Ser Tyr Ile Leu Cys Leu Gly Phe Thr
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Gly Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Ala
    130                 135                 140

Gly Val Thr Gln Asn Gly Lys Ser Phe Ser Cys Ile Arg Gly Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240
```

```
Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 17
<211> LENGTH: 1583
<212> TYPE: RNA
<213> ORGANISM: Artificial Sequence
<220> FEATURE:
<223> OTHER INFORMATION: Synthetic

<400> SEQUENCE: 17

```
gggaaauaag agagaaaaga agaguaagaa gaaauauaag accccggcgc cgccaccaug      60

aacccgaacc agaagaucau caccaucggc agcgugagcc ugaccaucag caccaucugc     120

uucuucaugc agaucgccau ccugaucacc accgugaccc ugcacuucaa gcaguacgag     180
```

-continued

```
uucaacagcc ugcccaacaa ccaggugaug cugugcgagc ccaccaucau cgagcggaac    240

aucaccgaga ucguguaccu gaccaacacc accaucgaga aggagaucug ccccaagccc    300

gccgaguacc ggaacuggag caagccccag ugcggcauca ccggcuucgc cccauucagc    360

aaggacaaca gcaucagacu gagugccggc ggcgacaucu gggugacccg ggagcccuac    420

gugagcugcg accuggacaa gugcuaccag uucgcccugg gacagggcac cacccugaac    480

aacgugcaca gcaacaacac ugugcgggac cggaccccau accggacccu gcugaugaac    540

gagcugggcg ugcccuucca ccugggcacc aagcaggugu gcaucgccug gagcagcagc    600

agcugccacg acggcaaggc cuggcugcac gugugcauua ccggcgacga caagaacgcc    660

accgccagcu ucaucuacaa cggcaggcug guggacagcg uggugagcug gagcaacgac    720

auccugcgga cccaggagag cgagugcgug ugcaucaacg gcaccugcac cgugguggaug    780

acugacggca acgccaccgg caaggccgac accaagaucc uguucaucga ggaggggaag    840

aucgugcaca ccagcaagcu gucuggcagc gcccagcacg uggaggagug cagcugcuac    900

ccucgguacc ccggcgugag gugcgugugc cgggacaacu ggaagggcag caaccggccc    960

aucaucgaca ucaacaucaa ggaccacagc auagugagca gcuacgugug cagcggucug   1020

gugggcgaca cuccccggaa gagcgacagc agcuccagca gccacugccu gaaccccaac   1080

aacgaggagg gugguacacgg cgugaagggc ugggccuucg acgacggcaa cgacgugugg   1140

augggccgga ccaucaacga gaccagcaga cugggcuacg agaccuucaa gguggugggag   1200

ggcuggagca aucccaagag caagcugcag aucaaccggc aggugaucgu cgaucggggc   1260

gaucggagcg gcuacagcgg caucuucagc guggagggca agagcugcau caaccggugc   1320

uucuacgugg agcugauccg gggccggaag gaggagaccg aggugcugug gaccagcaac   1380

agcaucgugg uguucugcgg caccagcggc accuacggca ccggauccug gccagacggc   1440

gccgaucuga accugaugca caucugauaa uaggcuggag ccucgguggc cuagcuucuu   1500

gccccuuggg ccucccccca gccccuccuc cccuuccugc acccguaccc ccgugguucuu   1560

ugaauaaagu cugagugggc ggc                                           1583
```

<210> SEQ ID NO 18
<211> LENGTH: 1407
<212> TYPE: RNA
<213> ORGANISM: Artificial Sequence
<220> FEATURE:
<223> OTHER INFORMATION: Synthetic

<400> SEQUENCE: 18

```
augaacccga accagaagau caucaccauc ggcagcguga gccugaccau cagcaccauc     60

ugcuucuuca ugcagaucgc cauccugauc accaccguga cccugcacuu caagcaguac    120

gaguucaaca gccugcccaa caaccaggug augcugugcg agcccaccau caucgagcgg    180

aacaucaccg agaucgugua ccugaccaac accaccaucg agaaggagau cugccccaag    240

cccgccgagu accggaacug gagcaagccc cagugcggca ucaccggcuu cgccccauuc    300

agcaaggaca acagcaucag acugagugcc ggcggcgaca ucugggugac ccgggagccc    360

uacgugagcu gcgaccugga caagugcuac caguucgccc ugggacaggg caccacccug    420

aacaacgugc acagcaacaa cacugugcgg gaccggaccc cauaccggac ccugcugaug    480

aacgagcugg gcgugcccuu ccaccugggc accaagcagg ugugcaucgc cuggagcagc    540

agcagcugcc acgacggcaa ggccuggcug cacgugugca uuaccggcga cgacaagaac    600

gccaccgcca gcuucaucua caacggcagg cugguggaca gcguggugag cuggagcaac    660
```

-continued

```
gacauccugc ggacccagga gagcgagugc gugugcauca acggcaccug caccguggug    720

augacugacg gcaacgccac cggcaaggcc gacaccaaga uccuguucau cgaggagggg    780

aagaucgugc acaccagcaa gcugucuggc agcgcccagc acguggagga gugcagcugc    840

uacccucggu accccggcgu gaggugcgug ugccgggaca acuggaaggg cagcaaccgg    900

cccaucaucg acaucaacau caaggaccac agcauaguga gcagcuacgu gugcagcggu    960

cuggugggcg acacuccccg gaagagcgac agcagcucca gcagccacug ccugaacccc   1020

aacaacgagg agggugguca cggcgugaag ggcugggccu ucgacgacgg caacgacgug   1080

uggaugggcc ggaccaucaa cgagaccagc agacugggcu acgagaccuu caagguggug   1140

gagggcugga gcaaucccaa gagcaagcug cagaucaacc ggcaggugau cgucgaucgg   1200

ggcgaucgga gcggcuacag cggcaucuuc agcguggagg gcaagagcug caucaaccgg   1260

ugcuucuacg uggagcugau ccggggccgg aaggaggaga ccgaggugcu guggaccagc   1320

aacagcaucg ugguguucug cggcaccagc ggcaccuacg gcaccggauc cuggccagac   1380

ggcgccgauc ugaaccugau gcacauc                                       1407


<210> SEQ ID NO 19
<211> LENGTH: 469
<212> TYPE: PRT
<213> ORGANISM: Artificial Sequence
<220> FEATURE:
<223> OTHER INFORMATION: Synthetic

<400> SEQUENCE: 19

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Leu Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Asn Asp Ile Leu Arg
    210                 215                 220
```

```
Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Ile Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Ser Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465
```

<210> SEQ ID NO 20
<211> LENGTH: 1583
<212> TYPE: RNA
<213> ORGANISM: Artificial Sequence
<220> FEATURE:
<223> OTHER INFORMATION: Synthetic

<400> SEQUENCE: 20

```
gggaaauaag agagaaaaga agaguaagaa gaaauauaag accccggcgc cgccaccaug      60

aacccgaacc agaagaucau caccaucggc agcgugagcc ugaccaucag caccaucugc     120

uucuucaugc agaucgccau ccugaucacc accgugaccc ugcacuucaa gcaguacgag     180

uucaacagcc ugcccaacaa ccaggugaug cugugcgagc ccaccaucau cgagcggaac     240

aucaccgaga ucguguaccu gaccaacacc accaucgaga aggagaucug ccccaagccc     300

gccgaguacc ggaacuggag caagccccag ugcggcauca ccggcuucgc cccauucagc     360

aaggacaaca gcaucagacu gagugccggc ggcgacaucu gggugacccg ggagcccuac     420

gugagcugcg accuggacaa gugcuaccag uucgcccugg gacagggcac cacccugaac     480

aacgugcaca gcaacaacac ugugcggggc cggaccccau accggacccu gcugaugaac     540

gagcugggcg ugcccuucca ccugggcacc aagcaggugu gcaucgccug gagcagcagc     600

agcugccacg acggcaaggc cuggcugcac gugugcauua ccggcgacga caagaacgcc     660
```

-continued accgccagcu ucaucuacaa cggcaggcug guggacagcg uggugagcug gagcaacgac 720
auccugcgga cccaggagag cgagugcgug ugcaucaacg gcaccugcac cguggugaug 780
acugacggca acgccaccgg caaggccgac accaagaucc uguucaucga ggaggggaag 840
aucgugcaca ccagcaagcu gucuggcagc gcccagcacg uggaggagug cagcugcuac 900
ccucgguacc ccggcgugag gugcgugugc cgggacaacu ggaagggcag caaccggccc 960
aucaucgaca ucaacaucaa ggaccacagc auagugagca gcuacgugug cagcggucug 1020
gugggcgaca cuccccggaa gagcgacagc agcuccagca gccacugccu gaaccccaac 1080
aacgaggagg gugguucacgg cgugaagggc ugggccuucg acgacggcaa cgacgugugg 1140
augggccgga ccaucaacga gaccagcaga cugggcuacg agaccuucaa ggugguggag 1200
ggcuggagca aucccaagag caagcugcag aucaaccggc aggugaucgu cgaucggggc 1260
gaucggagcg gcuacagcgg caucuucagc guggagggca agagcugcau caaccggugc 1320
uucuacgugg agcugauccg ggccggaag gaggagaccg aggugcugug gaccagcaac 1380
agcaucgugg uguucugcgg caccagcggc accuacggca ccggauccug gccagacggc 1440
gccgaucuga accugaugca caucugauaa uaggcuggag ccucggugge cuagcuucuu 1500 gccccuuggg ccucccccca gccccuccuc cccuuccugc acccguaccc ccguggucuu 1560
ugaauaaagu cugagugggc ggc 1583

<210> SEQ ID NO 21
<211> LENGTH: 1407
<212> TYPE: RNA
<213> ORGANISM: Artificial Sequence
<220> FEATURE:
<223> OTHER INFORMATION: Synthetic

<400> SEQUENCE: 21
augaacccga accagaagau caucaccauc ggcagcguga gccugaccau cagcaccauc 60
ugcuucuuca ugcagaucgc cauccugauc accaccguga cccugcacuu caagcaguac 120
gaguucaaca gccugcccaa caaccaggug augcugugcg agcccaccau caucgagcgg 180
aacaucaccg agaucgugua ccugaccaac accaccaucg agaaggagau cugccccaag 240
cccgccgagu accggaacug gagcaagccc cagugcggca ucaccggcuu cgccccauuc 300
agcaaggaca acagcaucag acugagugcc ggcggcgaca ucugggugac ccgggagccc 360
uacgugagcu gcgaccugga caagugcuac caguucgccc ugggacaggg caccacccug 420
aacaacgugc acagcaacaa cacugugcgg ggccggaccc cauaccggac ccugcugaug 480
aacgagcugg gcgugcccuu ccaccugggc accaagcagg ugugcaucgc cuggagcagc 540
agcagcugcc acgacggcaa ggccuggcug cacgugugca uuaccggcga cgacaagaac 600
gccaccgcca gcuucaucua caacggcagg cugguggaca gcguggugag cuggagcaac 660
gacauccugc ggacccagga gagcgagugc gugugcauca acggcaccug caccguggug 720
augacugacg gcaacgccac cggcaaggcc gacaccaaga uccuguucau cgaggagggg 780
aagaucgugc acaccagcaa gcugucuggc agcgcccagc acguggagga gugcagcugc 840
uacccucggu accccggcgu gaggugcgug ugccgggaca acuggaaggg cagcaaccgg 900
cccaucaucg acaucaacau caaggaccac agcauaguga gcagcuacgu gugcagcggu 960
cuggugggcg acacuccccg gaagagcgac agcagcucca gcagccacug ccugaacccc 1020
aacaacgagg agggugguca cggcgugaag ggcugggccu ucgacgacgg caacgacgug 1080

```
uggaugggcc ggaccaucaa cgagaccagc agacugggcu acgagaccuu caagguggug   1140

gagggcugga gcaaucccaa gagcaagcug cagaucaacc ggcaggugau cgucgaucgg   1200

ggcgaucgga gcggcuacag cggcaucuuc agcguggagg gcaagagcug caucaaccgg   1260

ugcuucuacg uggagcugau ccggggccgg aaggaggaga ccgaggugcu guggaccagc   1320

aacagcaucg ugguguucug cggcaccagc ggcaccuacg gcaccggauc cuggccagac   1380

ggcgccgauc ugaaccugau gcacauc                                       1407


<210> SEQ ID NO 22
<211> LENGTH: 469
<212> TYPE: PRT
<213> ORGANISM: Artificial Sequence
<220> FEATURE:
<223> OTHER INFORMATION: Synthetic

<400> SEQUENCE: 22

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Leu Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Gly Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Asn Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Ile Asp
    290                 295                 300
```

```
Ile Asn Ile Lys Asp His Ser Ile Val Ser Ser Tyr Val Cys Ser Gly
305                 310                 315                 320

Leu Val Gly Asp Thr Pro Arg Lys Ser Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465


<210> SEQ ID NO 23
<211> LENGTH: 1921
<212> TYPE: RNA
<213> ORGANISM: Artificial Sequence
<220> FEATURE:
<223> OTHER INFORMATION: Synthetic

<400> SEQUENCE: 23

gggaaauaag agagaaaaga agaguaagaa gaaauauaag accccggcgc cgccaccaug      60

aaggccauca ucgugcuguu aaugguggug accagcaacg ccgaccggau cugcaccggc     120

aucaccucua gcaacagccc ucacguggug aagaccgcca cacagggcga ggugaacgug     180

accggcguga uuccccugac caccaccccu accaagagcc acuucgccaa ccugaaggga     240

accgagaccc ggggcaagcu gugucccaag ugccugaacu gcaccgaccu ggacguggcc     300

cugggcagac ccaagugcac cggcaagauc cccagcgccc gggugucuau ccugcacgaa     360

gugcggcccg ugacuagcgg cugcuucccc aucaugcacg accggaccaa gauccggcag     420

cugcccaacc ugcugcgggg cuacgagcac gugcggcuga gcacccacaa cgugaucaac     480

gccgaagacg cacccgggag accauacgag aucggcacca gcggcucuug ccccaacauc     540

accaacggca acggcuucuu cgcuaccaug gccugggccg ugccaaagaa caagacugcc     600

accaacccuc ugaccaucga ggugcccuac aucugcaccg agggcgagga ccagaucacc     660

gugugggggcu uccacagcga cagcgagacc cagauggcca agcuguacgg cgacagcaag     720

ccccagaagu ucaccagcag cgccaacggc gugaccaccc acuacgugag ccagaucggc     780

ggcuucccca accagaccga ggacggcggc uuaccccaga gcggccggau cgugguggac     840

uacauggugc agaagagcgg caagaccggc accaucaccu accagcgggg cauccugcug     900

ccacagaagg uguggugcgc cucagggcgg ucaaagguga ucaagggcag ccugccacug     960

auuggcgagg ccgacugccu gcacgagaag uacggcggcc ugaacaagag caagcccuac    1020

uacaccggcg agcacgccaa ggcaaucggc aacugcccca ucugggugaa gacaccccug    1080
```

-continued

```
aagcuggcca acggcaccaa guaccggcca cccgccaaac ugcugaagga gcggggcuuc   1140

uucggcgcca uugccggcuu ccucgaaggc gguugggagg gcaugaucgc cggcuggcac   1200

ggcuacacua gccacggcgc acacggagua gcaguggccg ccgaccugaa gagcacccag   1260

gaggccauca acaagaucac caagaaccug aacagccuga gcgagcugga ggugaagaau   1320

cugcagcggc ugucuggcgc uauggacgag cugcacaacg agauccugga gcuggacgag   1380

aagguggacg acuuacgggc cgacaccauc agcagccaga ucgagcuggc cgugcugcug   1440

agcaacgagg gcaucaucaa cagcgaggac gagcaccugc uggcccugga gggaagcuga   1500

agaagaugcu gggcccuucu gccguggaga ucgguaacgg cugcuucgag accaagcaca   1560

agugcaacca gaccugccug gaucggaucg cagccggcac cuuugacgcc ggggaguuca   1620

gccugcccac cuucgacagc cugaacauca ccgccgccag ccugaacgac gacggccugg   1680

acaaccacac cauccugcug uacuacucua cagccgcuag cagccuggcc gugacccuga   1740

ugaucgccau cuucguggug uacaugguga gccgggacaa cgugagcugc agcaucugcc   1800

ugugauaaua ggcuggagcc ucgguggccu agcuucuugc cccuugggcc ucccccagc    1860

cccuccuccc cuuccugcac ccguaccccc guggucuuug aauaaagucu gagugggcgg   1920

c                                                                    1921
```

<210> SEQ ID NO 24
<211> LENGTH: 1745
<212> TYPE: RNA
<213> ORGANISM: Artificial Sequence
<220> FEATURE:
<223> OTHER INFORMATION: Synthetic

<400> SEQUENCE: 24

```
augaaggcca ucaucgugcu guuaauggug gugaccagca acgccgaccg gaucugcacc     60

ggcaucaccu cuagcaacag cccucacgug gugaagaccg ccacacaggg cgaggugaac    120

gugaccggcg ugauuccccu gaccaccacc ccuaccaaga gccacuucgc caaccugaag    180

ggaaccgaga cccggggcaa gcuguguccc aagugccuga acugcaccga ccuggacgug    240

gcccugggca gacccaagug caccggcaag auccccagcg cccgggguguc uauccugcac    300

gaagugcggc ccgugacuag cggcugcuuc cccaucaugc acgaccggac caagauccgg    360

cagcugccca accugcugcg gggcuacgag cacgugcggc ugagcaccca caacgugauc    420

aacgccgaag acgcacccgg gagaccauac gagaucggca ccagcggcuc uugccccaac    480

aucaccaacg gcaacggcuu cuucgcuacc auggccuggg ccgugccaaa gaacaagacu    540

gccaccaacc cucugaccau cgaggugccc uacaucugca ccgagggcga ggaccagauc    600

accguguggg gcuuccacag cgacagcgag acccagaugg ccaagcugua cggcgacagc    660

aagccccaga aguucaccag cagcgccaac ggcgugacca cccacuacgu gagccagauc    720

ggcggcuucc ccaaccagac cgaggacggc ggcuuacccc agagcggccg gaucguggug    780

gacuacaugg ugcagaagag cggcaagacc ggcaccauca ccuaccagcg gggcauccug    840

cugccacaga aggugugggug cgccucaggg cggucaaagg ugaucaaggg cagccugcca    900

cugauuggcg aggccgacug ccugcacgag aaguacggcg gccugaacaa gagcaagccc    960

uacuacaccg gcgagcacgc caaggcaauc ggcaacugcc ccaucugggu gaagacaccc   1020

cugaagcugg ccaacggcac caaguaccgg ccacccgcca aacugcugaa ggagcggggc   1080

uucuucggcg ccauugccgg cuuccucgaa ggcgguuggg agggcaugau cgccggcugg   1140

cacggcuaca cuagccacgg cgcacacgga guagcagugg ccgccgaccu gaagagcacc   1200
```

-continued caggaggcca ucaacaagau caccaagaac cugaacagcc ugagcgagcu ggaggugaag 1260
aaucugcagc ggcugucugg cgcuauggac gagcugcaca acgagauccu ggagcuggac 1320
gagaaggugg acgacuuacg ggccgacacc aucagcagcc agaucgagcu ggccgugcug 1380
cugagcaacg agggcaucau caacagcgag gacgagcacc ugcuggcccu ggagggaagc 1440
ugaagaagau gcugggcccu ucugccgugg agaucgguaa cggcugcuuc gagaccaagc 1500
acaagugcaa ccagaccugc cuggaucgga ucgcagccgg caccuuugac gccggggagu 1560
ucagccugcc caccuucgac agccugaaca ucaccgccgc cagccugaac gacgacggcc 1620
uggacaacca caccauccug cuguacuacu cuacagccgc uagcagccug gccgugaccc 1680
ugaugaucgc caucuucgug guguacaugg ugagccggga caacgugagc ugcagcaucu 1740
gccug 1745

<210> SEQ ID NO 25
<211> LENGTH: 582
<212> TYPE: PRT
<213> ORGANISM: Artificial Sequence
<220> FEATURE:
<223> OTHER INFORMATION: Synthetic

<400> SEQUENCE: 25

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Val Arg Leu Ser Thr His Asn Val Ile Asn Ala Glu Asp
    130                 135                 140

Ala Pro Gly Arg Pro Tyr Glu Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Lys Thr Ala Thr Asn Pro Leu Thr Ile Glu Val Pro Tyr Ile
            180                 185                 190

Cys Thr Glu Gly Glu Asp Gln Ile Thr Val Trp Gly Phe His Ser Asp
        195                 200                 205

Ser Glu Thr Gln Met Ala Lys Leu Tyr Gly Asp Ser Lys Pro Gln Lys
    210                 215                 220

Phe Thr Ser Ser Ala Asn Gly Val Thr Thr His Tyr Val Ser Gln Ile
225                 230                 235                 240

Gly Gly Phe Pro Asn Gln Thr Glu Asp Gly Gly Leu Pro Gln Ser Gly
                245                 250                 255

-continued

```
Arg Ile Val Val Asp Tyr Met Val Gln Lys Ser Gly Lys Thr Gly Thr
            260                 265                 270

Ile Thr Tyr Gln Arg Gly Ile Leu Leu Pro Gln Lys Val Trp Cys Ala
        275                 280                 285

Ser Gly Arg Ser Lys Val Ile Lys Gly Ser Leu Pro Leu Ile Gly Glu
    290                 295                 300

Ala Asp Cys Leu His Glu Lys Tyr Gly Gly Leu Asn Lys Ser Lys Pro
305                 310                 315                 320

Tyr Tyr Thr Gly Glu His Ala Lys Ala Ile Gly Asn Cys Pro Ile Trp
                325                 330                 335

Val Lys Thr Pro Leu Lys Leu Ala Asn Gly Thr Lys Tyr Arg Pro Pro
            340                 345                 350

Ala Lys Leu Leu Lys Glu Arg Gly Phe Phe Gly Ala Ile Ala Gly Phe
        355                 360                 365

Leu Glu Gly Gly Trp Glu Gly Met Ile Ala Gly Trp His Gly Tyr Thr
    370                 375                 380

Ser His Gly Ala His Gly Val Ala Val Ala Ala Asp Leu Lys Ser Thr
385                 390                 395                 400

Gln Glu Ala Ile Asn Lys Ile Thr Lys Asn Leu Asn Ser Leu Ser Glu
                405                 410                 415

Leu Glu Val Lys Asn Leu Gln Arg Leu Ser Gly Ala Met Asp Glu Leu
            420                 425                 430

His Asn Glu Ile Leu Glu Leu Asp Glu Lys Val Asp Asp Leu Arg Ala
        435                 440                 445

Asp Thr Ile Ser Ser Gln Ile Glu Leu Ala Val Leu Leu Ser Asn Glu
    450                 455                 460

Gly Ile Ile Asn Ser Glu Asp Glu His Leu Leu Ala Leu Glu Arg Lys
465                 470                 475                 480

Leu Lys Lys Met Leu Gly Pro Ser Ala Val Glu Ile Gly Asn Gly Cys
                485                 490                 495

Phe Glu Thr Lys His Lys Cys Asn Gln Thr Cys Leu Asp Arg Ile Ala
            500                 505                 510

Ala Gly Thr Phe Asp Ala Gly Glu Phe Ser Leu Pro Thr Phe Asp Ser
        515                 520                 525

Leu Asn Ile Thr Ala Ala Ser Leu Asn Asp Asp Gly Leu Asp Asn His
    530                 535                 540

Thr Ile Leu Leu Tyr Tyr Ser Thr Ala Ala Ser Ser Leu Ala Val Thr
545                 550                 555                 560

Leu Met Ile Ala Ile Phe Val Val Tyr Met Val Ser Arg Asp Asn Val
                565                 570                 575

Ser Cys Ser Ile Cys Leu
            580
```

<210> SEQ ID NO 26
<211> LENGTH: 1574
<212> TYPE: RNA
<213> ORGANISM: Artificial Sequence
<220> FEATURE:
<223> OTHER INFORMATION: Synthetic

<400> SEQUENCE: 26

```
gggaaauaag agagaaaaga agaguaagaa gaaauauaag accccggcgc cgccaccaug      60

cugcccagca ccauccagac ccugacccug uuucugacca gcggaggcgu gcugcugagc     120

cuguacguga gcgccagccu gagcuaccug cuguacagcg acauccugcu gaaguucagc     180
```

-continued

```
cccaccgaga ucaccgcacc caccaugccc cuggacugcg ccaacgccag caacgugcag    240

gccgugaacc ggagcgccac aaagggcgug acccugcugc ugcccgagcc agaguggaca    300

uauccucggc ugagcugccc uggcagcacc uuccagaagg cccugcugau cagcccacac    360

cgguucggcg agaccaaggg caacagcgca ccccugauca uccgggagcc cuucguggcc    420

uguggcccca acgagugcaa gcacuucgcc cugacacacu acgcugcuca gcccggugge    480

uacuacaacg gcacccgggg ugaucggaac aagcugcggc accugaucag cgugaagcug    540

ggcaagaucc ccaccgugga gaacagcauc uuccacaugg ccgccugguc aggaagcgcc    600

ugccacgacg gcaaggagug gaccuacauc ggcguggacg gcccugacaa caacgcccug    660

cugaagguga aguacggcga ggccuacacc gacaccuacc acagcuacgc caacaacauc    720

cugcggaccc aggagagcgc cugcaacugc aucggcggca acugcuaccu gaugaucacc    780

gacggcagcg cuucuggcgu gagcgagugc cgguuccuga agauccggga gggccggauc    840

aucaaggaga ucuuucccac cggccgggug aagcacaccg aggagugcac cugcggcuuc    900

gccagcaaca agaccaucga gugcgccugc cgggacaauc gguacaccgc caagcggccc    960

uucgugaagc ugaacgugga gaccgacacc gccgagaucc ggcugaugug caccgacacu   1020

uaucuggaca ccccucggcc uaacgacggc agcaucaccg gcccuugcga gagcgacggc   1080

gacaagggaa gcggcggcau caagggcggu uucgugcacc agcggaugaa gagcaagauc   1140

ggccgguggu acagccggac caugagcaag accgagcgga ugggcauggg ccuguacgua   1200

aaguacggag gggaucccug ggcugacagc gacgcccuga ccuucagcgg cgugauggug   1260

agcaugaagg agcccggcug guacagcuuc ggcuucgaga ucaaggacaa gaagugcgac   1320

gugcccugca ucggcaucga gauggugcac gacggcggca aggagaccug gcacucugcc   1380

gccacugcca ucuacugccu gaugggcagc ggccagcugc ugugggacac cgugaccggc   1440

guggacaugg cccugugaua auaggcugga gccucggugg ccuagcuucu ugccccuugg   1500

gccucccccc agccccuccu ccccuuccug cacccguacc cccguggucu uugaauaaag   1560

ucugaguggg cggc                                                     1574
```

<210> SEQ ID NO 27
<211> LENGTH: 1398
<212> TYPE: RNA
<213> ORGANISM: Artificial Sequence
<220> FEATURE:
<223> OTHER INFORMATION: Synthetic

<400> SEQUENCE: 27

```
augcugccca gcaccaucca gacccugacc cuguuucuga ccagcggagg cgugcugcug     60

agccuguacg ugagcgccag ccugagcuac cugcuguaca gcgacauccu gcugaaguuc    120

agccccaccg agaucaccgc acccaccaug ccccuggacu gcgccaacgc cagcaacgug    180

caggccguga accggagcgc cacaaagggc gugacccugc ugcugcccga gccagagugg    240

acauauccuc ggcugagcug cccuggcagc accuuccaga aggcccugcu gaucagccca    300

caccgguucg gcgagaccaa gggcaacagc gcaccccuga ucauccggga gcccuucgug    360

gccuguggcc ccaacgagug caagcacuuc gcccugacac acuacgcugc ucagcccggu    420

ggcuacuaca acggcacccg gggugaucgg aacaagcugc ggcaccugau cagcgugaag    480

cugggcaaga uccccaccgu ggagaacagc aucuuccaca uggccgccug gucaggaagc    540

gccugccacg acggcaagga guggaccuac aucggcgugg acggcccuga caacaacgcc    600

cugcugaagg ugaaguacgg cgaggccuac accgacaccu accacagcua cgccaacaac    660
```

auccugcgga cccaggagag cgccugcaac ugcaucggcg gcaacugcua ccugaugauc 720
accgacggca gcgcuucugg cgugagcgag ugccgguucc ugaagauccg ggagggccgg 780
aucaucaagg agaucuuucc caccggccgg gugaagcaca ccgaggagug caccugcggc 840
uucgccagca acaagaccau cgagugcgcc ugccgggaca aucgguacac cgccaagcgg 900
cccuucguga agcugaacgu ggagaccgac accgccgaga uccggcugau gugcaccgac 960
acuuaucugg acaccccucg gccuaacgac ggcagcauca ccggcccuug cgagagcgac 1020
ggcgacaagg gaagcggcgg caucaagggc gguuucgugc accagcggau gaagagcaag 1080
aucggccggu gguacagccg gaccaugagc aagaccgagc ggaugggcau gggccuguac 1140
guaaaguacg gaggggaucc cugggcugac agcgacgccc ugaccuucag cggcgugaug 1200
gugagcauga aggagcccgg cugguacagc uucggcuucg agaucaagga caagaagugc 1260
gacgugcccu gcaucggcau cgagauggug cacgacggcg gcaaggagac cuggcacucu 1320
gccgccacug ccaucuacug ccugaugggc agcggccagc ugcuguggga caccgugacc 1380
ggcguggaca uggcccug 1398

<210> SEQ ID NO 28
<211> LENGTH: 466
<212> TYPE: PRT
<213> ORGANISM: Artificial Sequence
<220> FEATURE:
<223> OTHER INFORMATION: Synthetic

<400> SEQUENCE: 28

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Val Ala Cys Gly Pro Asn Glu Cys Lys
        115                 120                 125

His Phe Ala Leu Thr His Tyr Ala Ala Gln Pro Gly Gly Tyr Tyr Asn
    130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Asn Ile Leu Arg Thr
    210                 215                 220
```

-continued

Gln Glu Ser Ala Cys Asn Cys Ile Gly Gly Asn Cys Tyr Leu Met Ile
225 230 235 240

Thr Asp Gly Ser Ala Ser Gly Val Ser Glu Cys Arg Phe Leu Lys Ile
245 250 255

Arg Glu Gly Arg Ile Ile Lys Glu Ile Phe Pro Thr Gly Arg Val Lys
260 265 270

His Thr Glu Glu Cys Thr Cys Gly Phe Ala Ser Asn Lys Thr Ile Glu
275 280 285

Cys Ala Cys Arg Asp Asn Arg Tyr Thr Ala Lys Arg Pro Phe Val Lys
290 295 300

Leu Asn Val Glu Thr Asp Thr Ala Glu Ile Arg Leu Met Cys Thr Asp
305 310 315 320

Thr Tyr Leu Asp Thr Pro Arg Pro Asn Asp Gly Ser Ile Thr Gly Pro
325 330 335

Cys Glu Ser Asp Gly Asp Lys Gly Ser Gly Gly Ile Lys Gly Gly Phe
340 345 350

Val His Gln Arg Met Lys Ser Lys Ile Gly Arg Trp Tyr Ser Arg Thr
355 360 365

Met Ser Lys Thr Glu Arg Met Gly Met Gly Leu Tyr Val Lys Tyr Gly
370 375 380

Gly Asp Pro Trp Ala Asp Ser Asp Ala Leu Thr Phe Ser Gly Val Met
385 390 395 400

Val Ser Met Lys Glu Pro Gly Trp Tyr Ser Phe Gly Phe Glu Ile Lys
405 410 415

Asp Lys Lys Cys Asp Val Pro Cys Ile Gly Ile Glu Met Val His Asp
420 425 430

Gly Gly Lys Glu Thr Trp His Ser Ala Ala Thr Ala Ile Tyr Cys Leu
435 440 445

Met Gly Ser Gly Gln Leu Leu Trp Asp Thr Val Thr Gly Val Asp Met
450 455 460

Ala Leu
465

<210> SEQ ID NO 29
<211> LENGTH: 1574
<212> TYPE: RNA
<213> ORGANISM: Artificial Sequence
<220> FEATURE:
<223> OTHER INFORMATION: Synthetic

<400> SEQUENCE: 29
gggaaauaag agagaaaaga agaguaagaa gaaauauaag accccggcgc cgccaccaug 60
cugcccagca ccauccagac ccugacccug uuucugacca gcggaggcgu gcugcugagc 120
cuguacguga gcgccagccu gagcuaccug cuguacagcg acauccugcu gaaguucagc 180
cccaccgaga ucaccgcacc caccaugccc cuggacugcg ccaacgccag caacgugcag 240
gccgugaacc ggagcgccac aaagggcgug acccugcugc ugcccgagcc agaguggaca 300
uauccucggc ugagcugccc uggcagcacc uuccagaagg cccugcugau cagcccacac 360
cgguucggcg agaccaaggg caacagcgca ccccugauca uccgggagcc cuucguggcc 420
uguggcccca acgagugcaa gcacuucgcc cugacacacu acgcugcuca gcccggguggc 480 uacuacaacg gcacccgggg uggccggaac aagcugcggc accugaucag cgugaagcug 540
ggcaagaucc ccaccgugga gaacagcauc uuccacaugg ccgccugguc aggaagcgcc 600
ugccacgacg gcaaggagug gaccuacauc ggcguggacg gcccugacaa caacgcccug 660
cugaagguga aguacggcga ggccuacacc gacaccuacc acagcuacgc caacaacauc 720
cugcggaccc aggagagcgc cugcaacugc aucggcggca acugcuaccu gaugaucacc 780
gacggcagcg cuucuggcgu gagcgagugc cgguuccuga agauccggga gggccggauc 840
aucaaggaga ucuuucccac cggccgggug aagcacaccg aggagugcac cugcggcuuc 900
gccagcaaca agaccaucga gugcgccugc cgggacaauc gguacaccgc caagcggccc 960
uucgugaagc ugaacgugga gaccgacacc gccgagaucc ggcugaugug caccgacacu 1020
uaucuggaca ccccucggcc uaacgacggc agcaucaccg gcccuugcga gagcgacggc 1080
gacaagggaa gcggcggcau caagggcggu uucgugcacc agcggaugaa gagcaagauc 1140
ggccgguggu acagccggac caugagcaag accgagcgga ugggcauggg ccuguacgua 1200
aaguacggag ggaucccug ggcugacagc gacgcccuga ccuucagcgg cgugauggug 1260
agcaugaagg agcccggcug guacagcuuc ggcuucgaga ucaaggacaa gaagugcgac 1320
gugcccugca ucggcaucga gauggugcac gacggcggca aggagaccug gcacucugcc 1380
gccacugcca ucuacugccu gaugggcagc ggccagcugc ugugggacac cgugaccggc 1440
guggacaugg cccugugaua auaggcugga gccucggugg ccuagcuucu ugccccuugg 1500 gccuccccc agccccuccu ccccuuccug cacccguacc cccguggucu uugaauaaag 1560
ucugaguggg cggc 1574

<210> SEQ ID NO 30
<211> LENGTH: 1398
<212> TYPE: RNA
<213> ORGANISM: Artificial Sequence
<220> FEATURE:
<223> OTHER INFORMATION: Synthetic

<400> SEQUENCE: 30
augcugccca gcaccaucca gacccugacc cuguuucuga ccagcggagg cgugcugcug 60
agccuguacg ugagcgccag ccugagcuac cugcuguaca gcgacauccu gcugaaguuc 120
agccccaccg agaucaccgc acccaccaug ccccuggacu gcgccaacgc cagcaacgug 180
caggccguga accggagcgc cacaaagggc gugacccugc ugcugcccga gccagagugg 240
acauauccuc ggcugagcug cccuggcagc accuuccaga aggcccugcu gaucagccca 300
caccgguucg gcgagaccaa gggcaacagc gcaccccuga ucauccggga gcccuucgug 360
gccuguggcc ccaacgagug caagcacuuc gcccugacac acuacgcugc ucagcccggu 420
ggcuacuaca acggcacccg gggugggcgg aacaagcugc ggcaccugau cagcgugaag 480
cugggcaaga uccccaccgu ggagaacagc aucuuccaca uggccgccug gucaggaagc 540
gccugccacg acggcaagga guggaccuac aucggcgugg acggcccuga caacaacgcc 600
cugcugaagg ugaaguacgg cgaggccuac accgacaccu accacagcua cgccaacaac 660
auccugcgga cccaggagag cgccugcaac ugcaucggcg gcaacugcua ccugaugauc 720
accgacggca gcgcuucugg cgugagcgag ugccgguucc ugaagauccg ggagggccgg 780
aucaucaagg agaucuuucc caccggccgg gugaagcaca ccgaggagug caccugcggc 840
uucgccagca acaagaccau cgagugcgcc ugccgggaca aucgguacac cgccaagcgg 900
cccuucguga agcugaacgu ggagaccgac accgccgaga uccggcugau gugcaccgac 960
acuuaucugg acaccccucg gccuaacgac ggcagcauca ccggcccuug cgagagcgac 1020
ggcgacaagg gaagcggcgg caucaagggc gguuucgugc accagcggau gaagagcaag 1080

```
aucggccggu gguacagccg gaccaugagc aagaccgagc ggaugggcau gggccuguac   1140

guaaaguacg gaggggaucc cugggcugac agcgacgccc ugaccuucag cggcgugaug   1200

gugagcauga aggagcccgg cugguacagc uucggcuucg agaucaagga caagaagugc   1260

gacgugcccu gcaucggcau cgagauggug cacgacggcg gcaaggagac cuggcacucu   1320

gccgccacug ccaucuacug ccugaugggc agcggccagc ugcuguggga caccgugacc   1380

ggcguggaca uggcccug                                                  1398


<210> SEQ ID NO 31
<211> LENGTH: 466
<212> TYPE: PRT
<213> ORGANISM: Artificial Sequence
<220> FEATURE:
<223> OTHER INFORMATION: Synthetic

<400> SEQUENCE: 31

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Val Ala Cys Gly Pro Asn Glu Cys Lys
        115                 120                 125

His Phe Ala Leu Thr His Tyr Ala Ala Gln Pro Gly Gly Tyr Tyr Asn
    130                 135                 140

Gly Thr Arg Gly Gly Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Arg Tyr Thr Ala Lys Arg Pro Phe Val Lys
    290                 295                 300
```

Leu Asn Val Glu Thr Asp Thr Ala Glu Ile Arg Leu Met Cys Thr Asp
305 310 315 320

Thr Tyr Leu Asp Thr Pro Arg Pro Asn Asp Gly Ser Ile Thr Gly Pro
325 330 335

Cys Glu Ser Asp Gly Asp Lys Gly Ser Gly Gly Ile Lys Gly Gly Phe
340 345 350

Val His Gln Arg Met Lys Ser Lys Ile Gly Arg Trp Tyr Ser Arg Thr
355 360 365

Met Ser Lys Thr Glu Arg Met Gly Met Gly Leu Tyr Val Lys Tyr Gly
370 375 380

Gly Asp Pro Trp Ala Asp Ser Asp Ala Leu Thr Phe Ser Gly Val Met
385 390 395 400

Val Ser Met Lys Glu Pro Gly Trp Tyr Ser Phe Gly Phe Glu Ile Lys
405 410 415

Asp Lys Lys Cys Asp Val Pro Cys Ile Gly Ile Glu Met Val His Asp
420 425 430

Gly Gly Lys Glu Thr Trp His Ser Ala Ala Thr Ala Ile Tyr Cys Leu
435 440 445

Met Gly Ser Gly Gln Leu Leu Trp Asp Thr Val Thr Gly Val Asp Met
450 455 460

Ala Leu
465

<210> SEQ ID NO 32
<211> LENGTH: 1928
<212> TYPE: RNA
<213> ORGANISM: Artificial Sequence
<220> FEATURE:
<223> OTHER INFORMATION: Synthetic

<400> SEQUENCE: 32
gggaaauaag agagaaaaga agaguaagaa gaaauauaag accccggcgc cgccaccaug 60
aaggccauca ucgugcuacu gauggugggug accagcaacg ccgaccggau cugcaccggc 120
aucaccagca gcaacagccc gcacguggug aagaccgcca cccaaggcga ggugaacgug 180
accggcguga ucccacugac caccacuccc accaagagcu acuucgccaa ccugaagggc 240
acacggacuc ggggcaagcu gugccccgac ugccugaacu gcaccgaccu ggacguggcc 300
cugggcagac ccaugugcgu gggcaccacc ccuucugcca aggccagcau ccugcacgag 360
gugagacccg ugaccagcgg gugcuucccc aucaugcacg accggaccaa gauccggcag 420
cugcccaacc ugcugcgggg cuacgagaag auccggcuga gcacccagaa cgugaucgac 480
gccgagaagg ccccuggagg ucccuaccgg cugggcacca gcggaagcug ccccaacgcc 540
accagcaaga ucggcuucuu cgccaccaug gccugggcug ugcccaagga caacuacaag 600
aacgccacca auccccugac cguggaggug cccuacaucu gcaccgaggg cgaggaccag 660
aucaccgugu ggggcuucca cagcgacaac aagacccaga ugaagagccu guacggcgac 720
agcaaucccc agaaguucac aagcagcgcc aacggcguga ccacccacua cgugagccag 780
aucggcgacu uccccgacca gaccgaggac ggagggcugc cucagagugg ccggaucgug 840
guggacuaca ugaugcagaa gcccggcaag accggcacca ucguguacca gcggggcgug 900
cuguugccuc agaaaguuug gugugccagc ggcaggagca aggugaucaa gggcagccug 960
ccccugaucg gcgaggcaga cugccuccac gaggaguacg gcggccugaa caagagcaag 1020
cccuacuaca ccggcaagca cgccaaggcc aucggcaacu gccccaucug ggugaagacc 1080

-continued ccucugaagc uggccaacgg caccaaguac cggccaccag ccaagcugcu gaaggagcgg 1140
ggcuucuuug gcgccauugc cggcuucuc gagggaggcu gggagggcau gaucgccggc 1200
uggcacggcu acacaagcca cggcgcacac ggaguggcug uggcugccga ccugaagagc 1260
acccaggagg ccaucaacaa gaucaccaag aaccugaaca gccugagcga gcuggaggug 1320
aagaaccugc agcggcuguc aggcgccaug gacgagcugc acaacgagau ccuggagcug 1380
gacgagaagg uggacgaccu gcgugccgac accaucagca gccagaucga gcuggccgug 1440
cugcugagca acgagggcau caucaacagc gaggacgagc accugcuggc ccuggagcgg 1500
aaacugaaga agaugcuggg acccucugcc guggacaucg gcaacggcug cuucgagacc 1560
aagcacaagu gcaaccagac cugccuggau cggaucgccg ccggaaccuu caacgccggc 1620
gaguucagcc ugcccaccuu cgacagccug aacaucaccg ccgccagccu gaacgacgac 1680
ggccuggaca accacaccau ccugcuguac uacagcacug ccgccucaag ccuggccgug 1740
acccugaugc uggccaucuu caucguguac auggugagcc gggacaacgu gagcugcagc 1800
aucugccugu gauaauaggc uggagccucg guggccuagc uucuugcccc uugggccucc 1860
ccccagcccc uccuccccuu ccugcacccg uacccccgug gucuuugaau aaagucugag 1920
ugggcggc 1928

<210> SEQ ID NO 33
<211> LENGTH: 1752
<212> TYPE: RNA
<213> ORGANISM: Artificial Sequence
<220> FEATURE:
<223> OTHER INFORMATION: Synthetic

<400> SEQUENCE: 33
augaaggcca ucaucgugcu acugauggug gugaccagca acgccgaccg gaucugcacc 60
ggcaucacca gcagcaacag cccgcacgug gugaagaccg ccacccaagg cgaggugaac 120
gugaccggcg ugaucccacu gaccaccacu cccaccaaga gcuacuucgc caaccugaag 180
ggcacacgga cucggggcaa gcugugcccc gacugccuga acugcaccga ccuggacgug 240
gcccugggca gacccaugug cgugggcacc accccuucug ccaaggccag cauccugcac 300
gaggugagac ccgugaccag cgggugcuuc cccaucaugc acgaccggac caagauccgg 360
cagcugccca accugcugcg gggcuacgag aagauccggc ugagcaccca gaacgugauc 420
gacgccgaga aggccccugg agguccuac cggcugggca ccagcggaag cugccccaac 480
gccaccagca agaucggcuu cuucgccacc auggccuggg cugugcccaa ggacaacuac 540
aagaacgcca ccaaucccu gaccguggag gugcccuaca ucugcaccga gggcgaggac 600
cagaucaccg uguggggcuu ccacagcgac aacaagaccc agaugaagag ccuguacggc 660
gacagcaauc cccagaaguu cacaagcagc gccaacggcg ugaccaccca cuacgugagc 720
cagaucggcg acuuccccga ccagaccgag gacggagggc ugccucagag uggccggauc 780 guggugggacu acaugaugca gaagcccggc aagaccggca ccaucgugua ccagcggggc 840
gugcuguugc cucagaaagu uuggugugcc agcggcagga gcaaggugau caagggcagc 900
cugccccuga ucggcgaggc agacugccuc cacgaggagu acggcggccu gaacaagagc 960
aagcccuacu acaccggcaa gcacgccaag gccaucggca acugccccau cugggugaag 1020
accccucuga agcuggccaa cggcaccaag uaccggccac cagccaagcu gcugaaggag 1080
cggggcuucu uuggcgccau ugccggcuuc cucgagggag gcugggaggg caugaucgcc 1140
ggcuggcacg gcuacacaag ccacggcgca cacggagugg cuguggcugc cgaccugaag 1200
agcacccagg aggccaucaa caagaucacc aagaaccuga acagccugag cgagcuggag 1260
gugaagaacc ugcagcggcu gucaggcgcc auggacgagc ugcacaacga gauccuggag 1320
cuggacgaga agguggacga ccugcgugcc gacaccauca gcagccagau cgagcuggcc 1380
gugcugcuga gcaacgaggg caucaucaac agcgaggacg agcaccugcu ggcccuggag 1440
cggaaacuga agaagaugcu gggacccucu gccguggaca ucggcaacgg cugcuucgag 1500
accaagcaca agugcaacca gaccugccug gaucggaucg ccgccggaac cuucaacgcc 1560
ggcgaguuca gccugcccac cuucgacagc cugaacauca ccgccgccag ccugaacgac 1620
gacggccugg acaaccacac cauccugcug uacuacagca cugccgccuc aagccuggcc 1680
gugacccuga ugcuggccau cuucaucgug uacaugguga gccgggacaa cgugagcugc 1740
agcaucugcc ug 1752

<210> SEQ ID NO 34
<211> LENGTH: 584
<212> TYPE: PRT
<213> ORGANISM: Artificial Sequence
<220> FEATURE:
<223> OTHER INFORMATION: Synthetic

<400> SEQUENCE: 34

Met Lys Ala Ile Ile Val Leu Leu Met Val Val Thr Ser Asn Ala Asp
1 5 10 15

Arg Ile Cys Thr Gly Ile Thr Ser Ser Asn Ser Pro His Val Val Lys
20 25 30

Thr Ala Thr Gln Gly Glu Val Asn Val Thr Gly Val Ile Pro Leu Thr
35 40 45

Thr Thr Pro Thr Lys Ser Tyr Phe Ala Asn Leu Lys Gly Thr Arg Thr
50 55 60

Arg Gly Lys Leu Cys Pro Asp Cys Leu Asn Cys Thr Asp Leu Asp Val
65 70 75 80

Ala Leu Gly Arg Pro Met Cys Val Gly Thr Thr Pro Ser Ala Lys Ala
85 90 95

Ser Ile Leu His Glu Val Arg Pro Val Thr Ser Gly Cys Phe Pro Ile
100 105 110

Met His Asp Arg Thr Lys Ile Arg Gln Leu Pro Asn Leu Leu Arg Gly
115 120 125

Tyr Glu Lys Ile Arg Leu Ser Thr Gln Asn Val Ile Asp Ala Glu Lys
130 135 140

Ala Pro Gly Gly Pro Tyr Arg Leu Gly Thr Ser Gly Ser Cys Pro Asn
145 150 155 160

Ala Thr Ser Lys Ile Gly Phe Phe Ala Thr Met Ala Trp Ala Val Pro
165 170 175

Lys Asp Asn Tyr Lys Asn Ala Thr Asn Pro Leu Thr Val Glu Val Pro
180 185 190

Tyr Ile Cys Thr Glu Gly Glu Asp Gln Ile Thr Val Trp Gly Phe His
195 200 205

Ser Asp Asn Lys Thr Gln Met Lys Ser Leu Tyr Gly Asp Ser Asn Pro
210 215 220

Gln Lys Phe Thr Ser Ser Ala Asn Gly Val Thr Thr His Tyr Val Ser
225 230 235 240

Gln Ile Gly Asp Phe Pro Asp Gln Thr Glu Asp Gly Gly Leu Pro Gln
245 250 255

-continued

```
Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Glu Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580
```

<210> SEQ ID NO 35
<211> LENGTH: 1574
<212> TYPE: RNA
<213> ORGANISM: Artificial Sequence
<220> FEATURE:
<223> OTHER INFORMATION: Synthetic

<400> SEQUENCE: 35

```
gggaaauaag agagaaaaga agaguaagaa gaaauauaag accccggcgc cgccaccaug      60

cugcccagca ccauccagac ccugacccug uuccugacca gcggaggcgu gcugcugagc     120

cuguacguca gcgccagccu gagcuaccug cuguacagcg acauccugcu gaaguucagc     180
```

-continued

```
cggaccgagg ugaccgcucc caucaugccc cuggacugcg ccaacgccag caacgugcag    240
gccgugaauc ggagcgccac caagggcgug acucccccugc ugcccgagcc ugaguggacu    300
uauccucggc ugagcugccc aggcagcacc uuccagaagg cccugcugau cagcccacac    360
cgguucggcg agaccaaggg caacagcgcu ccccugauca uccgggagcc cuucaucgcc    420
ugcggcccca aggagugcaa gcacuucgcc cugacccacu acgcugccca acccggaggc    480
uacuacaacg gcaccagaga ggaccggaac aagcugcggc accugaucag cgugaagcug    540
ggcaagaucc ccaccgugga gaacagcauc uuccacaugg cugcuugguc uggaagugcu    600
ugucacgacg gccgggagug gaccuacauc ggcguggacg gcccagacag caacgcccug    660
cugaagauca aguacggcga ggccuacacc gacaccuacc acagcuacgc caagaacauc    720
cugcggaccc aggagagcgc cugcaacugc aucggcggcg acugcuaccu gaugaucacc    780
gacggcccag caucuggcau cagcgagugc cgguuccuga agauccggga gggccggauc    840
aucaaggaga ucuuccccac cgggagagug aagcacaccg aggagugcac cugcggcuuc    900
gccagcaaca agaccaucga gugcgccugc cgggacaaca gcuacaccgc caagcggccc    960
uucgugaagc ugaacgugga gaccgacacc gccgagaucc ggcugaugug caccaagacc   1020
uaccuggaca ccccucggcc caacgacgga agcaucaccg gacccugcga gagcgacggg   1080
gacgaaggaa gcggcggaau caagggcggc uucgugcacc agcggauggc cagcaagauc   1140
ggccggugu acagccggac caugagcaag accaagcgga ugggcauggg ccuguacgug   1200
aaguacgacg gcgaccccug gacagacagc gaagcccugg cccugucugg cgugauggug   1260
agcauggagg agcccggcug guacagcuuc ggcuucgaga ucaaggacaa gaagugcgac   1320
gugcccugca ucggcaucga gauggugcac gacggcggca agaccaccug gcauagcgcc   1380
gcaaccgcga ucuacugccu gaugggcagc ggccagcugc ugugggacac cgugaccggc   1440
gugaacauga cccugugaua auaggcugga gccucggugg ccuagcuucu ugccccuugg   1500
gccucccccc agccccuccu ccccuuccug cacccguacc cccguggucu uugaauaaag   1560
ucugaguggg cggc                                                      1574
```

<210> SEQ ID NO 36
<211> LENGTH: 1398
<212> TYPE: RNA
<213> ORGANISM: Artificial Sequence
<220> FEATURE:
<223> OTHER INFORMATION: Synthetic

<400> SEQUENCE: 36

```
augcugccca gcaccaucca gacccugacc cuguuccuga ccagcggagg cgugcugcug     60
agccuguacg ucagcgccag ccugagcuac cugcuguaca gcgacauccu gcugaaguuc    120
agccggaccg aggugaccgc ucccaucaug ccccuggacu gcgccaacgc cagcaacgug    180
caggccguga aucggagcgc caccaagggc gugacucccc ugcugcccga gccugagugg    240
acuuauccuc ggcugagcug cccaggcagc accuuccaga aggcccugcu gaucagccca    300
caccgguucg gcgagaccaa gggcaacagc gcuccccuga ucauccggga gcccuucauc    360
gccugcggcc ccaaggagug caagcacuuc gcccugaccc acuacgcugc ccaacccgga    420
ggcuacuaca acggcaccag agaggaccgg aacaagcugc ggcaccugau cagcgugaag    480
cugggcaaga uccccaccgu ggagaacagc aucuuccaca uggcugcuug gucuggaagu    540
gcuugucacg acggccggga guggaccuac aucggcgugg acggcccaga cagcaacgcc    600
cugcugaaga ucaaguacgg cgaggccuac accgacaccu accacagcua cgccaagaac    660
```

```
auccugcgga cccaggagag cgccugcaac ugcaucggcg gcgacugcua ccugaugauc    720

accgacggcc cagcaucugg caucagcgag ugccgguucc ugaagauccg ggagggccgg    780

aucaucaagg agaucuuccc caccgggaga gugaagcaca ccgaggagug caccugcggc    840

uucgccagca acaagaccau cgagugcgcc ugccgggaca acagcuacac cgccaagcgg    900

cccuucguga agcugaacgu ggagaccgac accgccgaga uccggcugau gugcaccaag    960

accuaccugg acaccccucg gcccaacgac ggaagcauca ccggacccug cgagagcgac   1020

ggggacgaag gaagcggcgg aaucaagggc ggcuucgugc accagcggau ggccagcaag   1080

aucggccggu gguacagccg gaccaugagc aagaccaagc ggaugggcau gggccuguac   1140

gugaaguacg acggcgaccc cuggacagac agcgaagccc uggcccuguc uggcgugaug   1200

gugagcaugg aggagcccgg cugguacagc uucggcuucg agaucaagga caagaagugc   1260

gacgugcccu gcaucggcau cgagauggug cacgacggcg gcaagaccac cuggcauagc   1320

gccgcaaccg cgaucuacug ccugaugggc agcggccagc ugcuguggga caccgugacc   1380

ggcgugaaca ugacccug                                                 1398
```

<210> SEQ ID NO 37
<211> LENGTH: 466
<212> TYPE: PRT
<213> ORGANISM: Artificial Sequence
<220> FEATURE:
<223> OTHER INFORMATION: Synthetic

<400> SEQUENCE: 37

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Val Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Thr Pro Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220
```

-continued

Gln Glu Ser Ala Cys Asn Cys Ile Gly Gly Asp Cys Tyr Leu Met Ile
225 230 235 240

Thr Asp Gly Pro Ala Ser Gly Ile Ser Glu Cys Arg Phe Leu Lys Ile
245 250 255

Arg Glu Gly Arg Ile Ile Lys Glu Ile Phe Pro Thr Gly Arg Val Lys
260 265 270

His Thr Glu Glu Cys Thr Cys Gly Phe Ala Ser Asn Lys Thr Ile Glu
275 280 285

Cys Ala Cys Arg Asp Asn Ser Tyr Thr Ala Lys Arg Pro Phe Val Lys
290 295 300

Leu Asn Val Glu Thr Asp Thr Ala Glu Ile Arg Leu Met Cys Thr Lys
305 310 315 320

Thr Tyr Leu Asp Thr Pro Arg Pro Asn Asp Gly Ser Ile Thr Gly Pro
325 330 335

Cys Glu Ser Asp Gly Asp Glu Gly Ser Gly Gly Ile Lys Gly Gly Phe
340 345 350

Val His Gln Arg Met Ala Ser Lys Ile Gly Arg Trp Tyr Ser Arg Thr
355 360 365

Met Ser Lys Thr Lys Arg Met Gly Met Gly Leu Tyr Val Lys Tyr Asp
370 375 380

Gly Asp Pro Trp Thr Asp Ser Glu Ala Leu Ala Leu Ser Gly Val Met
385 390 395 400

Val Ser Met Glu Glu Pro Gly Trp Tyr Ser Phe Gly Phe Glu Ile Lys
405 410 415

Asp Lys Lys Cys Asp Val Pro Cys Ile Gly Ile Glu Met Val His Asp
420 425 430

Gly Gly Lys Thr Thr Trp His Ser Ala Ala Thr Ala Ile Tyr Cys Leu
435 440 445

Met Gly Ser Gly Gln Leu Leu Trp Asp Thr Val Thr Gly Val Asn Met
450 455 460

Thr Leu
465

<210> SEQ ID NO 38
<211> LENGTH: 1574
<212> TYPE: RNA
<213> ORGANISM: Artificial Sequence
<220> FEATURE:
<223> OTHER INFORMATION: Synthetic

<400> SEQUENCE: 38
gggaaauaag agagaaaaga agaguaagaa gaaauauaag accccggcgc cgccaccaug 60
cugcccagca ccauccagac ccugacccug uuccugacca gcggaggcgu gcugcugagc 120
cuguacguca gcgccagccu gagcuaccug cuguacagcg acauccugcu gaaguucagc 180
cggaccgagg ugaccgcucc caucaugccc cuggacugcg ccaacgccag caacgugcag 240
gccgugaauc ggagcgccac caagggcgug acuccccugc ugcccgagcc ugaguggacu 300
uauccucggc ugagcugccc aggcagcacc uuccagaagg cccugcugau cagcccacac 360
cgguucggcg agaccaaggg caacagcgcu ccccugauca uccgggagcc cuucaucgcc 420
ugcggcccca aggagugcaa gcacuucgcc cugacccacu acgcugccca acccggaggc 480
uacuacaacg gcaccagaga gggccggaac aagcugcggc accugaucag cgugaagcug 540
ggcaagaucc ccaccgugga gaacagcauc uuccacaugg cugcuugguc uggaagugcu 600
ugucacgacg gccgggagug gaccuacauc ggcguggacg gcccagacag caacgcccug 660

```
cugaagauca aguacggcga ggccuacacc gacaccuacc acagcuacgc caagaacauc    720
cugcggaccc aggagagcgc cugcaacugc aucggcggcg acugcuaccu gaugaucacc    780
gacggcccag caucuggcau cagcgagugc cgguuccuga agauccggga gggccggauc    840
aucaaggaga ucuuccccac cgggagagug aagcacaccg aggagugcac cugcggcuuc    900
gccagcaaca agaccaucga gugcgccugc cgggacaaca gcuacaccgc caagcggccc    960
uucgugaagc ugaacgugga gaccgacacc gccgagaucc ggcugaugug caccaagacc   1020
uaccuggaca ccccucggcc caacgacgga agcaucaccg gacccugcga gagcgacggg   1080
gacgaaggaa gcggcggaau caagggcggc uucgugcacc agcggauggc cagcaagauc   1140
ggccgguggu acagccggac caugagcaag accaagcgga ugggcauggg ccuguacgug   1200
aaguacgacg gcgaccccug gacagacagc gaagcccugg cccugucugg cgugauggug   1260
agcauggagg agcccggcug guacagcuuc ggcuucgaga ucaaggacaa gaagugcgac   1320
gugcccugca ucggcaucga gauggugcac gacggcggca agaccaccug gcauagcgcc   1380
gcaaccgcga ucuacugccu gaugggcagc ggccagcugc ugugggacac cgugaccggc   1440
gugaacauga cccugugaua auaggcugga gccucggugg ccuagcuucu ugccccuugg   1500
gccucccccc agccccuccu ccccuuccug cacccguacc cccguggucu uugaauaaag   1560
ucugaguggg cggc                                                     1574
```

<210> SEQ ID NO 39
<211> LENGTH: 1398
<212> TYPE: RNA
<213> ORGANISM: Artificial Sequence
<220> FEATURE:
<223> OTHER INFORMATION: Synthetic

<400> SEQUENCE: 39

```
augcugccca gcaccaucca gacccugacc cuguuccuga ccagcggagg cgugcugcug     60
agccuguacg ucagcgccag ccugagcuac cugcuguaca gcgacauccu gcugaaguuc    120
agccggaccg aggugaccgc ucccaucaug ccccuggacu gcgccaacgc cagcaacgug    180
caggccguga aucggagcgc caccaagggc gugacucccc ugcugcccga gccugagugg    240
acuuauccuc ggcugagcug cccaggcagc accuuccaga aggcccugcu gaucagccca    300
caccgguucg gcgagaccaa gggcaacagc gcuccccuga ucauccggga gcccuucauc    360
gccugcggcc ccaaggagug caagcacuuc gcccugaccc acuacgcugc ccaacccgga    420
ggcuacuaca acggcaccag agagggccgg aacaagcugc ggcaccugau cagcgugaag    480
cugggcaaga uccccaccgu ggagaacagc aucuuccaca uggcugcuug gucuggaagu    540
gcuugucacg acggccggga guggaccuac aucggcgugg acggcccaga cagcaacgcc    600
cugcugaaga ucaaguacgg cgaggccuac accgacaccu accacagcua cgccaagaac    660
auccugcgga cccaggagag cgccugcaac ugcaucggcg gcgacugcua ccugaugauc    720
accgacggcc cagcaucugg caucagcgag ugccgguucc ugaagauccg ggagggccgg    780
aucaucaagg agaucuuccc caccgggaga gugaagcaca ccgaggagug caccugcggc    840
uucgccagca acaagaccau cgagugcgcc ugccgggaca acagcuacac cgccaagcgg    900
cccuucguga agcugaacgu ggagaccgac accgccgaga uccggcugau gugcaccaag    960
accuaccugg acaccccucg gcccaacgac ggaagcauca ccggacccug cgagagcgac   1020
ggggacgaag gaagcggcgg aaucaagggc ggcuucgugc accagcggau ggccagcaag   1080
```

```
aucggccggu gguacagccg gaccaugagc aagaccaagc ggaugggcau gggccuguac   1140

gugaaguacg acggcgaccc cuggacagac agcgaagccc uggcccuguc uggcgugaug   1200

gugagcaugg aggagcccgg cugguacagc uucggcuucg agaucaagga caagaagugc   1260

gacgugcccu gcaucggcau cgagauggug cacgacggcg gcaagaccac cuggcauagc   1320

gccgcaaccg cgaucuacug ccugaugggc agcggccagc ugcuguggga caccgugacc   1380

ggcgugaaca ugacccug                                                 1398


<210> SEQ ID NO 40
<211> LENGTH: 466
<212> TYPE: PRT
<213> ORGANISM: Artificial Sequence
<220> FEATURE:
<223> OTHER INFORMATION: Synthetic

<400> SEQUENCE: 40

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Val Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Thr Pro Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Gly Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300
```

```
Leu Asn Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Glu Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Thr Thr Trp His Ser Ala Ala Thr Ala Ile Tyr Cys Leu
        435                 440                 445

Met Gly Ser Gly Gln Leu Leu Trp Asp Thr Val Thr Gly Val Asn Met
    450                 455                 460

Thr Leu
465
```

<210> SEQ ID NO 41
<211> LENGTH: 1874
<212> TYPE: RNA
<213> ORGANISM: Artificial Sequence
<220> FEATURE:
<223> OTHER INFORMATION: Synthetic

<400> SEQUENCE: 41

```
gggaaauaag agagaaaaga agaguaagaa gaaauauaag accccggcgc cgccaccaug     60

aaggccaucc uggucgugau gcuguacacc uucaccaccg ccaacgccga cacccugugc    120

aucggcuacc acgccaacaa cagcaccgac accguggaca ccgugcugga gaagaacgug    180

accgugaccc acagcgugaa ccugcuggag gacaagcaca acggcaagcu gugcaagcug    240

aggggagugg caccccugca ccugggcaag ugcaacaucg ccggcuggau ccugggcaac    300

cccgagugcg agagccugag cacagcccgg agcuggagcu acaucgugga gaccagcaac    360

agcgacaacg gcaccuguua ccccggcgac uucaucaacu acgaggagcu gcgggagcag    420

cugagcagcg ugagcagcuu cgagcgguuc gagaucuucc ccaagaccag cagcuggccc    480

aaccacgaca gcgacaacgg cgugacagca gccuguccac acgccggagc caagagcuuc    540

uacaagaacc ugaucuggcu ggugaagaag ggcaagagcu accccaagau caaccagacc    600

uacaucaacg acaagggcaa ggaggugcug gugcuguggg gcauccacca cccaccuacc    660

aucgccgacc agcagagccu guaccagaac gccgacgccu acguguucgu gggcaccagc    720

cgguacagca agaaguucaa gccagagauc gccacccggc ccaaggugag agaccaggag    780

ggccggauga acuacuacug gacccuggug gagcccggag acaagauuac cuucgaggcc    840

accggcaacc ugguggcccc ucgguacgcc uucaccaugg aacgggacgc uggcagcggc    900

aucaucauca gcgacacucc cgugcacgac ugcaacacca ccugccagac ucccgagggc    960

gcuaucaaca ccagccugcc cuuccagaac gugcacccca ucaccaucgg caagugcccc   1020

aaguacguaa agagcaccaa auugcggcug gccaccggac ucaggaacgu gcccagcauc   1080
```

caaagccggg gccuguuugg cgcaaucgcc ggcuucaucg agggcggcug gacuggcaug 1140
guggacggcu gguacggcua ccaccaccag aacgaacagg ggagcggcua cgcagcugac 1200
cugaagagca cccagaacgc caucgacaag aucaccaaca aggugaacag cgugaucgag 1260
aagaugaaca cccaguucac cgccgugggc aaggaguuca accaccugga gaagcggauc 1320
gagaaccuga acaagaaggu ggacgacggc uuccuggaca ucuggaccua caacgccgag 1380
cugcugguuc ugcuggagaa cgagcggacc cuggacuauc acgacagcaa cgugaagaac 1440
cuguacgaga aggugcggaa ccagcugaag aacaacgcca aggagaucgg caacggcugc 1500
uucgaguucu accacaagug cgacaacacc ugcauggaga gcgugaagaa cggcaccuac 1560
gacuacccca aguacagcga ggaggccaag cugaaccggg agaagaucga cggcgugaag 1620
cuggacagca cccggaucua ccagauccug gccaucuaca gcaccguggc cagcagccug 1680
gugcuggugg ugagccuggg cgccaucagc uucuggaugu gcagcaacgg cagccugcag 1740
ugccggaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 42
<211> LENGTH: 1698
<212> TYPE: RNA
<213> ORGANISM: Artificial Sequence
<220> FEATURE:
<223> OTHER INFORMATION: Synthetic

<400> SEQUENCE: 42
augaaggcca uccuggucgu gaugcuguac accuucacca ccgccaacgc cgacacccug 60
ugcaucggcu accacgccaa caacagcacc gacaccgugg acaccgugcu ggagaagaac 120
gugaccguga cccacagcgu gaaccugcug gaggacaagc acaacggcaa gcugugcaag 180
cugaggggag uggcaccccu gcaccugggc aagugcaaca ucgccggcug gauccugggc 240
aaccccgagu gcgagagccu gagcacagcc cggagcugga gcuacaucgu ggagaccagc 300
aacagcgaca acggcaccug uuaccccggc gacuucauca acuacgagga gcugcgggag 360
cagcugagca gcgugagcag cuucgagcgg uucgagaucu uccccaagac cagcagcugg 420
cccaaccacg acagcgacaa cggcgugaca gcagccuguc cacacgccgg agccaagagc 480
uucuacaaga accugaucug gcuggugaag aagggcaaga gcuaccccaa gaucaaccag 540
accuacauca acgacaaggg caaggaggug cuggugcugu ggggcaucca ccacccaccu 600
accaucgccg accagcagag ccuguaccag aacgccgacg ccuacguguu cgugggcacc 660
agccgguaca gcaagaaguu caagccagag aucgccaccc ggcccaaggu gagagaccag 720
gagggccgga ugaacuacua cuggacccug guggagcccg gagacaagau uaccuucgag 780
gccaccggca accugguggc cccucgguac gccuucacca uggaacggga cgcuggcagc 840
ggcaucauca ucagcgacac ucccgugcac gacugcaaca ccaccugcca gacucccgag 900
ggcgcuauca acaccagccu gcccuuccag aacgugcacc ccaucaccau cggcaagugc 960
cccaaguacg uaaagagcac caaauugcgg cuggccaccg gacucaggaa cgugcccagc 1020
auccaaagcc ggggccuguu uggcgcaauc gccggcuuca ucgagggcgg cuggacuggc 1080
augguggacg gcugguacgg cuaccaccac cagaacgaac aggggagcgg cuacgcagcu 1140
gaccugaaga gcacccagaa cgccaucgac aagaucacca acaaggugaa cagcgugauc 1200
gagaagauga acacccaguu caccgccgug ggcaaggagu ucaaccaccu ggagaagcgg 1260
aucgagaacc ugaacaagaa gguggacgac ggcuuccugg acaucuggac cuacaacgcc 1320
gagcugcugg uucugcugga gaacgagcgg acccuggacu aucacgacag caacgugaag 1380
aaccuguacg agaaggugcg gaaccagcug aagaacaacg ccaaggagau cggcaacggc 1440
ugcuucgagu ucuaccacaa gugcgacaac accugcaugg agagcgugaa gaacggcacc 1500
uacgacuacc ccaaguacag cgaggaggcc aagcugaacc gggagaagau cgacggcgug 1560
aagcuggaca gcacccggau cuaccagauc cuggccaucu acagcaccgu ggccagcagc 1620
cuggugcugg uggugagccu gggcgccauc agcuucugga ugugcagcaa cggcagccug 1680
cagugccgga ucugcauc 1698

<210> SEQ ID NO 43
<211> LENGTH: 566
<212> TYPE: PRT
<213> ORGANISM: Artificial Sequence
<220> FEATURE:
<223> OTHER INFORMATION: Synthetic

<400> SEQUENCE: 43

Met Lys Ala Ile Leu Val Val Met Leu Tyr Thr Phe Thr Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Arg Ser Trp Ser Tyr Ile
85 90 95

Val Glu Thr Ser Asn Ser Asp Asn Gly Thr Cys Tyr Pro Gly Asp Phe
100 105 110

Ile Asn Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asp Asn Gly Val Thr Ala Ala Cys Pro His Ala Gly Ala Lys Ser
145 150 155 160

Phe Tyr Lys Asn Leu Ile Trp Leu Val Lys Lys Gly Lys Ser Tyr Pro
165 170 175

Lys Ile Asn Gln Thr Tyr Ile Asn Asp Lys Gly Lys Glu Val Leu Val
180 185 190

Leu Trp Gly Ile His His Pro Pro Thr Ile Ala Asp Gln Gln Ser Leu
195 200 205

Tyr Gln Asn Ala Asp Ala Tyr Val Phe Val Gly Thr Ser Arg Tyr Ser
210 215 220

Lys Lys Phe Lys Pro Glu Ile Ala Thr Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Ala Pro Arg Tyr Ala Phe
260 265 270

Thr Met Glu Arg Asp Ala Gly Ser Gly Ile Ile Ile Ser Asp Thr Pro

-continued

```
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Asp Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

```
<210> SEQ ID NO 44
<211> LENGTH: 1583
<212> TYPE: RNA
<213> ORGANISM: Artificial Sequence
<220> FEATURE:
<223> OTHER INFORMATION: Synthetic

<400> SEQUENCE: 44

gggaaauaag agagaaaaga agaguaagaa gaaauauaag accccggcgc cgccaccaug      60

aaccccaacc agaagaucau caccaucggc agcaucugca ugaccaucgg caccgccaac     120

cugauccugc aaaucggcaa caucaucagc aucugggga gccacagcau ccagaucggc     180

aaccagagcc agaucgagac cugcaacaag agcgugauca ccuacgagaa caacaccugg     240

gugaaccaga ccuucgugaa caucagcaac accaacagcg ccgcucggca gucaguggcc     300

agcgugaagc uggccggcaa cagcagccug ugccccguua guggcugggc caucuacagc     360

aaggacaaca gcgugcggau cggcagcaag ggcgacgugu ucgugauccg ggagcccuuc     420
```

-continued

```
aucagcugca gcccgcuuga gugccgcacc uucuuccuga cccagggcgc ucugcugaac    480

gacaagcaca gcaacggcac caucaaggac cggagcccu aucggacccu gaugagcugc    540

cccauuggcg aggugcccag ccccuacaac agccgguucg agucuguggc cuggagcgcc    600

ucugccugcc acgacggcac caacuggcug accaucggga ucagcggacc cgauagcgga    660

gcaguggccg ugcugaagua caacggcauc aucaccgaca ccaucaagag cuggcggaac    720

aagauccugc ggacccagga gagcgagugc gccugcguga acggcagcug cuucaccauc    780

augaccgacg gcccuagcga cggacaggcc agcuacaaga ucuuccggau cgagaagggc    840

aagaucauca agagcgugga gaugaaggca cccaacuacc acuacgagga gugcagcugc    900

uaccccgaca gcagcgagau caccugcgug ugccgggaca acuggcacgg gagcaacagg    960

cccuggguga gcuucaacca gaaccuggag uaccagaugg gcuacaucug cagcggcgug   1020

uucggcgaca acccacggcc caacgacaag acuggcagcu gcgguccggu gagcagcaac   1080

ggcgccaacg gcgugaaggg cuucagcuuc aaguacggca acggcgugug gaucggccgg   1140

accaagagca ucagcagccg gaagggcuuc gagaugaucu gggaccccaa cggcuggacc   1200

ggcaccgaca acaaguucag caagaagcag gacaucgugg gcaucaacga guggagcggc   1260

uacagcggca gcuucgugca gcaccccgag cugacuggcc ugaacugcau ccggcccugc   1320

uucugggugg aacugauacg gggacggccc gaggagaaca ccaucuggac cagcggcagc   1380

agcaucagcu ucugcggcgu ggacagcgau aucgugggcu ggagcuggcc agacggagcc   1440

gagcugcccu ucaccaucga caagugauaa uaggcuggag ccucggugge cuagcuucuu   1500

gccccuuggg ccucccccca gccccuccuc cccuuccugc acccguaccc ccguggucuu   1560

ugaauaaagu cugagugggc ggc                                            1583
```

<210> SEQ ID NO 45
<211> LENGTH: 1407
<212> TYPE: RNA
<213> ORGANISM: Artificial Sequence
<220> FEATURE:
<223> OTHER INFORMATION: Synthetic

<400> SEQUENCE: 45

```
augaacccca accagaagau caucaccauc ggcagcaucu gcaugaccau cggcaccgcc     60

aaccugaucc ugcaaaucgg caacaucauc agcaucuggg ugagccacag cauccagauc    120

ggcaaccaga gccagaucga gaccugcaac aagagcguga ucaccuacga gaacaacacc    180

ugggugaacc agaccuucgu gaacaucagc aacaccaaca gcgccgcucg gcagucagug    240

gccagcguga agcuggccgg caacagcagc cugugccccg uuaguggcug ggccaucuac    300

agcaaggaca acagcgugcg gaucggcagc aagggcgacg uguucgugau ccgggagccc    360

uucaucagcu gcagcccgcu ugagugccgc accuucuucc ugacccaggg cgcucugcug    420

aacgacaagc acagcaacgg caccaucaag gaccggagcc ccuaucggac ccugaugagc    480

ugccccauug gcgaggugcc cagccccuac aacagccggu ucgagucugu ggccuggagc    540

gccucugccu gccacgacgg caccaacugg cugaccaucg ggaucagcgg acccgauagc    600

ggagcagugg ccgugcugaa guacaacggc aucaucaccg acaccaucaa gagcuggcgg    660

aacaagaucc ugcggaccca ggagagcgag ugcgccugcg ugaacggcag cugcuucacc    720

aucaugaccg acggcccuag cgacggacag gccagcuaca agaucuuccg gaucgagaag    780

ggcaagauca ucaagagcgu ggagaugaag gcacccaacu accacuacga ggagugcagc    840
```

```
ugcuaccccg acagcagcga gaucaccugc gugugccggg acaacuggca cgggagcaac    900

aggcccuggg ugagcuucaa ccagaaccug gaguaccaga ugggcuacau cugcagcggc    960

guguucggcg acaacccacg gcccaacgac aagacuggca gcugcggucc ggugagcagc   1020

aacggcgcca acggcgugaa gggcuucagc uucaaguacg gcaacggcgu guggaucggc   1080

cggaccaaga gcaucagcag ccggaagggc uucgagauga ucugggaccc caacggcugg   1140

accggcaccg acaacaaguu cagcaagaag caggacaucg ugggcaucaa cgaguggagc   1200

ggcuacagcg gcagcuucgu gcagcacccc gagcugacug gccugaacug cauccggccc   1260

ugcuucuggg uggaacugau acggggacgg cccgaggaga acaccaucug gaccagcggc   1320

agcagcauca gcuucugcgg cguggacagc gauaucgugg gcuggagcug gccagacgga   1380

gccgagcugc ccuucaccau cgacaag                                       1407
```

<210> SEQ ID NO 46
<211> LENGTH: 469
<212> TYPE: PRT
<213> ORGANISM: Artificial Sequence
<220> FEATURE:
<223> OTHER INFORMATION: Synthetic

<400> SEQUENCE: 46

```
Met Asn Pro Asn Gln Lys Ile Ile Thr Ile Gly Ser Ile Cys Met Thr
1               5                   10                  15

Ile Gly Thr Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Lys Ser Val Ile Thr Tyr Glu Asn Asn Thr Trp Val Asn Gln
    50                  55                  60

Thr Phe Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
```

260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Met Gly Tyr Ile Cys Ser Gly
305 310 315 320

Val Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Ile Ser Ser Arg
355 360 365

Lys Gly Phe Glu Met Ile Trp Asp Pro Asn Gly Trp Thr Gly Thr Asp
370 375 380

Asn Lys Phe Ser Lys Lys Gln Asp Ile Val Gly Ile Asn Glu Trp Ser
385 390 395 400

Gly Tyr Ser Gly Ser Phe Val Gln His Pro Glu Leu Thr Gly Leu Asn
405 410 415

Cys Ile Arg Pro Cys Phe Trp Val Glu Leu Ile Arg Gly Arg Pro Glu
420 425 430

Glu Asn Thr Ile Trp Thr Ser Gly Ser Ser Ile Ser Phe Cys Gly Val
435 440 445

Asp Ser Asp Ile Val Gly Trp Ser Trp Pro Asp Gly Ala Glu Leu Pro
450 455 460

Phe Thr Ile Asp Lys
465

<210> SEQ ID NO 47
<211> LENGTH: 1583
<212> TYPE: RNA
<213> ORGANISM: Artificial Sequence
<220> FEATURE:
<223> OTHER INFORMATION: Synthetic

<400> SEQUENCE: 47
gggaaauaag agagaaaaga agaguaagaa gaaauauaag accccggcgc cgccaccaug 60
aaccccaacc agaagaucau caccaucggc agcaucugca ugaccaucgg caccgccaac 120
cugauccugc aaaucggcaa caucaucagc aucuggguga gccacagcau ccagaucggc 180
aaccagagcc agaucgagac cugcaacaag agcgugauca ccuacgagaa caacaccugg 240
gugaaccaga ccuucgugaa caucagcaac accaacagcg ccgcucggca gucaguggcc 300
agcgugaagc uggccggcaa cagcagccug ugccccguua guggcugggc caucuacagc 360
aaggacaaca gcgugcggau cggcagcaag ggcgacgugu ucgugauccg ggagcccuuc 420
aucagcugca gcccgcuuga gugccgcacc uucuuccuga cccagggcgc ucugcugaac 480
gacaagcaca gcaacggcac caucaagggc cggagccccu aucggacccu gaugagcugc 540
cccauuggcg aggugcccag ccccuacaac agccgguucg agucuguggc cuggagcgcc 600
ucugccugcc acgacggcac caacuggcug accaucggga ucagcggacc cgauagcgga 660
gcaguggccg ugcugaagua caacggcauc aucaccgaca ccaucaagag cuggcggaac 720
aagauccugc ggacccagga gagcgagugc gccugcguga acggcagcug cuucaccauc 780
augaccgacg gcccuagcga cggacaggcc agcuacaaga ucuuccggau cgagaagggc 840

-continued aagaucauca agagcgugga gaugaaggca cccaacuacc acuacgagga gugcagcugc 900
uaccccgaca gcagcgagau caccugcgug ugccgggaca acuggcacgg gagcaacagg 960
cccuggguga gcuucaacca gaaccuggag uaccagaugg gcuacaucug cagcggcgug 1020
uucggcgaca acccacggcc caacgacaag acuggcagcu gcgguccggu gagcagcaac 1080
ggcgccaacg gcgugaaggg cuucagcuuc aaguacggca acggcgugug gaucggccgg 1140
accaagagca ucagcagccg gaagggcuuc gagaugaucu gggaccccaa cggcuggacc 1200
ggcaccgaca acaaguucag caagaagcag gacaucgugg gcaucaacga guggagcggc 1260
uacagcggca gcuucgugca gcaccccgag cugacuggcc ugaacugcau ccggcccugc 1320
uucugggugg aacugauacg gggacggccc gaggagaaca ccaucuggac cagcggcagc 1380
agcaucagcu ucugcggcgu ggacagcgau aucgugggcu ggagcuggcc agacggagcc 1440
gagcugcccu ucaccaucga caagugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 48
<211> LENGTH: 1407
<212> TYPE: RNA
<213> ORGANISM: Artificial Sequence
<220> FEATURE:
<223> OTHER INFORMATION: Synthetic

<400> SEQUENCE: 48
augaacccca accagaagau caucaccauc ggcagcaucu gcaugaccau cggcaccgcc 60
aaccugaucc ugcaaaucgg caacaucauc agcaucuggg ugagccacag cauccagauc 120
ggcaaccaga gccagaucga gaccugcaac aagagcguga ucaccuacga gaacaacacc 180 uggguggaacc agaccuucgu gaacaucagc aacaccaaca gcgccgcucg gcagucagug 240
gccagcguga agcuggccgg caacagcagc cugugccccg uuaguggcug ggccaucuac 300
agcaaggaca acagcgugcg gaucggcagc aagggcgacg uguucgugau ccgggagccc 360
uucaucagcu gcagcccgcu ugagugccgc accuucuucc ugacccaggg cgcucugcug 420
aacgacaagc acagcaacgg caccaucaag ggccggagcc ccuaucggac ccugaugagc 480
ugccccauug gcgaggugcc cagccccuac aacagccggu ucgagucugu ggccuggagc 540
gccucugccu gccacgacgg caccaacugg cugaccaucg ggaucagcgg acccgauagc 600
ggagcagugg ccgugcugaa guacaacggc aucaucaccg acaccaucaa gagcuggcgg 660
aacaagaucc ugcggaccca ggagagcgag ugcgccugcg ugaacggcag cugcuucacc 720
aucaugaccg acggcccuag cgacggacag gccagcuaca agaucuuccg gaucgagaag 780
ggcaagauca ucaagagcgu ggagaugaag gcacccaacu accacuacga ggagugcagc 840
ugcuaccccg acagcagcga gaucaccugc gugugccggg acaacuggca cgggagcaac 900
aggcccuggg ugagcuucaa ccagaaccug gaguaccaga ugggcuacau cugcagcggc 960
guguucggcg acaacccacg gcccaacgac aagacuggca gcugcggucc ggugagcagc 1020
aacggcgcca acggcgugaa gggcuucagc uucaaguacg gcaacggcgu guggaucggc 1080
cggaccaaga gcaucagcag ccggaagggc uucgagauga ucugggaccc caacggcugg 1140
accggcaccg acaacaaguu cagcaagaag caggacaucg ugggcaucaa cgaguggagc 1200
ggcuacagcg gcagcuucgu gcagcacccc gagcugacug gccugaacug cauccggccc 1260
ugcuucuggg uggaacugau acggggacgg cccgaggaga acaccaucug gaccagcggc 1320
agcagcauca gcuucugcgg cguggacagc gauaucgugg gcuggagcug gccagacgga 1380
gccgagcugc ccuucaccau cgacaag 1407

<210> SEQ ID NO 49
<211> LENGTH: 469
<212> TYPE: PRT
<213> ORGANISM: Artificial Sequence
<220> FEATURE:
<223> OTHER INFORMATION: Synthetic

<400> SEQUENCE: 49

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Ile Gly Asn Gln Ser Gln Ile Glu Thr
35 40 45

Cys Asn Lys Ser Val Ile Thr Tyr Glu Asn Asn Thr Trp Val Asn Gln
50 55 60

Thr Phe Val Asn Ile Ser Asn Thr Asn Ser Ala Ala Arg Gln Ser Val
65 70 75 80

Ala Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Gly Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Thr Asn Trp Leu Thr
180 185 190

Ile Gly Ile Ser Gly Pro Asp Ser Gly Ala Val Ala Val Leu Lys Tyr
195 200 205

Asn Gly Ile Ile Thr Asp Thr Ile Lys Ser Trp Arg Asn Lys Ile Leu
210 215 220

Arg Thr Gln Glu Ser Glu Cys Ala Cys Val Asn Gly Ser Cys Phe Thr
225 230 235 240

Ile Met Thr Asp Gly Pro Ser Asp Gly Gln Ala Ser Tyr Lys Ile Phe
245 250 255

Arg Ile Glu Lys Gly Lys Ile Ile Lys Ser Val Glu Met Lys Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Met Gly Tyr Ile Cys Ser Gly
305 310 315 320

Val Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys

-continued

```
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465


<210> SEQ ID NO 50
<211> LENGTH: 1874
<212> TYPE: RNA
<213> ORGANISM: Artificial Sequence
<220> FEATURE:
<223> OTHER INFORMATION: Synthetic

<400> SEQUENCE: 50

gggaaauaag agagaaaaga agaguaagaa gaaauauaag accccggcgc cgccaccaug      60

aagaccauca ucgcccugag cuacaucetg ugccugggcu ucacccagaa gaucccccggc    120

aacgauaaca gcaccgccac ccugugucug ggacaccacg ccgugcccaa cggcaccauc    180

gugaagacua ucaccaacga ccggaucgag gugaccaacg ccaccgagcu ggugcagaac    240

agcagcaucg gcgagaucug cgacagcccu caccagaucc uggacggcgg caacugcacc    300

cugaucgacg cacugcuggg cgacccucag ugcgacggcu uucagaacaa gaagugggac    360

cuguucgugg agagaucgcg ggccuacagc aacugcuacc ccuacgacgu ccccgacuac    420

gcaagccuga gaagccucgu ggccucaagc ggcacccugg aguucaagaa cgagagcuuc    480

aacugggccg gcgugaccca gaacggcaag ucauucagcu gcauccgggg cuccagcagc    540

agcuucuucu cacggcugaa cuggcugacc caccugaacu acaccuaccc cgcccugaac    600

gugaccaugc ccaacaagga gcaguucgac aagcuguaca ucuggggagu gcaccauccc    660

ggcaccgaca aggaccagau uagccuguac gcccagucua gcggccggau caccgugagc    720

accaagcgga gccagcaggc cgugaucccc aacaucggcu cucggcccag aauccgggac    780

auccccagcc ggaucagcau cuacuggacc auugugaagc ccggcgacau ccugcugauc    840

aacuccaccg gcaaccugau cgccccucgg ggcuauuuca agauccggag cggcaagagc    900

agcaucaugc ggagcgacgc cccuaucggc aagugcaaga gcgagugcau cacacccaac    960

ggaagcaucc ccaacgacaa gcccuuccag aacgugaacc ggauaaccua cggcgccugc   1020

ccuagauacg ugaagcagaa cacccugaag cuggccaccg gcaugcggaa cgugcccgag   1080

aagcagacuc ggggcaucuu cggcgccauc gccggcuuca ucgagaacgg cugggagggc   1140

augguggacg gcugguacgg cuuccggcac cagaacucug agggcagagg acaggccgca   1200

gaccugaaga gcacccaggc cgccaucgac cagaucaacg gcaagcugaa ccggcugauc   1260

ggcaagacca acgagaaguu ccaccagauc gagaaggagu ucagcgaggu ggagggcagg   1320
```

guacaggacc uggagaagua cguggaggac accaagaucg accuguggag cuacaacgcc 1380
gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau cuccugcuuc 1680
cugcugugcg uggcccugcu ggguuucauc augugggccu gccagaaggg caacauccgg 1740
ugcaacaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 51
<211> LENGTH: 1698
<212> TYPE: RNA
<213> ORGANISM: Artificial Sequence
<220> FEATURE:
<223> OTHER INFORMATION: Synthetic

<400> SEQUENCE: 51
augaagacca ucaucgcccu gagcuacauc cugugccugg gcuucaccca gaagaucccc 60
ggcaacgaua acagcaccgc cacccugugu cugggacacc acgccgugcc caacggcacc 120
aucgugaaga cuaucaccaa cgaccggauc gaggugacca acgccaccga gcuggugcag 180
aacagcagca ucggcgagau cugcgacagc ccucaccaga uccuggacgg cggcaacugc 240
acccugaucg acgcacugcu gggcgacccu cagugcgacg gcuuucagaa caagaagugg 300
gaccuguucg uggagagauc gcgggccuac agcaacugcu accccuacga cguccccgac 360
uacgcaagcc ugagaagccu cguggccuca agcggcaccc uggaguucaa gaacgagagc 420
uucaacuggg ccggcgugac ccagaacggc aagucauuca gcugcauccg gggcuccagc 480
agcagcuucu ucucacggcu gaacuggcug acccaccuga acuacaccua ccccgcccug 540
aacgugacca ugcccaacaa ggagcaguuc gacaagcugu acaucugggg agugcaccau 600
cccggcaccg acaaggacca gauuagccug uacgcccagu cuagcggccg gaucaccgug 660
agcaccaagc ggagccagca ggccgugauc cccaacaucg gcucucggcc cagaauccgg 720
gacaucccca gccggaucag caucuacugg accauuguga agcccggcga cauccugcug 780
aucaacucca ccggcaaccu gaucgccccu cggggcuauu ucaagauccg gagcggcaag 840
agcagcauca ugcggagcga cgccccuauc ggcaagugca agagcgagug caucacaccc 900
aacggaagca uccccaacga caagcccuuc cagaacguga accggauaac cuacggcgcc 960
ugcccuagau acgugaagca gaacacccug aagcuggcca ccggcaugcg gaacgugccc 1020
gagaagcaga cucggggcau cuucggcgcc aucgccggcu ucaucgagaa cggcugggag 1080
ggcauggugg acggcuggua cggcuuccgg caccagaacu cugagggcag aggacaggcc 1140
gcagaccuga agagcaccca ggccgccauc gaccagauca acggcaagcu gaaccggcug 1200
aucggcaaga ccaacgagaa guuccaccag aucgagaagg aguucagcga gguggagggc 1260
aggguacagg accuggagaa guacguggag gacaccaaga ucgaccugug gagcuacaac 1320
gccgagcugc ugguagcccu ggagaaccag cacaccaucg accugaccga cagcgagaug 1380
aacaagcugu ucgagaagac caagaagcag cugcgggaga acgccgagga caugggcaac 1440

```
ggcugcuuca agaucuacca caagugcgac aacgccugca ucggcagcau ccggaacgag   1500

accuacgacc acaacgugua ccgggacgag gcccugaaca accgguucca gaucaagggc   1560

guggagcuga agagcggcua caaggacugg auccugugga ucagcuucgc caucuccugc   1620

uuccugcugu gcguggcccu gcuggguuuc aucauguggg ccugccagaa gggcaacauc   1680

cggugcaaca ucugcauc                                                 1698


<210> SEQ ID NO 52
<211> LENGTH: 566
<212> TYPE: PRT
<213> ORGANISM: Artificial Sequence
<220> FEATURE:
<223> OTHER INFORMATION: Synthetic

<400> SEQUENCE: 52

Met Lys Thr Ile Ile Ala Leu Ser Tyr Ile Leu Cys Leu Gly Phe Thr
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Gly Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Ala
    130                 135                 140

Gly Val Thr Gln Asn Gly Lys Ser Phe Ser Cys Ile Arg Gly Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320
```

```
Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 53
<211> LENGTH: 1874
<212> TYPE: RNA
<213> ORGANISM: Artificial Sequence
<220> FEATURE:
<223> OTHER INFORMATION: Synthetic

<400> SEQUENCE: 53

```
gggaaauaag agagaaaaga agaguaagaa gaaauauaag accccggcgc cgccaccaug     60

aagaccauca ucgcccugag cuacaucug ugccugggcu ucacccagaa gauccccggc    120

aacgauaaca ugaccgccac ccugugucug ggacaccacg ccgugcccaa cggcaccauc    180

gugaagacua ucaccaacga ccggaucgag gugaccaacg ccaccgagcu ggugcagaac    240

agcagcaucg gcgagaucug cgacagcccu caccagaucc uggacggcgg caacugcacc    300

cugaucgacg cacugcuggg cgacccucag ugcgacggcu uucagaacaa gaagugggac    360

cuguucgugg agagaucgcg ggccuacagc aacugcuacc ccuacgacgu ccccgacuac    420

gcaagccuga gaagccucgu ggccucaagc ggcacccugg aguucaagaa cgagagcuuc    480

aacugggccg gcgugaccca gaacggcaag ucauucagcu gcauccgggg cuccagcagc    540

agcuucuucu cacggcugaa cuggcugacc caccugaacu acaccuaccc cgcccugaac    600
```

-continued

```
gugaccaugc ccaacaagga gcaguucgac aagcuguaca ucuggggagu gcaccauccc    660

ggcaccgaca aggaccagau uagccuguac gcccagucua gcggccggau caccgugagc    720

accaagcgga gccagcaggc cgugaucccc aacaucggcu cucggcccag aauccgggac    780

auccccagcc ggaucagcau cuacuggacc auugugaagc ccggcgacau ccugcugauc    840

aacuccaccg gcaaccugau cgccccucgg ggcuauuuca agauccggag cggcaagagc    900

agcaucaugc ggagcgacgc cccuaucggc aagugcaaga gcgagugcau cacacccaac    960

ggaagcaucc ccaacgacaa gcccuuccag aacgugaacc ggauaaccua cggcgccugc   1020

ccuagauacg ugaagcagaa cacccugaag cuggccaccg gcaugcggaa cgugcccgag   1080

aagcagacuc ggggcaucuu cggcgccauc gccggcuuca ucgagaacgg cugggagggc   1140

augguggacg gcugguacgg cuuccggcac cagaacucug agggcagagg acaggccgca   1200

gaccugaaga gcacccaggc cgccaucgac cagaucaacg gcaagcugaa ccggcugauc   1260

ggcaagacca acgagaaguu ccaccagauc gagaaggagu ucagcgaggu ggagggcagg   1320

guacaggacc uggagaagua cguggaggac accaagaucg accuguggag cuacaacgcc   1380

gagcugcugg uagcccugga gaaccagcac accaucgacc ugaccgacag cgagaugaac   1440

aagcuguucg agaagaccaa gaagcagcug cgggagaacg ccgaggacau gggcaacggc   1500

ugcuucaaga ucuaccacaa gugcgacaac gccugcaucg gcagcauccg gaacgagacc   1560

uacgaccaca acguguaccg ggacgaggcc cugaacaacc gguuccagau caagggcgug   1620

gagcugaaga gcggcuacaa ggacuggauc cuguggauca gcuucgccau cuccugcuuc   1680

cugcugugcg uggcccugcu ggguuucauc augugggccu gccagaaggg caacauccgg   1740

ugcaacaucu gcaucugaua auaggcugga gccucggugg ccuagcuucu ugccccuugg   1800

gccucccccc agccccuccu ccccuuccug cacccguacc cccgugguu uugaauaaag   1860

ucugaguggg cggc                                                     1874
```

<210> SEQ ID NO 54
<211> LENGTH: 1698
<212> TYPE: RNA
<213> ORGANISM: Artificial Sequence
<220> FEATURE:
<223> OTHER INFORMATION: Synthetic

<400> SEQUENCE: 54

```
augaagacca ucaucgcccu gagcuacauc cugugccugg gcuucaccca gaagaucccc     60

ggcaacgaua acaugaccgc cacccugugu cugggacacc acgccgugcc caacggcacc    120

aucgugaaga cuaucaccaa cgaccggauc gaggugacca acgccaccga gcuggugcag    180

aacagcagca ucggcgagau cugcgacagc ccucaccaga uccuggacgg cggcaacugc    240

acccugaucg acgcacugcu gggcgacccu cagugcgacg gcuuucagaa caagaagugg    300

gaccuguucg uggagagauc gcgggccuac agcaacugcu accccuacga cguccccgac    360

uacgcaagcc ugagaagccu cguggccuca agcggcaccc uggaguucaa gaacgagagc    420

uucaacuggg ccggcgugac ccagaacggc aagucauuca gcugcauccg gggcuccagc    480

agcagcuucu ucucacggcu gaacuggcug acccaccuga acuacaccua ccccgcccug    540

aacgugacca ugcccaacaa ggagcaguuc gacaagcugu acaucugggg agugcaccau    600

cccggcaccg acaaggacca gauuagccug uacgcccagu cuagcggccg gaucaccgug    660

agcaccaagc ggagccagca ggccgugauc cccaacaucg gcucucggcc cagaauccgg    720

gacaucccca gccggaucag caucuacugg accauuguga agcccggcga cauccugcug    780
```

```
aucaacucca ccggcaaccu gaucgccccu cggggcuauu ucaagauccg gagcggcaag    840

agcagcauca ugcggagcga cgccccuauc ggcaagugca agagcgagug caucacaccc    900

aacggaagca uccccaacga caagcccuuc cagaacguga accggauaac cuacggcgcc    960

ugcccuagau acgugaagca gaacacccug aagcuggcca ccggcaugcg gaacgugccc   1020

gagaagcaga cucggggcau cuucggcgcc aucgccggcu ucaucgagaa cggcugggag   1080

ggcauggugg acggcuggua cggcuuccgg caccagaacu cugagggcag aggacaggcc   1140

gcagaccuga agagcaccca ggccgccauc gaccagauca acggcaagcu gaaccggcug   1200

aucggcaaga ccaacgagaa guuccaccag aucgagaagg aguucagcga gguggagggc   1260

aggguacagg accuggagaa guacguggag gacaccaaga ucgaccugug gagcuacaac   1320

gccgagcugc ugguagcccu ggagaaccag cacaccaucg accugaccga cagcgagaug   1380

aacaagcugu ucgagaagac caagaagcag cugcgggaga acgccgagga caugggcaac   1440

ggcugcuuca agaucuacca caagugcgac aacgccugca ucggcagcau ccggaacgag   1500

accuacgacc acaacgugua ccgggacgag gcccugaaca accgguucca gaucaagggc   1560

guggagcuga agagcggcua caaggacugg auccugugga ucagcuucgc caucuccugc   1620

uuccugcugu gcguggcccu gcuggguuuc aucauguggg ccugccagaa gggcaacauc   1680

cggugcaaca ucugcauc                                                 1698
```

<210> SEQ ID NO 55
<211> LENGTH: 566
<212> TYPE: PRT
<213> ORGANISM: Artificial Sequence
<220> FEATURE:
<223> OTHER INFORMATION: Synthetic

<400> SEQUENCE: 55

```
Met Lys Thr Ile Ile Ala Leu Ser Tyr Ile Leu Cys Leu Gly Phe Thr
1               5                   10                  15

Gln Lys Ile Pro Gly Asn Asp Asn Met Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Gly Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Ala
    130                 135                 140

Gly Val Thr Gln Asn Gly Lys Ser Phe Ser Cys Ile Arg Gly Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190
```

-continued

```
Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 56
<211> LENGTH: 1874
<212> TYPE: RNA
<213> ORGANISM: Artificial Sequence
<220> FEATURE:
<223> OTHER INFORMATION: Synthetic

<400> SEQUENCE: 56
gggaaauaag agagaaaaga agaguaagaa gaaauauaag accccggcgc cgccaccaug 60
aagaccauca ucgcccugag cuacauccug ugccugggcu ucacccagaa gauccccggc 120
aacgauaaca ugaccgccac ccugugucug ggacaccacg ccgugcccaa cggcaccauc 180
gugaagacua ucaccaacga ccggaucgag gugaccaacg ccaccgagcu ggugcagaac 240
agcagcaucg gcgagaucug cgacagcccu caccagaucc uggacggcgg caacugcacc 300
cugaucgacg cacugcuggg cgacccucag ugcgacggcu uucagaacaa gaaguggac 360 cuguucgugg agagaucgcg ggccuacagc aacugcuacc ccuacgacgu ccccgacuac 420
gcaagccuga gaagccucgu ggccucaagc ggcacccugg aguucaagaa cgagagcuuc 480
aacugggccg gcgugaccca gaacggcaag ucauucagcu gcauccgggg cuccagcagc 540
agcuucuucu cacggcugaa cuggcugacc caccugaacu acaccuaccc cgcccugaac 600
gugaccaugc ccaacaagga gcaguucgac aagcuguaca ucuggggagu gcaccauccc 660
ggcaccgaca aggaccagau uagccuguac gcccagucua gcggccggau caccgugagc 720
accaagcgga gccagcaggc cgugaucccc aacaucggcu cucggcccag aauccgggac 780
auccccagcc ggaucagcau cuacuggacc auugugaagc ccggcgacau ccugcugauc 840
aacuccaccg gcaaccugau cgccccucgg ggcuauuuca agauccggag cggcaagagc 900
agcaucaugc ggagcgacgc ccccuaucggc aagugcaaga gcgagugcau cacacccaac 960
ggaagcaucc ccaacgacaa gcccuuccag aacgugaacc ggauaaccua cggcgccugc 1020
ccuagauacg ugaagcagaa cacccugaag cuggccaccg gcaugcggaa cgugcccgag 1080
aagcagacuc ggggcaucuu cggcgccauc gccggcuuca ucgagaacgg cugggagggc 1140
augguggacg gcugguacgg cuuccggcac cagaacucug agggcagagg acaggccgca 1200
gaccugaaga gcacccaggc cgccaucgac cagaucaacg gcaagcugaa ccggcugauc 1260
ggcaagacca acgagaaguu ccaccagauc gagaaggagu ucagcgaggu ggagggcagg 1320
guacaggacc uggagaagua cguggaggac accaagaucg accuguggag cuacaacgcc 1380
gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau cuccugcuuc 1680
cugcugugcg uggcccugcu ggguuucauc augugggccu gccagaaggg caacauccgg 1740
ugcaacaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 57
<211> LENGTH: 1698
<212> TYPE: RNA
<213> ORGANISM: Artificial Sequence
<220> FEATURE:
<223> OTHER INFORMATION: Synthetic

<400> SEQUENCE: 57
augaagacca ucaucgcccu gagcuacauc cugugccugg gcuucaccca gaagaucccc 60
ggcaacgaua acaugaccgc cacccugugu cugggacacc acgccgugcc caacggcacc 120
aucgugaaga cuaucaccaa cgaccggauc gaggugacca acgccaccga gcuggugcag 180
aacagcagca ucggcgagau cugcgacagc ccucaccaga uccuggacgg cggcaacugc 240
acccugaucg acgcacugcu gggcgacccu cagugcgacg gcuuucagaa caagaagugg 300
gaccuguucg uggagagauc gcgggccuac agcaacugcu accccuacga cguccccgac 360
uacgcaagcc ugagaagccu cguggccuca agcggcaccc uggaguucaa gaacgagagc 420
uucaacuggg ccggcgugac ccagaacggc aagucauuca gcugcauccg gggcuccagc 480
agcagcuucu ucucacggcu gaacuggcug acccaccuga acuacaccua ccccgcccug 540
aacgugacca ugcccaacaa ggagcaguuc gacaagcugu acaucugggg agugcaccau 600
cccggcaccg acaaggacca gauuagccug uacgcccagu cuagcggccg gaucaccgug 660
agcaccaagc ggagccagca ggccgugauc cccaacaucg gcucucggcc cagaauccgg 720
gacaucccca gccggaucag caucuacugg accauuguga agcccggcga cauccugcug 780
aucaacucca ccggcaaccu gaucgccccu cggggcuauu ucaagauccg gagcggcaag 840
agcagcauca ugcggagcga cgccccuauc ggcaagugca agagcgagug caucacaccc 900
aacggaagca uccccaacga caagcccuuc cagaacguga accggauaac cuacggcgcc 960
ugcccuagau acgugaagca gaacacccug aagcuggcca ccggcaugcg gaacgugccc 1020
gagaagcaga cucggggcau cuucggcgcc aucgccggcu ucaucgagaa cggcugggag 1080
ggcauggugg acggcuggua cggcuuccgg caccagaacu cugagggcag aggacaggcc 1140
gcagaccuga agagcaccca ggccgccauc gaccagauca acggcaagcu gaaccggcug 1200
aucggcaaga ccaacgagaa guuccaccag aucgagaagg aguucagcga ggtggagggc 1260
aggguacagg accuggagaa guacguggag gacaccaaga ucgaccugug gagcuacaac 1320
gccgagcugc ugguagcccu ggagaaccag cacaccaucg accugaccga cagcgagaug 1380
aacaagcugu ucgagaagac caagaagcag cugcgggaga acgccgagga caugggcaac 1440
ggcugcuuca agaucuacca caagugcgac aacgccugca ucggcagcau ccggaacgag 1500
accuacgacc acaacgugua ccgggacgag gcccugaaca accgguucca gaucaagggc 1560
guggagcuga agagcggcua caaggacugg auccugugga ucagcuucgc caucuccugc 1620
uuccugcugu gcguggcccu gcuggguuuc aucauguggg ccugccagaa gggcaacauc 1680
cggugcaaca ucugcauc 1698

<210> SEQ ID NO 58
<211> LENGTH: 566
<212> TYPE: PRT
<213> ORGANISM: Artificial Sequence
<220> FEATURE:
<223> OTHER INFORMATION: Synthetic

<400> SEQUENCE: 58

Met Lys Thr Ile Ile Ala Leu Ser Tyr Ile Leu Cys Leu Gly Phe Thr
1 5 10 15

Gln Lys Ile Pro Gly Asn Asp Asn Met Thr Ala Thr Leu Cys Leu Gly
20 25 30

His His Ala Val Pro Asn Gly Thr Ile Val Lys Thr Ile Thr Asn Asp
35 40 45

Arg Ile Glu Val Thr Asn Ala Thr Glu Leu Val Gln Asn Ser Ser Ile
50 55 60

Gly Glu Ile Cys Asp Ser Pro His Gln Ile Leu Asp Gly Gly Asn Cys

-continued

```
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Ala
    130                 135                 140

Gly Val Thr Gln Asn Gly Lys Ser Phe Ser Cys Ile Arg Gly Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495
```

```
Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 59
<211> LENGTH: 1568
<212> TYPE: RNA
<213> ORGANISM: Artificial Sequence
<220> FEATURE:
<223> OTHER INFORMATION: Synthetic

<400> SEQUENCE: 59

gggaaauaag agagaaaaga agaguaagaa gaaauauaag accccggcgc cgccaccaug      60

aucaucacca ucggcagcau cugcaugacc aucggcaccg ccaaccugau ccugcaaauc     120

ggcaacauca ucagcaucug ggugagccac agcauccaga ucggcaacca gagccagauc     180

gagaccugca acaagagcgu gaucaccuac gagaacaaca ccugggugaa ccagaccuuc     240

gugaacauca gcaacaccaa cagcgccgcu cggcagucag uggccagcgu gaagcuggcc     300

ggcaacagca gccugugccc cguuaguggc ugggccaucu acagcaagga caacagcgug     360

cggaucggca gcaagggcga cguguucgug auccgggagc ccuucaucag cugcagcccg     420

cuugagugcc gcaccuucuu ccugacccag ggcgcucugc ugaacgacaa gcacagcaac     480

ggcaccauca aggaccggag ccccuaucgg acccugauga gcugccccau uggcgaggug     540

cccagccccu acaacagccg guucgagucu guggccugga gcgccucugc cugccacgac     600

ggcaccaacu ggcugaccau cgggaucagc ggacccgaua gcggagcagu ggccgugcug     660

aaguacaacg gcaucaucac cgacaccauc aagagcuggc ggaacaagau ccugcggacc     720

caggagagcg agugcgccug cgugaacggc agcugcuuca ccaucaugac cgacggcccu     780

agcgacggac aggccagcua caagaucuuc cggaucgaga agggcaagau caucaagagc     840

guggagauga aggcacccaa cuaccacuac gaggagugca gcugcuaccc cgacagcagc     900

gagaucaccu gcgugugccg ggacaacugg cacgggagca acaggcccug ggugagcuuc     960

aaccagaacc uggaguacca gaugggcuac aucugcagcg gcguguucgg cgacaaccca    1020

cggcccaacg acaagacugg cagcugcggu ccggugagca gcaacggcgc caacggcgug    1080

aagggcuuca gcuucaagua cggcaacggc guguggaucg gccggaccaa gagcaucagc    1140

agccggaagg gcuucgagau gaucugggac ccccaacggcu ggaccggcac cgacaacaag    1200

uucagcaaga agcaggacau cgugggcauc aacgagugga gcggcuacag cggcagcuuc    1260

gugcagcacc ccgagcugac uggccugaac ugcauccggc ccugcuucug gguggaacug    1320

auacggggac ggcccgagga gaacaccauc uggaccagcg gcagcagcau cagcuucugc    1380

ggcguggaca gcgauaucgu gggcuggagc uggccagacg gagccgagcu gcccuucacc    1440

aucgacaagu gauaauaggc uggagccucg guggccuagc uucuugcccc uugggccucc    1500

ccccagcccc uccuccccuu ccugcacccg uacccccgug gucuuugaau aaagucugag    1560

ugggcggc                                                             1568
```

<210> SEQ ID NO 60
<211> LENGTH: 1392
<212> TYPE: RNA
<213> ORGANISM: Artificial Sequence
<220> FEATURE:
<223> OTHER INFORMATION: Synthetic

<400> SEQUENCE: 60
augaucauca ccaucggcag caucugcaug accaucggca ccgccaaccu gauccugcaa 60
aucggcaaca ucaucagcau cugggugagc cacagcaucc agaucggcaa ccagagccag 120
aucgagaccu gcaacaagag cgugaucacc uacgagaaca acaccugggu gaaccagacc 180
uucgugaaca ucagcaacac caacagcgcc gcucggcagu caguggccag cgugaagcug 240
gccggcaaca gcagccugug ccccguuagu ggcugggcca ucuacagcaa ggacaacagc 300
gugcggaucg gcagcaaggg cgacguguuc gugauccggg agcccuucau cagcugcagc 360
ccgcuugagu gccgcaccuu cuuccugacc cagggcgcuc ugcugaacga caagcacagc 420
aacggcacca ucaaggaccg gagccccuau cggacccuga ugagcugccc cauuggcgag 480
gugcccagcc ccuacaacag ccgguucgag ucuguggccu ggagcgccuc ugccugccac 540
gacggcacca acuggcugac caucgggauc agcggacccg auagcggagc aguggccgug 600
cugaaguaca acggcaucau caccgacacc aucaagagcu ggcggaacaa gauccugcgg 660
acccaggaga gcgagugcgc cugcgugaac ggcagcugcu ucaccaucau gaccgacggc 720
ccuagcgacg gacaggccag cuacaagauc uuccggaucg agaagggcaa gaucaucaag 780
agcguggaga ugaaggcacc caacuaccac uacgaggagu gcagcugcua ccccgacagc 840
agcgagauca ccugcgugug ccgggacaac uggcacggga gcaacaggcc cugggugagc 900
uucaaccaga accuggagua ccagaugggc uacaucugca gcggcguguu cggcgacaac 960
ccacggccca acgacaagac uggcagcugc gguccgguga gcagcaacgg cgccaacggc 1020
gugaagggcu ucagcuucaa guacggcaac ggcgugugga ucggccggac caagagcauc 1080
agcagccgga agggcuucga gaugaucugg gaccccaacg gcuggaccgg caccgacaac 1140
aaguucagca agaagcagga caucgugggc aucaacgagu ggagcggcua cagcggcagc 1200
uucgugcagc accccgagcu gacuggccug aacugcaucc ggcccugcuu cuggguggaa 1260
cugauacggg gacggcccga ggagaacacc aucuggacca gcggcagcag caucagcuuc 1320
ugcggcgugg acagcgauau cgugggcugg agcuggccag acggagccga gcugcccuuc 1380
accaucgaca ag 1392

<210> SEQ ID NO 61
<211> LENGTH: 464
<212> TYPE: PRT
<213> ORGANISM: Artificial Sequence
<220> FEATURE:
<223> OTHER INFORMATION: Synthetic

<400> SEQUENCE: 61

Met Ile Ile Thr Ile Gly Ser Ile Cys Met Thr Ile Gly Thr Ala Asn
1 5 10 15

Leu Ile Leu Gln Ile Gly Asn Ile Ile Ser Ile Trp Val Ser His Ser
20 25 30

Ile Gln Ile Gly Asn Gln Ser Gln Ile Glu Thr Cys Asn Lys Ser Val
35 40 45

Ile Thr Tyr Glu Asn Asn Thr Trp Val Asn Gln Thr Phe Val Asn Ile

```
    50                  55                  60

Ser Asn Thr Asn Ser Ala Ala Arg Gln Ser Val Ala Ser Val Lys Leu
65                  70                  75                  80

Ala Gly Asn Ser Ser Leu Cys Pro Val Ser Gly Trp Ala Ile Tyr Ser
                85                  90                  95

Lys Asp Asn Ser Val Arg Ile Gly Ser Lys Gly Asp Val Phe Val Ile
            100                 105                 110

Arg Glu Pro Phe Ile Ser Cys Ser Pro Leu Glu Cys Arg Thr Phe Phe
        115                 120                 125

Leu Thr Gln Gly Ala Leu Leu Asn Asp Lys His Ser Asn Gly Thr Ile
    130                 135                 140

Lys Asp Arg Ser Pro Tyr Arg Thr Leu Met Ser Cys Pro Ile Gly Glu
145                 150                 155                 160

Val Pro Ser Pro Tyr Asn Ser Arg Phe Glu Ser Val Ala Trp Ser Ala
                165                 170                 175

Ser Ala Cys His Asp Gly Thr Asn Trp Leu Thr Ile Gly Ile Ser Gly
            180                 185                 190

Pro Asp Ser Gly Ala Val Ala Val Leu Lys Tyr Asn Gly Ile Ile Thr
        195                 200                 205

Asp Thr Ile Lys Ser Trp Arg Asn Lys Ile Leu Arg Thr Gln Glu Ser
    210                 215                 220

Glu Cys Ala Cys Val Asn Gly Ser Cys Phe Thr Ile Met Thr Asp Gly
225                 230                 235                 240

Pro Ser Asp Gly Gln Ala Ser Tyr Lys Ile Phe Arg Ile Glu Lys Gly
                245                 250                 255

Lys Ile Ile Lys Ser Val Glu Met Lys Ala Pro Asn Tyr His Tyr Glu
            260                 265                 270

Glu Cys Ser Cys Tyr Pro Asp Ser Ser Glu Ile Thr Cys Val Cys Arg
        275                 280                 285

Asp Asn Trp His Gly Ser Asn Arg Pro Trp Val Ser Phe Asn Gln Asn
    290                 295                 300

Leu Glu Tyr Gln Met Gly Tyr Ile Cys Ser Gly Val Phe Gly Asp Asn
305                 310                 315                 320

Pro Arg Pro Asn Asp Lys Thr Gly Ser Cys Gly Pro Val Ser Ser Asn
                325                 330                 335

Gly Ala Asn Gly Val Lys Gly Phe Ser Phe Lys Tyr Gly Asn Gly Val
            340                 345                 350

Trp Ile Gly Arg Thr Lys Ser Ile Ser Ser Arg Lys Gly Phe Glu Met
        355                 360                 365

Ile Trp Asp Pro Asn Gly Trp Thr Gly Thr Asp Asn Lys Phe Ser Lys
    370                 375                 380

Lys Gln Asp Ile Val Gly Ile Asn Glu Trp Ser Gly Tyr Ser Gly Ser
385                 390                 395                 400

Phe Val Gln His Pro Glu Leu Thr Gly Leu Asn Cys Ile Arg Pro Cys
                405                 410                 415

Phe Trp Val Glu Leu Ile Arg Gly Arg Pro Glu Glu Asn Thr Ile Trp
            420                 425                 430

Thr Ser Gly Ser Ser Ile Ser Phe Cys Gly Val Asp Ser Asp Ile Val
        435                 440                 445

Gly Trp Ser Trp Pro Asp Gly Ala Glu Leu Pro Phe Thr Ile Asp Lys
    450                 455                 460
```

<210> SEQ ID NO 62

<211> LENGTH: 1538
<212> TYPE: RNA
<213> ORGANISM: Artificial Sequence
<220> FEATURE:
<223> OTHER INFORMATION: Synthetic

<400> SEQUENCE: 62
gggaaauaag agagaaaaga agaguaagaa gaaauauaag accccggcgc cgccaccaug 60
aaccccaacc agaagaucau caccaucggc agcaucugca ugaccaucgg caccgccaac 120
cugauccugc aaaucggcaa caucaucagc aucugggug a gccacagcau ccagaccggc 180
agccagagcc agaucgagac cugcaaccag agcauuauca ccuacgagaa uaacaccugg 240
gugaaggaca ccaccagcgu gauccugacc ggcaacagca gccugugccc cguuaguggc 300
ugggccaucu acagcaagga caacagcgug cggaucggca gcaagggcga cguguucgug 360
auccgggagc ccuucaucag cugcagcccg cuugagugcc gcaccuucuu ccugacccag 420
ggcgcucugc ugaacgacaa gcacagcaac ggcaccauca aggaccggag ccccuaucgg 480
acccugauga gcugccccau uggcgaggug cccagccccu acaacagccg guucgagucu 540
guggccugga gcgccucugc cugccacgac ggcaccaacu ggcugaccau cgggaucagc 600
ggacccgaua gcggagcagu ggccgugcug aaguacaacg gcaucaucac cgacaccauc 660
aagagcuggc ggaacaagau ccugcggacc caggagagcg agugcgccug cgugaacggc 720
agcugcuuca ccaucaugac cgacggcccu agcgacggac aggccagcua caagaucuuc 780
cggaucgaga agggcaagau caucaagagc guggagauga aggcacccaa cuaccacuac 840
gaggagugca gcugcuaccc cgacagcagc gagaucaccu gcgugugccg ggacaacugg 900
cacgggagca acaggcccug ggugagcuuc aaccagaacc uggaguacca gaugggcuac 960
aucugcagcg gcguguucgg cgacaaccca cggcccaacg acaagacugg cagcugcggu 1020
ccggugagca gcaacggcgc caacggcgug aagggcuuca gcuucaagua cggcaacggc 1080
guguggaucg gccggaccaa gagcaucagc agccggaagg gcuucgagau gaucugggac 1140
cccaacggcu ggaccggcac cgacaacaag uucagcaaga agcaggacau cgugggcauc 1200
aacgagugga gcggcuacag cggcagcuuc gugcagcacc ccgagcugac uggccugaac 1260
ugcauccggc ccugcuucug gguggaacug auacggggac ggcccgagga gaacaccauc 1320
uggaccagcg gcagcagcau cagcuucugc ggcguggaca gcgauaucgu gggcuggagc 1380
uggccagacg gagccgagcu gcccuucacc aucgacaagu gauaauaggc uggagccucg 1440
guggccuagc uucuugcccc uugggccucc ccccagcccc uccuccccuu ccugcacccg 1500
uacccccgug gucuuugaau aaagucugag ugggcggc 1538

<210> SEQ ID NO 63
<211> LENGTH: 1362
<212> TYPE: RNA
<213> ORGANISM: Artificial Sequence
<220> FEATURE:
<223> OTHER INFORMATION: Synthetic

<400> SEQUENCE: 63
augaacccca accagaagau caucaccauc ggcagcaucu gcaugaccau cggcaccgcc 60
aaccugaucc ugcaaaucgg caacaucauc agcaucuggg ugagccacag cauccagacc 120
ggcagccaga gccagaucga gaccugcaac cagagcauua ucaccuacga gaauaacacc 180
ugggugaagg acaccaccag cgugauccug accggcaaca gcagccugug ccccguuagu 240
ggcugggcca ucuacagcaa ggacaacagc gugcggaucg gcagcaaggg cgacguguuc 300
gugauccggg agcccuucau cagcugcagc ccgcuugagu gccgcaccuu cuuccugacc 360
cagggcgcuc ugcugaacga caagcacagc aacggcacca ucaaggaccg gagccccuau 420
cggacccuga ugagcugccc cauuggcgag gugcccagcc ccuacaacag ccgguucgag 480
ucuguggccu ggagcgccuc ugccugccac gacggcacca acuggcugac caucgggauc 540
agcggacccg auagcggagc aguggccgug cugaaguaca acggcaucau caccgacacc 600
aucaagagcu ggcggaacaa gauccugcgg acccaggaga gcgagugcgc cugcgugaac 660
ggcagcugcu ucaccaucau gaccgacggc ccuagcgacg gacaggccag cuacaagauc 720
uuccggaucg agaagggcaa gaucaucaag agcguggaga ugaaggcacc caacuaccac 780
uacgaggagu gcagcugcua ccccgacagc agcgagauca ccugcgugug ccgggacaac 840
uggcacggga gcaacaggcc cugggugagc uucaaccaga accuggagua ccagaugggc 900
uacaucugca gcggcguguu cggcgacaac ccacggccca acgacaagac uggcagcugc 960
gguccgguga gcagcaacgg cgccaacggc gugaagggcu ucagcuucaa guacggcaac 1020
ggcgugugga ucggccggac caagagcauc agcagccgga agggcuucga gaugaucugg 1080
gaccccaacg gcuggaccgg caccgacaac aaguucagca agaagcagga caucgugggc 1140
aucaacgagu ggagcggcua cagcggcagc uucgugcagc accccgagcu gacuggccug 1200
aacugcaucc ggcccugcuu cugggugga cugauacggg gacggcccga ggagaacacc 1260
aucuggacca gcggcagcag caucagcuuc ugcggcgugg acagcgauau cgugggcugg 1320
agcuggccag acggagccga gcugcccuuc accaucgaca ag 1362

<210> SEQ ID NO 64
<211> LENGTH: 454
<212> TYPE: PRT
<213> ORGANISM: Artificial Sequence
<220> FEATURE:
<223> OTHER INFORMATION: Synthetic

<400> SEQUENCE: 64

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Thr Gly Ser Gln Ser Gln Ile Glu Thr
35 40 45

Cys Asn Gln Ser Ile Ile Thr Tyr Glu Asn Asn Thr Trp Val Lys Asp
50 55 60

Thr Thr Ser Val Ile Leu Thr Gly Asn Ser Ser Leu Cys Pro Val Ser
65 70 75 80

Gly Trp Ala Ile Tyr Ser Lys Asp Asn Ser Val Arg Ile Gly Ser Lys
85 90 95

Gly Asp Val Phe Val Ile Arg Glu Pro Phe Ile Ser Cys Ser Pro Leu
100 105 110

Glu Cys Arg Thr Phe Phe Leu Thr Gln Gly Ala Leu Leu Asn Asp Lys
115 120 125

His Ser Asn Gly Thr Ile Lys Asp Arg Ser Pro Tyr Arg Thr Leu Met
130 135 140

Ser Cys Pro Ile Gly Glu Val Pro Ser Pro Tyr Asn Ser Arg Phe Glu
145 150 155 160

Ser Val Ala Trp Ser Ala Ser Ala Cys His Asp Gly Thr Asn Trp Leu
165 170 175

Thr Ile Gly Ile Ser Gly Pro Asp Ser Gly Ala Val Ala Val Leu Lys
180 185 190

Tyr Asn Gly Ile Ile Thr Asp Thr Ile Lys Ser Trp Arg Asn Lys Ile
195 200 205

Leu Arg Thr Gln Glu Ser Glu Cys Ala Cys Val Asn Gly Ser Cys Phe
210 215 220

Thr Ile Met Thr Asp Gly Pro Ser Asp Gly Gln Ala Ser Tyr Lys Ile
225 230 235 240

Phe Arg Ile Glu Lys Gly Lys Ile Ile Lys Ser Val Glu Met Lys Ala
245 250 255

Pro Asn Tyr His Tyr Glu Glu Cys Ser Cys Tyr Pro Asp Ser Ser Glu
260 265 270

Ile Thr Cys Val Cys Arg Asp Asn Trp His Gly Ser Asn Arg Pro Trp
275 280 285

Val Ser Phe Asn Gln Asn Leu Glu Tyr Gln Met Gly Tyr Ile Cys Ser
290 295 300

Gly Val Phe Gly Asp Asn Pro Arg Pro Asn Asp Lys Thr Gly Ser Cys
305 310 315 320

Gly Pro Val Ser Ser Asn Gly Ala Asn Gly Val Lys Gly Phe Ser Phe
325 330 335

Lys Tyr Gly Asn Gly Val Trp Ile Gly Arg Thr Lys Ser Ile Ser Ser
340 345 350

Arg Lys Gly Phe Glu Met Ile Trp Asp Pro Asn Gly Trp Thr Gly Thr
355 360 365

Asp Asn Lys Phe Ser Lys Lys Gln Asp Ile Val Gly Ile Asn Glu Trp
370 375 380

Ser Gly Tyr Ser Gly Ser Phe Val Gln His Pro Glu Leu Thr Gly Leu
385 390 395 400

Asn Cys Ile Arg Pro Cys Phe Trp Val Glu Leu Ile Arg Gly Arg Pro
405 410 415

Glu Glu Asn Thr Ile Trp Thr Ser Gly Ser Ser Ile Ser Phe Cys Gly
420 425 430

Val Asp Ser Asp Ile Val Gly Trp Ser Trp Pro Asp Gly Ala Glu Leu
435 440 445

Pro Phe Thr Ile Asp Lys
450

<210> SEQ ID NO 65
<211> LENGTH: 1493
<212> TYPE: RNA
<213> ORGANISM: Artificial Sequence
<220> FEATURE:
<223> OTHER INFORMATION: Synthetic

<400> SEQUENCE: 65
gggaaauaag agagaaaaga agaguaagaa gaaauauaag accccggcgc cgccaccaug 60
aaccccaacc agaagaucau caccaucggc agcaucugca ugaccaucgg caccgccaac 120
cugauccugc aaaucggcaa caucaucagc aucugggua gccacagcau ccagaucggc 180
aaccagagcc agaucgagac cugcaaccag agcgugaucc ugaccggcaa cagcagccug 240
ugccccguua guggcugggc caucuacagc aaggacaaca gcgugcggau cggcagcaag 300
ggcgacgugu ucgugauccg ggagcccuuc aucagcugca gcccgcuuga gugccgcacc 360
uucuuccuga cccagggcgc ucugcugaac gacaagcaca gcaacggcac caucaaggac 420

```
cggagccccu aucggacccu gaugagcugc cccauuggcg aggugcccag ccccuacaac    480

agccgguucg agucuguggc cuggagcgcc ucugccugcc acgacggcac caacuggcug    540

accaucggga ucagcggacc cgauagcgga gcaguggccg ugcugaagua caacggcauc    600

aucaccgaca ccaucaagag cuggcggaac aagauccugc ggacccagga gagcgagugc    660

gccugcguga acggcagcug cuucaccauc augaccgacg gcccuagcga cggacaggcc    720

agcuacaaga ucuuccggau cgagaagggc aagaucauca agagcgugga gaugaaggca    780

cccaacuacc acuacgagga gugcagcugc uaccccgaca gcagcgagau caccugcgug    840

ugccgggaca acuggcacgg gagcaacagg cccugggug a gcuucaacca gaaccuggag    900

uaccagaugg gcuacaucug cagcggcgug uucggcgaca acccacggcc caacgacaag    960

acuggcagcu gcgguccggu gagcagcaac ggcgccaacg gcgugaaggg cuucagcuuc   1020

aaguacggca acggcgugug gaucggccgg accaagagca ucagcagccg gaagggcuuc   1080

gagaugaucu gggaccccaa cggcuggacc ggcaccgaca acaaguucag caagaagcag   1140

gacaucgugg gcaucaacga guggagcggc uacagcggca gcuucgugca gcacccc gag   1200

cugacuggcc ugaacugcau ccggcccugc uucugggugg aacugauacg gggacggccc   1260

gaggagaaca ccaucuggac cagcggcagc agcaucagcu ucugcggcgu ggacagcgau   1320

aucgugggcu ggagcuggcc agacggagcc gagcugcccu ucaccaucga caagugauaa   1380

uaggcuggag ccucgguggc cuagcuucuu gccccuuggg ccucccccca gccccuccuc   1440

cccuuccugc acccguaccc ccguggucuu ugaauaaagu cugagugggc ggc          1493
```

<210> SEQ ID NO 66
<211> LENGTH: 1317
<212> TYPE: RNA
<213> ORGANISM: Artificial Sequence
<220> FEATURE:
<223> OTHER INFORMATION: Synthetic

<400> SEQUENCE: 66

```
augaacccca accagaagau caucaccauc ggcagcaucu gcaugaccau cggcaccgcc     60

aaccugaucc ugcaaaucgg caacaucauc agcaucuggg ugagccacag cauccagauc    120

ggcaaccaga gccagaucga gaccugcaac cagagcguga uccugaccgg caacagcagc    180

cugugccccg uuaguggcug ggccaucuac agcaaggaca acagcgugcg gaucggcagc    240

aagggcgacg uguucgugau ccgggagccc uucaucagcu gcagcccgcu ugagugccgc    300

accuucuucc ugacccaggg cgcucugcug aacgacaagc acagcaacgg caccaucaag    360

gaccggagcc ccuaucggac ccugaugagc ugccccauug gcgaggugcc cagccccuac    420

aacagccggu ucgagucugu ggccuggagc gccucugccu gccacgacgg caccaacugg    480

cugaccaucg ggaucagcgg acccgauagc ggagcagugg ccgugcugaa guacaacggc    540

aucaucaccg acaccaucaa gagcuggcgg aacaagaucc ugcggaccca ggagagcgag    600

ugcgccugcg ugaacggcag cugcuucacc aucaugaccg acggcccuag cgacggacag    660

gccagcuaca agaucuuccg gaucgagaag ggcaagauca ucaagagcgu ggagaugaag    720

gcacccaacu accacuacga ggagugcagc ugcuaccccg acagcagcga gaucaccugc    780

gugugccggg acaacuggca cgggagcaac aggcccuggg ugagcuucaa ccagaaccug    840

gaguaccaga ugggcuacau cugcagcggc guguucggcg acaacccacg gcccaacgac    900

aagacuggca gcugcggucc ggugagcagc aacggcgcca acggcgugaa gggcuucagc    960

uucaaguacg gcaacggcgu guggaucggc cggaccaaga gcaucagcag ccggaagggc   1020
```

uucgagauga ucugggaccc caacggcugg accggcaccg acaacaaguu cagcaagaag 1080
caggacaucg ugggcaucaa cgaguggagc ggcuacagcg gcagcuucgu gcagcacccc 1140
gagcugacug gccugaacug cauccggccc ugcuucuggg uggaacugau acggggacgg 1200
cccgaggaga acaccaucug gaccagcggc agcagcauca gcuucugcgg cguggacagc 1260
gauaucgugg gcuggagcug gccagacgga gccgagcugc ccuucaccau cgacaag 1317

<210> SEQ ID NO 67
<211> LENGTH: 439
<212> TYPE: PRT
<213> ORGANISM: Artificial Sequence
<220> FEATURE:
<223> OTHER INFORMATION: Synthetic

<400> SEQUENCE: 67

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Ile Gly Asn Gln Ser Gln Ile Glu Thr
35 40 45

Cys Asn Gln Ser Val Ile Leu Thr Gly Asn Ser Ser Leu Cys Pro Val
50 55 60

Ser Gly Trp Ala Ile Tyr Ser Lys Asp Asn Ser Val Arg Ile Gly Ser
65 70 75 80

Lys Gly Asp Val Phe Val Ile Arg Glu Pro Phe Ile Ser Cys Ser Pro
85 90 95

Leu Glu Cys Arg Thr Phe Phe Leu Thr Gln Gly Ala Leu Leu Asn Asp
100 105 110

Lys His Ser Asn Gly Thr Ile Lys Asp Arg Ser Pro Tyr Arg Thr Leu
115 120 125

Met Ser Cys Pro Ile Gly Glu Val Pro Ser Pro Tyr Asn Ser Arg Phe
130 135 140

Glu Ser Val Ala Trp Ser Ala Ser Ala Cys His Asp Gly Thr Asn Trp
145 150 155 160

Leu Thr Ile Gly Ile Ser Gly Pro Asp Ser Gly Ala Val Ala Val Leu
165 170 175

Lys Tyr Asn Gly Ile Ile Thr Asp Thr Ile Lys Ser Trp Arg Asn Lys
180 185 190

Ile Leu Arg Thr Gln Glu Ser Glu Cys Ala Cys Val Asn Gly Ser Cys
195 200 205

Phe Thr Ile Met Thr Asp Gly Pro Ser Asp Gly Gln Ala Ser Tyr Lys
210 215 220

Ile Phe Arg Ile Glu Lys Gly Lys Ile Ile Lys Ser Val Glu Met Lys
225 230 235 240

Ala Pro Asn Tyr His Tyr Glu Glu Cys Ser Cys Tyr Pro Asp Ser Ser
245 250 255

Glu Ile Thr Cys Val Cys Arg Asp Asn Trp His Gly Ser Asn Arg Pro
260 265 270

Trp Val Ser Phe Asn Gln Asn Leu Glu Tyr Gln Met Gly Tyr Ile Cys
275 280 285

Ser Gly Val Phe Gly Asp Asn Pro Arg Pro Asn Asp Lys Thr Gly Ser
290 295 300

Cys Gly Pro Val Ser Ser Asn Gly Ala Asn Gly Val Lys Gly Phe Ser

```
305                 310                 315                 320

Phe Lys Tyr Gly Asn Gly Val Trp Ile Gly Arg Thr Lys Ser Ile Ser
                325                 330                 335

Ser Arg Lys Gly Phe Glu Met Ile Trp Asp Pro Asn Gly Trp Thr Gly
            340                 345                 350

Thr Asp Asn Lys Phe Ser Lys Lys Gln Asp Ile Val Gly Ile Asn Glu
        355                 360                 365

Trp Ser Gly Tyr Ser Gly Ser Phe Val Gln His Pro Glu Leu Thr Gly
    370                 375                 380

Leu Asn Cys Ile Arg Pro Cys Phe Trp Val Glu Leu Ile Arg Gly Arg
385                 390                 395                 400

Pro Glu Glu Asn Thr Ile Trp Thr Ser Gly Ser Ser Ile Ser Phe Cys
                405                 410                 415

Gly Val Asp Ser Asp Ile Val Gly Trp Ser Trp Pro Asp Gly Ala Glu
            420                 425                 430

Leu Pro Phe Thr Ile Asp Lys
        435
```

<210> SEQ ID NO 68
<211> LENGTH: 1628
<212> TYPE: RNA
<213> ORGANISM: Artificial Sequence
<220> FEATURE:
<223> OTHER INFORMATION: Synthetic

<400> SEQUENCE: 68

```
gggaaauaag agagaaaaga agaguaagaa gaaauauaag accccggcgc cgccaccaug     60

aaccccaacc agaagaucau caccaucggc agcaucugca ugaccaucgg caccgccaac    120

cugauccugc aaaucggcaa caucaucagc aucuggguga gccacagcau ccagaucggc    180

aaccagagcc agaucgagac cugcaacaag agcgugauca ccuacgagaa caacaccugg    240

gugaaccaga ccuucgugaa caucagcaac accaacagcg ccgcucggaa caucaccgag    300

aucguguacc ugaccaacac caccaucgag aaacagucag uggccagcgu gaagcuggcc    360

ggcaacagca gccugugccc cguuaguggc ugggccaucu acagcaagga caacagcgug    420

cggaucggca gcaagggcga cguguucgug auccgggagc ccuucaucag cugcagcccg    480

cuugagugcc gcaccuucuu ccugacccag ggcgcucugc ugaacgacaa gcacagcaac    540

ggcaccauca aggaccggag ccccuaucgg acccugauga gcugccccau uggcgaggug    600

cccagccccu acaacagccg guucgagucu guggccugga gcgccucugc cugccacgac    660

ggcaccaacu ggcugaccau cgggaucagc ggacccgaua gcggagcagu ggccgugcug    720

aaguacaacg gcaucaucac cgacaccauc aagagcuggc ggaacaagau ccugcggacc    780

caggagagcg agugcgccug cgugaacggc agcugcuuca ccaucaugac cgacggcccu    840

agcgacggac aggccagcua caagaucuuc cggaucgaga agggcaagau caucaagagc    900

guggagauga aggcacccaa cuaccacuac gaggagugca gcugcuaccc cgacagcagc    960

gagaucaccu gcgugugccg ggacaacugg cacgggagca acaggcccug ggugagcuuc   1020

aaccagaacc uggaguacca gaugggcuac aucugcagcg gcguguucgg cgacaaccca   1080

cggcccaacg acaagacugg cagcugcggu ccggugagca gcaacggcgc caacggcgug   1140

aagggcuuca gcuucaagua cggcaacggc guguggaucg gccggaccaa gagcaucagc   1200

agccggaagg gcuucgagau gaucugggac cccaacggcu ggaccggcac cgacaacaag   1260

uucagcaaga agcaggacau cgugggcauc aacgagugga gcggcuacag cggcagcuuc   1320
```

gugcagcacc ccgagcugac uggccugaac ugcauccggc ccugcuucug gguggaacug 1380
auacggggac ggcccgagga gaacaccauc uggaccagcg gcagcagcau cagcuucugc 1440
ggcguggaca gcgauaucgu gggcuggagc uggccagacg gagccgagcu gcccuucacc 1500
aucgacaagu gauaauaggc uggagccucg guggccuagc uucuugcccc uugggccucc 1560
ccccagcccc uccuccccuu ccugcacccg uacccccgug gucuuugaau aaagucugag 1620
ugggcggc 1628

<210> SEQ ID NO 69
<211> LENGTH: 1452
<212> TYPE: RNA
<213> ORGANISM: Artificial Sequence
<220> FEATURE:
<223> OTHER INFORMATION: Synthetic

<400> SEQUENCE: 69
augaacccca accagaagau caucaccauc ggcagcaucu gcaugaccau cggcaccgcc 60
aaccugaucc ugcaaaucgg caacaucauc agcaucuggg ugagccacag cauccagauc 120
ggcaaccaga gccagaucga gaccugcaac aagagcguga ucaccuacga gaacaacacc 180
ugggugaacc agaccuucgu gaacaucagc aacaccaaca gcgccgcucg gaacaucacc 240
gagaucgugu accugaccaa caccaccauc gagaaacagu caguggccag cgugaagcug 300
gccggcaaca gcagccugug ccccguuagu ggcugggcca ucuacagcaa ggacaacagc 360
gugcggaucg gcagcaaggg cgacguguuc gugauccggg agcccuucau cagcugcagc 420
ccgcuugagu gccgcaccuu cuuccugacc cagggcgcuc ugcugaacga caagcacagc 480
aacggcacca ucaaggaccg gagccccuau cggacccuga ugagcugccc cauuggcgag 540
gugcccagcc ccuacaacag ccgguucgag ucuguggccu ggagcgccuc ugccugccac 600
gacggcacca acuggcugac caucgggauc agcggacccg auagcggagc aguggccgug 660
cugaaguaca acggcaucau caccgacacc aucaagagcu ggcggaacaa gauccugcgg 720
acccaggaga gcgagugcgc cugcgugaac ggcagcugcu ucaccaucau gaccgacggc 780
ccuagcgacg gacaggccag cuacaagauc uuccggaucg agaagggcaa gaucaucaag 840
agcguggaga ugaaggcacc caacuaccac uacgaggagu gcagcugcua ccccgacagc 900
agcgagauca ccugcgugug ccgggacaac uggcacggga gcaacaggcc cugggugagc 960
uucaaccaga accuggagua ccagaugggc uacaucugca gcggcguguu cggcgacaac 1020
ccacggccca acgacaagac uggcagcugc gguccgguga gcagcaacgg cgccaacggc 1080
gugaagggcu ucagcuucaa guacggcaac ggcgugugga ucggccggac caagagcauc 1140
agcagccgga agggcuucga gaugaucugg gaccccaacg gcuggaccgg caccgacaac 1200
aaguucagca agaagcagga caucgugggc aucaacgagu ggagcggcua cagcggcagc 1260
uucgugcagc accccgagcu gacuggccug aacugcaucc ggcccugcuu cuggguggaa 1320
cugauacggg gacggcccga ggagaacacc aucuggacca gcggcagcag caucagcuuc 1380
ugcggcgugg acagcgauau cgugggcugg agcuggccag acggagccga gcugcccuuc 1440
accaucgaca ag 1452

<210> SEQ ID NO 70
<211> LENGTH: 484
<212> TYPE: PRT
<213> ORGANISM: Artificial Sequence
<220> FEATURE:

<223> OTHER INFORMATION: Synthetic

<400> SEQUENCE: 70

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Ile Gly Asn Gln Ser Gln Ile Glu Thr
35 40 45

Cys Asn Lys Ser Val Ile Thr Tyr Glu Asn Asn Thr Trp Val Asn Gln
50 55 60

Thr Phe Val Asn Ile Ser Asn Thr Asn Ser Ala Ala Arg Asn Ile Thr
65 70 75 80

Glu Ile Val Tyr Leu Thr Asn Thr Thr Ile Glu Lys Gln Ser Val Ala
85 90 95

Ser Val Lys Leu Ala Gly Asn Ser Ser Leu Cys Pro Val Ser Gly Trp
100 105 110

Ala Ile Tyr Ser Lys Asp Asn Ser Val Arg Ile Gly Ser Lys Gly Asp
115 120 125

Val Phe Val Ile Arg Glu Pro Phe Ile Ser Cys Ser Pro Leu Glu Cys
130 135 140

Arg Thr Phe Phe Leu Thr Gln Gly Ala Leu Leu Asn Asp Lys His Ser
145 150 155 160

Asn Gly Thr Ile Lys Asp Arg Ser Pro Tyr Arg Thr Leu Met Ser Cys
165 170 175

Pro Ile Gly Glu Val Pro Ser Pro Tyr Asn Ser Arg Phe Glu Ser Val
180 185 190

Ala Trp Ser Ala Ser Ala Cys His Asp Gly Thr Asn Trp Leu Thr Ile
195 200 205

Gly Ile Ser Gly Pro Asp Ser Gly Ala Val Ala Val Leu Lys Tyr Asn
210 215 220

Gly Ile Ile Thr Asp Thr Ile Lys Ser Trp Arg Asn Lys Ile Leu Arg
225 230 235 240

Thr Gln Glu Ser Glu Cys Ala Cys Val Asn Gly Ser Cys Phe Thr Ile
245 250 255

Met Thr Asp Gly Pro Ser Asp Gly Gln Ala Ser Tyr Lys Ile Phe Arg
260 265 270

Ile Glu Lys Gly Lys Ile Ile Lys Ser Val Glu Met Lys Ala Pro Asn
275 280 285

Tyr His Tyr Glu Glu Cys Ser Cys Tyr Pro Asp Ser Ser Glu Ile Thr
290 295 300

Cys Val Cys Arg Asp Asn Trp His Gly Ser Asn Arg Pro Trp Val Ser
305 310 315 320

Phe Asn Gln Asn Leu Glu Tyr Gln Met Gly Tyr Ile Cys Ser Gly Val
325 330 335

Phe Gly Asp Asn Pro Arg Pro Asn Asp Lys Thr Gly Ser Cys Gly Pro
340 345 350

Val Ser Ser Asn Gly Ala Asn Gly Val Lys Gly Phe Ser Phe Lys Tyr
355 360 365

Gly Asn Gly Val Trp Ile Gly Arg Thr Lys Ser Ile Ser Ser Arg Lys
370 375 380

Gly Phe Glu Met Ile Trp Asp Pro Asn Gly Trp Thr Gly Thr Asp Asn
385 390 395 400

```
Lys Phe Ser Lys Lys Gln Asp Ile Val Gly Ile Asn Glu Trp Ser Gly
                405                 410                 415

Tyr Ser Gly Ser Phe Val Gln His Pro Glu Leu Thr Gly Leu Asn Cys
            420                 425                 430

Ile Arg Pro Cys Phe Trp Val Glu Leu Ile Arg Gly Arg Pro Glu Glu
        435                 440                 445

Asn Thr Ile Trp Thr Ser Gly Ser Ser Ile Ser Phe Cys Gly Val Asp
    450                 455                 460

Ser Asp Ile Val Gly Trp Ser Trp Pro Asp Gly Ala Glu Leu Pro Phe
465                 470                 475                 480

Thr Ile Asp Lys
```

<210> SEQ ID NO 71
<211> LENGTH: 1583
<212> TYPE: RNA
<213> ORGANISM: Artificial Sequence
<220> FEATURE:
<223> OTHER INFORMATION: Synthetic

<400> SEQUENCE: 71

```
gggaaauaag agagaaaaga agaguaagaa gaaauauaag accccggcgc cgccaccaug     60

aaccccaacc agaagaucau caccaucggc agcaucugca ugaccaucgg caccgccaac    120

cugauccugc aaaucggcaa caucaucagc aucuggguga gccacagcau ccagaucggc    180

aaccagagcc agaucgagac cugcaacaag agcgugauca ccuacgagaa caacaccugg    240

gugaaccaga ccuucgugaa caucagcaac accaacagcg ccgcucggca gucaguggcc    300

agcgugaagc uggccggcaa cagcagccug ugccccguua guggcugggc caucuacagc    360

aaggacaaca gcgugcggau cggcagcaag ggcgacgugu ucgugaucaa ggagcccuuc    420

aucagcugca gcccgcuuga gugccgcacc uucuuccuga cccagggcgc ucugcugaac    480

gacaagcaca gcaacggcac caucaaggac cggagccccu aucggacccu gaugagcugc    540

cccauuggcg aggugcccag ccccuacaac agccgguucg agucuguggc cuggagcgcc    600

ucugccugcc acgacggcac caacuggcug accaucggga ucagcggacc cgauagcgga    660

gcaguggccg ugcugaagua caacggcauc aucaccgaca ccaucaagag cuggcggaac    720

aagauccugc ggacccagga gagcgagugc gccugcguga acggcagcug cuucaccauc    780

augaccgacg gcccuagcga cggacaggcc agcuacaaga ucuuccggau cgagaagggc    840

aagaucauca agagcgugga gaugaaggca cccaacuacc acuacgagga gugcagcugc    900

uaccccgaca gcagcgagau caccugcgug ugccgggaca acuggcacgg gagcaacagg    960

cccuggguga gcuucaacca gaaccuggag uaccagaugg gcuacaucug cagcggcgug   1020

uucggcgaca acccacggcc caacgacaag acuggcagcu gcgguccggu gagcagcaac   1080

ggcgccaacg gcgugaaggg cuucagcuuc aaguacggca acggcgugug gaucggccgg   1140

accaagagca ucagcagccg gaagggcuuc gagaugaucu gggaccccaa cggcuggacc   1200

ggcaccgaca acaaguucag caagaagcag gacaucgugg gcaucaacga guggagcggc   1260

uacagcggca gcuucgugca gcaccccgag cugacuggcc ugaacugcau ccggcccugc   1320

uucugggugg aacugauacg gggacggccc gaggagaaca ccaucuggac cagcggcagc   1380

agcaucagcu ucugcggcgu ggacagcgau aucgugggcu ggagcuggcc agacggagcc   1440

gagcugcccu ucaccaucga caagugauaa uaggcuggag ccucgguggc cuagcuucuu   1500

gccccuuggg ccucccccca gccccuccuc cccuuccugc acccguaccc ccguggucuu   1560
```

ugaauaaagu cugagugggc ggc 1583

<210> SEQ ID NO 72
<211> LENGTH: 1407
<212> TYPE: RNA
<213> ORGANISM: Artificial Sequence
<220> FEATURE:
<223> OTHER INFORMATION: Synthetic

<400> SEQUENCE: 72
augaacccca accagaagau caucaccauc ggcagcaucu gcaugaccau cggcaccgcc 60
aaccugaucc ugcaaaucgg caacaucauc agcaucuggg ugagccacag cauccagauc 120
ggcaaccaga gccagaucga gaccugcaac aagagcguga ucaccuacga gaacaacacc 180
ugggugaacc agaccuucgu gaacaucagc aacaccaaca gcgccgcucg gcagucagug 240
gccagcguga agcuggccgg caacagcagc cugugccccg uuaguggcug ggccaucuac 300
agcaaggaca acagcgugcg gaucggcagc aagggcgacg uguucgugau caaggagccc 360
uucaucagcu gcagcccgcu ugagugccgc accuucuucc ugacccaggg cgcucugcug 420
aacgacaagc acagcaacgg caccaucaag gaccggagcc ccuaucggac ccugaugagc 480
ugccccauug gcgaggugcc cagccccuac aacagccggu ucgagucugu ggccuggagc 540
gccucugccu gccacgacgg caccaacugg cugaccaucg ggaucagcgg acccgauagc 600
ggagcagugg ccgugcugaa guacaacggc aucaucaccg acaccaucaa gagcuggcgg 660
aacaagaucc ugcggaccca ggagagcgag ugcgccugcg ugaacggcag cugcuucacc 720
aucaugaccg acggcccuag cgacggacag gccagcuaca agaucuuccg gaucgagaag 780
ggcaagauca ucaagagcgu ggagaugaag gcacccaacu accacuacga ggagugcagc 840
ugcuaccccg acagcagcga gaucaccugc gugugccggg acaacuggca cgggagcaac 900
aggcccuggg ugagcuucaa ccagaaccug gaguaccaga ugggcuacau cugcagcggc 960
guguucggcg acaacccacg gcccaacgac aagacuggca gcugcggucc ggugagcagc 1020
aacggcgcca acggcgugaa gggcuucagc uucaaguacg gcaacggcgu guggaucggc 1080
cggaccaaga gcaucagcag ccggaagggc uucgagauga ucugggaccc caacggcugg 1140
accggcaccg acaacaaguu cagcaagaag caggacaucg ugggcaucaa cgaguggagc 1200
ggcuacagcg gcagcuucgu gcagcacccc gagcugacug gccugaacug cauccggccc 1260
ugcuucuggg uggaacugau acggggacgg cccgaggaga acaccaucug gaccagcggc 1320
agcagcauca gcuucugcgg cguggacagc gauaucgugg gcuggagcug gccagacgga 1380
gccgagcugc ccuucaccau cgacaag 1407

<210> SEQ ID NO 73
<211> LENGTH: 469
<212> TYPE: PRT
<213> ORGANISM: Artificial Sequence
<220> FEATURE:
<223> OTHER INFORMATION: Synthetic

<400> SEQUENCE: 73

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Ile Gly Asn Gln Ser Gln Ile Glu Thr
35 40 45

-continued

```
Cys Asn Lys Ser Val Ile Thr Tyr Glu Asn Asn Thr Trp Val Asn Gln
    50                  55                  60

Thr Phe Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Lys Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
```

465

<210> SEQ ID NO 74
<211> LENGTH: 1583
<212> TYPE: RNA
<213> ORGANISM: Artificial Sequence
<220> FEATURE:
<223> OTHER INFORMATION: Synthetic

<400> SEQUENCE: 74
gggaaauaag agagaaaaga agaguaagaa gaaauauaag accccggcgc cgccaccaug 60
aaccccaacc agaagaucau caccaucggc agcaucugca ugaccaucgg caccgccaac 120
cugauccugc aaaucggcaa caucaucagc aucuggguga gccacagcau ccagaucggc 180
aaccagagcc agaucgagac cugcaacaag agcgugauca ccuacgagaa caacaccugg 240
gugaaccaga ccuucgugaa caucagcaac accaacagcg ccgcucggca gucaguggcc 300
agcgugaagc uggccggcaa cagcagccug ugccccguua guggcugggc caucuacagc 360
aaggacaaca gcgugcggau cggcagcaag ggcgacgugu ucgugauccg ggagcccuuc 420
aucagcugca gcccgcuuga gugccgcacc uucuuccuga cccagggcgc ucugcugaac 480
gacaagcaca gcaacggcac caucaaggac cggagccccu aucggacccu gaugagcugc 540
cccauuggcg aggugcccag ccccuacaac agccgguucg agucuguggc cuggagcgcc 600
ucugccugcc acgacggcac caacuggcug accaucggga ucagcggacc cgauagcgga 660
gcaguggccg ugcugaagua caacggcauc aucaccgaca ccaucaagag cuggcggaac 720
aagauccugc ggacccagga cagcgagugc gccugcguga acggcagcug cuucaccauc 780
augaccgacg gcccuagcga cggacaggcc agcuacaaga ucuuccggau cgagaagggc 840
aagaucauca agagcgugga gaugaaggca cccaacuacc acuacgagga gugcagcugc 900
uaccccgaca gcagcgagau caccugcgug ugccgggaca acuggcacgg gagcaacagg 960
cccuggguga gcuucaacca gaaccuggag uaccagaugg gcuacaucug cagcggcgug 1020
uucggcgaca acccacggcc caacgacaag acuggcagcu gcgguccggu gagcagcaac 1080
ggcgccaacg gcgugaaggg cuucagcuuc aaguacggca acggcgugug gaucggccgg 1140
accaagagca ucagcagccg gaagggcuuc gagaugaucu gggaccccaa cggcuggacc 1200
ggcaccgaca acaaguucag caagaagcag gacaucgugg gcaucaacga guggagcggc 1260
uacagcggca gcuucgugca gcaccccgag cugacuggcc ugaacugcau ccggcccugc 1320
uucugggugg aacugauacg gggacggccc gaggagaaca ccaucuggac cagcggcagc 1380
agcaucagcu ucugcggcgu ggacagcgau aucgugggcu ggagcuggcc agacggagcc 1440
gagcugcccu ucaccaucga caagugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 75
<211> LENGTH: 1407
<212> TYPE: RNA
<213> ORGANISM: Artificial Sequence
<220> FEATURE:
<223> OTHER INFORMATION: Synthetic

<400> SEQUENCE: 75
augaacccca accagaagau caucaccauc ggcagcaucu gcaugaccau cggcaccgcc 60
aaccugaucc ugcaaaucgg caacaucauc agcaucuggg ugagccacag cauccagauc 120
ggcaaccaga gccagaucga gaccugcaac aagagcguga ucaccuacga gaacaacacc 180
ugggugaacc agaccuucgu gaacaucagc aacaccaaca gcgccgcucg gcagucagug 240
gccagcguga agcuggccgg caacagcagc cugugccccg uuaguggcug ggccaucuac 300
agcaaggaca acagcgugcg gaucggcagc aagggcgacg uguucgugau ccgggagccc 360
uucaucagcu gcagcccgcu ugagugccgc accuucuucc ugacccaggg cgcucugcug 420
aacgacaagc acagcaacgg caccaucaag gaccggagcc ccuaucggac ccugaugagc 480
ugccccauug gcgaggugcc cagccccuac aacagccggu ucgagucugu ggccuggagc 540
gccucugccu gccacgacgg caccaacugg cugaccaucg ggaucagcgg acccgauagc 600
ggagcagugg ccgugcugaa guacaacggc aucaucaccg acaccaucaa gagcuggcgg 660
aacaagaucc ugcggaccca ggacagcgag ugcgccugcg ugaacggcag cugcuucacc 720
aucaugaccg acggcccuag cgacggacag gccagcuaca agaucuuccg gaucgagaag 780
ggcaagauca ucaagagcgu ggagaugaag gcacccaacu accacuacga ggagugcagc 840
ugcuaccccg acagcagcga gaucaccugc gugugccggg acaacuggca cgggagcaac 900
aggcccuggg ugagcuucaa ccagaaccug gaguaccaga ugggcuacau cugcagcggc 960
guguucggcg acaacccacg gcccaacgac aagacuggca gcugcggucc ggugagcagc 1020
aacggcgcca acggcgugaa gggcuucagc uucaaguacg gcaacggcgu guggaucggc 1080
cggaccaaga gcaucagcag ccggaagggc uucgagauga ucugggaccc caacggcugg 1140
accggcaccg acaacaaguu cagcaagaag caggacaucg ugggcaucaa cgaguggagc 1200
ggcuacagcg gcagcuucgu gcagcacccc gagcugacug gccugaacug cauccggccc 1260
ugcuucuggg uggaacugau acggggacgg cccgaggaga acaccaucug gaccagcggc 1320
agcagcauca gcuucugcgg cguggacagc gauaucgugg gcuggagcug gccagacgga 1380
gccgagcugc ccuucaccau cgacaag 1407

<210> SEQ ID NO 76
<211> LENGTH: 469
<212> TYPE: PRT
<213> ORGANISM: Artificial Sequence
<220> FEATURE:
<223> OTHER INFORMATION: Synthetic

<400> SEQUENCE: 76

Met Asn Pro Asn Gln Lys Ile Ile Thr Ile Gly Ser Ile Cys Met Thr
1 5 10 15

Ile Gly Thr Ala Asn Leu Ile Leu Gln Ile Gly Asn Ile Ile Ser Ile
20 25 30

Trp Val Ser His Ser Ile Gln Ile Gly Asn Gln Ser Gln Ile Glu Thr
35 40 45

Cys Asn Lys Ser Val Ile Thr Tyr Glu Asn Asn Thr Trp Val Asn Gln
50 55 60

Thr Phe Val Asn Ile Ser Asn Thr Asn Ser Ala Ala Arg Gln Ser Val
65 70 75 80

Ala Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Asp Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465

<210> SEQ ID NO 77
<211> LENGTH: 1583
<212> TYPE: RNA
<213> ORGANISM: Artificial Sequence
<220> FEATURE:
<223> OTHER INFORMATION: Synthetic

<400> SEQUENCE: 77
gggaaauaag agagaaaaga agaguaagaa gaaauauaag accccggcgc cgccaccaug 60
aaccccaacc agaagaucau caccaucggc agcaucugca ugaccaucgg caccgccaac 120

```
cugauccugc aaaucggcaa caucaucagc aucuggguga gccacagcau ccagaucggc    180

aaccagagcc agaucgagac cugcaacaag agcgugauca ccuacgagaa caacaccugg    240

gugaaccaga ccuucgugaa caucagcaac accaacagcg ccgcucggca gucaguggcc    300

agcgugaagc uggccggcaa cagcagccug ugccccguua guggcugggc caucuacagc    360

aaggacaaca gcgugcggau cggcagcaag ggcgacgugu ucgugaucaa ggagcccuuc    420

aucagcugca gcccgcuuga gugccgcacc uucuuccuga cccagggcgc ucugcugaac    480

gacaagcaca gcaacggcac caucaagggc cggagcccu aucggacccu gaugagcugc    540

cccauuggcg aggugcccag ccccuacaac agccgguucg agucuguggc cuggagcgcc    600

ucugccugcc acgacggcac caacuggcug accaucggga ucagcggacc cgauagcgga    660

gcaguggccg ugcugaagua caacggcauc aucaccgaca ccaucaagag cuggcggaac    720

aagauccugc ggacccagga gagcgagugc gccugcguga acggcagcug cuucaccauc    780

augaccgacg gcccuagcga cggacaggcc agcuacaaga ucuuccggau cgagaagggc    840

aagaucauca agagcgugga gaugaaggca cccaacuacc acuacgagga gugcagcugc    900

uaccccgaca gcagcgagau caccugcgug ugccgggaca acuggcacgg gagcaacagg    960

cccuggguga gcuucaacca gaaccuggag uaccagaugg gcuacaucug cagcggcgug   1020

uucggcgaca acccacggcc caacgacaag acuggcagcu gcgguccggu gagcagcaac   1080

ggcgccaacg gcgugaaggg cuucagcuuc aaguacggca acggcgugug gaucggccgg   1140

accaagagca ucagcagccg gaagggcuuc gagaugaucu gggaccccaa cggcuggacc   1200

ggcaccgaca acaaguucag caagaagcag gacaucgugg gcaucaacga guggagcggc   1260

uacagcggca gcuucgugca gcaccccgag cugacuggcc ugaacugcau ccggcccugc   1320

uucugggugg aacugauacg gggacggccc gaggagaaca ccaucuggac cagcggcagc   1380

agcaucagcu ucugcggcgu ggacagcgau aucgugggcu ggagcuggcc agacggagcc   1440

gagcugcccu ucaccaucga caagugauaa uaggcuggag ccucggugge cuagcuucuu   1500

gccccuuggg ccucccccca gccccuccuc cccuuccugc acccguaccc ccguggucuu   1560

ugaauaaagu cugagugggc ggc                                           1583
```

<210> SEQ ID NO 78
<211> LENGTH: 1407
<212> TYPE: RNA
<213> ORGANISM: Artificial Sequence
<220> FEATURE:
<223> OTHER INFORMATION: Synthetic

<400> SEQUENCE: 78

```
augaacccca accagaagau caucaccauc ggcagcaucu gcaugaccau cggcaccgcc     60

aaccugaucc ugcaaaucgg caacaucauc agcaucuggg ugagccacag cauccagauc    120

ggcaaccaga gccagaucga gaccugcaac aagagcguga ucaccuacga gaacaacacc    180

ugggugaacc agaccuucgu gaacaucagc aacaccaaca gcgccgcucg gcagucagug    240

gccagcguga agcuggccgg caacagcagc cugugccccg uuaguggcug ggccaucuac    300

agcaaggaca acagcgugcg gaucggcagc aagggcgacg uguucgugau caaggagccc    360

uucaucagcu gcagcccgcu ugagugccgc accuucuucc ugacccaggg cgcucugcug    420

aacgacaagc acagcaacgg caccaucaag ggccggagcc ccuaucggac ccugaugagc    480

ugccccauug gcgaggugcc cagccccuac aacagccggu ucgagucugu ggccuggagc    540
```

```
gccucugccu gccacgacgg caccaacugg cugaccaucg ggaucagcgg acccgauagc    600

ggagcagugg ccgugcugaa guacaacggc aucaucaccg acaccaucaa gagcuggcgg    660

aacaagaucc ugcggaccca ggagagcgag ugcgccugcg ugaacggcag cugcuucacc    720

aucaugaccg acggcccuag cgacggacag gccagcuaca agaucuuccg gaucgagaag    780

ggcaagauca ucaagagcgu ggagaugaag gcacccaacu accacuacga ggagugcagc    840

ugcuaccccg acagcagcga gaucaccugc gugugccggg acaacuggca cgggagcaac    900

aggcccuggg ugagcuucaa ccagaaccug gaguaccaga ugggcuacau cugcagcggc    960

guguucggcg acaacccacg gcccaacgac aagacuggca gcugcggucc ggugagcagc   1020

aacggcgcca acggcgugaa gggcuucagc uucaaguacg gcaacggcgu guggaucggc   1080

cggaccaaga gcaucagcag ccggaagggc uucgagauga ucugggaccc caacggcugg   1140

accggcaccg acaacaaguu cagcaagaag caggacaucg ugggcaucaa cgaguggagc   1200

ggcuacagcg gcagcuucgu gcagcacccc gagcugacug gccugaacug cauccggccc   1260

ugcuucuggg uggaacugau acggggacgg cccgaggaga acaccaucug gaccagcggc   1320

agcagcauca gcuucugcgg cguggacagc gauaucgugg gcuggagcug gccagacgga   1380

gccgagcugc ccuucaccau cgacaag                                       1407
```

```
<210> SEQ ID NO 79
<211> LENGTH: 469
<212> TYPE: PRT
<213> ORGANISM: Artificial Sequence
<220> FEATURE:
<223> OTHER INFORMATION: Synthetic

<400> SEQUENCE: 79

Met Asn Pro Asn Gln Lys Ile Ile Thr Ile Gly Ser Ile Cys Met Thr
1               5                   10                  15

Ile Gly Thr Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Lys Ser Val Ile Thr Tyr Glu Asn Asn Thr Trp Val Asn Gln
    50                  55                  60

Thr Phe Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Lys Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Gly Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205
```

```
Asn Gly Ile Ile Thr Asp Thr Ile Lys Ser Trp Arg Asn Lys Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465
```

<210> SEQ ID NO 80
<211> LENGTH: 1583
<212> TYPE: RNA
<213> ORGANISM: Artificial Sequence
<220> FEATURE:
<223> OTHER INFORMATION: Synthetic

<400> SEQUENCE: 80

```
gggaaauaag agagaaaaga agaguaagaa gaaauauaag accccggcgc cgccaccaug      60

aaccccaacc agaagaucau caccaucggc agcaucugca ugaccaucgg caccgccaac     120

cugauccugc aaaucggcaa caucaucagc aucuggguga gccacagcau ccagaucggc     180

aaccagagcc agaucgagac cugcaacaag agcgugauca ccuacgagaa caacaccugg     240

gugaaccaga ccuucgugaa caucagcaac accaacagcg ccgcucggca gucaguggcc     300

agcgugaagc uggccggcaa cagcagccug ugccccguua guggcugggc caucuacagc     360

aaggacaaca gcgugcggau cggcagcaag ggcgacgugu ucgugauccg ggagcccuuc     420

aucagcugca gcccgcuuga gugccgcacc uucuuccuga cccagggcgc ucugcugaac     480

gacaagcaca gcaacggcac caucaagggc cggagccccu aucggacccu gaugagcugc     540
```

-continued

```
cccauuggcg aggugcccag ccccuacaac agccgguucg agucuguggc cuggagcgcc    600

ucugccugcc acgacggcac caacuggcug accaucggga ucagcggacc cgauagcgga    660

gcaguggccg ugcugaagua caacggcauc aucaccgaca ccaucaagag cuggcggaac    720

aagauccugc ggacccagga cagcgagugc gccugcguga acggcagcug cuucaccauc    780

augaccgacg gcccuagcga cggacaggcc agcuacaaga ucuuccggau cgagaagggc    840

aagaucauca agagcgugga gaugaaggca cccaacuacc acuacgagga gugcagcugc    900

uaccccgaca gcagcgagau caccugcgug ugccgggaca acuggcacgg gagcaacagg    960

cccugggguga gcuucaacca gaaccuggag uaccagaugg gcuacaucug cagcggcgug   1020

uucggcgaca acccacggcc caacgacaag acuggcagcu gcgguccggu gagcagcaac   1080

ggcgccaacg gcgugaaggg cuucagcuuc aaguacggca acggcgugug gaucggccgg   1140

accaagagca ucagcagccg gaagggcuuc gagaugaucu gggaccccaa cggcuggacc   1200

ggcaccgaca acaaguucag caagaagcag gacaucgugg gcaucaacga guggagcggc   1260

uacagcggca gcuucgugca gcaccccgag cugacuggcc ugaacugcau ccggcccugc   1320

uucugggugg aacugauacg gggacggccc gaggagaaca ccaucuggac cagcggcagc   1380

agcaucagcu ucugcggcgu ggacagcgau aucgugggcu ggagcuggcc agacggagcc   1440

gagcugcccu ucaccaucga caagugauaa uaggcuggag ccucgguggc cuagcuucuu   1500

gccccuuggg ccucccccca gccccuccuc cccuuccugc acccguaccc ccguggucuu   1560

ugaauaaagu cugagugggc ggc                                            1583
```

<210> SEQ ID NO 81
<211> LENGTH: 1407
<212> TYPE: RNA
<213> ORGANISM: Artificial Sequence
<220> FEATURE:
<223> OTHER INFORMATION: Synthetic

<400> SEQUENCE: 81

```
augaacccca accagaagau caucaccauc ggcagcaucu gcaugaccau cggcaccgcc     60

aaccugaucc ugcaaaucgg caacaucauc agcaucuggg ugagccacag cauccagauc    120

ggcaaccaga gccagaucga gaccugcaac aagagcguga ucaccuacga gaacaacacc    180

ugggugaacc agaccuucgu gaacaucagc aacaccaaca gcgccgcucg gcagucagug    240

gccagcguga agcuggccgg caacagcagc cugugccccg uuaguggcug ggccaucuac    300

agcaaggaca acagcgugcg gaucggcagc aagggcgacg uguucgugau ccgggagccc    360

uucaucagcu gcagcccgcu ugagugccgc accuucuucc ugacccaggg cgcucugcug    420

aacgacaagc acagcaacgg caccaucaag ggccggagcc ccuaucggac ccugaugagc    480

ugccccauug gcgaggugcc cagccccuac aacagccggu ucgagucugu ggccuggagc    540

gccucugccu gccacgacgg caccaacugg cugaccaucg ggaucagcgg acccgauagc    600

ggagcagugg ccgugcugaa guacaacggc aucaucaccg acaccaucaa gagcuggcgg    660

aacaagaucc ugcggaccca ggacagcgag ugcgccugcg ugaacggcag cugcuucacc    720

aucaugaccg acggcccuag cgacggacag gccagcuaca agaucuuccg gaucgagaag    780

ggcaagauca ucaagagcgu ggagaugaag gcacccaacu accacuacga ggagugcagc    840

ugcuaccccg acagcagcga gaucaccugc gugugccggg acaacuggca cgggagcaac    900

aggcccuggg ugagcuucaa ccagaaccug gaguaccaga ugggcuacau cugcagcggc    960

guguucggcg acaacccacg gcccaacgac aagacuggca gcugcggucc ggugagcagc   1020
```

```
aacggcgcca acggcgugaa gggcuucagc uucaaguacg gcaacggcgu guggaucggc   1080

cggaccaaga gcaucagcag ccggaagggc uucgagauga ucugggaccc caacggcugg   1140

accggcaccg acaacaaguu cagcaagaag caggacaucg ugggcaucaa cgaguggagc   1200

ggcuacagcg gcagcuucgu gcagcacccc gagcugacug gccugaacug cauccggccc   1260

ugcuucuggg uggaacugau acggggacgg cccgaggaga acaccaucug gaccagcggc   1320

agcagcauca gcuucugcgg cguggacagc gauaucgugg gcuggagcug gccagacgga   1380

gccgagcugc ccuucaccau cgacaag                                        1407
```

<210> SEQ ID NO 82
<211> LENGTH: 469
<212> TYPE: PRT
<213> ORGANISM: Artificial Sequence
<220> FEATURE:
<223> OTHER INFORMATION: Synthetic

<400> SEQUENCE: 82

```
Met Asn Pro Asn Gln Lys Ile Ile Thr Ile Gly Ser Ile Cys Met Thr
1               5                   10                  15

Ile Gly Thr Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Lys Ser Val Ile Thr Tyr Glu Asn Asn Thr Trp Val Asn Gln
    50                  55                  60

Thr Phe Val Asn Ile Ser Asn Thr Asn Ser Ala Ala Arg Gln Ser Val
65                  70                  75                  80

Ala Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Gly Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Asp Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
        275                 280                 285
```

-continued

```
Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Lys Lys Gln Asp Ile Val Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Ile Val Gly Trp Ser Trp Pro Asp Gly Ala Glu Leu Pro
    450                 455                 460

Phe Thr Ile Asp Lys
465


<210> SEQ ID NO 83
<211> LENGTH: 3272
<212> TYPE: RNA
<213> ORGANISM: Artificial Sequence
<220> FEATURE:
<223> OTHER INFORMATION: Synthetic

<400> SEQUENCE: 83

gggaaauaag agagaaaaga agaguaagaa gaaauauaag accccggcgc cgccaccaug     60

aagaccauca ucgcccugag cuacauccug ugccugggcu ucacccagaa gauccccggc    120

aacgauaaca gcaccgccac ccugugucug ggacaccacg ccgugcccaa cggcaccauc    180

gugaagacua ucaccaacga ccggaucgag gugaccaacg ccaccgagcu ggugcagaac    240

agcagcaucg gcgagaucug cgacagcccu caccagaucc uggacggcgg caacugcacc    300

cugaucgacg cacugcuggg cgacccucag ugcgacggcu uucagaacaa gaagugggac    360

cuguucgugg agagaucgcg ggccuacagc aacugcuacc ccuacgacgu ccccgacuac    420

gcaagccuga gaagccucgu ggccucaagc ggcacccugg aguucaagaa cgagagcuuc    480

aacugggccg gcgugaccca gaacggcaag ucauucagcu gcauccgggg cuccagcagc    540

agcuucuucu cacggcugaa cuggcugacc caccugaacu acaccuaccc cgcccugaac    600

gugaccaugc ccaacaagga gcaguucgac aagcuguaca ucuggggagu gcaccauccc    660

ggcaccgaca aggaccagau uagccuguac gcccagucua gcggccggau caccgugagc    720

accaagcgga gccagcaggc cgugaucccc aacaucggcu cucggcccag aauccgggac    780

auccccagcc ggaucagcau cuacuggacc auugugaagc ccggcgacau ccugcugauc    840

aacuccaccg gcaaccugau cgccccucgg ggcuauuuca agauccggag cggcaagagc    900

agcaucaugc ggagcgacgc cccuaucggc aagugcaaga gcgagugcau cacacccaac    960

ggaagcaucc ccaacgacaa gcccuuccag aacgugaacc ggauaaccua cggcgccugc   1020
```

ccuagauacg ugaagcagaa cacccugaag cuggccaccg gcaugcggaa cgugcccgag 1080
aagcagacuc ggggcaucuu cggcgccauc gccggcuuca ucgagaacgg cugggagggc 1140
augguggacg gcugguacgg cuuccggcac cagaacucug agggcagagg acaggccgca 1200
gaccugaaga gcacccaggc cgccaucgac cagaucaacg gcaagcugaa ccggcugauc 1260
ggcaagacca acgagaaguu ccaccagauc gagaaggagu ucagcgaggu ggagggcagg 1320
guacaggacc uggagaagua cguggaggac accaagaucg accuguggag cuacaacgcc 1380
gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau cuccugcuuc 1680
cugcugugcg uggcccugcu ggguuucauc augugggccu gccagaaggg caacauccgg 1740
ugcaacaucu gcaucggcuc uggcagcggc agcaccagcc ugcugggacu ggccgugcgg 1800
cugcugcugu uucagccugc ccugauggug uucugggcaa gccaggugcg gcagaacugc 1860
cggaacggca gcuacgagau cagcgugcug augauggaca acagcgccua caaggagccc 1920
augcagaacc ugcgggaggc cguggaggag ggccuggaca ucgugcggaa gcggcugcgg 1980
gaagccgacc ugaacgugac cgugaacgcc accuucaucu acagcgacgg ccugauccac 2040
aagagcggcg acugccggag cagcaccugc gaggggcugg accugcugcg ggagaucacc 2100
cgggaccaca agaugggcug cgcccugaug ggccccagcu gcaccuacag cacuuuccag 2160
auguaccugg acaccgagcu gaacuacccc augaucagcg caggcagcua cggccugagc 2220
ugcgacuaca aggagacccu gacccggauc cugccacccg cccggaagcu gauguacuuc 2280
cucguggacu ucuggaaggu gaacaacgcc agcuucaagc ccuucagcug gaacagcagc 2340
uacguguaca agaacggcag cgagcccgag gacugcuucu gguaccugaa cgcucuggag 2400
gccggggugu gcuacuucag cgaggugcug aacuucaagg acgugcugcg gcggagcgag 2460
caguuccagg agauccugac cggccacaac cggaagagca acgugaucgu gaugugcggc 2520
accccggaga gcuucuacga cgugaagggc gaccugcagg uggccgagga caccguggug 2580
auccuggugg accuguucag caaccacuac uucgaggaga acaccaccgc cccugaguac 2640
auggacaacg ugcuggugcu gacccugccc agcgagcaga gcaccagcaa caccagcgug 2700
gccgagcggu ucagcagcgg ccggagcgac uucagccugg ccuaccugga gggcacccug 2760
cuguucggcc acaugcugca gaccuuccug gagaacggcg agaacguaac cggccccaag 2820
uucgcccggg ccuuccggaa ccugaccuuc cagggcuucg caggccccgu gacccuggac 2880
gacagcggcg acaucgacaa caucaugagc cugcuguacg ugagccugga cacccggaag 2940
uacaaggugc ugaugaagua cgacacccac aagaacaaga ccaucccccgu ggccgagaac 3000 cccaacuuca ucuggaagaa ccacaagcug cccaacgacg ugcccggucu gggaccgcag 3060
auccugauga ucgccguguu cacccugacc ggcauccugg uggugcugcu gcugaucgcc 3120
cugcuggucc ugcggaagua ccggcgggac cacugauaau aggcuggagc cucgguggcc 3180
uagcuucuug ccccuugggc cucccccag ccccuccucc ccuuccugca cccguacccc 3240
cguggucuuu gaauaaaguc ugagugggcg gc 3272

<210> SEQ ID NO 84

-continued

<211> LENGTH: 3096
<212> TYPE: RNA
<213> ORGANISM: Artificial Sequence
<220> FEATURE:
<223> OTHER INFORMATION: Synthetic

<400> SEQUENCE: 84
augaagacca ucaucgcccu gagcuacauc cugugccugg gcuucaccca gaagaucccc 60
ggcaacgaua acagcaccgc cacccugugu cugggacacc acgccgugcc caacggcacc 120
aucgugaaga cuaucaccaa cgaccggauc gaggugacca acgccaccga gcuggugcag 180
aacagcagca ucggcgagau cugcgacagc ccucaccaga uccuggacgg cggcaacugc 240
acccugaucg acgcacugcu gggcgacccu cagugcgacg gcuuucagaa caagaagugg 300
gaccuguucg uggagagauc gcgggccuac agcaacugcu accccuacga cguccccgac 360
uacgcaagcc ugagaagccu cguggccuca agcggcaccc uggaguucaa gaacgagagc 420
uucaacuggg ccggcgugac ccagaacggc aagucauuca gcugcauccg gggcuccagc 480
agcagcuucu ucucacggcu gaacuggcug acccaccuga acuacaccua ccccgcccug 540
aacgugacca ugcccaacaa ggagcaguuc gacaagcugu acaucugggg agugcaccau 600
cccggcaccg acaaggacca gauuagccug uacgcccagu cuagcggccg gaucaccgug 660
agcaccaagc ggagccagca ggccgugauc cccaacaucg gcucucggcc cagaauccgg 720
gacaucccca gccggaucag caucuacugg accauuguga agcccggcga cauccugcug 780
aucaacucca ccggcaaccu gaucgccccu cggggcuauu ucaagauccg gagcggcaag 840
agcagcauca ugcggagcga cgccccuauc ggcaagugca agagcgagug caucacaccc 900
aacggaagca uccccaacga caagcccuuc cagaacguga accggauaac cuacggcgcc 960
ugcccuagau acgugaagca gaacacccug aagcuggcca ccggcaugcg gaacgugccc 1020
gagaagcaga cucggggcau cuucggcgcc aucgccggcu ucaucgagaa cggcugggag 1080
ggcauggugg acggcuggua cggcuuccgg caccagaacu cugagggcag aggacaggcc 1140
gcagaccuga agagcaccca ggccgccauc gaccagauca acggcaagcu gaaccggcug 1200
aucggcaaga ccaacgagaa guuccaccag aucgagaagg aguucagcga gguggagggc 1260
aggguacagg accuggagaa guacguggag gacaccaaga ucgaccugug gagcuacaac 1320
gccgagcugc ugguagcccu ggagaaccag cacaccaucg accugaccga cagcgagaug 1380
aacaagcugu ucgagaagac caagaagcag cugcgggaga acgccgagga caugggcaac 1440
ggcugcuuca agaucuacca caagugcgac aacgccugca ucggcagcau ccggaacgag 1500
accuacgacc acaacgugua ccgggacgag gcccugaaca accgguucca gaucaagggc 1560
guggagcuga agagcggcua caaggacugg auccugugga ucagcuucgc caucuccugc 1620
uuccugcugu gcguggcccu gcuggguuuc aucauguggg ccugccagaa gggcaacauc 1680
cggugcaaca ucugcaucgg cucuggcagc ggcagcacca gccugcuggg acuggccgug 1740
cggcugcugc uguuucagcc ugcccugaug guguucuggg caagccaggu gcggcagaac 1800
ugccggaacg gcagcuacga gaucagcgug cugaugaugg acaacagcgc cuacaaggag 1860
cccaugcaga accugcggga ggccguggag gagggccugg acaucgugcg gaagcggcug 1920
cgggaagccg accugaacgu gaccgugaac gccaccuuca ucuacagcga cggccugauc 1980
cacaagagcg gcgacugccg gagcagcacc ugcgaggggc uggaccugcu gcgggagauc 2040
acccgggacc acaagauggg cugcgcccug augggcccca gcugcaccua cagcacuuuc 2100
cagauguacc uggacaccga gcugaacuac cccaugauca gcgcaggcag cuacggccug 2160

-continued agcugcgacu acaaggagac ccugacccgg auccugccac ccgcccggaa gcugauguac 2220
uuccucgugg acuucuggaa ggugaacaac gccagcuuca agcccuucag cuggaacagc 2280
agcuacgugu acaagaacgg cagcgagccc gaggacugcu ucugguaccu gaacgcucug 2340
gaggccgggg ugagcuacuu cagcgaggug cugaacuuca aggacgugcu gcggcggagc 2400
gagcaguucc aggagauccu gaccggccac aaccggaaga gcaacgugau cgugaugugc 2460
ggcaccccgg agagcuucua cgacgugaag ggcgaccugc agguggccga ggacaccgug 2520
gugauccugg uggaccuguu cagcaaccac uacuucgagg agaacaccac cgccccugag 2580
uacauggaca acgugcuggu gcugacccug cccagcgagc agagcaccag caacaccagc 2640
guggccgagc gguucagcag cggccggagc gacuucagcc uggccuaccu ggagggcacc 2700
cugcuguucg gccacaugcu gcagaccuuc cuggagaacg gcgagaacgu aaccggcccc 2760
aaguucgccc gggccuuccg gaaccugacc uuccagggcu ucgcaggccc cgugacccug 2820
gacgacagcg gcgacaucga caacaucaug agccugcugu acgugagccu ggacacccgg 2880
aaguacaagg ugcugaugaa guacgacacc cacaagaaca agaccauccc cguggccgag 2940
aaccccaacu ucaucuggaa gaaccacaag cugcccaacg acgugcccgg ucugggaccg 3000
cagauccuga ugaucgccgu guucacccug accggcaucc ugguggugcu gcugcugauc 3060
gcccugcugg uccugcggaa guaccggcgg gaccac 3096

<210> SEQ ID NO 85
<211> LENGTH: 1032
<212> TYPE: PRT
<213> ORGANISM: Artificial Sequence
<220> FEATURE:
<223> OTHER INFORMATION: Synthetic

<400> SEQUENCE: 85

Met Lys Thr Ile Ile Ala Leu Ser Tyr Ile Leu Cys Leu Gly Phe Thr
1 5 10 15

Gln Lys Ile Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Arg Ile Glu Val Thr Asn Ala Thr Glu Leu Val Gln Asn Ser Ser Ile
50 55 60

Gly Glu Ile Cys Asp Ser Pro His Gln Ile Leu Asp Gly Gly Asn Cys
65 70 75 80

Thr Leu Ile Asp Ala Leu Leu Gly Asp Pro Gln Cys Asp Gly Phe Gln
85 90 95

Asn Lys Lys Trp Asp Leu Phe Val Glu Arg Ser Arg Ala Tyr Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Lys Asn Glu Ser Phe Asn Trp Ala
130 135 140

Gly Val Thr Gln Asn Gly Lys Ser Phe Ser Cys Ile Arg Gly Ser Ser
145 150 155 160

Ser Ser Phe Phe Ser Arg Leu Asn Trp Leu Thr His Leu Asn Tyr Thr
165 170 175

Tyr Pro Ala Leu Asn Val Thr Met Pro Asn Lys Glu Gln Phe Asp Lys
180 185 190

```
Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile Gly Ser Gly Ser Gly Ser Thr Ser Leu Leu
                565                 570                 575

Gly Leu Ala Val Arg Leu Leu Leu Phe Gln Pro Ala Leu Met Val Phe
            580                 585                 590

Trp Ala Ser Gln Val Arg Gln Asn Cys Arg Asn Gly Ser Tyr Glu Ile
        595                 600                 605

Ser Val Leu Met Met Asp Asn Ser Ala Tyr Lys Glu Pro Met Gln Asn
```

-continued

```
    610                 615                 620

Leu Arg Glu Ala Val Glu Glu Gly Leu Asp Ile Val Arg Lys Arg Leu
625                 630                 635                 640

Arg Glu Ala Asp Leu Asn Val Thr Val Asn Ala Thr Phe Ile Tyr Ser
                645                 650                 655

Asp Gly Leu Ile His Lys Ser Gly Asp Cys Arg Ser Ser Thr Cys Glu
            660                 665                 670

Gly Leu Asp Leu Leu Arg Glu Ile Thr Arg Asp His Lys Met Gly Cys
        675                 680                 685

Ala Leu Met Gly Pro Ser Cys Thr Tyr Ser Thr Phe Gln Met Tyr Leu
    690                 695                 700

Asp Thr Glu Leu Asn Tyr Pro Met Ile Ser Ala Gly Ser Tyr Gly Leu
705                 710                 715                 720

Ser Cys Asp Tyr Lys Glu Thr Leu Thr Arg Ile Leu Pro Pro Ala Arg
                725                 730                 735

Lys Leu Met Tyr Phe Leu Val Asp Phe Trp Lys Val Asn Asn Ala Ser
            740                 745                 750

Phe Lys Pro Phe Ser Trp Asn Ser Ser Tyr Val Tyr Lys Asn Gly Ser
        755                 760                 765

Glu Pro Glu Asp Cys Phe Trp Tyr Leu Asn Ala Leu Glu Ala Gly Val
    770                 775                 780

Ser Tyr Phe Ser Glu Val Leu Asn Phe Lys Asp Val Leu Arg Arg Ser
785                 790                 795                 800

Glu Gln Phe Gln Glu Ile Leu Thr Gly His Asn Arg Lys Ser Asn Val
                805                 810                 815

Ile Val Met Cys Gly Thr Pro Glu Ser Phe Tyr Asp Val Lys Gly Asp
            820                 825                 830

Leu Gln Val Ala Glu Asp Thr Val Val Ile Leu Val Asp Leu Phe Ser
        835                 840                 845

Asn His Tyr Phe Glu Glu Asn Thr Thr Ala Pro Glu Tyr Met Asp Asn
    850                 855                 860

Val Leu Val Leu Thr Leu Pro Ser Glu Gln Ser Thr Ser Asn Thr Ser
865                 870                 875                 880

Val Ala Glu Arg Phe Ser Ser Gly Arg Ser Asp Phe Ser Leu Ala Tyr
                885                 890                 895

Leu Glu Gly Thr Leu Leu Phe Gly His Met Leu Gln Thr Phe Leu Glu
            900                 905                 910

Asn Gly Glu Asn Val Thr Gly Pro Lys Phe Ala Arg Ala Phe Arg Asn
        915                 920                 925

Leu Thr Phe Gln Gly Phe Ala Gly Pro Val Thr Leu Asp Asp Ser Gly
    930                 935                 940

Asp Ile Asp Asn Ile Met Ser Leu Leu Tyr Val Ser Leu Asp Thr Arg
945                 950                 955                 960

Lys Tyr Lys Val Leu Met Lys Tyr Asp Thr His Lys Asn Lys Thr Ile
                965                 970                 975

Pro Val Ala Glu Asn Pro Asn Phe Ile Trp Lys Asn His Lys Leu Pro
            980                 985                 990

Asn Asp Val Pro Gly Leu Gly Pro  Gln Ile Leu Met Ile  Ala Val Phe
        995                 1000                1005

Thr Leu  Thr Gly Ile Leu Val  Val Leu Leu Leu Ile  Ala Leu Leu
    1010                1015                1020

Val Leu  Arg Lys Tyr Arg Arg  Asp His
1025                1030
```

<210> SEQ ID NO 86
<211> LENGTH: 1874
<212> TYPE: RNA
<213> ORGANISM: Artificial Sequence
<220> FEATURE:
<223> OTHER INFORMATION: Synthetic

<400> SEQUENCE: 86
gggaaauaag agagaaaaga agaguaagaa gaaauauaag accccggcgc cgccaccaug 60
aagaccauca ucgcccugag cuacauccug ugccugggcu ucacccagaa gaucccggc 120 aacgauaaca gcaccgccac ccugugucug ggacaccacg ccgugcccaa cggcaccauc 180
gugaagacua ucaccaacga ccggaucgag gugaccaacg ccaccgagcu ggugcagaac 240
agcagcaucg gcgagaucug cgacagcccu caccagaucc uggacggcgg caacugcacc 300
cugaucgacg cacugcuggg cgacccucag ugcgacggcu uucagaacaa gaagugggac 360
cuguucgugg agagaucgcg ggccuacagc aacugcuacc ccuacgacgu ccccgacuac 420
gcaagccuga gaagccucgu ggccucaagc ggcacccugg aguucaagaa cgagagcuuc 480
aacugggccg gcgugaccca gaacggcaag ucauucagcu gcauccgggg cuccagcagc 540
agcuucuucu cacggcugaa cuggcugacc caccugaacu acaccuaccc cgcccugaac 600
gugaccaugc ccaacaagga gcaguucgac aagcuguaca ucuggggagu gcaccauccc 660
ggcaccgaca aggaccagau uagccuguac gcccagucua gcggccggau caccgugagc 720
accaagcgga gccagcaggc cgugaucccc aacaucggcu cucggcccag aauccgggac 780
auccccagcc ggaucagcau cuacuggacc auugugaagc ccggcgacau ccugcugauc 840
aacuccaccg gcaaccugau cgccccucgg ggcuauuuca agauccggag cggcaagagc 900
agcaucaugc ggagcgacgc ccccuaucggc aagugcaaga gcgagugcau cacacccaac 960
ggaagcaucc ccaacgacaa gcccuuccag aacgugaacc ggauaaccua cggcgccugc 1020
ccuagauacg ugaagcagaa cacccugaag cuggccaccg gcaugcggaa cgugcccgag 1080
aagcagacuc ggggcaucuu cggcgccauc gccggcuuca ucgagaacgg cugggagggc 1140
augguggacg gcugguacgg cuuccggcac cagaacucug agggcagagg acaggccgca 1200
gaccugaaga gcacccaggc cgccaucgac cagaucaacg gcaagcugaa ccggcugauc 1260
ggcaagacca acgagaaguu ccaccagauc gagaaggagu ucagcgaggu ggagggcagg 1320
guacaggacc uggagaagua cguggaggac accaagaucg accuguggag cuacaacgcc 1380
gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau cuccugcuuc 1680
cugcugugcg uggcccugcu ggguuucauc augugggccu gccagaaggg caacauccgg 1740
ugcaacaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 87
<211> LENGTH: 1698
<212> TYPE: RNA

<213> ORGANISM: Artificial Sequence
<220> FEATURE:
<223> OTHER INFORMATION: Synthetic

<400> SEQUENCE: 87

```
augaagacca ucaucgcccu gagcuacauc cugugccugg gcuucaccca gaagaucccc     60

ggcaacgaua acagcaccgc cacccugugu cugggacacc acgccgugcc caacggcacc    120

aucgugaaga cuaucaccaa cgaccggauc gaggugacca acgccaccga gcuggugcag    180

aacagcagca ucggcgagau cugcgacagc ccucaccaga uccuggacgg cggcaacugc    240

acccugaucg acgcacugcu gggcgacccu cagugcgacg gcuuucagaa caagaagugg    300

gaccuguucg uggagagauc gcgggccuac agcaacugcu accccuacga cguccccgac    360

uacgcaagcc ugagaagccu cguggccuca agcggcaccc uggaguucaa gaacgagagc    420

uucaacuggg ccggcgugac ccagaacggc aagucauuca gcugcauccg gggcuccagc    480

agcagcuucu ucucacggcu gaacuggcug acccaccuga acuacaccua ccccgcccug    540

aacgugacca ugcccaacaa ggagcaguuc gacaagcugu acaucugggg agugcaccau    600

cccggcaccg acaaggacca gauuagccug uacgcccagu cuagcggccg gaucaccgug    660

agcaccaagc ggagccagca ggccgugauc cccaacaucg gcucucggcc cagaauccgg    720

gacaucccca gccggaucag caucuacugg accauuguga agcccggcga cauccugcug    780

aucaacucca ccggcaaccu gaucgccccu cggggcuauu ucaagauccg gagcggcaag    840

agcagcauca ugcggagcga cgccccuauc ggcaagugca agagcgagug caucacaccc    900

aacggaagca uccccaacga caagcccuuc cagaacguga accggauaac cuacggcgcc    960

ugcccuagau acgugaagca gaacacccug aagcuggcca ccggcaugcg gaacgugccc   1020

gagaagcaga cucggggcau cuucggcgcc aucgccggcu ucaucgagaa cggcugggag   1080

ggcauggugg acggcuggua cggcuuccgg caccagaacu cugagggcag aggacaggcc   1140

gcagaccuga agagcaccca ggccgccauc gaccagauca acggcaagcu gaaccggcug   1200

aucggcaaga ccaacgagaa guuccaccag aucgagaagg aguucagcga gguggagggc   1260

aggguacagg accuggagaa guacguggag gacaccaaga ucgaccugug gagcuacaac   1320

gccgagcugc ugguagcccu ggagaaccag cacaccaucg accugaccga cagcgagaug   1380

aacaagcugu ucgagaagac caagaagcag cugcgggaga acgccgagga caugggcaac   1440

ggcugcuuca agaucuacca caagugcgac aacgccugca ucggcagcau ccggaacgag   1500

accuacgacc acaacgugua ccgggacgag gcccugaaca accgguucca gaucaagggc   1560

guggagcuga agagcggcua caaggacugg auccugugga ucagcuucgc caucuccugc   1620

uuccugcugu gcguggcccu gcuggguuuc aucauguggg ccugccagaa gggcaacauc   1680

cggugcaaca ucugcauc                                                 1698
```

<210> SEQ ID NO 88
<211> LENGTH: 566
<212> TYPE: PRT
<213> ORGANISM: Artificial Sequence
<220> FEATURE:
<223> OTHER INFORMATION: Synthetic

<400> SEQUENCE: 88

```
Met Lys Thr Ile Ile Ala Leu Ser Tyr Ile Leu Cys Leu Gly Phe Thr
1               5                   10                  15

Gln Lys Ile Pro Gly Asn Asp Asn Ser Thr Ala Thr Leu Cys Leu Gly
            20                  25                  30
```

-continued

```
His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Gly Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Ala
    130                 135                 140

Gly Val Thr Gln Asn Gly Lys Ser Phe Ser Cys Ile Arg Gly Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445
```

```
Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 89
<211> LENGTH: 1874
<212> TYPE: RNA
<213> ORGANISM: Artificial Sequence
<220> FEATURE:
<223> OTHER INFORMATION: Synthetic

<400> SEQUENCE: 89

gggaaauaag agagaaaaga agaguaagaa gaaauauaag accccggcgc cgccaccaug     60

aagaccauca ucgcccugag cuacauccug ugccuggugu ucgcccagaa gauccccggc    120

aacgauaaca gcaccgccac ccugugucug ggacaccacg ccgugcccaa cggcaccauc    180

gugaagacua ucaccaacga ccggaucgag gugaccaacg ccaccgagcu ggugcagaac    240

agcagcaucg gcgagaucug cgacagcccu caccagaucc uggacggcgg caacugcacc    300

cugaucgacg cacugcuggg cgacccucag ugcgacggcu uucagaacaa ggagugggac    360

cuguucgugg agagaucgcg ggccaacagc aacugcuacc ccuacgacgu ccccgacuac    420

gcaagccuga gaagccucgu ggccucaagc ggcacccugg aguucaagaa cgagagcuuc    480

aacuggaccg gcgugaagca gaacggcacc ucaagcgccu gcauccgggg cuccagcagc    540

agcuucuucu cacggcugaa cuggcugacc caccugaacu acaccuaccc cgcccugaac    600

gugaccaugc ccaacaacga gcaguucgac aagcuguaca ucuggggagu gcaccauccc    660

agcaccgaca aggaccagau uagccuguuc gcccagccca gcggccggau caccgugagc    720

accaagcgga gccagcaggc cgugaucccc aacaucggcu cucggcccag aauccgggac    780

auccccagcc ggaucagcau cuacuggacc auugugaagc ccggcgacau ccugcugauc    840

aacuccaccg gcaaccugau cgccccucgg ggcuauuuca agauccggag cggcaagagc    900

agcaucaugc ggagcgacgc cccuaucggc aagugcaaga gcgagugcau cacacccaac    960

ggaagcaucc ccaacgacaa gcccuuccag aacgugaacc ggauaaccua cggcgccugc   1020

ccuagauacg ugaagcagag cacccugaag cuggccaccg gcaugcggaa cgugcccgag   1080

aagcagacuc ggggcaucuu cggcgccauc gccggcuuca ucgagaacgg cugggagggc   1140

augguggacg gcugguacgg cuuccggcac cagaacucug agggcagagg acaggccgca   1200

gaccugaaga gcacccaggc cgccaucgac cagaucaacg gcaagcugaa ccggcugauc   1260

ggcaagacca acgagaaguu ccaccagauc gagaaggagu ucagcgaggu ggagggcagg   1320

guacaggacc uggagaagua cguggaggac accaagaucg accuguggag cuacaacgcc   1380
```

gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau guccugcuuc 1680
cugcugugca ucgcccugcu ggguuucauc augugggccu gccagaaggg caacauccgg 1740
ugcaacaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 90
<211> LENGTH: 1698
<212> TYPE: RNA
<213> ORGANISM: Artificial Sequence
<220> FEATURE:
<223> OTHER INFORMATION: Synthetic

<400> SEQUENCE: 90
augaagacca ucaucgcccu gagcuacauc cugugccugg uguucgccca gaagaucccc 60
ggcaacgaua acagcaccgc cacccugugu cugggacacc acgccgugcc caacggcacc 120
aucgugaaga cuaucaccaa cgaccggauc gaggugacca acgccaccga gcuggugcag 180
aacagcagca ucggcgagau cugcgacagc ccucaccaga uccuggacgg cggcaacugc 240
acccugaucg acgcacugcu gggcgacccu cagugcgacg gcuuucagaa caaggagugg 300
gaccuguucg uggagagauc gcgggccaac agcaacugcu accccuacga cguccccgac 360
uacgcaagcc ugagaagccu cguggccuca agcggcaccc uggaguucaa gaacgagagc 420
uucaacugga ccggcgugaa gcagaacggc accucaagcg ccugcauccg gggcuccagc 480
agcagcuucu ucucacggcu gaacuggcug acccaccuga acuacaccua ccccgcccug 540
aacgugacca ugcccaacaa cgagcaguuc gacaagcugu acaucugggg agugcaccau 600
cccagcaccg acaaggacca gauuagccug uucgcccagc ccagcggccg gaucaccgug 660
agcaccaagc ggagccagca ggccgugauc cccaacaucg gcucucggcc cagaauccgg 720
gacaucccca gccggaucag caucuacugg accauuguga agcccggcga cauccugcug 780
aucaacucca ccggcaaccu gaucgccccu cggggcuauu ucaagauccg gagcggcaag 840
agcagcauca ugcggagcga cgccccuauc ggcaagugca agagcgagug caucacaccc 900
aacggaagca uccccaacga caagcccuuc cagaacguga accggauaac cuacggcgcc 960
ugcccuagau acgugaagca gagcacccug aagcuggcca ccggcaugcg gaacgugccc 1020
gagaagcaga cucggggcau cuucggcgcc aucgccggcu ucaucgagaa cggcugggag 1080
ggcauggugg acggcuggua cggcuuccgg caccagaacu cugagggcag aggacaggcc 1140
gcagaccuga agagcaccca ggccgccauc gaccagauca acggcaagcu gaaccggcug 1200
aucggcaaga ccaacgagaa guuccaccag aucgagaagg aguucagcga gguggagggc 1260
aggguacagg accuggagaa guacguggag gacaccaaga ucgaccugug gagcuacaac 1320
gccgagcugc ugguagcccu ggagaaccag cacaccaucg accugaccga cagcgagaug 1380
aacaagcugu ucgagaagac caagaagcag cugcgggaga acgccgagga caugggcaac 1440
ggcugcuuca agaucuacca caagugcgac aacgccugca ucggcagcau ccggaacgag 1500
accuacgacc acaacgugua ccgggacgag gcccugaaca accgguucca gaucaagggc 1560
guggagcuga agagcggcua caaggacugg auccugugga ucagcuucgc cauguccugc 1620
uuccugcugu gcaucgcccu gcuggguuuc aucauguggg ccugccagaa gggcaacauc 1680
cggugcaaca ucugcauc 1698

<210> SEQ ID NO 91
<211> LENGTH: 566
<212> TYPE: PRT
<213> ORGANISM: Artificial Sequence
<220> FEATURE:
<223> OTHER INFORMATION: Synthetic

<400> SEQUENCE: 91

Met Lys Thr Ile Ile Ala Leu Ser Tyr Ile Leu Cys Leu Val Phe Ala
1 5 10 15

Gln Lys Ile Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Arg Ile Glu Val Thr Asn Ala Thr Glu Leu Val Gln Asn Ser Ser Ile
50 55 60

Gly Glu Ile Cys Asp Ser Pro His Gln Ile Leu Asp Gly Gly Asn Cys
65 70 75 80

Thr Leu Ile Asp Ala Leu Leu Gly Asp Pro Gln Cys Asp Gly Phe Gln
85 90 95

Asn Lys Glu Trp Asp Leu Phe Val Glu Arg Ser Arg Ala Asn Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Lys Asn Glu Ser Phe Asn Trp Thr
130 135 140

Gly Val Lys Gln Asn Gly Thr Ser Ser Ala Cys Ile Arg Gly Ser Ser
145 150 155 160

Ser Ser Phe Phe Ser Arg Leu Asn Trp Leu Thr His Leu Asn Tyr Thr
165 170 175

Tyr Pro Ala Leu Asn Val Thr Met Pro Asn Asn Glu Gln Phe Asp Lys
180 185 190

Leu Tyr Ile Trp Gly Val His His Pro Ser Thr Asp Lys Asp Gln Ile
195 200 205

Ser Leu Phe Ala Gln Pro Ser Gly Arg Ile Thr Val Ser Thr Lys Arg
210 215 220

Ser Gln Gln Ala Val Ile Pro Asn Ile Gly Ser Arg Pro Arg Ile Arg
225 230 235 240

Asp Ile Pro Ser Arg Ile Ser Ile Tyr Trp Thr Ile Val Lys Pro Gly
245 250 255

Asp Ile Leu Leu Ile Asn Ser Thr Gly Asn Leu Ile Ala Pro Arg Gly
260 265 270

Tyr Phe Lys Ile Arg Ser Gly Lys Ser Ser Ile Met Arg Ser Asp Ala
275 280 285

Pro Ile Gly Lys Cys Lys Ser Glu Cys Ile Thr Pro Asn Gly Ser Ile
290 295 300

Pro Asn Asp Lys Pro Phe Gln Asn Val Asn Arg Ile Thr Tyr Gly Ala
305 310 315 320

Cys Pro Arg Tyr Val Lys Gln Ser Thr Leu Lys Leu Ala Thr Gly Met

```
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Met Ser Cys Phe Leu Leu Cys
    530                 535                 540

Ile Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 92
<211> LENGTH: 1874
<212> TYPE: RNA
<213> ORGANISM: Artificial Sequence
<220> FEATURE:
<223> OTHER INFORMATION: Synthetic

<400> SEQUENCE: 92

```
gggaaauaag agagaaaaga agaguaagaa gaaauauaag accccggcgc cgccaccaug     60

aaggccaucc uggucgugau gcuguacacc uucaccaccg ccaacgccga cacccugugc    120

aucggcuacc acgccaacaa cagcaccgac accguggaca ccgugcugga gaagaacgug    180

accgugaccc acagcgugaa ccugcuggag gacaagcaca acggcaagcu gugcaagcug    240

aggggagugg caccccugca ccugggcaag ugcaacaucg ccggcuggau ccugggcaac    300

cccgagugcg agagccugag cacagcccgg agcuggagcu acaucgugga gaccagcaac    360

agcgacaacg gcaccuguua ccccggcgac uucaucaacu acgaggagcu gcgggagcag    420

cugagcagcg ugagcagcuu cgagcgguuc gagaucuucc ccaagaccag cagcuggccc    480

aaccacgaca gcgacaacgg cgugacagca gccuguccac acgccggagc caagagcuuc    540

uacaagaacc ugaucuggcu ggugaagaag ggcaagagcu accccaagau caaccagacc    600

uacaucaacg acaagggcaa ggaggugcug gugcuguggg gcauccacca cccaccuacc    660
```

aucgccgacc agcagagccu guaccagaac gccgacgccu acguguucgu gggcaccagc 720
cgguacagca agaaguucaa gccagagauc gccacccggc ccaaggugag agaccaggag 780
ggccggauga acuacuacug gacccuggug gagcccggag acaagauuac cuucgaggcc 840
accggcaacc ugguggcccc ucgguacgcc uucaccaugg aacgggacgc uggcagcggc 900
aucaucauca gcgacacucc cgugcacgac ugcaacacca ccugccagac ucccgagggc 960
gcuaucaaca ccagccugcc cuuccagaac gugcacccca ucaccaucgg caagugcccc 1020
aaguacguaa agagcaccaa auugcggcug gccaccggac ucaggaacgu gcccagcauc 1080
caaagccggg gccuguuugg cgcaaucgcc ggcuucaucg agggcggcug gacuggcaug 1140
guggacggcu gguacggcua ccaccaccag aacgaacagg ggagcggcua cgcagcugac 1200
cugaagagca cccagaacgc caucgacaag aucaccaaca aggugaacag cgugaucgag 1260
aagaugaaca cccaguucac cgccgugggc aaggaguuca accaccugga gaagcggauc 1320
gagaaccuga acaagaaggu ggacgacggc uuccuggaca ucuggaccua caacgccgag 1380
cugcugguuc ugcuggagaa cgagcggacc cuggacuauc acgacagcaa cgugaagaac 1440
cuguacgaga aggugcggaa ccagcugaag aacaacgcca aggagaucgg caacggcugc 1500
uucgaguucu accacaagug cgacaacacc ugcauggaga gcgugaagaa cggcaccuac 1560
gacuacccca aguacagcga ggaggccaag cugaaccggg agaagaucga cggcgugaag 1620
cuggacagca cccggaucua ccagauccug gccaucuaca gcaccguggc cagcagccug 1680
gugcuggugg ugagccuggg cgccaucagc uucuggaugu gcagcaacgg cagccugcag 1740
ugccggaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 93
<211> LENGTH: 1698
<212> TYPE: RNA
<213> ORGANISM: Artificial Sequence
<220> FEATURE:
<223> OTHER INFORMATION: Synthetic

<400> SEQUENCE: 93
augaaggcca uccuggucgu gaugcuguac accuucacca ccgccaacgc cgacacccug 60
ugcaucggcu accacgccaa caacagcacc gacaccgugg acaccgugcu ggagaagaac 120
gugaccguga cccacagcgu gaaccugcug gaggacaagc acaacggcaa gcugugcaag 180
cugaggggag uggcaccccu gcaccugggc aagugcaaca ucgccggcug gauccugggc 240
aaccccgagu gcgagagccu gagcacagcc cggagcugga gcuacaucgu ggagaccagc 300
aacagcgaca acggcaccug uuaccccggc gacuucauca acuacgagga gcugcgggag 360
cagcugagca gcgugagcag cuucgagcgg uucgagaucu uccccaagac cagcagcugg 420
cccaaccacg acagcgacaa cggcgugaca gcagccuguc cacacgccgg agccaagagc 480
uucuacaaga accugaucug gcuggugaag aagggcaaga gcuaccccaa gaucaaccag 540
accuacauca acgacaaggg caaggaggug cuggugcugu ggggcaucca ccacccaccu 600
accaucgccg accagcagag ccuguaccag aacgccgacg ccuacguguu cgugggcacc 660
agccgguaca gcaagaaguu caagccagag aucgccaccc ggcccaaggu gagagaccag 720
gagggccgga ugaacuacua cuggacccug guggagcccg gagacaagau uaccuucgag 780
gccaccggca accugguggc cccucgguac gccuucacca uggaacggga cgcuggcagc 840

-continued

```
ggcaucauca ucagcgacac ucccgugcac gacugcaaca ccaccugcca gacucccgag     900

ggcgcuauca acaccagccu gcccuuccag aacgugcacc ccaucaccau cggcaagugc     960

cccaaguacg uaaagagcac caaauugcgg cuggccaccg gacucaggaa cgugcccagc    1020

auccaaagcc ggggccuguu uggcgcaauc gccggcuuca ucgagggcgg cuggacuggc    1080

augguggacg gcugguacgg cuaccaccac cagaacgaac aggggagcgg cuacgcagcu    1140

gaccugaaga gcacccagaa cgccaucgac aagaucacca acaaggugaa cagcgugauc    1200

gagaagauga acacccaguu caccgccgug ggcaaggagu ucaaccaccu ggagaagcgg    1260

aucgagaacc ugaacaagaa gguggacgac ggcuuccugg acaucuggac cuacaacgcc    1320

gagcugcugg uucugcugga gaacgagcgg acccuggacu aucacgacag caacgugaag    1380

aaccuguacg agaaggugcg gaaccagcug aagaacaacg ccaaggagau cggcaacggc    1440

ugcuucgagu ucuaccacaa gugcgacaac accugcaugg agagcgugaa gaacggcacc    1500

uacgacuacc ccaaguacag cgaggaggcc aagcugaacc gggagaagau cgacggcgug    1560

aagcuggaca gcacccggau cuaccagauc cuggccaucu acagcaccgu ggccagcagc    1620

cuggugcugg uggugagccu gggcgccauc agcuucugga ugugcagcaa cggcagccug    1680

cagugccgga ucugcauc                                                  1698
```

<210> SEQ ID NO 94
<211> LENGTH: 566
<212> TYPE: PRT
<213> ORGANISM: Artificial Sequence
<220> FEATURE:
<223> OTHER INFORMATION: Synthetic

<400> SEQUENCE: 94

```
Met Lys Ala Ile Leu Val Val Met Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Arg Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asp Asn Gly Val Thr Ala Ala Cys Pro His Ala Gly Ala Lys Ser
145                 150                 155                 160

Phe Tyr Lys Asn Leu Ile Trp Leu Val Lys Lys Gly Lys Ser Tyr Pro
                165                 170                 175

Lys Ile Asn Gln Thr Tyr Ile Asn Asp Lys Gly Lys Glu Val Leu Val
            180                 185                 190

Leu Trp Gly Ile His His Pro Pro Thr Ile Ala Asp Gln Gln Ser Leu
        195                 200                 205
```

```
Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Ala Pro Arg Tyr Ala Phe
            260                 265                 270

Thr Met Glu Arg Asp Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Asp Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 95
<211> LENGTH: 1874
<212> TYPE: RNA
<213> ORGANISM: Artificial Sequence
<220> FEATURE:
<223> OTHER INFORMATION: Synthetic

<400> SEQUENCE: 95
gggaaauaag agagaaaaga agaguaagaa gaaauauaag accccggcgc cgccaccaug 60
aaggccaucc uggucgugau gcuguacacc uucaccaccg ccaacgccga cacccugugc 120
aucggcuacc acgccaacaa cagcaccgac accguggaca ccgugcugug caagaacgug 180
accgugaccc acagcgugaa ccugcuggag gacaagcaca acggcaagcu gugcaagcug 240
aggggagugg caccccugca ccugggcaag ugcaacaucg ccggcuggau ccugggcaac 300
cccgagugcg agagccugag cacagcccgg agcuggagcu acaucgugga gaccagcaac 360
agcgacaacg gcaccuguua ccccggcgac uucaucaacu acgaggagcu gcgggagcag 420
cugagcagcg ugagcagcuu cgagcgguuc gagaucuucc ccaagaccag cagcuggccc 480
aaccacgaca gcgacaacgg cgugacagca gccuguccac acgccggagc caagagcuuc 540
uacaagaacc ugaucuggcu ggugaagaag ggcaagagcu accccaagau caaccagacc 600
uacaucaacg acaagggcaa ggaggugcug gugcuguggg gcauccacca cccaccuacc 660
aucgccgacc agcagagccu guaccagaac gccgacgccu acguguucgu gggcaccagc 720
cgguacagca agaaguucaa gccagagauc gccacccggc ccaaggugag agaccaggag 780
ggccggauga acuacuacug gacccuggug gagcccggag acaagauuac cuucgaggcc 840
accggcaacc ugguggcccc ucgguacgcc uucaccaugg aacgggacgc uggcagcggc 900
aucaucauca gcgacacucc cgugcacgac ugcaacacca ccugccagac ucccgagggc 960
gcuaucaaca ccagccugcc cuuccagaac gugcacccca ucaccaucgg caagugcccc 1020
aaguacguaa agagcaccaa auugcggcug gccaccggac ucaggaacgu gcccagcauc 1080
caaagccggg gccuguuugg cgcaaucgcc ggcuucaucg agggcggcug gacuggcaug 1140
guggacggcu gguacggcua ccaccaccag aacgaacagg ggagcggcua cgcagcugac 1200
cugaagagca cccagaacgc caucgacugc aucaccaaca aggugaacag cgugaucgag 1260
aagaugaaca cccaguucac cgccgugggc aaggaguuca accaccugga gaagcggauc 1320
gagaaccuga acaagaaggu ggacgacggc uuccuggaca ucuggaccua caacgccgag 1380
cugcugguuc ugcuggagaa cgagcggacc cuggacuauc acgacagcaa cgugaagaac 1440
cuguacgaga aggugcggaa ccagcugaag aacaacgcca aggagaucgg caacggcugc 1500
uucgaguucu accacaagug cgacaacacc ugcauggaga gcgugaagaa cggcaccuac 1560
gacuacccca aguacagcga ggaggccaag cugaaccggg agaagaucga cggcgugaag 1620
cuggacagca cccggaucua ccagauccug gccaucuaca gcaccguggc cagcagccug 1680
gugcuggugg ugagccuggg cgccaucagc uucuggaugu gcagcaacgg cagccugcag 1740
ugccggaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 96
<211> LENGTH: 1698
<212> TYPE: RNA
<213> ORGANISM: Artificial Sequence
<220> FEATURE:
<223> OTHER INFORMATION: Synthetic

<400> SEQUENCE: 96
augaaggcca uccuggucgu gaugcuguac accuucacca ccgccaacgc cgacacccug 60
ugcaucggcu accacgccaa caacagcacc gacaccgugg acaccgugcu gugcaagaac 120

-continued

```
gugaccguga cccacagcgu gaaccugcug gaggacaagc acaacggcaa gcugugcaag    180

cugaggggag uggcaccccu gcaccugggc aagugcaaca ucgccggcug gauccugggc    240

aaccccgagu gcgagagccu gagcacagcc cggagcugga gcuacaucgu ggagaccagc    300

aacagcgaca acggcaccug uuaccccggc gacuucauca acuacgagga gcugcgggag    360

cagcugagca gcgugagcag cuucgagcgg uucgagaucu uccccaagac cagcagcugg    420

cccaaccacg acagcgacaa cggcgugaca gcagccuguc cacacgccgg agccaagagc    480

uucuacaaga accugaucug gcuggugaag aagggcaaga gcuaccccaa gaucaaccag    540

accuacauca acgacaaggg caaggaggug cuggugcugu ggggcaucca ccacccaccu    600

accaucgccg accagcagag ccuguaccag aacgccgacg ccuacguguu cgugggcacc    660

agccgguaca gcaagaaguu caagccagag aucgccaccc ggcccaaggu gagagaccag    720

gagggccgga ugaacuacua cuggacccug guggagcccg gagacaagau uaccuucgag    780

gccaccggca accugguggc cccucgguac gccuucacca uggaacggga cgcuggcagc    840

ggcaucauca ucagcgacac ucccgugcac gacugcaaca ccaccugcca gacucccgag    900

ggcgcuauca acaccagccu gcccuuccag aacgugcacc ccaucaccau cggcaagugc    960

cccaaguacg uaaagagcac caaauugcgg cuggccaccg gacucaggaa cgugcccagc   1020

auccaaagcc ggggccuguu uggcgcaauc gccggcuuca ucgagggcgg cuggacuggc   1080

augguggacg gcugguacgg cuaccaccac cagaacgaac aggggagcgg cuacgcagcu   1140

gaccugaaga gcacccagaa cgccaucgac ugcaucacca acaaggugaa cagcgugauc   1200

gagaagauga acacccaguu caccgccgug ggcaaggagu ucaaccaccu ggagaagcgg   1260

aucgagaacc ugaacaagaa gguggacgac ggcuuccugg acaucuggac cuacaacgcc   1320

gagcugcugg uucugcugga gaacgagcgg acccuggacu aucacgacag caacgugaag   1380

aaccuguacg agaaggugcg gaaccagcug aagaacaacg ccaaggagau cggcaacggc   1440

ugcuucgagu ucuaccacaa gugcgacaac accugcaugg agagcgugaa gaacggcacc   1500

uacgacuacc ccaaguacag cgaggaggcc aagcugaacc gggagaagau cgacggcgug   1560

aagcuggaca gcacccggau cuaccagauc cuggccaucu acagcaccgu ggccagcagc   1620

cuggugcugg uggugagccu gggcgccauc agcuucugga ugugcagcaa cggcagccug   1680

cagugccgga ucugcauc                                                 1698
```

```
<210> SEQ ID NO 97
<211> LENGTH: 566
<212> TYPE: PRT
<213> ORGANISM: Artificial Sequence
<220> FEATURE:
<223> OTHER INFORMATION: Synthetic

<400> SEQUENCE: 97

Met Lys Ala Ile Leu Val Val Met Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Cys Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80
```

-continued

```
Asn Pro Glu Cys Glu Ser Leu Ser Thr Ala Arg Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asp Asn Gly Val Thr Ala Ala Cys Pro His Ala Gly Ala Lys Ser
145                 150                 155                 160

Phe Tyr Lys Asn Leu Ile Trp Leu Val Lys Lys Gly Lys Ser Tyr Pro
                165                 170                 175

Lys Ile Asn Gln Thr Tyr Ile Asn Asp Lys Gly Lys Glu Val Leu Val
            180                 185                 190

Leu Trp Gly Ile His His Pro Pro Thr Ile Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Ala Pro Arg Tyr Ala Phe
            260                 265                 270

Thr Met Glu Arg Asp Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Cys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

-continued

```
            500                 505                 510

Asn Arg Glu Lys Ile Asp Gly Val Lys Leu Asp Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 98
<211> LENGTH: 1874
<212> TYPE: RNA
<213> ORGANISM: Artificial Sequence
<220> FEATURE:
<223> OTHER INFORMATION: Synthetic

<400> SEQUENCE: 98

gggaaauaag agagaaaaga agaguaagaa gaaauauaag accccggcgc cgccaccaug     60

aaggccaucc uggucgugau gcuguacacc uucaccaccg ccaacgccga cacccugugc    120

aucggcuacc acgccaacaa cagcaccgac accguggaca ccgugcugug caagaacgug    180

accgugaccc acagcgugaa ccugcuggag gacaagcaca acggcaagcu gugcaagcug    240

aggggagugg caccccugca ccugggcaag ugcaacaucg ccggcuggau ccugggcaac    300

cccgagugcg agagccugag cacagcccgg agcuggagcu acaucgugga gaccagcaac    360

agcgacaacg gcaccuguua ccccggcgac uucaucaacu acgaggagcu gcgggagcag    420

cugagcagcg ugagcagcuu cgagcgguuc gagaucuucc ccaagaccag cagcuggccc    480

aaccacgaca gcgacaacgg cgugacagca gccuguccac acgccggagc caagagcuuc    540

uacaagaacc ugaucuggcu ggugaagaag ggcaagagcu accccaagau caaccagacc    600

uacaucaacg acaagggcaa ggaggugcug gugcuguggg gcauccacca cccaccuacc    660

aucgccgacc agcagagccu guaccagaac gccgacgccu acguguucgu gggcaccagc    720

cgguacagca agaaguucaa gccagagauc gccacccggc ccaaggugag agaccaggag    780

ggccggauga acuacuacug gacccuggug gagcccggag acaagauuac cuucgaggcc    840

accggcaacc ugguggcccc ucgguacgcc uucaccaugg aacgggacgc uggcagcggc    900

aucaucauca gcgacacucc cgugcacgac ugcaacacca ccugccagac ucccgagggc    960

gcuaucaaca ccagccugcc cuuccagaac gugcacccca ucaccaucgg caagugcccc   1020

aaguacguaa agagcaccaa auugcggcug gccaccggac ucaggaacgu gcccagcauc   1080

caagccgccg gccuguuugg cgcaaucgcc ggcuucaucg agggcggcug gacuggcaug   1140

guggacggcu gguacggcua ccaccaccag aacgaacagg ggagcggcua cgcagcugac   1200

cugaagagca cccagaacgc caucgacugc aucaccaaca aggugaacag cgugaucgag   1260

aagaugaaca cccaguucac cgccgugggc aaggaguuca accaccugga gaagcggauc   1320

gagaaccuga acaagaaggu ggacgacggc uuccuggaca ucuggaccua caacgccgag   1380

cugcugguuc ugcuggagaa cgagcggacc cuggacuauc acgacagcaa cgugaagaac   1440

cuguacgaga aggugcggaa ccagcugaag aacaacgcca aggagaucgg caacggcugc   1500

uucgaguucu accacaagug cgacaacacc ugcauggaga gcgugaagaa cggcaccuac   1560

gacuacccca aguacagcga ggaggccaag cugaaccggg agaagaucga cggcgugaag   1620

cuggacagca cccggaucua ccagauccug gccaucuaca gcaccguggc cagcagccug   1680
```

-continued gugcuggugg ugagccuggg cgccaucagc uucuggaugu gcagcaacgg cagccugcag 1740
ugccggaucu gcaucugaua auaggcugga gccucggugg ccuagcuucu ugccccuugg 1800
gccucccccc agccccuccu ccccuuccug cacccguacc cccguggucu uugaauaaag 1860
ucugaguggg cggc 1874

<210> SEQ ID NO 99
<211> LENGTH: 1698
<212> TYPE: RNA
<213> ORGANISM: Artificial Sequence
<220> FEATURE:
<223> OTHER INFORMATION: Synthetic

<400> SEQUENCE: 99
augaaggcca uccuggucgu gaugcuguac accuucacca ccgccaacgc cgacacccug 60
ugcaucggcu accacgccaa caacagcacc gacaccgugg acaccgugcu gugcaagaac 120
gugaccguga cccacagcgu gaaccugcug gaggacaagc acaacggcaa gcugugcaag 180
cugaggggag uggcaccccu gcaccugggc aagugcaaca ucgccggcug gauccugggc 240
aaccccgagu gcgagagccu gagcacagcc cggagcugga gcuacaucgu ggagaccagc 300
aacagcgaca acggcaccug uuaccccggc gacuucauca acuacgagga gcugcgggag 360
cagcugagca gcgugagcag cuucgagcgg uucgagaucu uccccaagac cagcagcugg 420
cccaaccacg acagcgacaa cggcgugaca gcagccuguc cacacgccgg agccaagagc 480
uucuacaaga accugaucug gcuggugaag aagggcaaga gcuaccccaa gaucaaccag 540
accuacauca acgacaaggg caaggaggug cuggugcugu ggggcaucca ccacccaccu 600
accaucgccg accagcagag ccuguaccag aacgccgacg ccuacguguu cgugggcacc 660
agccgguaca gcaagaaguu caagccagag aucgccaccc ggcccaaggu gagagaccag 720
gagggccgga ugaacuacua cuggacccug guggagcccg gagacaagau uaccuucgag 780
gccaccggca accugguggc cccucgguac gccuucacca uggaacggga cgcuggcagc 840
ggcaucauca ucagcgacac ucccgugcac gacugcaaca ccaccugcca gacucccgag 900
ggcgcuauca acaccagccu gcccuuccag aacgugcacc ccaucaccau cggcaagugc 960
cccaaguacg uaaagagcac caaauugcgg cuggccaccg gacucaggaa cgugcccagc 1020
auccaagccg ccggccuguu uggcgcaauc gccggcuuca ucgagggcgg cuggacuggc 1080
augguggacg gcugguacgg cuaccaccac cagaacgaac aggggagcgg cuacgcagcu 1140
gaccugaaga gcacccagaa cgccaucgac ugcaucacca acaaggugaa cagcgugauc 1200
gagaagauga acacccaguu caccgccgug ggcaaggagu ucaaccaccu ggagaagcgg 1260
aucgagaacc ugaacaagaa gguggacgac ggcuuccugg acaucuggac cuacaacgcc 1320
gagcugcugg uucugcugga gaacgagcgg acccuggacu aucacgacag caacgugaag 1380
aaccuguacg agaaggugcg gaaccagcug aagaacaacg ccaaggagau cggcaacggc 1440
ugcuucgagu ucuaccacaa gugcgacaac accugcaugg agagcgugaa gaacggcacc 1500
uacgacuacc ccaaguacag cgaggaggcc aagcugaacc gggagaagau cgacggcgug 1560
aagcuggaca gcacccggau cuaccagauc cuggccaucu acagcaccgu ggccagcagc 1620
cuggugcugg uggugagccu gggcgccauc agcuucugga ugugcagcaa cggcagccug 1680
cagugccgga ucugcauc 1698

<210> SEQ ID NO 100

<211> LENGTH: 566
<212> TYPE: PRT
<213> ORGANISM: Artificial Sequence
<220> FEATURE:
<223> OTHER INFORMATION: Synthetic

<400> SEQUENCE: 100

```
Met Lys Ala Ile Leu Val Val Met Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Cys Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Arg Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asp Asn Gly Val Thr Ala Ala Cys Pro His Ala Gly Ala Lys Ser
145                 150                 155                 160

Phe Tyr Lys Asn Leu Ile Trp Leu Val Lys Lys Gly Lys Ser Tyr Pro
                165                 170                 175

Lys Ile Asn Gln Thr Tyr Ile Asn Asp Lys Gly Lys Glu Val Leu Val
            180                 185                 190

Leu Trp Gly Ile His His Pro Pro Thr Ile Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Ala Pro Arg Tyr Ala Phe
            260                 265                 270

Thr Met Glu Arg Asp Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ala Ala Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380
```

```
Thr Gln Asn Ala Ile Asp Cys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Asp Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 101
<211> LENGTH: 1868
<212> TYPE: RNA
<213> ORGANISM: Artificial Sequence
<220> FEATURE:
<223> OTHER INFORMATION: Synthetic

<400> SEQUENCE: 101

```
gggaaauaag agagaaaaga agaguaagaa gaaauauaag accccggcgc cgccaccaug      60

gagaacauug uguuacugcu ggccauugug ucacugguga aauccgacca gauuugcauu     120

gguuaccacg ccaauaacuc aaccgagcag guggauacua ucauggagaa gaacguaacc     180

gucacccacg cccaggacau uuuggagaag acacauaacg guaaacucug ugaccugaac     240

ggggugaagc ccuugauacu gaaggauugc ucuguagcgg gcuggcuacu cggaaauccu     300

augugcgacg aauuuauucg cguaccugag uggaguuaua ucguugagag agccaaucca     360

gcuaacgauc ugugcuaucc uggcagucug aacgauuacg aagagcuuaa acaccuccug     420

ucccggauua accauuucga gaagauauug auaaucccga agagcagcug gccaaaucac     480

gaaaccuccc ugggagugag cgcugcuugc cccuaccagg gagccccuuc auucuucagg     540

aacgugguuu ggcugaucaa gaagaacgac gcauacccaa cuauuaagau cuccuacaau     600

aauaccaacc gggaggaccu gcuaaucuug uggggguaucc aucacagcaa caacgcagaa     660

gagcaaacua accuguauaa gaacccgacc accuauaucu cggucggaac aagcacguua     720

aaccagcggu uggucccgaa gaucgccaca aggucucagg ugaacggcca gagaggaaga     780

auggacuucu ucuggaccau auugaagcca gacgacgcaa uacauuucga gucuaacgga     840

aacuucauug cuccggaaua cgcguacaag auuguuaaga agggcgauuc gaccauuaug     900

aaaucagggg uggaauacgg ucacuguaac accaagugcc aaacuccugu gggcgcuauu     960
```

-continued

```
aacucaucaa ugcccuucca caauauucac ccacugacua uuggugagug cccgaaauac   1020
guaaagucua auaaacucgu guuggcgacc ggccuaagaa acagcccaca gaucgagacc   1080
aggggcuugu uuggggcgau ugcaggauuu aucgaaggcg gcuggcaggg uaugguggac   1140
ggcugguacg gauaucauca cagcaacgaa caagggucag gauacgccgc agacaaagaa   1200
ucgacucaga aagcuauaga cggagugacg aacaaaguga acucgaucau ugauaagaug   1260
aauacacagu uugaagcggu cggcagagaa uuuaacaacu uggaacggag aauugagaau   1320
cugaacaaga agauggagga cggcuuucug gacgugugga cuuauaacgc cgagcuccuc   1380
gugcugaugg agaacgaaag gacucuugac uuucacgauu caaacgucaa gaaccuguac   1440
gacaagguua gauugcagcu gcgggacaac gccaaagaac uggguaacgg cuguuucgag   1500
uucuaccaua agugcgauaa cgagugcaug gaaucuguca gaaacgguac cuacgacuau   1560
ccccaguauu cugaagaggc ccgccucaaa cgagaggaga ucucuggagu gaagcuggag   1620
uccauuggca cguaccaaau ucugucaauc uacuccaccg cugcaucaag ccuagcucug   1680
gcgaucauga uggcggggcu cagucugugg auguguucaa acgguucccu gcagugucgc   1740
auuuguaucu gauaaauaggc uggagccucg guggccuagc uucuugcccc uugggccucc   1800
ccccagcccc uccuccccuu ccugcacccg uacccccgug gucuuugaau aaagucugag   1860
ugggcggc                                                            1868
```

```
<210> SEQ ID NO 102
<211> LENGTH: 1692
<212> TYPE: RNA
<213> ORGANISM: Artificial Sequence
<220> FEATURE:
<223> OTHER INFORMATION: Synthetic

<400> SEQUENCE: 102
```

```
auggagaaca uuguguuacu gcuggccauu gugucacugg ugaaauccga ccagauuugc     60
auugguuacc acgccaauaa cucaaccgag cagguggaua cuaucaugga gaagaacgua    120
accgucaccc acgcccagga cauuuuggag aagacacaua acgguaaacu cugugaccug    180
aacgggguga agcccuugau acugaaggau ugcucuguag cgggcuggcu acucggaaau    240
ccuaugugcg acgaauuuau ucgcguaccu gaguggaguu auaucguuga gagagccaau    300
ccagcuaacg aucugugcua ucccuggcagu cugaacgauu acgaagagcu uaaacaccuc    360
cuguccccgga uuaaccauuu cgagaagaua uugauaaucc cgaagagcag cuggccaaau    420
cacgaaaccu cccugggagu gagcgcugcu ugccccuacc agggagcccc uucauucuuc    480
aggaacgugg uuuggcugau caagaagaac gacgcauacc caacuauuaa gaucuccuac    540
aauaauacca accgggagga ccugcuaauc uugugggggua uccaucacag caacaacgca    600
gaagagcaaa cuaaccugua uaagaacccg accaccuaua ucucggucgg aacaagcacg    660
uuaaaccagc gguuggucccc gaagaucgcc acaaggucuc aggugaacgg ccagagagga    720
agaauggacu ucuucuggac cauauugaag ccagacgacg caauacauuu cgagucuaac    780
ggaaacuuca uugcuccgga auacgcguac aagauuguua agaagggcga uucgaccauu    840
augaaaucag gggugaaua cggucacugu aacaccaagu gccaaacucc ugugggcgcu    900
auuaacucau caaugccccuu ccacaauauu cacccacuga cuauugguga gugcccgaaa    960
uacguaaagu cuaauaaacu cguguuggcg accggccuaa gaaacagccc acagaucgag   1020
accaggggcu uguuuggggc gauugcagga uuuaucgaag gcggcuggca ggguauggug   1080
gacggcuggu acggauauca ucacagcaac gaacaagggu caggauacgc cgcagacaaa   1140
```

```
gaaucgacuc agaaagcuau agacggagug acgaacaaag ugaacucgau cauugauaag   1200

augaauacac aguuugaagc ggucggcaga gaauuuaaca acuuggaacg gagaauugag   1260

aaucugaaca agaagaugga ggacggcuuu cuggacgugu ggacuuauaa cgccgagcuc   1320

cucgugcuga uggagaacga aaggacucuu gacuuucacg auucaaacgu caagaaccug   1380

uacgacaagg uuagauugca gcugcgggac aacgccaaag aacuggguaa cggcuguuuc   1440

gaguucuacc auaagugcga uaacgagugc auggaaucug ucagaaacgg uaccuacgac   1500

uauccccagu auucugaaga ggcccgccuc aaacgagagg agaucucugg agugaagcug   1560

gaguccauug gcacguacca aauucuguca aucuacucca ccgcugcauc aagccuagcu   1620

cuggcgauca ugauggcggg gcucagucug uggauguguu caaacgguuc ccugcagugu   1680

cgcauuugua uc                                                        1692
```

```
<210> SEQ ID NO 103
<211> LENGTH: 564
<212> TYPE: PRT
<213> ORGANISM: Artificial Sequence
<220> FEATURE:
<223> OTHER INFORMATION: Synthetic

<400> SEQUENCE: 103

Met Glu Asn Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Ser Leu Asn
            100                 105                 110

Asp Tyr Glu Glu Leu Lys His Leu Leu Ser Arg Ile Asn His Phe Glu
        115                 120                 125

Lys Ile Leu Ile Ile Pro Lys Ser Ser Trp Pro Asn His Glu Thr Ser
    130                 135                 140

Leu Gly Val Ser Ala Ala Cys Pro Tyr Gln Gly Ala Pro Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Glu Glu Gln Thr Asn Leu Tyr Lys
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Gln Val Asn Gly Gln Arg Gly
225                 230                 235                 240

Arg Met Asp Phe Phe Trp Thr Ile Leu Lys Pro Asp Asp Ala Ile His
                245                 250                 255
```

```
Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Gly Val Glu Tyr Gly
        275                 280                 285

His Cys Asn Thr Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Ile Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Ala Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile
```

```
<210> SEQ ID NO 104
<211> LENGTH: 1877
<212> TYPE: RNA
<213> ORGANISM: Artificial Sequence
<220> FEATURE:
<223> OTHER INFORMATION: Synthetic

<400> SEQUENCE: 104

gggaaauaag agagaaaaga agaguaagaa gaaauauaag accccggcgc cgccaccaug      60

gagaacauug uguuacugcu ggccauugug ucacugguga aauccgacca gauuugcauu     120

gguuaccacg ccaauaacuc aaccgagcag guggauacua ucauggagaa gaacguaacc     180

gucacccacg cccaggacau uuuggagaag acacauaacg guaaacucug ugaccugaac     240

ggggugaagc ccuugauacu gaaggauugc ucuguagcgg gcuggcuacu cggaaauccu     300
```

-continued

```
augugcgacg aauuuauucg cguaccugag uggaguuaua ucguugagag agccaaucca    360

gcuaacgauc ugugcuaucc uggcagucug aacgauuacg aagagcuuaa acaccuccug    420

ucccggauua accauuucga gaagauauug auaaucccga agagcagcug gccaaaucac    480

gaaaccuccc ugggagugag cgcugcuugc ccuaccagg gagccccuuc auucuucagg    540

aacgugguuu ggcugaucaa gaagaacgac gcauacccaa cuauuaagau cuccuacaau    600

aauaccaacc gggaggaccu gcuaaucuug uggggguaucc aucacagcaa caacgcagaa    660

gagcaaacua accuguauaa gaacccgacc accuauaucu cggucggaac aagcacguua    720

aaccagcggu ugguccccgaa gaucgccaca aggucucagg ugaacggcca gagaggaaga    780

auggacuucu ucuggaccau auugaagcca gacgacgcaa uacauuucga gucuaacgga    840

aacuucauug cuccggaaua cgcguacaag auuguuaaga agggcgauuc gaccauuaug    900

aaaucagggg uggaauacgg ucacuguaac accaagugcc aaacuccugu gggcgcuauu    960

aacucaucaa ugcccuucca caauauucac ccacugacua uuggugagug cccgaaauac   1020

guaaagucua auaaacucgu guuggcgacc ggccuaagaa acagcccacu ucgcgagaag   1080

aggcggaaga ggggcuuguu uggggcgauu gcaggauuua ucgaaggcgg cuggcagggu   1140

augguggacg gcugguacgg auaucaucac agcaacgaac aagggucagg auacgccgca   1200

gacaaagaau cgacucagaa agcuauagac ggagugacga acaaagugaa cucgaucauu   1260

gauaagauga auacacaguu ugaagcgguc ggcagagaau uuaacaacuu ggaacggaga   1320

auugagaauc ugaacaagaa gauggaggac ggcuuucugg acguguggac uuauaacgcc   1380

gagcuccucg ugcugaugga gaacgaaagg acucuugacu uucacgauuc aaacgucaag   1440

aaccuguacg acaagguuag auugcagcug cgggacaacg ccaaagaacu ggguaacggc   1500

uguuucgagu ucuaccauaa gugcgauaac gagugcaugg aaucugucag aaacgguacc   1560

uacgacuauc cccaguauuc ugaagaggcc cgccucaaac gagaggagau cucuggagug   1620

aagcuggagu ccauuggcac guaccaaauu cugucaaucu acuccaccgc ugcaucaagc   1680

cuagcucugg cgaucaugau ggcggggcuc agucugugga uguguucaaa cgguucccug   1740

cagugucgca uuuguaucug auaauaggcu ggagccucgg uggccuagcu ucuugcccu   1800

ugggccuccc cccagccccu ccuccccuuc cugcacccgu acccccgugg ucuuugaaua   1860

aagucugagu gggcggc                                                  1877
```

<210> SEQ ID NO 105
<211> LENGTH: 1701
<212> TYPE: RNA
<213> ORGANISM: Artificial Sequence
<220> FEATURE:
<223> OTHER INFORMATION: Synthetic

<400> SEQUENCE: 105

```
auggagaaca uuguguuacu gcuggccauu gugucacugg ugaaauccga ccagauuugc     60

auugguuacc acgccaauaa cucaaccgag cagguggaua cuaucaugga gaagaacgua    120

accgucaccc acgcccagga cauuuuggag aagacacaua acgguaaacu cugugaccug    180

aacgggguga agcccuugau acugaaggau ugcucuguag cgggcuggcu acucggaaau    240

ccuaugugcg acgaauuuau ucgcguaccu gaguggaguu auaucguuga gagagccaau    300

ccagcuaacg aucugugcua uccuggcagu cugaacgauu acgaagagcu uaaacaccuc    360

cugucccgga uuaaccauuu cgagaagaua uugauaaucc cgaagagcag cuggccaaau    420

cacgaaaccu cccugggagu gagcgcugcu ugccccuacc agggagcccc uucauucuuc    480
```

-continued

```
aggaacgugg uuuggcugau caagaagaac gacgcauacc caacuauuaa gaucuccuac    540

aauaauacca accgggagga ccugcuaauc uuguggggua uccaucacag caacaacgca    600

gaagagcaaa cuaaccugua uaagaacccg accaccuaua ucucggucgg aacaagcacg    660

uuaaaccagc gguugguccc gaagaucgcc acaaggucuc aggugaacgg ccagagagga    720

agaauggacu ucuucuggac cauauugaag ccagacgacg caauacauuu cgagucuaac    780

ggaaacuuca uugcuccgga auacgcguac aagauuguua agaagggcga uucgaccauu    840

augaaaucag ggguggaaua cggucacugu aacaccaagu gccaaacucc ugugggcgcu    900

auuaacucau caaugcccuu ccacaauauu cacccacuga cuauuggug a gugcccgaaa    960

uacguaaagu cuaauaaacu cguguuggcg accggccuaa gaaacagccc acuucgcgag   1020

aagaggcgga agaggggcuu guuuggggcg auugcaggau uuaucgaagg cggcuggcag   1080

gguaugugg acggcuggua cggauaucau cacagcaacg aacaagggc aggauacgcc   1140

gcagacaaag aaucgacuca gaaagcuaua gacggaguga cgaacaaagu gaacucgauc   1200

auugauaaga ugaauacaca guuugaagcg gucggcagag aauuuaacaa cuuggaacgg   1260

agaauugaga aucugaacaa gaagauggag gacggcuuuc uggacgugug gacuuauaac   1320

gccgagcucc ucgugcugau ggagaacgaa aggacucuug acuuucacga uucaaacguc   1380

aagaaccugu acgacaaggu uagauugcag cugcgggaca acgccaaaga acugguaac   1440

ggcuguuucg aguucuacca uaagugcgau aacgagugca uggaaucugu cagaaacggu   1500

accuacgacu auccccagua uucugaagag gcccgccuca aacgagagga gaucucugga   1560

gugaagcugg aguccauugg cacguaccaa auucugucaa ucuacuccac cgcugcauca   1620

agccuagcuc uggcgaucau gauggcgggg cucagucugu ggauguguuc aaacgguucc   1680

cugcaguguc gcauuuguau c                                              1701
```

```
<210> SEQ ID NO 106
<211> LENGTH: 567
<212> TYPE: PRT
<213> ORGANISM: Artificial Sequence
<220> FEATURE:
<223> OTHER INFORMATION: Synthetic

<400> SEQUENCE: 106

Met Glu Asn Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Ser Leu Asn
            100                 105                 110

Asp Tyr Glu Glu Leu Lys His Leu Leu Ser Arg Ile Asn His Phe Glu
        115                 120                 125

Lys Ile Leu Ile Ile Pro Lys Ser Ser Trp Pro Asn His Glu Thr Ser
    130                 135                 140
```

```
Leu Gly Val Ser Ala Ala Cys Pro Tyr Gln Gly Ala Pro Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Glu Glu Gln Thr Asn Leu Tyr Lys
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Gln Val Asn Gly Gln Arg Gly
225                 230                 235                 240

Arg Met Asp Phe Phe Trp Thr Ile Leu Lys Pro Asp Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Gly Val Glu Tyr Gly
        275                 280                 285

His Cys Asn Thr Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Lys Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Ala Ala Ser Ser Leu Ala Leu
    530                 535                 540

Ala Ile Met Met Ala Gly Leu Ser Leu Trp Met Cys Ser Asn Gly Ser
545                 550                 555                 560
```

Leu Gln Cys Arg Ile Cys Ile
565

<210> SEQ ID NO 107
<211> LENGTH: 1583
<212> TYPE: RNA
<213> ORGANISM: Artificial Sequence
<220> FEATURE:
<223> OTHER INFORMATION: Synthetic

<400> SEQUENCE: 107
gggaaauaag agagaaaaga agaguaagaa gaaauauaag accccggcgc cgccaccaug 60
aacccgaacc agaagaucau caccaucggc agcgugagcc ugaccaucag caccaucugc 120
uucuucaugc agaucgccau ccugaucacc accgugaccc ugcacuucaa gcaguacgag 180
uucaacagcc ugcccaacaa ccaggugaug cugugcgagc ccaccaucau cgagcggaac 240
aucaccgaga ucguguaccu gaccaacacc accaucgaga aggagaucug ccccaagccc 300
gccgaguacc ggaacuggag caagccccag ugcggcauca ccggcuucgc cccauucagc 360
aaggacaaca gcaucagacu gagugccggc ggcgacaucu gggugacccg ggagcccuac 420
gugagcugcg accuggacaa gugcuaccag uucgcccugg gacagggcac cacccugaac 480
aacgugcaca gcaacaacac ugugcgggac cggaccccau accggacccu gcugaugaac 540
gagcugggcg ugcccuucca ccugggcacc aagcaggugu gcaucgccug gagcagcagc 600
agcugccacg acggcaaggc cuggcugcac gugugcauua ccggcgacga caagaacgcc 660
accgccagcu ucaucuacaa cggcaggcug guggacagcg uggugagcug gagcaacgac 720
auccugcgga cccaggagag cgagugcgug ugcaucaacg gcaccugcac cgugguguaug 780 acugacggca acgccaccgg caaggccgac accaagaucc uguucaucga ggaggggaag 840
aucgugcaca ccagcaagcu gucuggcagc gcccagcacg uggaggagug cagcugcuac 900
ccucgguacc ccggcgugag gugcgugugc cgggacaacu ggaagggcag caaccggccc 960
aucaucgaca ucaacaucaa ggaccacagc auagugagca gcuacgugug cagcggucug 1020
gugggcgaca cucccggaa gagcgacagc agcuccagca gccacugccu gaaccccaac 1080
aacgaggagg gugguacgg cgugaagggc ugggccuucg acgacggcaa cgacgugugg 1140
augggccgga ccaucaacga gaccagcaga cugggcuacg agaccuucaa ggugguggag 1200
ggcuggagca aucccaagag caagcugcag aucaaccggc aggugaucgu cgaucggggc 1260
gaucggagcg gcuacagcgg caucuucagc guggagggca agagcugcau caaccggugc 1320
uucuacgugg agcugauccg ggccggaag gaggagaccg aggugcugug gaccagcaac 1380
agcaucgugg uguucugcgg caccagcggc accuacggca ccggauccug gccagacggc 1440
gccgaucuga accugaugca caucugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 108
<211> LENGTH: 1407
<212> TYPE: RNA
<213> ORGANISM: Artificial Sequence
<220> FEATURE:
<223> OTHER INFORMATION: Synthetic

<400> SEQUENCE: 108
augaacccga accagaagau caucaccauc ggcagcguga gccugaccau cagcaccauc 60

-continued

```
ugcuucuuca ugcagaucgc cauccugauc accaccguga cccugcacuu caagcaguac    120

gaguucaaca gccugcccaa caaccaggug augcugugcg agcccaccau caucgagcgg    180

aacaucaccg agaucgugua ccugaccaac accaccaucg agaaggagau cugccccaag    240

cccgccgagu accggaacug gagcaagccc cagugcggca ucaccggcuu cgccccauuc    300

agcaaggaca acagcaucag acugagugcc ggcggcgaca ucugggugac ccgggagccc    360

uacgugagcu gcgaccugga caagugcuac caguucgccc ugggacaggg caccacccug    420

aacaacgugc acagcaacaa cacugugcgg gaccggaccc cauaccggac ccugcugaug    480

aacgagcugg gcgugcccuu ccaccugggc accaagcagg ugugcaucgc cuggagcagc    540

agcagcugcc acgacggcaa ggccuggcug cacgugugca uuaccggcga cgacaagaac    600

gccaccgcca gcuucaucua caacggcagg cugguggaca gcguggugag cuggagcaac    660

gacauccugc ggacccagga gagcgagugc gugugcauca acggcaccug caccguggug    720

augacugacg gcaacgccac cggcaaggcc gacaccaaga uccuguucau cgaggagggg    780

aagaucgugc acaccagcaa gcugucuggc agcgcccagc acguggagga gugcagcugc    840

uacccucggu accccggcgu gaggugcgug ugccgggaca acuggaaggg cagcaaccgg    900

cccaucaucg acaucaacau caaggaccac agcauaguga gcagcuacgu gugcagcggu    960

cugguggcg acacuccccg gaagagcgac agcagcucca gcagccacug ccugaacccc   1020

aacaacgagg agggugguca cggcgugaag ggcugggccu ucgacgacgg caacgacgug   1080

uggaugggcc ggaccaucaa cgagaccagc agacugggcu acgagaccuu caagguggug   1140

gagggcugga gcaaucccaa gagcaagcug cagaucaacc ggcaggugau cgucgaucgg   1200

ggcgaucgga gcggcuacag cggcaucuuc agcguggagg gcaagagcug caucaaccgg   1260

ugcuucuacg uggagcugau ccggggccgg aaggaggaga ccgaggugcu guggaccagc   1320

aacagcaucg uggguucug cggcaccagc ggcaccuacg gcaccggauc cuggccagac   1380

ggcgccgauc ugaaccugau gcacauc                                       1407
```

```
<210> SEQ ID NO 109
<211> LENGTH: 469
<212> TYPE: PRT
<213> ORGANISM: Artificial Sequence
<220> FEATURE:
<223> OTHER INFORMATION: Synthetic

<400> SEQUENCE: 109

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Leu Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125
```

Cys Tyr Gln Phe Ala Leu Gly Gln Gly Thr Thr Leu Asn Asn Val His
130 135 140

Ser Asn Asn Thr Val Arg Asp Arg Thr Pro Tyr Arg Thr Leu Leu Met
145 150 155 160

Asn Glu Leu Gly Val Pro Phe His Leu Gly Thr Lys Gln Val Cys Ile
165 170 175

Ala Trp Ser Ser Ser Ser Cys His Asp Gly Lys Ala Trp Leu His Val
180 185 190

Cys Ile Thr Gly Asp Asp Lys Asn Ala Thr Ala Ser Phe Ile Tyr Asn
195 200 205

Gly Arg Leu Val Asp Ser Val Val Ser Trp Ser Asn Asp Ile Leu Arg
210 215 220

Thr Gln Glu Ser Glu Cys Val Cys Ile Asn Gly Thr Cys Thr Val Val
225 230 235 240

Met Thr Asp Gly Asn Ala Thr Gly Lys Ala Asp Thr Lys Ile Leu Phe
245 250 255

Ile Glu Glu Gly Lys Ile Val His Thr Ser Lys Leu Ser Gly Ser Ala
260 265 270

Gln His Val Glu Glu Cys Ser Cys Tyr Pro Arg Tyr Pro Gly Val Arg
275 280 285

Cys Val Cys Arg Asp Asn Trp Lys Gly Ser Asn Arg Pro Ile Ile Asp
290 295 300

Ile Asn Ile Lys Asp His Ser Ile Val Ser Ser Tyr Val Cys Ser Gly
305 310 315 320

Leu Val Gly Asp Thr Pro Arg Lys Ser Asp Ser Ser Ser Ser Ser His
325 330 335

Cys Leu Asn Pro Asn Asn Glu Glu Gly Gly His Gly Val Lys Gly Trp
340 345 350

Ala Phe Asp Asp Gly Asn Asp Val Trp Met Gly Arg Thr Ile Asn Glu
355 360 365

Thr Ser Arg Leu Gly Tyr Glu Thr Phe Lys Val Val Glu Gly Trp Ser
370 375 380

Asn Pro Lys Ser Lys Leu Gln Ile Asn Arg Gln Val Ile Val Asp Arg
385 390 395 400

Gly Asp Arg Ser Gly Tyr Ser Gly Ile Phe Ser Val Glu Gly Lys Ser
405 410 415

Cys Ile Asn Arg Cys Phe Tyr Val Glu Leu Ile Arg Gly Arg Lys Glu
420 425 430

Glu Thr Glu Val Leu Trp Thr Ser Asn Ser Ile Val Val Phe Cys Gly
435 440 445

Thr Ser Gly Thr Tyr Gly Thr Gly Ser Trp Pro Asp Gly Ala Asp Leu
450 455 460

Asn Leu Met His Ile
465

<210> SEQ ID NO 110
<211> LENGTH: 1583
<212> TYPE: RNA
<213> ORGANISM: Artificial Sequence
<220> FEATURE:
<223> OTHER INFORMATION: Synthetic

<400> SEQUENCE: 110
gggaaauaag agagaaaaga agaguaagaa gaaauauaag accccggcgc cgccaccaug 60
aacccgaacc agaagaucau caccaucggc agcgugagcc ugaccaucag caccaucugc 120
uucuucaugc agaucgccau ccugaucacc accgugaccc ugcacuucaa gcaguacgag 180
uucaacagcc cucccaacaa ccaggugaug cugugcgagc ccaccaucau cgagcggaac 240
augaccgaga ucguguaccu gaccaacacc accaucgaga aggagaucug ccccaagccc 300
gccgaguacc ggaacuggag caagccccag ugcggcauca ccggcuucgc cccauucagc 360
aaggacaaca gcaucagacu gagugccggc ggcgacaucu gggugacccg ggagcccuac 420
gugagcugcg accuggacaa gugcuaccag uucgcccugg gacagggcac cacccugaac 480
aacgugcaca gcaacaacac ugugcgggac cggaccccau accggacccu gcugaugaac 540
gagcugggcg ugcccuucca ccugggcacc aagcaggugu gcaucgccug gagcagcagc 600
agcugccacg acggcaaggc cuggcugcac gugugcauua ccggcgacga caagaacgcc 660
accgccagcu ucaucuacaa cggcaggcug guggacagcg uggugagcug gagcaacgac 720
auccugcgga cccaggagag cgagugcgug ugcaucaacg gcaccugcac cgugguguaug 780 acugacggca acgccaccgg caaggccgac accaagaucc uguucaucga ggaggggaag 840
aucgugcaca ccagcaagcu gucuggcagc gcccagcacg uggaggagug cagcugcuac 900
ccucgguacc ccggcgugag gugcgugugc cgggacaacu ggaagggcag caaccggccc 960
aucaucgaca ucaacaucaa ggaccacagc auagugagca gauacgugug cagcggucug 1020
gugggcgaca cucccccggaa gagcgacagc agcuccagca gccacugccu gaaccccaac 1080
aacgagaagg gugaccacgg cgugaagggc ugggccuucg acgacggcaa cgacgugugg 1140
augggccgga ccaucaacga gaccagcaga cugggcuacg agaccuucaa ggugguggag 1200
ggcuggagca aucccaagag caagcugcag aucaaccggc aggugaucgu cgaucggggc 1260
gaucggagcg gcuacagcgg caucuucagc guggagggca agagcugcau caaccggugc 1320
uucuacgugg agcugauccg gggccggaag gaggagaccg aggugcugug gaccagcaac 1380
agcaucgugg uguucugcgg caccagcggc accuacggca ccggauccug gccagacggc 1440
gccaaccuga gccugaugca caucugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 111
<211> LENGTH: 1407
<212> TYPE: RNA
<213> ORGANISM: Artificial Sequence
<220> FEATURE:
<223> OTHER INFORMATION: Synthetic

<400> SEQUENCE: 111
augaacccga accagaagau caucaccauc ggcagcguga gccugaccau cagcaccauc 60
ugcuucuuca ugcagaucgc cauccugauc accaccguga cccugcacuu caagcaguac 120
gaguucaaca gcccucccaa caaccaggug augcugugcg agcccaccau caucgagcgg 180
aacaugaccg agaucgugua ccugaccaac accaccaucg agaaggagau cugccccaag 240
cccgccgagu accggaacug gagcaagccc cagugcggca ucaccggcuu cgccccauuc 300
agcaaggaca acagcaucag acugagugcc ggcggcgaca ucugggugac ccgggagccc 360
uacgugagcu gcgaccugga caagugcuac caguucgccc ugggacaggg caccacccug 420
aacaacgugc acagcaacaa cacugugcgg gaccggaccc cauaccggac ccugcugaug 480
aacgagcugg gcgugcccuu ccaccugggc accaagcagg ugugcaucgc cuggagcagc 540

```
agcagcugcc acgacggcaa ggccuggcug cacgugugca uuaccggcga cgacaagaac     600

gccaccgcca gcuucaucua caacggcagg cugguggaca gcguggugag cuggagcaac     660

gacauccugc ggacccagga gagcgagugc gugugcauca acggcaccug caccguggug     720

augacugacg gcaacgccac cggcaaggcc gacaccaaga uccuguucau cgaggagggg     780

aagaucgugc acaccagcaa gcugucuggc agcgcccagc acguggagga gugcagcugc     840

uacccucggu accccggcgu gaggugcgug ugccgggaca acuggaaggg cagcaaccgg     900

cccaucaucg acaucaacau caaggaccac agcauaguga gcagauacgu gugcagcggu     960

cuggugggcg acacuccccg gaagagcgac agcagcucca gcagccacug ccugaacccc    1020

aacaacgaga agggugacca cggcgugaag ggcugggccu ucgacgacgg caacgacgug    1080

uggaugggcc ggaccaucaa cgagaccagc agacugggcu acgagaccuu caagguggug    1140

gagggcugga gcaaucccaa gagcaagcug cagaucaacc ggcaggugau cgucgaucgg    1200

ggcgaucgga gcggcuacag cggcaucuuc agcguggagg gcaagagcug caucaaccgg    1260

ugcuucuacg uggagcugau ccggggccgg aaggaggaga ccgaggugcu guggaccagc    1320

aacagcaucg uggguguucug cggcaccagc ggcaccuacg gcaccggauc cuggccagac    1380

ggcgccaacc ugagccugau gcacauc                                         1407


<210> SEQ ID NO 112
<211> LENGTH: 469
<212> TYPE: PRT
<213> ORGANISM: Artificial Sequence
<220> FEATURE:
<223> OTHER INFORMATION: Synthetic

<400> SEQUENCE: 112

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Met Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205
```

```
Gly Arg Leu Val Asp Ser Val Val Ser Trp Ser Asn Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Ile Asp
    290                 295                 300

Ile Asn Ile Lys Asp His Ser Ile Val Ser Arg Tyr Val Cys Ser Gly
305                 310                 315                 320

Leu Val Gly Asp Thr Pro Arg Lys Ser Asp Ser Ser Ser Ser Ser His
                325                 330                 335

Cys Leu Asn Pro Asn Asn Glu Lys Gly Asp His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asn Leu
    450                 455                 460

Ser Leu Met His Ile
465
```

<210> SEQ ID NO 113
<211> LENGTH: 1583
<212> TYPE: RNA
<213> ORGANISM: Artificial Sequence
<220> FEATURE:
<223> OTHER INFORMATION: Synthetic

<400> SEQUENCE: 113

```
gggaaauaag agagaaaaga agaguaagaa gaaauauaag accccggcgc cgccaccaug     60

aacccgaacc agaagaucau caccaucggc agcgugagcc ugaccaucag caccaucugc    120

uucuucaugc agaucgccau ccugaucacc accgugaccc ugcacuucaa gcaguacgag    180

uucaacagcc cucccaacaa ccaggugaug cugugcgagc ccaccaucau cgagcggaac    240

augaccgaga ucguguaccu gaccaacacc accaucgaga aggagaucug ccccaagccc    300

gccgaguacc ggaacuggag caagccccag ugcggcauca ccggcuucgc cccauucagc    360

aaggacaaca gcaucagacu gagugccggc ggcgacaucu gggugacccg ggagcccuac    420

gugagcugcg accuggacaa gugcuaccag uucgcccugg gacagggcac cacccugaac    480

aacgugcaca gcaacaacac ugugcggggc cggaccccau accggacccu gcugaugaac    540
```

-continued gagcugggcg ugcccuucca ccugggcacc aagcaggugu gcaucgccug gagcagcagc 600
agcugccacg acggcaaggc cuggcugcac gugugcauua ccggcgacga caagaacgcc 660
accgccagcu ucaucuacaa cggcaggcug guggacagcg uggugagcug gagcaacgac 720
auccugcgga cccaggagag cgagugcgug ugcaucaacg gcaccugcac cgugguguaug 780 acugacggca acgccaccgg caaggccgac accaagaucc uguucaucga ggaggggaag 840
aucgugcaca ccagcaagcu gucuggcagc gcccagcacg uggaggagug cagcugcuac 900
ccucgguacc ccggcgugag gugcgugugc cgggacaacu ggaagggcag caaccggccc 960
aucaucgaca ucaacaucaa ggaccacagc auagugagca gauacgugug cagcggucug 1020
gugggcgaca cuccccggaa gagcgacagc agcuccagca gccacugccu gaaccccaac 1080
aacgagaagg gugaccacgg cgugaagggc ugggccuucg acgacggcaa cgacgugugg 1140
augggccgga ccaucaacga gaccagcaga cugggcuacg agaccuucaa ggugguggag 1200
ggcuggagca aucccaagag caagcugcag aucaaccggc aggugaucgu cgaucggggc 1260
gaucggagcg gcuacagcgg caucuucagc guggagggca agagcugcau caaccggugc 1320
uucuacgugg agcugauccg ggccggaagg gaggagaccg aggugcugug gaccagcaac 1380
agcaucgugg uguucugcgg caccagcggc accuacggca ccggauccug gccagacggc 1440
gccaaccuga gccugaugca caucugauaa uaggcuggag ccucggguggc cuagcuucuu 1500 gccccuuggg ccucccccca gccccuccuc cccuuccugc acccguaccc ccguggucuu 1560
ugaauaaagu cugagugggc ggc 1583

<210> SEQ ID NO 114
<211> LENGTH: 1407
<212> TYPE: RNA
<213> ORGANISM: Artificial Sequence
<220> FEATURE:
<223> OTHER INFORMATION: Synthetic

<400> SEQUENCE: 114
augaacccga accagaagau caucaccauc ggcagcguga gccugaccau cagcaccauc 60
ugcuucuuca ugcagaucgc cauccugauc accaccguga cccugcacuu caagcaguac 120
gaguucaaca gcccucccaa caaccaggug augcugugcg agcccaccau caucgagcgg 180
aacaugaccg agaucgugua ccugaccaac accaccaucg agaaggagau cugccccaag 240
cccgccgagu accggaacug gagcaagccc cagugcggca ucaccggcuu cgccccauuc 300
agcaaggaca acagcaucag acugagugcc ggcggcgaca ucugggugac ccgggagccc 360
uacgugagcu gcgaccugga caagugcuac caguucgccc ugggacaggg caccacccug 420
aacaacgugc acagcaacaa cacugugcgg ggccggaccc cauaccggac ccugcugaug 480
aacgagcugg gcgugcccuu ccaccugggc accaagcagg ugugcaucgc cuggagcagc 540
agcagcugcc acgacggcaa ggccuggcug cacgugugca uuaccggcga cgacaagaac 600
gccaccgcca gcuucaucua caacggcagg cugguggaca gcguggugag cuggagcaac 660
gacauccugc ggacccagga gagcgagugc gugugcauca acggcaccug caccguggug 720
augacugacg gcaacgccac cggcaaggcc gacaccaaga uccuguucau cgaggagggg 780
aagaucgugc acaccagcaa gcugucuggc agcgcccagc acguggagga gugcagcugc 840
uacccucggu accccggcgu gaggugcgug ugccgggaca acuggaaggg cagcaaccgg 900
cccaucaucg acaucaacau caaggaccac agcauaguga gcagauacgu gugcagcggu 960

```
cuggugggcg acacuccccg gaagagcgac agcagcucca gcagccacug ccugaacccc   1020

aacaacgaga agggugacca cggcgugaag ggcugggccu ucgacgacgg caacgacgug   1080

uggaugggcc ggaccaucaa cgagaccagc agacugggcu acgagaccuu caagguggug   1140

gagggcugga gcaaucccaa gagcaagcug cagaucaacc ggcaggugau cgucgaucgg   1200

ggcgaucgga gcggcuacag cggcaucuuc agcguggagg gcaagagcug caucaaccgg   1260

ugcuucuacg uggagcugau ccggggccgg aaggaggaga ccgaggugcu guggaccagc   1320

aacagcaucg uggu guucug cggcaccagc ggcaccuacg gcaccggauc cuggccagac   1380

ggcgccaacc ugagccugau gcacauc                                        1407
```

<210> SEQ ID NO 115
<211> LENGTH: 469
<212> TYPE: PRT
<213> ORGANISM: Artificial Sequence
<220> FEATURE:
<223> OTHER INFORMATION: Synthetic

<400> SEQUENCE: 115

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Met Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Gly Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Asn Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285
```

Cys Val Cys Arg Asp Asn Trp Lys Gly Ser Asn Arg Pro Ile Ile Asp
    290                 295                 300

Ile Asn Ile Lys Asp His Ser Ile Val Ser Arg Tyr Val Cys Ser Gly
305                 310                 315                 320

Leu Val Gly Asp Thr Pro Arg Lys Ser Asp Ser Ser Ser Ser Ser His
                325                 330                 335

Cys Leu Asn Pro Asn Asn Glu Lys Gly Asp His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asn Leu
    450                 455                 460

Ser Leu Met His Ile
465

<210> SEQ ID NO 116
<211> LENGTH: 1583
<212> TYPE: RNA
<213> ORGANISM: Artificial Sequence
<220> FEATURE:
<223> OTHER INFORMATION: Synthetic

<400> SEQUENCE: 116
gggaaauaag agagaaaaga agaguaagaa gaaauauaag accccggcgc cgccaccaug 60
aacccgaacc agaagaucau caccaucggc agcgugagcc ugaccaucag caccaucugc 120
uucuucaugc agaucgccau ccugaucacc accgugaccc ugcacuucaa gcaguacgag 180
uucaacagcc cucccaacaa ccaggugaug cugugcgagc ccaccaucau cgagcggaac 240
augaccgaga ucguguaccu gaccaacacc accaucgaga aggagaucug ccccaagccc 300
gccgaguacc ggaacuggag caagccccag ugcggcauca ccggcuucgc cccauucagc 360
aaggacaaca gcaucagacu gagugccggc ggcgacaucu gggugacccg ggagcccuac 420
gugagcugcg accuggacaa gugcuaccag uucgcccugg gacagggcac cacccugaac 480
aacgugcaca gcaacaacac ugugcgggac cggaccccau accggacccu gcugaugaac 540
gagcugggcg ugcccuucca ccugggcacc aagcaggugu gcaucgccug gagcagcagc 600
agcugccacg acggcaaggc cuggcugcac gugugcauua ccggcgacga caagaacgcc 660
accgccagcu ucaucuacaa cggcaggcug guggacagcg uggugagcug gagcaacgac 720
auccugcgga cccaggacag cgagugcgug ugcaucaacg gcaccugcac cgguggugaug 780 acugacggca acgccaccgg caaggccgac accaagaucc uguucaucga ggaggggaag 840
aucgugcaca ccagcaagcu gucuggcagc gcccagcacg uggaggagug cagcugcuac 900
ccucgguacc ccggcgugag gugcgugugc cgggacaacu ggaagggcag caaccggccc 960
aucaucgaca ucaacaucaa ggaccacagc auagugagca gauacgugug cagcggucug 1020
gugggcgaca cuccccggaa gagcgacagc agcuccagca gccacugccu gaaccccaac 1080
aacgagaagg gugaccacgg cgugaagggc ugggccuucg acgacggcaa cgacguguggg 1140 augggccgga ccaucaacga gaccagcaga cugggcuacg agaccuucaa ggugguggag 1200
ggcuggagca aucccaagag caagcugcag aucaaccggc aggugaucgu cgaucggggc 1260
gaucggagcg gcuacagcgg caucuucagc guggagggca agagcugcau caaccggugc 1320
uucuacgugg agcugauccg gggccggaag gaggagaccg aggugcugug gaccagcaac 1380
agcaucgugg uguucugcgg caccagcggc accuacggca ccggauccug gccagacggc 1440
gccaaccuga gccugaugca caucugauaa uaggcuggag ccucgguggc cuagcuucuu 1500
gccccuuggg ccucccccca gccccuccuc cccuuccugc acccguaccc ccguggucuu 1560
ugaauaaagu cugagugggc ggc 1583

<210> SEQ ID NO 117
<211> LENGTH: 1407
<212> TYPE: RNA
<213> ORGANISM: Artificial Sequence
<220> FEATURE:
<223> OTHER INFORMATION: Synthetic

<400> SEQUENCE: 117
augaacccga accagaagau caucaccauc ggcagcguga gccugaccau cagcaccauc 60
ugcuucuuca ugcagaucgc cauccugauc accaccguga cccugcacuu caagcaguac 120
gaguucaaca gcccucccaa caaccaggug augcugugcg agcccaccau caucgagcgg 180
aacaugaccg agaucgugua ccugaccaac accaccaucg agaaggagau cugccccaag 240
cccgccgagu accggaacug gagcaagccc cagugcggca ucaccggcuu cgccccauuc 300
agcaaggaca acagcaucag acugagugcc ggcggcgaca ucugggugac ccgggagccc 360
uacgugagcu gcgaccugga caagugcuac caguucgccc ugggacaggg caccacccug 420
aacaacgugc acagcaacaa cacugugcgg gaccggaccc cauaccggac ccugcugaug 480
aacgagcugg gcgugcccuu ccaccugggc accaagcagg ugugcaucgc cuggagcagc 540
agcagcugcc acgacggcaa ggccuggcug cacgugugca uuaccggcga cgacaagaac 600
gccaccgcca gcuucaucua caacggcagg cugguggaca gcguggugag cuggagcaac 660
gacauccugc ggacccagga cagcgagugc gugugcauca acggcaccug caccguggug 720
augacugacg gcaacgccac cggcaaggcc gacaccaaga uccuguucau cgaggagggg 780
aagaucgugc acaccagcaa gcugucuggc agcgcccagc acguggagga gugcagcugc 840
uacccucggu accccggcgu gaggugcgug ugccgggaca acuggaaggg cagcaaccgg 900
cccaucaucg acaucaacau caaggaccac agcauaguga gcagauacgu gugcagcggu 960
cuggugggcg acacuccccg gaagagcgac agcagcucca gcagccacug ccugaacccc 1020
aacaacgaga agggugacca cggcgugaag ggcugggccu ucgacgacgg caacgacgug 1080
uggaugggcc ggaccaucaa cgagaccagc agacugggcu acgagaccuu caagguggug 1140
gagggcugga gcaaucccaa gagcaagcug cagaucaacc ggcaggugau cgucgaucgg 1200
ggcgaucgga gcggcuacag cggcaucuuc agcguggagg gcaagagcug caucaaccgg 1260
ugcuucuacg uggagcugau ccggggccgg aaggaggaga ccgaggugcu guggaccagc 1320
aacagcaucg ugguguucug cggcaccagc ggcaccuacg gcaccggauc cuggccagac 1380
ggcgccaacc ugagccugau gcacauc 1407

<210> SEQ ID NO 118
<211> LENGTH: 469
<212> TYPE: PRT
<213> ORGANISM: Artificial Sequence
<220> FEATURE:
<223> OTHER INFORMATION: Synthetic

<400> SEQUENCE: 118

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Met Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Leu Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Asn Asp Ile Leu Arg
    210                 215                 220

Thr Gln Asp Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Ile Asp
    290                 295                 300

Ile Asn Ile Lys Asp His Ser Ile Val Ser Arg Tyr Val Cys Ser Gly
305                 310                 315                 320

Leu Val Gly Asp Thr Pro Arg Lys Ser Asp Ser Ser Ser Ser Ser His
                325                 330                 335

Cys Leu Asn Pro Asn Asn Glu Lys Gly Asp His Gly Val Lys Gly Trp
            340                 345                 350

Ala Phe Asp Asp Gly Asn Asp Val Trp Met Gly Arg Thr Ile Asn Glu
        355                 360                 365
```

```
Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asn Leu
    450                 455                 460

Ser Leu Met His Ile
465
```

<210> SEQ ID NO 119
<211> LENGTH: 1586
<212> TYPE: RNA
<213> ORGANISM: Artificial Sequence
<220> FEATURE:
<223> OTHER INFORMATION: Synthetic

<400> SEQUENCE: 119

```
gggaaauaag agagaaaaga agaguaagaa gaaauauaag accccggcgc cgccaccaug     60

aacccuaauc agaagauugc gaccauuggc agcauuucuc uuggccucgu gguguucaac    120

gucuugcugc acgcccuauc caucauccuc augguccugg cccuugguaa gagcgagaac    180

aacgguauuu guaagggaac aaucaucaga gaguacaacg agaccguucg gaucgagaag    240

guaacacagu gguacaauac gucaguugug gaguacgugc cgcacuggaa cgagggcgcu    300

uauauuaaca acaccgagcc aaucugcgac gugaagggcu uugcgccuuu uagcaaagac    360

aacggaaucc gaaucggaag cagagggcau aucuuuguua uuagggaacc auuugugucu    420

uguagucccg ucgagugccg aaccuucuuc cuuacacagg gcgcauugcu gaacgauaag    480

cauuccaacg gcaccguuaa ggacaggagc ccauucagga cacugauguc aguggaaguu    540

ggucaaucgc cuaacguuua ucaggcacgc uuugaggccg uggccuggag ugcaaccgcc    600

ugucacgacg gcaagaagug gaugacaauu ggggugacug guccugacag caaggcaauc    660

gcaguuguuc acuacggcgg uguccccacg gacaucguga auucgugggc cggagacauc    720

cugcggacuc aggaaucuuc guguaccugc auccagggca acuguuacug gguaaugacu    780

gacgguccua guaaccguca ggcccaauau agaauauaca aggccaacca gggcaagauu    840

auugaccaag ccgacguauc cuucuccggc ggccauaucg aggagugcuc uuguuauccu    900

aacgacggaa aggucgagug ugugugccgc gacaacugga ucgggaccaa ccgcccugug    960

cuggucauau cuccugaucu gucauaucgu gugggauauc uuugugcagg auugccaucc   1020

gauacacccc gaggugagga cgcccaguuc guagggagcu guacuagccc uaugggaaau   1080

cagggauacg gcguuaaggg uuuuggauuc cgccaaggua ccgacgucug gaugggcagg   1140

accauaagca ggaccagcag auccggauuu gaaaucauca ggaucaagaa cggguggacc   1200

cagacgucua aagagcaaau ucgucggcaa gugguuguag acaaucuaaa uuggucuggc   1260

uauagcggaa guuucacucu uccaguugaa cucagcggcc gugagugucu ggugccgugc   1320

uuuugggugg aaaugaucag aggcaggccc gaggagcgua caaucuggac aucuucuucc   1380

uccaucguga ugugugggguu ugaucacgag aucgcagacu ggagcuggca cgacggugcg   1440
```

auacugccau ucgacauuga cggaauguga uaauaggcug gagccucggu ggccuagcuu 1500
cuugccccuu gggccucccc ccagccccuc cuccccuucc ugcacccgua cccccguggu 1560
cuuugaauaa agucugagug ggcggc 1586

<210> SEQ ID NO 120
<211> LENGTH: 1410
<212> TYPE: RNA
<213> ORGANISM: Artificial Sequence
<220> FEATURE:
<223> OTHER INFORMATION: Synthetic

<400> SEQUENCE: 120
augaacccua aucagaagau ugcgaccauu ggcagcauuu cucuuggccu cgugguguuc 60
aacgucuugc ugcacgcccu auccaucauc cucauggucc uggcccuugg uaagagcgag 120
aacaacggua uuuguaaggg aacaaucauc agagaguaca acgagaccgu ucggaucgag 180
aagguaacac agugguacaa uacgucaguu guggaguacg ugccgcacug gaacgagggc 240
gcuuauauua acaacaccga gccaaucugc gacgugaagg gcuuugcgcc uuuuagcaaa 300
gacaacggaa uccgaaucgg aagcagaggg cauaucuuug uuauuaggga accauuugug 360
ucuuguaguc ccgucgagug ccgaaccuuc uuccuuacac agggcgcauu gcugaacgau 420
aagcauucca acggcaccgu uaaggacagg agcccauuca ggacacugau gucaguggaa 480
guuggucaau cgccuaacgu uuaucaggca cgcuuugagg ccguggccug gagugcaacc 540
gccugucacg acggcaagaa guggaugaca auuggggug a cugguccuga cagcaaggca 600
aucgcaguug uucacuacgg cgguguccccc acggacaucg ugaauucgug ggccggagac 660
auccugcgga cucaggaauc uucguguacc ugcauccagg gcaacuguua cuggguaaug 720
acugacgguc cuaguaaccg ucaggcccaa uauagaauau acaaggccaa ccagggcaag 780
auuauugacc aagccgacgu auccuucucc ggcggccaua ucgaggagug cucuuguuau 840
ccuaacgacg gaaaggucga gugugugugc cgcgacaacu ggaucgggac caaccgcccu 900
gugcugguca uaucuccuga ucugucauau cgugugggau aucuuugugc aggauugcca 960
uccgauacac cccgagguga ggacgcccag uucguaggga gcuguacuag cccuauggga 1020
aaucagggau acggcguuaa ggguuuugga uuccgccaag guaccgacgu cuggaugggc 1080
aggaccauaa gcaggaccag cagauccgga uuugaaauca ucaggaucaa gaacgggugg 1140
acccagacgu cuaaagagca aauucgucgg caagugguug uagacaaucu aaauuggucu 1200
ggcuauagcg gaaguuucac ucuuccaguu gaacucagcg gccgugagug ucuggugccg 1260
ugcuuuuggg uggaaaugau cagaggcagg cccgaggagc guacaaucug gacaucuucu 1320
uccuccaucg ugaugugugg gguugaucac gagaucgcag acuggagcug gcacgacggu 1380
gcgauacugc cauucgacau ugacggaaug 1410

<210> SEQ ID NO 121
<211> LENGTH: 470
<212> TYPE: PRT
<213> ORGANISM: Artificial Sequence
<220> FEATURE:
<223> OTHER INFORMATION: Synthetic

<400> SEQUENCE: 121

Met Asn Pro Asn Gln Lys Ile Ala Thr Ile Gly Ser Ile Ser Leu Gly
1 5 10 15

Leu Val Val Phe Asn Val Leu Leu His Ala Leu Ser Ile Ile Leu Met

-continued

```
            20                  25                  30

Val Leu Ala Leu Gly Lys Ser Glu Asn Asn Gly Ile Cys Lys Gly Thr
        35                  40                  45

Ile Ile Arg Glu Tyr Asn Glu Thr Val Arg Ile Glu Lys Val Thr Gln
    50                  55                  60

Trp Tyr Asn Thr Ser Val Val Glu Tyr Val Pro His Trp Asn Glu Gly
65                  70                  75                  80

Ala Tyr Ile Asn Asn Thr Glu Pro Ile Cys Asp Val Lys Gly Phe Ala
                85                  90                  95

Pro Phe Ser Lys Asp Asn Gly Ile Arg Ile Gly Ser Arg Gly His Ile
            100                 105                 110

Phe Val Ile Arg Glu Pro Phe Val Ser Cys Ser Pro Val Glu Cys Arg
        115                 120                 125

Thr Phe Phe Leu Thr Gln Gly Ala Leu Leu Asn Asp Lys His Ser Asn
    130                 135                 140

Gly Thr Val Lys Asp Arg Ser Pro Phe Arg Thr Leu Met Ser Val Glu
145                 150                 155                 160

Val Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
            180                 185                 190

Val Thr Gly Pro Asp Ser Lys Ala Ile Ala Val Val His Tyr Gly Gly
        195                 200                 205

Val Pro Thr Asp Ile Val Asn Ser Trp Ala Gly Asp Ile Leu Arg Thr
    210                 215                 220

Gln Glu Ser Ser Cys Thr Cys Ile Gln Gly Asn Cys Tyr Trp Val Met
225                 230                 235                 240

Thr Asp Gly Pro Ser Asn Arg Gln Ala Gln Tyr Arg Ile Tyr Lys Ala
                245                 250                 255

Asn Gln Gly Lys Ile Ile Asp Gln Ala Asp Val Ser Phe Ser Gly Gly
            260                 265                 270

His Ile Glu Glu Cys Ser Cys Tyr Pro Asn Asp Gly Lys Val Glu Cys
        275                 280                 285

Val Cys Arg Asp Asn Trp Ile Gly Thr Asn Arg Pro Val Leu Val Ile
    290                 295                 300

Ser Pro Asp Leu Ser Tyr Arg Val Gly Tyr Leu Cys Ala Gly Leu Pro
305                 310                 315                 320

Ser Asp Thr Pro Arg Gly Glu Asp Ala Gln Phe Val Gly Ser Cys Thr
                325                 330                 335

Ser Pro Met Gly Asn Gln Gly Tyr Gly Val Lys Gly Phe Gly Phe Arg
            340                 345                 350

Gln Gly Thr Asp Val Trp Met Gly Arg Thr Ile Ser Arg Thr Ser Arg
        355                 360                 365

Ser Gly Phe Glu Ile Ile Arg Ile Lys Asn Gly Trp Thr Gln Thr Ser
    370                 375                 380

Lys Glu Gln Ile Arg Arg Gln Val Val Val Asp Asn Leu Asn Trp Ser
385                 390                 395                 400

Gly Tyr Ser Gly Ser Phe Thr Leu Pro Val Glu Leu Ser Gly Arg Glu
                405                 410                 415

Cys Leu Val Pro Cys Phe Trp Val Glu Met Ile Arg Gly Arg Pro Glu
            420                 425                 430

Glu Arg Thr Ile Trp Thr Ser Ser Ser Ser Ile Val Met Cys Gly Val
        435                 440                 445
```

```
Asp His Glu Ile Ala Asp Trp Ser Trp His Asp Gly Ala Ile Leu Pro
    450                 455                 460

Phe Asp Ile Asp Gly Met
465                 470


<210> SEQ ID NO 122
<211> LENGTH: 1586
<212> TYPE: RNA
<213> ORGANISM: Artificial Sequence
<220> FEATURE:
<223> OTHER INFORMATION: Synthetic

<400> SEQUENCE: 122

gggaaauaag agagaaaaga agaguaagaa gaaauauaag accccggcgc cgccaccaug      60

aacccuaauc agaagauugc gaccauuggc agcauuucuc uuggccucgu gguguucaac     120

gucuugcugc acgcccuauc caucaucctc augguccugg cccuugguaa gagcgagaac     180

aacgguauuu guaagggaac aaucaucaga gaguacaacg agaccguucg gaucgagaag     240

guaacacagu gguacaauac gucaguugug gaguacgugc cgcacuggaa cgagggcgcu     300

uauauuaaca acaccgagcc aaucugcgac gugaagggcu uugcgccuuu uagcaaagac     360

aacggaaucc gaaucggaag cagagggcau aucuuuguua uuagggaacc auuugugucu     420

uguagucccg ucgagugccg aaccuucuuc cuuacacagg gcgcauugcu gaacgauaag     480

cauuccaacg gcaccguuaa gggcaggagc ccauucagga cacugauguc aguggaaguu     540

ggucaaucgc cuaacguuua ucaggcacgc uuugaggccg uggccuggag ugcaaccgcc     600

ugucacgacg gcaagaagug gaugacaauu ggggugacug guccugacag caaggcaauc     660

gcaguuguuc acuacggcgg uguccccacg gacaucguga auucgugggc cggagacauc     720

cugcggacuc aggaaucuuc guguaccugc auccagggca acuguuacug gguaaugacu     780

gacgguccua guaaccguca ggcccaauau agaauauaca aggccaacca gggcaagauu     840

auugaccaag ccgacguauc cuucuccggc ggccauaucg aggagugcuc uuguuauccu     900

aacgacggaa aggucgagug ugugugccgc gacaacugga ucgggaccaa ccgcccugug     960

cuggucauau cuccugaucu gucauaucgu gugggauauc uuugugcagg auugccaucc    1020

gauacacccc gaggugagga cgcccaguuc guagggagcu guacuagccc uaugggaaau    1080

cagggauacg gcguuaaggg uuuuggauuc cgccaaggua ccgacgucug gaugggcagg    1140

accauaagca ggaccagcag auccggauuu gaaaucauca ggaucaagaa cggguggacc    1200

cagacgucua aagagcaaau ucgucggcaa gugguuguag acaaucuaaa uuggucuggc    1260

uauagcggaa guuucacucu uccaguugaa cucagcggcc gugagugucu ggugccgugc    1320

uuuugggugg aaaugaucag aggcaggccc gaggagcgua caaucuggac aucuucuucc    1380

uccaucguga ugugugggu ugaucacgag aucgcagacu ggagcuggca cgacggugcg    1440

auacugccau ucgacauuga cggaauguga uaauaggcug gagccucggu ggccuagcuu    1500

cuugccccuu gggccucccc ccagccccuc cuccccuucc ugcacccgua cccccguggu    1560

cuuugaauaa agucugagug ggcggc                                         1586


<210> SEQ ID NO 123
<211> LENGTH: 1410
<212> TYPE: RNA
<213> ORGANISM: Artificial Sequence
<220> FEATURE:
<223> OTHER INFORMATION: Synthetic
```

<400> SEQUENCE: 123

```
augaacccua aucagaagau ugcgaccauu ggcagcauuu cucuuggccu cgugguguuc     60
aacgucuugc ugcacgcccu auccaucauc cucauggucc uggcccuugg uaagagcgag    120
aacaacggua uuuguaaggg aacaaucauc agagaguaca acgagaccgu ucggaucgag    180
aagguaacac agugguacaa uacgucaguu guggaguacg ugccgcacug gaacgagggc    240
gcuuauauua acaacaccga gccaaucugc gacgugaagg gcuuugcgcc uuuuagcaaa    300
gacaacggaa uccgaaucgg aagcagaggg cauaucuuug uuauuaggga accauuugug    360
ucuuguaguc ccgucgagug ccgaaccuuc uuccuuacac agggcgcauu gcugaacgau    420
aagcauucca acggcaccgu uaagggcagg agcccauuca ggacacugau gucaguggaa    480
guuggucaau cgccuaacgu uuaucaggca cgcuuugagg ccguggccug gagugcaacc    540
gccugucacg acggcaagaa guggaugaca auuggggguga cugguccuga cagcaaggca    600
aucgcaguug uucacuacgg cggugucccc acggacaucg ugaauucgug ggccggagac    660
auccugcgga cucaggaauc uucguguacc ugcauccagg gcaacuguua cuggguaaug    720
acugacgguc cuaguaaccg ucaggcccaa uauagaauau acaaggccaa ccagggcaag    780
auuauugacc aagccgacgu auccuucucc ggcggccaua ucgaggagug cucuuguuau    840
ccuaacgacg gaaaggucga gugugugugc cgcgacaacu ggaucgggac caaccgcccu    900
gugcugguca uaucuccuga ucugucauau cgugugggau aucuuugugc aggauugcca    960
uccgauacac cccgagguga ggacgcccag uucguaggga gcuguacuag cccuauggga   1020
aaucagggau acggcguuaa ggguuuugga uuccgccaag guaccgacgu cuggaugggc   1080
aggaccauaa gcaggaccag cagauccgga uuugaaauca ucaggaucaa gaacgggugg   1140
acccagacgu cuaaagagca aauucgucgg caagugguug uagacaaucu aaauuggucu   1200
ggcuauagcg gaaguuucac ucuuccaguu gaacucagcg gccgugagug ucuggugccg   1260
ugcuuuuggg uggaaaugau cagaggcagg cccgaggagc guacaaucug gacaucuucu   1320
uccuccaucg ugaugugugg gguugaucac gagaucgcag acuggagcug gcacgacggu   1380
gcgauacugc cauucgacau ugacggaaug                                    1410
```

<210> SEQ ID NO 124
<211> LENGTH: 470
<212> TYPE: PRT
<213> ORGANISM: Artificial Sequence
<220> FEATURE:
<223> OTHER INFORMATION: Synthetic

<400> SEQUENCE: 124

```
Met Asn Pro Asn Gln Lys Ile Ala Thr Ile Gly Ser Ile Ser Leu Gly
1               5                   10                  15

Leu Val Val Phe Asn Val Leu Leu His Ala Leu Ser Ile Ile Leu Met
            20                  25                  30

Val Leu Ala Leu Gly Lys Ser Glu Asn Asn Gly Ile Cys Lys Gly Thr
        35                  40                  45

Ile Ile Arg Glu Tyr Asn Glu Thr Val Arg Ile Glu Lys Val Thr Gln
    50                  55                  60

Trp Tyr Asn Thr Ser Val Val Glu Tyr Val Pro His Trp Asn Glu Gly
65                  70                  75                  80

Ala Tyr Ile Asn Asn Thr Glu Pro Ile Cys Asp Val Lys Gly Phe Ala
                85                  90                  95

Pro Phe Ser Lys Asp Asn Gly Ile Arg Ile Gly Ser Arg Gly His Ile
```

```
            100                 105                 110

Phe Val Ile Arg Glu Pro Phe Val Ser Cys Ser Pro Val Glu Cys Arg
        115                 120                 125

Thr Phe Phe Leu Thr Gln Gly Ala Leu Leu Asn Asp Lys His Ser Asn
    130                 135                 140

Gly Thr Val Lys Gly Arg Ser Pro Phe Arg Thr Leu Met Ser Val Glu
145                 150                 155                 160

Val Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
            180                 185                 190

Val Thr Gly Pro Asp Ser Lys Ala Ile Ala Val Val His Tyr Gly Gly
        195                 200                 205

Val Pro Thr Asp Ile Val Asn Ser Trp Ala Gly Asp Ile Leu Arg Thr
    210                 215                 220

Gln Glu Ser Ser Cys Thr Cys Ile Gln Gly Asn Cys Tyr Trp Val Met
225                 230                 235                 240

Thr Asp Gly Pro Ser Asn Arg Gln Ala Gln Tyr Arg Ile Tyr Lys Ala
                245                 250                 255

Asn Gln Gly Lys Ile Ile Asp Gln Ala Asp Val Ser Phe Ser Gly Gly
            260                 265                 270

His Ile Glu Glu Cys Ser Cys Tyr Pro Asn Asp Gly Lys Val Glu Cys
        275                 280                 285

Val Cys Arg Asp Asn Trp Ile Gly Thr Asn Arg Pro Val Leu Val Ile
    290                 295                 300

Ser Pro Asp Leu Ser Tyr Arg Val Gly Tyr Leu Cys Ala Gly Leu Pro
305                 310                 315                 320

Ser Asp Thr Pro Arg Gly Glu Asp Ala Gln Phe Val Gly Ser Cys Thr
                325                 330                 335

Ser Pro Met Gly Asn Gln Gly Tyr Gly Val Lys Gly Phe Gly Phe Arg
            340                 345                 350

Gln Gly Thr Asp Val Trp Met Gly Arg Thr Ile Ser Arg Thr Ser Arg
        355                 360                 365

Ser Gly Phe Glu Ile Ile Arg Ile Lys Asn Gly Trp Thr Gln Thr Ser
    370                 375                 380

Lys Glu Gln Ile Arg Arg Gln Val Val Val Asp Asn Leu Asn Trp Ser
385                 390                 395                 400

Gly Tyr Ser Gly Ser Phe Thr Leu Pro Val Glu Leu Ser Gly Arg Glu
                405                 410                 415

Cys Leu Val Pro Cys Phe Trp Val Glu Met Ile Arg Gly Arg Pro Glu
            420                 425                 430

Glu Arg Thr Ile Trp Thr Ser Ser Ser Ser Ile Val Met Cys Gly Val
        435                 440                 445

Asp His Glu Ile Ala Asp Trp Ser Trp His Asp Gly Ala Ile Leu Pro
    450                 455                 460

Phe Asp Ile Asp Gly Met
465                 470
```

<210> SEQ ID NO 125
<211> LENGTH: 1586
<212> TYPE: RNA
<213> ORGANISM: Artificial Sequence
<220> FEATURE:
<223> OTHER INFORMATION: Synthetic

<400> SEQUENCE: 125
gggaaauaag agagaaaaga agaguaagaa gaaauauaag accccggcgc cgccaccaug 60
aacccuaauc agaagauugc gaccauuggc agcauuucuc uuggccucgu gguguucaac 120
gucuugcugc acgcccuauc caucauccuc augguccugg cccuugguaa gagcgagaac 180
aacgguauuu guaagggaac aaucaucaga gaguacaacg agaccguucg gaucgagaag 240
guaacacagu gguacaauac gucaguugug gaguacgugc cgcacuggaa cgagggcgcu 300
uauauuaaca acaccgagcc aaucugcgac gugaagggcu uugcgccuuu uagcaaagac 360
aacggaaucc gaaucggaag cagagggcau aucuuuguua uuagggaacc auuugugucu 420
uguagucccg ucgagugccg aaccuucuuc cuuacacagg gcgcauugcu gaacgauaag 480
cauuccaacg gcaccguuaa ggacaggagc ccauucagga cacugauguc aguggaaguu 540
ggucaaucgc cuaacguuua ucaggcacgc uuugaggccg uggccuggag ugcaaccgcc 600
ugucacgacg gcaagaagug gaugacaauu ggggugacug guccugacag caaggcaauc 660
gcaguuguuc acuacggcgg uguccccacg gacaucguga auucgugggc cggagacauc 720
cugcggacuc aggacucuuc guguaccugc auccagggca acuguuacug gguaaugacu 780
gacgguccua guaaccguca ggcccaauau agaauauaca aggccaacca gggcaagauu 840
auugaccaag ccgacguauc cuucuccggc ggccauaucg aggagugcuc uuguuauccu 900
aacgacggaa aggucgagug ugugugccgc gacaacugga ucgggaccaa ccgcccugug 960
cuggucauau cuccugaucu gucauaucgu gugggauauc uuugugcagg auugccaucc 1020
gauacacccc gaggugagga cgcccaguuc guagggagcu guacuagccc uaugggaaau 1080
cagggauacg gcguuaaggg uuuuggauuc cgccaaggua ccgacgucug gaugggcagg 1140
accauaagca ggaccagcag auccggauuu gaaaucauca ggaucaagaa cggguggacc 1200
cagacgucua aagagcaaau ucgucggcaa gugguuguag acaaucuaaa uuggucuggc 1260
uauagcggaa guuucacucu uccaguugaa cucagcggcc gugagugucu ggugccgugc 1320
uuuugggugg aaaugaucag aggcaggccc gaggagcgua caaucuggac aucuucuucc 1380
uccaucguga ugugugggu ugaucacgag aucgcagacu ggagcuggca cgacggugcg 1440
auacugccau ucgacauuga cggaauguga uaauaggcug gagccucggu ggccuagcuu 1500
cuugccccuu gggccucccc ccagccccuc cuccccuucc ugcacccgua cccccguggu 1560
cuuugaauaa agucugagug ggcggc 1586

<210> SEQ ID NO 126
<211> LENGTH: 1410
<212> TYPE: RNA
<213> ORGANISM: Artificial Sequence
<220> FEATURE:
<223> OTHER INFORMATION: Synthetic

<400> SEQUENCE: 126
augaacccua aucagaagau ugcgaccauu ggcagcauuu cucuuggccu cgugguguuc 60
aacgucuugc ugcacgcccu auccaucauc cucauggucc uggcccuugg uaagagcgag 120
aacaacggua uuuguaaggg aacaaucauc agagaguaca acgagaccgu ucggaucgag 180
aagguaacac agugguacaa uacgucaguu guggaguacg ugccgcacug gaacgagggc 240
gcuuauauua acaacaccga gccaaucugc gacgugaagg gcuuugcgcc uuuuagcaaa 300
gacaacggaa uccgaaucgg aagcagaggg cauaucuuug uuauuaggga accauuugug 360
ucuuguaguc ccgucgagug ccgaaccuuc uuccuuacac agggcgcauu gcugaacgau 420

```
aagcauucca acggcaccgu uaaggacagg agcccauuca ggacacugau gucaguggaa    480

guuggucaau cgccuaacgu uuaucaggca cgcuuugagg ccguggccug gagugcaacc    540

gccugucacg acggcaagaa guggaugaca auugggguga cugguccuga cagcaaggca    600

aucgcaguug uucacuacgg cggugucccc acggacaucg ugaauucgug ggccggagac    660

auccugcgga cucaggacuc uucguguacc ugcauccagg gcaacuguua cuggguaaug    720

acugacgguc cuaguaaccg ucaggcccaa uauagaauau acaaggccaa ccagggcaag    780

auuauugacc aagccgacgu auccuucucc ggcggccaua ucgaggagug cucuuguuau    840

ccuaacgacg gaaaggucga gugugugugc cgcgacaacu ggaucgggac caaccgcccu    900

gugcugguca uaucuccuga ucugucauau cgugugggau aucuuugugc aggauugcca    960

uccgauacac cccgagguga ggacgcccag uucguaggga gcuguacuag cccuauggga   1020

aaucagggau acggcguuaa ggguuuugga uuccgccaag guaccgacgu cuggaugggc   1080

aggaccauaa gcaggaccag cagauccgga uuugaaauca ucaggaucaa gaacgggugg   1140

acccagacgu cuaaagagca aauucgucgg caaguggauug uagacaaucu aaauuggucu   1200

ggcuauagcg gaaguuucac ucuuccaguu gaacucagcg gccgugagug ucuggugccg   1260

ugcuuuuggg uggaaaugau cagaggcagg cccgaggagc guacaaucug gacaucuucu   1320

uccuccaucg ugaugugugg gguugaucac gagaucgcag acuggagcug gcacgacggu   1380

gcgauacugc cauucgacau ugacggaaug                                     1410


<210> SEQ ID NO 127
<211> LENGTH: 470
<212> TYPE: PRT
<213> ORGANISM: Artificial Sequence
<220> FEATURE:
<223> OTHER INFORMATION: Synthetic

<400> SEQUENCE: 127

Met Asn Pro Asn Gln Lys Ile Ala Thr Ile Gly Ser Ile Ser Leu Gly
1               5                   10                  15

Leu Val Val Phe Asn Val Leu Leu His Ala Leu Ser Ile Ile Leu Met
            20                  25                  30

Val Leu Ala Leu Gly Lys Ser Glu Asn Asn Gly Ile Cys Lys Gly Thr
        35                  40                  45

Ile Ile Arg Glu Tyr Asn Glu Thr Val Arg Ile Glu Lys Val Thr Gln
    50                  55                  60

Trp Tyr Asn Thr Ser Val Val Glu Tyr Val Pro His Trp Asn Glu Gly
65                  70                  75                  80

Ala Tyr Ile Asn Asn Thr Glu Pro Ile Cys Asp Val Lys Gly Phe Ala
                85                  90                  95

Pro Phe Ser Lys Asp Asn Gly Ile Arg Ile Gly Ser Arg Gly His Ile
            100                 105                 110

Phe Val Ile Arg Glu Pro Phe Val Ser Cys Ser Pro Val Glu Cys Arg
        115                 120                 125

Thr Phe Phe Leu Thr Gln Gly Ala Leu Leu Asn Asp Lys His Ser Asn
    130                 135                 140

Gly Thr Val Lys Asp Arg Ser Pro Phe Arg Thr Leu Met Ser Val Glu
145                 150                 155                 160

Val Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
```

```
            180                 185                 190

Val Thr Gly Pro Asp Ser Lys Ala Ile Ala Val Val His Tyr Gly Gly
        195                 200                 205

Val Pro Thr Asp Ile Val Asn Ser Trp Ala Gly Asp Ile Leu Arg Thr
    210                 215                 220

Gln Asp Ser Ser Cys Thr Cys Ile Gln Gly Asn Cys Tyr Trp Val Met
225                 230                 235                 240

Thr Asp Gly Pro Ser Asn Arg Gln Ala Gln Tyr Arg Ile Tyr Lys Ala
                245                 250                 255

Asn Gln Gly Lys Ile Ile Asp Gln Ala Asp Val Ser Phe Ser Gly Gly
            260                 265                 270

His Ile Glu Glu Cys Ser Cys Tyr Pro Asn Asp Gly Lys Val Glu Cys
        275                 280                 285

Val Cys Arg Asp Asn Trp Ile Gly Thr Asn Arg Pro Val Leu Val Ile
    290                 295                 300

Ser Pro Asp Leu Ser Tyr Arg Val Gly Tyr Leu Cys Ala Gly Leu Pro
305                 310                 315                 320

Ser Asp Thr Pro Arg Gly Glu Asp Ala Gln Phe Val Gly Ser Cys Thr
                325                 330                 335

Ser Pro Met Gly Asn Gln Gly Tyr Gly Val Lys Gly Phe Gly Phe Arg
            340                 345                 350

Gln Gly Thr Asp Val Trp Met Gly Arg Thr Ile Ser Arg Thr Ser Arg
        355                 360                 365

Ser Gly Phe Glu Ile Ile Arg Ile Lys Asn Gly Trp Thr Gln Thr Ser
    370                 375                 380

Lys Glu Gln Ile Arg Arg Gln Val Val Val Asp Asn Leu Asn Trp Ser
385                 390                 395                 400

Gly Tyr Ser Gly Ser Phe Thr Leu Pro Val Glu Leu Ser Gly Arg Glu
                405                 410                 415

Cys Leu Val Pro Cys Phe Trp Val Glu Met Ile Arg Gly Arg Pro Glu
            420                 425                 430

Glu Arg Thr Ile Trp Thr Ser Ser Ser Ser Ile Val Met Cys Gly Val
        435                 440                 445

Asp His Glu Ile Ala Asp Trp Ser Trp His Asp Gly Ala Ile Leu Pro
    450                 455                 460

Phe Asp Ile Asp Gly Met
465                 470
```

<210> SEQ ID NO 128
<211> LENGTH: 9
<212> TYPE: RNA
<213> ORGANISM: Artificial Sequence
<220> FEATURE:
<223> OTHER INFORMATION: Synthetic

<400> SEQUENCE: 128 ccrccaugg 9

<210> SEQ ID NO 129
<211> LENGTH: 1867
<212> TYPE: RNA
<213> ORGANISM: Artificial Sequence
<220> FEATURE:
<223> OTHER INFORMATION: Synthetic

<400> SEQUENCE: 129
gggaaauaag agagaaaaga agaguaagaa gaaauauaag accccggcgc cgccaccaug 60
aagaccauca ucgcccugag cuacauccug ugccuggugu ucgcccagaa gauccccggc 120
aacgauaaca gcaccgccac ccugugucug ggacaccacg ccgugcccaa cggcaccauc 180
gugaagacua ucaccaacga ccggaucgag gugaccaacg ccaccgagcu ggugcagaac 240
agcagcaucg gcgagaucug cgacagcccu caccagaucc uggacggcgg caacugcacc 300
cugaucgacg cacugcuggg cgacccucag ugcgacggcu uucagaacaa ggagugggac 360
cuguucgugg agagaucgcg ggccaacagc aacugcuacc ccuacgacgu ccccgacuac 420
gcaagccuga gaagccucgu ggccucaagc ggcacccugg aguucaagaa cgagagcuuc 480
aacuggaccg gcgugaagca gaacggcacc ucaagcgccu gcauccgggg cuccagcagc 540
agcuucuucu cacggcugaa cuggcugacc caccugaacu acaccuaccc cgcccugaac 600
gugaccaugc ccaacaacga gcaguucgac aagcuguaca ucuggggagu gcaccauccc 660
agcaccgaca aggaccagau uagccuguuc gcccagccca gcggccggau caccgugagc 720
accaagcgga gccagcaggc cgugaucccc aacaucggcu cucggcccag aauccgggac 780
auccccagcc ggaucagcau cuacuggacc auugugaagc ccggcgacau ccugcugauc 840
aacuccaccg gcaaccugau cgccccucgg ggcuauuuca agauccggag cggcaagagc 900
agcaucaugc ggagcgacgc cccuaucggc aagugcaaga gcgagugcau cacacccaac 960
ggaagcaucc ccaacgacaa gcccuuccag aacgugaacc ggauaaccua cggcgccugc 1020
ccuagauacg ugaagcagag cacccugaag cuggccaccg gcaugcggaa cgugcccgag 1080
aagcagacuc ggggcaucuu cggcgccauc gccggcuuca ucgagaacgg cugggagggc 1140
augguggacg gcugguacgg cuuccggcac cagaacucug agggcagagg acaggccgca 1200
gaccugaaga gcacccaggc cgccaucgac cagaucaacg gcaagcugaa ccggcugauc 1260
ggcaagacca acgagaaguu ccaccagauc gagaaggagu ucagcgaggu ggagggcagg 1320
guacaggacc uggagaagua cguggaggac accaagaucg accuguggag cuacaacgcc 1380
gagcugcugg uagcccugga gaaccagcac accaucgacc ugaccgacag cgagaugaac 1440
aagcuguucg agaagaccaa gaagcagcug cgggagaacg ccgaggacau gggcaacggc 1500
ugcuucaaga ucuaccacaa gugcgacaac gccugcaucg gcagcauccg gaacgagacc 1560
uacgaccaca acguguaccg ggacgaggcc cugaacaacc gguuccagau caagggcgug 1620
gagcugaaga gcggcuacaa ggacuggauc cuguggauca gcuucgccau guccugcuuc 1680
cugcugugca ucgcccugcu ggguuucauc augugggccu gccagaaggg caacauccgg 1740
ugcaacaucu gcaucugaua auaggcugga gccucggugg cacgagaacg gcaccaucac 1800
cccucccccc agccccuccu ccccuuccug caggaagugg ucuuugaaua aagucugagu 1860
gggcggc 1867

<210> SEQ ID NO 130
<211> LENGTH: 112
<212> TYPE: RNA
<213> ORGANISM: Artificial Sequence
<220> FEATURE:
<223> OTHER INFORMATION: Synthetic

<400> SEQUENCE: 130
ugauaauagg cuggagccuc gguggcacga gaacggcacc aucaccccuc cccccagccc 60
cuccuccccu uccugcagga aguggucuuu gaauaaaguc ugagugggcg gc 112

<210> SEQ ID NO 131

<211> LENGTH: 1915
<212> TYPE: RNA
<213> ORGANISM: Artificial Sequence
<220> FEATURE:
<223> OTHER INFORMATION: Synthetic

<400> SEQUENCE: 131
gggaaauaag agagaaaaga agaguaagaa gaaauauaag accccggcgc cgccaccaug 60
aaggccauca ucgugcuguu aauggguggug accagcaacg ccgaccggau cugcaccggc 120
aucaccucua gcaacagccc ucacguggug aagaccgcca cacagggcga ggugaacgug 180
accggcguga uuccccugac caccaccccu accaagagcc acuucgccaa ccugaaggga 240
accgagaccc ggggcaagcu gugucccaag ugccugaacu gcaccgaccu ggacguggcc 300
cugggcagac ccaagugcac cggcaagauc cccagcgccc gggugucuau ccugcacgaa 360
gugcggcccg ugacuagcgg cugcuucccc aucaugcacg accggaccaa gauccggcag 420
cugcccaacc ugcugcgggg cuacgagcac gugcggcuga gcacccacaa cgugaucaac 480
gccgaagacg cacccgggag accauacgag aucggcacca gcggcucuug ccccaacauc 540
accaacggca acggcuucuu cgcuaccaug gccugggccg ugccaaagaa caagacugcc 600
accaacccuc ugaccaucga ggugcccuac aucugcaccg agggcgagga ccagaucacc 660 gugugggggcu uccacagcga cagcgagacc cagauggcca agcuguacgg cgacagcaag 720
ccccagaagu ucaccagcag cgccaacggc gugaccaccc acuacgugag ccagaucggc 780
ggcuucccca accagaccga ggacggcggc uuaccccaga gcggccggau cgugguggac 840
uacauggugc agaagagcgg caagaccggc accaucaccu accagcgggg cauccugcug 900
ccacagaagg ugugguggcgc cucagggcgg ucaaagguga ucaagggcag ccugccacug 960
auuggcgagg ccgacugccu gcacgagaag uacggcggcc ugaacaagag caagcccuac 1020
uacaccggcg agcacgccaa ggcaaucggc aacugcccca ucugggguga gacaccccug 1080
aagcuggcca acggcaccaa guaccggcca cccgccaaac ugcugaagga gcggggcuuc 1140
uucggcgcca uugccggcuu ccucgaaggc gguugggagg gcaugaucgc cggcuggcac 1200
ggcuacacua gccacggcgc acacggagua gcaguggccg ccgaccugaa gagcacccag 1260
gaggccauca acaagaucac caagaaccug aacagccuga gcgagcugga ggugaagaau 1320
cugcagcggc ugucuggcgc uauggacgag cugcacaacg agauccugga gcuggacgag 1380
aagguggacg acuuacgggc cgacaccauc agcagccaga ucgagcuggc cgugcugcug 1440
agcaacgagg gcaucaucaa cagcgaggac gagcaccugc uggcccugga gggaagcuga 1500
agaagaugcu gggcccuucu gccguggaga ucgguaacgg cugcuucgag accaagcaca 1560
agugcaacca gaccugccug gaucggaucg cagccggcac cuuugacgcc ggggaguuca 1620
gccugcccac cuucgacagc cugaacauca ccgccgccag ccugaacgac gacggccugg 1680
acaaccacac cauccugcug uacuacucua cagccgcuag cagccuggcc gugacccuga 1740
ugaucgccau cuucguggug uacaugguga gccgggacaa cgugagcugc agcaucugcc 1800
ugugauaaua ggcuggagcc ucgguggcaa ccuacgccga agaccacgcc uccccccagc 1860
cccuccuccc cuuccugcag guuaguggguc uuugaauaaa gucugagugg gcggc 1915

<210> SEQ ID NO 132
<211> LENGTH: 113
<212> TYPE: RNA
<213> ORGANISM: Artificial Sequence
<220> FEATURE:
<223> OTHER INFORMATION: Synthetic

<400> SEQUENCE: 132
ugauaauagg cuggagccuc gguggcaacc uacgccgaag accacgccuc cccccagccc 60
cuccuccccu uccugcaggu uaguggucuu ugaauaaagu cugagugggc ggc 113

<210> SEQ ID NO 133
<211> LENGTH: 1923
<212> TYPE: RNA
<213> ORGANISM: Artificial Sequence
<220> FEATURE:
<223> OTHER INFORMATION: Synthetic

<400> SEQUENCE: 133
gggaaauaag agagaaaaga agaguaagaa gaaauauaag accccggcgc cgccaccaug 60
aaggccauca ucgugcuacu gaugguggug accagcaacg ccgaccggau cugcaccggc 120
aucaccagca gcaacagccc gcacguggug aagaccgcca cccaaggcga ggugaacgug 180
accggcguga ucccacugac caccacuccc accaagagcu acuucgccaa ccugaagggc 240
acacggacuc ggggcaagcu gugccccgac ugccugaacu gcaccgaccu ggacguggcc 300
cugggcagac ccaugugcgu gggcaccacc ccuucugcca aggccagcau ccugcacgag 360
gugagacccg ugaccagcgg gugcuucccc aucaugcacg accggaccaa gauccggcag 420
cugcccaacc ugcugcgggg cuacgagaag auccggcuga gcacccagaa cgugaucgac 480
gccgagaagg ccccuggagg ucccuaccgg cugggcacca gcggaagcug ccccaacgcc 540
accagcaaga ucggcuucuu cgccaccaug gccugggcug ugcccaagga caacuacaag 600
aacgccacca aucccugac cguggaggug cccuacaucu gcaccgaggg cgaggaccag 660
aucaccgugu ggggcuucca cagcgacaac aagacccaga ugaagagccu guacggcgac 720
agcaaucccc agaaguucac aagcagcgcc aacggcguga ccacccacua cgugagccag 780
aucggcgacu uccccgacca gaccgaggac ggagggcugc cucagagugg ccggaucgug 840
guggacuaca ugaugcagaa gcccggcaag accggcacca ucguguacca gcggggcgug 900
cuguugccuc agaaaguuug gugugccagc ggcaggagca aggugaucaa gggcagccug 960
ccccugaucg gcgaggcaga cugccuccac gaggaguacg gcggccugaa caagagcaag 1020
cccuacuaca ccggcaagca cgccaaggcc aucggcaacu gccccaucug ggugaagacc 1080
ccucugaagc uggccaacgg caccaaguac cggccaccag ccaagcugcu gaaggagcgg 1140
ggcuucuuug gcgccauugc cggcuucCuc gagggaggcu gggagggcau gaucgccggc 1200
uggcacggcu acacaagcca cggcgcacac ggaguggcug uggcugccga ccugaagagc 1260
acccaggagg ccaucaacaa gaucaccaag aaccugaaca gccugagcga gcuggaggug 1320
aagaaccugc agcggcuguc aggcgccaug gacgagcugc acaacgagau ccuggagcug 1380
gacgagaagg uggacgaccu gcgugccgac accaucagca gccagaucga gcuggccgug 1440
cugcugagca acgagggcau caucaacagc gaggacgagc accugcuggc ccuggagcgg 1500
aaacugaaga agaugcuggg acccucugcc guggacaucg gcaacggcug cuucgagacc 1560
aagcacaagu gcaaccagac cugccuggau cggaucgccg ccggaaccuu caacgccggc 1620
gaguucagcc ugcccaccuu cgacagccug aacaucaccg ccgccagccu gaacgacgac 1680
ggccuggaca accacaccau ccugcuguac uacagcacug ccgccucaag ccuggccgug 1740
acccugaugc uggccaucuu caucguguac auggugagcc gggacaacgu gagcugcagc 1800
aucugccugu gauaauaggc uggagccucg guggcaacga cccugccgca gcaaaccucc 1860

-continued ccccagcccc uccuccccuu ccugcaggac caguggucuu ugaauaaagu cugagugggc 1920
ggc 1923

<210> SEQ ID NO 134
<211> LENGTH: 114
<212> TYPE: RNA
<213> ORGANISM: Artificial Sequence
<220> FEATURE:
<223> OTHER INFORMATION: Synthetic

<400> SEQUENCE: 134
ugauaauagg cuggagccuc gguggcaacg acccugccgc agcaaaccuc cccccagccc 60
cuccuccccu uccugcagga ccaguggucu uugaauaaag ucugaguggg cggc 114

<210> SEQ ID NO 135
<211> LENGTH: 1870
<212> TYPE: RNA
<213> ORGANISM: Artificial Sequence
<220> FEATURE:
<223> OTHER INFORMATION: Synthetic

<400> SEQUENCE: 135
gggaaauaag agagaaaaga agaguaagaa gaaauauaag accccggcgc cgccaccaug 60
aaggccaucc uggucgugau gcuguacacc uucaccaccg ccaacgccga cacccugugc 120
aucggcuacc acgccaacaa cagcaccgac accguggaca ccgugcugga gaagaacgug 180
accgugaccc acagcgugaa ccugcuggag gacaagcaca acggcaagcu gugcaagcug 240
aggggagugg caccccugca ccugggcaag ugcaacaucg ccggcuggau ccugggcaac 300
cccgagugcg agagccugag cacagcccgg agcuggagcu acaucgugga gaccagcaac 360
agcgacaacg gcaccuguua ccccggcgac uucaucaacu acgaggagcu gcgggagcag 420
cugagcagcg ugagcagcuu cgagcgguuc gagaucuucc ccaagaccag cagcuggccc 480
aaccacgaca gcgacaacgg cgugacagca gccuguccac acgccggagc caagagcuuc 540
uacaagaacc ugaucuggcu ggugaagaag ggcaagagcu accccaagau caaccagacc 600
uacaucaacg acaagggcaa ggaggugcug gugcuguggg gcauccacca cccaccuacc 660
aucgccgacc agcagagccu guaccagaac gccgacgccu acguguucgu gggcaccagc 720
cgguacagca agaaguucaa gccagagauc gccacccggc ccaaggugag agaccaggag 780
ggccggauga acuacuacug gacccuggug gagcccggag acaagauuac cuucgaggcc 840
accggcaacc ugguggcccc ucgguacgcc uucaccaugg aacgggacgc uggcagcggc 900
aucaucauca gcgacacucc cgugcacgac ugcaacacca ccugccagac ucccgagggc 960
gcuaucaaca ccagccugcc cuuccagaac gugcacccca ucaccaucgg caagugcccc 1020
aaguacguaa agagcaccaa auugcggcug gccaccggac ucaggaacgu gcccagcauc 1080
caaagccggg gccuguuugg cgcaaucgcc ggcuucaucg agggcggcug gacuggcaug 1140
guggacggcu gguacggcua ccaccaccag aacgaacagg ggagcggcua cgcagcugac 1200
cugaagagca cccagaacgc caucgacaag aucaccaaca aggugaacag cgugaucgag 1260
aagaugaaca cccaguucac cgccgugggc aaggaguuca accaccugga gaagcggauc 1320
gagaaccuga acaagaaggu ggacgacggc uuccuggaca ucuggaccua caacgccgag 1380
cugcugguuc ugcuggagaa cgagcggacc cuggacuauc acgacagcaa cgugaagaac 1440
cuguacgaga aggugcggaa ccagcugaag aacaacgcca aggagaucgg caacggcugc 1500
uucgaguucu accacaagug cgacaacacc ugcauggaga gcgugaagaa cggcaccuac 1560

-continued gacuacccca aguacagcga ggaggccaag cugaaccggg agaagaucga cggcgugaag 1620
cuggacagca cccggaucua ccagauccug gccaucuaca gcaccguggc cagcagccug 1680
gugcuggugg ugagccuggg cgccaucagc uucuggaugu gcagcaacgg cagccugcag 1740
ugccggaucu gcaucugaua auaggcugga gccucggugg ccaccgaagc agccaucagc 1800 accuccccc agccccuccu ccccuuccug caggccaaag uggucuuuga auaaagucug 1860
agugggcggc 1870

<210> SEQ ID NO 136
<211> LENGTH: 115
<212> TYPE: RNA
<213> ORGANISM: Artificial Sequence
<220> FEATURE:
<223> OTHER INFORMATION: Synthetic

<400> SEQUENCE: 136
ugauaauagg cuggagccuc gguggccacc gaagcagcca ucagcaccuc cccccagccc 60
cuccuccccu uccugcaggc caaagugguc uuugaauaaa gucugagugg gcggc 115

<210> SEQ ID NO 137
<211> LENGTH: 9
<212> TYPE: PRT
<213> ORGANISM: Artificial Sequence
<220> FEATURE:
<223> OTHER INFORMATION: Synthetic

<400> SEQUENCE: 137

Ile Tyr Ser Thr Val Ala Ser Ser Leu
1               5

<210> SEQ ID NO 138
<211> LENGTH: 11
<212> TYPE: RNA
<213> ORGANISM: Artificial Sequence
<220> FEATURE:
<223> OTHER INFORMATION: Synthetic

<400> SEQUENCE: 138
gggauccuac c 11

<210> SEQ ID NO 139
<211> LENGTH: 4
<212> TYPE: PRT
<213> ORGANISM: Artificial Sequence
<220> FEATURE:
<223> OTHER INFORMATION: Synthetic

<400> SEQUENCE: 139

Arg Ile Ile Val
1

<210> SEQ ID NO 140
<211> LENGTH: 5
<212> TYPE: PRT
<213> ORGANISM: Artificial Sequence
<220> FEATURE:
<223> OTHER INFORMATION: Synthetic

<400> SEQUENCE: 140

Gly Arg Phe Tyr Gln
1               5

-continued

<210> SEQ ID NO 141
<211> LENGTH: 4
<212> TYPE: PRT
<213> ORGANISM: Artificial Sequence
<220> FEATURE:
<223> OTHER INFORMATION: Synthetic

<400> SEQUENCE: 141

Thr Tyr Asp Pro
1

<210> SEQ ID NO 142
<211> LENGTH: 4
<212> TYPE: PRT
<213> ORGANISM: Artificial Sequence
<220> FEATURE:
<223> OTHER INFORMATION: Synthetic

<400> SEQUENCE: 142

Glu Gly Leu Val
1

<210> SEQ ID NO 143
<211> LENGTH: 5
<212> TYPE: PRT
<213> ORGANISM: Artificial Sequence
<220> FEATURE:
<223> OTHER INFORMATION: Synthetic

<400> SEQUENCE: 143

Gly Phe Arg Tyr Gln
1 5

UNITED STATES PATENT AND TRADEMARK OFFICE
CERTIFICATE OF CORRECTION

PATENT NO. : 12,329,811 B2
APPLICATION NO. : 17/572465
DATED : June 17, 2025
INVENTOR(S) : Raffael Nachbagauer, Carole Henry and Patricia Jorquera It is certified that error appears in the above-identified patent and that said Letters Patent is hereby corrected as shown below:

In the Claims

In Claim 1 at Column 399, Lines 55-56, please delete "the lipid nanoparticle" and insert --a lipid nanoparticle--.

In Claim 16 at Column 403, Lines 54-55, please delete "the lipid nanoparticle" and insert --a lipid nanoparticle--.

Signed and Sealed this
Fourth Day of November, 2025

John A. Squires
*Director of the United States Patent and Trademark Office*